US008367658B2

(12) United States Patent
Collins et al.

(10) Patent No.: US 8,367,658 B2
(45) Date of Patent: Feb. 5, 2013

(54) PYRAZIN-2-YL-PYRIDIN-2-YL-AMINE AND PYRAZIN-2-YL-PYRIMIDIN-4-YL-AMINE COMPOUNDS AND THEIR USE

(75) Inventors: Ian Collins, Sutton (GB); John Charles Reader, Linton (GB); Thomas Peter Matthews, Sutton (GB); Kwai Ming Cheung, Sutton (GB); Nicolas Proisy, Sutton (GB); David Hugh Williams, Melbourn (GB); Sukhbinder Singh Klair, Sawston (GB); Jane Elizabeth Scanlon, Sawston (GB); Nelly Piton, Saffron Walden (GB); Glynn Jonathan Addison, Babraham (GB); Michael Cherry, Haddenham (GB)

(73) Assignee: Cancer Research Technology Limited, London (GB)

( * ) Notice: Subject to any disclaimer, the term of this patent is extended or adjusted under 35 U.S.C. 154(b) by 0 days.

(21) Appl. No.: 13/241,887

(22) Filed: Sep. 23, 2011

(65) Prior Publication Data

US 2012/0040967 A1 Feb. 16, 2012

Related U.S. Application Data

(63) Continuation of application No. 12/680,891, filed as application No. PCT/GB2008/003362 on Oct. 6, 2008, now Pat. No. 8,058,045.

(60) Provisional application No. 60/977,700, filed on Oct. 5, 2007.

(30) Foreign Application Priority Data

Oct. 5, 2007 (GB) .................................. 0719644.7

(51) Int. Cl.
*A61K 31/55* (2006.01)
*A61K 31/5377* (2006.01)
*A61K 31/497* (2006.01)
*A61K 31/506* (2006.01)

(52) U.S. Cl. ........... 514/217.05; 514/235.8; 514/252.11; 514/255.05

(58) Field of Classification Search .............. 514/217.05, 514/255.05, 235.8, 252.11
See application file for complete search history.

(56) References Cited

U.S. PATENT DOCUMENTS

| 8,058,045 B2 | 11/2011 | Collins et al. |
| 2010/0311730 A1 | 12/2010 | Collins et al. |
| 2010/0331328 A1 | 12/2010 | Collins et al. |

FOREIGN PATENT DOCUMENTS

| WO | WO 03/032984 | 4/2003 |
| WO | WO 03/035065 | 5/2003 |
| WO | WO 03/093297 | 11/2003 |
| WO | WO 03/101444 | 12/2003 |
| WO | WO 2005/011597 | 2/2005 |
| WO | WO 2005/034869 | 4/2005 |
| WO | WO 2005/037285 | 4/2005 |
| WO | WO 2005/121126 | 12/2005 |
| WO | WO 2006/039718 | 4/2006 |
| WO | WO 2007/000240 | 1/2007 |
| WO | WO 2008/077554 | 7/2008 |
| WO | WO 2008/115369 | 9/2008 |

OTHER PUBLICATIONS

Balaint and Vousden, 2001, "Activation and activities of the p53 tumour suppressor protein," *Br. J. Cancer*, vol. 85, pp. 1813-1823.
Bartek and Lukas, 2003, "Chk1 and Chk2 kinases in checkpoint control and cancer," *Cancer Cell*, vol. 3, pp. 421-429.
Carson and Lois, 1995, "Cancer progression and p53," *Lancet*, vol. 346, pp. 1009-1011.
Dixon and Norbury, 2002, "Therapeutic exploitation of checkpoint defects in cancer cells lacking p53 function," *Cell Cycle*, vol. 1, pp. 362-368.
Greenblatt et al., 1994, "Mutations in the p53 tumor suppressor gene: clues to cancer etiology and molecular pathogenesis," *Cancer Res.*, vol. 54, pp. 4855-4878.
Itoh et al., 2002, "Efficient synthesis of substituted 2-aminopyrazines: FeCl3-promoted condensation of hydroxyiminoketones with aminoacetonitriles", *Tetrahedron Lett.*, vol. 43, pp. 9287-9290.
Liu et al., 2000, "Chk1 is an essential kinase that is regulated by Atr and required for the G(2)/M DNA damage checkpoint," *Genes Dev.*, vol. 14, pp. 1448-1459.
Sanchez et al., 1997, "Conservation of the Chk1 checkpoint pathway in mammals: linkage of DNA damage to Cdk regulation through Cdc25," *Science*, vol. 277, pp. 1497-1501.
Sorensen et al., 2005, "Cell-cycle checkpoint kinase Chk1 is required for mammalian homologous recombination repair," *Nat. Cell Biol.*, vol. 7, pp. 195-201.
Tao and Lin, 2006, "Chk1 inhibitors for novel cancer treatment," *Anti-Cancer Agents in Medicinal Chemistry*, vol. 6, pp. 377-388.
Wang et al., 1996, "UCN-01: a potent abrogator of G2 checkpoint function in cancer cells with disrupted p53," *J. Natl. Cancer Inst.*, vol. 8, pp. 956-965.
Weinert and Hartwell, 1989, "Control of G2 delay by the rad9 gene of *Saccharomyces cerevisiae*," *J. Cell Sci. Suppl.*, vol. 12, pp. 145-148.

(Continued)

*Primary Examiner* — Kristin Bianchi
(74) *Attorney, Agent, or Firm* — Swanson & Bratschun, L.L.C.

(57) ABSTRACT

The present invention pertains generally to the field of therapeutic compounds, and more specifically to certain biarylamine compounds (referred to herein as BAA compounds), and especially certain pyrazin-2-yl-pyridin-2-yl-amine and pyrazine-2-yl-pyrimidin-4-yl-amine compounds, which, inter alia, inhibit Checkpoint Kinase 1 (CHK1) kinase function. The present invention also pertains to pharmaceutical compositions comprising such compounds, and the use of such compounds and compositions, both in vitro and in vivo, to inhibit CHK1 kinase function, and in the treatment of diseases and conditions that are mediated by CHK1, that are ameliorated by the inhibition of CHK1 kinase function, etc., including proliferative conditions such as cancer, etc., optionally in combination with another agent, for example, (a) a DNA topoisomerase I or II inhibitor; (b) a DNA damaging agent; (c) an antimetabolite or TS inhibitor; (d) a microtubule targeted agent; and (e) ionising radiation.

19 Claims, No Drawings

OTHER PUBLICATIONS

White et al., 1967, "Gattermann reaction of 3,5-dimethoxyphenylacetonitrile. Synthesis of 6,8-dioxyisoquinolines" *J. Org. Chem.*, vol. 32, pp. 2689-2692.

Xiao et al., 2006, "Differential roles of checkpoint kinase 1, checkpoint kinase 2, and mitogen-activated protein kinase-activated protein kinase 2 in mediating DNA damage-induced cell cycle arrest: implications for cancer therapy," *Mol. Cancer Ther.*, vol. 5, pp. 1935-1943.

Zachos et al., 2003, "Chk1-deficient tumour cells are viable but exhibit multiple checkpoint and survival defects," *EMBO J.*, vol. 22, pp. 713-723.

Zhao et al., 2002, "Disruption of the checkpoint kinase 1/cell division cycle 25A pathway abrogates ionizing radiation-induced S and G2 checkpoints," *Proc. Natl. Acad. Sci. USA*, vol. 99, pp. 14795-14800.

International Search Report (ISR) and Written Opinion of International Searching Authority (WOISA) for PCT/GB2008/003362, 2008.

International Preliminary Report on Patentability (IPRP) for PCT/GB2008/003362, 2008.

International Search Report (ISR) and Written Opinion of International Searching Authority (WOISA) for PCT/GB2009/000438, 2009.

International Preliminary Report on Patentability (IPRP) for PCT/GB2009/000438, 2009.

UK Search Report for GB 0719644.7, 2008.

UK Search Report for GB 0803018.1, 2008.

PYRAZIN-2-YL-PYRIDIN-2-YL-AMINE AND PYRAZIN-2-YL-PYRIMIDIN-4-YL-AMINE COMPOUNDS AND THEIR USE

RELATED APPLICATIONS

This application is a continuation application of U.S. application Ser. No. 12/680,891, filed Aug. 25, 2010 now U.S. Pat. No. 8,058,045, entitled "Pyrazin-2-yl-pyridin-2-yl-amine and pyrazin-2-yl-pyrimidin-4-yl-amine Compounds and Their Use." U.S. application Ser. No. 12/680,891 is a 35 U.S.C. §371 national phase application of PCT/GB2008/003362 (WO 2009/044162), filed Oct. 6, 2008. PCT/GB2008/003362 is a non-provisional application of U.S. Provisional Patent Application Ser. No. 60/977,700, filed Oct. 5, 2007 and United Kingdom Patent Application Serial No. 0719644.7, filed Oct. 5, 2007, the contents of all of which are incorporated herein by reference in their entirety.

TECHNICAL FIELD

The present invention pertains generally to the field of therapeutic compounds, and more specifically to certain biarylamine compounds (referred to herein as BAA compounds), and especially certain pyrazin-2-yl-pyridin-2-yl-amine and pyrazine-2-yl-pyrimidin-4-yl-amine compounds, which, inter alia, inhibit Checkpoint Kinase 1 (CHK1) kinase function. The present invention also pertains to pharmaceutical compositions comprising such compounds, and the use of such compounds and compositions, both in vitro and in vivo, to inhibit CHK1 kinase function, and in the treatment of diseases and conditions that are mediated by CHK1, that are ameliorated by the inhibition of CHK1 kinase function, etc., including proliferative conditions such as cancer, etc., optionally in combination with another agent, for example, (a) a DNA topoisomerase I or II inhibitor; (b) a DNA damaging agent; (c) an antimetabolite or TS inhibitor; (d) a microtubule targeted agent; and (e) ionising radiation.

BACKGROUND

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Checkpoint Kinase 1 (CHK1)

Progression through the cell division cycle is a tightly regulated process and is monitored at several positions known as cell cycle checkpoints (see, e.g., Weinert and Hartwell, 1989; Bartek and Lukas, 2003). These checkpoints are found in all four stages of the cell cycle; G1, S (DNA replication), G2 and M (Mitosis) and they ensure that key events which control the fidelity of DNA replication and cell division are completed correctly. Cell cycle checkpoints are activated by a number of stimuli, including DNA damage and DNA errors caused by defective replication. When this occurs, the cell cycle will arrest, allowing time for either DNA repair to occur or, if the damage is too severe, for activation of cellular processes leading to controlled cell death.

All cancers, by definition, have some form of aberrant cell division cycle. Frequently, the cancer cells possess one or more defective cell cycle checkpoints, or harbour defects in a particular DNA repair pathway. These cells are therefore often more dependent on the remaining cell cycle checkpoints and repair pathways, compared to non-cancerous cells (where all checkpoints and DNA repair pathways are intact). The response of cancer cells to DNA damage is frequently a critical determinant of whether they continue to proliferate or activate cell death processes and die. For example, tumour cells that contain a mutant form(s) of the tumour suppressor p53 are defective in the G1 DNA damage checkpoint. Thus inhibitors of the G2 or S-phase checkpoints are expected to further impair the ability of the tumour cell to repair damaged DNA.

Many known cancer treatments cause DNA damage by either physically modifying the cell's DNA or disrupting vital cellular processes that can affect the fidelity of DNA replication and cell division, such as DNA metabolism, DNA synthesis, DNA transcription and microtubule spindle formation. Such treatments include for example, radiotherapy, which causes DNA strand breaks, and a variety of chemotherapeutic agents including topoisomerase inhibitors, antimetabolites, DNA-alkylating agents, and platinum-containing cytotoxic drugs. A significant limitation to these genotoxic treatments is drug resistance. One of the most important mechanisms leading to this resistance is attributed to activation of cell cycle checkpoints, giving the tumour cell time to repair damaged DNA. By abrogating a particular cell cycle checkpoint, or inhibiting a particular form of DNA repair, it may therefore be possible to circumvent tumour cell resistance to the genotoxic agents and augment tumour cell death induced by DNA damage, thus increasing the therapeutic index of these cancer treatments.

CHK1 is a serine/threonine kinase involved in regulating cell cycle checkpoint signals that are activated in response to DNA damage and errors in DNA caused by defective replication (see, e.g., Bartek and Lukas, 2003). CHK1 transduces these signals through phosphorylation of substrates involved in a number of cellular activities including cell cycle arrest and DNA repair. Two key substrates of CHK1 are the Cdc25A and Cdc25C phosphatases that dephosphorylate CDK1 leading to its activation, which is a requirement for exit from G2 into mitosis (M phase) (see, e.g., Sanchez et al., 1997). Phosphorylation of Cdc25C and the related Cdc25A by CHK1 blocks their ability to activate CDK1, thus preventing the cell from exiting G2 into M phase. The role of CHK1 in the DNA damage-induced G2 cell cycle checkpoint has been demonstrated in a number of studies where CHK1 function has been knocked out (see, e.g., Liu et al., 2000; Zhao et al., 2002; Zachos et al., 2003).

The reliance of the DNA damage-induced G2 checkpoint upon CHK1 provides one example of a therapeutic strategy for cancer treatment, involving targeted inhibition of CHK1. Upon DNA damage, the p53 tumour suppressor protein is stabilised and activated to give a p53-dependent G1 arrest, leading to apoptosis or DNA repair (Balaint and Vousden, 2001). Over half of all cancers are functionally defective for p53, which can make them resistant to genotoxic cancer treatments such as ionising radiation (IR) and certain forms of chemotherapy (see, e.g., Greenblatt et al., 1994; Carson and Lois, 1995). These p53 deficient cells fail to arrest at the G1 checkpoint or undergo apoptosis or DNA repair, and consequently may be more reliant on the G2 checkpoint for viability and replication fidelity. Therefore abrogation of the G2 checkpoint through inhibition of the CHK1 kinase function may selectively sensitise p53 deficient cancer cells to genotoxic cancer therapies, and this has been demonstrated (see, e.g., Wang et al., 1996; Dixon and Norbury, 2002).

In addition, CHK1 has also been shown to be involved in S phase cell cycle checkpoints and DNA repair by homologous recombination. Thus, inhibition of CHK1 kinase in those cancers that are reliant on these processes after DNA damage, may provide additional therapeutic strategies for the treatment of cancers using CHK1 inhibitors (see, e.g., Sorensen et al., 2005). Recent data using CHK1 selective siRNA supports the selective inhibition of CHK1 as a relevant therapeutic approach, and suggests that combined inhibition with certain other checkpoint kinases provides no additional benefit and may be non-productive (see, e.g., Xiao et al., 2006). Small-molecule selective inhibitors of CHK1 kinase function from various chemical classes have been described (see, e.g., Tao and Lin, 2006).

Wang et al., 2005, describe certain pyrazine compounds of the following formula which allegedly are useful as potassium ion channel modulators.

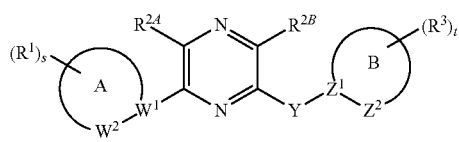

SUMMARY OF THE INVENTION

One aspect of the invention pertains to certain biarylamine compounds (referred to herein as BAA compounds), as described herein.

Another aspect of the invention pertains to a composition (e.g., a pharmaceutical composition) comprising a BAA compound, as described herein, and a pharmaceutically acceptable carrier or diluent.

Another aspect of the invention pertains to method of preparing a composition (e.g., a pharmaceutical composition) comprising the step of admixing a BAA compound, as described herein, and a pharmaceutically acceptable carrier or diluent.

Another aspect of the present invention pertains to a method of inhibiting CHK1 kinase function in a cell, in vitro or in vivo, comprising contacting the cell with an effective amount of a BAA compound, as described herein.

In one embodiment, the method further comprises contacting the cell with one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

Another aspect of the present invention pertains to a method of regulating (e.g., inhibiting) cell proliferation (e.g., proliferation of a cell), inhibiting cell cycle progression, promoting apoptosis, or a combination of one or more these, in vitro or in vivo, comprising contacting a cell with an effective amount of a BAA compound, as described herein.

In one embodiment, the method further comprises contacting the cell with one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

Another aspect of the present invention pertains to a method of treatment comprising administering to a subject in need of treatment a therapeutically-effective amount of a BAA compound, as described herein, preferably in the form of a pharmaceutical composition.

In one embodiment, the method further comprises administering to the subject one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

Another aspect of the present invention pertains to a BAA compound as described herein for use in a method of treatment of the human or animal body by therapy.

In one embodiment, the method of treatment comprises treatment with both (i) a BAA compound and (ii) one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

Another aspect of the present invention pertains to use of a BAA compound, as described herein, in the manufacture of a medicament for use in treatment.

In one embodiment, the treatment comprises treatment with both (i) a medicament comprising a BAA compound and (ii) one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

In one embodiment, the treatment is treatment of a disease or condition that is mediated by CHK1.

In one embodiment, the treatment is treatment of a disease or condition that is ameliorated by the inhibition of CHK1 kinase function.

In one embodiment, the treatment is treatment of a proliferative condition.

In one embodiment, the treatment is treatment of cancer.

In one embodiment, the treatment is treatment of: p53 negative cancer.

In one embodiment, the treatment is treatment of: lung cancer, breast cancer, ovarian cancer, colorectal cancer, melanoma, or glioma.

Another aspect of the present invention pertains to a kit comprising (a) a BAA compound, as described herein, preferably provided as a pharmaceutical composition and in a suitable container and/or with suitable packaging; and (b) instructions for use, for example, written instructions on how to administer the compound.

In one embodiment, the kit further comprises one or more other agents selected from: (a) a DNA topoisomerase I or II inhibitor; (b) a DNA damaging agent; (c) an antimetabolite or TS inhibitor; and (d) a microtubule targeted agent.

Another aspect of the present invention pertains to a BAA compound obtainable by a method of synthesis as described herein, or a method comprising a method of synthesis as described herein.

Another aspect of the present invention pertains to a BAA compound obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspect of the invention.

DETAILED DESCRIPTION OF THE INVENTION

Compounds

One aspect of the present invention relates to certain biarylamines (for convenience, collectively referred to herein as "biarylamine compounds" or "BAA compounds") which are pyrazin-2-yl-pyridin-2-yl-amines or pyrazine-2-yl-pyrimidin-4-yl-amines.

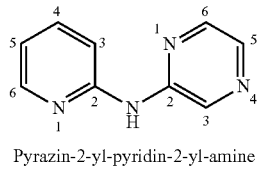
Pyrazin-2-yl-pyridin-2-yl-amine

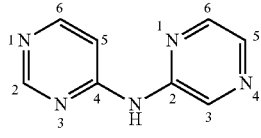
Pyrazin-2-yl-pyrimidin-2-yl-amine

In one embodiment, the compounds are selected from compounds of the following formula, and pharmaceutically acceptable salts, solvates, chemically protected forms, and prodrugs thereof:

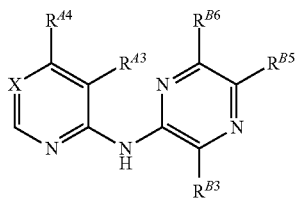

wherein:
—X= is independently —CR$^{A5}$= or —N=;
—R$^{A5}$ is independently —H or -Q$^{A5}$;
—R$^{A3}$ is independently —H or -Q$^{A3}$;
—R$^{A4}$ is independently —NH$_2$, -Q$^{A4N}$, —OH, —O-Q$^{A4O}$, —SH, or —S-Q$^{A4S}$;
—R$^{B3}$ is independently —H or -Q$^{B3}$;
—R$^{B5}$ is independently —H or -Q$^{B5}$; and
—R$^{B6}$ is independently —H or -Q$^{B6}$.

The Group —X=
In one embodiment, —X= is independently —CR$^{A5}$= or —N=.
In one embodiment, —X= is independently —CR$^{A5}$=.
In one embodiment, —X= is independently —N=.

The Group —R$^{A5}$
In one embodiment, —R$^{A5}$, if present, is independently —H or -Q$^{A5}$.
In one embodiment, —R$^{A5}$, if present, is independently —H.
In one embodiment, —R$^{A5}$, if present, is independently -Q$^{A5}$.

The Group —R$^{A3}$
In one embodiment, —R$^{A3}$ is independently —H or -Q$^{A3}$.
In one embodiment, —R$^{A3}$ is independently —H.
In one embodiment, —R$^{A3}$ is independently -Q$^{A3}$.

The Group —R$^{A4}$
In one embodiment, —R$^{A4}$ is independently —NH$_2$, -Q$^{A4N}$, —OH, —O-Q$^{A4O}$, —SH, or —S-Q$^{A4S}$.
In one embodiment, —R$^{A4}$ is independently —NH$_2$ or -Q$^{A4N}$.
In one embodiment, —R$^{A4}$ is independently -Q$^{A4N}$.
In one embodiment, —R$^{A4}$ is independently —NH$_2$.
In one embodiment, —R$^{A4}$ is independently —OH or —O-Q$^{A4O}$.
In one embodiment, —R$^{A4}$ is independently —OH.
In one embodiment, —R$^{A4}$ is independently —O-Q$^{A4O}$.
In one embodiment, —R$^{A4}$ is independently —SH or —S-Q$^{A4S}$.
In one embodiment, —R$^{A4}$ is independently —SH.
In one embodiment, —R$^{A4}$ is independently —S-Q$^{A4S}$.

The Group —R$^{B3}$
In one embodiment, —R$^{B3}$ is independently —H or -Q$^{B3}$.
In one embodiment, —R$^{B3}$ is independently —H.
In one embodiment, —R$^{B3}$ is independently -Q$^{B3}$.

The Group —R$^{B5}$
In one embodiment, —R$^{B5}$ is independently —H or -Q$^{B5}$.
In one embodiment, —R$^{B5}$ is independently —H.
In one embodiment, —R$^{B5}$ is independently -Q$^{B5}$.

The Group —R$^{B6}$
In one embodiment, —R$^{B6}$ is independently —H or -Q$^{B6}$.
In one embodiment, —R$^{B6}$ is independently —H.
In one embodiment, —R$^{B6}$ is independently -Q$^{B6}$.

The Group -Q$^{A4N}$
In one embodiment, -Q$^{A4N}$, if present, is independently -Q$^{A4N1}$ or -Q$^{A4N2}$.
In one embodiment, -Q$^{A4N}$, if present, is independently -Q$^{A4N1}$.
In one embodiment, -Q$^{A4N}$, if present, is independently -Q$^{A4N2}$.

The Group -Q$^{A4N1}$
In one embodiment, -Q$^{A4N1}$, if present, is independently —NHR$^{QN1}$ or NR$^{QN1}_2$.
In one embodiment, -Q$^{A4N1}$, if present, is independently —NHR$^{QN1}$.
In one embodiment, -Q$^{A4N1}$, if present, is independently —NR$^{QN1}_2$.

In one embodiment, each —R$^{QN1}$, if present, is independently:
—R$^{J1}$, —R$^{J2}$, —R$^{J3}$, —R$^{J4}$, —R$^{J5}$, —R$^{J6}$, —R$^{J7}$, —R$^{J8}$, -L$^{I}$-R$^{J4}$, -L$^{I}$-R$^{J5}$, -L$^{I}$-R$^{J6}$, -L$^{I}$-R$^{J7}$, or -L$^{I}$-R$^{J8}$;

wherein:
each —R$^{J1}$ is independently saturated aliphatic C$_{1-6}$alkyl;
each —R$^{J2}$ is independently aliphatic C$_{2-6}$alkenyl;
each —R$^{J3}$ is independently aliphatic C$_{2-6}$alkynyl;
each —R$^{J4}$ is independently saturated C$_{3-6}$cycloalkyl;

each —$R^{J5}$ is independently $C_{3-6}$cycloalkenyl;
each —$R^{J6}$ is independently non-aromatic $C_{3-8}$heterocyclyl;
each —$R^{J7}$ is independently $C_{6-10}$carboaryl;
each —$R^{J8}$ is independently $C_{5-10}$heteroaryl;
each -$L^J$- is independently saturated aliphatic $C_{1-3}$alkylene;

and wherein:
each $C_{1-6}$alkyl, $C_{2-6}$alkenyl, $C_{2-6}$alkynyl, $C_{3-6}$cycloalkyl, $C_{3-6}$cycloalkenyl, non-aromatic $C_{3-8}$heterocyclyl, $C_{6-10}$carboaryl, $C_{5-10}$heteroaryl, and $C_{1-3}$alkylene is optionally substituted, for example, with one or more substituents —$R^{J9}$, wherein each —$R^{J9}$ is independently:
—F, —Cl, —Br, —I,
—$R^{L1}$,
—$CF_3$, —$OCF_3$,
—OH, -$L^L$-OH, —O-$L^L$-OH,
—$OR^{L1}$, -$L^L$-$OR^{L1}$, —O-$L^L$-$OR^{L1}$,
—SH, —$SR^{L1}$,
—CN,
—$NO_2$,
—$NH_2$, —$NHR^{L1}$, —$NR^{L1}_2$, —$NR^{L2}R^{L3}$,
-$L^L$-$NH_2$, -$L^L$-$NHR^{L1}$, -$L^L$-$NR^{L1}_2$, -$L^L$-$NR^{L2}R^{L3}$,
—O-$L^L$-$NH_2$, —O-$L^L$-$NHR^{L1}$, —O-$L^L$-$NR^{L1}_2$, —O-$L^L$-$NR^{L2}R^{L3}$,
—C(=O)OH, —C(=O)$OR^{L1}$,
—C(=O)$NH_2$, —C(=O)$NHR^{L1}$, —C(=O)$NR^{L1}_2$, —C(=O)$NR^{L2}R^{L3}$,
—NHC(=O)$R^{L1}$, —$NR^{L1}$C(=O)$R^{L1}$,
—NHC(=O)$OR^{L1}$, —$NR^{L1}$C(=O)$OR^{L1}$,
—OC(=O)$NH_2$, —OC(=O)$NHR^{L1}$, —OC(=O)$NR^{L1}_2$, —OC(=O)$NR^{L2}R^{L3}$,
—C(=O)$R^{L1}$,
—NHC(=O)$NH_2$, —NHC(=O)$NHR^{L1}$,
—NHC(=O)$NR^{L1}_2$, —NHC(=O)$NR^{L2}R^{L3}$,
—$NR^{L1}$C(=O)$NH_2$, —$NR^{L1}$C(=O)$NHR^{L1}$,
—$NR^{L1}$C(=O)$NR^{L1}_2$, —$NR^{L1}$C(=O)$NR^{L2}R^{L3}$,
—NHS(=O)$_2R^{L1}$, —$NR^{L1}$S(=O)$_2R^{L1}$,
—S(=O)$_2NH_2$, —S(=O)$_2NHR^{L1}$, —S(=O)$_2NR^{L1}_2$,
—S(=O)$_2NR^{L2}R^{L3}$,
—S(=O)$R^{L1}$, —S(=O)$_2R^{L1}$, —OS(=O)$_2R^{L1}$, or
—S(=O)$_2OR^{L1}$;
wherein:
each -$L^L$- is independently saturated aliphatic $C_{1-8}$alkylene;
in each group —$NR^{L2}R^{L3}$, $R^{L2}$ and $R^{L3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;
each —$R^{L1}$ is independently:
—$R^{Z1}$, —$R^{Z4}$, —$R^{Z6}$, —$R^{Z7}$, —$R^{Z8}$,
-$L^Z$-$R^{Z4}$, -$L^Z$-$R^{Z6}$, -$L^Z$-$R^{Z7}$ or -$L^Z$-$R^{Z8}$;
wherein:
each —$R^{Z1}$ is independently saturated aliphatic $C_{1-6}$alkyl;
each —$R^{Z4}$ is independently saturated $C_{3-6}$cycloalkyl;
each —$R^{Z6}$ is independently non-aromatic $C_{3-8}$heterocyclyl;
each —$R^{Z7}$ is independently $C_{6-10}$carboaryl;
each —$R^{Z8}$ is independently $C_{5-10}$heteroaryl;
each -$L^Z$- is independently saturated aliphatic $C_{1-3}$alkylene;

and wherein:
each $C_{1-6}$alkyl, $C_{3-6}$cycloalkyl, non-aromatic $C_{3-8}$heterocyclyl, $C_{6-10}$carboaryl, $C_{5-10}$heteroaryl, and $C_{1-3}$alkylene is optionally substituted, for example, with one or more substituents —$R^{Z9}$, wherein each —$R^{Z9}$ is independently:
—F, —Cl, —Br, —I,
—$R^{ZZ1}$,
—$CF_3$, —$OCF_3$,
—OH, -$L^{ZZ}$-OH,
—$OR^{ZZ1}$, -$L^{ZZ}$-$OR^{ZZ1}$,
—SH, —$SR^{ZZ1}$,
—CN,
—$NO_2$,
—$NH_2$, —$NHR^{ZZ1}$, —$NR^{ZZ1}_2$, —$NR^{ZZ2}R^{ZZ3}$,
-$L^{ZZ}$-$NH_2$, -$L^{ZZ}$-$NHR^{ZZ1}$, -$L^{ZZ}$-$NR^{ZZ1}_2$, -$L^{ZZ}$-$NR^{ZZ2}R^{ZZ3}$,
—C(=O)OH, —C(=O)$OR^{ZZ1}$,
—C(=O)$NH_2$, —C(=O)$NHR^{ZZ1}$, —C(=O)$NR^{ZZ1}_2$, or —C(=O)$NR^{ZZ2}R^{ZZ3}$;
wherein:
each —$R^{ZZ1}$ is independently saturated aliphatic $C_{1-4}$alkyl, phenyl, or benzyl;
each -$L^{ZZ}$- is independently saturated aliphatic $C_{1-5}$alkylene; and
in each group —$NR^{ZZ2}R^{ZZ3}$, $R^{ZZ2}$ and $R^{ZZ3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.

In one embodiment, each —$R^{QN1}$, if present, is independently:
—$R^{J2}$, —$R^{J4}$, —$R^{J6}$, —$R^{J7}$, —$R^{J8}$,
-$L^J$-$R^{J4}$, -$L^J$-$R^{J6}$, -$L^J$-$R^{J7}$, or -$L^J$-$R^{J8}$.

In one embodiment, each —$R^{QN1}$, if present, is independently:
—$R^{J1}$, —$R^{J4}$, —$R^{J6}$, —$R^{J8}$,
-$L^J$-$R^{J4}$, -$L^J$-$R^{J6}$, or -$L^J$-$R^{J8}$.

In one embodiment, each —$R^{QN1}$, if present, is independently —$R^{J1}$, —$R^{J6}$, or -$L^J$-$R^{J6}$.

In one embodiment, each —$R^{QN1}$, if present, is independently —$R^{J1}$.

In one embodiment, each —$R^{QN1}$, if present, is independently —$R^{J6}$.

In one embodiment, each —$R^{QN1}$, if present, is independently -$L^J$-$R^{J6}$.

In one embodiment, each —$R^{QN1}$, if present, is independently —$R^{J7}$ or -$L^J$-$R^{J7}$.

In one embodiment, each —$R^{QN1}$, if present, is independently —$R^{J6}$ or -$L^J$-$R^{J6}$.

In one embodiment, each —$R^{J1}$, if present, is independently a saturated aliphatic $C_{1-5}$alkyl.

In one embodiment, each -$L^J$-, if present, is independently —$CH_2$— or —$CH_2CH_2$—.

In one embodiment, each -$L^J$-, if present, is independently —$CH_2$—.

In one embodiment, each —$R^{J4}$-, if present, is independently cyclohexyl, and is optionally substituted.

In one embodiment, each —$R^{J6}$, if present, is a $C_{3-8}$heterocyclyl group that is a 4-, 5-, 6-, or 7-membered non-aromatic monocyclic ring or a 7- or 8-membered non-aromatic bicyclic ring, said ring having exactly 1 ring heteroatom or exactly 2 ring heteroatoms, wherein each of said ring heteroatoms is independently N, O, or S; and is optionally substituted.

In one embodiment, each —$R^{J6}$, if present, is independently azetidinyl, pyrrolidinyl, imidazolidinyl, pyrazolidinyl, piperidinyl, piperazinyl, morpholinyl, azepinyl, diazepinyl, oxetanyl, tetrahydrofuranyl, tetrahydropyranyl, dioxanyl, 3-aza-bicyclo[3.2.1]octanyl, 8-aza-bicyclo[3.2.1]octanyl, 3,8-diaza-bicyclo[3.2.1]octanyl, 3-aza-bicyclo[3.1.1]heptanyl, 6-aza-bicyclo[3.1.1]heptanyl, 3,6-diaza-bicyclo[3.1.1]heptanyl, 2-azabicyclo[2.2.2]octanyl, 1-azabicyclo[2.2.1]heptanyl, quinuclidinyl, or 9-azabicyclo[3.3.1]nonanyl; and is optionally substituted.

For convenience, the structures of the following groups are illustrated:

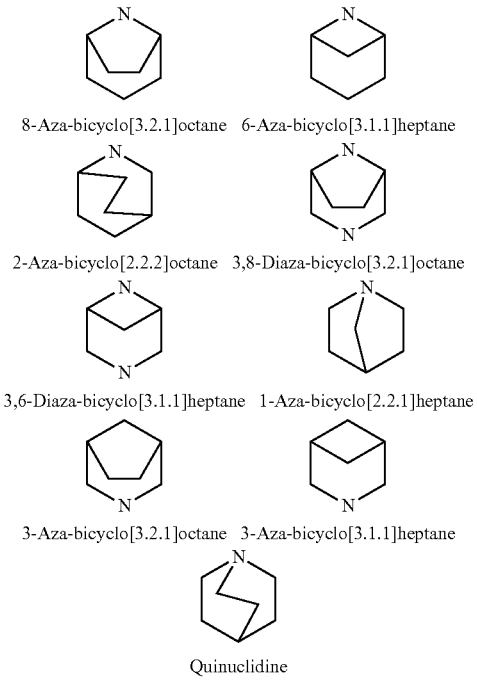

8-Aza-bicyclo[3.2.1]octane   6-Aza-bicyclo[3.1.1]heptane

2-Aza-bicyclo[2.2.2]octane   3,8-Diaza-bicyclo[3.2.1]octane 3,6-Diaza-bicyclo[3.1.1]heptane   1-Aza-bicyclo[2.2.1]heptane 3-Aza-bicyclo[3.2.1]octane   3-Aza-bicyclo[3.1.1]heptane Quinuclidine In one embodiment, each —$R^{J6}$, if present, is independently pyrrolidinyl, piperidinyl, piperazinyl, morpholinyl, tetrahydrofuranyl, tetrahydropyranyl, or 8-aza-bicyclo[3.2.1]octanyl, and is optionally substituted.

In one embodiment, each —$R^{J6}$, if present, is independently pyrrolidinyl, piperidinyl, tetrahydrofuranyl, tetrahydropyranyl, or 8-aza-bicyclo[3.2.1]octanyl; and is optionally substituted.

In one embodiment, each —$R^{J6}$, if present, is independently piperidinyl or 8-aza-bicyclo[3.2.1]octanyl; and is optionally substituted.

In one embodiment, each —$R^{J6}$, if present, is independently piperidinyl; and is optionally substituted.

In one embodiment, each —$R^{J6}$, if present, is independently 8-aza-bicyclo[3.2.1]octanyl; and is optionally substituted.

In one embodiment, each —$R^{J7}$, if present, is independently phenyl, and is optionally substituted.

In one embodiment, each —$R^{J8}$, if present, is independently $C_{5-6}$heteroaryl, and is optionally substituted.

In one embodiment, each —$R^{J8}$, if present, is independently furanyl, thienyl, pyrrolyl, imidazolyl, pyrazolyl, triazolyl, oxazolyl, isoxazolyl, thiazolyl, isothiazolyl, pyridyl, pyrimidinyl, or pyridazinyl, and is optionally substituted.

In one embodiment, each —$R^{J8}$, if present is independently pyridyl, and is optionally substituted.

In one embodiment, each —$R^{J9}$, if present, is independently:

—F, —Cl, —Br, —I,
—$R^{L1}$,
—$CF_3$, —$OCF_3$,
—OH, -$L^L$-OH,
—$OR^{L1}$, -$L^L$-$OR^{L1}$,
—CN,
—$NH_2$, —$NHR^{L1}$, —$NR^{L1}_2$, —$NR^{L2}R^{L3}$,
-$L^L$-$NH_2$, -$L^L$-$NHR^{L1}$, -$L^L$-$NR^{L1}_2$, -$L^L$-$NR^{L2}R^{L3}$,
—O-$L^L$-$NH_2$, —O-$L^L$-$NHR^{L1}$, —O-$L^L$-$NR^{L1}_2$, —O-$L^L$-$NR^{L2}R^{L3}$,
—C(=O)OH, —C(=O)$OR^{L1}$,
—C(=O)$NH_2$, —C(=O)$NHR^{L1}$, —C(=O)$NR^{L1}_2$, —C(=O)$NR^{L2}R^{L3}$,
—NHC(=O)$R^{L1}$, —$NR^{L1}$C(=O)$R^{L1}$,
—NHC(=O)$OR^{L1}$, —$NR^{L1}$C(=O)$OR^{L1}$,
—OC(=O)$NH_2$, —OC(=O)$NHR^{L1}$, —OC(=O)$NR^{L1}_2$, —OC(=O)$NR^{L2}R^{L3}$,
—C(=O)$R^{L1}$,
—S(=O)$_2NH_2$, —S(=O)$_2NHR^{L1}$, —S(=O)$_2NR^{L1}_2$, —S(=O)$_2NR^{L2}R^{L3}$,
—S(=O)$R^{L1}$, —S(=O)$_2R^{L1}$, or —S(=O)$_2OR^{L1}$.

In one embodiment, each —$R^{J9}$, if present, is independently:
—$R^{L1}$,
—OH, —$OR^{L1}$,
—$NH_2$, —$NHR^{L1}$, —$NR^{L1}_2$, —$NR^{L2}R^{L3}$,
—C(=O)$NH_2$, —C(=O)$NHR^{L1}$, —C(=O)$NR^{L1}_2$, or —C(=O)$NR^{L2}R^{L3}$.

In one embodiment, each -$L^L$-, if present, is independently saturated aliphatic $C_{1-3}$alkylene.

In one embodiment, each —$NR^{L2}R^{L3}$, if present, is independently azetidino, pyrrolidino, imidazolidino, pyrazolidino, piperidino, piperazino, morpholino, azepino, or diazepino, and is optionally substituted, for example, with one or more groups selected from $C_{1-3}$alkyl and —$CF_3$.

In one embodiment, each —$NR^{L2}R^{L3}$, if present, is independently pyrrolidino, piperidino, piperazino, or morpholino, and is optionally substituted, for example, with one or more groups selected from $C_{1-3}$alkyl and —$CF_3$.

In one embodiment, each —$R^{L1}$, if present, is independently:
—$R^{Z1}$, —$R^{Z4}$, —$R^{Z7}$, —$R^{Z8}$,
-$L^Z$-$R^{Z4}$, -$L^Z$-$R^{Z7}$, or -$L^Z$-$R^{Z8}$.

In one embodiment, each —$R^{L1}$, if present, is independently:
—$R^{Z1}$, —$R^{Z4}$, —$R^{Z7}$,
-$L^Z$-$R^{Z4}$, or -$L^Z$-$R^{Z7}$.

In one embodiment, each —$R^{L1}$, if present, is independently —$R^{Z1}$, —$R^{Z7}$, or -$L^Z$-$R^{Z7}$.

In one embodiment, each —$R^{L1}$, if present, is independently —$R^{Z1}$.

In one embodiment, each -$L^Z$-, if present, is independently —$CH_2$—.

In one embodiment, each —$R^{Z1}$, if present, is independently a saturated aliphatic $C_{1-3}$alkyl.

In one embodiment, each —$R^{Z6}$, if present, is a $C_{3-8}$heterocyclyl group that is a 4-, 5-, 6-, or 7-membered non-aromatic monocyclic ring or a 7- or 8-membered non-aromatic bicyclic ring, said ring having exactly 1 ring heteroatom or exactly 2 ring heteroatoms, wherein each of said ring heteroatoms is independently N, O, or S; and is optionally substituted.

In one embodiment, each —$R^{Z6}$, if present, is independently azetidinyl, pyrrolidinyl, imidazolidinyl, pyrazolidinyl, piperidinyl, piperazinyl, morpholinyl, azepinyl, diazepinyl, tetrahydrofuranyl, tetrahydropyranyl, dioxanyl, 8-aza-bicyclo[3.2.1]octanyl, 3,8-diaza-bicyclo[3.2.1]octanyl, 6-aza-bicyclo[3.1.1]heptanyl, or 3,6-diaza-bicyclo[3.1.1]heptanyl; and is optionally substituted.

In one embodiment, each —$R^{Z6}$, if present, is independently pyrrolidinyl, piperidinyl, piperazinyl, morpholinyl, tetrahydrofuranyl, or tetrahydropyranyl; and is optionally substituted.

In one embodiment, each —$R^{Z7}$, if present, is independently phenyl, and is optionally substituted.

In one embodiment, each —$R^{Z8}$, if present, is independently $C_{3-6}$heteroaryl, and is optionally substituted.

In one embodiment, each —$R^{Z8}$, if present, is independently furanyl, thienyl, pyrrolyl, imidazolyl, pyrazolyl, triazolyl, oxazolyl, isoxazolyl, thiazolyl, isothiazolyl, pyridyl, pyrimidinyl, or pyridazinyl, and is optionally substituted.

In one embodiment, each —$R^{Z9}$, if present, is independently:
—F, —Cl, —Br, —I,
$R^{ZZ1}$,
—$CF_3$, —$OCF_3$,
—OH, -$L^{ZZ}$-OH,
—$OR^{ZZ1}$, -$L^{ZZ}$-$OR^{ZZ1}$,
—$NH_2$, —$NHR^{ZZ1}$, —$NR^{ZZ1}{}_2$, —$NR^{ZZ2}R^{ZZ3}$,
-$L^{ZZ}$-$NH_2$, -$L^{ZZ}$-$NHR^{ZZ1}$, -$L^{ZZ}$-$NR^{ZZ1}{}_2$, -$L^{ZZ}$-$NR^{ZZ2}R^{ZZ3}$,
—C(=O)OH, —C(=O)$OR^{ZZ1}$,
—C(=O)$NH_2$, —C(=O)$NHR^{ZZ1}$, —C(=O)$NR^{ZZ1}{}_2$, or —C(=O)$NR^{ZZ2}R^{ZZ3}$.

In one embodiment, each -$L^{ZZ}$, if present, is independently saturated aliphatic $C_{1-3}$alkylene.

In one embodiment, each —$R^{ZZ1}$, if present, is independently $C_{1-4}$alkyl.

In one embodiment, each —$NR^{ZZ2}R^{ZZ3}$, if present, is independently azetidino, pyrrolidino, imidazolidino, pyrazolidino, piperidino, piperazino, morpholino, azepino, or diazepino, and is optionally substituted, for example, with one or more groups selected from $C_{1-3}$alkyl and —$CF_3$.

In one embodiment, each —$NR^{ZZ2}R^{ZZ3}$, if present is independently pyrrolidino, piperidino, piperazino, or morpholino, and is optionally substituted, for example, with one or more groups selected from $C_{1-3}$alkyl and —$CF_3$.

In one embodiment, each —$R^{Z9}$, if present, is independently —F, —Cl, —Br, —I, -Me, -Et, —$CF_3$, —OH, —$CH_2$OH, —$CH_2CH_2$OH, —OMe, —OEt, —$CH_2$OMe, —$CH_2CH_2$OMe, —$OCF_3$, —SMe, —CN, —$NO_2$, —$NH_2$, —NHMe, —$NMe_2$, —$CH_2NH_2$, —$CH_2$NHMe, —$CH_2NMe_2$, —$CH_2CH_2NH_2$, —$CH_2CH_2$NHMe, —$CH_2CH_2NMe_2$, —C(=O)OH, —C(=O)OMe, —C(=O)$NH_2$, —C(=O)NHMe, —C(=O)$NMe_2$, —C(=O)NHPh, —C(=O)N(Me)Ph, —C(=O)$NHCH_2$Ph, —C(=O)N(Me)$CH_2$Ph, —$CH_2$-Ph, or -Ph.

In one embodiment, -$Q^{44N1}$, if present, is independently selected from groups of the following formulae, wherein n1 is independently 1, 2, 3, or 4; n2 is independently 1, 2, 3, or 4; and n3 is independently 1 or 2:

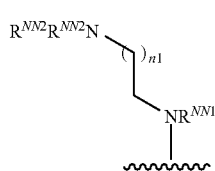

(A4N1-A)

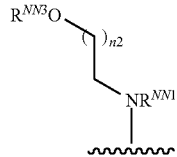

(A4N1-B)

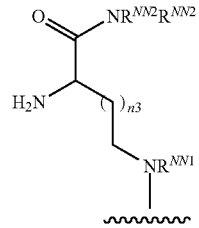

(A4N1-C)

In one embodiment, -$Q^{44N1}$, if present, is independently a group of formula (A4N1-A).

In one embodiment, -$Q^{44N1}$, if present, is independently a group of formula (A4N1-B).

In one embodiment, -$Q^{44N1}$, if present, is independently a group of formula (A4N1-C).

In one embodiment, -$Q^{44N1}$, if present, is independently selected from groups of the following formulae, wherein n4 is independently 1 or 2:

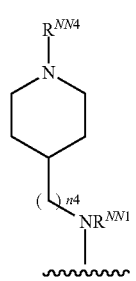

(A4N1-D)

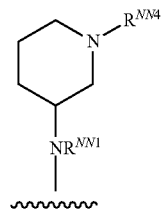

(A4N1-E)

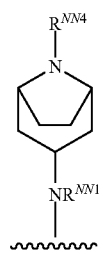

(A4N1-F)

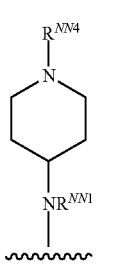

(A4N1-G)

In one embodiment, -$Q^{A4N1}$, if present, is independently selected from groups of the following formulae, wherein n4 is independently 1 or 2:

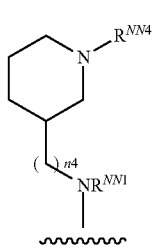

(A4N1-H)

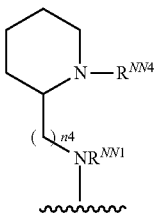

(A4N1-I)

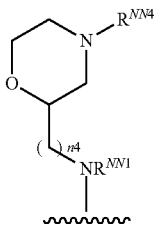

(A4N1-J)

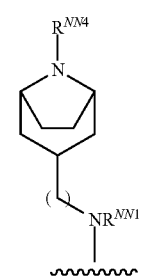

(A4N1-K)

In one embodiment, -$Q^{A4N1}$, if present, is independently a group of formula (A4N1-D).

In one embodiment, -$Q^{A4N1}$, if present, is independently a group of formula (A4N1-E).

In one embodiment, -$Q^{A4N1}$, if present, is independently a group of formula (A4N1-F).

In one embodiment, -$Q^{A4N1}$, if present, is independently a group of formula (A4N1-G).

In one embodiment, -$Q^{A4N1}$, if present, is independently a group of formula (A4N1-H).

In one embodiment, -$Q^{A4N1}$, if present, is independently a group of formula (A4N1-I).

In one embodiment, -$Q^{A4N1}$, if present, is independently a group of formula (A4N1-J).

In one embodiment, -$Q^{A4N1}$, if present, is independently a group of formula (A4N1-K).

In one embodiment, n4 is independently 1.

In one embodiment, —$R^{NN1}$ is independently —H or saturated aliphatic $C_{1-4}$alkyl.

In one embodiment, —$R^{NN1}$ is independently —H or -Me.

In one embodiment, —$R^{NN1}$ is independently saturated aliphatic $C_{1-4}$alkyl.

In one embodiment, —$R^{NN1}$ is independently -Me.

In one embodiment, —$R^{NN1}$ is independently —H.

In one embodiment, each —$R^{NN2}$ is independently —H, saturated aliphatic $C_{1-4}$alkyl, phenyl, or benzyl; or, the group —$NR^{NN2}R^{NN2}$ is independently azetidino, pyrrolidino, imidazolidino, pyrazolidino, piperidino, piperazino, morpholino, azepino, or diazepino, and is optionally substituted, for example, with one or more groups selected from $C_{1-3}$alkyl and —$CF_3$.

In one embodiment, each —$R^{NN2}$ is independently —H, saturated aliphatic $C_{1-4}$alkyl, phenyl, or benzyl; or, the group —$NR^{NN2}R^{NN2}$ is independently pyrrolidino, piperidino, piperazino, or morpholino, and is optionally substituted, for example, with one or more groups selected from $C_{1-3}$alkyl and —$CF_3$.

In one embodiment, each —$R^{NN2}$ is independently —H, saturated aliphatic $C_{1-4}$alkyl, phenyl, or benzyl.

In one embodiment, each —$R^{NN2}$ is independently —H or saturated aliphatic $C_{1-4}$alkyl.

In one embodiment, each —$R^{NN2}$ is independently —H or -Me.

In one embodiment, each —$R^{NN2}$ is independently —H.

In one embodiment, —$R^{NN3}$, if present, is independently —H or saturated aliphatic $C_{1-4}$alkyl.

In one embodiment, —$R^{NN3}$, if present, is independently —H or -Me.

In one embodiment, —$R^{NN3}$, if present, is independently —H.

In one embodiment, —$R^{NN4}$, if present, is independently —H, saturated aliphatic $C_{1-4}$alkyl, phenyl, or benzyl.

In one embodiment, —$R^{NN4}$, if present, is independently —H or saturated aliphatic $C_{1-4}$alkyl.

In one embodiment, —$R^{NN4}$, if present, is independently —H or -Me.

In one embodiment, —$R^{NN4}$, if present, is independently —H.

In one embodiment, —$R^{NN4}$, if present, is independently -Me.

In one embodiment, -$Q^{A4N1}$, if present, is independently selected from those substituents exemplified under the heading "Some Preferred Embodiments."

The Group -$Q^{A4N2}$

In one embodiment, -$Q^{A4N2}$, if present, is independently —$NR^{QN2}R^{QN3}$.

In one embodiment, in the group —$NR^{QN2}R^{QN3}$, if present, $R^{QN2}$ and $R^{QN3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.

In one embodiment, —$NR^{QN2}R^{QN3}$, if present, is independently azetidino, pyrrolidino, imidazolidino, pyrazolidino, piperidino, piperazino, morpholino, azepino, or diazepino, and is optionally substituted.

In one embodiment, —NR$^{QN2}$R$^{QN3}$, if present, is independently pyrrolidino, piperidino, piperazino, or morpholino, and is optionally substituted.

In one embodiment, —NR$^{QN2}$R$^{QN3}$, if present, is independently piperidino, piperazino, or morpholino, and is optionally substituted.

In one embodiment, —NR$^{QN2}$R$^{QN3}$ is optionally substituted, for example, with one or more substituents —R$^{QNR}$, wherein each —R$^{QNR}$ is independently:
- —F,
- —R$^{AA1}$,
- —CF$_3$,
- —OH, -L$^{AA}$-OH, —O-L$^{AA}$-OH,
- —OR$^{AA1}$, -L$^{AA}$-OR$^{AA1}$, —O-L$^{AA}$-OR$^{AA1}$,
- —SH, —SR$^{AA1}$,
- —CN,
- —NH$_2$, —NHR$^{AA1}$, —NR$^{AA1}_2$, —NR$^{AA2}$R$^{AA3}$,
- -L$^{AA}$-NH$_2$, -L$^{AA}$-NHR$^{AA1}$, -L$^{AA}$-NR$^{AA1}_2$, -L$^{AA}$-NR$^{AA2}$R$^{AA3}$,
- —O-L$^{AA}$-NH$_2$, —O-L$^{AA}$-NHR$^{AA1}$, —O-L$^{AA}$-NR$^{AA1}_2$, —O-L$^{AA}$-NR$^{AA2}$R$^{AA3}$,
- —C(=O)OH, —C(=O)OR$^{AA1}$,
- —C(=O)NH$_2$, —C(=O)NHR$^{AA1}$, —C(=O)NR$^{AA1}_2$, —C(=O)NR$^{AA2}$R$^{AA3}$,
- —NHC(=O)R$^{AA1}$, —NR$^{AA1}$C(=O)R$^{AA1}$,
- —NHC(=O)OR$^{AA1}$, —NR$^{AA1}$C(=O)OR$^{AA1}$,
- —OC(=O)NH$_2$, —OC(=O)NHR$^{AA1}$, —OC(=O)NR$^{AA1}_2$, —OC(=O)NR$^{AA2}$R$^{AA3}$,
- —C(=O)R$^{AA1}$,
- —NHC(=O)NH$_2$, —NHC(=O)NHR$^{AA1}$,
- —NHC(=O)NR$^{AA1}_2$, —NHC(=O)NR$^{AA2}$R$^{AA3}$,
- —NR$^{AA1}$C(=O)NH$_2$, —NR$^{AA1}$C(=O)NHR$^{AA1}$,
- —NR$^{AA1}$C(=O)NR$^{AA1}_2$, —NR$^{AA1}$C(=O)NR$^{AA2}$R$^{AA3}$,
- —NHS(=O)$_2$R$^{AA1}$, —NR$^{AA1}$S(=O)$_2$R$^{AA1}$,
- —S(=O)$_2$NH$_2$, —S(=O)$_2$NHR$^{AA1}$, —S(=O)$_2$NR$^{AA1}_2$,
- —S(=O)$_2$NR$^{AA2}$R$^{AA3}$,
- —S(=O)R$^{AA1}$, —S(=O)$_2$R$^{AA1}$, —OS(=O)$_2$R$^{AA1}$, or —S(=O)$_2$OR$^{AA1}$;

wherein:
  each -L$^{AA}$- is independently saturated aliphatic C$_{1-5}$alkylene;
  in each group —NR$^{AA2}$R$^{AA3}$, R$^{AA2}$ and R$^{AA3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;
  each —R$^{AA1}$ is independently:
    —R$^{BB1}$, —R$^{BB4}$, —R$^{BB6}$, —R$^{BB7}$, —R$^{BB8}$,
    -L$^{BB}$-R$^{BB4}$, -L$^{BB}$-R$^{BB6}$, -L$^{BB}$-R$^{BB7}$, or -L$^{BB}$-R$^{BB8}$;
  wherein:
    each —R$^{BB1}$ is independently saturated aliphatic C$_{1-6}$alkyl;
    each —R$^{BB4}$ is independently saturated C$_{3-6}$cycloalkyl;
    each —R$^{BB6}$ is independently non-aromatic C$_{3-8}$heterocyclyl;
    each —R$^{BB7}$ is independently C$_{6-10}$carboaryl;
    each —R$^{BB8}$ is independently C$_{5-10}$heteroaryl;
    each -L$^{BB}$- is independently saturated aliphatic C$_{1-3}$alkylene;
  and wherein:
    each C$_{1-6}$alkyl, C$_{3-6}$cycloalkyl, non-aromatic C$_{3-8}$heterocyclyl, C$_{6-10}$carboaryl, C$_{5-10}$heteroaryl, and C$_{1-3}$alkylene is optionally substituted, for example, with one or more substituents —R$^{BB9}$, wherein each —R$^{BB9}$ is independently:
      —F, —Cl, —Br, —I,
      —R$^{CC1}$,
      —CF$_3$, —OCF$_3$,
      —OH, -L$^{CC}$-OH,
      —OR$^{CC1}$, -L$^{CC}$-OR$^{CC1}$,
      —SH, —SR$^{CC1}$,
      —CN,
      —NO$_2$,
      —NH$_2$, —NHR$^{CC1}$, —NR$^{CC1}_2$, —NR$^{CC2}$R$^{CC3}$,
      -L$^{CC}$-NH$_2$, -L$^{CC}$-NHR$^{CC1}$, -L$^{CC}$-NR$^{CC1}_2$, -L$^{CC}$-NR$^{CC2}$R$^{CC3}$,
      —C(=O)OH, —C(=O)OR$^{CC1}$,
      —C(=O)NH$_2$, —C(=O)NHR$^{CC1}$, —C(=O)NR$^{CC1}_2$, or —C(=O)NR$^{CC2}$R$^{CC3}$;

wherein:
  each —R$^{CC1}$ is independently saturated aliphatic C$_{1-4}$alkyl, phenyl, or benzyl;
  each -L$^{CC}$- is independently saturated aliphatic C$_{1-5}$alkylene; and
  in each group —NR$^{CC2}$R$^{CC3}$, R$^{CC2}$ and R$^{CC3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.

In one embodiment, each —R$^{QNR}$, if present, is independently:
- —F,
- —R$^{AA1}$,
- —CF$_3$,
- —OH, -L$^{AA}$-OH, —O-L$^{AA}$-OH,
- —OR$^{AA1}$, -L$^{AA}$-OR$^{AA1}$, —O-L$^{AA}$-OR$^{AA1}$,
- —CN,
- —NH$_2$, —NHR$^{AA1}$, —NR$^{AA1}_2$, —NR$^{AA2}$R$^{AA3}$,
- -L$^{AA}$-NH$_2$, -L$^{AA}$-NHR$^{AA1}$, -L$^{AA}$-NR$^{AA1}_2$, -L$^{AA}$-NR$^{AA2}$R$^{AA3}$,
- —O-L$^{AA}$-NH$_2$, —O-L$^{AA}$-NHR$^{AA1}$, —O-L$^{AA}$-NR$^{AA1}_2$, —O-L$^{AA}$-NR$^{AA2}$R$^{AA3}$;
- —C(=O)OH, —C(=O)OR$^{AA1}$,
- —C(=O)NH$_2$, —C(=O)NHR$^{AA1}$, —C(=O)NR$^{AA1}_2$, —C(=O)NR$^{AA2}$R$^{AA3}$,
- —NHC(=O)R$^{AA1}$, —NR$^{AA1}$C(=O)R$^{AA1}$,
- —NHS(=O)$_2$R$^{AA1}$, —NR$^{AA1}$S(=O)$_2$R$^{AA1}$,
- —S(=O)$_2$NH$_2$, —S(=O)$_2$NHR$^{AA1}$, —S(=O)$_2$NR$^{AA1}_2$,
- —S(=O)$_2$NR$^{AA2}$R$^{AA3}$,
- —S(=O)R$^{AA1}$, or —S(=O)$_2$R$^{AA1}$.

In one embodiment, each —R$^{QNR}$, if present, is independently:
- —R$^{AA1}$,
- —NH$_2$, —NHR$^{AA1}$, —NR$^{AA1}_2$, —NR$^{AA2}$R$^{AA3}$,
- -L$^{AA}$-NH$_2$, -L$^{AA}$-NHR$^{AA1}$, -L$^{AA}$-NR$^{AA1}_2$, or -L$^{AA}$-NR$^{AA2}$R$^{AA3}$.

In one embodiment, each —R$^{QNR}$, if present, is independently —R$^{AA1}$, —NH$_2$, or -L$^{AA}$-NH$_2$.

In one embodiment, each —R$^{QNR}$, if present, is independently —NH$_2$ or -L$^{AA}$-NH$_2$.

In one embodiment, each -L$^{AA}$-, if present, is independently saturated aliphatic C$_{1-3}$alkylene.

In one embodiment, each -L$^{AA}$-, if present, is independently —CH$_2$— or —CH$_2$CH$_2$—.

In one embodiment, each -L$^{AA}$-, if present, is independently —CH$_2$—.

In one embodiment, each —NR$^{AA2}$R$^{AA3}$, if present, is independently azetidino, pyrrolidino, imidazolidino, pyrazolidino, piperidino, piperazino, morpholino, azepino, or diazepino, and is optionally substituted, for example, with one or more groups selected from $C_{1-3}$alkyl and —$CF_3$.

In one embodiment, each —$NR^{AA2}R^{AA3}$, if present, is independently pyrrolidino, piperidino, piperazino, or morpholino, and is optionally substituted, for example, with one or more groups selected from $C_{1-3}$alkyl and —$CF_3$.

In one embodiment, each —$R^{AA1}$, if present, is independently:
—$R^{BB1}$, —$R^{BB4}$, —$R^{BB7}$, —$R^{BB8}$,
-$L^{BB}$-$R^{BB4}$, -$L^{BB}$-$R^{BB7}$, or -$L^{BB}$-$R^{BB8}$.

In one embodiment, each —$R^{AA1}$, if present, is independently:
—$R^{BB1}$, —$R^{BB4}$, —$R^{BB7}$,
-$L^{BB}$-$R^{BB4}$, or -$L^{BB}$-$R^{BB7}$.

In one embodiment, each —$R^{AA1}$, if present, is independently —$R^{BB1}$, —$R^{BB7}$, or -$L^{BB}$-$R^{BB7}$.

In one embodiment, each —$R^{AA1}$, if present, is independently —$R^{BB1}$.

In one embodiment, each —$R^{AA1}$, if present, is independently -$L^{BB}$-$R^{BB7}$.

In one embodiment, each -$L^{BB}$-, if present, is independently —$CH_2$—.

In one embodiment, each —$R^{BB1}$, if present, is independently a saturated aliphatic $C_{1-3}$alkyl.

In one embodiment, each —$R^{BB6}$, if present, is a $C_{3-8}$heterocyclyl group that is a 4-, 5-, 6-, or 7-membered non-aromatic monocyclic ring, said ring having exactly 1 ring heteroatom or exactly 2 ring heteroatoms, wherein each of said ring heteroatoms is independently N, O, or S; and is optionally substituted.

In one embodiment, each —$R^{BB6}$, if present, is independently azetidinyl, pyrrolidinyl, imidazolidinyl, pyrazolidinyl, piperidinyl, piperazinyl, morpholinyl, azepinyl, diazepinyl, tetrahydrofuranyl, tetrahydropyranyl, dioxanyl, and is optionally substituted.

In one embodiment, each —$R^{BB6}$, if present, is independently pyrrolidinyl, piperidinyl, piperazinyl, morpholinyl, tetrahydrofuranyl, or tetrahydropyranyl, and is optionally substituted.

In one embodiment, each —$R^{BB7}$, if present, is independently phenyl, and is optionally substituted.

In one embodiment, each —$R^{BB8}$, if present, is independently $C_{5-6}$heteroaryl, and is optionally substituted.

In one embodiment, each —$R^{BB8}$, if present, is independently furanyl, thienyl, pyrrolyl, imidazolyl, pyrazolyl, triazolyl, oxazolyl, isoxazolyl, thiazolyl, isothiazolyl, pyridyl, pyrimidinyl, or pyridazinyl, and is optionally substituted.

In one embodiment, each —$R^{BB9}$, if present, is independently:
—F, —Cl, —Br, —I,
—$R^{CC1}$,
—$CF_3$, —$OCF_3$,
—OH, -$L^{CC}$-OH,
—$OR^{CC1}$, -$L^{CC}$-$OR^{CC1}$,
—$NH_2$, —$NHR^{CC1}$, —$NR^{CC1}{}_2$, —$NR^{CC2}R^{CC3}$,
-$L^{CC}$-$NH_2$, -$L^{CC}$-$NHR^{CC1}$, -$L^{CC}$-$NR^{CC1}{}_2$, -$L^{CC}$-$NR^{CC2}R^{CC3}$,
—C(=O)OH, —C(=O)$OR^{CC1}$,
—C(=O)$NH_2$, —C(=O)$NHR^{CC1}$, —C(=O)$NR^{CC1}{}_2$, or —C(=O)$NR^{CC2}R^{CC3}$.

In one embodiment, each —$R^{BB9}$, if present, is independently:

—$R^{CC1}$,
—$NH_2$, —$NHR^{CC1}$, —$NR^{CC1}{}_2$, or —$NR^{CC2}R^{CC3}$.

In one embodiment, each -$L^{CC}$-, if present, is independently saturated aliphatic $C_{1-3}$alkylene.

In one embodiment, each —$R^{CC1}$, if present, is independently $C_{1-4}$alkyl.

In one embodiment, each —$R^{CC1}$, if present, is independently phenyl.

In one embodiment, each —$NR^{CC2}R^{CC3}$, if present, is independently azetidino, pyrrolidino, imidazolidino, pyrazolidino, piperidino, piperazino, morpholino, azepino, or diazepino, and is optionally substituted, for example, with one or more groups selected from $C_{1-3}$alkyl and —$CF_3$.

In one embodiment, each —$NR^{CC2}R^{CC3}$, if present, is independently pyrrolidino, piperidino, piperazino, or morpholino, and is optionally substituted, for example, with one or more groups selected from $C_{1-3}$alkyl and —$CF_3$.

In one embodiment, each —$R^{BB9}$, if present, is independently —F, —Cl, —Br, —I, -Me, -Et, —$CF_3$, —OH, —$CH_2OH$, —$CH_2CH_2OH$, —OMe, —OEt, —$CH_2OMe$, —$CH_2CH_2OMe$, —$OCF_3$, —SMe, —CN, —$NO_2$, —$NH_2$, —NHMe, —$NMe_2$, —$CH_2NH_2$, —$CH_2CH_2NH_2$, —O—$CH_2CH_2$—$NH_2$, —C(=O)OH, —C(=O)OMe, —C(=O)$NH_2$, —C(=O)NHMe, —C(=O)$NMe_2$, —$SO_2NH_2$, —$SO_2NHMe$, —$SO_2NMe_2$, —$SO_2Me$, —$CH_2$-Ph, or -Ph.

In one embodiment, -$Q^{A4N2}$, if present, is independently selected from groups of the following formulae, wherein m1 is independently 1 or 2, and each —$R^{MM1}$ is independently —H or saturated aliphatic $C_{1-4}$alkyl:

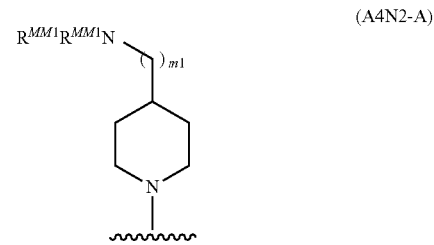

(A4N2-A)

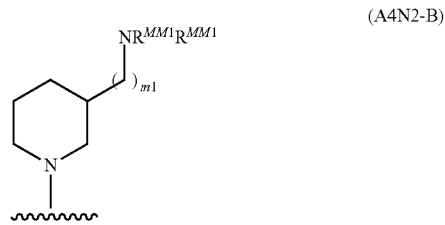

(A4N2-B)

In one embodiment, -$Q^{A4N2}$, if present, is independently a group of formula (A4N2-A).

In one embodiment, -$Q^{A4N2}$, if present, is independently a group of formula (A4N2-B).

In one embodiment, each —$R^{MM1}$ is independently —H or -Me.

In one embodiment, each —$R^{MM1}$ is independently —H.

In one embodiment, -$Q^{A4N2}$, if present, is independently the following group, wherein each —$R^{MM2}$ is independently —H or saturated aliphatic $C_{1-4}$alkyl:

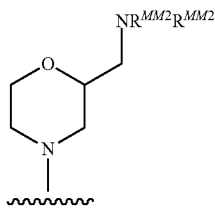

(A4N2-C)

In one embodiment, each —$R^{MM2}$ is independently —H or -Me.

In one embodiment, each —$R^{MM2}$ is independently —H.

In one embodiment, -$Q^{44N2}$, if present, is independently selected from those substituents exemplified under the heading "Some Preferred Embodiments."

The group -$Q^{44O}$

In one embodiment, -$Q^{44O}$, if present, is independently —$R^{C1}$, wherein —$R^{C1}$ is independently:
—$R^{D1}$, —$R^{D2}$, —$R^{D3}$, —$R^{D4}$, —$R^{D5}$, —$R^{D6}$, —$R^{D7}$, —$R^{D8}$,
-$L^D$-$R^{D4}$, -$L^D$-$R^{D5}$, -$L^D$-$R^{D6}$, -$L^D$-$R^{D7}$, or -$L^D$-$R^{D8}$;
wherein:
each —$R^{D1}$ is independently saturated aliphatic $C_{1-6}$alkyl;
each —$R^{D2}$ is independently aliphatic $C_{2-6}$alkenyl;
each —$R^{D3}$ is independently aliphatic $C_{2-6}$alkynyl;
each —$R^{D4}$ is independently saturated $C_{3-6}$cycloalkyl;
each —$R^{D5}$ is independently $C_{3-6}$cycloalkenyl;
each —$R^{D6}$ is independently non-aromatic $C_{3-8}$heterocyclyl;
each —$R^{D7}$ is independently $C_{6-10}$carboaryl;
each —$R^{D8}$ is independently $C_{5-10}$heteroaryl;
each -$L^D$- is independently saturated aliphatic $C_{1-3}$alkylene;
and wherein:
each $C_{1-6}$alkyl, $C_{2-6}$alkenyl, $C_{2-6}$alkynyl, $C_{3-6}$cycloalkyl, $C_{3-6}$cycloalkenyl, non-aromatic $C_{3-8}$heterocyclyl, $C_{6-10}$carboaryl, $C_{5-10}$heteroaryl, and $C_{1-3}$alkylene is optionally substituted, for example, with one or more substituents —$R^{D9}$, wherein each —$R^{D9}$ is independently:
—F, —Cl, —Br, —I,
—$R^{E1}$,
—$CF_3$, —$OCF_3$,
—OH, -$L^E$-OH, —O-$L^E$-OH,
—$OR^{E1}$, -$L^E$-$OR^{E1}$, —O-$L^E$-$OR^{E1}$,
—SH, —$SR^{E1}$,
—CN,
—$NO_2$,
—$NH_2$, —$NHR^{E1}$, —$NR^{E1}_2$, —$NR^{E2}R^{E3}$,
-$L^E$-$NH_2$, -$L^E$-$NHR^{E1}$, -$L^E$-$NR^{E1}_2$, -$L^E$-$NR^{E2}R^{E3}$,
—O-$L^E$-$NH_2$, —O-$L^E$-$NHR^{E1}$, —O-$L^E$-$NR^{E1}_2$,
—O-$L^E$-$NR^{E2}R^{E3}$,
—C(=O)OH, —C(=O)$OR^{E1}$,
—C(=O)$NH_2$, —C(=O)$NHR^{E1}$, —C(=O)$NR^{E1}_2$, or
—C(=O)$NR^{E2}R^{E3}$;
wherein:
each —$R^{E1}$ is independently saturated aliphatic $C_{1-4}$alkyl, phenyl, or benzyl;
each -$L^E$- is independently saturated aliphatic $C_{1-5}$alkylene; and
in each group —$NR^{E2}R^{E3}$, $R^{E2}$ and $R^{E3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.

In one embodiment, —$R^{C1}$, if present, is independently:
—$R^{D1}$, —$R^{D4}$, —$R^{D6}$, —$R^{D7}$, —$R^{D8}$;
-$L^D$-$R^{D4}$, -$L^D$-$R^{D6}$, -$L^D$-$R^{D7}$, or -$L^D$-$R^{D8}$.

In one embodiment, $R^{C1}$, if present, is independently:
—$R^{D1}$, —$R^{D6}$, —$R^{D7}$, —$R^{D8}$,
-$L^D$-$R^{D6}$, -$L^D$-$R^{D7}$, or -$L^D$-$R^{D8}$.

In one embodiment, —$R^{C1}$, if present, is independently —$R^{D6}$ or -$L^D$-$R^{D6}$.

In one embodiment, —$R^{C1}$, if present, is independently —$R^{D6}$.

In one embodiment, —$R^{C1}$, if present, is independently -$L^D$-$R^{D6}$.

In one embodiment, each -$L^D$-, if present, is independently —$CH_2$— or —$CH_2CH_2$—.

In one embodiment, each -$L^D$-, if present, is independently —$CH_2$—.

In one embodiment, each —$R^{D1}$, if present, is independently a saturated aliphatic $C_{1-3}$alkyl.

In one embodiment, each —$R^{D6}$, if present, is a $C_{3-8}$heterocyclyl group that is a 4-, 5-, 6-, or 7-membered non-aromatic monocyclic ring or a 7- or 8-membered non-aromatic bicyclic ring, said ring having exactly 1 ring heteroatom or exactly 2 ring heteroatoms, wherein each of said ring heteroatoms is independently N, O, or S; and is optionally substituted.

In one embodiment, each —$R^{D6}$, if present, is independently azetidinyl, pyrrolidinyl, imidazolidinyl, pyrazolidinyl, piperidinyl, piperazinyl, morpholinyl, azepinyl, diazepinyl, oxetanyl, tetrahydrofuranyl, tetrahydropyranyl, dioxanyl, 3-aza-bicyclo[3.2.1]octanyl, 8-aza-bicyclo[3.2.1]octanyl, 3,8-diaza-bicyclo[3.2.1]octanyl, 3-aza-bicyclo[3.1.1]heptanyl, 6-aza-bicyclo[3.1.1]heptanyl, 3,6-diaza-bicyclo[3.1.1]heptanyl, 2-azabicyclo[2.2.2]octanyl, 1-azabicyclo[2.2.1]heptanyl, quinuclidinyl, or 9-azabicyclo[3.3.1]nonanyl, and is optionally substituted.

In one embodiment, each —$R^{D6}$, if present, is independently pyrrolidinyl, piperidinyl, piperazinyl, morpholinyl, tetrahydrofuranyl, or tetrahydropyranyl, and is optionally substituted.

In one embodiment, each —$R^{D7}$, if present, is independently phenyl, and is optionally substituted.

In one embodiment, each —$R^{D8}$, if present, is independently $C_{5-6}$heteroaryl, and is optionally substituted.

In one embodiment, each —$R^{D8}$, if present, is independently furanyl, thienyl, pyrrolyl, imidazolyl, pyrazolyl, triazolyl, oxazolyl, isoxazolyl, thiazolyl, isothiazolyl, pyridyl, pyrimidinyl, or pyridazinyl, and is optionally substituted.

In one embodiment, each —$R^{D8}$, if present is independently imidazolyl, pyrazolyl, triazolyl, pyridyl, pyrimidinyl, and is optionally substituted In one embodiment, each —$R^{D8}$, if present, is independently $C_{9-10}$heteroaryl, and is Optionally substituted.

In one embodiment, each —$R^{D9}$, if present, is independently:
—F, —Cl, —Br, —I,
—$R^{E1}$,
—$CF_3$, —$OCF_3$,
—OH, -$L^E$-OH, —O-$L^E$-OH,
—$OR^{E1}$, -$L^E$-$OR^{E1}$, —O-$L^E$-$OR^{E1}$,
—$NH_2$, —$NHR^{E1}$, —$NR^{E1}_2$, —$NR^{E2}R^{E3}$,
-$L^E$-$NH_2$, -$L^E$-$NHR^{E1}$, -$L^E$-$NR^{E1}_2$, -$L^E$-$NR^{E2}R^{E3}$,
—O-$L^E$-$NH_2$, —O-$L^E$-$NHR^{E1}$, —O-$L^E$-$NR^{E1}_2$, —O-$L^E$-$NR^{E2}R^{E3}$,
—C(=O)OH, —C(=O)$OR^{E1}$, —C(=O)NH$_2$, —C(=O)NHR$^{E1}$, —C(=O)NR$^{E1}$$_2$, or —C(=O)NR$^{E2}$R$^{E3}$;

In one embodiment, each -L$^E$-, if present, is independently saturated aliphatic C$_{1-3}$alkylene.

In one embodiment, each —R$^{E1}$, if present, is independently C$_{1-4}$alkyl.

In one embodiment, each —NR$^{E2}$R$^{E3}$, if present, is independently azetidino, pyrrolidino, imidazolidino, pyrazolidino, piperidino, piperazino, morpholino, azepino, or diazepino, and is optionally substituted, for example, with one or more groups selected from C$_{1-3}$alkyl and —CF$_3$.

In one embodiment, each —NR$^{E2}$R$^{E3}$, if present, is independently pyrrolidino, piperidino, piperazino, or morpholino, and is optionally substituted, for example, with one or more groups selected from C$_{1-3}$alkyl and —CF$_3$.

In one embodiment, each —R$^{D9}$, if present, is independently —F, —Cl, —Br, —I, -Me, -Et, —CF$_3$, —OH, —CH$_2$CH$_2$OH, —O—CH$_2$CH$_2$OH, —OMe, —OEt, —CH$_2$CH$_2$OMe, —O—CH$_2$CH$_2$OMe, —OCF$_3$, —SMe, —CN, —NO$_2$, —NH$_2$, —NHMe, —NMe$_2$, —CH$_2$CH$_2$NH$_2$, —CH$_2$CH$_2$NHMe, —CH$_2$CH$_2$NMe$_2$, —CH$_2$-(morpholino), —O—CH$_2$CH$_2$-(morpholino), —O—CH$_2$CH$_2$—NH$_2$, —C(=O)OH, —C(=O)OMe, —C(=O)NH$_2$, —C(=O)NHMe, —C(=O)NMe$_2$, —SO$_2$NH$_2$, —SO$_2$NHMe, —SO$_2$NMe$_2$, —SO$_2$Me, —CH$_2$-Ph, or -Ph.

In one embodiment, each -Q$^{A4O}$, if present, is independently selected from those substituents exemplified under the heading "Some Preferred Embodiments."

The Group -Q$^{A4S}$

In one embodiment, -Q$^{A4S}$, if present, is independently —R$^{F1}$, wherein —R$^{F1}$ is independently:
—R$^{G1}$, —R$^{G2}$, —R$^{G3}$, —R$^{G4}$, —R$^{G5}$, —R$^{G6}$, —R$^{G7}$, —R$^{G8}$,
-L$^G$-R$^{G4}$, -L$^G$-R$^{G5}$, -L$^G$-R$^{G6}$, -L$^G$-R$^{G7}$, or -L$^G$-R$^{G8}$;

wherein:
each —R$^{G1}$ is independently saturated aliphatic C$_{1-6}$alkyl;
each —R$^{G2}$ is independently aliphatic C$_{2-6}$alkenyl;
each —R$^{G3}$ is independently aliphatic C$_{2-6}$alkynyl;
each —R$^{G4}$ is independently saturated C$_{3-6}$cycloalkyl;
each —R$^{G5}$ is independently C$_{3-6}$cycloalkenyl;
each —R$^{G6}$ is independently non-aromatic C$_{3-8}$heterocyclyl;
each —R$^{G7}$ is independently C$_{6-10}$carboaryl;
each —R$^{G8}$ is independently C$_{5-10}$heteroaryl;
each -L$^G$- is independently saturated aliphatic C$_{1-3}$alkylene;

and wherein:
each C$_{1-6}$alkyl, C$_{2-6}$alkenyl, C$_{2-6}$alkynyl, C$_{3-6}$cycloalkyl, C$_{3-6}$cycloalkenyl, non-aromatic C$_{3-8}$heterocyclyl, C$_{6-10}$carboaryl, C$_{5-10}$heteroaryl, and C$_{1-3}$alkylene is optionally substituted, for example, with one or more substituents —R$^{G9}$, wherein each —R$^{G9}$ is independently:
—F, —Cl, —Br, —I,
—R$^{H1}$,
—CF$_3$, —OCF$_3$,
—OH, -L$^H$-OH, —O-L$^H$-OH,
—OR$^{H1}$, -L$^H$-OR$^{H1}$, —O-L$^H$-OR$^{H1}$,
—SH, —SR$^{H1}$,
—CN,
—NO$_2$,
—NH$_2$, —NHR$^{H1}$, —NR$^{H1}$$_2$, —NR$^{H2}$R$^{H3}$,
-L$^H$-NH$_2$, -L$^H$-NHR$^{H1}$, -L$^H$-NR$^{H1}$$_2$, -L$^H$-NR$^{H2}$R$^{H3}$,
—O-L$^H$-NH$_2$, —O-L$^H$-NHR$^{H1}$, —O-L$^H$-NR$^{H1}$$_2$,
—O-L$^H$-NR$^{H2}$R$^{H3}$,
—C(=O)OH, —C(=O)OR$^{H1}$,
—C(=O)NH$_2$, —C(=O)NHR$^{H1}$, —C(=O)NR$^{H1}$$_2$, or —C(=O)NR$^{H2}$R$^{H3}$;

wherein:
each —R$^{H1}$ is independently saturated aliphatic C$_{1-4}$alkyl, phenyl, or benzyl;
each -L$^H$- is independently saturated aliphatic C$_{1-5}$alkylene; and
in each group —NR$^{H2}$R$^{H3}$, R$^{H2}$ and R$^{H3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.

In one embodiment, —R$^{F1}$, if present, is independently:
—R$^{G1}$, —R$^{G4}$, —R$^{G6}$, —R$^{G7}$, —R$^{G8}$,
-L$^G$-R$^{G4}$, -L$^G$-R$^{G6}$, -L$^G$-R$^{G7}$, or -L$^G$-R$^{G8}$.

In one embodiment, R$^{F1}$, if present, is independently:
—R$^{G1}$, —R$^{G6}$, —R$^{G7}$, —R$^{G8}$,
-L$^G$-R$^{G6}$, -L$^G$-R$^{G7}$, or -L$^G$-R$^{G8}$.

In one embodiment, —R$^{F1}$, if present, is independently —R$^{G6}$ or -L$^G$-R$^{G6}$.

In one embodiment, —R$^{F1}$, if present, is independently —R$^{G6}$.

In one embodiment, —R$^{F1}$, if present, is independently -L$^G$-R$^{G6}$.

In one embodiment, each -L$^G$-, if present, is independently —CH$_2$— or —CH$_2$CH$_2$—.

In one embodiment, each -L$^G$-, if present, is independently —CH$_2$—.

In one embodiment, each —R$^{G1}$, if present, is independently a saturated aliphatic C$_{1-3}$alkyl.

In one embodiment, each —R$^{G6}$, if present, is a C$_{3-8}$heterocyclyl group that is a 4-, 5-, 6-, or 7-membered non-aromatic monocyclic ring or a 7- or 8-membered non-aromatic bicyclic ring, said ring having exactly 1 ring heteroatom or exactly 2 ring heteroatoms, wherein each of said ring heteroatoms is independently N, O, or S; and is optionally substituted.

In one embodiment, each —R$^{G6}$, if present, is independently is independently azetidinyl, pyrrolidinyl, imidazolidinyl, pyrazolidinyl, piperidinyl, piperazinyl, morpholinyl, azepinyl, diazepinyl, oxetanyl, tetrahydrofuranyl, tetrahydropyranyl, dioxanyl, 3-aza-bicyclo[3.2.1]octanyl, 8-aza-bicyclo[3.2.1]octanyl, 3,8-diaza-bicyclo[3.2.1]octanyl, 3-aza-bicyclo[3.1.1]heptanyl, 6-aza-bicyclo[3.1.1]heptanyl, 3,6-diaza-bicyclo[3.1.1]heptanyl, 2-azabicyclo[2.2.2]octanyl, 1-azabicyclo[2.2.1]heptanyl, quinuclidinyl, or 9-azabicyclo[3.3.1]nonanyl, and is optionally substituted.

In one embodiment, each —R$^{G6}$, if present, is independently pyrrolidinyl, piperidinyl, piperazinyl, morpholinyl, tetrahydrofuranyl, or tetrahydropyranyl, and is optionally substituted.

In one embodiment, each —R$^{G7}$, if present, is independently phenyl, and is optionally substituted.

In one embodiment, each —R$^{G8}$, if present, is independently C$_{5-6}$heteroaryl, and is optionally substituted.

In one embodiment, each —R$^{G8}$, if present, is independently furanyl, thienyl, pyrrolyl, imidazolyl, pyrazolyl, triazolyl, oxazolyl, isoxazolyl, thiazolyl, isothiazolyl, pyridyl, pyrimidinyl, or pyridazinyl, and is optionally substituted.

In one embodiment, each —R$^{G8}$, if present, is independently imidazolyl, pyrazolyl, triazolyl, pyridyl, or pyrimidinyl, and is optionally substituted.

In one embodiment, each —R$^{G8}$, if present, is independently C$_{9-10}$heteroaryl, and is optionally substituted.

In one embodiment, each —$R^{G9}$, if present, is independently:
- —F, —Cl, —Br, —I,
- —$R^{H1}$,
- —$CF_3$, —$OCF_3$,
- —OH, -$L^H$-OH, —O-$L^H$-OH,
- —$OR^{H1}$, -$L^H$-$OR^{H1}$, —O-$L^H$-$OR^{H1}$,
- —$NH_2$, —$NHR^{H1}$, —$NR^{H1}_2$, —$NR^{H2}R^{H3}$,
- -$L^H$-$NH_2$, -$L^H$-$NHR^{H1}$, -$L^H$-$NR^{H1}_2$, -$L^H$-$NR^{H2}R^{H3}$,
- —O-$L^H$-$NH_2$, —O-$L^H$-$NHR^{H1}$, —O-$L^H$-$NR^{H1}_2$, —O-$L^H$-$NR^{H2}R^{H3}$,
- —C(=O)OH, —C(=O)$OR^{H1}$,
- —C(=O)$NH_2$, —C(=O)$NHR^{H1}$, —C(=O)$NR^{H1}_2$, or —C(=O)$NR^{H2}R^{H3}$.

In one embodiment, each -$L^H$-, if present, is independently saturated aliphatic $C_{1-3}$alkylene.

In one embodiment, each —$R^{H1}$, if present, is independently $C_{1-4}$alkyl.

In one embodiment, each —$NR^{H2}R^{H3}$, if present, is independently azetidino, pyrrolidino, imidazolidino, pyrazolidino, piperidino, piperazino, morpholino, azepino, or diazepino, and is optionally substituted, for example, with one or more groups selected from $C_{1-3}$alkyl and —$CF_3$.

In one embodiment, each —$NR^{H2}R^{H3}$, if present, is independently pyrrolidino, piperidino, piperazino, or morpholino, and is optionally substituted, for example, with one or more groups selected from $C_{1-3}$alkyl and —$CF_3$.

In one embodiment, each —$R^{G9}$, if present, is independently —F, —Cl, —Br, —I, -Me, -Et, —$CF_3$, —OH, —$CH_2CH_2OH$, —O—$CH_2CH_2OH$, —OMe, —OEt, —$CH_2CH_2OMe$, —O—$CH_2CH_2OMe$, —$OCF_3$, —SMe, —CN, —$NO_2$, —$NH_2$, —NHMe, —$NMe_2$, —$CH_2CH_2NH_2$, —$CH_2CH_2NHMe$, —$CH_2CH_2NMe_2$, —$CH_2$-(morpholino), —O—$CH_2CH_2$-(morpholino), —O—$CH_2CH_2$—$NH_2$, —C(=O)OH, —C(=O)OMe, —C(=O)$NH_2$, —C(=O)NHMe, —C(=O)$NMe_2$, —$SO_2NH_2$, —$SO_2NHMe$, —$SO_2NMe_2$, —$SO_2Me$, —$CH_2$-Ph, or -Ph.

In one embodiment, -$Q^{44S}$, if present, is independently selected from those substituents exemplified under the heading "Some Preferred Embodiments."

The Group $Q^{45}$

In one embodiment, $Q^{45}$, if present, is independently:
- —F, —Cl, —Br, —I,
- —$R^{J1}$,
- —$CF_3$, —$OCF_3$,
- —OH, -$L^J$-OH, —O-$L^J$-OH,
- —$OR^{J1}$, -$L^J$-$OR^{J1}$, —O-$L^J$-$OR^{J1}$,
- —SH, —$SR^{J1}$,
- —CN,
- —$NO_2$,
- —$NH_2$, —$NHR^{J1}$, —$NR^{J1}_2$, —$NR^{J2}R^{J3}$,
- -$L^J$-$NH_2$, -$L^J$-$NHR^{J1}$, -$L^J$-$NR^{J1}_2$, -$L^J$-$NR^{J2}R^{J3}$,
- —O-$L^J$-$NH_2$, —O-$L^J$-$NHR^{J1}$, —O-$L^J$-$NR^{J1}_2$, —O-$L^J$-$NR^{J2}R^{J3}$,
- —C(=O)OH, —C(=O)$OR^{J1}$,
- —C(=O)$NH_2$, —C(=O)$NHR^{J1}$, —C(=O)$NR^{J1}_2$, —C(=O)$NR^{J2}R^{J3}$,
- —NHC(=O)$R^{J1}$, —$NR^{J1}$C(=O)$R^{J1}$,
- —NHC(=O)$OR^{J1}$, —$NR^{J1}$C(=O)$OR^{J1}$,
- —OC(=O)$NH_2$, —OC(=O)$NHR^{J1}$, —OC(=O)$NR^{J1}_2$, —OC(=O)$NR^{J2}R^{J3}$,
- —C(=O)$R^{J1}$,
- —NHC(=O)$NH_2$, —NHC(=O)$NHR^{J1}$,
- —NHC(=O)$NR^{J1}_2$, —NHC(=O)$NR^{J2}R^{J3}$,
- —$NR^{J1}$C(=O)$NH_2$, —$NR^{J1}$C(=O)$NHR^{J1}$,
- —$NR^{J1}$C(=O)$NR^{J1}_2$, —$NR^{J1}$C(=O)$NR^{J2}R^{J3}$,
- —$NHS(=O)_2R^{J1}$, —$NR^{J1}S(=O)_2R^{J1}$,
- —$S(=O)_2NH_2$, —$S(=O)_2NHR^{J1}$, —$S(=O)_2NR^{J1}_2$, —$S(=O)_2NR^{J2}R^{J3}$,
- —$S(=O)R^{J1}$, —$S(=O)_2R^{J1}$, —$OS(=O)_2R^{J1}$, or —$S(=O)_2OR^{J1}$;

wherein:

each -$L^J$- is independently saturated aliphatic $C_{1-5}$alkylene;

in each group —$NR^{J2}R^{J3}$, $R^{J2}$ and $R^{J3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;

each —$R^{J1}$ is independently:
- $R^{K1}$, $R^{K2}$, $R^{K3}$, $R^{K4}$, $R^{K5}$, $R^{K6}$, $R^{K7}$, $R^{K8}$,
- -$L^K$-$R^{K4}$, -$L^K$-$R^{K5}$, -$L^K$-$R^{K6}$, -$L^K$-$R^{K7}$, or -$L^K$-$R^{K8}$;

wherein:
- each —$R^{K1}$ is independently saturated aliphatic $C_{1-6}$alkyl;
- each —$R^{K2}$ is independently aliphatic $C_{2-6}$alkenyl;
- each —$R^{K3}$ is independently aliphatic $C_{2-6}$alkynyl;
- each —$R^{K4}$ is independently saturated $C_{3-6}$cycloalkyl;
- each —$R^{K5}$ is independently $C_{3-6}$cycloalkenyl;
- each —$R^{K6}$ is independently non-aromatic $C_{3-8}$heterocyclyl;
- each —$R^{K7}$ is independently $C_{6-10}$carboaryl;
- each —$R^{K8}$ is independently $C_{5-10}$heteroaryl;
- each -$L^K$- is independently saturated aliphatic $C_{1-3}$alkylene;

and wherein:

each $C_{1-6}$alkyl, $C_{2-6}$alkenyl, $C_{2-6}$alkynyl, $C_{3-6}$cycloalkyl, $C_{3-6}$cycloalkenyl, non-aromatic $C_{3-8}$heterocyclyl, $C_{6-10}$carboaryl, $C_{5-10}$heteroaryl, and $C_{1-3}$alkylene is optionally substituted, for example, with one or more substituents —$R^{K9}$, wherein each —$R^{K9}$ is independently:
- —F, —Cl, —Br, —I,
- —$R^{M1}$,
- —$CF_3$, —$OCF_3$,
- —OH, -$L^M$-OH, —O-$L^M$-OH,
- —$OR^{M1}$, -$L^M$-$OR^{M1}$, —O-$L^M$-$OR^{M1}$,
- —SH, —$SR^{M1}$,
- —CN,
- —$NO_2$,
- —$NH_2$, —$NHR^{M1}$, —$NR^{M1}_2$, —$NR^{M2}R^{M3}$,
- -$L^M$-$NH_2$, -$L^M$-$NHR^{M1}$, -$L^M$-$NR^{M1}_2$, -$L^M$-$NR^{M2}R^{M3}$,
- —C(=O)OH, —C(=O)$OR^{M1}$,
- —C(=O)$NH_2$, —C(=O)$NHR^{M1}$, —C(=O)$NR^{M1}_2$, or —C(=O)$NR^{M2}R^{M3}$;

wherein:

each —$R^{M1}$ is independently saturated aliphatic $C_{1-4}$alkyl, phenyl, or benzyl;

each -$L^M$- is independently saturated aliphatic $C_{1-5}$alkylene; and in each group —$NR^{M2}R^{M3}$, $R^{M2}$ and $R^{M3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.

In one embodiment, each -$Q^{45}$, if present, is independently:
- —F, —Cl, —Br, —I,
- —$R^{J1}$,
- —$CF_3$, —$OCF_3$, —OH, -L$^J$-OH, —O-L$^J$-OH,
—OR$^{J1}$, -L$^J$-OR$^{J1}$, —O-L$^J$-OR$^{J1}$,
—CN,
—NH$_2$, —NHR$^{J1}$, —NR$^{J1}{}_2$, —NR$^{J2}$R$^{J3}$,
-L$^J$-NH$_2$, -L$^J$-NHR$^{J1}$, -L$^J$-NR$^{J1}{}_2$, -L$^J$-NR$^{J2}$R$^{J3}$,
—O-L$^J$-NH$_2$, —O-L$^J$-NHR$^{J1}$, —O-L$^J$-NR$^{J1}{}_2$, —O-L$^J$-NR$^{J2}$R$^{J3}$,
—C(=O)OH, —C(=O)OR$^{J1}$,
—C(=O)NH$_2$, —C(=O)NHR$^{J1}$, —C(=O)NR$^{J1}{}_2$, —C(=O)NR$^{J2}$R$^{J3}$,
—NHC(=O)R$^{J1}$, —NR$^{J1}$C(=O)R$^{J1}$,
—NHS(=O)$_2$R$^{J1}$, —NR$^{J1}$S(=O)$_2$R$^{J1}$, or
—C(=O)R$^{J1}$.

In one embodiment, each -Q$^{45}$, if present, is independently:
—F, —Cl, —Br, —I,
—R$^{J1}$,
—NH$_2$, —NHR$^{J1}$, —NR$^{J1}{}_2$, —NR$^{J2}$R$^{J3}$,
—C(=O)OH, —C(=O)OR$^{J1}$
—C(=O)NH$_2$, —C(=O)NHR$^{J1}$, —C(=O)NR$^{J1}{}_2$, —C(=O)NR$^{J2}$R$^{J3}$,
—NHC(=O)R$^{J1}$, —NR$^{J1}$C(=O)R$^{J1}$,
—NHS(=O)$_2$R$^{J1}$, or —NR$^{J1}$S(=O)$_2$R$^{J1}$.

In one embodiment, each -Q$^{45}$, if present, is independently:
—F, —Cl, —Br, —I, or —R$^{J1}$.

In one embodiment, each -Q$^{45}$, if present, is independently:
—NH$_2$, —NHR$^{J1}$, —NR$^{J1}{}_2$, —NR$^{J2}$R$^{J3}$,
—NHC(=O)R$^{J1}$, —NR$^{J1}$C(=O)R$^{J1}$,
—NHS(=O)$_2$R$^{J1}$, or —NR$^{J1}$S(=O)$_2$R$^{J1}$.

In one embodiment, each -Q$^{45}$, if present, is independently:
—NH$_2$, —NHR$^{J1}$, —NR$^{J1}{}_2$, —NR$^{J2}$R$^{J3}$,
—NHC(=O)R$^{J1}$, or —NR$^{J1}$C(=O)R$^{J1}$.

In one embodiment, each -Q$^{45}$, if present, is independently:
—NHS(=O)$_2$R$^{J1}$ or —NR$^{J1}$S(=O)$_2$R$^{J1}$.

In one embodiment, each -Q$^{45}$, if present, is independently:
—C(=O)OH, —C(=O)OR$^{J1}$,
—C(=O)NH$_2$, —C(=O)NHR$^{J1}$, —C(=O)NR$^{J1}{}_2$, or —C(=O)NR$^{J2}$R$^{J3}$.

In one embodiment, each -Q$^{45}$, if present, is independently:
—C(=O)NH$_2$, —C(=O)NHR$^{J1}$, —C(=O)NR$^{J1}{}_2$, or —C(=O)NR$^{J2}$R$^{J3}$.

In one embodiment, each -Q$^{45}$, if present, is independently —C(=O)OR$^{J1}$.

In one embodiment, each -Q$^{45}$, if present, is independently —C(=O)NHR$^{J1}$.

In one embodiment, each -Q$^{45}$, if present, is independently —R$^{J1}$.

In one embodiment, each -L$^J$-, if present, is independently saturated aliphatic C$_{1-3}$alkylene.

In one embodiment, each —NR$^{J2}$R$^{J3}$, if present, is independently azetidino, pyrrolidino, imidazolidino, pyrazolidino, piperidino, piperazino, morpholino, azepino, or diazepino, and is optionally substituted, for example, with one or more groups selected from C$_{1-3}$alkyl and —CF$_3$.

In one embodiment, each —NR$^{J2}$R$^{J3}$, if present, is independently pyrrolidino, piperidino, piperazino, or morpholino, and is optionally substituted, for example, with one or more groups selected from C$_{1-3}$alkyl and —CF$_3$.

In one embodiment, each —R$^{J1}$, if present, is independently:
—R$^{K1}$, —R$^{K4}$, —R$^{K6}$, —R$^{K7}$, —R$^{K8}$,
-L$^K$-R$^{K4}$, -L$^K$-R$^{K6}$, -L$^K$-R$^{K7}$, or -L$^K$-R$^{K8}$.

In one embodiment, each —R$^{J1}$, if present, is independently:
—R$^{K1}$, —R$^{K6}$, —R$^{K7}$, —R$^{K8}$,
-L$^K$-R$^{K6}$, -L$^K$-R$^{K7}$, or -L$^K$-R$^{K8}$.

In one embodiment, each —R$^{J1}$, if present, is independently —R$^{K1}$, —R$^{K7}$, or -L$^K$-R$^{K7}$.

In one embodiment, each —R$^{J1}$, if present, is independently —R$^{K6}$, -L$^K$-R$^{K6}$, R$^{K8}$, or -L$^K$-R$^{K8}$.

In one embodiment, each —R$^{J1}$, if present, is independently —R$^{K6}$, or -L$^K$-R$^{K6}$.

In one embodiment, each —R$^{J1}$, if present, is independently —R$^{K1}$.

In one embodiment, each —R$^{J1}$, if present, is independently —R$^{K2}$.

In one embodiment, each —R$^{J1}$, if present, is independently —R$^{K3}$.

In one embodiment, each —R$^{J1}$, if present, is independently —R$^{K7}$.

In one embodiment, each -R$^{J1}$, if present, is independently —R$^{K8}$.

In one embodiment, each -L$^K$-, if present, is independently —CH$_2$— or —CH$_2$CH$_2$—.

In one embodiment, each -L$^K$-, if present, is independently —CH$_2$—.

In one embodiment, each —R$^{K1}$, if present, is independently a saturated aliphatic C$_{1-3}$alkyl.

In one embodiment, each —R$^{K1}$, if present, is independently -Me.

In one embodiment, each —R$^{K1}$, if present, is independently —CH$_2$CH$_2$CH$_2$—OH or —CH$_2$CH$_2$CH$_2$—OMe.

In one embodiment, each —R$^{K2}$, if present, is independently —CH=CH—CH$_2$—OH, —CH=CH—CH$_2$—OMe, —CH=CH—CH$_2$CH$_2$—OH, or —CH=CH—CH$_2$CH$_2$—OMe.

In one embodiment, each —R$^{K3}$, if present, is independently —C≡C—CH$_2$—OH, —C≡C—CH$_2$-OMe, —C≡C—C(Me)$_2$-OH, or —C≡C—C(Me)$_2$-OMe.

In one embodiment, each —R$^{K6}$, if present, is a C$_{3-8}$heterocyclyl group that is a 4-, 5-, 6-, or 7-membered non-aromatic monocyclic ring or a 7- or 8-membered non-aromatic bicyclic ring, said ring having exactly 1 ring heteroatom or exactly 2 ring heteroatoms, wherein each of said ring heteroatoms is independently N, O, or S; and is optionally substituted.

In one embodiment, each —R$^{K6}$, if present, is independently azetidinyl, pyrrolidinyl, imidazolidinyl, pyrazolidinyl, piperidinyl, piperazinyl, morpholinyl, azepinyl, diazepinyl, tetrahydrofuranyl, tetrahydropyranyl, dioxanyl, and is optionally substituted.

In one embodiment, each —R$^{K6}$, if present, is independently pyrrolidinyl, piperidinyl, piperazinyl, morpholinyl, tetrahydrofuranyl, or tetrahydropyranyl, and is optionally substituted.

In one embodiment, each —R$^{K7}$, if present, is independently phenyl, and is optionally substituted.

In one embodiment, each —R$^{K8}$, if present, is independently C$_{5-6}$heteroaryl, and is optionally substituted.

In one embodiment, each —R$^{K8}$, if present, is independently furanyl, thienyl, pyrrolyl, imidazolyl, pyrazolyl, triazolyl, oxazolyl, isoxazolyl, thiazolyl, isothiazolyl, oxadiazolyl, pyridyl, pyrimidinyl, or pyridazinyl, and is optionally substituted.

In one embodiment, each —R$^{K8}$, if present is independently thiazolyl, oxazolyl, isoxazolyl, or oxadiazolyl, and is optionally substituted.

In one embodiment, each —R$^{K8}$, if present, is independently thienyl or pyrazolyl, and is optionally substituted.

In one embodiment, each —R$^{K8}$, if present, is independently selected from:

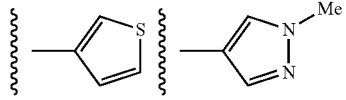

In one embodiment, each —R$^{K8}$, if present, is independently C$_{3-10}$heteroaryl, and is optionally substituted.

In one embodiment, each —R$^{K8}$, if present, is independently benzofuranyl, benzothienyl, indolyl, benzoimidazolyl, indazolyl, benzotriazolyl, benzooxazolyl, benzoisoxazolyl, benzothiazolyl, benzoisothiazolyl, quinolinyl, isoquinolinyl, quinazolinyl, cinnolinyl, phthalazinyl, or quinoxalinyl, and is optionally substituted.

In one embodiment, each —R$^{K8}$, if present is independently benzothiazolyl or benzoxazolyl, and is optionally substituted.

In one embodiment, each —R$^{K9}$, if present, is independently:
—F, —Cl, —Br, —I,
—R$^{M1}$,
—CF$_3$, —OCF$_3$,
—OH, -L$^M$-OH,
—OR$^{M1}$, -L$^M$-OR$^{M1}$, —O-L$^M$-OR$^{M1}$,
—NH$_2$, —NHR$^{M1}$, —NR$^{M1}{}_2$, —NR$^{M2}$R$^{M3}$,
-L$^M$-NH$_2$, -L$^M$-NHR$^{M1}$, -L$^M$-NR$^{M1}{}_2$, -L$^M$-NR$^{M2}$R$^{M3}$,
—C(=O)OH, —C(=O)OR$^{M1}$,
—C(=O)NH$_2$, —C(=O)NHR$^{M1}$, —C(=O)NR$^{M1}{}_2$, or —C(=O)NR$^{M2}$R$^{M3}$.

In one embodiment, each —R$^{K9}$, if present, is independently:
—F, —Cl, —Br, —I,
—R$^{M1}$,
—CF$_3$, —OCF$_3$,
—OH, -L$^M$-OH,
—OR$^{M1}$, -L$^M$-OR$^{M1}$,
—NH$_2$, —NHR$^{M1}$, —NR$^{M1}{}_2$, —NR$^{M2}$R$^{M3}$,
-L$^M$-NH$_2$, -L$^M$-NHR$^{M1}$, -L$^M$-NR$^{M1}{}_2$, -L$^M$-NR$^{M2}$R$^{M3}$,
—C(=O)OH, —C(=O)OR$^{M1}$,
—C(=O)NH$_2$, —C(=O)NHR$^{M1}$, —C(=O)NR$^{M1}{}_2$, or —C(=O)NR$^{M2}$R$^{M3}$.

In one embodiment, each —R$^{K9}$, if present, is independently:
—OR$^{M1}$,
—NH$_2$, —NHR$^{M1}$, —NR$^{M1}{}_2$, or —NR$^{M2}$R$^{M3}$.

In one embodiment, each —R$^{K9}$, if present, is independently:
—F, —OR$^{M1}$, -L$^M$-OR$^{M1}$, or —O-L$^M$-OR$^{M1}$.

In one embodiment, each —R$^{K9}$, if present, is independently:
—F, —OMe, —CH$_2$OMe, or —OCH$_2$CH$_2$OMe.

In one embodiment, each -L$^M$-, if present, is independently saturated aliphatic C$_{1-3}$alkylene.

In one embodiment, each —R$^{M1}$, if present, is independently C$_{1-4}$alkyl.

In one embodiment, each —NR$^{M2}$R$^{M3}$, if present, is independently azetidino, pyrrolidino, imidazolidino, pyrazolidino, piperidino, piperazino, morpholino, azepino, or diazepino, and is optionally substituted, for example, with one or more groups selected from C$_{1-3}$alkyl and —CF$_3$.

In one embodiment, each —NR$^{M2}$R$^{M3}$, if present, is independently pyrrolidino, piperidino, piperazino, or morpholino, and is optionally substituted, for example, with one or more groups selected from C$_{1-3}$alkyl and —CF$_3$.

In one embodiment, each —R$^{K9}$, if present, is independently —F, —Cl, —Br, —I, -Me, -Et, —CF$_3$, —OH, —CH$_2$CH$_2$OH, —OCH$_2$CH$_2$OH, —OMe, —OEt, —CH$_2$CH$_2$OMe, —OCH$_2$CH$_2$OMe, —OCF$_3$, —SMe, —CN, —NO$_2$, —NH$_2$, —NHMe, —NMe$_2$, —CH$_2$CH$_2$NH$_2$, —CH$_2$-(morpholino), —O—CH$_2$CH$_2$-(morpholino), —O—CH$_2$CH$_2$—NH$_2$, —C(=O)OH, —C(=O)OMe, —C(=O)NH$_2$, —C(=O)NHMe, —C(=O)NMe$_2$, —SO$_2$NH$_2$, —SO$_2$NHMe, —SO$_2$NMe$_2$, —SO$_2$Me, —CH$_2$-Ph, or -Ph.

In one embodiment, each -Q$^{45}$, if present, is independently selected from those substituents exemplified under the heading "Some Preferred Embodiments."

The Group -Q$^{43}$

In one embodiment, -Q$^{43}$, if present, is independently:
—F, —Cl, —Br, —I,
—R$^{N1}$,
—CF$_3$, —OCF$_3$,
—OH, —OR$^{N1}$,
—SH, —SR$^{N1}$,
—NH$_2$, —NHR$^{N1}$, —NR$^{N1}{}_2$, or —NR$^{N2}$R$^{N3}$;
wherein:
  each —R$^{N1}$ is independently saturated aliphatic C$_{1-6}$alkyl; and
  in each group —NR$^{N2}$R$^{N3}$, R$^{N2}$ and R$^{N3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.

In one embodiment, each —NR$^{N2}$R$^{N3}$, if present, is independently azetidino, pyrrolidino, imidazolidino, pyrazolidino, piperidino, piperazino, morpholino, azepino, or diazepino, and is optionally substituted, for example, with one or more groups selected from C$_{1-3}$alkyl and —CF$_3$.

In one embodiment, each —NR$^{N2}$R$^{N3}$, if present, is independently pyrrolidino, piperidino, piperazino, or morpholino, and is optionally substituted, for example, with one or more groups selected from C$_{1-3}$alkyl and —CF$_3$.

In one embodiment, -Q$^{43}$, if present, is independently —F, —Cl, —Br, —I, -Me, -Et, -nPr, -iPr, —CF$_3$, —OH, —OMe, —OEt, —OCF$_3$, —SH, —SMe, —NH$_2$, —NHMe, or —NMe$_2$.

In one embodiment, -Q$^{43}$, if present, is independently selected from those substituents exemplified under the heading "Some Preferred Embodiments."

The Group Q$^{B3}$

In one embodiment, -Q$^{B3}$, if present, is independently:
—F, —Cl, —Br, —I,
—R$^{Q1}$,
—CF$_3$, —OCF$_3$,
—OH, —OR$^{Q1}$,
—SH, —SR$^{Q1}$,
—NH$_2$, —NHR$^{Q1}$, —NR$^{Q1}{}_2$, or —NR$^{Q2}$R$^{Q3}$;
wherein:
  each —R$^{Q1}$ is independently saturated aliphatic C$_{1-6}$alkyl; and
  in each group —NR$^{Q2}$R$^{Q3}$, R$^{Q2}$ and R$^{Q3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.

In one embodiment, -$Q^{B3}$, if present, is independently:
—$R^{Q1}$,
—OH, —$OR^{Q1}$,
—SH, —$SR^{Q1}$,
—$NH_2$, —$NHR^{Q1}$, —$NR^{Q1}{}_2$, or —$NR^{Q2}R^{Q3}$.

In one embodiment, each —$NR^{Q2}R^{Q3}$, if present, is independently azetidino, pyrrolidino, imidazolidino, pyrazolidino, piperidino, piperazino, morpholino, azepino, or diazepino, and is optionally substituted, for example, with one or more groups selected from $C_{1-3}$alkyl and —$CF_3$.

In one embodiment, each —$NR^{Q2}R^{Q3}$, if present, is independently pyrrolidino, piperidino, piperazino, or morpholino, and is optionally substituted, for example, with one or more groups selected from $C_{1-3}$alkyl and —$CF_3$.

In one embodiment, -$Q^{B3}$, if present, is independently -Me, -Et, —OH, —OMe, —OEt, —$OCF_3$, —$NH_2$, —NHMe, —$NMe_2$, —SH, or —SMe.

In one embodiment, -$Q^{B3}$, if present, is independently selected from those substituents exemplified under the heading "Some Preferred Embodiments."

The Group $Q^{B5}$

In one embodiment, -$Q^{B5}$, if present, is independently:
—F, —Cl, —Br, —I,
—$R^{T1}$,
—$CF_3$, —$OCF_3$,
—OH, -$L^T$-OH, —O-$L^T$-OH,
—$OR^{T1}$, -$L^T$-$OR^{T1}$, —O-$L^T$-$OR^{T1}$,
—SH, —$SR^{T1}$,
—CN,
—$NO_2$,
—$NH_2$, —$NHR^{T1}$, —$NR^{T1}{}_2$, —$NR^{T2}R^{T3}$,
-$L^T$-$NH_2$, -$L^T$-$NHR^{T1}$, -$L^T$-$NR^{T1}{}_2$, -$L^T$-$NR^{T2}R^{T3}$,
—O-$L^T$-$NH_2$, —O-$L^T$-$NHR^{T1}$, —O-$L^T$-$NR^{T1}{}_2$, —O-$L^T$-$NR^{T2}R^{T3}$,
—C(=O)OH, —C(=O)$OR^{T1}$,
—C(=O)$NH_2$, —C(=O)$NHR^{T1}$, —C(=O)$NR^{T1}{}_2$, —C(=O)$NR^{T2}R^{T3}$,
—NHC(=O)$R^{T1}$, —$NR^{T1}$C(=O)$R^{T1}$,
—NHC(=O)$OR^{T1}$, —$NR^{T1}$C(=O)$OR^{T1}$,
—OC(=O)$NH_2$, —OC(=O)$NHR^{T1}$, —OC(=O)$NR^{T1}{}_2$, —OC(=O)$NR^{T2}R^{T3}$,
—C(=O)$R^{T1}$,
—NHC(=O)$NH_2$, —NHC(=O)$NHR^{T1}$,
—NHC(=O)$NR^{T1}{}_2$, —NHC(=O)$NR^{T2}R^{T3}$,
—$NR^{T1}$C(=O)$NH_2$, —$NR^{T1}$C(=O)$NHR^{T1}$,
—$NR^{T1}$C(=O)$NR^{T1}{}_2$, —$NR^{T1}$C(=O)$NR^{T2}R^{T3}$,
—NHS(=O)$_2R^{T1}$, —$NR^{T1}$S(=O)$_2R^{T1}$,
—S(=O)$_2NH_2$, —S(=O)$_2NHR^{T1}$, —S(=O)$_2NR^{T1}{}_2$, —S(=O)$_2NR^{T2}R^{T3}$,
—S(=O)$R^{T1}$, —S(=O)$_2R^{T1}$, —OS(=O)$_2R^{T1}$ or —S(=O)$_2OR^{T1}$;
wherein:
each -$L^T$- is independently saturated aliphatic $C_{1-5}$alkylene;
in each group —$NR^{T2}R^{T3}$, $R^{T2}$ and $R^{T3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O,
each —$R^{T1}$ is independently:
$R^{U1}$, $R^{U2}$, $R^{U3}$, $R^{U4}$, $R^{U5}$, $R^{U6}$, $R^{U7}$, $R^{U8}$,
-$L^U$-$R^{U4}$, -$L^U$-$R^{U5}$, -$L^U$-$R^{U6}$, -$L^U$-$R^{U7}$, or -$L^U$-$R^{U8}$;

wherein:
each —$R^{U1}$ is independently saturated aliphatic $C_{1-6}$alkyl;
each —$R^{U2}$ is independently aliphatic $C_{2-6}$alkenyl;
each —$R^{U3}$ is independently aliphatic $C_{2-6}$alkynyl;
each —$R^{U4}$ is independently saturated $C_{3-6}$cycloalkyl;
each —$R^{U5}$ is independently $C_{3-6}$cycloalkenyl;
each —$R^{U6}$ is independently non-aromatic $C_{3-8}$heterocyclyl;
each —$R^{U7}$ is independently $C_{6-10}$carboaryl;
each —$R^{U8}$ is independently $C_{5-10}$heteroaryl;
each -$L^U$- is independently saturated aliphatic $C_{1-3}$alkylene;
and wherein:
each $C_{1-6}$alkyl, $C_{2-6}$alkenyl, $C_{2-6}$alkynyl, $C_{3-6}$cycloalkyl, $C_{3-6}$cycloalkenyl, non-aromatic $C_{3-8}$heterocyclyl, $C_{6-10}$carboaryl, $C_{5-10}$heteroaryl, and $C_{1-3}$alkylene is optionally substituted, for example, with one or more substituents —$R^{U9}$, wherein each —$R^{U9}$ is independently:
—F, —Cl, —Br, —I,
—$R^{V1}$,
—$CF_3$, —$OCF_3$,
—OH, -$L^V$-OH,
—$OR^{V1}$, -$L^V$-$OR^{V1}$,
—SH, —$SR^{V1}$,
—CN,
—$NO_2$,
—$NH_2$, —$NHR^{V1}$, —$NR^{V1}{}_2$, —$NR^{V2}R^{V3}$,
-$L^V$-$NH_2$, -$L^V$-$NHR^{V1}$, -$L^V$-$NR^{V1}{}_2$, -$L^V$-$NR^{V2}R^{V3}$,
—C(=O)OH, —C(=O)$OR^{V1}$,
—C(=O)$NH_2$, —C(=O)$NHR^{V1}$, —C(=O)$NR^{V1}{}_2$, or —C(=O)$NR^{V2}R^{V3}$;
wherein:
each —$R^{V1}$ is independently saturated aliphatic $C_{1-4}$alkyl, phenyl, or benzyl;
each -$L^V$- is independently saturated aliphatic $C_{1-5}$alkylene; and
in each group —$NR^{V2}R^{V3}$, $R^{V2}$ and $R^{V3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.

In one embodiment, -$Q^{B5}$, if present, is independently:
—$R^{T1}$,
—$CF_3$, —$OCF_3$,
—OH, -$L^T$-OH, —O-$L^T$-OH,
—$OR^{T1}$, -$L^T$-$OR^{T1}$, —O-$L^T$-$OR^{T1}$,
—CN,
—$NO_2$,
—$NH_2$, —$NHR^{T1}$, —$NR^{T1}{}_2$, —$NR^{T2}R^{T3}$
-$L^T$-$NH_2$, -$L^T$-$NHR^{T1}$, -$L^T$-$NR^{T1}{}_2$, -$L^T$-$NR^{T2}R^{T3}$
—O-$L^T$-$NH_2$, —O-$L^T$-$NHR^{T1}$, —O-$L^T$-$NR^{T1}{}_2$, —O-$L^T$-$NR^{T2}R^{T3}$,
—C(=O)OH, —C(=O)$OR^{T1}$,
—C(=O)$NH_2$, —C(=O)$NHR^{T1}$, —C(=O)$NR^{T1}{}_2$, —C(=O)$NR^{T2}R^{T3}$,
—NHC(=O)$R^{T1}$, or —$NR^{T1}$C(=O)$R^{T1}$.

In one embodiment, -$Q^{B5}$, if present, is independently:
$R^{T1}$,
—$CF_3$,
—OH, -$L^T$-OH,
—$OR^{T1}$, -$L^T$-$OR^{T1}$,
—CN, —C(=O)NH$_2$, —C(=O)NHR$^{T1}$, —C(=O)NR$^{T1}$$_2$, —C(=O)NR$^{T2}$R$^{T3}$,
—NHC(=O)R$^{T1}$, or —NR$^{T1}$C(=O)R$^{T1}$.

In one embodiment, -Q$^{B5}$, if present, is independently:
—R$^{T1}$,
—OR$^{T1}$,
—CN,
—C(=O)NH$_2$, —C(=O)NHR$^{T1}$, —C(=O)NR$^{T1}$$_2$, or —C(=O)NR$^{T2}$R$^{T3}$.

In one embodiment, each -L$^T$-, if present, is independently saturated aliphatic C$_{1-3}$alkylene.

In one embodiment, each —NR$^{T2}$R$^{T3}$, if present, is independently azetidino, pyrrolidino, imidazolidino, pyrazolidino, piperidino, piperazino, morpholino, azepino, or diazepino, and is optionally substituted, for example, with one or more groups selected from C$_{1-3}$alkyl and —CF$_3$.

In one embodiment, each —NR$^{T2}$R$^{T3}$, if present, is independently pyrrolidino, piperidino, piperazino, or morpholino, and is optionally substituted, for example, with one or more groups selected from C$_{1-3}$alkyl and —CF$_3$.

In one embodiment, each —R$^{T1}$, if present, is independently:
—R$^{U1}$, —R$^{U3}$, —R$^{U4}$, —R$^{U6}$, —R$^{U7}$, —R$^{U8}$,
-L$^U$-R$^{U4}$, -L$^U$-R$^{U6}$, -L$^U$-R$^{U7}$, or -L$^U$-R$^{U8}$.

In one embodiment, each —R$^{T1}$, if present, is independently —R$^{U1}$.

In one embodiment, each -L$^U$-, if present, is independently —CH$_2$—.

In one embodiment, each —R$^{U1}$, if present, is independently a saturated aliphatic C$_{1-3}$alkyl.

In one embodiment, each —R$^{U1}$, if present, is independently —CH$_3$.

In one embodiment, each —R$^{U3}$, if present, is independently an aliphatic C$_{2-4}$alkynyl.

In one embodiment, each —R$^{U3}$, if present, is independently an aliphatic C$_3$alkynyl.

In one embodiment, each —R$^{U6}$, if present, is a C$_{3-8}$heterocyclyl group that is a 4-, 5-, 6-, or 7-membered non-aromatic monocyclic ring or a 7- or 8-membered non-aromatic bicyclic ring, said ring having exactly 1 ring heteroatom or exactly 2 ring heteroatoms, wherein each of said ring heteroatoms is independently N, O, or S; and is optionally substituted.

In one embodiment, each —R$^{U6}$, if present, is independently azetidinyl, pyrrolidinyl, imidazolidinyl, pyrazolidinyl, piperidinyl, piperazinyl, morpholinyl, azepinyl, diazepinyl, tetrahydrofuranyl, tetrahydropyranyl, dioxanyl, and is optionally substituted.

In one embodiment, each —R$^{U6}$, if present, is independently pyrrolidinyl, piperidinyl, piperazinyl, morpholinyl, tetrahydrofuranyl, or tetrahydropyranyl, and is optionally substituted.

In one embodiment, each —R$^{U7}$, if present, is independently phenyl, and is optionally substituted.

In one embodiment, each —R$^{U8}$, if present, is independently C$_{5-6}$heteroaryl, and is optionally substituted.

In one embodiment, each —R$^{U8}$, if present, is independently furanyl, thienyl, pyrrolyl, imidazolyl, pyrazolyl, triazolyl, oxazolyl, isoxazolyl, thiazolyl, isothiazolyl, pyridyl, pyrimidinyl, or pyridazinyl, and is optionally substituted.

In one embodiment, each —R$^{U8}$, if present, is independently imidazolyl, pyrazolyl, or triazolyl, and is optionally substituted.

In one embodiment, each —R$^{U9}$, if present, is independently —F, —Cl, —Br, —I, -Me, -Et, —CF$_3$, —OH, —CH$_2$OH, —CH$_2$CH$_2$OH, —O—CH$_2$CH$_2$OH, —OMe, —OEt, —CH$_2$OMe, —CH$_2$CH$_2$OMe, —O—CH$_2$CH$_2$OMe, —OCF$_3$, —SH, —SMe, —CN, —NO$_2$, —NH$_2$, —NHMe, —NMe$_2$, —CH$_2$NH$_2$, —CH$_2$NHMe, —CH$_2$NMe$_2$, —CH$_2$CH$_2$NH$_2$, —CH$_2$—(morpholino), —O—CH$_2$CH$_2$—(morpholino), —O—CH$_2$CH$_2$—NH$_2$, —C(=O)OH, —C(=O)OMe, —C(=O)NH$_2$, —C(=O)NHMe, —C(=O)NMe$_2$, —SO$_2$NH$_2$, —SO$_2$NHMe, —SO$_2$NMe$_2$, —SO$_2$Me, —CH$_2$-Ph, or -Ph.

In one embodiment, each —R$^{U9}$, if present, is independently —F, —Cl, -Me, -Et, —CF$_3$, —OH, —CH$_2$OH, —CH$_2$CH$_2$OH, —OMe, —CH$_2$OMe, —CH$_2$CH$_2$OMe, —CN, —NO$_2$, —NH$_2$, —NHMe, —NMe$_2$, —CH$_2$CH$_2$NH$_2$, —O—CH$_2$CH$_2$—NH$_2$, —C(=O)OH, —C(=O)OMe, —C(=O)NH$_2$, —C(=O)NHMe, —C(=O)NMe$_2$, —SO$_2$NH$_2$, —SO$_2$NHMe, or —SO$_2$NMe$_2$.

In one embodiment, -Q$^{B5}$, if present, is independently -Me, —OMe, —CN, —C≡C—CH$_2$OH, or —C(=O)NH$_2$.

In one embodiment, -Q$^{B5}$, if present, is independently -Me, —OMe, or —CN.

In one embodiment, -Q$^{B5}$, if present, is independently -Me or —CN.

In one embodiment, -Q$^{B5}$, if present, is independently —CN.

In one embodiment, -Q$^{B5}$, if present, is independently selected from those substituents exemplified under the heading "Some Preferred Embodiments."

The Group Q$^{B6}$

In one embodiment, -Q$^{B6}$, if present, is independently:
—R$^{W1}$,
—CF$_3$, —OCF$_3$,
—OH, -L$^W$-OH, —O-L$^W$-OH,
—OR$^{W1}$, -L$^W$-OR$^{W1}$, —O-L$^W$-OR$^{W1}$,
—SH, —SR$^{W1}$,
—CN,
—NO$_2$,
—NH$_2$, —NHR$^{W1}$, —NR$^{W1}$$_2$, —NR$^{W2}$R$^{W3}$,
-L$^W$-NH$_2$, -L$^W$-NHR$^{W1}$, -L$^W$-NR$^{W1}$$_2$, -L$^W$-NR$^{W2}$R$^{W3}$,
—O-L$^W$-NH$_2$, —O-L$^W$-NHR$^{W1}$, —O-L$^W$-NR$^{W1}$$_2$, —O-L$^W$-NR$^{W2}$R$^{W3}$,
—C(=O)OH, —C(=O)OR$^{W1}$,
—C(=O)NH$_2$, —C(=O)NHR$^{W1}$, —C(=O)NR$^{W1}$$_2$, —C(=O)NR$^{W2}$R$^{W3}$,
—NHC(=O)R$^{W1}$, —NR$^{W1}$C(=O)R$^{W1}$,
—NHC(=O)OR$^{W1}$, —NR$^{W1}$C(=O)OR$^{W1}$,
OC(=O)NH$_2$, —OC(=O)NHR$^{W1}$, —OC(=O)NR$^{W1}$$_2$, —OC(=O)NR$^{W2}$R$^{W3}$,
—C(=O)R$^{W1}$,
—NHC(=O)NH$_2$, —NHC(=O)NHR$^{W1}$,
—NHC(=O)NR$^{W1}$$_2$, —NHC(=O)NR$^{W2}$R$^{W3}$,
—NR$^{W1}$C(=O)NH$_2$, —NR$^{W1}$C(=O)NHR$^{W1}$,
—NR$^{W1}$C(=O)NRW$^{W1}$$_2$, —NR$^{W1}$C(=O)NR$^{W2}$R$^{W3}$,
—NHS(=O)$_2$R$^{W1}$, —NR$^{W1}$S(=O)$_2$R$^{W1}$,
—S(=O)$_2$NH$_2$, —S(=O)$_2$NHR$^{W1}$, —S(=O)$_2$NR$^{W1}$$_2$,
—S(=O)$_2$NR$^{W2}$R$^{W3}$,
—S(=O)R$^{W1}$, —S(=O)$_2$R$^{W1}$, —OS(=O)$_2$R$^{W1}$, or —S(=O)$_2$OR$^{W1}$;

wherein:
each -L$^W$- is independently saturated aliphatic C$_{1-5}$alkylene;
in each group —NR$^{W2}$R$^{W3}$, R$^{W2}$ and R$^{W3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;

each —$R^{W1}$ is independently:
—$R^{X1}$, —$R^{X2}$, —$R^{X3}$, —$R^{X4}$, —$R^{X5}$, —$R^{X6}$, —$R^{X7}$, —$R^{X8}$,
-$L^X$-$R^{X4}$, -$L^X$-$R^{X5}$, -$L^X$-$R^{X6}$, -$L^X$-$R^{X7}$, or -$L^X$-$R^{X8}$;
wherein:
each —$R^{X1}$ is independently saturated aliphatic $C_{1-6}$alkyl;
each —$R^{X2}$ is independently aliphatic $C_{2-6}$alkenyl;
each —$R^{X3}$ is independently aliphatic $C_{2-6}$alkynyl;
each —$R^{X4}$ is independently saturated $C_{3-6}$cycloalkyl;
each —$R^{X5}$ is independently $C_{3-6}$cycloalkenyl;
each —$R^{X6}$ is independently non-aromatic $C_{3-8}$heterocyclyl;
each —$R^{X7}$ is independently $C_{6-10}$carboaryl;
each —$R^{X8}$ is independently $C_{3-10}$heteroaryl;
each -$L^X$- is independently saturated aliphatic $C_{1-3}$alkylene;
and wherein:
each $C_{1-6}$alkyl, $C_{2-6}$alkenyl, $C_{2-6}$alkynyl, $C_{3-6}$cycloalkyl, $C_{3-6}$cycloalkenyl, non-aromatic $C_{3-8}$heterocyclyl, $C_{6-10}$carboaryl, $C_{8-18}$heteroaryl, and $C_{1-3}$alkylene is optionally substituted, for example, with one or more substituents —$R^{X9}$, wherein each —$R^{X9}$ is independently:
—F, —Cl, —Br, —I,
—$R^{Y1}$,
—$CF_3$, —$OCF_3$,
—OH, -$L^Y$-OH,
—$OR^{Y1}$, -$L^Y$-$OR^{Y1}$,
—SH, —$SR^{Y1}$,
—CN,
—$NO_2$,
—$NH_2$, —$NHR^{Y1}$, —$NR^{Y1}_2$, —$NR^{Y2}R^{Y3}$,
-$L^Y$-$NH_2$, -$L^Y$-$NHR^{Y1}$, -$L^Y$-$NR^{Y1}_2$, -$L^Y$-$NR^{Y2}R^{Y3}$,
—C(=O)OH, —C(=O)$OR^{Y1}$,
—C(=O)$NH_2$, —C(=O)$NHR^{Y1}$, —C(=O)$NR^{Y1}_2$, or —C(=O)$NR^{Y2}R^{Y3}$;
wherein:
each —$R^{Y1}$ is independently saturated aliphatic $C_{5-4}$alkyl, phenyl, or benzyl;
each -$L^Y$- is independently saturated aliphatic $C_{5-5}$alkylene; and
in each group —$NR^{Y2}R^{Y3}$, $R^{Y2}$ and $R^{Y3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.

In one embodiment, -$Q^{B6}$, if present, is independently:
—$R^{W1}$,
—$CF_3$, —$OCF_3$,
—OH, -$L^W$-OH, —O-$L^W$-OH,
—$OR^{W1}$, -$L^W$-$OR^{W1}$, —O-$L^W$-$OR^{W1}$,
—CN,
—$NH_2$, —$NHR^{W1}$, —$NR^{W1}_2$, —$NR^{W2}R^{W3}$,
-$L^W$-$NH_2$, -$L^W$-$NHR^{W1}$, -$L^W$-$NR^{W1}_2$, -$L^W$-$NR^{W2}R^{W3}$,
—O-$L^W$-$NH_2$, —O-$L^W$-$NHR^{W1}$, —O-$L^W$-$NR^{W1}_2$, —O-$L^W$-$NR^{W2}R^{W3}$,
—C(=O)OH, —C(=O)$OR^{W1}$,
—C(=O)$NH_2$, —C(=O)$NHR^{W1}$, —C(=O)$NR^{W1}_2$, —C(=O)$NR^{W2}R^{W3}$,
—NHC(=O)$R^{W1}$, —$NR^{W1}$C(=O)$R^{W1}$,
—NHC(=O)$OR^{W1}$, —$NR^{W1}$C(=O)$OR^{W1}$,
—OC(=O)$NH_2$, —OC(=O)$NHR^{W1}$, —OC(=O)$NR^{W1}_2$, —OC(=O)$NR^{W2}R^{W3}$,
—NHC(=O)$NH_2$, —NHC(=O)$NHR^{W1}$,
—NHC(=O)$NR^{W1}_2$, —NHC(=O)$NR^{W2}R^{W3}$,
—$NR^{W1}$C(=O)$NH_2$, —$NR^{W1}$C(=O)$NHR^{W1}$,
—$NR^{W1}$C(=O)$NR^{W1}_2$, —$NR^{W1}$C(=O)$NR^{W2}R^{W3}$,
—NHS(=O)$_2R^{W1}$, or —$NR^{W1}$S(=O)$_2R^{W1}$, In one embodiment, -$Q^{B6}$, if present, is independently:
—$R^{W1}$,
—$CF_3$, —$OCF_3$,
—OH, -$L^W$-OH, —O-$L^W$-OH,
—$OR^{W1}$, -$L^W$-$OR^{W1}$, —O-$L^W$-$OR^{W1}$,
—CN,
—$NH_2$, —$NHR^{W1}$, —$NR^{W1}_2$, —$NR^{W2}R^{W3}$,
-$L^W$-$NH_2$, -$L^W$-$NHR^{W1}$, -$L^W$-$NR^{W1}_2$, -$L^W$-$NR^{W2}R^{W3}$,
—O-$L^W$-$NH_2$, —O-$L^W$-$NHR^{W1}$, —O-$L^W$-$NR^{W1}_2$, or —O-$L^W$-$NR^{W2}R^{W3}$.

In one embodiment, each -$L^W$-, if present, is independently saturated aliphatic $C_{1-3}$alkylene.

In one embodiment, each —$NR^{W2}R^{W3}$, if present, is independently azetidino, pyrrolidino, imidazolidino, pyrazolidino, piperidino, piperazino, morpholino, azepino, or diazepino, and is optionally substituted, for example, with one or more groups selected from $C_{1-3}$alkyl and —$CF_3$.

In one embodiment, each —$NR^{W2}R^{W3}$, if present, is independently pyrrolidino, piperidino, piperazino, or morpholino, and is optionally substituted, for example, with one or more groups selected from $C_{1-3}$alkyl and —$CF_3$.

In one embodiment, each —$R^{W1}$, if present, is independently:
—$R^{X1}$, —$R^{X4}$, —$R^{X6}$, —$R^{X7}$, —$R^{X8}$,
-$L^X$-$R^{X4}$, -$L^X$-$R^{X6}$, -$L^X$-$R^{X7}$, or -$L^X$-$R^{X8}$.

In one embodiment, each —$R^W$, if present, is independently —$R^{X1}$.

In one embodiment, each -$L^{X1}$, if present, is independently —$CH_2$—.

In one embodiment, each —$R^{X1}$, if present, is independently a saturated aliphatic $C_{1-3}$alkyl.

In one embodiment, each —$R^{X6}$, if present, is a $C_{3-8}$heterocyclyl group that is a 4-, 5-, 6-, or 7-membered non-aromatic monocyclic ring or a 7- or 8-membered non-aromatic bicyclic ring, said ring having exactly 1 ring heteroatom or exactly 2 ring heteroatoms, wherein each of said ring heteroatoms is independently N, O, or S; and is optionally substituted.

In one embodiment, each —$R^{X6}$, if present, is independently azetidinyl, pyrrolidinyl, imidazolidinyl, pyrazolidinyl, piperidinyl, piperazinyl, morpholinyl, azepinyl, diazepinyl, tetrahydrofuranyl, tetrahydropyranyl, dioxanyl, 8-aza-bicyclo[3.2.1]octanyl, 3,8-diaza-bicyclo[3.2.1]octanyl, 6-aza-bicyclo[3.1.1]heptanyl, or 3,6-diaza-bicyclo[3.1.1]heptanyl, and is optionally substituted.

In one embodiment, each —$R^{X6}$, if present, is independently pyrrolidinyl, piperidinyl, piperazinyl, morpholinyl, tetrahydrofuranyl, or tetrahydropyranyl, and is optionally substituted.

In one embodiment, each —$R^{X7}$, if present, is independently phenyl, and is optionally substituted.

In one embodiment, each —$R^{X8}$, if present, is independently $C_{3-6}$heteroaryl, and is optionally substituted.

In one embodiment, each —$R^{X8}$, if present, is independently furanyl, thienyl, pyrrolyl, imidazolyl, pyrazolyl, triazolyl, oxazolyl, isoxazolyl, thiazolyl, isothiazolyl, pyridyl, pyrimidinyl, or pyridazinyl, and is optionally substituted.

In one embodiment, each —$R^{X9}$, if present, is independently:
—F, —Cl, —Br, —I,
—$R^{Y1}$,
—$CF_3$, —$OCF_3$,
—OH, -$L^Y$-OH,
—$OR^{Y1}$, -$L^Y$-$OR^{Y1}$, —NH$_2$, —NHR$^{Y1}$, —NR$^{Y1}{}_2$, —NR$^{Y2}$R$^{Y3}$,
-L$^Y$-NH$_2$, -L$^Y$-NHR$^{Y1}$, -L$^Y$-NR$^{Y1}{}_2$, -L$^Y$-NR$^{Y2}$R$^{Y3}$,
—C(=O)OH, —C(=O)OR$^{Y1}$,
—C(=O)NH$_2$, —C(=O)NHR$^{Y1}$, —C(=O)NR$^{Y1}{}_2$, or
—C(=O)NR$^{Y2}$R$^{Y3}$.

In one embodiment, each -L$^Y$-, if present, is independently saturated aliphatic C$_{1-3}$alkylene.

In one embodiment, each —R$^{Y1}$, if present, is independently C$_{1-4}$alkyl.

In one embodiment, each —NR$^{Y2}$R$^{Y3}$, if present, is independently azetidino, pyrrolidino, imidazolidino, pyrazolidino, piperidino, piperazino, morpholino, azepino, or diazepino, and is optionally substituted, for example, with one or more groups selected from C$_{1-3}$alkyl and —CF$_3$.

In one embodiment, each —NR$^{Y2}$R$^{Y3}$, if present, is independently pyrrolidino, piperidino, piperazino, or morpholino, and is optionally substituted, for example, with one or more groups selected from C$_{1-3}$alkyl and —CF$_3$.

In one embodiment, each —R$^{X9}$, if present, is independently —F, —Cl, —Br, —I, -Me, -Et, —CF$_3$, —OH, —CH$_2$OH, —CH$_2$CH$_2$OH, —O—CH$_2$CH$_2$OH, —OMe, —OEt, —CH$_2$OMe, —CH$_2$CH$_2$OMe, —O—CH$_2$CH$_2$OMe, —OCF$_3$, —SMe, —CN, —NO$_2$, —NH$_2$, —NHMe, —NMe$_2$, —CH$_2$NH$_2$, —CH$_2$NHMe, —CH$_2$NMe$_2$, —CH$_2$CH$_2$NH$_2$, —CH$_2$-(morpholino), —O—CH$_2$CH$_2$-(morpholino), —O—CH$_2$CH$_2$—NH$_2$, —C(=O)OH, —C(=O)OMe, —C(=O)NH$_2$, —C(=O)NHMe, —C(=O)NMe$_2$, —SO$_2$NH$_2$, —SO$_2$NHMe, —SO$_2$NMe$_2$, —SO$_2$Me, —CH$_2$-Ph, or -Ph.

In one embodiment, -Q$^{B6}$, if present, is independently -Me, -Et, -nPr, -iPr, —CF$_3$, —OH, —OMe, —OEt, —O(nPr), —O(iPr), —OCF$_3$, —CN, —NH$_2$, —NHMe, —NMe$_2$, —O—CH$_2$CH$_2$—OH, —O—CH$_2$CH$_2$—OMe, —O—CH$_2$CH$_2$—NH$_2$, —O—CH$_2$CH$_2$—NHMe, —O—CH$_2$CH$_2$—NMe$_2$, —O—CH$_2$CH$_2$CH$_2$—NH$_2$, —O—CH$_2$CH$_2$CH$_2$—NHMe, or —O—CH$_2$CH$_2$CH$_2$—NMe$_2$.

In one embodiment, -Q$^{B6}$, if present, is independently selected from those substituents exemplified under the heading "Some Preferred Embodiments."

Molecular Weight

In one embodiment, the BA compound has a molecular weight of from 187 to 1200.

In one embodiment, the bottom of range is 190, 200, 225, 250, 275, 300, or 350.

In one embodiment, the top of range is 1100, 1000, 900, 800, 700, or 600.

In one embodiment, the range is from 190 to 600.

Combinations

Each and every compatible combination of the embodiments described above is explicitly disclosed herein, as if each and every combination was individually and explicitly recited.

Examples of Specific Embodiments

In one embodiment, the compounds are selected from compounds of the following formulae and pharmaceutically acceptable salts, solvates, chemically protected forms, and prodrugs thereof:

| Compound No. | Synthesis No. | Structure |
|---|---|---|
| Y-001 | 44-D | 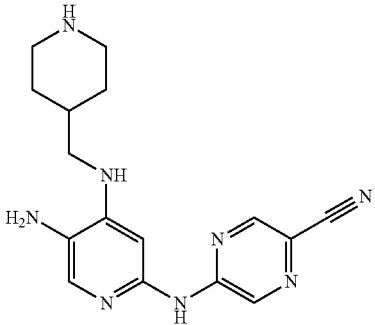 |
| Y-002 | 45 | 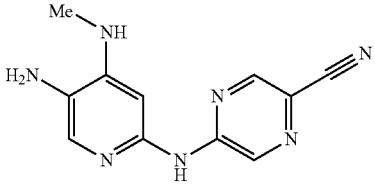 [SMILES: CNc1cc(Nc2cnc(C#N)cn2)ncc1N] |
| Y-003 | 46 | 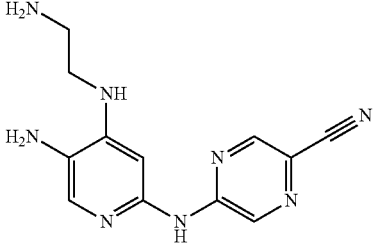 [SMILES: N#Cc1cnc(Nc2cc(NCCN)c(N)cn2)cn1] |

-continued
| Compound No. | Synthesis No. | Structure |
|---|---|---|
| Y-004 | 47 | 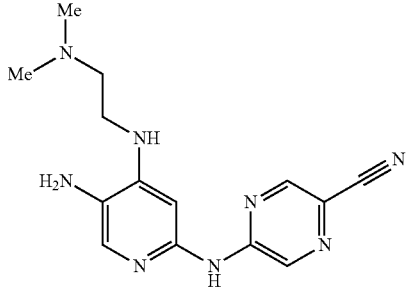 [SMILES: CN(C)CCNc1cc(Nc2cnc(C#N)cn2)ncc1N] |
| Y-005 | 48 | 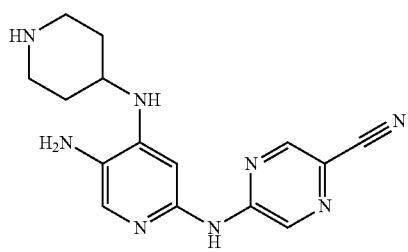 [SMILES: N#Cc1cnc(Nc2cc(NC3CCNCC3)c(N)cn2)cn1] |
| Y-006 | 49 | 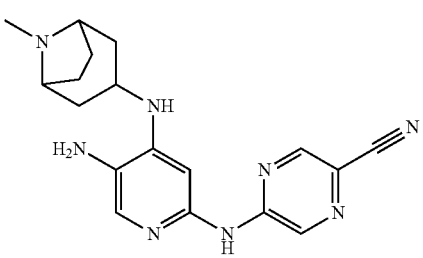 [SMILES: CN1C2CCC1CC(Nc1cc(Nc3cnc(C#N)cn3)ncc1N)C2] |
| Y-007 | 50 | 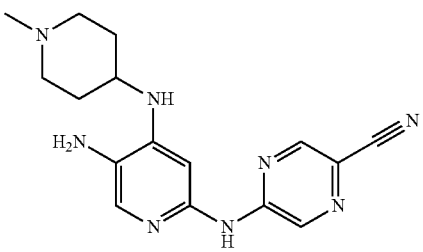 [SMILES: CN1CCC(Nc2cc(Nc3cnc(C#N)cn3)ncc2N)CC1] |
| Y-008 | 51 | 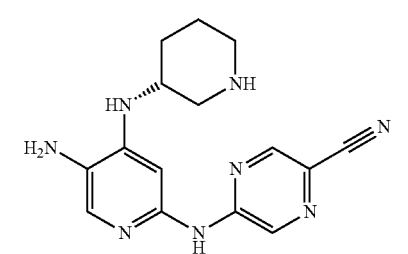 |
| Y-009 | 52 | 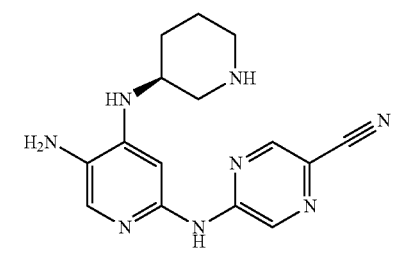 [SMILES: N#Cc1cnc(Nc2cc(N[C@H]3CCCNC3)c(N)cn2)cn1] |

-continued
| Compound No. | Synthesis No. | Structure |
|---|---|---|
| Y-010 | 53 | 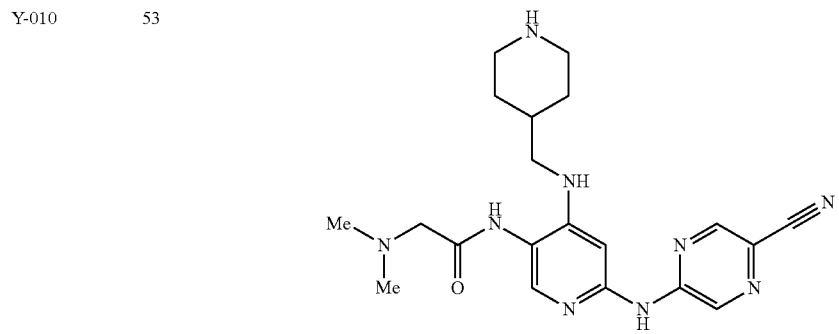 |
| Y-011 | 54 | 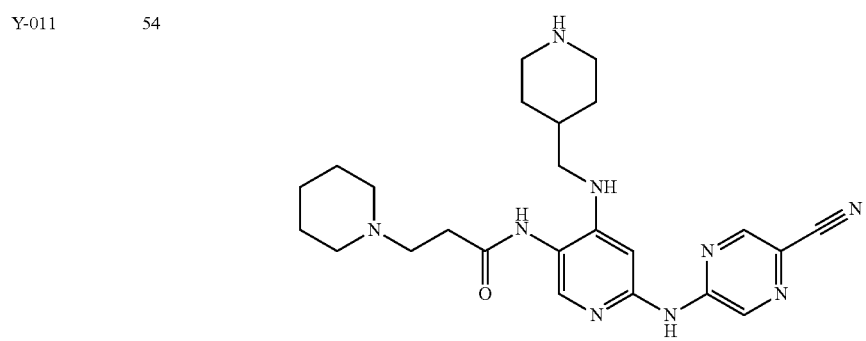 |
| Y-012 | 55 | 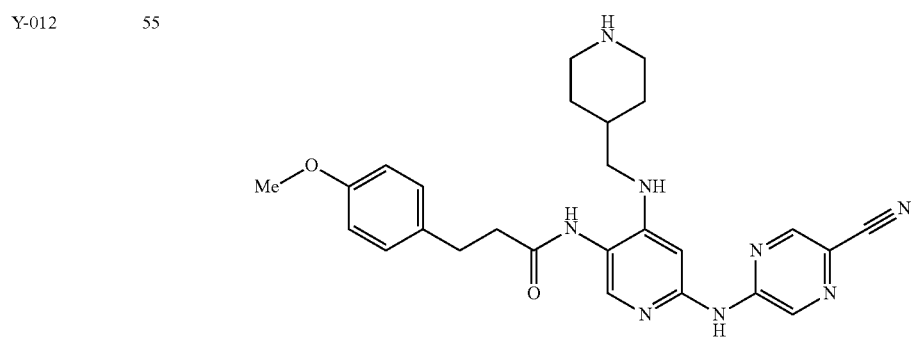 |
| Y-013 | 56 | 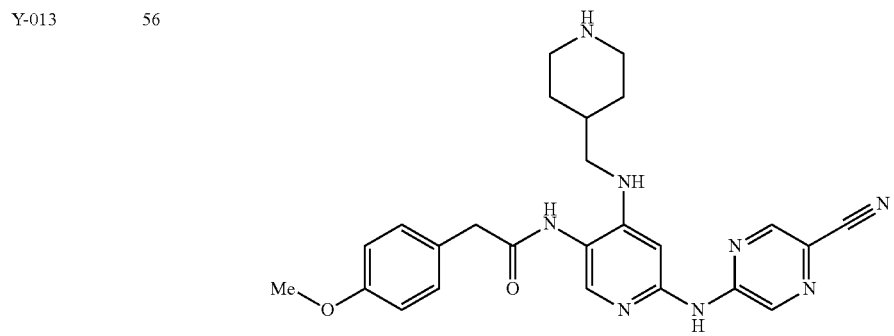 |

-continued

| Compound No. | Synthesis No. | Structure |
|---|---|---|
| Y-014 | 57 | 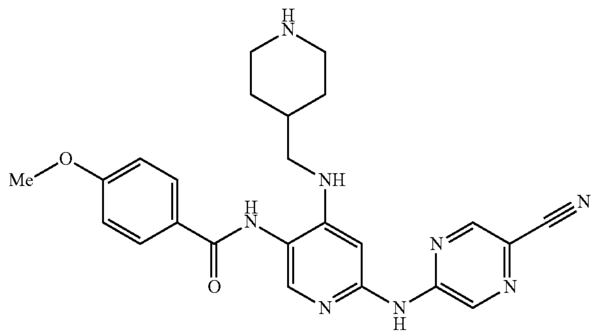 [SMILES: COc1ccc(C(=O)Nc2cnc(Nc3cnc(C#N)cn3)cc2NCC2CCNCC2)cc1] |
| Y-015 | 58 | 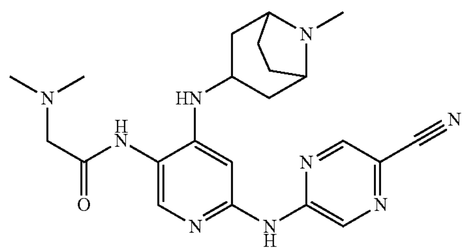 [SMILES: CN(C)CC(=O)Nc1cnc(Nc2cnc(C#N)cn2)cc1NC1CC2CCC(C1)N2C] |
| Y-016 | 59 | 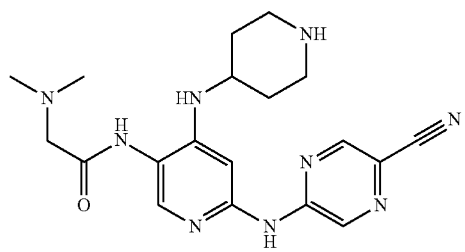 [SMILES: CN(C)CC(=O)Nc1cnc(Nc2cnc(C#N)cn2)cc1NC1CCNCC1] |
| Y-017 | 60 | 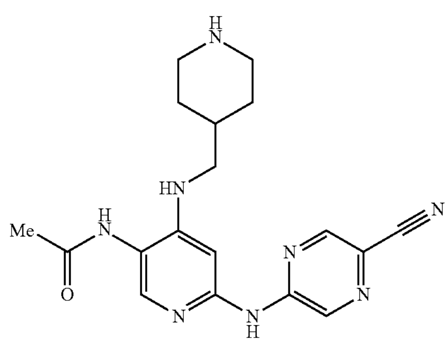 [SMILES: CC(=O)Nc1cnc(Nc2cnc(C#N)cn2)cc1NCC1CCNCC1] |
| Y-018 | 61 | 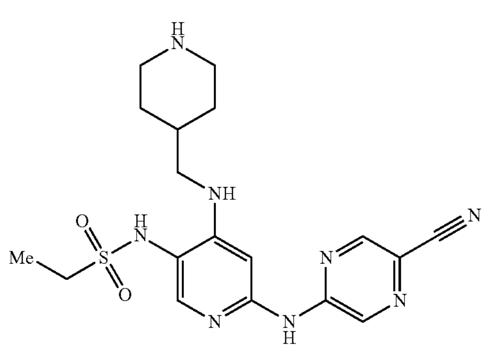 [SMILES: CCS(=O)(=O)Nc1cnc(Nc2cnc(C#N)cn2)cc1NCC1CCNCC1] |

| Compound No. | Synthesis No. | Structure |
|---|---|---|
| Y-019 | 62-C | 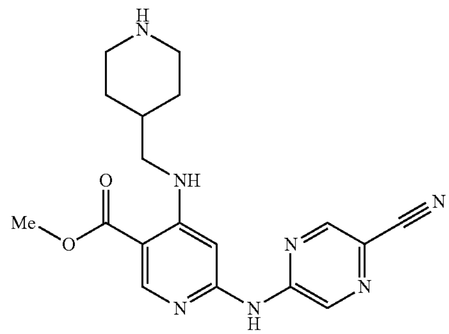 [SMILES: COC(=O)c1cnc(Nc2cnc(C#N)cn2)cc1NCC1CCNCC1] |
| Y-020 | 63 | 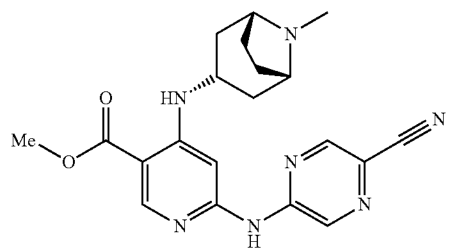 |
| Y-021 | 64 | 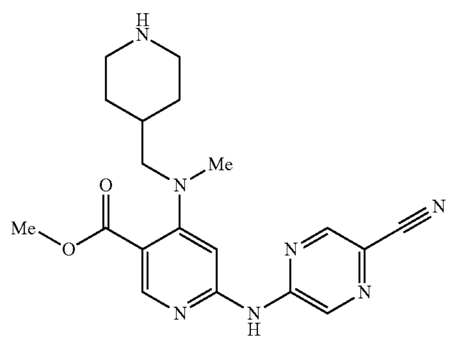 [SMILES: COC(=O)c1cnc(Nc2cnc(C#N)cn2)cc1N(C)CC1CCNCC1] |
| Y-022 | 65 | 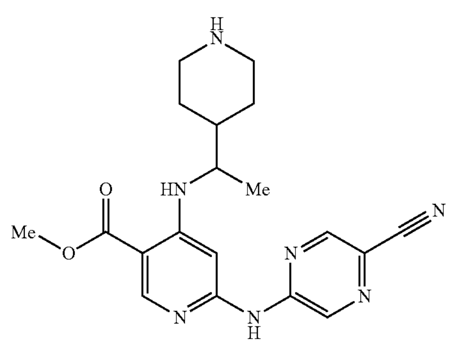 [SMILES: COC(=O)c1cnc(Nc2cnc(C#N)cn2)cc1NC(C)C1CCNCC1] |
| Y-023 | 66 | 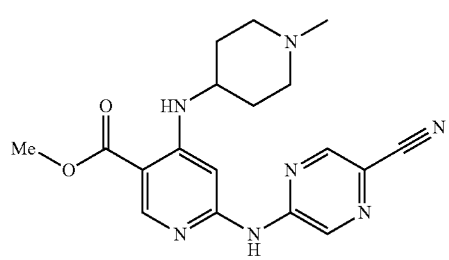 [SMILES: COC(=O)c1cnc(Nc2cnc(C#N)cn2)cc1NC1CCN(C)CC1] |

-continued
| Compound No. | Synthesis No. | Structure |
|---|---|---|
| Y-024 | 67 | 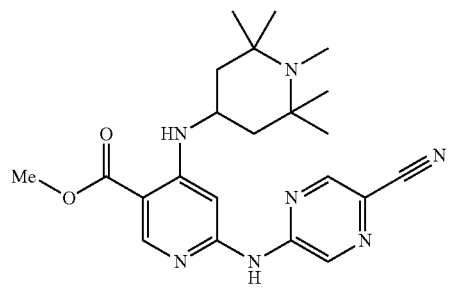 [SMILES: COC(=O)c1cnc(Nc2cnc(C#N)cn2)cc1NC1CC(C)(C)N(C)C(C)(C)C1] |
| Y-025 | 68 | 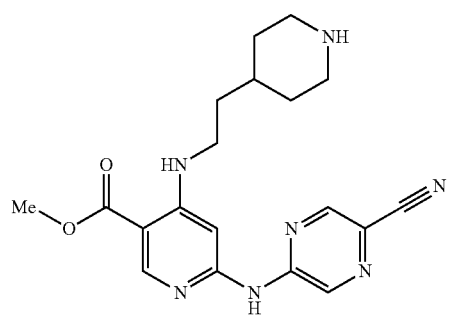 [SMILES: COC(=O)c1cnc(Nc2cnc(C#N)cn2)cc1NCCC1CCNCC1] |
| Y-026 | 69 | 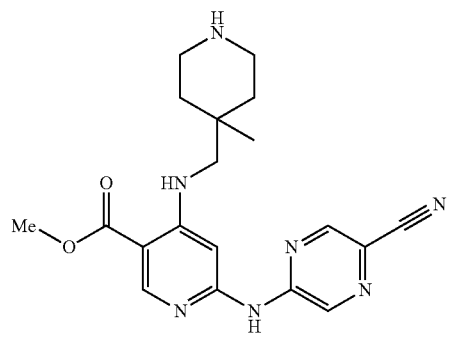 [SMILES: COC(=O)c1cnc(Nc2cnc(C#N)cn2)cc1NCC1(C)CCNCC1] |
| Y-027 | 70 | 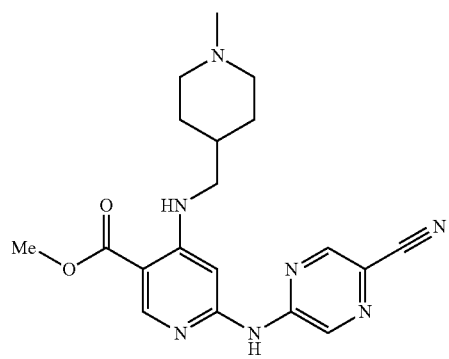 [SMILES: COC(=O)c1cnc(Nc2cnc(C#N)cn2)cc1NCC1CCN(C)CC1] |

-continued

| Compound No. | Synthesis No. | Structure |
|---|---|---|
| Y-028 | 71 | 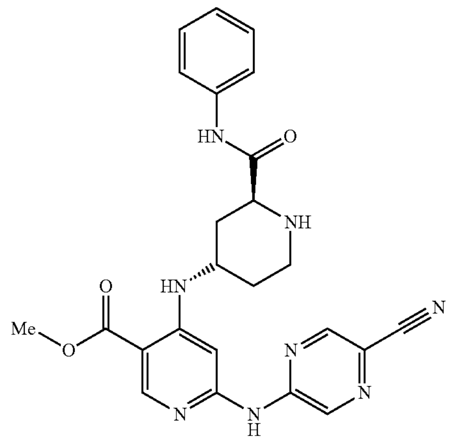 |
| Y-029 | 72 | 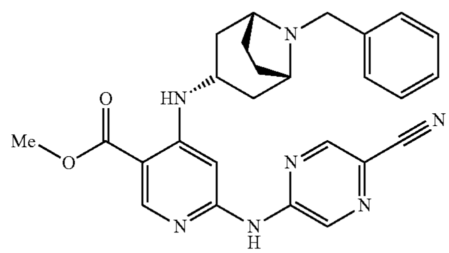 |
| Y-030 | 73 | 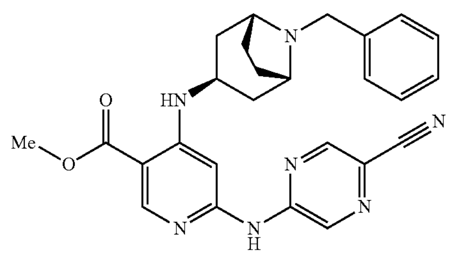 [SMILES: COC(=O)c1cnc(Nc2cnc(C#N)cn2)cc1N[C@H]1C[C@H]2CC[C@@H](C1)N2Cc1ccccc1] |
| Y-031 | 74 | 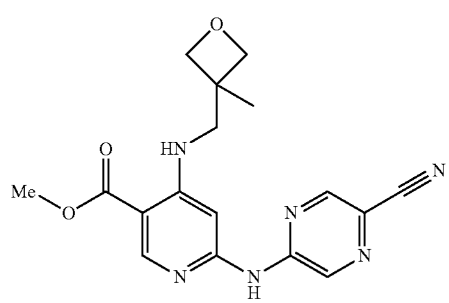 [SMILES: COC(=O)c1cnc(Nc2cnc(C#N)cn2)cc1NCC1(C)COC1] |
| Y-032 | 75-B | 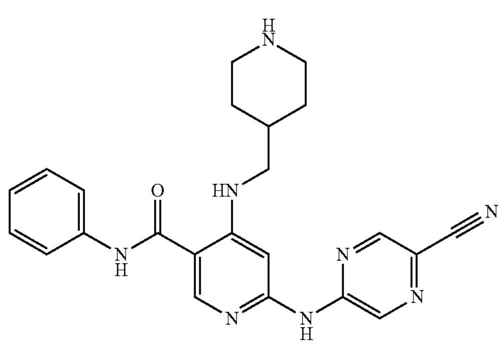 [SMILES: N#Cc1cnc(Nc2cc(NCC3CCNCC3)c(C(=O)Nc3ccccc3)cn2)cn1] |

-continued
| Compound No. | Synthesis No. | Structure |
|---|---|---|
| Y-033 | 76 | 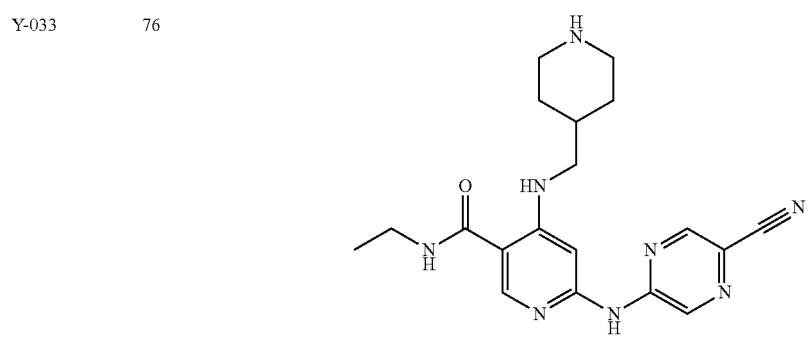 |
| Y-034 | 77 | 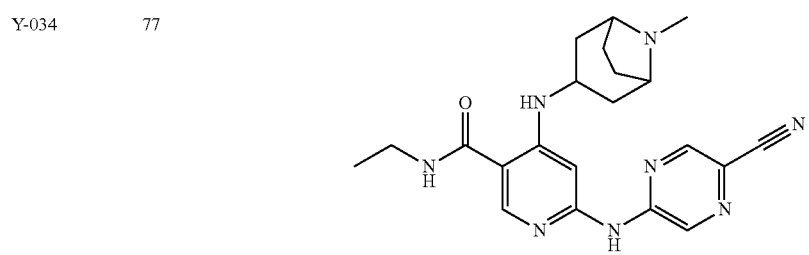 |
| Y-035 | 78-C | 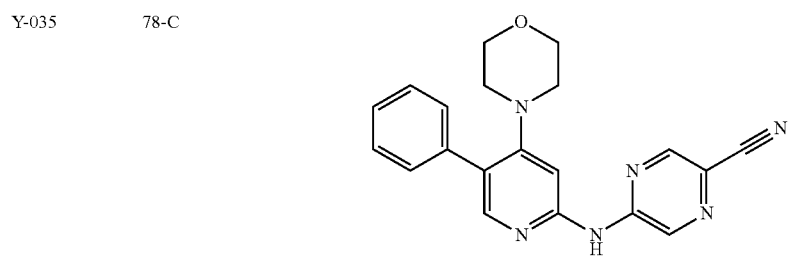 |
| Y-036 | 81 | 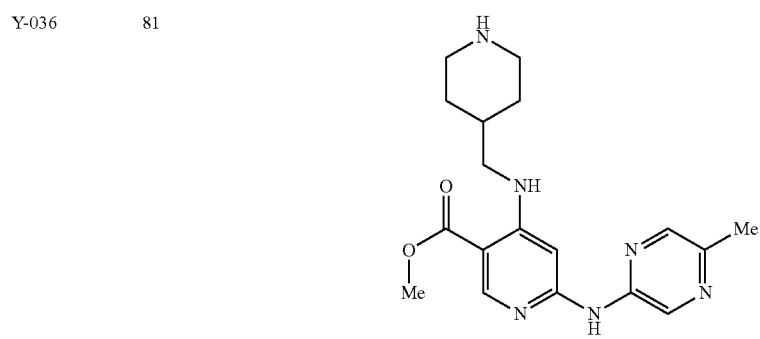 |
| Y-037 | 82-B | 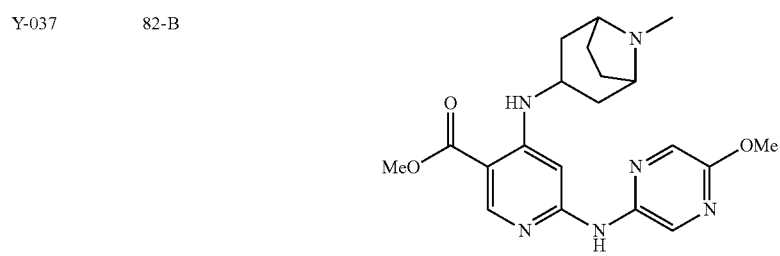 |

| Compound No. | Synthesis No. | Structure |
|---|---|---|
| Y-038 | 83-D | 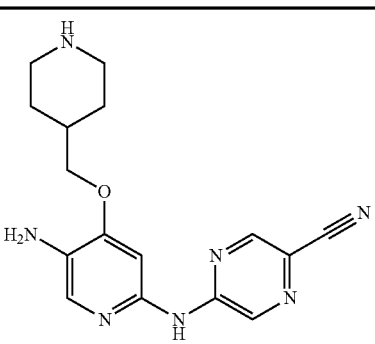 |
| Y-039 | 84-B | 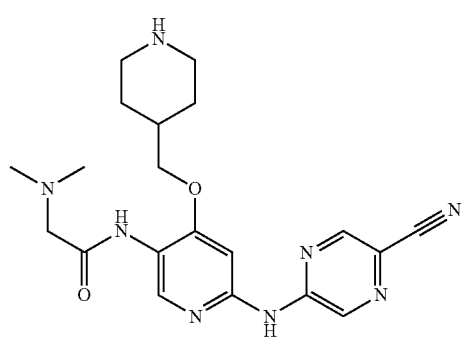 [SMILES: CN(C)CC(=O)Nc1cnc(Nc2cnc(C#N)cn2)cc1OCC1CCNCC1] |
In one embodiment, the compounds are selected from compounds of the following formulae and pharmaceutically acceptable salts, solvates, chemically protected forms, and prodrugs thereof:
| Compound No | Synthesis No | Structure |
|---|---|---|
| Y-040 | 85 | 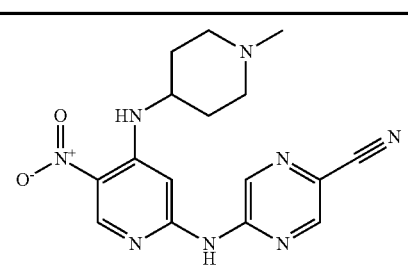 |
| Y-041 | 86 | 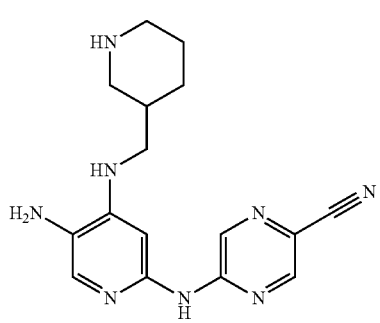 [SMILES: N#Cc1cnc(Nc2cc(NCC3CCCNC3)c(N)cn2)cn1] |

-continued
| Compound No | Synthesis No | Structure |
|---|---|---|
| Y-042 | 87 | 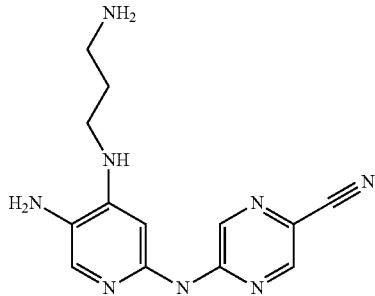 |
| Y-043 | 88 | 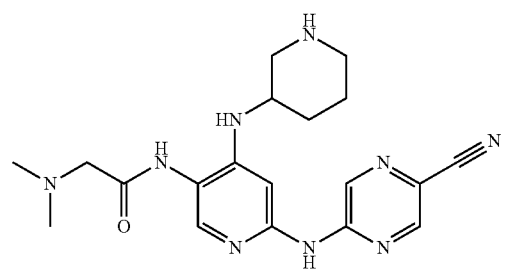 [SMILES: CN(C)CC(=O)Nc1cnc(Nc2cnc(C#N)cn2)cc1NC1CCCNC1] |
| Y-044 | 89 | 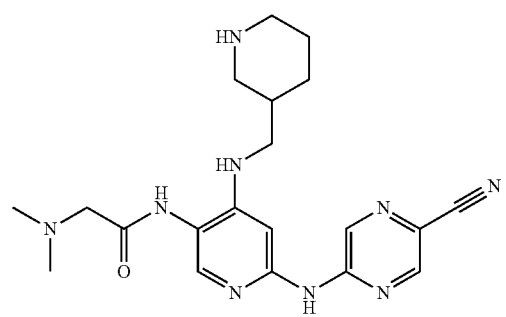 [SMILES: CN(C)CC(=O)Nc1cnc(Nc2cnc(C#N)cn2)cc1NCC1CCCNC1] |
| Y-045 | 90 | 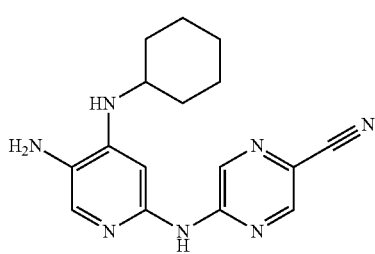 [SMILES: N#Cc1cnc(Nc2cc(NC3CCCCC3)c(N)cn2)cn1] |
| Y-046 | 91 | 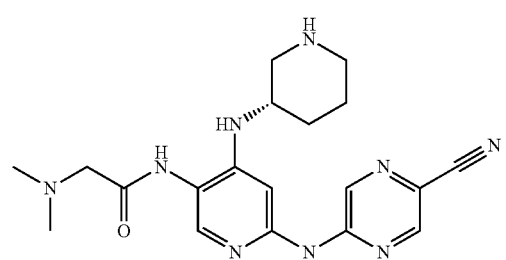 |

-continued
| Compound No | Synthesis No | Structure |
|---|---|---|
| Y-047 | 92 | 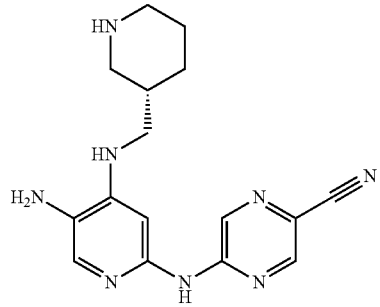 |
| Y-048 | 93 | 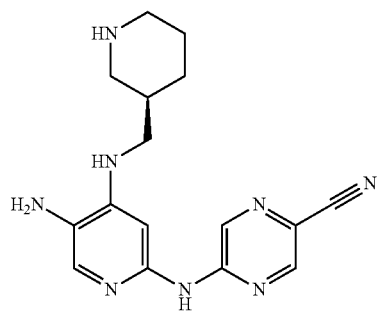 [SMILES: N#Cc1cnc(Nc2cc(NC[C@@H]3CCCNC3)c(N)cn2)cn1] |
| Y-049 | 94 | 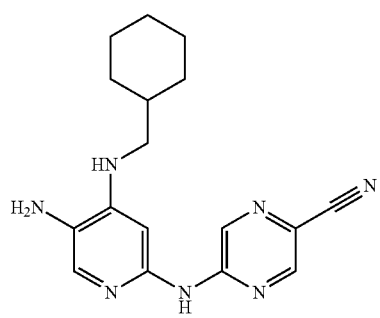 [SMILES: N#Cc1cnc(Nc2cc(NCC3CCCCC3)c(N)cn2)cn1] |
| Y-050 | 95 | 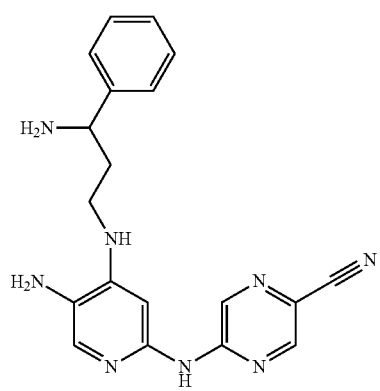 [SMILES: N#Cc1cnc(Nc2cc(NCCC(N)c3ccccc3)c(N)cn2)cn1] |

-continued

| Compound No | Synthesis No | Structure |
|---|---|---|
| Y-051 | 96 | 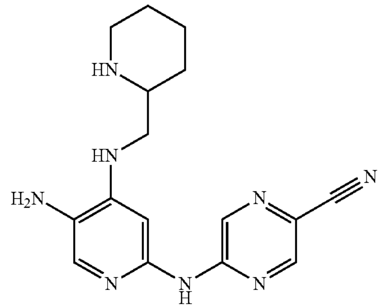 [SMILES: N#Cc1cnc(Nc2cc(NCC3CCCCN3)c(N)cn2)cn1] |
| Y-052 | 97 | 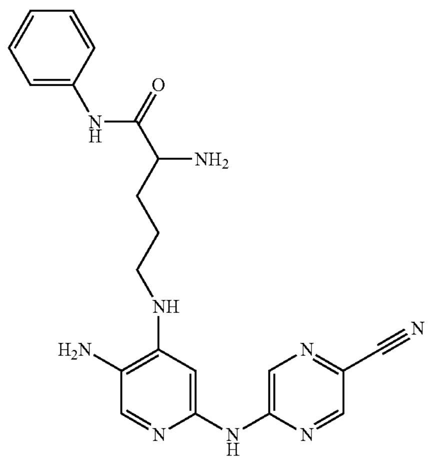 [SMILES: N#Cc1cnc(Nc2cc(NCCCC(N)C(=O)Nc3ccccc3)c(N)cn2)cn1] |
| Y-053 | 98 | 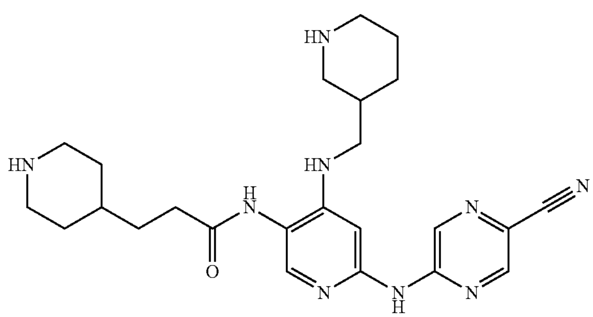 [SMILES: N#Cc1cnc(Nc2cc(NCC3CCCNC3)c(NC(=O)CCC3CCNCC3)cn2)cn1] |
| Y-054 | 99 | 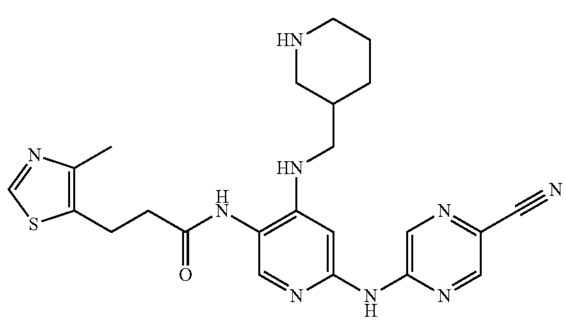 [SMILES: Cc1ncsc1CCC(=O)Nc1cnc(Nc2cnc(C#N)cn2)cc1NCC1CCCNC1] |

-continued

| Compound No | Synthesis No | Structure |
|---|---|---|
| Y-055 | 100 | 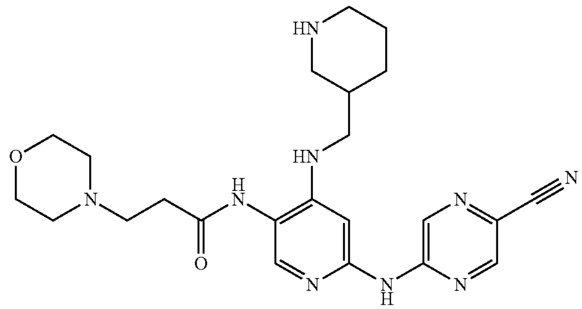 [SMILES: N#Cc1cnc(Nc2cc(NCC3CCCNC3)c(NC(=O)CCN3CCOCC3)cn2)cn1] |
| Y-056 | 101-D | 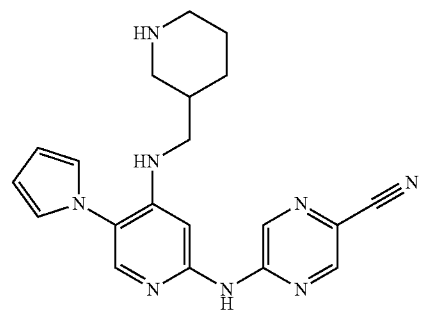 [SMILES: N#Cc1cnc(Nc2cc(NCC3CCCNC3)c(-n3cccc3)cn2)cn1] |
| Y-057 | 102 | 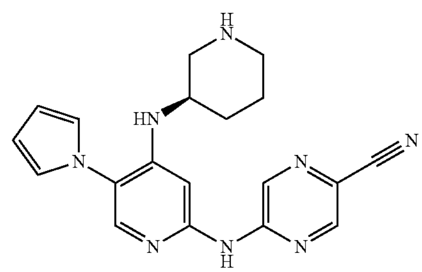 [SMILES: N#Cc1cnc(Nc2cc(N[C@@H]3CCCNC3)c(-n3cccc3)cn2)cn1] |
| Y-058 | 103 | 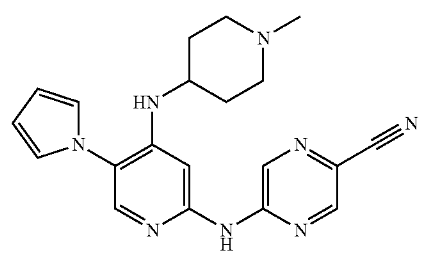 [SMILES: CN1CCC(Nc2cc(Nc3cnc(C#N)cn3)ncc2-n2cccc2)CC1] |
| Y-059 | 104 | 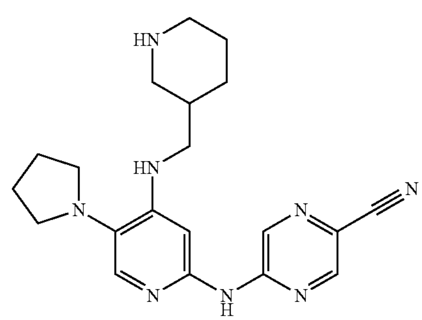 [SMILES: N#Cc1cnc(Nc2cc(NCC3CCCNC3)c(N3CCCC3)cn2)cn1] |

-continued
| Compound No | Synthesis No | Structure |
|---|---|---|
| Y-060 | 105 | 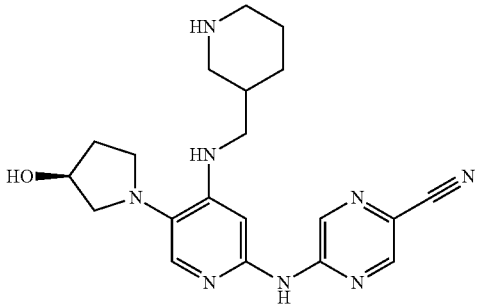 [SMILES: N#Cc1cnc(Nc2cc(NCC3CCCNC3)c(N3CC[C@H](O)C3)cn2)cn1] |
| Y-061 | 106 | 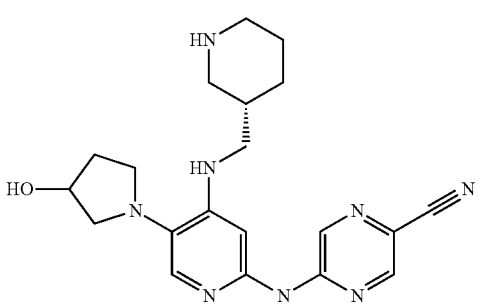 |
| Y-062 | 107-C | 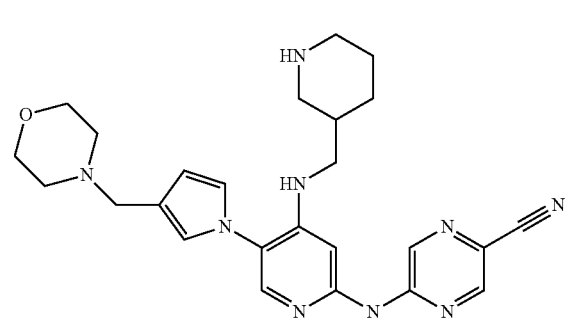 |
| Y-063 | 108 | 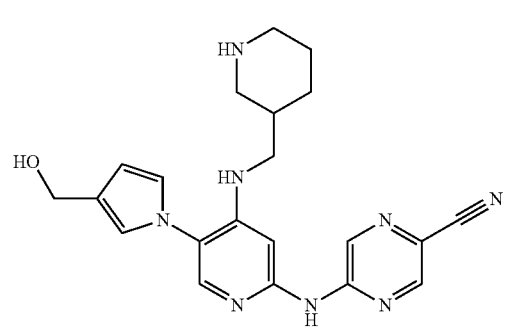 [SMILES: N#Cc1cnc(Nc2cc(NCC3CCCNC3)c(-n3ccc(CO)c3)cn2)cn1] |
| Y-064 | 109-D | 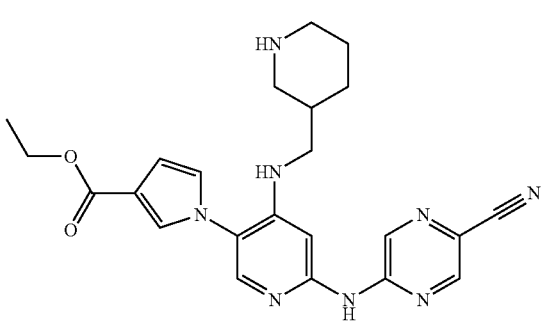 [SMILES: CCOC(=O)c1ccn(-c2cnc(Nc3cnc(C#N)cn3)cc2NCC2CCCNC2)c1] |

| Compound No | Synthesis No | Structure |
|---|---|---|
| Y-065 | 110-B | 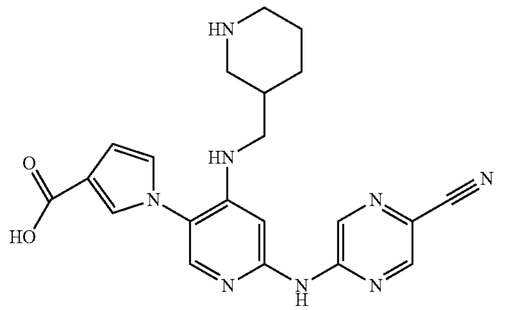 [SMILES: N#Cc1cnc(Nc2cc(NCC3CCCNC3)c(-n3ccc(C(=O)O)c3)cn2)cn1] |
| Y-066 | 111-B | 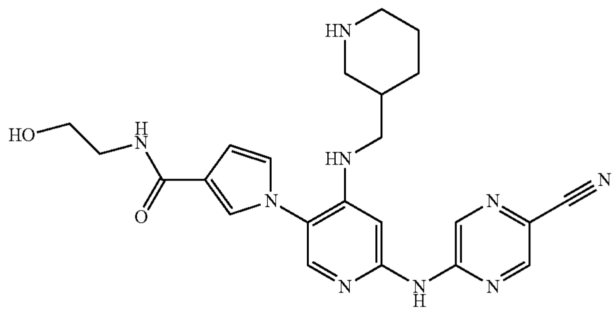 [SMILES: N#Cc1cnc(Nc2cc(NCC3CCCNC3)c(-n3ccc(C(=O)NCCO)c3)cn2)cn1] |
| Y-067 | 112 | 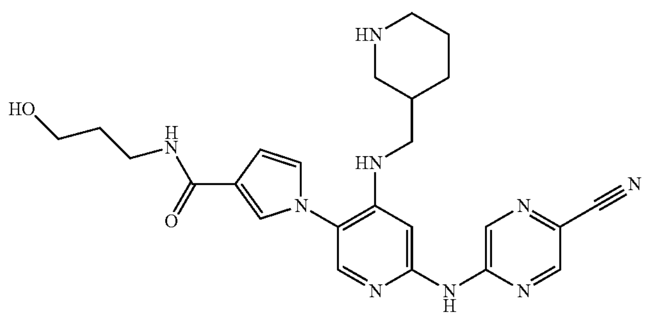 [SMILES: N#Cc1cnc(Nc2cc(NCC3CCCNC3)c(-n3ccc(C(=O)NCCCO)c3)cn2)cn1] |
| Y-068 | 113 | 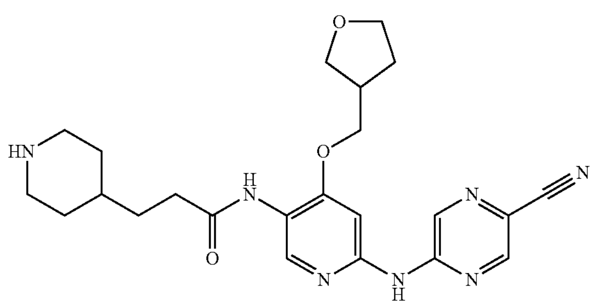 [SMILES: N#Cc1cnc(Nc2cc(OCC3CCOC3)c(NC(=O)CCC3CCNCC3)cn2)cn1] |
| Y-069 | 114 | 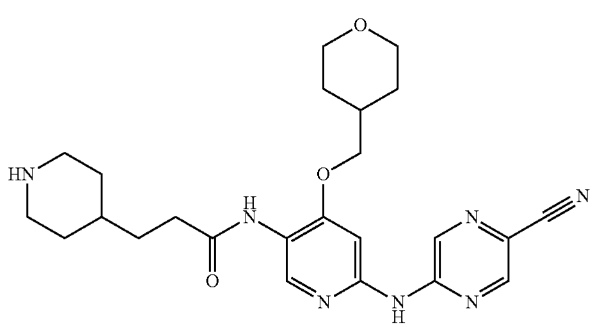 [SMILES: N#Cc1cnc(Nc2cc(OCC3CCOCC3)c(NC(=O)CCC3CCNCC3)cn2)cn1] |

| Compound No | Synthesis No | Structure |
|---|---|---|
| Y-070 | 115 | 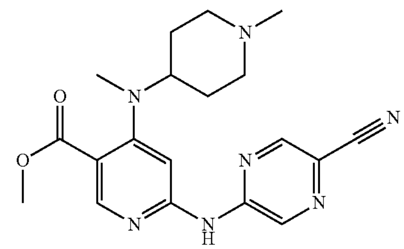 [SMILES: COC(=O)c1cnc(Nc2cnc(C#N)cn2)cc1N(C)C1CCN(C)CC1] |
| Y-071 | 116 | 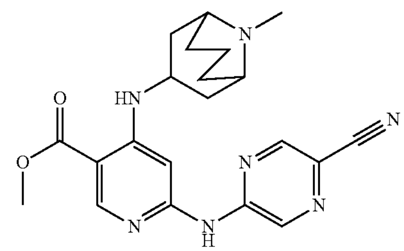 [SMILES: COC(=O)c1cnc(Nc2cnc(C#N)cn2)cc1NC1CC2CCCC(C1)N2C] |
| Y-072 | 117-B | 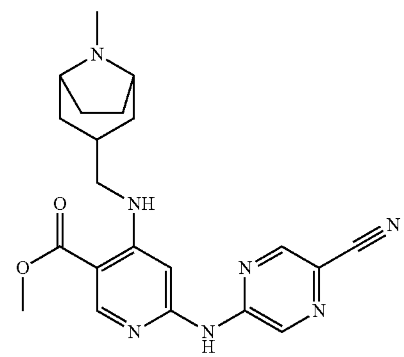 [SMILES: COC(=O)c1cnc(Nc2cnc(C#N)cn2)cc1NCC1CC2CCC(C1)N2C] |
| Y-073 | 118 | 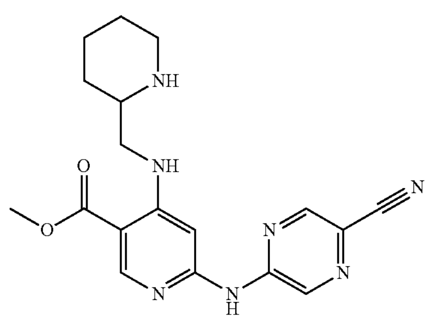 [SMILES: COC(=O)c1cnc(Nc2cnc(C#N)cn2)cc1NCC1CCCCN1] |
| Y-074 | 119 | 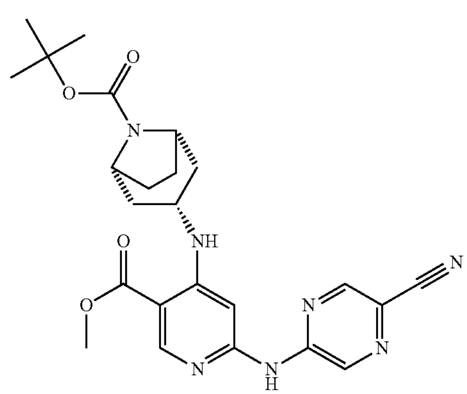 |

| Compound No | Synthesis No | Structure |
|---|---|---|
| Y-075 | 120 | 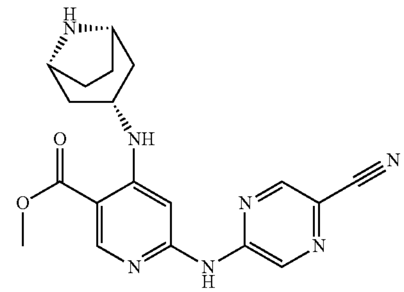 [SMILES: COC(=O)c1cnc(Nc2cnc(C#N)cn2)cc1N[C@@H]1C[C@H]2CC[C@@H](C1)N2] |
| Y-076 | 121 | 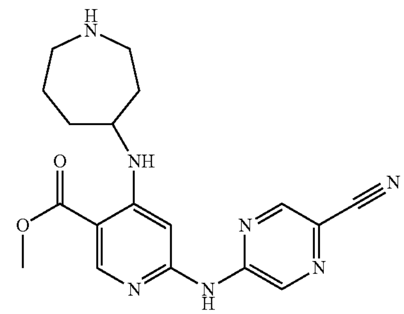 [SMILES: COC(=O)c1cnc(Nc2cnc(C#N)cn2)cc1NC1CCCNCC1] |
| Y-077 | 122 | 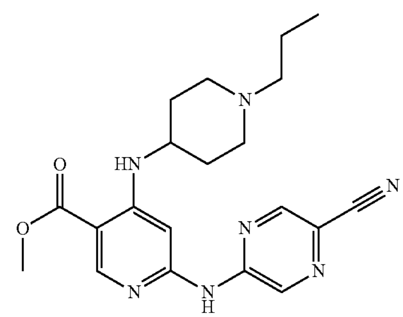 [SMILES: CCCN1CCC(Nc2cc(Nc3cnc(C#N)cn3)ncc2C(=O)OC)CC1] |
| Y-078 | 123 | 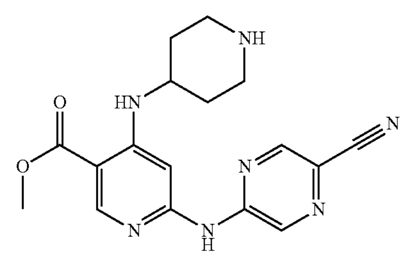 [SMILES: COC(=O)c1cnc(Nc2cnc(C#N)cn2)cc1NC1CCNCC1] |
| Y-079 | 124 | 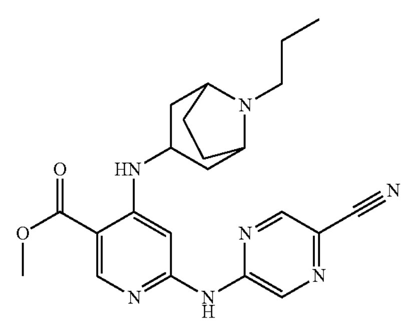 [SMILES: CCCN1C2CCC1CC(Nc1cc(Nc3cnc(C#N)cn3)ncc1C(=O)OC)C2] |

-continued
| Compound No | Synthesis No | Structure |
|---|---|---|
| Y-080 | 125 | 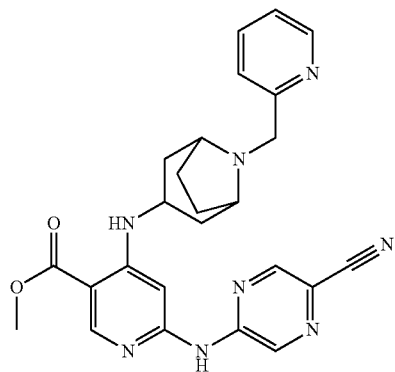 [SMILES: COC(=O)c1cnc(Nc2cnc(C#N)cn2)cc1NC1CC2CCC(C1)N2Cc1ccccn1] |
| Y-081 | 126 | 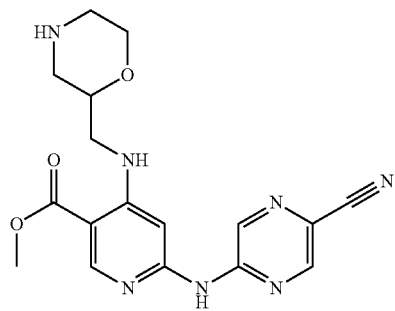 [SMILES: COC(=O)c1cnc(Nc2cnc(C#N)cn2)cc1NCC1CNCCO1] |
| Y-082 | 127 | 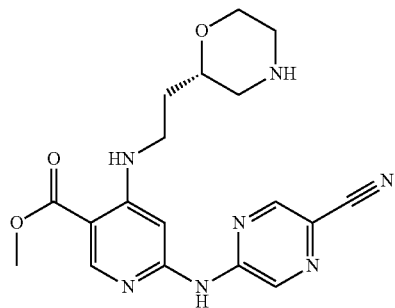 [SMILES: COC(=O)c1cnc(Nc2cnc(C#N)cn2)cc1NCC[C@H]1CNCCO1] |
| Y-083 | 128 | 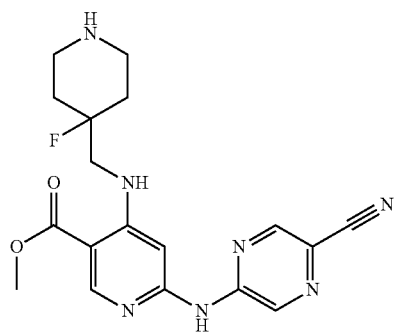 [SMILES: COC(=O)c1cnc(Nc2cnc(C#N)cn2)cc1NCC1(F)CCNCC1] |

-continued
| Compound No | Synthesis No | Structure |
|---|---|---|
| Y-084 | 129 | 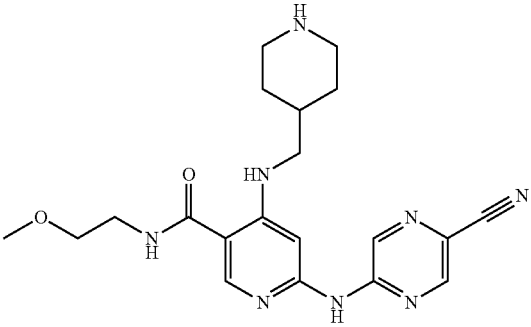 [SMILES: COCCNC(=O)c1cnc(Nc2cnc(C#N)cn2)cc1NCC1CCNCC1] |
| Y-085 | 130 | 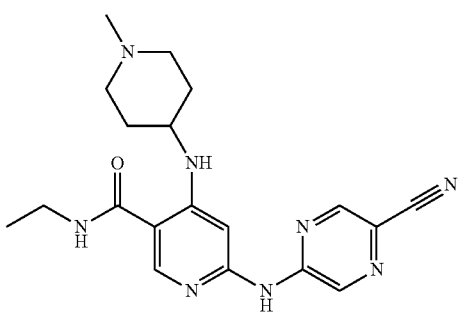 [SMILES: CCNC(=O)c1cnc(Nc2cnc(C#N)cn2)cc1NC1CCN(C)CC1] |
| Y-086 | 131 | 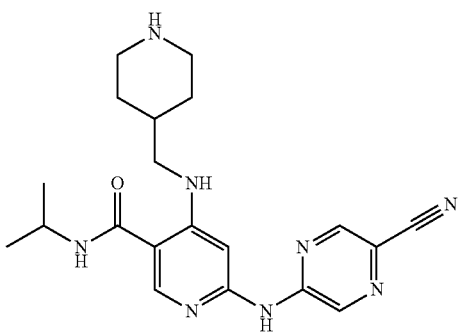 [SMILES: CC(C)NC(=O)c1cnc(Nc2cnc(C#N)cn2)cc1NCC1CCNCC1] |
| Y-087 | 132 | 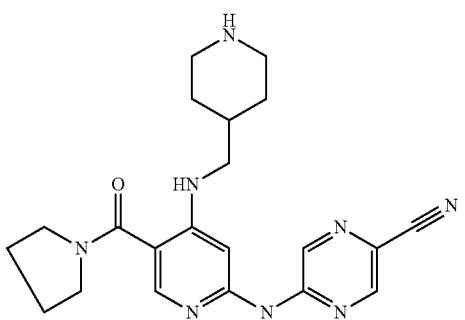 |

-continued
| Compound No | Synthesis No | Structure |
|---|---|---|
| Y-088 | 133 | 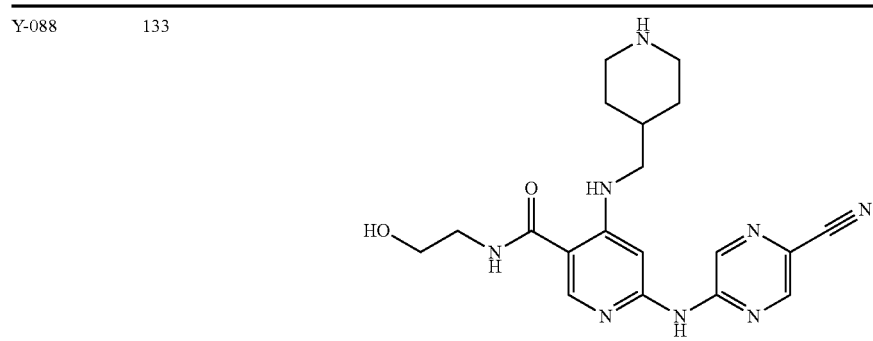 |
| Y-089 | 134 | 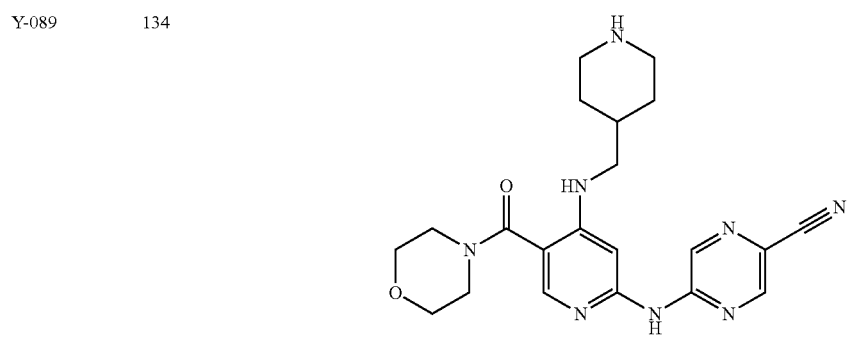 |
| Y-090 | 135 | 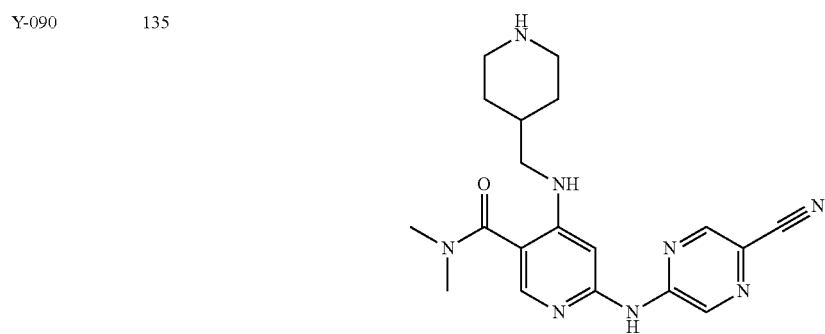 |
| Y-091 | 136 | 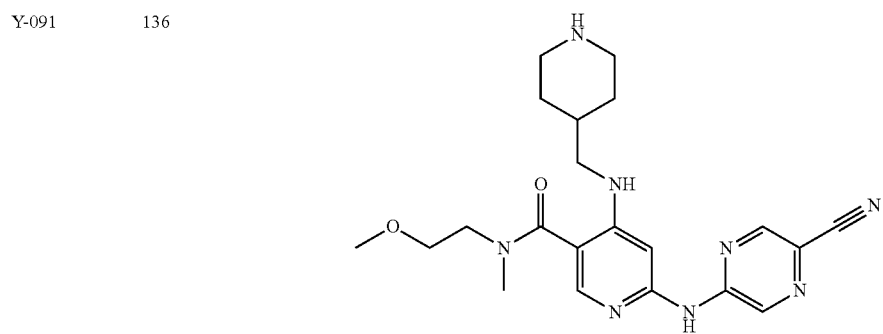 |

-continued
| Compound No | Synthesis No | Structure |
|---|---|---|
| Y-092 | 137 | 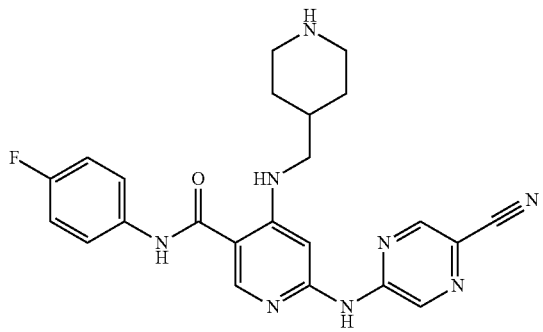 |
| Y-093 | 138 | 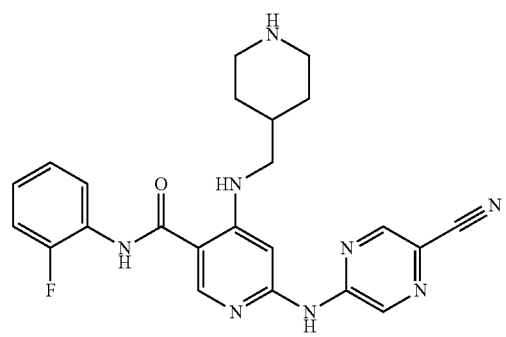 [SMILES: N#Cc1cnc(Nc2cc(NCC3CCNCC3)c(C(=O)Nc3ccccc3F)cn2)cn1] |
| Y-094 | 139 | 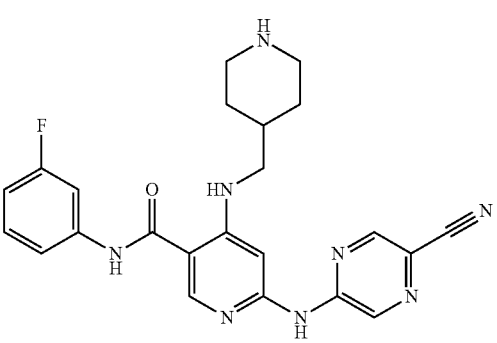 [SMILES: N#Cc1cnc(Nc2cc(NCC3CCNCC3)c(C(=O)Nc3cccc(F)c3)cn2)cn1] |
| Y-095 | 140 | 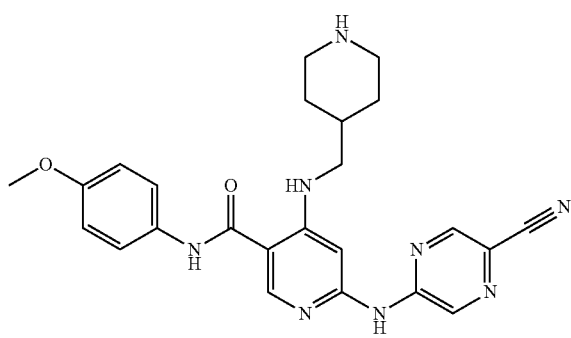 [SMILES: COc1ccc(NC(=O)c2cnc(Nc3cnc(C#N)cn3)cc2NCC2CCNCC2)cc1] |

-continued
| Compound No | Synthesis No | Structure |
|---|---|---|
| Y-096 | 141 | 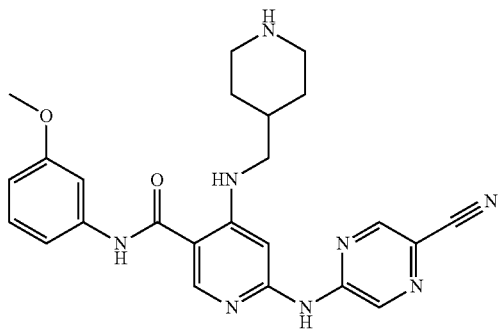 [SMILES: COc1cccc(NC(=O)c2cnc(Nc3cnc(C#N)cn3)cc2NCC2CCNCC2)c1] |
| Y-097 | 142 | 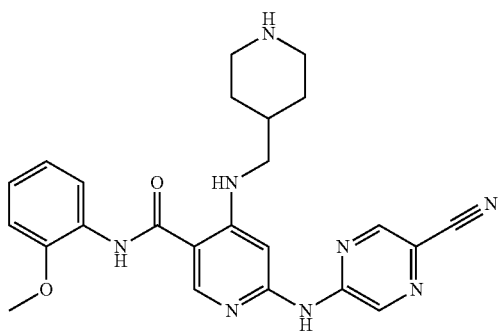 [SMILES: COc1ccccc1NC(=O)c1cnc(Nc2cnc(C#N)cn2)cc1NCC1CCNCC1] |
| Y-098 | 143 | 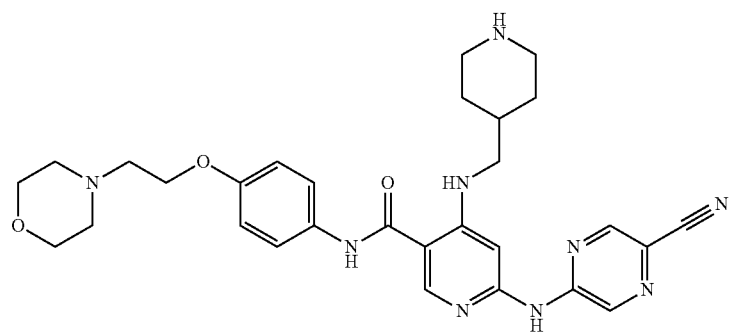 [SMILES: N#Cc1cnc(Nc2cc(NCC3CCNCC3)c(C(=O)Nc3ccc(OCCN4CCOCC4)cc3)cn2)cn1] |
| Y-099 | 144 | 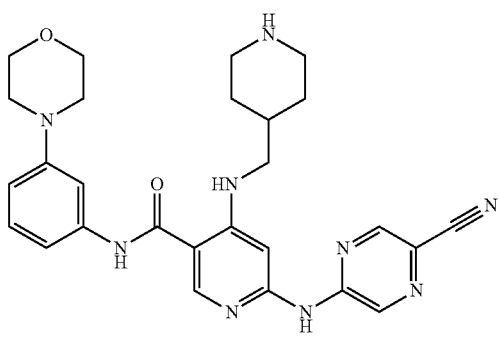 [SMILES: N#Cc1cnc(Nc2cc(NCC3CCNCC3)c(C(=O)Nc3cccc(N4CCOCC4)c3)cn2)cn1] |

-continued

| Compound No | Synthesis No | Structure |
|---|---|---|
| Y-100 | 145 | 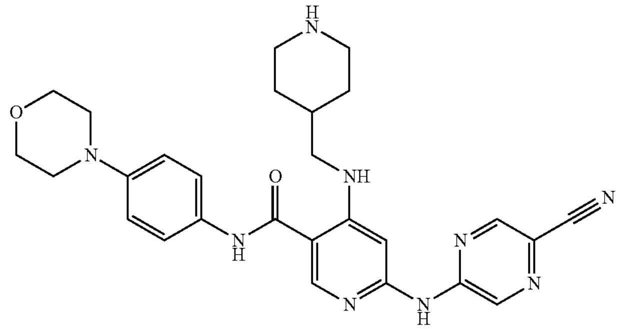 [SMILES: N#Cc1cnc(Nc2cc(NCC3CCNCC3)c(C(=O)Nc3ccc(N4CCOCC4)cc3)cn2)cn1] |
| Y-101 | 146 | 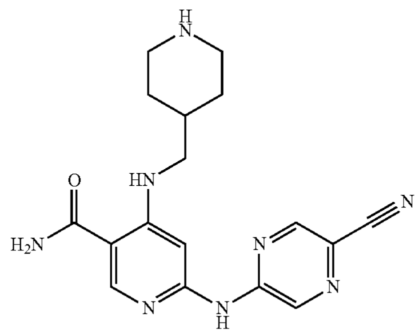 [SMILES: N#Cc1cnc(Nc2cc(NCC3CCNCC3)c(C(N)=O)cn2)cn1] |
| Y-102 | 147 | 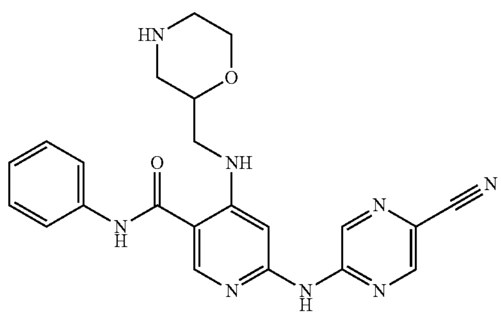 [SMILES: N#Cc1cnc(Nc2cc(NCC3CNCCO3)c(C(=O)Nc3ccccc3)cn2)cn1] |
| Y-103 | 148 | 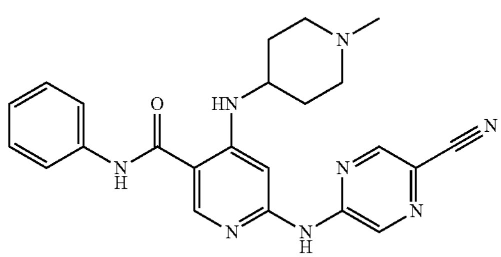 [SMILES: CN1CCC(Nc2cc(Nc3cnc(C#N)cn3)ncc2C(=O)Nc2ccccc2)CC1] |
| Y-104 | 149 | 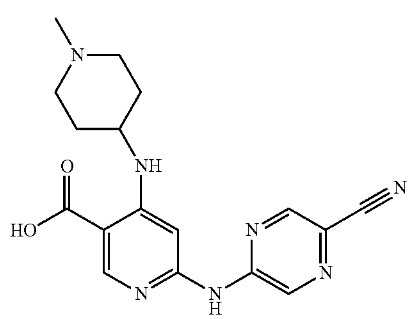 [SMILES: CN1CCC(Nc2cc(Nc3cnc(C#N)cn3)ncc2C(=O)O)CC1] |

-continued

| Compound No | Synthesis No | Structure |
|---|---|---|
| Y-105 | 150 | 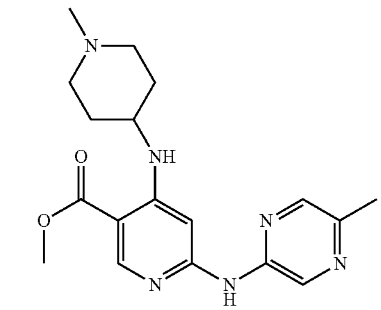 [SMILES: COC(=O)c1cnc(Nc2cnc(C)cn2)cc1NC1CCN(C)CC1] |
| Y-106 | 151 | 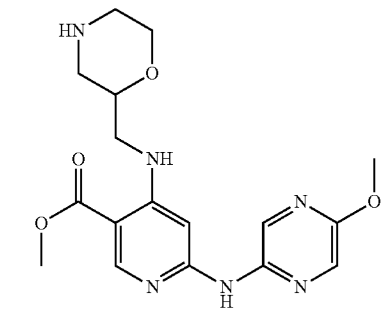 [SMILES: COC(=O)c1cnc(Nc2cnc(OC)cn2)cc1NCC1CNCCO1] |
| Y-107 | 152-C | 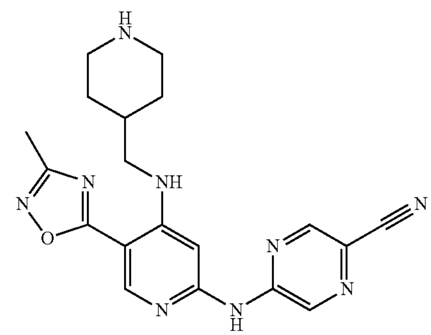 [SMILES: Cc1noc(-c2cnc(Nc3cnc(C#N)cn3)cc2NCC2CCNCC2)n1] |
| Y-108 | 153-E | 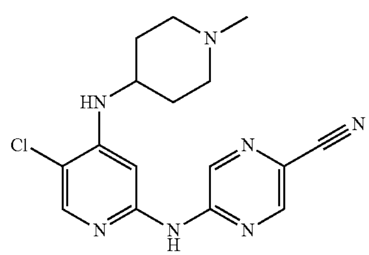 [SMILES: CN1CCC(Nc2cc(Nc3cnc(C#N)cn3)ncc2Cl)CC1] |
| Y-109 | 154 | 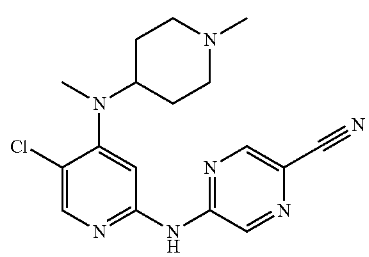 [SMILES: CN1CCC(N(C)c2cc(Nc3cnc(C#N)cn3)ncc2Cl)CC1] |

-continued
| Compound No | Synthesis No | Structure |
|---|---|---|
| Y-110 | 155-D | 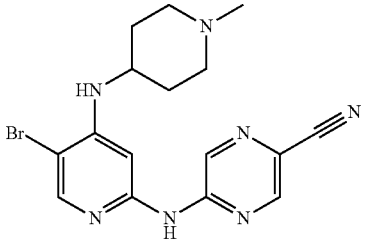 |
| Y-111 | 156-B | 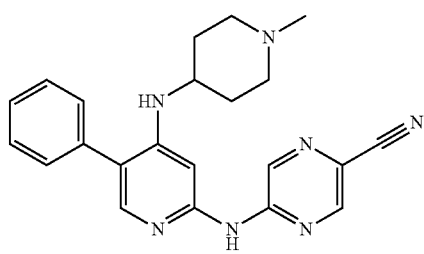 [SMILES: CN1CCC(Nc2cc(Nc3cnc(C#N)cn3)ncc2-c2ccccc2)CC1] |
| Y-112 | 157 | 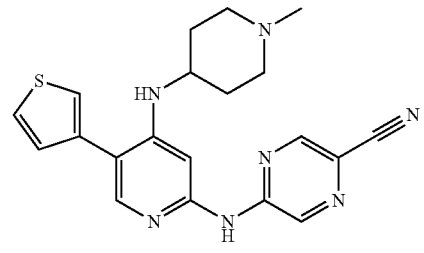 [SMILES: CN1CCC(Nc2cc(Nc3cnc(C#N)cn3)ncc2-c2ccsc2)CC1] |
| Y-113 | 158 | 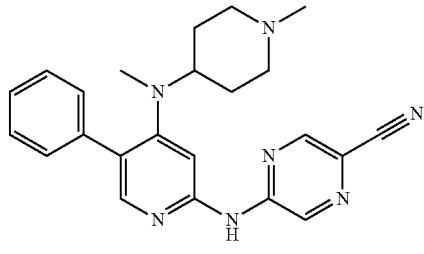 [SMILES: CN1CCC(N(C)c2cc(Nc3cnc(C#N)cn3)ncc2-c2ccccc2)CC1] |
| Y-114 | 159 | 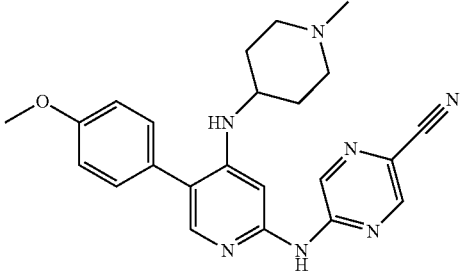 [SMILES: COc1ccc(-c2cnc(Nc3cnc(C#N)cn3)cc2NC2CCN(C)CC2)cc1] |
| Y-115 | 160 | 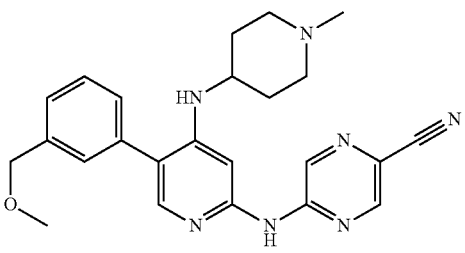 [SMILES: COCc1cccc(-c2cnc(Nc3cnc(C#N)cn3)cc2NC2CCN(C)CC2)c1] |

-continued

| Compound No | Synthesis No | Structure |
|---|---|---|
| Y-116 | 161 | 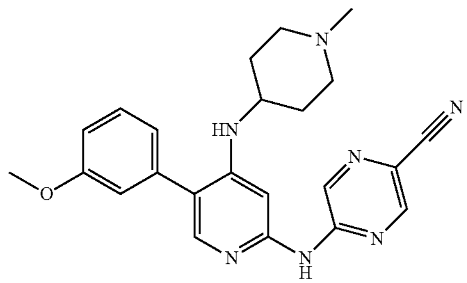 [SMILES: COc1cccc(-c2cnc(Nc3cnc(C#N)cn3)cc2NC2CCN(C)CC2)c1] |
| Y-117 | 162 | 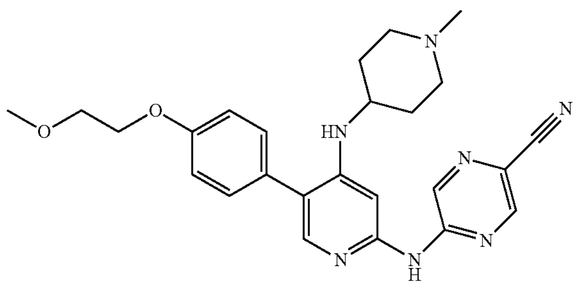 [SMILES: COCCOc1ccc(-c2cnc(Nc3cnc(C#N)cn3)cc2NC2CCN(C)CC2)cc1] |
| Y-118 | 163 | 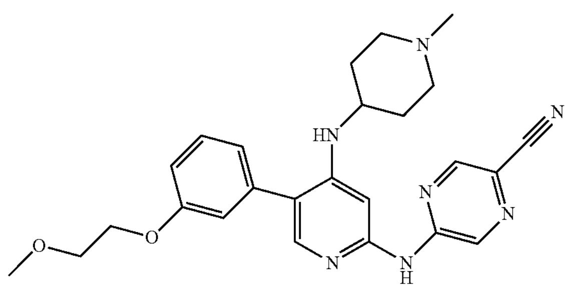 [SMILES: COCCOc1cccc(-c2cnc(Nc3cnc(C#N)cn3)cc2NC2CCN(C)CC2)c1] |
| Y-119 | 164 | 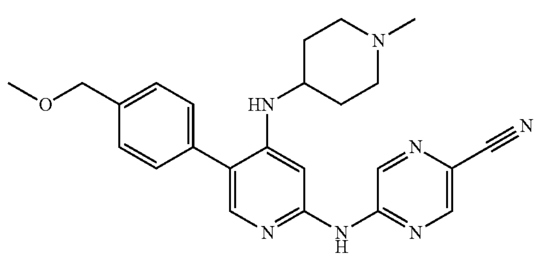 [SMILES: COCc1ccc(-c2cnc(Nc3cnc(C#N)cn3)cc2NC2CCN(C)CC2)cc1] |
| Y-120 | 165 | 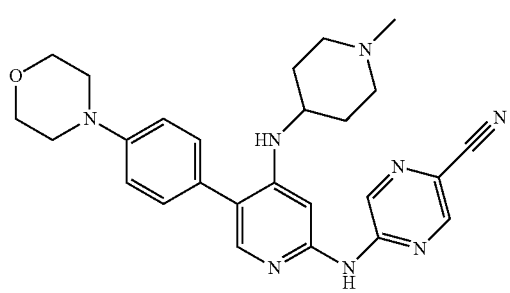 [SMILES: CN1CCC(Nc2cc(Nc3cnc(C#N)cn3)ncc2-c2ccc(N3CCOCC3)cc2)CC1] |

-continued

| Compound No | Synthesis No | Structure |
|---|---|---|
| Y-121 | 166 | 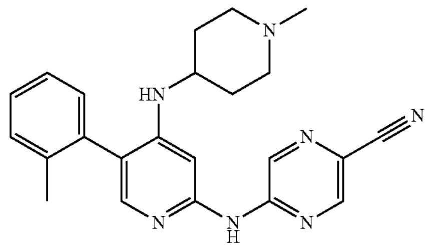 [SMILES: Cc1ccccc1-c1cnc(Nc2cnc(C#N)cn2)cc1NC1CCN(C)CC1] |
| Y-122 | 167-E | 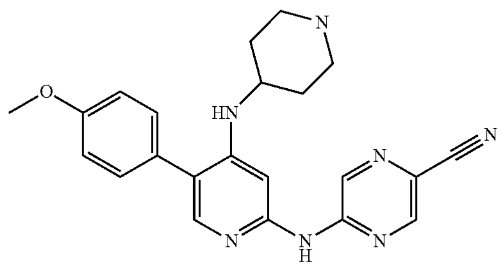 [SMILES: COc1ccc(-c2cnc(Nc3cnc(C#N)cn3)cc2NC2CCNCC2)cc1] |
| Y-123 | 168-B | 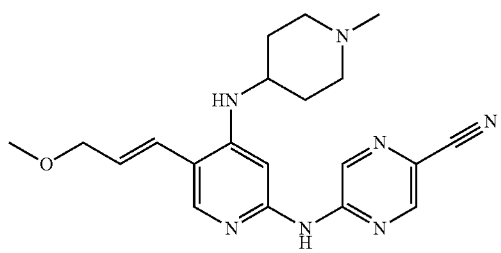 [SMILES: COC/C=C/c1cnc(Nc2cnc(C#N)cn2)cc1NC1CCN(C)CC1] |
| Y-124 | 169-D | 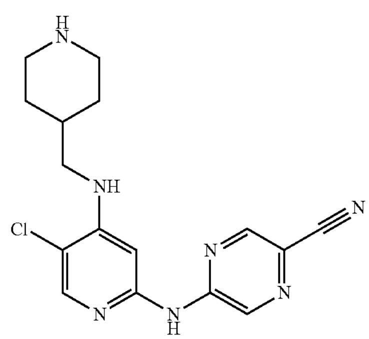 [SMILES: N#Cc1cnc(Nc2cc(NCC3CCNCC3)c(Cl)cn2)cn1] |
| Y-125 | 170-E | 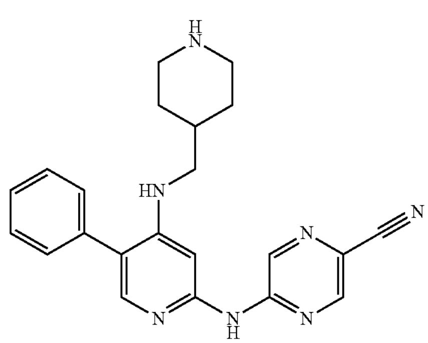 [SMILES: N#Cc1cnc(Nc2cc(NCC3CCNCC3)c(-c3ccccc3)cn2)cn1] |

-continued
| Compound No | Synthesis No | Structure |
|---|---|---|
| Y-126 | 171-E | 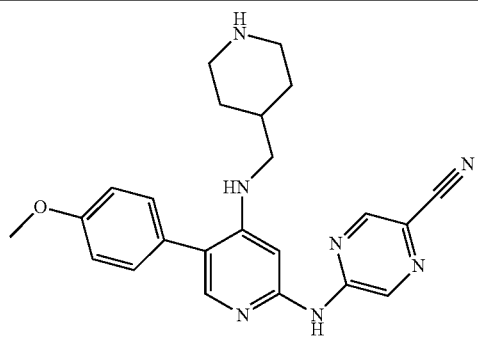 |
| Y-127 | 172 | 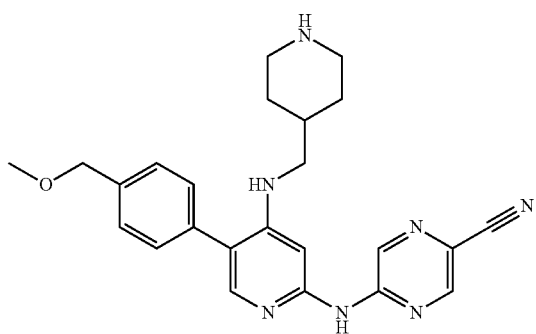 [SMILES: COCc1ccc(-c2cnc(Nc3cnc(C#N)cn3)cc2NCC2CCNCC2)cc1] |
| Y-128 | 173 | 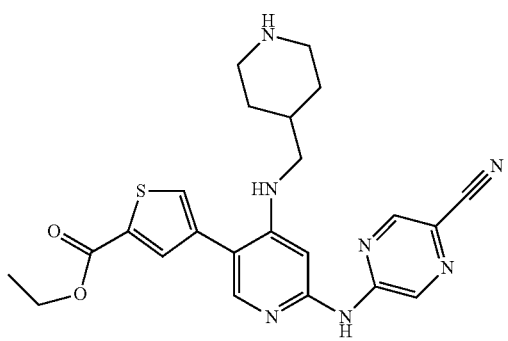 [SMILES: CCOC(=O)c1cc(-c2cnc(Nc3cnc(C#N)cn3)cc2NCC2CCNCC2)cs1] |
| Y-129 | 174 | 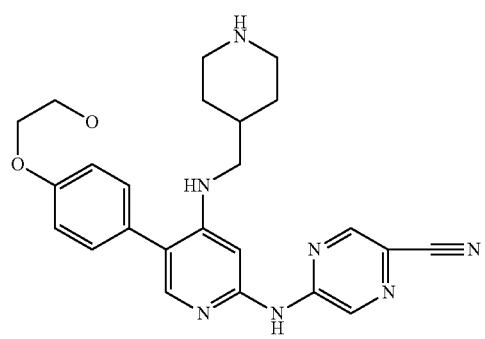 [SMILES: N#Cc1cnc(Nc2cc(NCC3CCNCC3)c(-c3ccc(OCCO)cc3)cn2)cn1] |

-continued
| Compound No | Synthesis No | Structure |
|---|---|---|
| Y-130 | 175 | 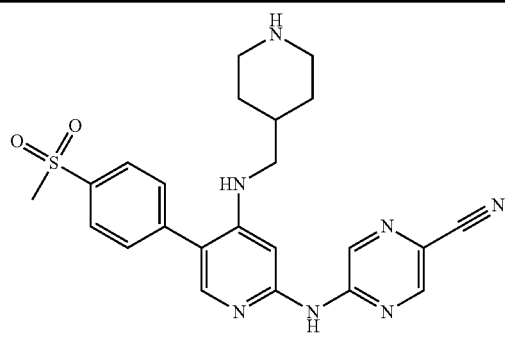 |
| Y-131 | 176 | 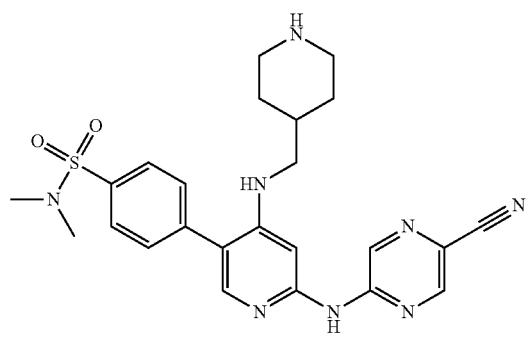 [SMILES: CN(C)S(=O)(=O)c1ccc(-c2cnc(Nc3cnc(C#N)cn3)cc2NCC2CCNCC2)cc1] |
| Y-132 | 177 | 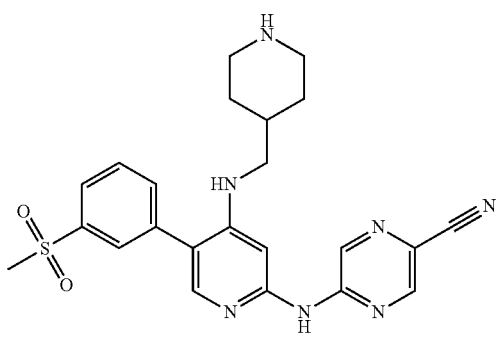 [SMILES: CS(=O)(=O)c1cccc(-c2cnc(Nc3cnc(C#N)cn3)cc2NCC2CCNCC2)c1] |
| Y-133 | 178 | 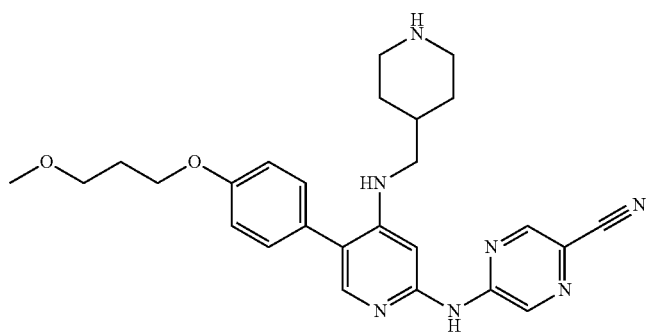 [SMILES: COCCCOc1ccc(-c2cnc(Nc3cnc(C#N)cn3)cc2NCC2CCNCC2)cc1] |

-continued
| Compound No | Synthesis No | Structure |
|---|---|---|
| Y-134 | 179 | 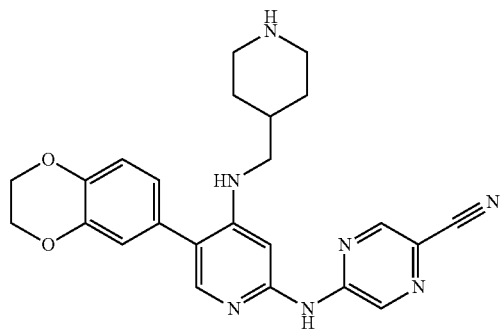 [SMILES: N#Cc1cnc(Nc2cc(NCC3CCNCC3)c(-c3ccc4c(c3)OCCO4)cn2)cn1] |
| Y-135 | 180 | 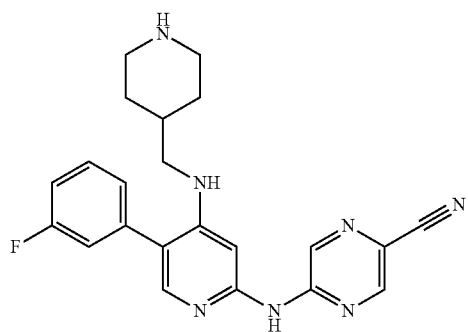 [SMILES: N#Cc1cnc(Nc2cc(NCC3CCNCC3)c(-c3cccc(F)c3)cn2)cn1] |
| Y-136 | 181 | 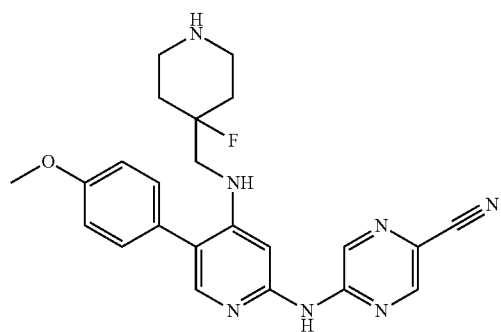 [SMILES: COc1ccc(-c2cnc(Nc3cnc(C#N)cn3)cc2NCC2(F)CCNCC2)cc1] |
| Y-137 | 182 | 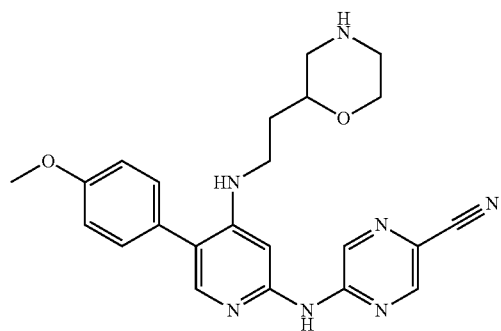 [SMILES: COc1ccc(-c2cnc(Nc3cnc(C#N)cn3)cc2NCCC2CNCCO2)cc1] |

| Compound No | Synthesis No | Structure |
|---|---|---|
| Y-138 | 183 | 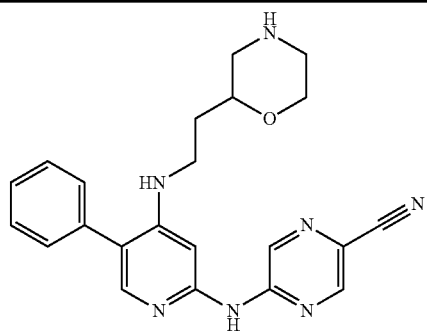 |
| Y-139 | 184-C | 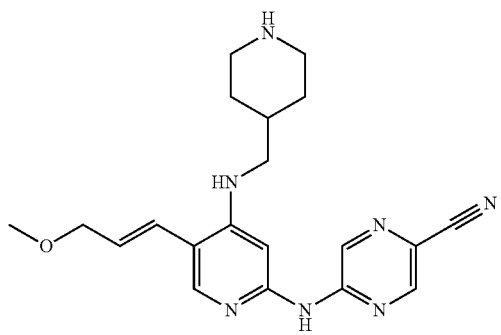 [SMILES: COC/C=C/c1cnc(Nc2cnc(C#N)cn2)cc1NCC1CCNCC1] |
| Y-140 | 185 | 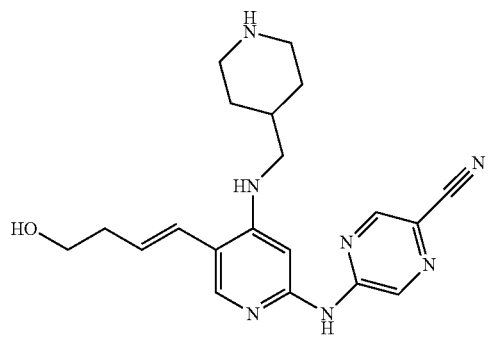 [SMILES: N#Cc1cnc(Nc2cc(NCC3CCNCC3)c(/C=C/CCO)cn2)cn1] |
| Y-141 | 186 | 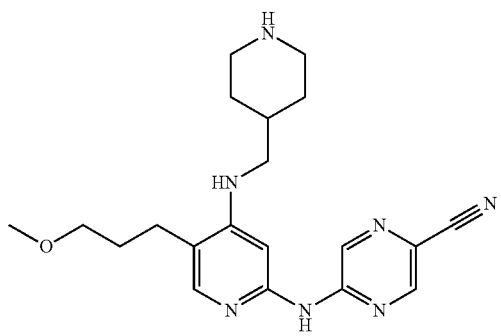 [SMILES: COCCCc1cnc(Nc2cnc(C#N)cn2)cc1NCC1CCNCC1] |

-continued
| Compound No | Synthesis No | Structure |
|---|---|---|
| Y-142 | 187 | 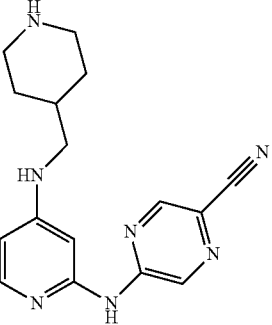 |
| Y-143 | 188 | 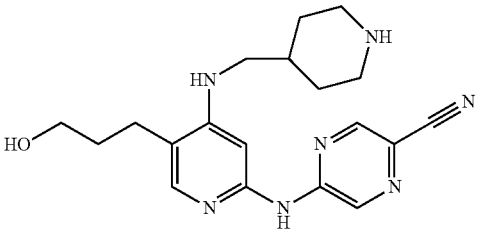 [SMILES: N#Cc1cnc(Nc2cc(NCC3CCNCC3)c(CCCO)cn2)cn1] |
| Y-144 | 189-B | 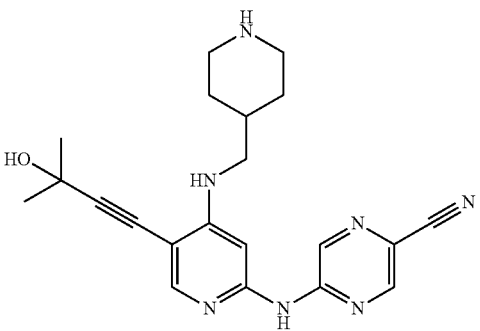 [SMILES: CC(C)(O)C#Cc1cnc(Nc2cnc(C#N)cn2)cc1NCC1CCNCC1] |
| Y-145 | 190 | 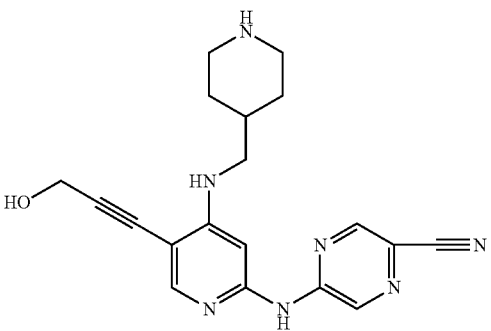 [SMILES: N#Cc1cnc(Nc2cc(NCC3CCNCC3)c(C#CCO)cn2)cn1] |
| Y-146 | 191-H | 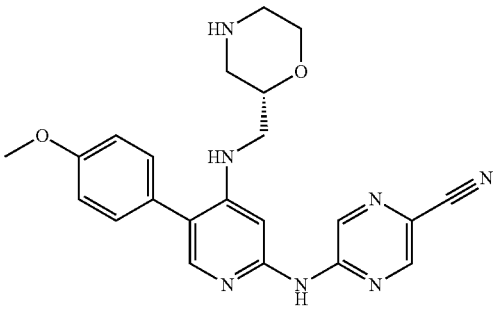 [SMILES: COc1ccc(-c2cnc(Nc3cnc(C#N)cn3)cc2NC[C@@H]2CNCCO2)cc1] |

-continued

| Compound No | Synthesis No | Structure |
|---|---|---|
| Y-147 | 192-H | 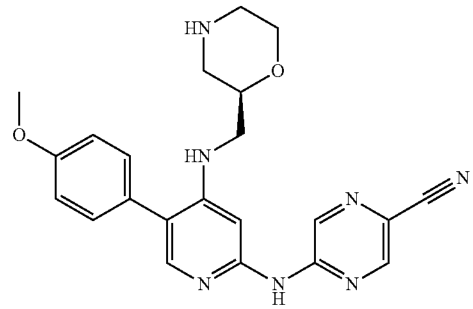 [SMILES: COc1ccc(-c2cnc(Nc3cnc(C#N)cn3)cc2NC[C@H]2CNCCO2)cc1] |
| Y-148 | 193 | 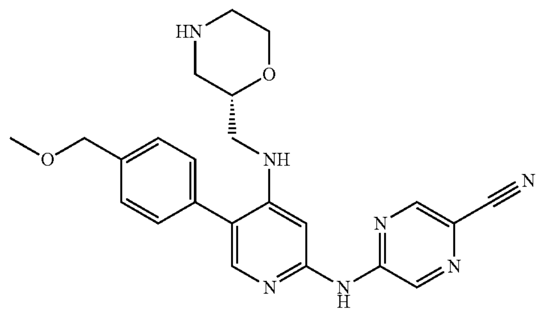 [SMILES: COCc1ccc(-c2cnc(Nc3cnc(C#N)cn3)cc2NC[C@@H]2CNCCO2)cc1] |
| Y-149 | 194 | 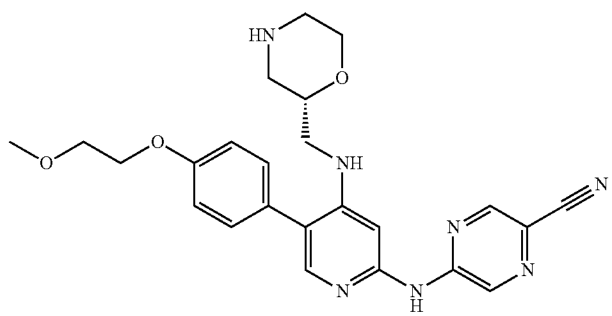 [SMILES: COCCOc1ccc(-c2cnc(Nc3cnc(C#N)cn3)cc2NC[C@@H]2CNCCO2)cc1] |
| Y-150 | 195 | 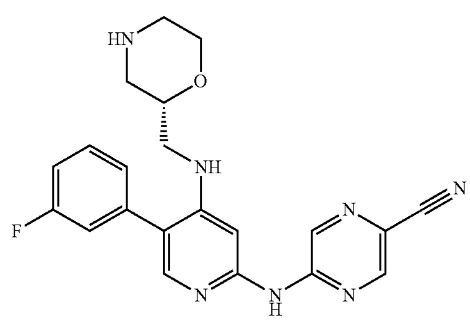 [SMILES: N#Cc1cnc(Nc2cc(NC[C@@H]3CNCCO3)c(-c3cccc(F)c3)cn2)cn1] |
| Y-151 | 196 | 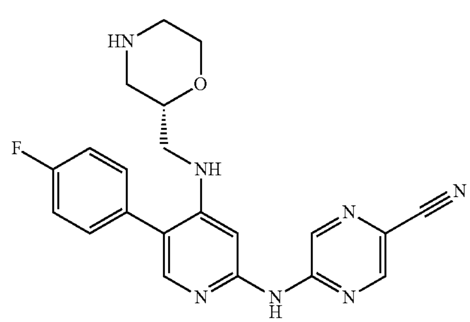 [SMILES: N#Cc1cnc(Nc2cc(NC[C@@H]3CNCCO3)c(-c3ccc(F)cc3)cn2)cn1] |

-continued
| Compound No | Synthesis No | Structure |
|---|---|---|
| Y-152 | 197 | 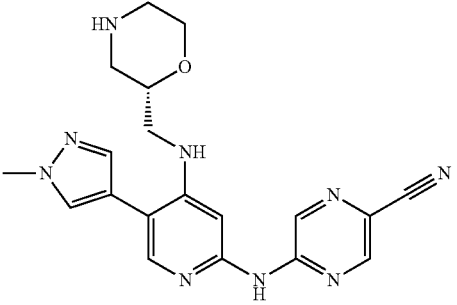 [SMILES: Cn1cc(-c2cnc(Nc3cnc(C#N)cn3)cc2NC[C@@H]2CNCCO2)cn1] |
| Y-153 | 198 | 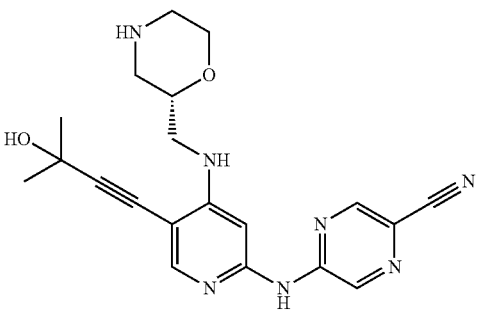 [SMILES: CC(C)(O)C#Cc1cnc(Nc2cnc(C#N)cn2)cc1NC[C@@H]1CNCCO1] |
| Y-154 | 199 | 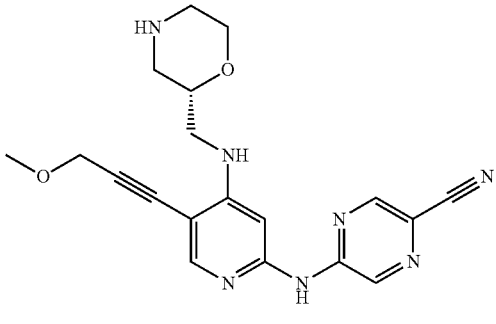 [SMILES: COCC#Cc1cnc(Nc2cnc(C#N)cn2)cc1NC[C@@H]1CNCCO1] |
| Y-155 | 200 | 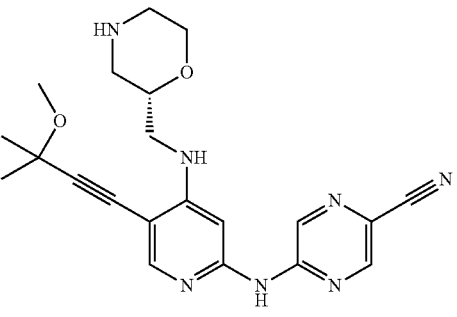 [SMILES: COC(C)(C)C#Cc1cnc(Nc2cnc(C#N)cn2)cc1NC[C@@H]1CNCCO1] |
| Y-156 | 201 | 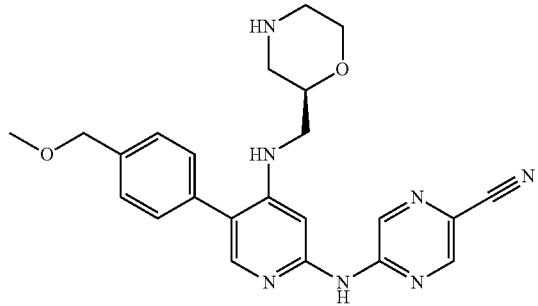 [SMILES: COCc1ccc(-c2cnc(Nc3cnc(C#N)cn3)cc2NC[C@H]2CNCCO2)cc1] |

| Compound No | Synthesis No | Structure |
|---|---|---|
| Y-157 | 202 | 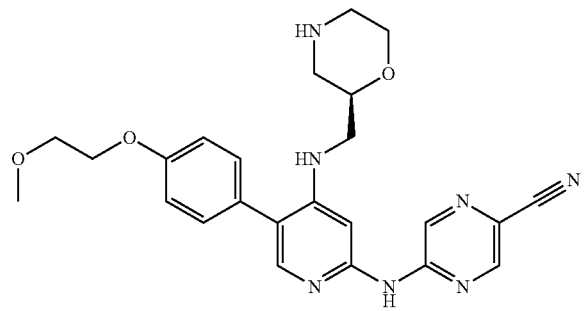 [SMILES: COCCOc1ccc(-c2cnc(Nc3cnc(C#N)cn3)cc2NC[C@H]2CNCCO2)cc1] |
| Y-158 | 203 | 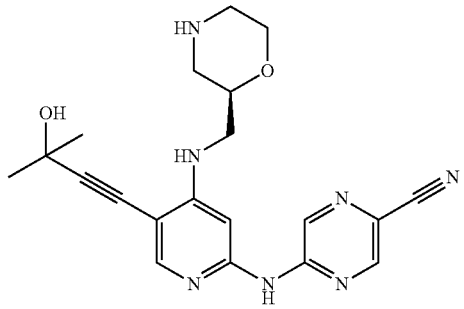 [SMILES: CC(C)(O)C#Cc1cnc(Nc2cnc(C#N)cn2)cc1NC[C@H]1CNCCO1] |
| Y-159 | 204 | 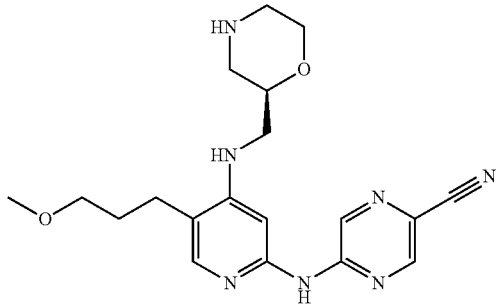 [SMILES: COCCCc1cnc(Nc2cnc(C#N)cn2)cc1NC[C@H]1CNCCO1] |

In one embodiment, the compounds are selected from compounds of the following formulae and pharmaceutically acceptable salts, solvates, chemically protected forms, and prodrugs thereof:
| Compound No. | Synthesis No. | Structure |
|---|---|---|
| Z-001 | 1-B | 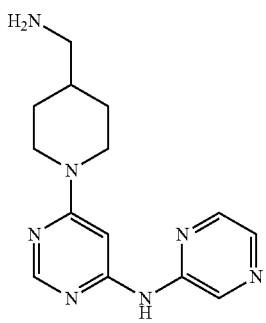 [SMILES: NCC1CCN(c2cc(Nc3cnccn3)ncn2)CC1] |
| Z-002 | 2 | 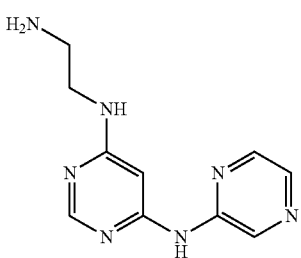 [SMILES: NCCNc1cc(Nc2cnccn2)ncn1] |
| Z-003 | 3 | 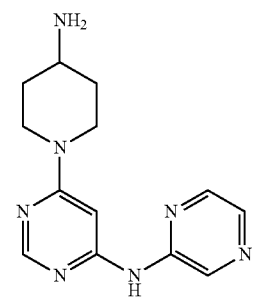 [SMILES: NC1CCN(c2cc(Nc3cnccn3)ncn2)CC1] |
| Z-004 | 4 | 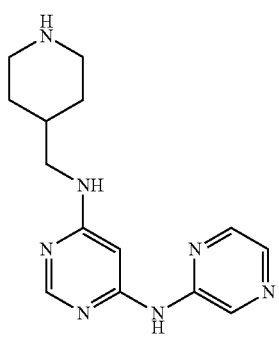 [SMILES: c1cnc(Nc2cc(NCC3CCNCC3)ncn2)cn1] |
| Z-005 | 5 | 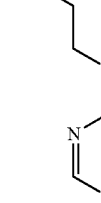 |
| Z-006 | 6 | 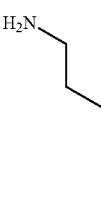 |
| Z-007 | 7-B | 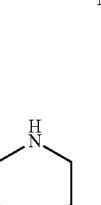 |
| Z-008 | 8 | 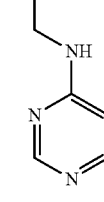 |
| Z-009 | 9 | 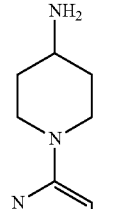 |

| Compound No. | Synthesis No. | Structure |
|---|---|---|
| Z-010 | 10 | 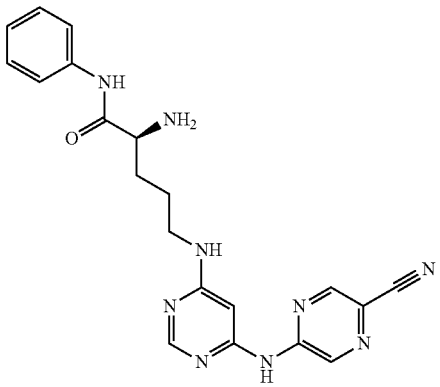 [SMILES: N#Cc1cnc(Nc2cc(NCCC[C@H](N)C(=O)Nc3ccccc3)ncn2)cn1] |
| Z-011 | 11 | 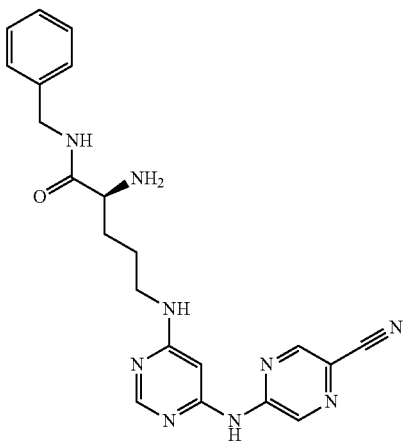 [SMILES: N#Cc1cnc(Nc2cc(NCCC[C@H](N)C(=O)NCc3ccccc3)ncn2)cn1] |
| Z-012 | 12 | 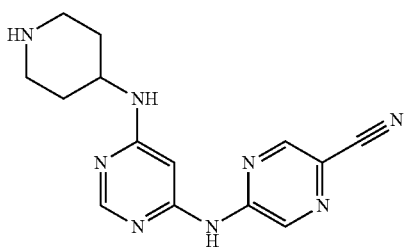 [SMILES: N#Cc1cnc(Nc2cc(NC3CCNCC3)ncn2)cn1] |
| Z-013 | 13 | 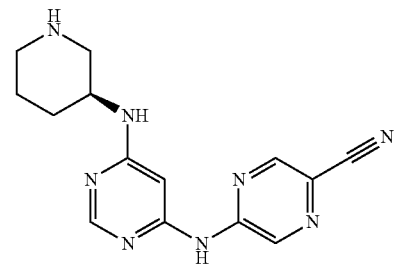 [SMILES: N#Cc1cnc(Nc2cc(N[C@H]3CCCNC3)ncn2)cn1] |
| Z-014 | 14 | 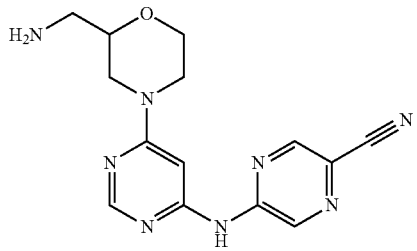 [SMILES: N#Cc1cnc(Nc2cc(N3CCOC(CN)C3)ncn2)cn1] |
| Z-015 | 15 | 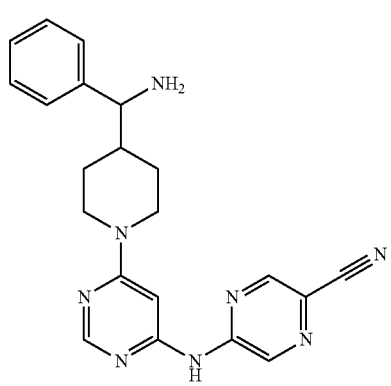 [SMILES: N#Cc1cnc(Nc2cc(N3CCC(C(N)c4ccccc4)CC3)ncn2)cn1] |
| Z-016 | 16 | 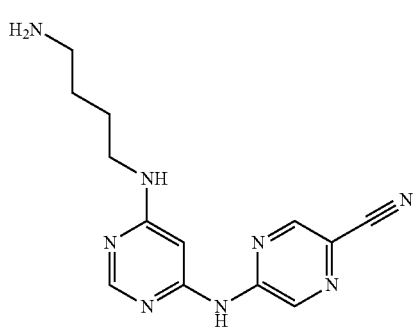 [SMILES: N#Cc1cnc(Nc2cc(NCCCCN)ncn2)cn1] |
| Z-017 | 17 | 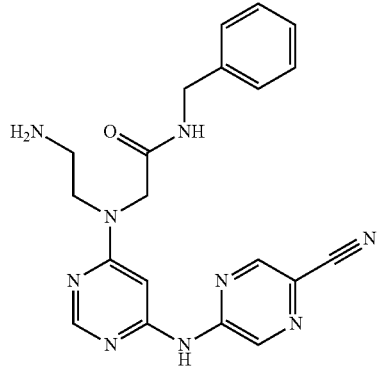 [SMILES: N#Cc1cnc(Nc2cc(N(CCN)CC(=O)NCc3ccccc3)ncn2)cn1] |

| Compound No. | Synthesis No. | Structure |
|---|---|---|
| Z-018 | 18 | 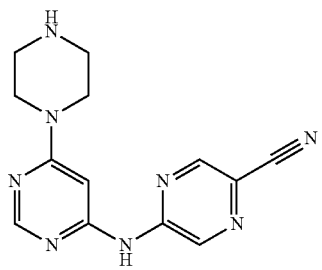 [SMILES: N#Cc1cnc(Nc2cc(N3CCNCC3)ncn2)cn1] |
| Z-019 | 19 | 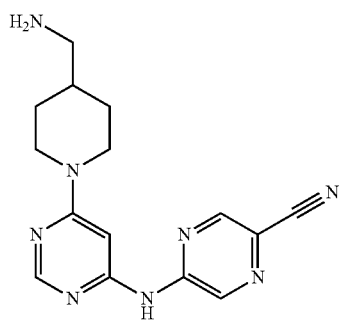 [SMILES: N#Cc1cnc(Nc2cc(N3CCC(CN)CC3)ncn2)cn1] |
| Z-020 | 20 | 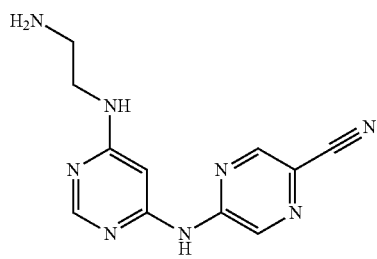 [SMILES: N#Cc1cnc(Nc2cc(NCCN)ncn2)cn1] |
| Z-021 | 21 | 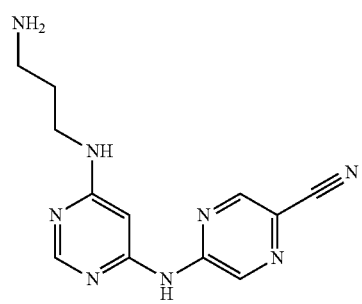 |
| Z-022 | 22 | 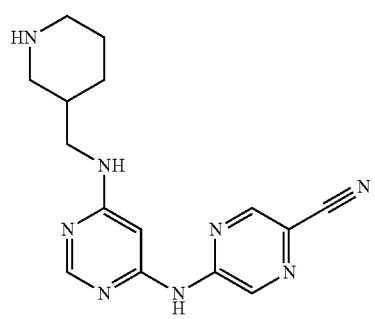 [SMILES: N#Cc1cnc(Nc2cc(NCC3CCCNC3)ncn2)cn1] |
| Z-023 | 23 | 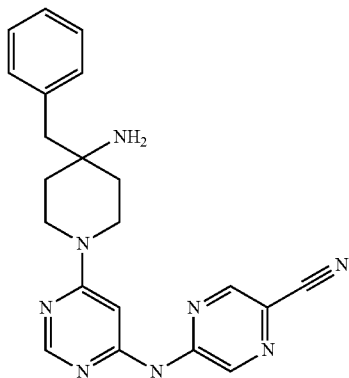 |
| Z-024 | 24 | 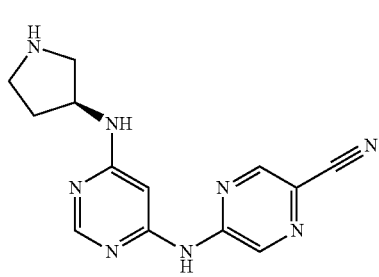 [SMILES: N#Cc1cnc(Nc2cc(N[C@H]3CCNC3)ncn2)cn1] |
| Z-025 | 25 | 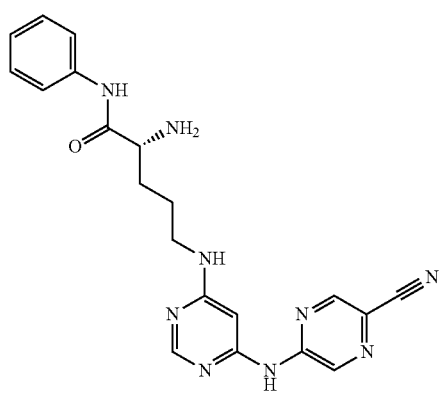 [SMILES: N#Cc1cnc(Nc2cc(NCCC[C@@H](N)C(=O)Nc3ccccc3)ncn2)cn1] |
| Z-026 | 26 | 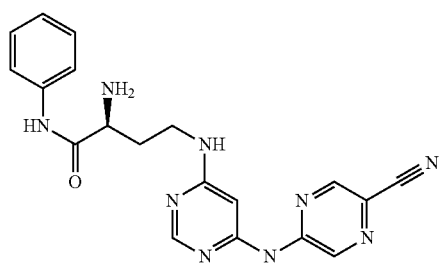 |
| Z-027 | 27 | 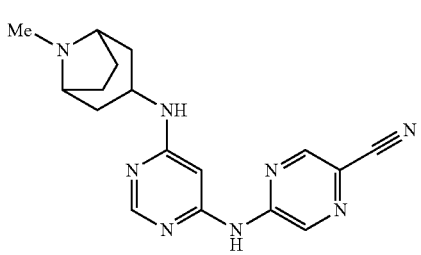 [SMILES: CN1C2CCC1CC(Nc1cc(Nc3cnc(C#N)cn3)ncn1)C2] |

-continued
| Compound No. | Synthesis No. | Structure |
|---|---|---|
| Z-028 | 28 | 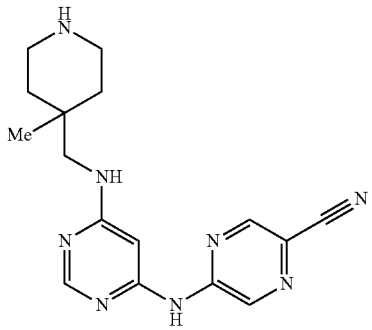 [SMILES: CC1(CNc2cc(Nc3cnc(C#N)cn3)ncn2)CCNCC1] |
| Z-029 | 29 | 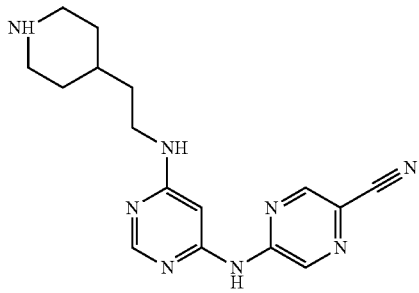 [SMILES: N#Cc1cnc(Nc2cc(NCCC3CCNCC3)ncn2)cn1] |
| Z-030 | 30 | 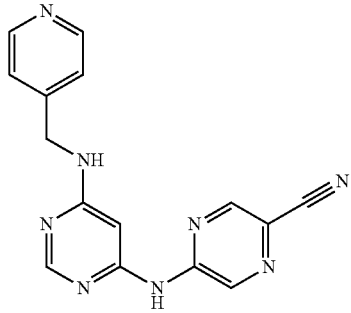 [SMILES: N#Cc1cnc(Nc2cc(NCc3ccncc3)ncn2)cn1] |
| Z-031 | 31 | 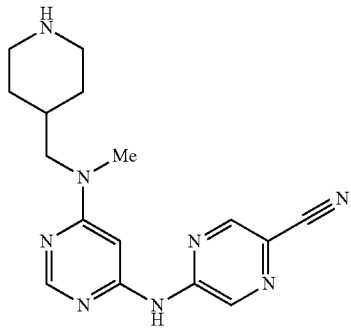 [SMILES: CN(CC1CCNCC1)c1cc(Nc2cnc(C#N)cn2)ncn1] |
-continued
| Compound No. | Synthesis No. | Structure |
|---|---|---|
| Z-032 | 32 | 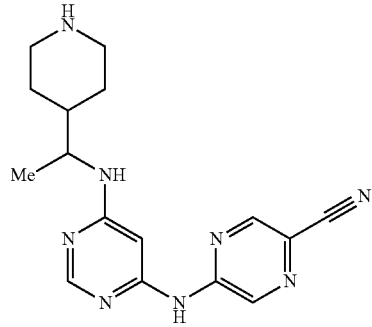 [SMILES: CC(Nc1cc(Nc2cnc(C#N)cn2)ncn1)C1CCNCC1] |
| Z-033 | 33 | 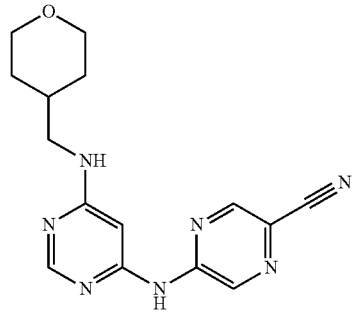 [SMILES: N#Cc1cnc(Nc2cc(NCC3CCOCC3)ncn2)cn1] |
| Z-034 | 34 | 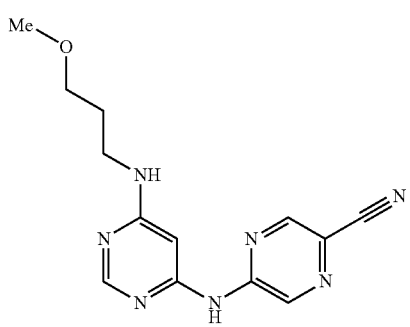 |
| Z-035 | 35 | 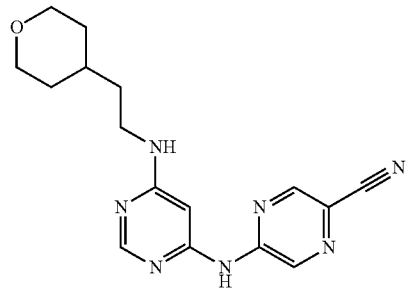 [SMILES: N#Cc1cnc(Nc2cc(NCCC3CCOCC3)ncn2)cn1] |
| Z-036 | 36 | 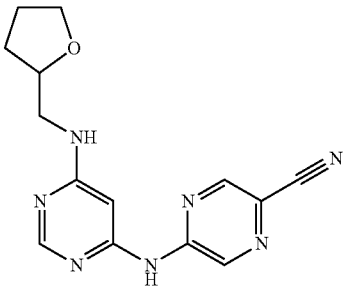 [SMILES: N#Cc1cnc(Nc2cc(NCC3CCCO3)ncn2)cn1] |

-continued
| Compound No. | Synthesis No. | Structure |
|---|---|---|
| Z-037 | 37 | 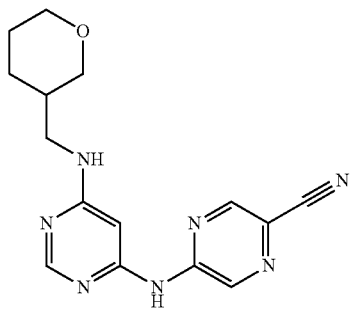 [SMILES: N#Cc1cnc(Nc2cc(NCC3CCCOC3)ncn2)cn1] |
| Z-038 | 38 | 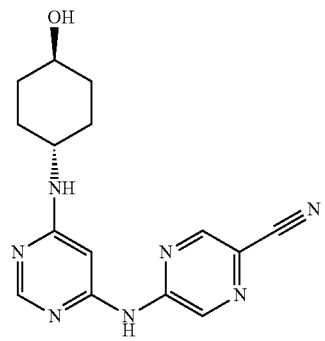 [SMILES: N#Cc1cnc(Nc2cc(N[C@H]3CC[C@H](O)CC3)ncn2)cn1] |
| Z-039 | 39 | 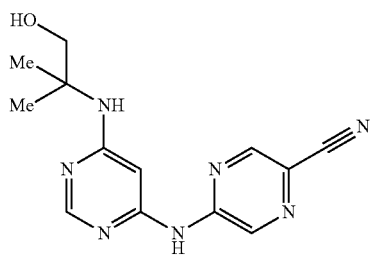 [SMILES: CC(C)(CO)Nc1cc(Nc2cnc(C#N)cn2)ncn1] |
| Z-040 | 40 | 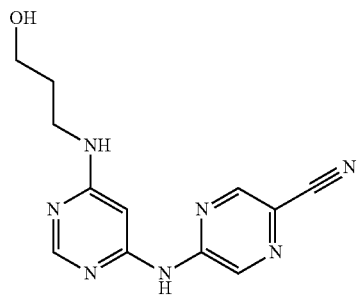 |
| Z-041 | 41 | 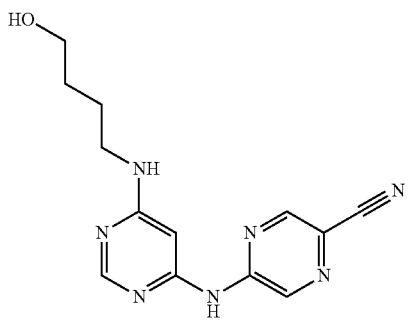 [SMILES: N#Cc1cnc(Nc2cc(NCCCCO)ncn2)cn1] |
-continued
| Compound No. | Synthesis No. | Structure |
|---|---|---|
| Z-042 | 42 | 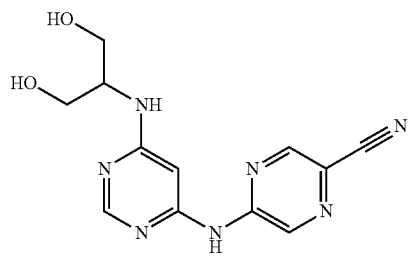 [SMILES: N#Cc1cnc(Nc2cc(NC(CO)CO)ncn2)cn1] |
| Z-043 | 43 | 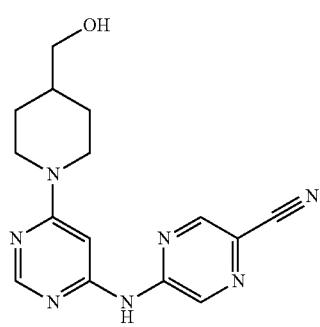 [SMILES: N#Cc1cnc(Nc2cc(N3CCC(CO)CC3)ncn2)cn1] |
| Z-044 | 79-E | 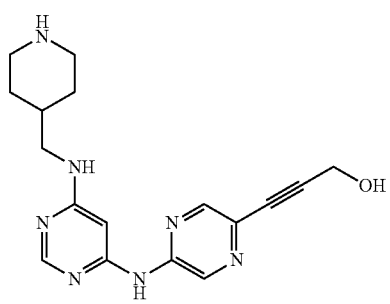 [SMILES: OCC#Cc1cnc(Nc2cc(NCC3CCNCC3)ncn2)cn1] |
| Z-045 | 80 | 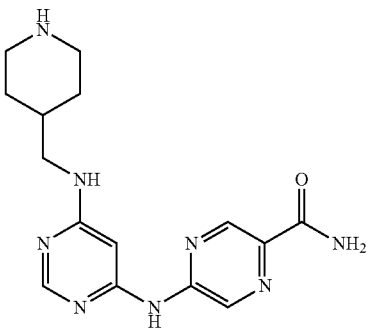 [SMILES: NC(=O)c1cnc(Nc2cc(NCC3CCNCC3)ncn2)cn1] |
In one embodiment, the compounds are selected from compounds of the following formula and pharmaceutically acceptable salts, solvates, chemically protected forms, and prodrugs thereof:

| Compound No | Synthesis No. | Structure |
|---|---|---|
| Z-046 | 205-D | 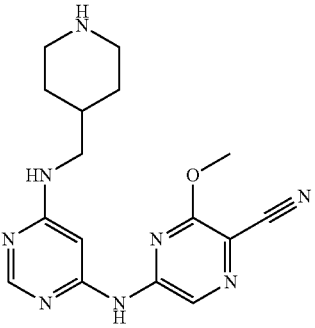 [SMILES: COc1nc(Nc2cc(NCC3CCNCC3)ncn2)cnc1C#N] |

Substantially Purified Forms

One aspect of the present invention pertains to BAA compounds, as described herein, in substantially purified form and/or in a form substantially free from contaminants.

In one embodiment, the substantially purified form is at least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to a equimolar mixture of enantiomers (i.e., a racemic mixture, a racemate). In one embodiment, the substantially purified form refers to one enantiomer, e.g., optically pure enantiomer.

In one embodiment, the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the substantially purified form is at least 60% optically pure (i.e., 60% of the compound, on a molar basis, is the desired stereoisomer or enantiomer, and 40% is the undesired stereoisomer or enantiomer), e.g., at least 70% optically pure, e.g., at least 80% optically pure, e.g., at least 90% optically pure, e.g., at least 95% optically pure, e.g., at least 97% optically pure, e.g., at least 98% optically pure, e.g., at least 99% optically pure.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

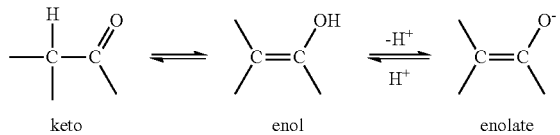

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COON may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Solvates and Hydrates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate and hydrate forms thereof.

Chemically Protected Forms

It may be convenient or desirable to prepare, purify, and/or handle the compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 4th Edition; John Wiley and Sons, 2006).

Unless otherwise specified, a reference to a particular compound also includes chemically protected forms thereof.

A wide variety of such "protecting," "blocking," or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)$CH_3$, —OAc).

For example, an aldehyde or ketone group may be protected as an acetal (R—CH(OR)$_2$) or ketal ($R_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—$CH_3$); a benzyloxy amide (—NHCO—$OCH_2C_6H_5$, —NH-Cbz); as a t-butoxy amide (—NHCO—$OC(CH_3)_3$, —NH-Boc); a 2-biphenyl-2-propoxy amide (—NHCO—$OC(CH_3)_2C_6H_4C_6H_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH-Psec); or, in suitable cases (e.g., cyclic amines), as a nitroxide radical (>N—O.).

For example, a carboxylic acid group may be protected as an ester for example, as: an $C_{1-7}$alkyl ester (e.g., a methyl ester; a t-butyl ester); a $C_{1-7}$haloalkyl ester (e.g., a $C_{1-7}$trihaloalkyl ester); a tri$C_{1-7}$alkylsilyl-$C_{1-7}$alkyl ester; or a $C_{5-20}$aryl-$C_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—$CH_2$NHC(=O)$CH_3$).

Prodrugs

It may be convenient or desirable to prepare, purify, and/or handle the compound in the form of a prodrug. The term "prodrug," as used herein, pertains to a compound which, when metabolised (e.g., in vivo), yields the desired active compound. Typically, the prodrug is inactive, or less active than the desired active compound, but may provide advantageous handling, administration, or metabolic properties.

Unless otherwise specified, a reference to a particular compound also includes prodrugs thereof.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Chemical Synthesis

Several methods for the chemical synthesis of biarylamine compounds of the present invention are described herein. These and/or other well known methods may be modified and/or adapted in known ways in order to facilitate the synthesis of additional compounds within the scope of the present invention.

In one approach (General Method A), compounds of type (iv) are prepared by a method as illustrated in the following scheme. Commercially available compounds (i) and (ii) are coupled, for example, under palladium mediated amination conditions, typically with heating and in the presence of base, to give diarylamine (iii). Subsequent reaction with an amine, usually in the presence of a tertiary base such as triethylamine at elevated temperatures in NMP using oil bath or microwave heating, followed by removal of any protecting groups on the amine component, gives the required compound (iv). Alternatively, the order of sequential displacement by the two amines can be reversed.

Scheme 1

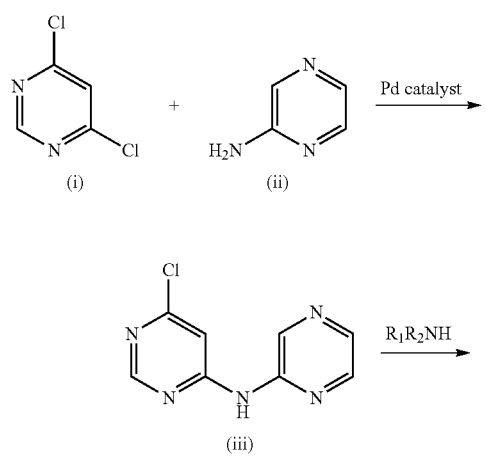

In another approach (General Method B), compounds of type (vii) are prepared by a method as illustrated in the following scheme. Commercially available compounds (i) and (v) are coupled, for example, under palladium mediated amination conditions, typically with heating and in the presence of base to give diarylamine (vi). Subsequent reaction with an amine, usually in the presence of a tertiary base such as triethylamine at elevated temperatures in NMP using oil bath or microwave heating, followed by removal of any protecting groups on the amine component, gives the required compound (vii). Alternatively, the order of sequential displacement by the two amines can be reversed.

Scheme 2

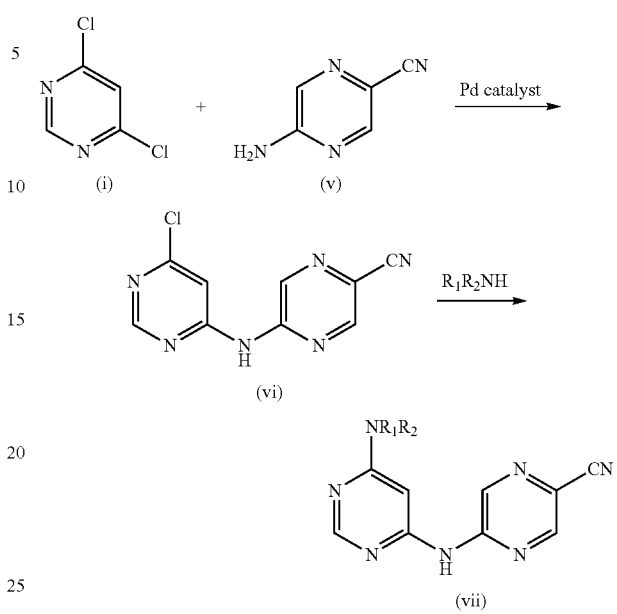

In another approach (General Method C), compounds of type (xi) are prepared by a method as illustrated in the following scheme. 2-Bromo-4-chloro-5-nitropyridine (viii) is treated with an amine, typically in acetonitrile and in the presence of a tertiary base to afford intermediate (ix). Treatment of this intermediate with 2-amino-5-cyanopyrazine (v) under palladium mediated amination conditions, typically with heating and in the presence of base, gives bisarylamine (x). Reduction of the nitro group using tin (II) chloride or a metal/acid mixture followed by removal of any protecting groups on the amine component gives compound (xi).

Scheme 3

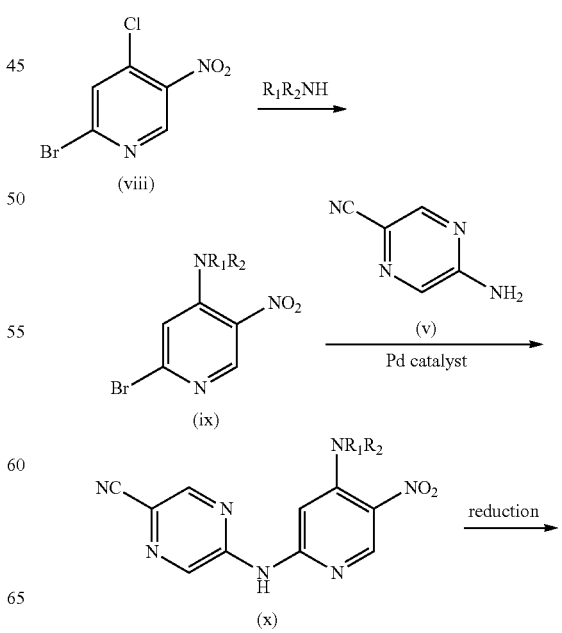

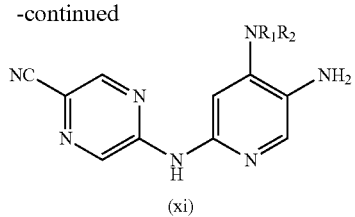

(xi)

Scheme 5

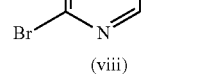

(viii)

In another approach (General Method D), compounds of type (xii) and (xiii) are prepared by a method as illustrated in the following scheme. Amine (xi) is treated with an acid under standard amide formation conditions using an activating agent such as EDC.

Alternatively, the amine is treated with an anhydride or other form of activated acid. Removal of any protecting groups on the amine component then gives amides (xii).

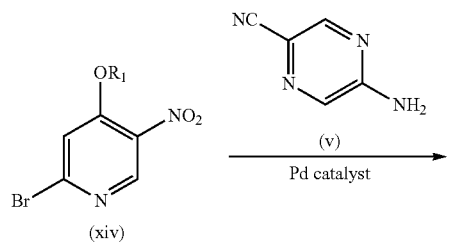

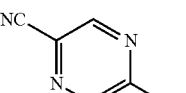

Scheme 4

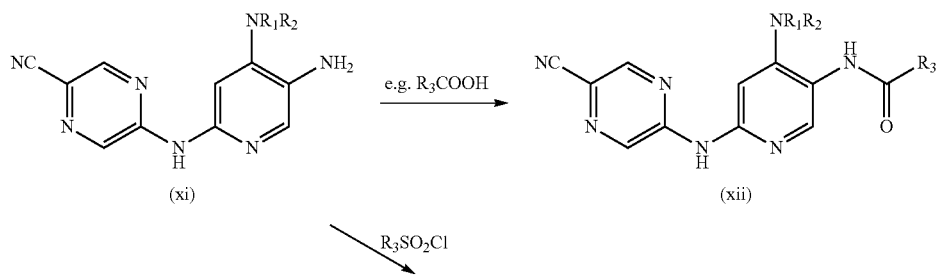

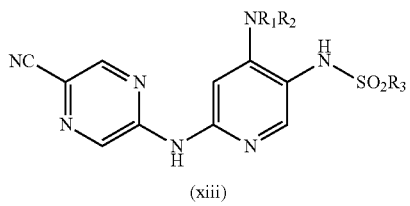

(xiii)

Treatment of amine (xi) with a sulphonyl chloride typically in the presence of a tertiary base such as triethylamine gives rise to sulphonamides (xiii).

In another approach (General Method E), compounds of type (xvi) are prepared by a method as illustrated in the following scheme. 2-Bromo-4-chloro-5-nitropyridine (viii) is treated with an alcohol and strong base such as sodium hydride, typically in DMF to afford intermediate (xiv). Treatment of this intermediate with 2-amino-5-cyanopyrazine (v) under palladium mediated amination conditions, typically with heating and in the presence of base, gives diarylamine (xv). Reduction of the nitro group using tin (II) chloride or a metal/acid mixture followed by removal of any protecting groups on the alcohol component then provides compound (xvi).

-continued

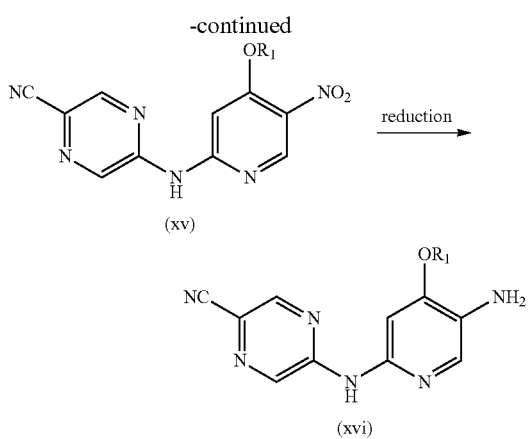

In another approach (General Method F), compounds of type (xvii) are prepared by a method as illustrated in the following scheme. Amine (xvi) is treated with an acid under standard amide formation conditions using an activating agent such as EDC. Alternatively, the amine is treated with an anhydride or other form of activated acid. Removal of any protecting groups on the amine component then gives amides (xvii).

Scheme 6

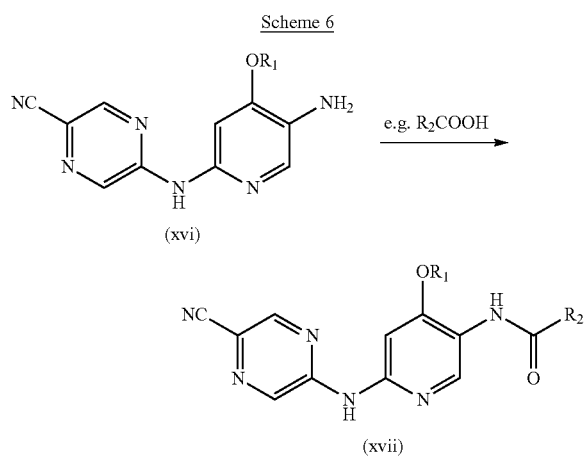

In another approach (General Method G), compounds of type (xxi) are prepared by a method as illustrated in the following scheme. Treatment of dichloropyrimidine (i) with an amine, typically with heating and in the presence of a tertiary base, provides intermediate (xviii). Sonagashira coupling of 2-bromo-5-aminopyrazine (xix) and an alkyne gives amine (xx). Treatment of intermediate (xviii) with (xx) under palladium mediated amination conditions, typically with heating and in the presence of base gives, after removal of any protecting groups, biarylamines (xxi).

Scheme 7

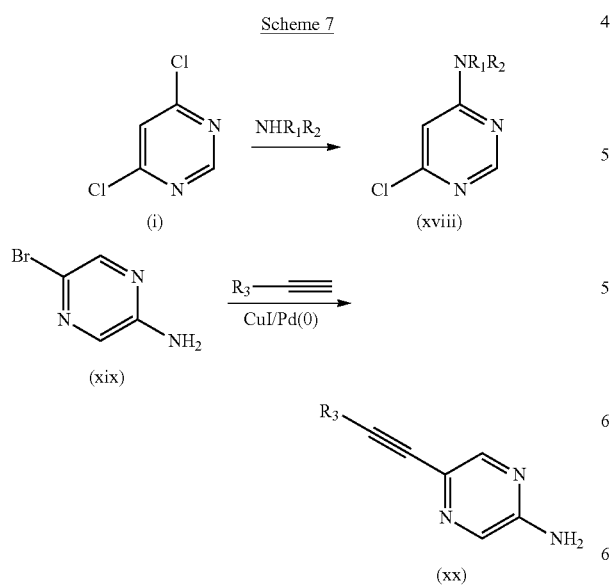

In another approach (General Method H), compounds of type (xxii) are prepared by a method as illustrated in the following scheme. Nitriles (vii) are treated with trifluoroacetic acid, typically with heating, to provide primary amides (xxii).

Scheme 8

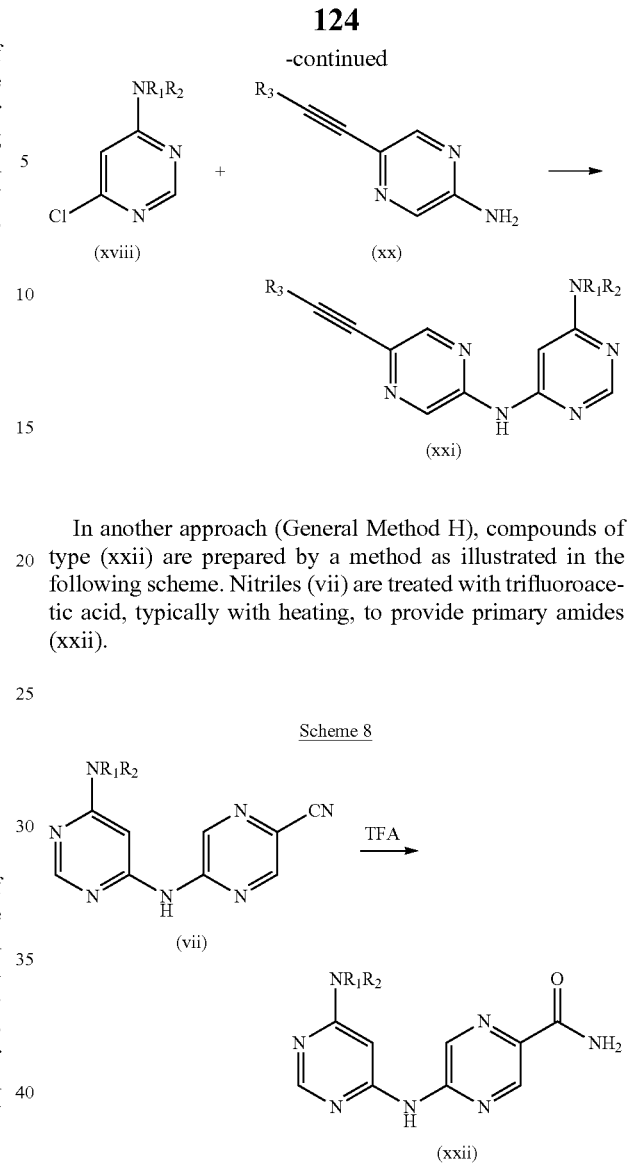

In another approach (General Method I), compounds of type (xxv) are prepared by a method as illustrated in the following scheme. 2,4-Dichloropyridine-5-carboxylates (xxiii) are treated with amines, typically with oil bath or microwave heating, and typically in the presence of a tertiary amine base, to provide pyridines (xxiv). Treatment of intermediates (xxiv) with (v) under palladium mediated amination conditions, typically with heating and in the presence of base gives, after removal of any protecting groups, biarylamines (xxv).

Scheme 9

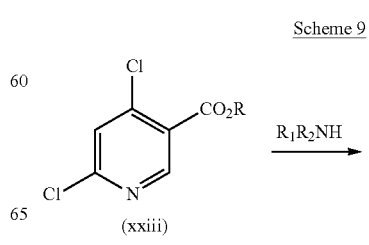

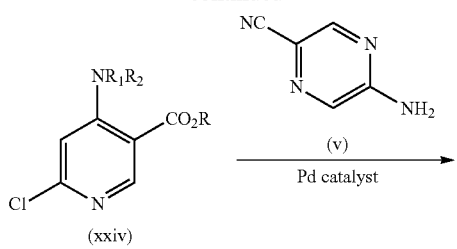

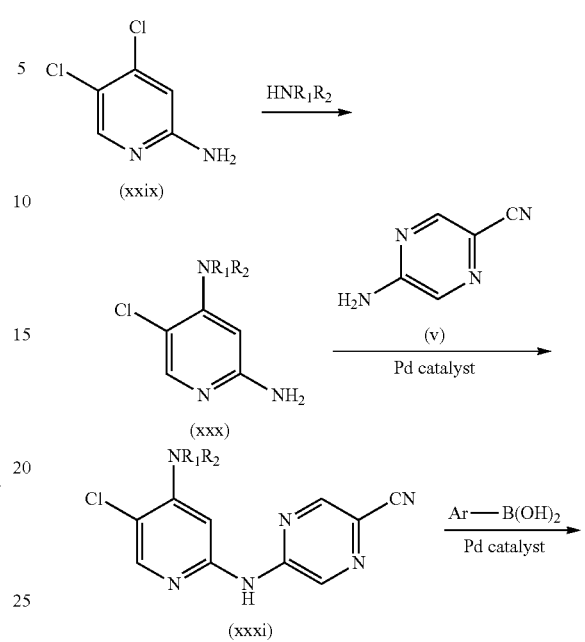

Scheme 11

In another approach (General Method J), compounds of type (xxviii) are prepared by a method as illustrated in the following scheme. Esters (xxvi) are hydrolysed to the acids (xxvii) with alkoxides, typically lithium hydroxide. The acids (xxvii) are treated with an amine under standard amide formation conditions using an activating agent such as TBTU.

Scheme 10

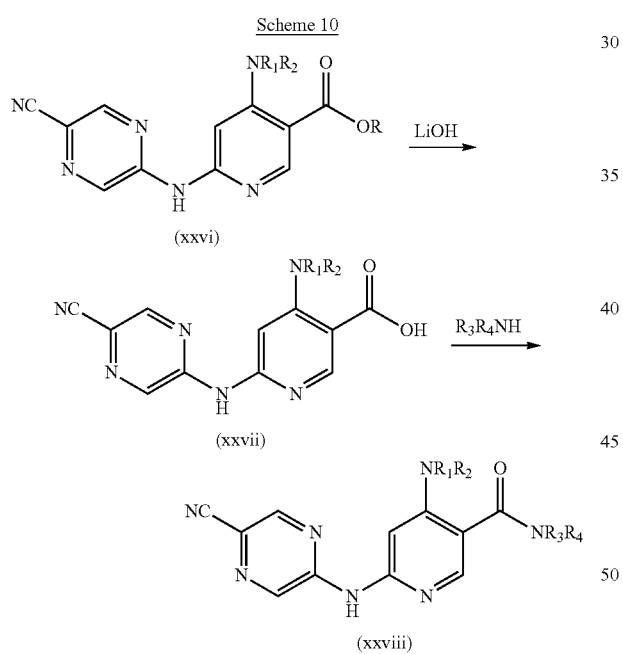

In another approach (General Method K), compounds of type (xxxii) are prepared by a method as illustrated in the following scheme. 2-Amino-4,5-dichloropyridine (xxix) is treated with an amine, typically with oil bath or microwave heating, to give the 5-chloropyridine (xxx). Treatment of intermediate (xxx) with (v) under palladium mediated amination conditions, typically with heating and in the presence of base gives intermediate (xxxi). Treatment of the intermediate (xxxi) with an arylboronic acid or arylboronic ester under palladium mediated cross-coupling conditions, typically with heating and in the presence of base gives, after removal of any protecting groups, biarylamines (xxxii).

In another approach (General Method L), compounds of type (xxxiv) are prepared by a method as illustrated in the following scheme. 2,4-Dichloropyridine-5-carboxylates (xxiii) are treated with amines, typically with oil bath or microwave heating, and typically in the presence of a tertiary amine base, to provide pyridines (xxiv). Treatment of intermediates (xxiv) with commercially available 2-amino-5-methylpyrazine (xxxiii) under palladium mediated amination conditions, typically with heating and in the presence of base gives, after removal of any protecting groups, biarylamines (xxxiv).

Scheme 12

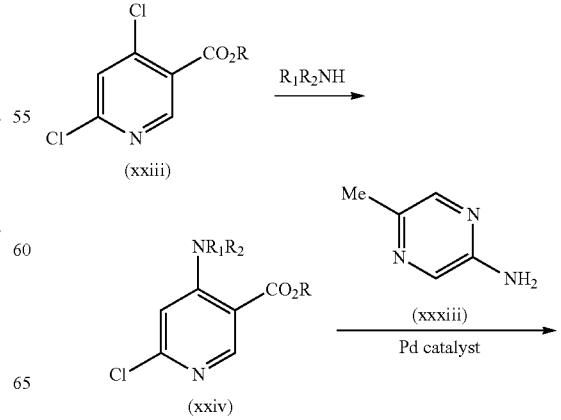

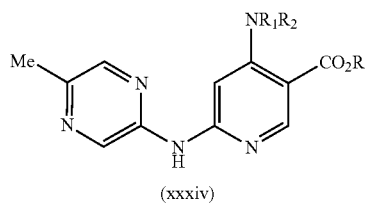

(xxxiv)

Scheme 14

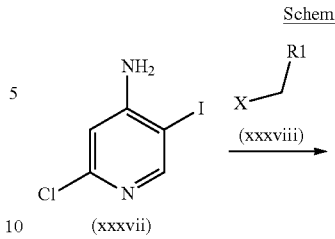

In another approach, (General Method M), compounds of type (xxxvi) are prepared by a method as illustrated in the following scheme. 2,4-Dichloropyridine-5-carboxylates (xxiii) are treated with amines, typically with oil bath or microwave heating, and typically in the presence of a tertiary amine base, to provide pyridines (xxiv). Treatment of intermediates (xxiv) with 2-amino-5-methoxypyrazine (xxxv) under palladium mediated amination conditions, typically with heating and in the presence of base gives, after removal of any protecting groups, biarylamines (xxxvi).

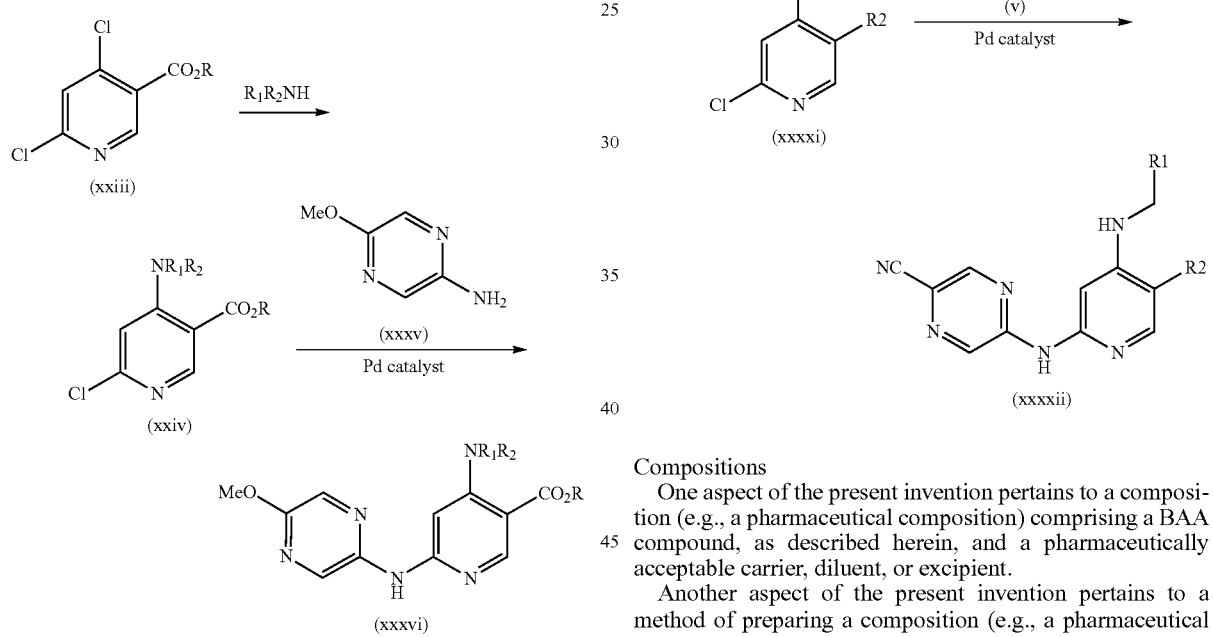

In another approach (General Method N), compounds of type (xxxxii) are prepared by a method illustrated in the following scheme. 2-Chloro-4-amino-5-iodopyridine (xxxvii) is alkylated with alkyl halides or alkyl tosylates (xxxviii) in the presence of a strong base, for example sodium hydride, typically with heating. The intermediates (xxxix) are treated with an aryl or alkenyl boronic acid (xxxx) in the presence of a palladium catalyst and base, typically palladium (0) tetrakis (triphenylphosphine) and sodium carbonate, in a suitable solvent such as acetonitrile, with oil bath or microwave heating, to give the intermediates (xxxxi). The intermediates (xxxxi) are reacted with 2-amino-4-cyanopyrazine (v) under palladium mediated amination conditions, typically with heating and in the presence of base, to give, after removal of any protecting groups, biarylamines (xxxxii).

Compositions

One aspect of the present invention pertains to a composition (e.g., a pharmaceutical composition) comprising a BAA compound, as described herein, and a pharmaceutically acceptable carrier, diluent, or excipient.

Another aspect of the present invention pertains to a method of preparing a composition (e.g., a pharmaceutical composition) comprising admixing a BAA compound, as described herein, and a pharmaceutically acceptable carrier, diluent, or excipient.

Uses

The compounds described herein are useful, for example, in the treatment of diseases and conditions that are ameliorated by the inhibition of CHK1 kinase function, such as, for example, proliferative conditions, cancer, etc.

Use in Methods of Inhibiting CHK1

One aspect of the present invention pertains to a method of inhibiting CHK1 kinase function, in vitro or in vivo, comprising contacting a CHK1 kinase with an effective amount of a BAA compound, as described herein.

One aspect of the present invention pertains to a method of inhibiting CHK1 kinase function in a cell, in vitro or in vivo, comprising contacting the cell with an effective amount of a BAA compound, as described herein.

In one embodiment, the method further comprises contacting the cell with one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

Suitable assays for determining CHK1 kinase function inhibition are described herein and/or are known in the art.

Use in Methods of Inhibiting Cell Proliferation, Etc.

The BAA compounds described herein, e.g., (a) regulate (e.g., inhibit) cell proliferation; (b) inhibit cell cycle progression; (c) promote apoptosis; or (d) a combination of one or more of these.

One aspect of the present invention pertains to a method of regulating (e.g., inhibiting) cell proliferation (e.g., proliferation of a cell), inhibiting cell cycle progression, promoting apoptosis, or a combination of one or more these, in vitro or in vivo, comprising contacting a cell with an effective amount of a BAA compound, as described herein.

In one embodiment, the method is a method of regulating (e.g., inhibiting) cell proliferation (e.g., proliferation of a cell), in vitro or in vivo, comprising contacting a cell with an effective amount of a BAA compound, as described herein.

In one embodiment, the method further comprises contacting the cell with one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

In one embodiment, the method is performed in vitro.

In one embodiment, the method is performed in vivo.

In one embodiment, the BAA compound is provided in the form of a pharmaceutically acceptable composition.

Any type of cell may be treated, including but not limited to, lung, gastrointestinal (including, e.g., bowel, colon), breast (mammary), ovarian, prostate, liver (hepatic), kidney (renal), bladder, pancreas, brain, and skin.

One of ordinary skill in the art is readily able to determine whether or not a candidate compound regulates (e.g., inhibits) cell proliferation, etc. For example, assays which may conveniently be used to assess the activity offered by a particular compound are described herein.

For example, a sample of cells (e.g., from a tumour) may be grown in vitro and a compound brought into contact with said cells, and the effect of the compound on those cells observed. As an example of "effect," the morphological status of the cells (e.g., alive or dead, etc.) may be determined. Where the compound is found to exert an influence on the cells, this may be used as a prognostic or diagnostic marker of the efficacy of the compound in methods of treating a patient carrying cells of the same cellular type.

Use in Methods of Therapy

Another aspect of the present invention pertains to a BAA compound, as described herein, for use in a method of treatment of the human or animal body by therapy.

In one embodiment, the method of treatment comprises treatment with both (i) a BAA compound, as described herein, and (ii) one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

Another aspect of the present invention pertains to (a) a DNA topoisomerase I or II inhibitor, (b) a DNA damaging agent, (c) an antimetabolite or TS inhibitor, or (d) a microtubule targeted agent, as described herein, for use in a method of treatment of the human or animal body by therapy, wherein the method of treatment comprises treatment with both (i) a BAA compound, as described herein, and (a) the DNA topoisomerase I or II inhibitor, (b) the DNA damaging agent, (c) the antimetabolite or TS inhibitor, or (d) the microtubule targeted agent.

Use in the Manufacture of Medicaments

Another aspect of the present invention pertains to use of a BAA compound, as described herein, in the manufacture of a medicament for use in treatment.

In one embodiment, the medicament comprises the BAA compound.

In one embodiment, the treatment comprises treatment with both (i) a medicament comprising a BAA compound, as described herein, and (ii) one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

Another aspect of the present invention pertains to use of (a) a DNA topoisomerase I or II inhibitor, (b) a DNA damaging agent, (c) an antimetabolite or TS inhibitor, or (d) a microtubule targeted agent, as described herein, in the manufacture of a medicament for use in a treatment, wherein the treatment comprises treatment with both (i) a BAA compound, as described herein, and (a) the DNA topoisomerase I or II inhibitor, (b) the DNA damaging agent, (c) the antimetabolite or TS inhibitor, or (d) the microtubule targeted agent.

Methods of Treatment

Another aspect of the present invention pertains to a method of treatment comprising administering to a patient in need of treatment a therapeutically effective amount of a BAA compound, as described herein, preferably in the form of a pharmaceutical composition.

In one embodiment, the method further comprises administering to the subject one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

Conditions Treated—Conditions Mediated by CHK1

In one embodiment (e.g., of use in methods of therapy, of use in the manufacture of medicaments, of methods of treatment), the treatment is treatment of a disease or condition that is mediated by CHK1.

Conditions Treated—Conditions Ameliorated by the Inhibition of CHK1 Kinase Function In one embodiment (e.g., of use in methods of therapy, of use in the manufacture of medicaments, of methods of treatment), the treatment is treatment of: a disease or condition that is ameliorated by the inhibition of CHK1 kinase function.

Conditions Treated—Proliferative Conditions and Cancer

In one embodiment (e.g., of use in methods of therapy, of use in the manufacture of medicaments, of methods of treatment), the treatment is treatment of: a proliferative condition.

The term "proliferative condition," as used herein, pertains to an unwanted or uncontrolled cellular proliferation of excessive or abnormal cells which is undesired, such as, neoplastic or hyperplastic growth.

In one embodiment, the treatment is treatment of: a proliferative condition characterised by benign, pre-malignant, or malignant cellular proliferation, including but not limited to, neoplasms, hyperplasias, and tumours (e.g., histocytoma, glioma, astrocyoma, osteoma), cancers (see below), psoriasis, bone diseases, fibroproliferative disorders (e.g., of connective tissues), pulmonary fibrosis, atherosclerosis, smooth muscle cell proliferation in the blood vessels, such as stenosis or restenosis following angioplasty.

In one embodiment, the treatment is treatment of: cancer.

In one embodiment, the treatment is treatment of: p53 negative cancer.

In one embodiment, the treatment is treatment of: lung cancer, small cell lung cancer, non-small cell lung cancer, gastrointestinal cancer, stomach cancer, bowel cancer, colon cancer, rectal cancer, colorectal cancer, thyroid cancer, breast cancer, ovarian cancer, endometrial cancer, prostate cancer, testicular cancer, liver cancer, kidney cancer, renal cell carcinoma, bladder cancer, pancreatic cancer, brain cancer, glioma, sarcoma, osteosarcoma, bone cancer, nasopharyngeal cancer (e.g., head cancer, neck cancer), skin cancer, squamous cancer, Kaposi's sarcoma, melanoma, malignant melanoma, lymphoma, or leukemia.

In one embodiment, the treatment is treatment of:

a carcinoma, for example a carcinoma of the bladder, breast, colon (e.g., colorectal carcinomas such as colon adenocarcinoma and colon adenoma), kidney, epidermal, liver, lung (e.g., adenocarcinoma, small cell lung cancer and non-small cell lung carcinomas), oesophagus, gall bladder, ovary, pancreas (e.g., exocrine pancreatic carcinoma), stomach, cervix, thyroid, prostate, skin (e.g., squamous cell carcinoma);

a hematopoietic tumour of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma;

a hematopoietic tumor of myeloid lineage, for example acute and chronic myelogenous leukemias, myelodysplastic syndrome, or promyelocytic leukemia;

a tumour of mesenchymal origin, for example fibrosarcoma or habdomyosarcoma;

a tumor of the central or peripheral nervous system, for example astrocytoma, neuroblastoma, glioma or schwannoma;

melanoma; seminoma; teratocarcinoma; osteosarcoma; xenoderoma pigmentoum; keratoctanthoma; thyroid follicular cancer; or Kaposi's sarcoma.

In one embodiment, the treatment is treatment of solid tumour cancer.

In one embodiment, the treatment is treatment of: lung cancer, breast cancer, ovarian cancer, colorectal cancer, melanoma, or glioma.

The anti-cancer effect may arise through one or more mechanisms, including but not limited to, the regulation of cell proliferation, the inhibition of cell cycle progression, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death). The compounds of the present invention may be used in the treatment of the cancers described herein, independent of the mechanisms discussed herein.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, alleviatiation of symptoms of the condition, amelioration of the condition, and cure of the condition. Treatment as a prophylactic measure (i.e., prophylaxis) is also included. For example, use with patients who have not yet developed the condition, but who are at risk of developing the condition, is encompassed by the term "treatment."

For example, treatment includes the prophylaxis of cancer, reducing the incidence of cancer, alleviating the symptoms of cancer, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents, for example, cytotoxic agents, anticancer agents, etc. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; photodynamic therapy; gene therapy; and controlled diets.

For example, it may be beneficial to combine treatment with a compound as described herein with one or more other (e.g., 1, 2, 3, 4) agents or therapies that regulates cell growth or survival or differentiation via a different mechanism, thus treating several characteristic features of cancer development.

One aspect of the present invention pertains to a compound as described herein, in combination with one or more additional therapeutic agents, as described below.

The particular combination would be at the discretion of the physician who would select dosages using his common general knowledge and dosing regimens known to a skilled practitioner.

The agents (i.e., the compound described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound described here, plus one or more other agents) may be formulated together in a single dosage form, or alternatively, the individual agents may be formulated separately and presented together in the form of a kit, optionally with instructions for their use.

Combination Therapies Employing DNA Damaging Agents

As discussed herein, in some embodiments, the BAA compound is employed in combination with (e.g., in conjunction with) with one or more other agents selected from: (a) a DNA topoisomerase I or II inhibitor; (b) a DNA damaging agent; (c) an antimetabolite or TS inhibitor; (d) a microtubule targeted agent; and (e) ionising radiation.

When both a BAA compound and one or more other agents are employed, they may be used (e.g., contacted, administered, etc.) in any order. Furthermore, they may be used (e.g., contacted, administered, etc.) together, as part of a single formulation, or separately, as separate formulations.

For example, in regard to methods of treatment employing both a BAA compound and one or more other agents, treatment with (e.g., administration of) the BAA compound may be prior to, concurrent with, or may follow, treatment with (e.g., administration of) the one or more other agents, or a combination thereof.

In one embodiment, treatment with (e.g., administration of) a BAA compound is concurrent with, or follows, treatment with (e.g., administration of) the one or more other agents.

In one embodiment, the one or more other agents is a DNA topoisomerase I or II inhibitor; for example, Etoposide, Toptecan, Camptothecin, Irinotecan, SN-38, Doxorubicin, Daunorubicin.

In one embodiment, the one or more other agents is a DNA damaging agent; for example, alkylating agents, platinating agents, or compounds that generate free radicals; for example, Temozolomide, Cisplatin, Carboplatin, Mitomycin C, Cyclophosphamide, BCNU, CCNU, Bleomycin.

In one embodiment, the one or more other agents is an antimetabolite or TS inhibitor; for example, 5-fluorouracil, hydroxyurea, Gemcitabine, Arabinosylcytosine, Fludarabine, Tomudex, ZD9331.

In one embodiment, the one or more other agents is a microtubule targeted agent; for example, Paclitaxel, Docetaxel, Vincristine, Vinblastine.

In one embodiment, the one or more other agents is ionising radiation (e.g., as part of radiotherapy).

Other Uses

The BAA compounds described herein may also be used as cell culture additives to inhibit CHK1 kinase function, e.g., to inhibit cell proliferation, etc.

The BAA compounds described herein may also be used as part of an in vitro assay, for example, in order to determine whether a candidate host is likely to benefit from treatment with the compound in question.

The BAA compounds described herein may also be used as a standard, for example, in an assay, in order to identify other compounds, other CHK1 kinase function inhibitors, other anti-proliferative agents, other anti-cancer agents, etc.

Kits

One aspect of the invention pertains to a kit comprising (a) a BAA compound as described herein, or a composition comprising a BAA compound as described herein, e.g., preferably provided in a suitable container and/or with suitable packaging; and (b) instructions for use, e.g., written instructions on how to administer the compound or composition.

In one embodiment, the kit further comprises one or more other agents selected from: (a) a DNA topoisomerase I or II inhibitor; (b) a DNA damaging agent; (c) an antimetabolite or TS inhibitor; and (d) a microtubule targeted agent.

The written instructions may also include a list of indications for which the active ingredient is a suitable treatment.

Routes of Administration

The BAA compound or pharmaceutical composition comprising the BAA compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

Formulations

While it is possible for the BAA compound to be administered alone, it is preferable to present it as a pharmaceutical formulation (e.g., composition, preparation, medicament) comprising at least one BAA compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one BAA compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences,* 18th edition, Mack Publishing Company, Easton, Pa., 1990; and *Handbook of Pharmaceutical Excipients,* 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or admixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the compound in a flavored basis, usually sucrose and acacia or tragacanth.

Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringers Solution, or Lactated Ringer's Injection. Typically, the concentration of the compound in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the BAA compounds, and compositions comprising the BAA compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular BAA compound, the route of administration, the time of administration, the rate of excretion of the BAA compound, the duration of the treatment, other drugs, compounds, and/or materials used in combination, the severity of the condition, and the species, sex, age, weight, condition, general health, and prior medical history of the patient. The amount of BAA compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the BAA compound is in the range of about 10 µg to about 250 mg (more typically about 100 µg to about 25 mg) per kilogram body weight of the subject per day. Where the compound is a salt, an ester, an amide, a prodrug, or the like, the amount administered is calculated on the basis of the parent compound and so the actual weight to be used is increased proportionately.

EXAMPLES

The following examples are provided solely to illustrate the present invention and are not intended to limit the scope of the invention, as described herein.

Chemical Synthesis

Liquid Chromatography-Mass Spectrometry (LC-MS) Methods

LC-MS (1) analyses were performed on a Micromass ZQ mass spectrometer/Waters Alliance 2795 HT HPLC with a Phenomenex Gemini 3 µm, C18, 30 mm×3 mm i.d. column at a temperature of 35° C. using the following solvent gradient and flow rates:

Solvent A: 0.02% Ammonia and 0.063% ammonium formate in water

Solvent B: 0.02% Ammonia and 5% Solvent A in acetonitrile.

0.00 to 2.50 minutes 95% A/5% B to 5% A/95% B (1.2 mL/minute)

2.50 to 2.75 minutes 5% A/95% B (1.2 mL/minute)

2.75 to 3.50 minutes 5% A/95% B (2.0 mL/minute)

3.50 to 3.65 minutes 5% A/95% B to 95% A/5% B (2.0 mL/minute)

3.65 to 4.00 minutes 95% A/5% B (1.2 mL/minute)

UV detection was at 220-400 nm using a Waters 996 photodiode array UV detector and ionisation was by positive or negative ion electrospray. Molecular weight scan range was 80-1000 amu.

LC-MS (2) analyses were performed on a Micromass ZQ mass spectrometer/Waters Alliance 2795 HT HPLC with a Phenomenex Gemini 5 µm, C18, 30 mm×4.6 mm i.d. column at a temperature of 35° C. and a flow rate of 2 mL/minute using the following solvent gradient:

Solvent A: 0.02% Ammonia and 0.063% ammonium formate in water

Solvent B: 0.02% Ammonia and 5% Solvent A in acetonitrile.

0.00 to 4.25 min 95% A/5% B to 5% A/95% B 4.25 to 5.80 min 5% A/95% B 5.80 to 5.90 min 5% A/95% B to 95% A/5% B 5.90 to 7.00 min 95% A/5% B UV detection was at 220-400 nm using a Waters 996 photodiode array UV detector and ionisation was by positive or negative ion electrospray. Molecular weight scan range was 80-1000 amu.

LC-MS (3) analyses were performed on a Micromass LCT/Waters Alliance 2795 HPLC system with a Discovery 5 µm, C18, 50 mm×4.6 mm or 30 mm×4.6 mm i.d. column from Supelco at a temperature of 22° C. and a flow rate of 1 mL/minute using the following solvent gradient:

Solvent A: Methanol.

Solvent B: 0.1% Formic acid in water.

0.0-0.3 minutes: 10% A/90% B.

0.3-0.6 minutes: 10% A/90% B to 20% A/80% B.

0.6-4.5 minutes: 20% A/80% B to 90% A/10% B.

4.5-5.4 minutes: 90% A/10% B.

5.4-5.7 minutes: 90% A/10% B to 10% A/90%.B.

5.7-6.0 minutes: 10% A/90% B.

UV detection was at 254 nm and ionisation was by positive or negative ion electrospray. Molecular weight scan range was 50-1000 amu.

LC-MS (3B) analyses were performed on a Micromass LCT/Waters Alliance 2795 HPLC system with a Phenomenex Gemini 3 μm, C18, 30 mm×4.6 mm i.d. column at a temperature of 30° C. and a flow rate of 1 mL/minute using the following solvent gradient:

Solvent A: Methanol.
Solvent B: 0.1% Formic acid in water.
0.0-0.3 minutes: 10% A/90% B.
0.3-0.6 minutes: 10% A/90% B to 20% A/80% B.
0.6-4.5 minutes: 20% A/80% B to 90% A/10% B.
4.5-5.4 minutes: 90% A/10% B.
5.4-5.7 minutes: 90% A/10% B to 10% A/90%.B.
5.7-6.0 minutes: 10% A/90% B.

UV detection was at 254 nm using a Waters 2487 photodiode array UV detector and ionisation was by positive or negative ion electrospray. Molecular weight scan range was 50-1000 amu.

LC-MS (4) analyses were performed on a Micromass LCT/Waters Alliance 2795 HPLC system with a Merck Chromolith SpeedROD RP-18e, 50 mm×4.6 mm column at a temperature of 25° C. and a flow rate of 2 mL/minute using the following solvent gradient:

Solvent A: Methanol.
Solvent B: 0.1% Formic acid in water.
0.0-2.25 minutes: 10% A/90% B to 90% A/10% B.
2.25-3.0 minutes: 90% A/10% B.
3.0-3.3 minutes: 90% A/10% B to 10% A/90% B.
3.3-3.5 minutes: 10% A/90% B.

UV detection was at 254 nm using a Waters 2487 photodiode array UV detector and ionisation was by positive or negative ion electrospray. Molecular weight scan range was 50-1000 amu.

Synthesis 1-A

6-Chloro-N-(pyrazin-2-yl)pyrimidin-4-amine

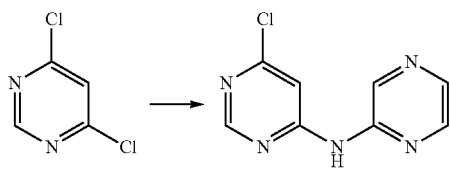 [SMILES: Clc1cc(Cl)ncn1 ; Clc1cc(Nc2cnccn2)ncn1]

A mixture of 2-aminopyrazine (230 mg, 2.42 mmol), sodium tert-butoxide (232 mg, 2.42 mmol) and bis(tri-t-butylphosphine)palladium (0) (51 mg, 0.1 mmol) in toluene (2 mL) was degassed under a stream of nitrogen over 10 min. 4,6-Dichloropyrimidine (300 mg, 2.01 mmol) was added to the mixture and the reaction was heated at 80° C. for 2 h. After cooling, the solution was passed through a PS-SH cartridge and the solvent removed in vacuo. The residue was triturated with dichloromethane and the resulting solid was collected and dried by vacuum filtration to give crude 6-chloro-N-(pyrazin-2-yl)pyrimidin-4-amine (333 mg) which was used without further purification.

LCMS (2) Rt=1.65 min; m/z (ESI$^+$) 208 (MH$^+$).

Synthesis 1-B

N-(6-(4-(aminomethyl)piperidin-1-yl)pyrimidin-4-yl)pyrazin-2-amine (Z-001)

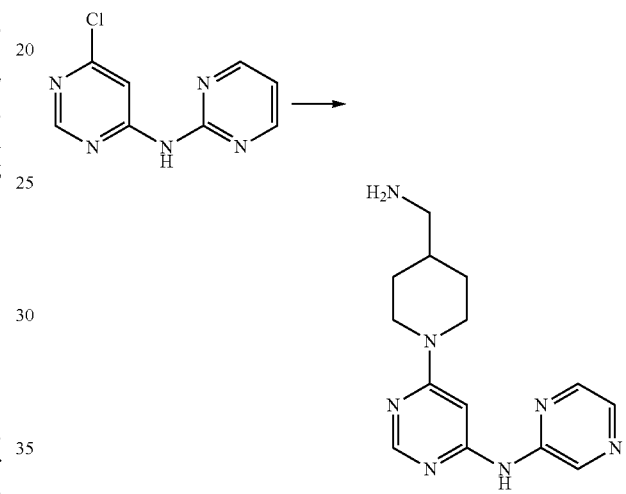

A mixture of 6-chloro-N-(pyrazin-2-yl)pyrimidin-4-amine (20 mg, 0.096 mmol), tert-butyl N-(4-piperidinylmethyl)carbamate (41 mg, 0.193 mmol) and triethylamine (27 μL, 0.193 mmol) in 1-methyl-2-pyrrolidinone (1 mL) was heated at 140° C. for 10 minutes using microwave irradiation. The mixture was concentrated in vacuo and the residue purified using preparative HPLC. The purified solid was dissolved in dichloromethane (4 mL) and treated with trifluoroacetic acid (4 mL) for 1 hour at room temperature. The solution was applied to a MP-TsOH SPE cartridge, washed, then eluted with 2N ammonia and concentrated to give N-(6-(4-(aminomethyl)piperidin-1-yl)pyrimidin-4-yl)pyrazin-2-amine (4.4 mg, 16%).

$^1$H NMR (DMSO-d$_6$, 400 MHz) δ 8.83 (d, 1H, J=1.3 Hz), 8.29 (dd, 1H, J=2.8, 1.3 Hz), 8.23 (d, 1H, J=1.0 Hz), 8.08 (d, 1H, J=2.8 Hz), 7.17 (d, 1H, J=1.0 Hz), 4.45 (d, 2H, J=10.9 Hz), 2.95 (m, 2H), 2.61 (d, 2H, J=6.7 Hz), 1.90 (d, 2H, J=12.3 Hz), 1.74 (m, 1H), 1.21 (m, 3H). LCMS (2) Rt=1.62 min; m/z (ESI$^+$) 286 [MH$^+$].

The following compounds were prepared in a similar manner to that described in Synthesis 1, using the appropriate protected or unprotected diamines in place of tert-butyl N-(4-piperidinylmethyl)carbamate in Synthesis 1-B.

Synthesis 2

N-(2-Aminoethyl)-N'-pyrazin-2-ylpyrimidine-4,6-diamine (Z-002)

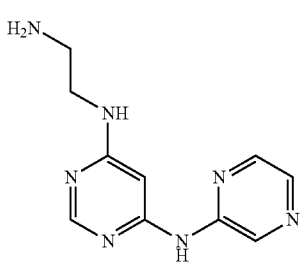

The title compound was prepared using methods analogous to those described in Synthesis 1, steps 1-A and 1-B.

$^1$H NMR (MeOD-d$_4$, 400 MHz) δ 8.69 (br s, 1H), 8.47 (dd, 1H, 1H, J=2.8, 1.5 Hz), 8.18 (d, 1H, J=1.0 Hz), 8.06 (d, 1H, J=2.8 Hz), 7.12 (br s, 1H), 3.44 (t, 2H, J=6.1 Hz), 2.89 (t, 2H, J=6.1 Hz). LCMS (2) Rt=1.10 min; m/z (ESI$^+$) 232 (MH$^+$).

Synthesis 3

6-(4-Aminopiperidin-1-yl)-N-pyrazin-2-ylpyrimidin-4-amine (Z-003)

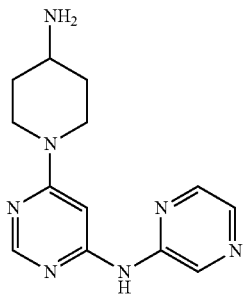 [SMILES: NC1CCN(c2cc(Nc3cnccn3)ncn2)CC1]

The title compound was prepared using methods analogous to those described in Synthesis 1, steps 1-A and 1-B.

$^1$H NMR (MeOD-d$_4$, 400 MHz) δ 8.80 (d, 1H, J=1.3 Hz), 8.27 (dd, 1H, J=2.8, 1.5 Hz), 8.21 (d, 1H, J=0.8 Hz), 8.05 (d, 1H, J=2.8 Hz), 7.15 (d, 1H, J=1.0 Hz), 4.37 (d, 2H, J=13.6 Hz), 3.01-2.94 (m, 3H), 1.95-1.91 (m, 2H), 1.40-1.29 (m, 2H). LCMS (2) Rt=1.43 min; m/z (ESI$^+$) 272 (MH$^+$).

Synthesis 4

N-(Piperidin-4-ylmethyl)-W-pyrazin-2-ylpyrimidine-4,6-diamine (Z-004)

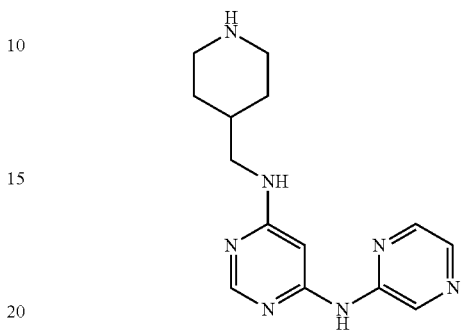

The title compound was prepared using methods analogous to those described in Synthesis 1, steps 1-A and 1-B.

$^1$H NMR (DMSO-d$_6$, 400 MHz) δ 9.7 (br s, 1H), 8.83 (s, 1H), 8.21 (dd, 1H, J=2.5, 1.5 Hz), 8.15 (d, 1H, J=0.8 Hz), 8.08 (d, 1H, J=2.5 Hz), 7.14 (br m, 1H), 6.90 (s, 1H), 3.1 (br m, 2H), 3.0 (br m, 2H), 2.4 (br m, 2H), 1.65-1.63 (m, 3H), 1.13-1.03 (m, 2H). LCMS (2) Rt=1.36 min; m/z (ESI$^+$) 286 (MH$^+$).

Synthesis 5

N-(3-Aminopropyl)-A-pyrazin-2-ylpyrimidine-4,6-diamine (Z-005)

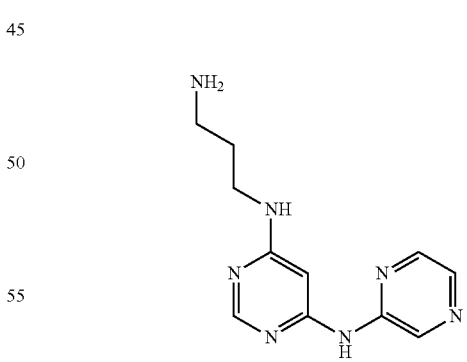

The title compound was prepared using methods analogous to those described in Synthesis 1, steps 1-A and 1-B.

$^1$H NMR (DMSO-d$_6$, 400 MHz) δ 8.84 (d, 1H, J=1.0 Hz), 8.22 (dd, 1H, J=2.5, 1.5 Hz), 8.18 (d, 1H, J=1.0 Hz), 8.08 (d, 1H, J=2.5 Hz), 7.31 (br s, 1H), 6.90 (s, 1H), 3.35-3.32 (m,

2H), 2.85-2.80 (m, 4H), 1.84-1.77 (m, 3H). LCMS (2) Rt=1.31 min; m/z (ESI⁺) 246 (MH⁺).

Synthesis 6

N-(4-Aminobutyl)-N'-pyrazin-2-ylpyrimidine-4,6-diamine (Z-006)

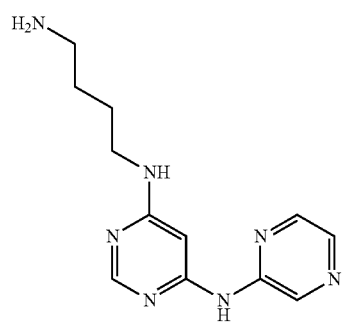 [SMILES: NCCCCNc1cc(Nc2cnccn2)ncn1]

The title compound was prepared using methods analogous to those described in Synthesis 1, steps 1A and 1B.

LCMS (2) Rt=1.21 min; m/z (ESI⁺) 260 (MH⁺).

Synthesis 7-A

5-(6-Chloropyrimidin-4-ylamino)pyrazine-2-carbonitrile

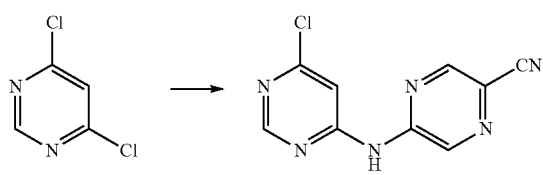 [SMILES: Clc1cc(Cl)ncn1 ; N#Cc1cnc(Nc2cc(Cl)ncn2)cn1]

A mixture of 4,6-dichloropyrimidine (1.00 g, 6.7 mmol), 2-amino-5-cyanopyrazine (806 mg, 6.7 mmol) and bis(triphenylphosphine)palladium (II) chloride (94 mg, 0.134 mmol) in dry THF (24 mL) was degassed under a stream of nitrogen gas for 10 minutes with stirring. Lithium bis(trimethylsilyl) amide in THF (1M, 7.38 mL, 7.4 mmol) was added and the mixture was heated at 135° C. for 20 minutes using microwave irradiation. The reaction mixture was adsorbed onto silica and purified by flash column chromatography, eluting with 30% ethyl acetate in hexane, to give 5-(6-chloropyrimidin-4-ylamino)pyrazine-2-carbonitrile (300 mg, 19%).

LCMS (1) Rt=1.64 min; m/z (ESI⁻) 231.

Synthesis 7-B

5-(6-(Piperidin-4-ylmethylamino)pyrimidin-4-ylamino)pyrazine-2-carbonitrile (Z-007)

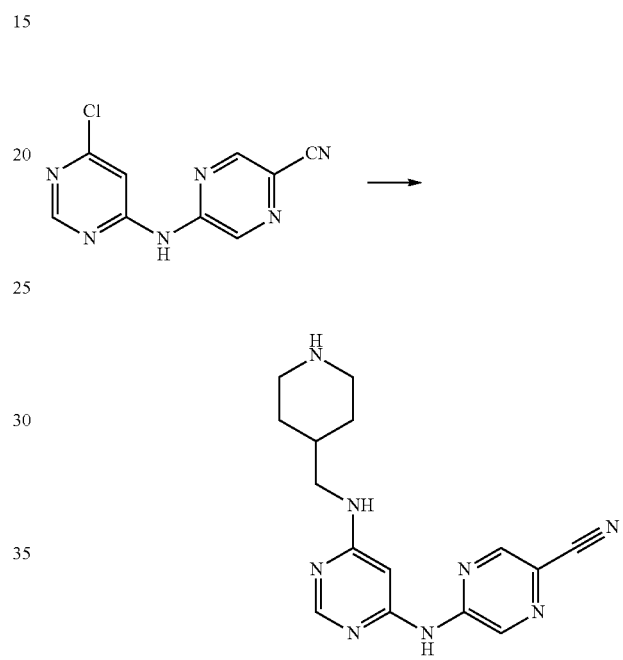

A mixture of 5-(6-chloropyrimidin-4-ylamino)pyrazine-2-carbonitrile (124 mg, 0.533 mmol), tert-butyl 4-(aminomethyl)piperidine-1-carboxylate (228 mg, 1.066 mmol) and triethylamine (150 µL, 1.07 mmol) in 1-methyl-2-pyrrolidinone (1 mL) was heated at 145° C. for 15 minutes using microwave irradiation. The mixture was concentrated in vacuo and the residue purified by preparative HPLC. The purified solid was dissolved in dichloromethane (2 mL) and trifluoroacetic acid (3 mL) and was stirred for 1 hour at room temperature before being applied to a MP-TsOH cartridge. After washing with methanol, the pure product was eluted using 7M ammonia to give 5-(6-(piperidin-4-ylmethylamino)pyrimidin-4-ylamino)pyrazine-2-carbonitrile (10.3 mg, 6%).

¹H NMR (DMSO-d₆, 400 MHz) δ 8.79 (br s, 1H), 8.62 (s, 1H), 8.21 (s, 1H), 7.14 (br s, 1H), 3.26 (br s, 1H), 3.18 (m, 2H), 2.71 (m, 2H), 1.85 (m, 4H), 1.30 (m, 3H).

The following compounds were prepared in a similar manner to that described in Synthesis 7, using the appropriate protected or unprotected diamines in place of tert-butyl 4-(aminomethyl)piperidine-1-carboxylate in Synthesis 7-B.

Synthesis 8

5-(6-(4-Aminopiperidin-1-yl)pyrimidin-4-ylamino)pyrazine-2-carbonitrile (Z-008)

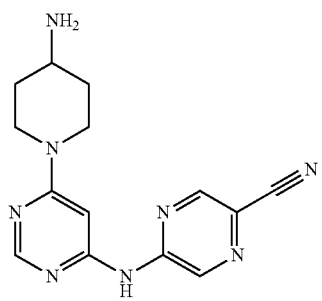 [SMILES: N#Cc1cnc(Nc2cc(N3CCC(N)CC3)ncn2)cn1]

The title compound was prepared using methods analogous to those described in Synthesis 7, steps 7-A and 7-B.

$^1$H NMR (DMSO-$d_6$, 400 MHz) δ 9.00 (d, 1H, J=1.3 Hz), 8.82 (d, 1H, J=1.0 Hz), 8.33 (s, 1H), 7.16 (s, 1H), 4.21 (br d, 2H, J=13.4 Hz), 3.05-2.91 (m, 3H), 1.80 (br d, 2H, J=12.6 Hz), 1.21 (m, 2H). LCMS (2) Rt=1.84 min; m/z (ESI$^+$) 297 (MH$^+$), (ESI$^-$) 295

Synthesis 9

2-((2-Aminoethyl)(6-(5-cyanopyrazin-2-ylamino)pyrimidin-4-yl)amino)acetamide (Z-009)

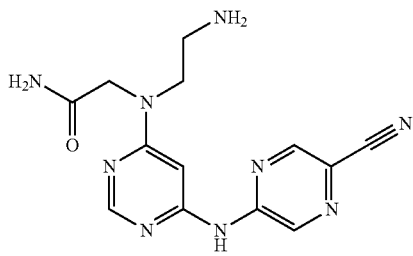 [SMILES: N#Cc1cnc(Nc2cc(N(CCN)CC(N)=O)ncn2)cn1]

The title compound was prepared using methods analogous to those described in Synthesis 7, steps 7-A and 7-B.

$^1$H NMR (DMSO-$d_6$, 400 MHz) δ 9.01 (br s, 2H), 9.00 (d, 1H, J=1.5 Hz), 8.85 (d, 1H, J=1.5 Hz), 8.77 (br s, 2H), 8.38 (d, 1H, J=0.8 Hz), 8.33 (br s, 2H), 8.25 (br s, 1H), 7.09 (s, 1H), 4.03 (s, 2H), 3.78 (t, 2H, J=5.8 Hz), 2.92 (t, 2H, J=6.5 Hz). LCMS (2) Rt=1.30 min; m/z (ESI$^+$) 314 (MH$^+$), (ESI$^-$) 312.

Synthesis 10

(S)-2-Amino-5-(6-(5-cyanopyrazin-2-ylamino)pyrimidin-4-ylamino)-N-phenylpentanamide (Z-010)

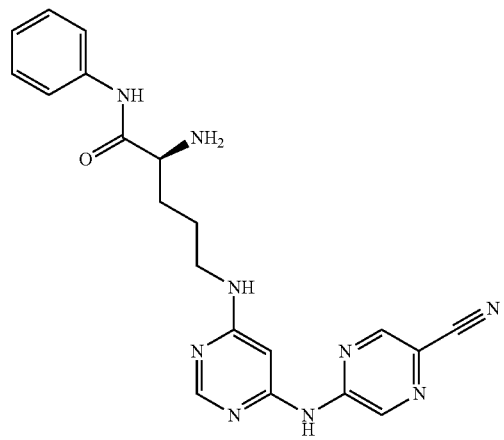 [SMILES: N#Cc1cnc(Nc2cc(NCCC[C@H](N)C(=O)Nc3ccccc3)ncn2)cn1]

The title compound was prepared using methods analogous to those described in Synthesis 7, steps 7-A and 7-B.

$^1$H NMR (DMSO-$d_6$, 400 MHz) δ 8.85 (br s, 1H), 8.77 (s, 1H), 8.22 (s, 1H), 7.62 (d, 2H, J=7.5 Hz), 7.54 (s, 1H), 7.30 (t, 2H, J=7.6 Hz), 7.05 (t, 1H, J=7.3 Hz), 7.03 (m, 1H), 3.38 (m, 5H), 1.75-1.47 (m, 4H). LCMS (2) Rt=2.11 min; m/z (ESI$^+$) 404 (MH$^+$), (ESI$^-$) 402.

Synthesis 11

(S)-2-Amino-N-benzyl-5-(6-(5-cyanopyrazin-2-ylamino)pyrimidin-4-ylamino)pentanamide (Z-011)

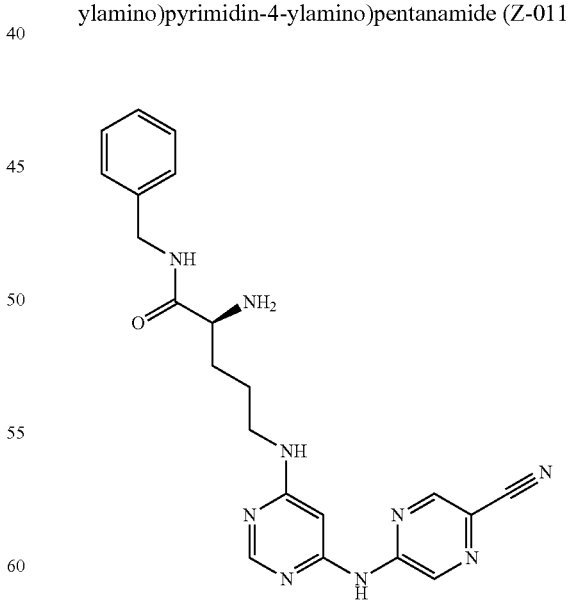

The title compound was prepared using methods analogous to those described in Synthesis 7, steps 7-A and 7-B.

$^1$H NMR (DMSO-$d_6$, 400 MHz) δ 8.85 (br s, 1H), 8.78 (s, 1H), 8.37 (t, 1H, J=6.1 Hz), 8.23 (s, 1H), 7.53 (br s, 1H), 7.31-7.19 (m, 6H), 7.03 (br s, 1H), 4.28 (d, 2H, J=5.8 Hz), 3.21 (m, 3H), 1.69-1.38 (m, 4H). LCMS (2) Rt=2.05 min; m/z (ESI⁺) 418 (MH⁺), 440 (MNa⁺), (ESI⁻) 416.

Synthesis 12

5-(6-(Piperidin-4-ylamino)pyrimidin-4-ylamino)pyrazine-2-carbonitrile (Z-012)

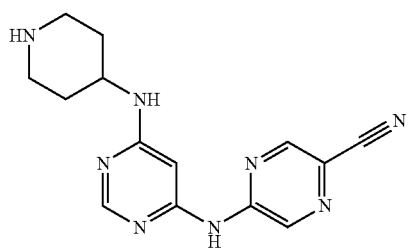 [SMILES: N#Cc1cnc(Nc2cc(NC3CCNCC3)ncn2)cn1]

The title compound was prepared using methods analogous to those described in Synthesis 7, steps 7-A and 7-B.

¹H NMR (DMSO-d₆, 400 MHz) δ 8.84 (br s, 1H), 8.77 (s, 1H), 8.23 (s, 1H), 7.48 (br s, 1H), 7.01 (br s, 1H), 3.89 (br s, 1H), 2.96 (d, 2H, J=12.6 Hz), 2.54 (m, 2H), 1.79 (d, 2H, J=12.3 Hz), 1.31 (m, 2H). LCMS (2) Rt=1.80 min; m/z (ESI⁺) 297 (MH⁺), (ESI⁻) 295.

Synthesis 13

(S)-5-(6-(Piperidin-3-ylamino)pyrimidin-4-ylamino)pyrazine-2-carbonitrile (Z-013)

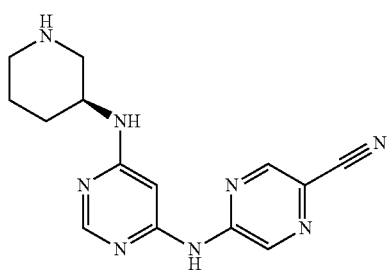 [SMILES: N#Cc1cnc(Nc2cc(N[C@H]3CCCNC3)ncn2)cn1]

The title compound was prepared using methods analogous to those described in Synthesis 7, steps 7-A and 7-B.

¹H NMR (DMSO-d₆, 400 MHz) δ 8.84 (br s, 1H), 8.77 (s, 1H), 8.24 (s, 1H), 7.41 (br s, 1H), 7.03 (br s, 1H), 3.90 (br s, 1H), 3.07 (d, 1H, J=12.4 Hz), 2.84 (d, 1H, J=12.4 Hz), 2.36 (t, 1H, J=12.4 Hz), 1.89 (m, 1H), 1.67 (m, 1H), 1.41 (m, 2H). LCMS (2) Rt=1.84 min; m/z (ESI⁺) 297 (MH⁺), (ESI⁻) 295.

Synthesis 14

5-(6-(2-(Aminomethyl)morpholino)pyrimidin-4-ylamino)pyrazine-2-carbonitrile (Z-014)

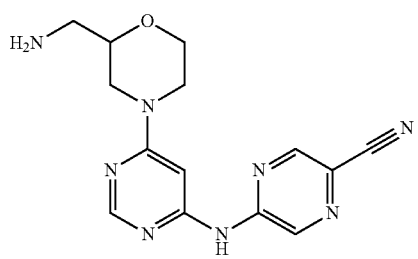 [SMILES: N#Cc1cnc(Nc2cc(N3CCOC(CN)C3)ncn2)cn1]

The title compound was prepared using methods analogous to those described in Synthesis 7, steps 7-A and 7-B.

¹H NMR (DMSO-d₆, 400 MHz) δ 9.00 (d, 1H, J=1.3 Hz), 8.81 (d, 1H, J=1.3 Hz), 8.36 (s, 1H), 7.16 (s, 1H), 4.28-4.02 (m, 3H), 3.97 (d, 2H, J=11.6 Hz), 3.51 (t, 2H, J=12.1 Hz), 2.98 (t, 1H, J=12.1 Hz), 2.73-2.63 (m, 4H). LCMS (2) Rt=1.75 min; m/z (ESI⁺) 313 (MH⁺), (ESI⁺) 311.

Synthesis 15

5-(6-(4-(Amino(phenyl)methyl)piperidin-1-yl)pyrimidin-4-ylamino)pyrazine-2-carbonitrile (Z-015)

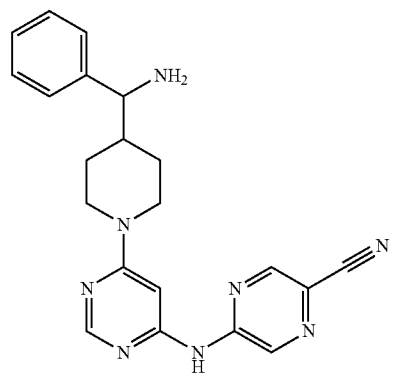 [SMILES: N#Cc1cnc(Nc2cc(N3CCC(C(N)c4ccccc4)CC3)ncn2)cn1]

The title compound was prepared using methods analogous to those described in Synthesis 7, steps 7-A and 7-B.

LCMS (2) Rt=2.61 min; m/z (ESI⁺) 387 (MH⁺).

Synthesis 16

5-(6-(4-Aminobutylamino)pyrimidin-4-ylamino)pyrazine-2-carbonitrile (Z-016)

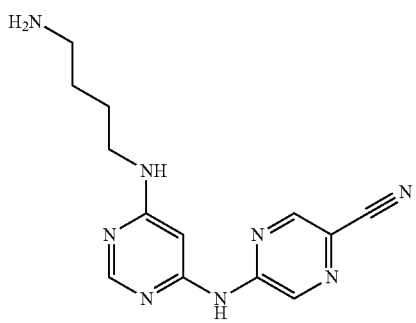 [SMILES: N#Cc1cnc(Nc2cc(NCCCCN)ncn2)cn1]

The title compound was prepared using methods analogous to those described in Synthesis 7, steps 7-A and 7-B.

$^1$H NMR (DMSO-d$_6$, 400 MHz) δ 8.86 (br s, 1H), 8.77 (s, 1H), 8.44 (s, 1H), 8.24 (s, 1H), 7.57 (br s, 1H), 7.02 (br s, 1H), 3.29 (m, 2H), 2.75 (m, 2H), 1.55 (m, 4H). LCMS (2) Rt=1.86 min; m/z (ESI$^+$) 285 (MH$^+$), (ESI$^-$) 283.

Synthesis 17

2-((2-Aminoethyl)(6-(5-cyanopyrazin-2-ylamino)pyrimidin-4-yl)amino)-N-benzylacetamide (Z-017)

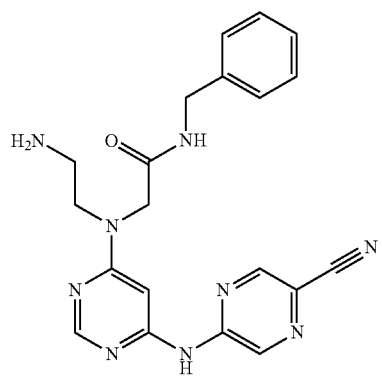 [SMILES: N#Cc1cnc(Nc2cc(N(CCN)CC(=O)NCc3ccccc3)ncn2)cn1]

The title compound was prepared using methods analogous to those described in Synthesis 7, steps 7-A and 7-B.

$^1$H NMR (DMSO-d$_6$, 400 MHz) δ 8.82 (br s, 1H), 8.17 (s, 1H), 7.16-6.92 (m, 7H), 4.14 (d, 2H, J=5.8 Hz), 4.04 (br s, 3H), 3.34 (m, 4H), 2.69 (t, 2H, J=6.0 Hz). LCMS (2) Rt=2.12 min; m/z (ESI$^+$) 404 (MH$^+$), 426 (MNa$^+$), (ESI$^-$) 402.

Synthesis 18

5-(6-(piperazin-1-yl)pyrimidin-4-ylamino)pyrazine-2-carbonitrile (Z-018)

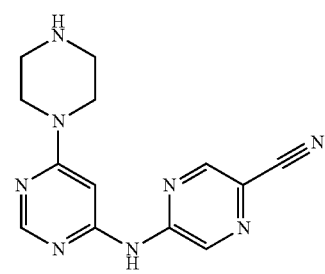 [SMILES: N#Cc1cnc(Nc2cc(N3CCNCC3)ncn2)cn1]

The title compound was prepared using methods analogous to those described in Synthesis 7, steps 7-A and 7-B.

$^1$H NMR (MeOD-d$_4$, 400 MHz) δ 8.96 (d, 1H, J=1.5 Hz), 8.66 (d, 1H, J=1.5 Hz), 8.50 (br s, 1H), 8.39 (d, 1H, J=1.0 Hz), 7.30 (d, 1H, J=1.0 Hz), 3.89 (t, 4H, J=5.3 Hz), 3.26 (t, 4H, J=5.3 Hz). LCMS (2) Rt=1.70 min; m/z (ESI$^+$) 283 (MH$^+$), (ESI$^-$) 281.

Synthesis 19

5-(6-(4-(Aminomethyl)piperidin-1-yl)pyrimidin-4-ylamino)pyrazine-2-carbonitrile (Z-019)

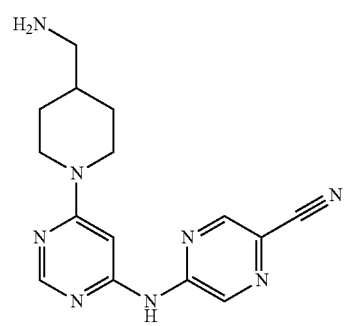 [SMILES: N#Cc1cnc(Nc2cc(N3CCC(CN)CC3)ncn2)cn1]

The title compound was prepared using methods analogous to those described in Synthesis 7, steps 7-A and 7-B.

$^1$H NMR (DMSO-d$_6$, 400 MHz) δ 11.91 (br s, 1H), 8.88 (m, 2H), 8.47 (s, 1H), 8.17 (br s, 3H), 7.16 (s, 1H), 3.75-3.65 (m, 2H), 3.59 (s, 1H), 3.09 (t, 2H, J=12.1 Hz), 2.73 (t, 2H,

J=5.8 Hz), 1.98 (br s, 1H), 1.88 (d, 2H, J=11.9 Hz), 1.26-1.16 (m, 2H). LCMS (2) Rt=2.08 min; m/z (ESI⁺) 311 (MH⁺), (ESI⁻) 309.

Synthesis 20

5-(6-(2-Aminoethylamino)pyrimidin-4-ylamino)pyrazine-2-carbonitrile (Z-020)

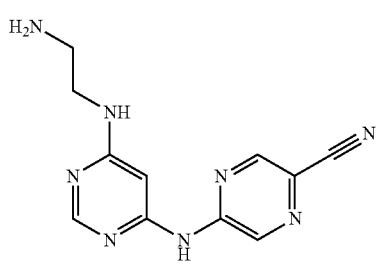 [SMILES: N#Cc1cnc(Nc2cc(NCCN)ncn2)cn1]

The title compound was prepared using methods analogous to those described in Synthesis 7, steps 7-A and 7-B.

¹H NMR (DMSO-d₆, 400 MHz) δ 8.88 (br s, 1H), 8.78 (d, 1H, J=1.3 Hz), 8.40 (br s, 1H), 8.27 (s, 1H), 7.84 (br s, 1H), 7.05 (br s, 1H), 3.45 (br s, 2H), 2.89 (t, 2H, J=6.1 Hz). LCMS (2) Rt=1.53 min; m/z (ESI⁺) 257 (MH⁺), (ESI⁻) 255.

Synthesis 21

5-(6-(3-Aminopropylamino)pyrimidin-4-ylamino)pyrazine-2-carbonitrile (Z-021)

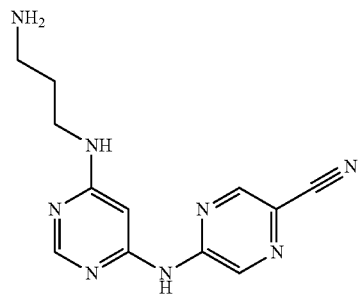

The title compound was prepared using methods analogous to those described in Synthesis 7, steps 7-A and 7-B.

¹H NMR (DMSO-d₆, 400 MHz) δ 8.63 (br s, 1H), 8.53 (s, 1H), 8.19 (br s, 1H), 8.00 (s, 1H), 7.44 (br s, 1H), 6.79 (br s, 1H), 3.10 (3H, br s), 2.53 (m, 3H), 1.51 (quin, 2H, J=7.1 Hz). LCMS (2) Rt=1.74 min; m/z (ESI⁺) 271 (MH⁺), (ESI⁻) 269.

Synthesis 22

5-(6-(Piperidin-3-ylmethylamino)pyrimidin-4-ylamino)pyrazine-2-carbonitrile (Z-022)

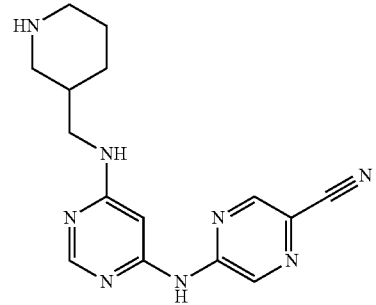

The title compound was prepared using methods analogous to those described in Synthesis 7, steps 7-A and 7-B.

¹H NMR (DMSO-d₆, 400 MHz) δ 11.57 (br s, 1H), 8.93-8.78 (m, 4H), 7.28 (s, 1H), 3.75 (m, 1H), 3.66 (s, 1H), 3.55 (m, 1H), 3.29 (m, 3H), 2.86-2.65 (m, 2H), 2.13 (m, 1H), 1.86 (m, 2H), 1.70 (m, 1H), 1.31 (m, 1H). LCMS (2) Rt=2.01 min; m/z (ESI⁺) 311 (MH⁺), (ESI⁻) 309.

Synthesis 23

5-(6-(4-Amino-4-benzylpiperidin-1-yl)pyrimidin-4-ylamino)pyrazine-2-carbonitrile (Z-023)

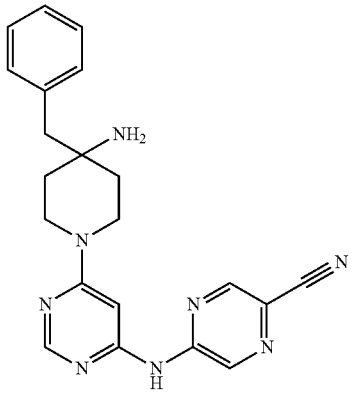 [SMILES: N#Cc1cnc(Nc2cc(N3CCC(N)(Cc4ccccc4)CC3)ncn2)cn1]

The title compound was prepared using methods analogous to those described in Synthesis 7, steps 7-A and 7-B.

¹H NMR (DMSO-d₆, 400 MHz) δ 8.99 (d, 1H, J=1.3 Hz), 8.81 (d, 1H, J=1.5 Hz), 8.30 (d, 1H, J=0.8 Hz), 7.31-7.19 (m, 5H), 7.14 (s, 1H), 3.38 (m, 4H), 2.66 (s, 2H), 1.49 (m, 2H), 1.35 (m, 2H). LCMS (2) Rt=2.69 min; m/z (ESI⁺) 387 (MH⁺), (ESI⁻) 385.

Synthesis 24

(S)-5-(6-(Pyrrolidin-3-ylamino)pyrimidin-4-ylamino)pyrazine-2-carbonitrile (Z-024)

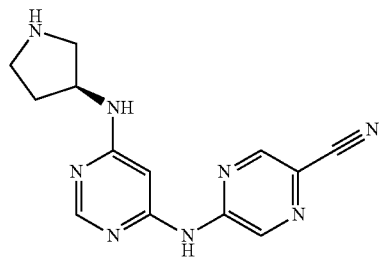 [SMILES: N#Cc1cnc(Nc2cc(N[C@H]3CCNC3)ncn2)cn1]

The title compound was prepared using methods analogous to those described in Synthesis 7, steps 7-A and 7-B.

$^1$H NMR (DMSO-$d_6$, 400 MHz) δ 8.86 (br s, 1H), 8.77 (d, 1H, J=1.3 Hz), 8.38 (s, 1H), 8.28 (s, 1H), 7.90 (br s, 1H), 7.03 (br s, 1H), 4.44 (br s, 1H), 3.24 (m, 1H), 3.17-3.01 (m, 3H), 2.89 (dd, 1H, J=4.0, 11.6 Hz), 2.13-2.02 (m, 1H), 1.82-1.74 (m, 1H). LCMS (2) Rt=1.75 min; m/z (ESI$^+$) 283 (MH$^+$), (ESI$^-$) 281.

Synthesis 25

(R)-2-Amino-5-(6-(5-cyanopyrazin-2-ylamino)pyrimidin-4-ylamino)-N-phenylpentanamide (Z-025)

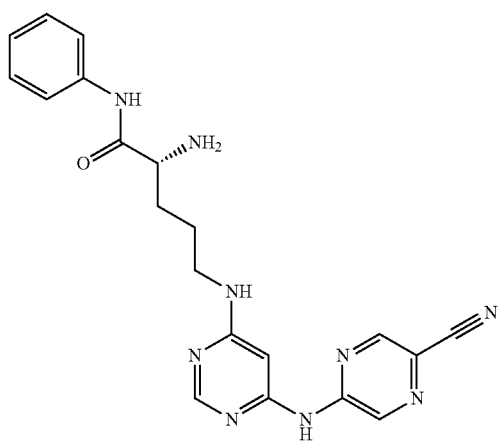 [SMILES: N#Cc1cnc(Nc2cc(NCCC[C@@H](N)C(=O)Nc3ccccc3)ncn2)cn1]

The title compound was prepared using methods analogous to those described in Synthesis 7, steps 7-A and 7-B.

$^1$H NMR (DMSO-$d_6$, 400 MHz) δ 8.85 (br s, 1H), 8.77 (d, 1H, J=1.0 Hz), 8.22 (s, 1H), 7.62 (d, 2H, J=7.6 Hz), 7.55 (br s, 1H), 7.30 (t, 2H, J=7.6 Hz), 7.03 (t, 1H, J=7.3 Hz), 3.38 (m, 2H), 1.75-1.51 (m, 5H).

Synthesis 26

(S)-2-Amino-4-(6-(5-cyanopyrazin-2-ylamino)pyrimidin-4-ylamino)-N-phenylbutanamide (Z-026)

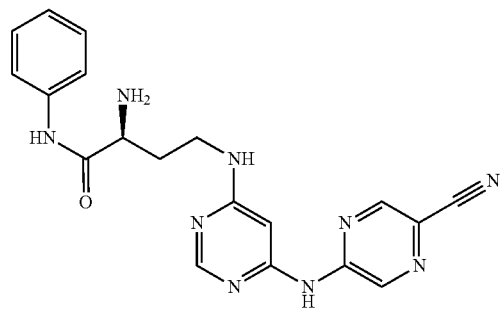 [SMILES: N#Cc1cnc(Nc2cc(NCC[C@H](N)C(=O)Nc3ccccc3)ncn2)cn1]

The title compound was prepared using methods analogous to those described in Synthesis 7, steps 7-A and 7-B.

$^1$H NMR (DMSO-$d_6$, 400 MHz) δ 8.85 (br s, 1H), 8.75 (s, 1H); 8.24 (s, 1H), 7.63 (d, 2H, J=7.6 Hz), 7.55 (br s, 1H), 7.30 (t, 2H, J=7.6 Hz), 7.04 (t, 1H, J=7.6 Hz), 7.03 (br s, 1H), 1.94 (m, 1H), 1.66 (m, 1H), 1.30 (d, 1H, J=7.1 Hz), 1.13 (t, 1H, J=6.8 Hz).

Synthesis 27

5-(6-((1R,3s,5S)-8-Methyl-8-azabicyclo[3.2.1]octan-3-ylamino)pyrimidin-4-ylamino)pyrazine-2-carbonitrile (Z-027)

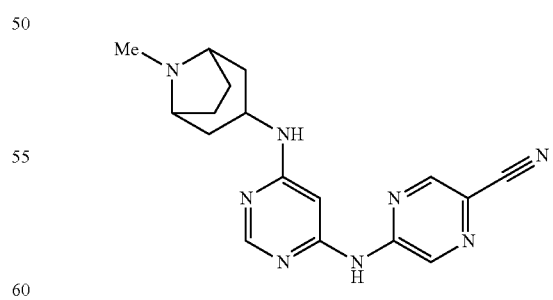

The title compound was prepared using methods analogous to those described in Synthesis 7, steps 7-A and 7-B.

$^1$H NMR (500 MHz, DMSO) δ 1.52-1.64 (4H, m), 1.67-1.75 (2H, m), 1.93-2.01 (2H, m), 2.23 (3H, s), 3.14 (2H, broad s), 4.20 (1H, broad s), 6.94 (1H, s), 7.28 (1H, s), 8.22 (1H, s), 8.74 (1H, s), 8.86 (1H, broad s), 10.58 (1H, broad s). LCMS (3) Rt 1.59 min; m/z (ESI⁺) 337 (MH⁺).

Synthesis 28

5-(6-((4-Methylpiperidin-4-yl)methylamino)pyrimidin-4-ylamino)pyrazine-2-carbonitrile (Z-028)

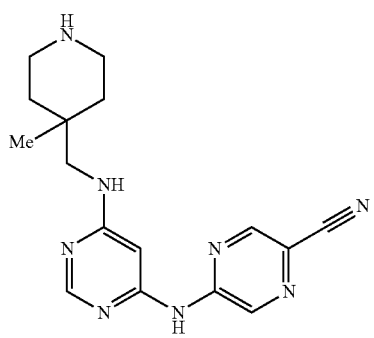 [SMILES: CC1(CNc2cc(Nc3cnc(C#N)cn3)ncn2)CCNCC1]

The title compound was prepared using methods analogous to those described in Synthesis 7, steps 7-A and 7-B.

¹H NMR (500 MHz, d₄-MeOD) δ 8.76 (1H, s), 8.61 (1H, s), 8.21 (1H, s), 7.20 (1H, s), 3.30-3.45 (2H, m), 2.95-3.10 (2H, m), 2.85-2.95 (2H, m), 1.55-1.70 (2H, m), 1.40-1.55 (2H, m), 1.07 (3H, s). LCMS (3) Rt 1.58 min; m/z (ESI⁺) 325 (MH⁺).

Synthesis 29

5-(6-(2-(Piperidin-4-yl)ethylamino)pyrimidin-4-ylamino)pyrazine-2-carbonitrile (Z-029)

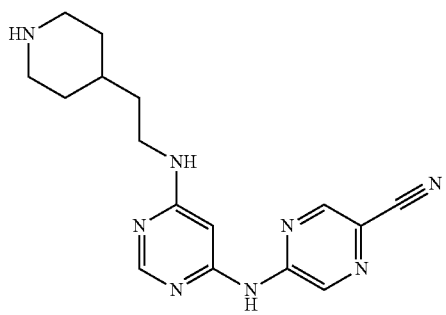 [SMILES: N#Cc1cnc(Nc2cc(NCCC3CCNCC3)ncn2)cn1]

The title compound was prepared using methods analogous to those described in Synthesis 7, steps 7-A and 7-B.

¹H NMR (500 MHz, d₄-MeOD) δ 8.80 (1H, s), 8.62 (1H, s), 8.22 (1H, s), 7.11 (1H, s), 3.35-3.50 (2H, m), 3.10-3.25 (2H, m), 2.70-2.85 (2H, m), 1.80-1.90 (2H, m), 1.50-1.70 (2H, m), 1.15-1.35 (3H, m). LCMS (3) Rt 1.58 min; m/z (ESI⁺) 325 (MH⁺).

Synthesis 30

5-(6-(Pyridin-4-ylmethylamino)pyrimidin-4-ylamino)pyrazine-2-carbonitrile (Z-030)

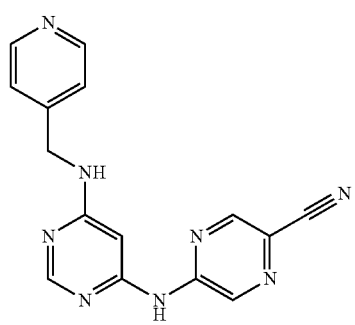 [SMILES: N#Cc1cnc(Nc2cc(NCc3ccncc3)ncn2)cn1]

The title compound was prepared using methods analogous to those described in Synthesis 7, steps 7-A and 7-B.

¹H NMR (500 MHz, DMSO) δ 4.54 (2H, s), 7.12 (1H, broad s), 7.29 (2H, d, J=5.0 Hz), 8.07 (1H, s), 8.23 (1H, s), 8.49 (2H, d, J=5.0 Hz), 8.76 (1H, s), 8.87 (1H, s), 10.68 (1H, s). LCMS (3) Rt 1.58 min; m/z (ESI⁺) 305 (MH⁺).

Synthesis 31

5-(6-(Methyl(piperidin-4-ylmethyl)amino)pyrimidin-4-ylamino)pyrazine-2-carbonitrile (Z-031)

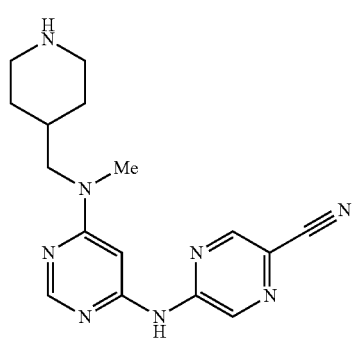 [SMILES: CN(CC1CCNCC1)c1cc(Nc2cnc(C#N)cn2)ncn1]

The title compound was prepared using methods analogous to those described in Synthesis 7, steps 7-A and 7-B.

¹H NMR (500 MHz, d₄-MeOD) δ 8.92 (1H, s), 8.63 (1H, s), 8.26 (1H, s), 7.08 (1H, s), 3.45-3.50 (2H, m), 3.05-3.15

(5H, m), 2.55-2.65 (2H, m), 1.90-2.05 (1H, m), 1.65-1.75 (2H, m), 1.20-1.35 (2H, m). LCMS (3) Rt 1.52 min; m/z (ESI+) 325 (MH+).

Synthesis 32

5-(6-(1-(Piperidin-4-yl)ethylamino)pyrimidin-4-ylamino)pyrazine-2-carbonitrile (Z-032)

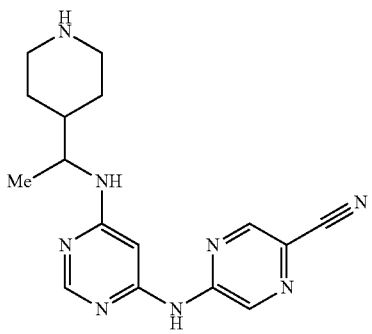 [SMILES: CC(Nc1cc(Nc2cnc(C#N)cn2)ncn1)C1CCNCC1]

The title compound was prepared using methods analogous to those described in Synthesis 7, steps 7-A and 7-B.

$^1$H NMR (500 MHz, d$_4$-MeOD) δ 8.83 (1H, s), 8.61 (1H, s), 8.20 (1H, s), 7.10 (1H, s), 3.05-3.15 (2H, m), 2.55-2.65 (2H, m), 1.70-1.90 (2H, m), 1.55-1.65 (1H, m), 1.25-1.35 (3H, m), 1.20 (3H, d, J=7.5 Hz). LCMS (3) Rt 1.50 min; m/z (ESI+) 325 (MH+)

Synthesis 33

5-(6-((Tetrahydro-2H-pyran-4-yl)methylamino)pyrimidin-4-ylamino)pyrazine-2-carbonitrile (Z-033)

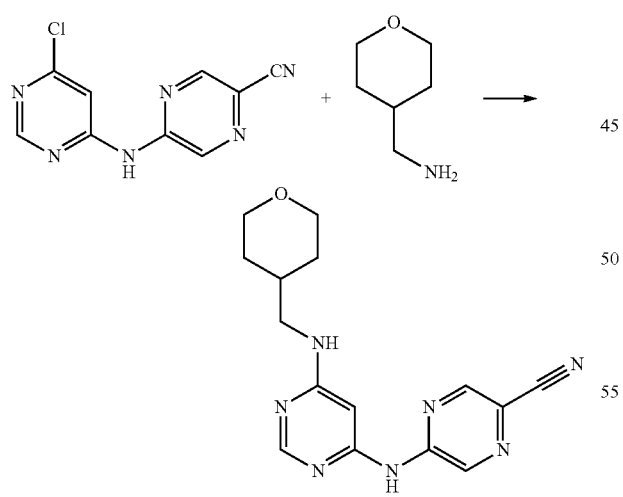

A solution of 5-(6-chloropyrimidin-4-ylamino)pyrazine-2-carbonitrile (20 mg, 0.086 mmol), 4-(aminomethyl)tetrahydropyran (18 mg, 0.17 mmol), and triethylamine (0.02 mL, 0.13 mmol) in MeCN (0.2 mL) was heated to 145° C. for 30 minutes by microwave irradiation. The mixture was cooled and solvent was removed by evaporation. The crude material was redissolved in a mixture of dichloromethane (89%), MeOH (10%), 0.88 s.g. NH$_3$ (1%) and adsorbed onto a solvent-conditioned Trikonex silica chromatography column. Elution with the same solvent mixture gave 5-(6-((tetrahydro-2H-pyran-4-yl)methylamino)pyrimidin-4-ylamino)pyrazine-2-carbonitrile as a yellow powder (11 mg, 41%).

$^1$H NMR (500 MHz, DMSO) δ 1.15-1.24 (2H, m), 1.60 (2H, d, J=12.5 Hz), 1.73-1.83 (1H, m), 3.15-3.28 (4H, m), 3.84 (2H, dd, J=3.0, 11.0 Hz), 7.00 (1H, br s), 7.50 (1H, br s), 8.22 (1H, s), 8.75 (1H, s), 8.86 (1H, br s), 10.59 (1H, br s). LCMS (3) Rt 2.79 min; m/z (ESI+) 312 (MH+).

The following compounds were prepared in a similar manner to that described in Synthesis 33, using the appropriate amines in place of 4-(aminomethyl)tetrahydropyran.

Synthesis 34

5-(6-(3-Methoxypropylamino)pyrimidin-4-ylamino)pyrazine-2-carbonitrile (Z-034)

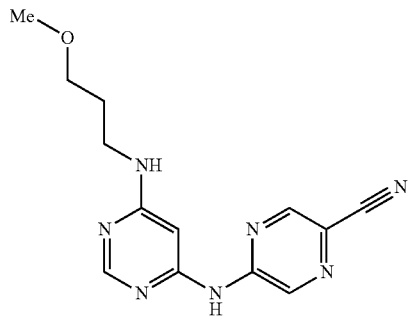 [SMILES: COCCCNc1cc(Nc2cnc(C#N)cn2)ncn1]

The title compound was prepared using methods analogous to those described in Synthesis 33.

$^1$H NMR (500 MHz, DMSO) δ 1.75 (1H, quin, J=6.5 Hz), 3.23 (2H, s), 3.38 (2H, t, J=6.5 Hz), 3.51 (3H, s), 6.97 (1H, br s), 7.44 (1H, br s), 8.23 (1H, s), 8.76 (1H, s), 8.88 (1H, br s), 10.60 (1H, br s). LCMS (3) Rt 2.58 min; m/z (ESI+) 286 (MH+).

Synthesis 35

5-(6-(2-(Tetrahydro-2H-pyran-4-yl)ethylamino)pyrimidin-4-ylamino)pyrazine-2-carbonitrile (Z-035)

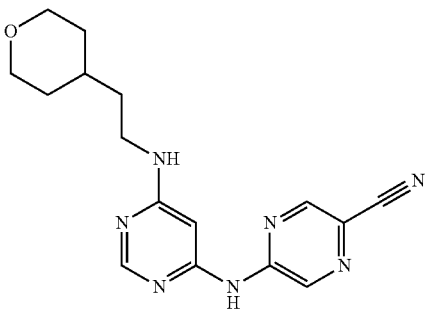 [SMILES: N#Cc1cnc(Nc2cc(NCCC3CCOCC3)ncn2)cn1]

The title compound was prepared using methods analogous to those described in Synthesis 33.

¹H NMR (500 MHz, DMSO) δ 1.11-1.26 (2H, m), 1.42-1.50 (2H, m), 1.53-1.64 (3H, m), 3.22-3.38 (4H, m), 3.82 (2H, dd, J=3.0, 11.0 Hz), 6.97 (1H, br s), 7.41 (1H, br s), 8.22 (1H, s), 8.75 (1H, s), 8.87 (1H, br s), 10.60 (1H, br s). LCMS (3) Rt 3.10 min; m/z (ESI⁺) 326 (MH⁺).

3.80 (1H. m), 7.00 (1H, br s), 7.47 (1H, br s), 8.22 (1H, s), 8.75 (1H, s), 8.86 (1H, br s), 10.60 (1H, s). LCMS (3) Rt 2.99 min; m/z (ESI⁺) 312 (MH⁺).

Synthesis 36

5-(6-((Tetrahydrofuran-2-yl)methylamino)pyrimidin-4-ylamino)pyrazine-2-carbonitrile (Z-036)

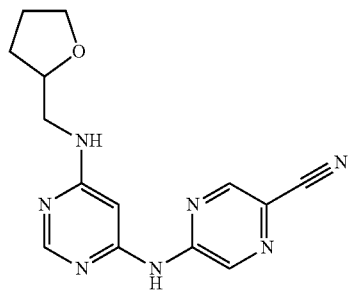 [SMILES: N#Cc1cnc(Nc2cc(NCC3CCCO3)ncn2)cn1]

The title compound was prepared using methods analogous to those described in Synthesis 33.

¹H NMR (500 MHz, DMSO) δ 1.51-1.60 (1H, m), 1.74-1.95 (3H, m), 3.32-3.39 (2H, m), 3.60-3.66 (1H, m), 3.74-3.81 (1H, m), 3.93-4.01 (1H, m), 7.02 (1H, br s), 7.51 (1H, br s), 8.22 (1H, s), 8.75 (1H, s), 8.88 (1H, br s), 10.60 (1H, br s). LCMS (3) Rt 2.73 min; m/z (ESI⁺) 298 (MH⁺).

Synthesis 38

5-(6-(((1r,4r)-4-Hydroxycyclohexylamino)pyrimidin-4-ylamino)pyrazine-2-carbonitrile (Z-038)

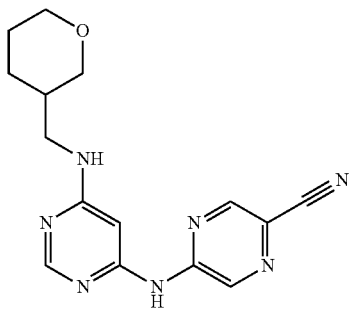 [SMILES: N#Cc1cnc(Nc2cc(NCC3CCCOC3)ncn2)cn1]

The title compound was prepared using methods analogous to those described in Synthesis 33.

¹H NMR (500 MHz, DMSO) δ 1.18-1.29 (4H, m), 1.79-1.91 (4H, m), 3.36-3.43 (1H, m), 3.73 (1H, broad s), 4.52 (1H, br s), 6.95 (1H, br s), 7.32 (1H, br s), 8.22 (1H, s), 8.75 (1H, s), 8.85 (1H, br s), 10.59 (1H, s).

LCMS (3) Rt 2.46 min; m/z (ESI⁺) 312 (MH⁺).

Synthesis 37

5-(6-((Tetrahydro-2H-pyran-3-yl)methylamino)pyrimidin-4-ylamino)pyrazine-2-carbonitrile (Z-037)

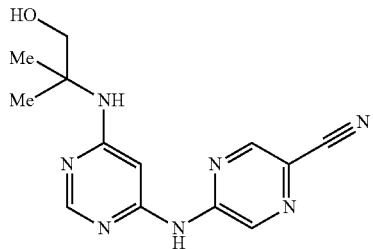 [SMILES: CC(C)(CO)Nc1cc(Nc2cnc(C#N)cn2)ncn1]

The title compound was prepared using methods analogous to those described in Synthesis 33.

¹H NMR (500 MHz, DMSO) δ 1.20-1.28 (1H, m), 1.40-1.50 (1H, m), 1.54-1.61 (1H, m), 1.75-1.83 (2H, m), 3.09-3.21 (3H, m), 3.30-3.35 (1H, m), 3.68-3.72 (1H, m), 3.76-

Synthesis 39

5-(6-(1-Hydroxy-2-methylpropan-2-ylamino)pyrimidin-4-ylamino)pyrazine-2-carbonitrile (Z-039)

The title compound was prepared using methods analogous to those described in Synthesis 33.

¹H NMR (500 MHz, DMSO) δ 1.31 (6H, s), 3.53 (2H, d, J=5.5 Hz), 5.05 (1H, t, J=5.5 Hz), 6.95 (1H, s), 7.06 (1H, d,

J=1.0 Hz), 8.22 (1H, d, J=1 Hz), 8.74 (1H, d, J=1 Hz), 8.85 (1H, d, J=1 Hz), 10.60 (1H, br s). LCMS (3) Rt 2.62 min; m/z (ESI+) 286 (MH+).

Synthesis 40

5-(6-(3-Hydroxypropylamino)pyrimidin-4-ylamino)pyrazine-2-carbonitrile (Z-040)

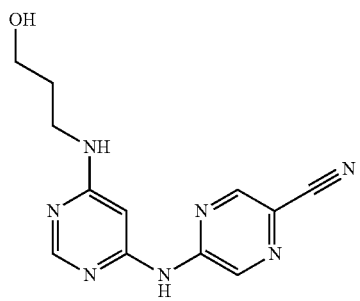 [SMILES: N#Cc1cnc(Nc2cc(NCCCO)ncn2)cn1]

The title compound was prepared using methods analogous to those described in Synthesis 33.

$^1$H NMR (500 MHz, DMSO) δ 1.67 (2H, dt, J=6.5, 7.0 Hz), 3.30 (2H, partially obscured by H$_2$O), 3.47 (2H, t, J=6.5 Hz), 4.46 (1H, br s), 6.97 (1H, br s), 7.41 (1H, br s), 8.23 (1H, s), 8.76 (1H, s), 8.88 (1H, br s), 10.61 (1H, br s). LCMS (3) Rt 2.03 min; m/z (ESI+) 272 (MH+).

Synthesis 41

5-(6-(4-Hydroxybutylamino)pyrimidin-4-ylamino)pyrazine-2-carbonitrile (Z-041)

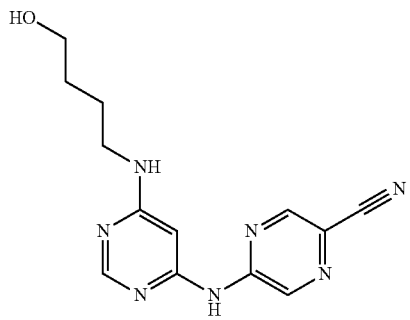 [SMILES: N#Cc1cnc(Nc2cc(NCCCCO)ncn2)cn1]

The title compound was prepared using methods analogous to those described in Synthesis 33.

$^1$H NMR (500 MHz, DMSO) δ 1.46 (2H, dt, J=6.5, 7.0 Hz), 1.54 (2H, dt, J=6.5, 7.0 Hz), 3.26 (2H, br s), 3.41 (2H, t, J=6.5 Hz), 4.37 (1H, br s), 6.97 (1H, br s), 7.42 (1H, br s), 8.22 (1H, s), 8.75 (1H, s), 8.87 (1H, br s), 10.59 (1H, br s). LCMS (3) Rt 2.22 min; m/z (ESI+) 286 (MH+).

Synthesis 42

5-(6-(1,3-Dihydroxypropan-2-ylamino)pyrimidin-4-ylamino)pyrazine-2-carbonitrile (Z-042)

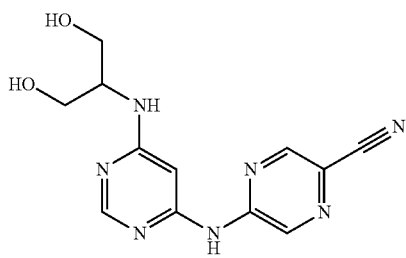 [SMILES: N#Cc1cnc(Nc2cc(NC(CO)CO)ncn2)cn1]

The title compound was prepared using methods analogous to those described in Synthesis 33.

LCMS (3) Rt 1.61 min; m/z (ESI+) 288 (MH+).

Synthesis 43

5-(6-(4-(Hydroxymethyl)piperidin-1-yl)pyrimidin-4-ylamino)pyrazine-2-carbonitrile (Z-043)

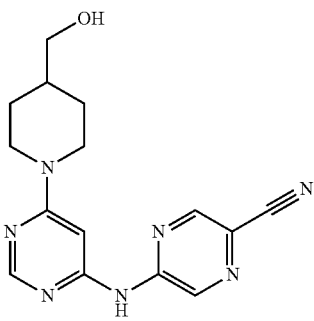 [SMILES: N#Cc1cnc(Nc2cc(N3CCC(CO)CC3)ncn2)cn1]

The title compound was prepared using methods analogous to those described in Synthesis 33.

$^1$H NMR (500 MHz, CDCl$_3$) δ 1.26 (2H, dq, J=4.0, 12.5 Hz), 1.81-1.94 (4H, m), 2.97 (2H, td, J=2.5, 12.0 Hz), 3.57 (2H, d, J=6.0 Hz), 4.48 (2H, d, J=12.0 Hz), 7.16 (1H, s), 8.37

(1H, s), 8.54 (1H, d, J=1.0 Hz), 8.72 (1H, d, J=1.0 Hz), 9.09 (1H, br s). LCMS (3) Rt 2.61 min; m/z (ESI⁺) 312 (MH⁺).

Synthesis 44-A tert-Butyl 4-((2-bromo-5-nitropyridin-4-ylamino)methyl)piperidine-1-carboxylate

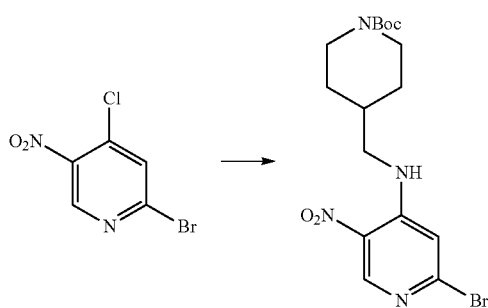 [SMILES: O=[N+]([O-])c1cnc(Br)cc1Cl ; CC(C)(C)OC(=O)N1CCC(CNc2cc(Br)ncc2[N+](=O)[O-])CC1]

A solution of 4-(aminomethyl)-1-boc-piperidine (370 mg, 1.73 mmol) in acetonitrile (1 mL) was added over 1 minute to a solution of 2-bromo-4-chloro-5-nitropyridine (373 mg, 1.57 mmol) and triethylamine (0.24 mL, 1.73 mmol) in acetonitrile (5 mL). The solution was stirred for 30 minutes then partitioned between dichloromethane and water. The aqueous phase was extracted with dichloromethane (×3) and the combined organic phases were dried (Na₂SO4) and concentrated to give tert-butyl 4-((2-bromo-5-nitropyridin-4-ylamino)methyl)piperidine-1-carboxylate as a light brown foam (640 mg, 98%) which was used without further purification.

¹H NMR (MeOD, 400 MHz) δ 8.82 (s, 1H), 7.25 (s, 1H), 4.14 (m, 3H), 3.35 (s, 1H), 1.97-1.88 (m, 1H), 1.80 (m, 3H), 1.27-1.17 (m, 3H). LCMS (1) Rt=2.35 min; m/z (ESI⁺) 415, 417 (MH⁺).

Synthesis 44-B tert-Butyl 4-((2-(5-cyanopyrazin-2-ylamino)-5-nitropyridin-4-ylamino)methyl)piperidine-1-carboxylate

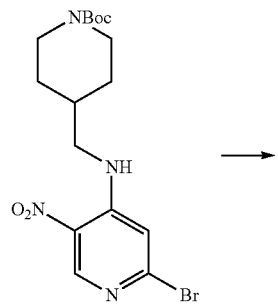

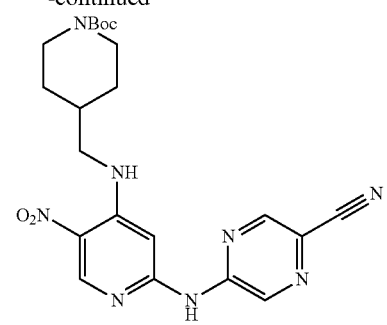

Palladium (II) acetate (32 mg, 0.14 mmol) was added to (±)-2,2"-bis(diphenylphosphino)-1,1"-binaphthalene (268 mg, 0.4 mmol) in DMF/toluene (1/1) and the resulting mixture was degassed under a stream of nitrogen gas for 10 minutes. 2-Amino-5-cyanopyrazine (172 mg, 1.43 mmol), sodium tert-butoxide (207 mg, 2.15 mmol) and tert-butyl 4-((2-bromo-5-nitropyridin-4-ylamino)methyl)piperidine-1-carboxylate (595 mg, 1.43 mmol) were added and the mixture was degassed for a further 5 minutes before being heated at 150° C. for 30 minutes using microwave irradiation. The mixture was concentrated in vacuo and partially purified by silica chromatography, eluting with 40% ethyl acetate-hexane, to give 273 mg of tert-butyl 4-((2-(5-cyanopyrazin-2-ylamino)-5-nitropyridin-4-ylamino)methyl)piperidine-1-carboxylate at a purity of 75% which was used without further purification.

LCMS (1) Rt=2.37 min; m/z (ESI⁻) 453.

Synthesis 44-C tert-Butyl 4-((5-amino-2-(5-cyanopyrazin-2-ylamino)pyridin-4-ylamino)methyl)piperidine-1-carboxylate

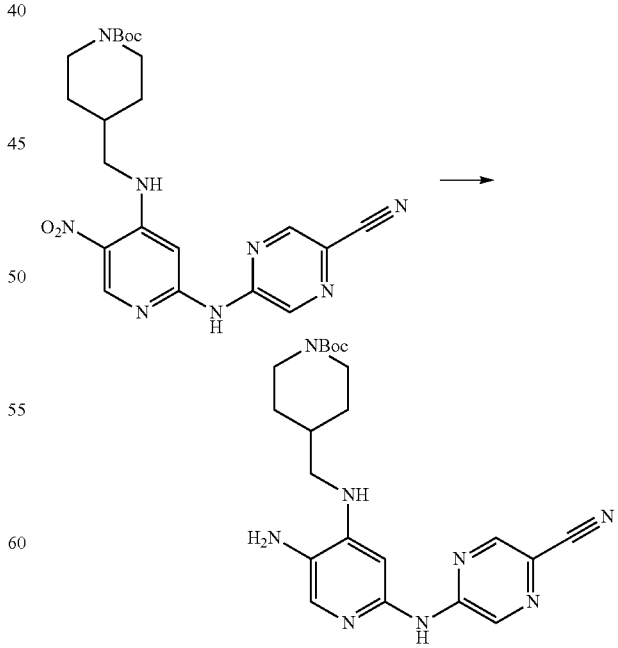

Tin (II) chloride hydrate (678 mg, 5 eq) was added to a solution of tert-butyl 4-((2-(5-cyanopyrazin-2-ylamino)-5- nitropyridin-4-ylamino)methyl)piperidine-1-carboxylate (273 mg) in ethanol (20 mL). The mixture was heated at 70° C. for 30 minutes then cooled to room temperature and evaporated to dryness. The residue was diluted with ethyl acetate and saturated aqueous sodium hydrogen carbonate. The suspension was filtered and the aqueous phase was separated and extracted twice with ethyl acetate. The combined organic layers were dried ($Na_2SO_4$) and concentrated to give crude tert-butyl 4-((5-amino-2-(5-cyanopyrazin-2-ylamino)pyridin-4-ylamino)methyl)piperidine-1-carboxylate (233 mg) as a yellow solid.

LCMS (1) Rt 1.94 min; m/z ($ESI^+$) 425 ($MH^+$), ($ESI^-$) 423.

Synthesis 44-D 5-(5-Amino-4-(piperidin-4-ylmethylamino)pyridin-2-ylamino)pyrazine-2-carbonitrile (Y-001)

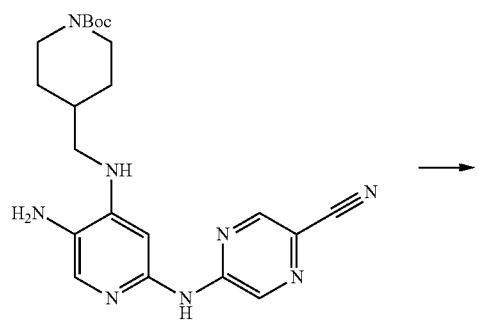

Crude tert-butyl 4-((5-amino-2-(5-cyanopyrazin-2-ylamino)pyridin-4-ylamino)methyl)piperidine-1-carboxylate (50 mg) was loaded onto a MP-TsOH SPE cartridge, then eluted after 20 minutes with 2 M ammonia in methanol. The basic fractions were concentrated. Preparative HPLC gave 5-(5-amino-4-(piperidin-4-ylmethylamino)pyridin-2-ylamino)pyrazine-2-carbonitrile (2.36 mg, 2.4% over 3 steps).

$^1$H NMR (DMSO-$d_6$, 400 MHz) δ 8.93 (br s, 1H), 8.63 (d, 1H, J=1.2 Hz), 8.34 (s, 1H), 7.45 (s, 1H), 6.86 (br s, 1H), 5.70 (m, 1H), 3.18 (m, 2H), 3.01 (t, 2H, J=5.6 Hz), 2.67-2.74 (m, 2H), 2.33 (m, 1H), 1.83 (d, 2H, J=11.2 Hz), 1.27 (m, 2H). LCMS (2) Rt=1.60 min; m/z ($ESI^+$) 325, ($ESI^-$) 323.

The following compounds were prepared in a similar manner to that described in Synthesis 44, using the appropriate protected or unprotected amines in place of 4-(aminomethyl)-1-boc-piperidine in Step 44-A.

Synthesis 45

5-(5-Amino-4-(methylamino)pyridin-2-ylamino)pyrazine-2-carbonitrile (Y-002)

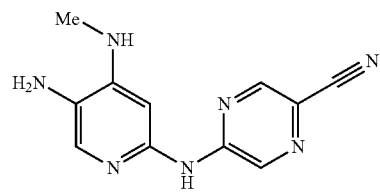 [SMILES: CNc1cc(Nc2cnc(C#N)cn2)ncc1N]

The title compound was prepared using methods analogous to those described in Synthesis 44, steps 44-A to 44-C.

LCMS (2) Rt=1.51 min; m/z ($ESI^+$) 242 ($MH^+$), ($ESI^-$) 240.

Synthesis 46

5-(5-Amino-4-(2-aminoethylamino)pyridin-2-ylamino)pyrazine-2-carbonitrile (Y-003)

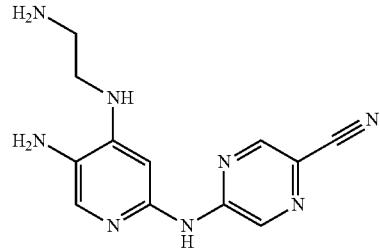 [SMILES: N#Cc1cnc(Nc2cc(NCCN)c(N)cn2)cn1]

The title compound was prepared using methods analogous to those described in Synthesis 44, steps 44-A to 44-C.

$^1$H NMR (DMSO-$d_6$, 400 MHz) δ 9.03 (br s, 1H), 8.71 (d, 1H, J=1.5 Hz), 8.42 (s, 2H), 7.58 (s, 1H), 6.92 (br s, 1H), 6.04

(m, 1H), 3.43-3.37 (m, 2H), 3.15 (m, 2H). LCMS (2) Rt=1.23 min; m/z (ESI⁺) 271 (MH⁺), (ESI⁻) 269.

Synthesis 47

5-(5-Amino-4-(2-(dimethylamino)ethylamino)pyridin-2-ylamino)pyrazine-2-carbonitrile (Y-004)

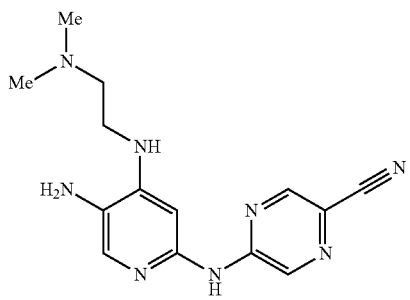 [SMILES: CN(C)CCNc1cc(Nc2cnc(C#N)cn2)ncc1N]

The title compound was prepared using methods analogous to those described in Synthesis 44, steps 44-A to 44-C.

LCMS (2) Rt=1.87 min; m/z (ESI⁺) 299 (MH⁺), (ESI⁻) 297.

Synthesis 48

5-(5-Amino-4-(piperidin-4-ylamino)pyridin-2-ylamino)pyrazine-2-carbonitrile (Y-005)

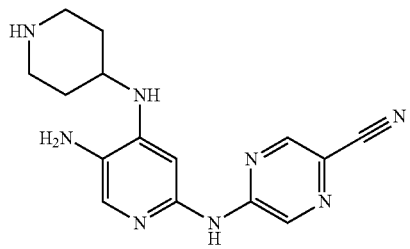 [SMILES: N#Cc1cnc(Nc2cc(NC3CCNCC3)c(N)cn2)cn1]

The title compound was prepared using methods analogous to those described in Synthesis 44, steps 44-A to 44-D.

¹H NMR (DMSO-d₆, 400 MHz) δ 8.92 (br s, 1H), 8.62 (d, 1H, J=1.5 Hz), 8.29 (s, 2H), 7.46 (s, 1H), 6.88 (br s, 1H), 5.40 (m, 1H), 3.25-3.14 (m, 2H), 2.89-2.79 (m, 2H), 2.69-2.67 (m, 1H), 2.08-2.00 (m, 2H), 1.57-1.46 (m, 2H). LCMS (2) Rt=1.68 min; m/z (ESI⁺) 311 (MH⁺), (ESI⁻) 309.

Synthesis 49

5-(5-Amino-4-(8-methyl-8-aza-bicyclo[3.2.1]octan-3-ylamino)-pyridin-2-ylamino)pyrazine-2-carbonitrile (Y-006)

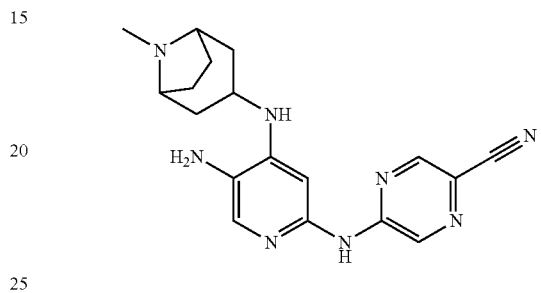

The title compound was prepared using methods analogous to those described in Synthesis 44, steps 44-A to 44-C.

¹H NMR (DMSO-d₆, 400 MHz) δ 8.98 (br s, 1H), 8.61 (d, 1H, J=1.5 Hz), 8.37 (s, 2H), 7.48 (s, 1H), 6.71 (br s, 1H), 5.18 (m, 1H), 3.10 (m, 2H), 2.68-2.66 (m, 1H), 2.34-2.31 (m, 1H), 2.23-2.07 (m, 5H), 1.94 (s, 2H), 1.79-1.73 (m, 2H), 1.69-1.63 (m, 1H). LCMS (2) Rt=1.92 min; m/z (ESI⁺) 351 (MH⁺), (ESI⁻) 349.

Synthesis 50

5-(5-Amino-4-(1-methylpiperidin-4-ylamino)pyridin-2-ylamino)pyrazine-2-carbonitrile (Y-007)

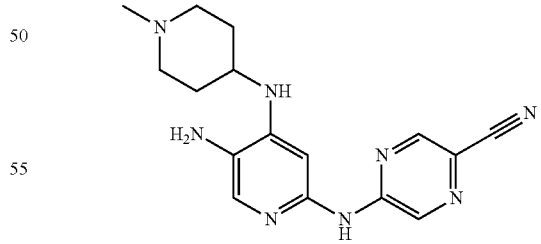

The title compound was prepared using methods analogous to those described in Synthesis 44, steps 44-A to 44-C.

¹H NMR (DMSO-d₆, 400 MHz) δ 8.97 (br s, 1H), 8.63 (d, 1H, J=1.5 Hz), 8.24 (s, 2H), 7.44 (s, 1H), 6.83 (br s, 1H), 5.30 (m, 1H), 2.84-2.77 (m, 2H), 2.69-2.66 (m, 1H), 2.20 (s, 2H), 2.09 (s, 3H), 2.07-1.91 (m, 2H), 1.52-1.40 (m, 2H). LCMS (2) Rt=1.66 min, m/z (ESI⁺) 325 (MH⁺), (ESI⁻) 323.

Synthesis 51

(R)-5-(5-Amino-4-(piperidin-3-ylamino)pyridin-2-ylamino)pyrazine-2-carbonitrile (Y-008)

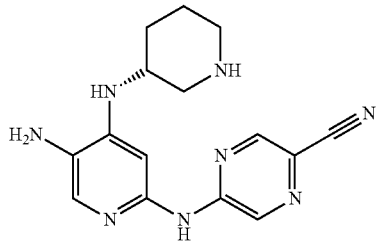

The title compound was prepared using methods analogous to those described in Synthesis 44, steps 44-A to 44-D.

¹H NMR (DMSO-d₆, 400 MHz) δ 8.94 (br s, 1H), 8.62 (d, 1H, J=1.3 Hz), 8.33 (s, 2H), 7.46 (s, 1H), 6.86 (br s, 1H), 5.36 (m, 1H), 3.38 (m, 2H), 3.22-3.17 (m, 1H), 2.93-2.89 (m, 2H), 2.55 (s, 1H), 2.03-1.96 (m, 1H), 1.76-1.70 (m, 1H), 1.57-1.41 (m, 2H). LCMS (2) Rt=1.44 min, m/z (ESI⁺) 311 (MH⁺), (ESI⁻) 309.

Synthesis 52

(S)-5-(5-Amino-4-(piperidin-3-ylamino)pyridin-2-ylamino)pyrazine-2-carbonitrile (Y-009)

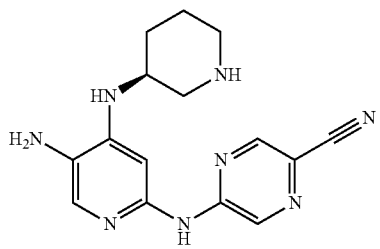 [SMILES: N#Cc1cnc(Nc2cc(N[C@H]3CCCNC3)c(N)cn2)cn1]

The title compound was prepared using methods analogous to those described in Synthesis 44, steps 44-A to 44-D.

¹H NMR (DMSO-d₆, 400 MHz) δ 8.80 (br s, 1H), 8.49 (d, 1H, J=1.5 Hz), 8.22 (br s, 2H), 7.33 (s, 1H), 6.75 (br s, 1H), 5.32 (d, 1H, J=7.1 Hz), 3.37-3.30 (m, 1H), 3.13-3.06 (m, 1H), 2.87-2.81 (m, 1H), 2.57-2.50 (m, 1H), 2.47-2.40 (m, 1H), 1.89-1.82 (m, 1H), 1.67-1.60 (m, 1H), 1.50-1.30 (m, 2H). LCMS (2) Rt=1.67 min, m/z (ESI⁺) 311 (MH⁺), (ESI⁻) 309.

Synthesis 53

N-(6-(5-Cyanopyrazin-2-ylamino)-4-(piperidin-4-ylmethylamino)pyridin-3-yl)-2-(dimethylamino)acetamide (Y-010)

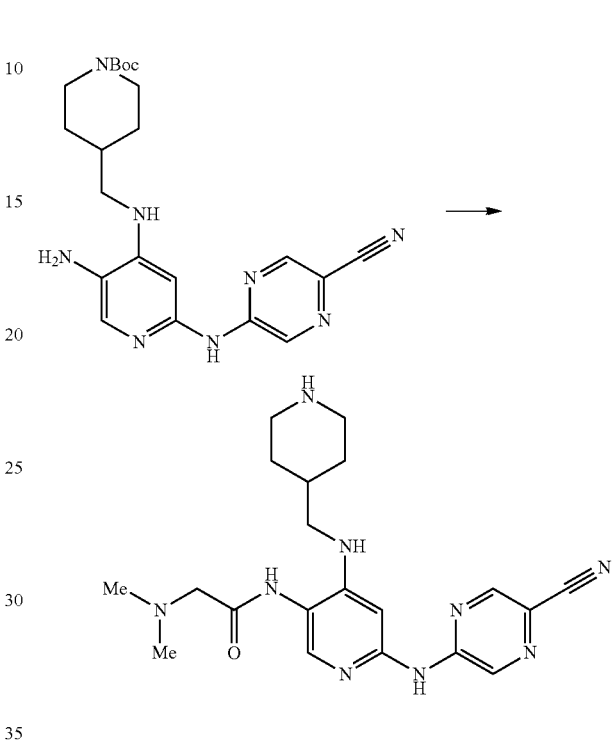

Diisopropylethylamine (16 μL, 0.092 mmol), N,N-dimethylglycine (7 mg, 0.067 mmol), HOBt (12 mg, 0.092 mmol) and EDC (17 mg, 0.092 mmol) were added to tert-butyl 4-((5-amino-2-(5-cyanopyrazin-2-ylamino)-pyridin-4-ylamino)-methyl)-piperidine-1-carboxylate (26 mg, 0.061 mmol) in DMF (1.5 mL). The mixture was stirred at room temperature for 6 hours and then partitioned between dichloromethane and water. The aqueous phase was extracted with dichloromethane. The combined organic layers were dried and concentrated. Preparative HPLC gave N-(6-(5-cyanopyrazin-2-ylamino)-4-(1-boc-piperidin-4-ylmethylamino)pyridin-3-yl)-2-(dimethylamino)acetamide as a white solid. The solid was dissolved in 20% trifluoroacetic acid in dichloromethane. After 20 minutes the mixture was loaded onto a MP-TsOH SPE cartridge and eluted with 2M ammonia in methanol. The basic fractions were combined and concentrated to give N-(6-(5-cyanopyrazin-2-ylamino)-4-(piperidin-4-ylmethylamino)pyridin-3-yl)-2-(dimethylamino)acetamide (7.52 mg, 30%) as a pale yellow solid.

¹H NMR (DMSO-d₆, 400 MHz) δ 10.47 (br s, 1H), 9.09 (s, 1H), 9.07 (s, 1H), 8.72 (d, 1H, J=1.6 Hz), 7.75 (s, 1H), 7.02 (br s, 1H), 5.95 (t, 1H, J=6.0 Hz), 3.09 (s, 2H), 3.01-2.95 (m, 3H), 2.55 (m, 3H), 2.46-2.41 (m, 2H), 2.30 (s, 6H), 1.68 (d, 2H, J=11.2 Hz), 1.13-1.02 (m, 2H). LCMS (2) Rt=1.78 min; m/z (ESI⁺) 410 (MH⁺), (ESI⁻) 408.

The following compounds were prepared in a similar manner to that described in Synthesis 53 starting from the appropriate 4-substituted-5-amino-2-(5-cyanopyrazin-2-ylamino)-pyridine, and using the appropriate acid in place of N,N-dimethylglycine.

Synthesis 54

N-(6-(5-Cyanopyrazin-2-ylamino)-4-(piperidin-4-ylmethylamino)pyridin-3-yl)-3-(piperidin-1-yl)propanamide (Y-011)

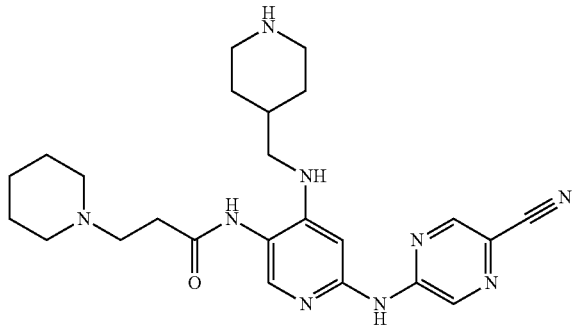 [SMILES: N#Cc1cnc(Nc2cc(NCC3CCNCC3)c(NC(=O)CCN3CCCCC3)cn2)cn1]

The title compound was prepared using methods analogous to those described in Synthesis 53.

LCMS (2) Rt=2.64 min; m/z (ESI$^+$) 464 (MH$^+$), (ESI$^-$) 462.

Synthesis 55

N-(6-(5-Cyanopyrazin-2-ylamino)-4-(piperidin-4-ylmethylamino)pyridin-3-yl)-3-(4-methoxyphenyl)propanamide (Y-012)

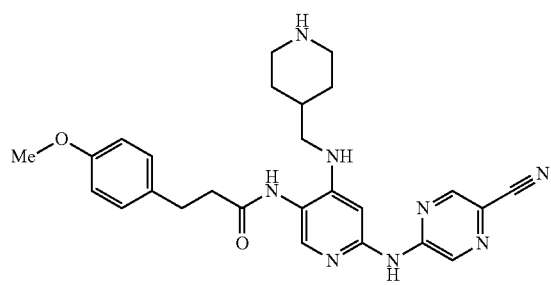 [SMILES: COc1ccc(CCC(=O)Nc2cnc(Nc3cnc(C#N)cn3)cc2NCC2CCNCC2)cc1]

The title compound was prepared using methods analogous to those described in Synthesis 53.

$^1$H NMR (DMSO-d$_6$, 400 MHz) δ 10.45 (br s, 1H), 9.10 (s, 1H), 9.07 (s, 1H), 8.71 (d, 1H, J=1.3 Hz), 7.72 (s, 1H), 7.18 (d, 2H, J=8.6 Hz), 6.99 (br s, 1H), 6.88 (d, 2H, J=8.6 Hz), 5.74 (t, 1H, J=6.0 Hz), 3.73 (s, 3H), 2.99-2.91 (m, 4H), 2.88-2.83 (t, 2H, J=7.2 Hz), 2.64 (t, 2H, J=7.6 Hz), 2.47-2.39 (t, 2H, J=11.6 Hz), 1.65 (m, 3H), 1.12-0.99 (m, 2H). LCMS (2) Rt=2.33 min; m/z (ESI$^+$) 487 (MH$^+$), (ESI$^-$) 485.

Synthesis 56

N-(6-(5-Cyanopyrazin-2-ylamino)-4-(piperidin-4-ylmethylamino)pyridin-3-yl)-2-(4-methoxyphenyl)acetamide (Y-013)

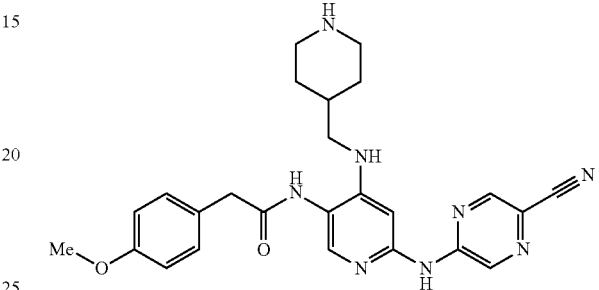

The title compound was prepared using methods analogous to those described in Synthesis 53.

$^1$H NMR (DMSO-d$_6$, 400 MHz) δ 10.51 (br s, 1H), 9.37 (s, 1H), 9.06 (s, 1H), 8.72 (d, 1H, J=1.5 Hz), 7.77 (s, 1H), 7.28 (m, 2H), 7.03 (br s, 1H), 6.90 (m, 2H), 5.88 (t, 1H, J=5.6 Hz), 3.74 (s, 3H), 3.58 (s, 2H), 3.17 (s, 1H), 3.02-2.93 (m, 4H), 2.49-2.45 (m, 2H), 1.66 (d, 3H, J=11.4 Hz), 1.16-1.04 (m, 2H). LCMS (2) Rt=2.19 min; m/z (ESI$^+$) 473 (MH$^+$), (ESI$^-$) 471.

Synthesis 57

N-(6-(5-Cyanopyrazin-2-ylamino)-4-(piperidin-4-ylmethylamino)pyridin-3-yl)-4-methoxybenzamide (Y-014)

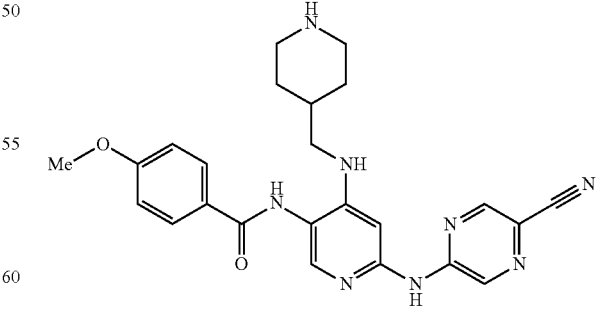

The title compound was prepared using methods analogous to those described in Synthesis 53.

$^1$H NMR (DMSO-d$_6$, 400 MHz) δ 10.44 (br s, 1H), 9.41 (s, 1H), 9.04 (s, 1H), 8.67 (d, 1H, J=1.5 Hz), 7.93 (d, 2H, J=8.8

Hz), 7.73 (s, 1H), 7.01 (s, 1H), 6.99 (d, 2H, J=8.8 Hz), 6.18 (t, 1H, J=5.3 Hz), 3.77 (s, 3H), 2.89-2.97 (m, 4H), 2.46-2.39 (m, 2H), 1.64 (d, 3H, J=11.4 Hz), 1.05 (m, 2H). LCMS (2) Rt=2.17 min; m/z (ESI+) 459 (MH+), (ESI−) 457.

Synthesis 58

N-(6-(5-Cyanopyrazin-2-ylamino)-4-(8-methyl-8-aza-bicyclo[3.2.1]octan-3-ylamino)pyridin-3-yl)-2-(dimethylamino)acetamide (Y-015)

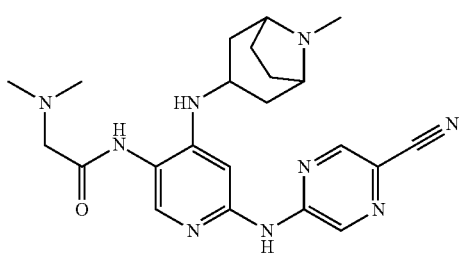 [SMILES: CN(C)CC(=O)Nc1cnc(Nc2cnc(C#N)cn2)cc1NC1CC2CCC(C1)N2C]

The title compound was prepared using methods analogous to those described in Synthesis 53.

¹H NMR (DMSO-d₆, 400 MHz) δ 9.39 (br s, 1H), 9.08 (br s, 1H), 8.72 (d, 1H, J=1.3 Hz), 7.89 (s, 1H), 6.96 (s, 1H), 5.58 (m, 1H), 3.15 (m, 2H), 3.11 (s, 2H), 2.31 (s, 6H), 2.24 (s, 3H), 2.20-2.12 (m, 2H), 1.98-1.93 (m, 2H), 1.86-1.80 (m, 2H), 1.74-1.69 (m, 2H), 1.57-1.52 (m, 2H). LCMS (2) Rt=1.71 min; m/z (ESI+) 436 (MH+), (ESI−) 434.

Synthesis 59

N-(6-(5-Cyanopyrazin-2-ylamino)-4-(piperidin-4-ylamino)pyridin-3-yl)-2-(dimethylamino)acetamide (Y-016)

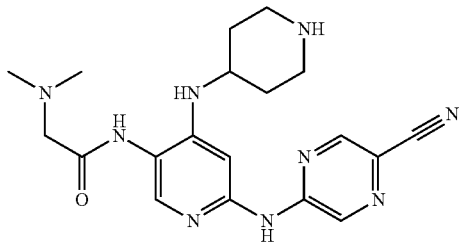 [SMILES: CN(C)CC(=O)Nc1cnc(Nc2cnc(C#N)cn2)cc1NC1CCNCC1]

The title compound was prepared using methods analogous to those described in Synthesis 53.

¹H NMR (DMSO-d₆, 400 MHz) δ 10.49 (br s, 1H), 9.18 (s, 1H), 9.06 (s, 1H), 8.74 (d, 1H, J=1.5 Hz), 8.36 (s, 1H), 7.85 (s, 1H), 7.12 (br s, 1H), 5.60 (m, 1H), 3.15-3.08 (m, 4H), 2.94- 2.91 (m, 1H), 2.79-2.70 (m, 2H), 2.30 (s, 6H), 2.00-1.93 (m, 2H), 1.51-1.40 (m, 2H). LCMS (2) Rt=1.48 min; m/z (ESI+) 396 (MH+), (ESI−) 394.

Synthesis 60

N-(6-(5-Cyanopyrazin-2-ylamino)-4-(piperidin-4-ylmethylamino)pyridin-3-yl)acetamide (Y-017)

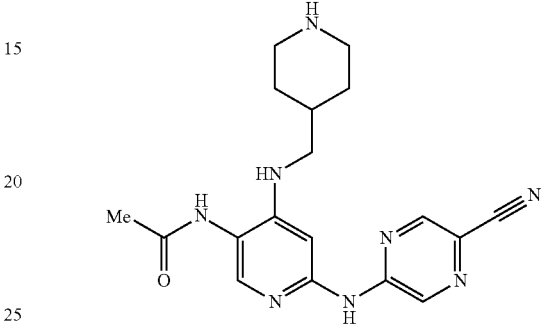

Triethylamine (11 µL, 0.082 mmol) and acetic anhydride (8 µL, 0.082 mmol) were added to a solution of tert-butyl 4-((5-amino-2-(5-cyanopyrazin-2-ylamino)-pyridin-4-ylamino)-methyl)-piperidine-1-carboxylate (29 mg, 0.068 mmol) in DMF (1 mL) at 0° C. After 2 hours, the mixture was loaded onto a MP-TsOH SPE cartridge, and eluted with 2M ammonia in methanol. The basic fractions were combined and concentrated. Purified by preparative HPLC gave N-(6-(5-cyanopyrazin-2-ylamino)-4-(piperidin-4-ylmethylamino) pyridin-3-yl)acetamide (7.4 mg, 32%).

¹H NMR (DMSO-d₆, 400 MHz) δ 10.51 (br s, 1H), 9.21 (s, 1H), 9.05 (s, 1H), 8.74 (d, 1H, J=1.5 Hz), 8.41 (s, 1H), 7.79 (s, 1H), 7.05 (br s, 1H), 6.25 (t, 1H, J=6.1 Hz), 3.16 (d, 3H, J=10.4 Hz), 3.04-2.97 (t, 2H, J=6.3 Hz), 2.67 (t, 2H, J=11.4 Hz), 2.04 (s, 3H), 1.79 (d, 2H, J=10.8 Hz), 1.32-1.20 (m, 2H). LCMS (2) Rt=1.57 min; m/z (ESI+) 367 (MH+), (ESI−) 365.

Synthesis 61

N-(6-(5-Cyanopyrazin-2-ylamino)-4-(piperidin-4-ylmethylamino)pyridin-3-yl)ethanesulfonamide (Y-018)

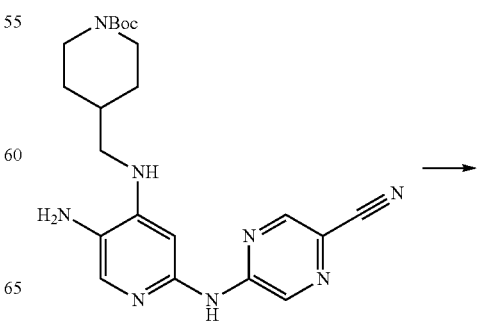

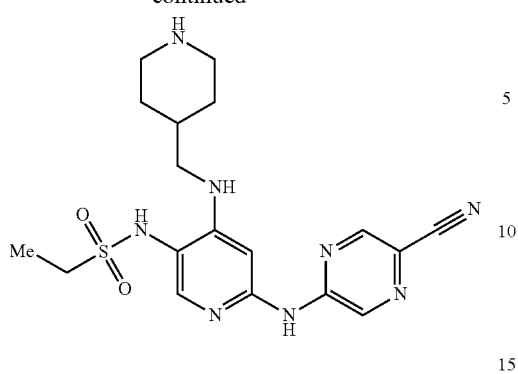

Triethylamine (15 µL, 0.11 mmol) and ethylsulfonylchloride (8 µL, 0.78 mmol) were added to a stirred solution of tert-butyl 4-((5-amino-2-(5-cyanopyrazin-2-ylamino)-pyridin-4-ylamino)-methyl)-piperidine-1-carboxylate (30.3 mg, 0.071 mmol) in DMF (1 mL) at 0° C. After 1.5 hours at room temperature, further ethylsulfonylchloride (5.5 µL, 0.53 mmol) and triethylamine (7.5 µL, 0.53 mmol) were added. After 1 hour the reaction mixture was partitioned between dichloromethane and water. The aqueous phase was extracted with dichloromethane. The combined organic phases were dried (Na$_2$SO$_4$) and concentrated. Preparative HPLC gave N-(6-(5-cyanopyrazin-2-ylamino)-4-(1-Boc-piperidin-4-ylmethylamino)pyridin-3-yl)ethanesulfonamide as a solid. The material was dissolved in 20% trifluoroacetic acid in dichloromethane. After 20 minutes the mixture was loaded onto a MP-TsOH SPE cartridge and eluted with 2M ammonia in methanol. The basic fractions were combined to give N-(6-(5-cyanopyrazin-2-ylamino)-4-(piperidin-4-ylmethylamino)pyridin-3-yl)ethanesulfonamide (2.28 mg, 8%).

$^1$H NMR (DMSO-d$_6$, 400 MHz) δ 9.05 (br s, 1H), 8.70 (s, 1H), 7.77 (s, 1H), 6.97 (s, 1H), 6.13 (s, 1H), 3.35 (m, 2H), 3.16 (s, 1H), 3.11-2.96 (m, 4H), 2.59 (m, 2H), 1.74 (d, 3H, J=10.4 Hz), 1.25-1.14 (m, 5H). LCMS (2) Rt=1.32 min; m/z (ESI$^+$) 417 (MH$^+$), (ESI$^-$) 415.

Synthesis 62-A

Methyl 4-((1-(tert-butoxycarbonyl)piperidin-4-yl)methylamino)-6-chloronicotinate

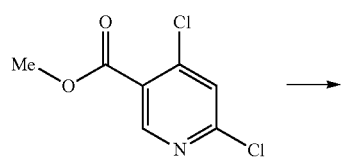

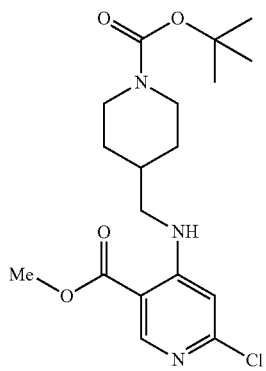

A solution of methyl 4,6-dichloronicotinate (1.20 g, 5.8 mmol), tert-butyl 4-(aminomethyl)piperidine-1-carboxylate (1.24 g, 5.8 mmol) and triethylamine (4.09 mL, 29.1 mmol) in n-butanol (13 mL) was heated at 120° C. for 90 minutes by microwave irradiation. The solvent was evaporated and the mixture was purified by flash chromatography on silica, eluting with ethyl acetate-hexane (1:4), to give methyl 4-((1-(tert-butoxycarbonyl)piperidin-4-yl)methylamino)-6-chloronicotinate as a colourless solid (1.87 g, 84%).

$^1$H NMR (500 MHz, CDCl$_3$) δ 1.14-1.27 (3H, m), 1.46 (9H, s) 1.76-1.78 (3H, m), 2.72 (2H, t, J=12.3 Hz), 3.10 (2H, t, J=5.6 Hz), 3.17 (3H, s), 4.16 (2H, s), 6.53 1H, s), 8.25 (1H, s), 8.66 (1H, s). LCMS (3) Rt 5.26 min; m/z (ESI$^+$) 386, 384 (MH$^+$).

Synthesis 62-B

Methyl 4-((1-(tert-butoxycarbonyl)piperidin-4-yl)methylamino)-6-(5-cyanopyrazin-2-ylamino)nicotinate

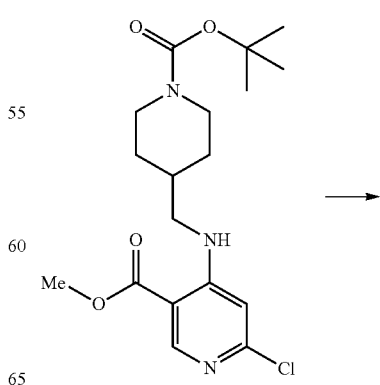

177
-continued

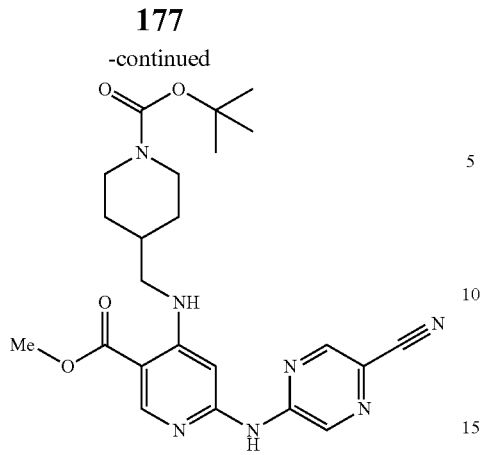

Methyl 4-((1-(tert-butoxycarbonyl)piperidin-4-yl)methylamino)-6-chloronicotinate (0.200 g, 0.52 mmol), 4-aminocyanopyrazine (0.094 g, 0.78 mmol), cesium carbonate (0.340 g, 1.04 mmol), Pd$_2$(dba)$_3$ (0.021 g, 0.02 mmol) and xantphos (0.024 g, 0.04 mmol) were mixed under an argon atmosphere before the addition of toluene (3 mL). The reaction mixture was heated at 130° C. for 30 minutes by microwave irradiation. The cooled mixture was dissolved in methanol-dichloromethane (1:1). The mixture was purified by ion exchange chromatography on SCX-II acidic resin (2 g) eluting with methanol, then 2M ammonia-methanol. The basic fractions were combined and evaporated. Flash column chromatography eluting with ethyl acetate-hexane (1:3) gave methyl 4-((1-(tert-butoxycarbonyl)piperidin-4-yl)methylamino)-6-(5-cyanopyrazin-2-ylamino)nicotinate as a yellow solid (0.090 g, 37%).

$^1$H NMR (500 MHz, CDCl$_3$) δ 1.19-1.28 (2H, m), 1.41 (9H, s), 1.79-1.82 (2H, m), 1.91-1.97 (1H, m), 2.70-2.80 (3H, m), 3.25 (2H, t, J=6.3 Hz), 3.86 (3H, s), 4.12-4.14 (2H, m), 6.53 (1H, s), 7.28 (1H, s), 8.23 (1H, t, J=5.3 Hz), 8.62 (1H, s), 8.66 (1H, d, J=1.2 Hz), 9.16 (1H, d, J=1.2 Hz) 9.58 (1H, s). LCMS (3) Rt 4.37 min; m/z (ESI$^+$) 468 (MH$^+$).

Synthesis 62-C

Methyl 6-(5-cyanopyrazin-2-ylamino)-4-(piperidin-4-ylmethylamino)-nicotinate (Y-019)

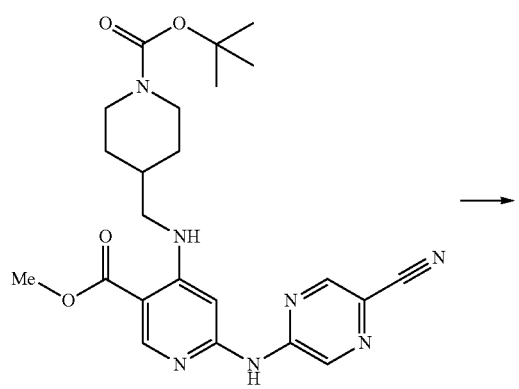

178
-continued

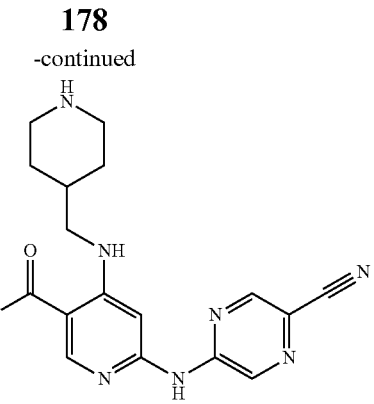

TFA (0.1 mL) was added to a solution of methyl 4-((1-(tert-butoxycarbonyl)piperidin-4-yl)methylamino)-6-(5-cyanopyrazin-2-ylamino)nicotinate (20 mg, 0.04 mmol) in dichloromethane (1 mL) at room temperature. After 20 minutes, the solution was evaporated to dryness and purified by ion exchange chromatography on SCX-II acidic resin (500 mg) eluting with methanol, then 2M ammonia-methanol. The basic fractions were combined and solvent was evaporated to give methyl 6-(5-cyanopyrazin-2-ylamino)-4-(piperidin-4-ylmethylamino)-nicotinate compound as a yellow solid (11 mg, 70%).

$^1$H NMR (500 MHz, CDCl$_3$) δ 1.21-1.29 (2H, m), 1.75-1.86 (3H, m), 2.05-2.09 (2H, m), 2.55-2.61 (3H, m), 3.04-3.07 (2H, m), 3.20 (2H, t, J=6.3 Hz), 3.87 (3H, s), 7.28 (1H, s), 8.22 (1H, s), 8.64 (1H, d, J=1.2 Hz), 8.66 (1H, d, J=1.2 Hz), 9.20 (1H, s). LCMS (3) R$_t$ 1.50 min; m/z (ESI$^+$) 368 (MH$^+$).

The following compounds were prepared in a similar manner to that described in Synthesis 62, using the appropriate protected or unprotected diamines in place of tert-butyl 4-(aminomethyl)piperidine-1-carboxylate in Synthesis 62-A.

Synthesis 63

Methyl 6-(5-cyanopyrazin-2-ylamino)-4-((1R,3s,5S)-8-methyl-8-azabicyclo[3.2.1]octan-3-ylamino)nicotinate (Y-020)

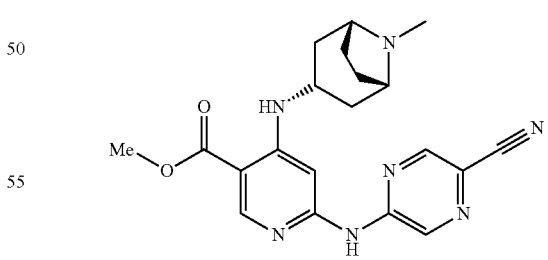

The title compound was prepared using methods analogous to those described in Synthesis 62, steps 62-A, 62-B and 62-C.

$^1$H NMR (500 MHz, d$_4$-MeOD) δ 1.80 (2H, t, J=11.7 Hz), 2.06-2.08 (2H, m), 2.25-2.28 (2H, m), 2.35-2.37 (2H, m), 2.61 (3H, s), 3.32 (2H, dt, J=3.2, 1.6 Hz), 3.68 (2H, s), 3.87

(3H, s), 3.95-4.01 (1H, m), 7.42 (1H, s), 8.60 (1H, d, J=1.3 Hz), 8.65 (1H, s), 8.92 (1H, d, J=1.3 Hz). LCMS (3) Rt 1.68 min; m/z (ESI⁺) 394 (MH⁺).

Synthesis 64

Methyl 6-(5-cyanopyrazin-2-ylamino)-4-(methyl (piperidin-4-ylmethyl)amino)nicotinate (Y-021)

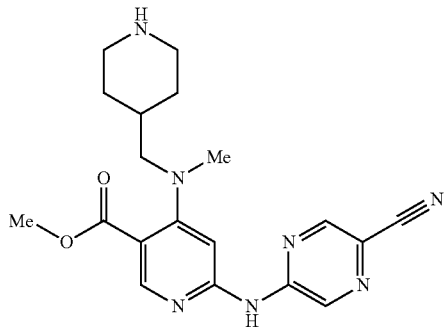 [SMILES: COC(=O)c1cnc(Nc2cnc(C#N)cn2)cc1N(C)CC1CCNCC1]

The title compound was prepared using methods analogous to those described in Synthesis 62, steps 62-A, 62-B and 62-C.

¹H NMR (500 MHz, d₄-MeOD) δ 8.92 (1H, s), 8.60 (1H, s), 8.38 (1H, s), 7.45 (1H, s), 3.89 (3H, s), 3.30 (2H, d, J=8.3 Hz), 3.10-3.20 (2H, m), 2.96 (3H, s), 2.60-2.70 (2H, m), 1.95-2.05 (1H, m), 1.75-1.85 (2H, m), 1.15-1.25 (2H, m). LCMS (3) Rt 1.57 min; m/z (ESI⁺) 382 (MH⁺).

Synthesis 65

Methyl 6-(5-cyanopyrazin-2-ylamino)-4-(1-(piperidin-4-yl)ethylamino)nicotinate (Y-022)

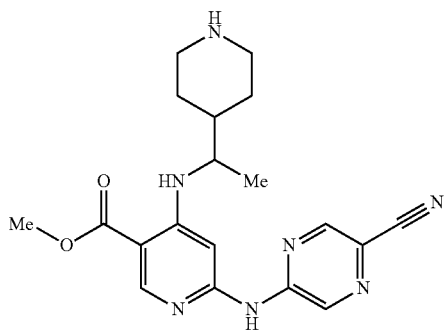 [SMILES: COC(=O)c1cnc(Nc2cnc(C#N)cn2)cc1NC(C)C1CCNCC1]

The title compound was prepared using methods analogous to those described in Synthesis 62, steps 62-A, 62-B and 62-C.

¹H NMR (500 MHz, d₄-MeOD) δ 8.91 (1H, s), 8.63 (1H, s), 8.60 (1H, s), 8.20 (1H, d, J=9.5 Hz), 7.25 (1H, s), 3.85 (3H, s), 3.50-3.60 (1H, m), 3.05-3.20 (2H, m), 2.55-2.70 (2H, m), 1.80-1.90 (1H, m), 1.65-1.80 (2H, m), 1.20-1.40 (3H, m), 1.25 (3H, d, J=7.5 Hz). LCMS (3) Rt 1.83 min; m/z (ESI⁺) 382 (MH⁺).

Synthesis 66

Methyl 6-(5-cyanopyrazin-2-ylamino)-4-(1-methylpiperidin-4-ylamino)nicotinate (Y-023)

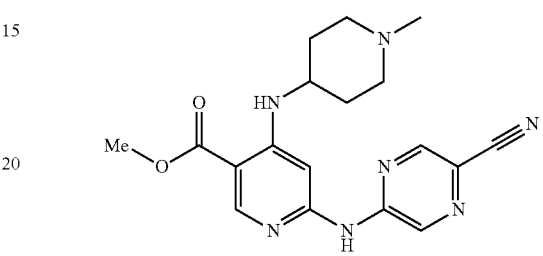

The title compound was prepared using methods analogous to those described in Synthesis 62, steps 62-A and 62-B.

¹H NMR (500 MHz, DMSO) δ 1.49-1.59 (2H, m), 1.96-2.03 (2H, m), 2.15-2.25 (5H, m), 2.22 (3H, s), 2.70 (2H, br s), 3.40 (1H, br s), 3.81 (3H, s), 7.28 (1H, s), 7.96 (1H, d, J=7.0 Hz), 8.61 (1H, s), 8.80 (1H, d, J=1.5 Hz), 9.01 (1H, d, J=1.5 Hz), 10.75 (1H, s). LCMS (3) Rt 1.38 min; m/z (ESI⁺) 368 (MH⁺).

Synthesis 67

Methyl 6-(5-cyanopyrazin-2-ylamino)-4-(1,2,2,6,6-pentamethylpiperidin-4-ylamino)nicotinate (Y-024)

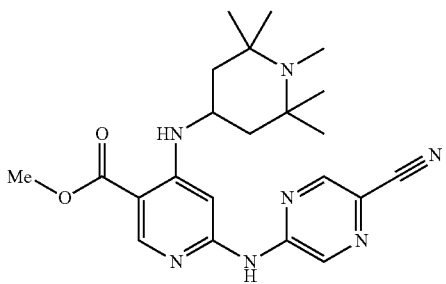 [SMILES: COC(=O)c1cnc(Nc2cnc(C#N)cn2)cc1NC1CC(C)(C)N(C)C(C)(C)C1]

The title compound was prepared using methods analogous to those described in Synthesis 62, steps 62-A and 62-B.

¹H NMR (500 MHz, DMSO) δ 1.12 (6H, s), 1.15 (6H, s), 1.32 (2H, t, J=12.0 Hz), 1.93 (2H, d, J=12.0 Hz), 2.23 (3H, s), 3.68-3.78 (1H, m), 3.81 (3H, s), 7.47 (1H, s), 7.83 (1H, d,

J=7.0 Hz), 8.61 (1H, s), 8.66 (1H, d, J=1.5 Hz), 8.89 (1H, d, J=1.5 Hz), 10.87 (1H, s). LCMS (3) Rt 1.99 min; m/z (ESI⁺) 424 (MH⁺).

Synthesis 68

Methyl 6-(5-cyanopyrazin-2-ylamino)-4-(2-(piperidin-4-yl)ethylamino)nicotinate (Y-025)

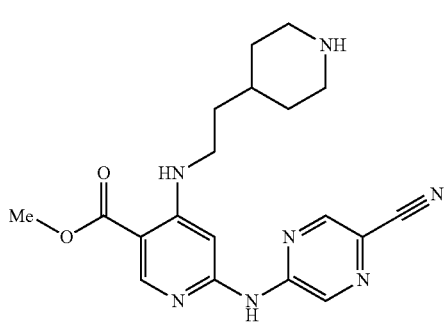 [SMILES: COC(=O)c1cnc(Nc2cnc(C#N)cn2)cc1NCCC1CCNCC1]

The title compound was prepared using methods analogous to those described in Synthesis 62, steps 62-A, 62-B and 62-C.

¹H NMR (500 MHz, MeOD) δ 8.88 (1H, s), 8.62 (1H, s), 8.60 (1H, s), 7.24 (1H, s), 3.87 (3H, s), 3.30-3.38 (2H, m), 3.05-3.15 (2H, m), 2.64-2.72 (2H, m), 1.80-1.86 (2H, m), 1.60-1.70 (3H, m), 1.20-1.35 (2H, m). LCMS (3) Rt 1.78 min; m/z (ESI⁺) 382 (MH⁺).

Synthesis 69

Methyl 6-(5-cyanopyrazin-2-ylamino)-4-((4-methylpiperidin-4-yl)methylamino)nicotinate (Y-026)

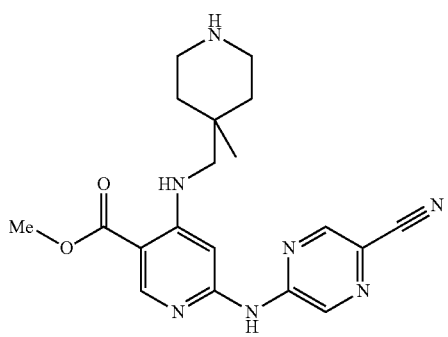 [SMILES: COC(=O)c1cnc(Nc2cnc(C#N)cn2)cc1NCC1(C)CCNCC1]

The title compound was prepared using methods analogous to those described in Synthesis 62, steps 62-A, 62-B and 62-C.

¹H NMR (500 MHz, MeOD) δ 8.90 (1H, s), 8.65 (1H, s), 8.60 (1H, s), 7.35 (1H, s), 3.89 (3H, s), 3.2-3.25 (2H, m), 2.95-3.10 (4H, m), 1.53-1.74 (4H, m), 1.16 (3H, s). LCMS (3) Rt 1.81 min; m/z (ESI⁺) 382 (MH⁺).

Synthesis 70

Methyl 6-(5-cyanopyrazin-2-ylamino)-4-((1-methylpiperidin-4-yl)methylamino)nicotinate (Y-027)

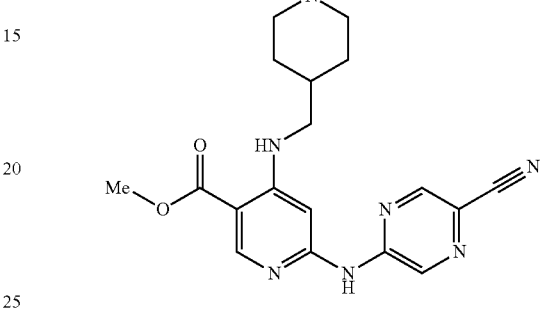

The title compound was prepared using methods analogous to those described in Synthesis 62, steps 62-A and 62-B.

¹H NMR (500 MHz, MeOD) δ 8.92 (1H, s), 8.65 (1H, s), 8.64 (1H, s), 7.29 (1H, s), 3.89 (3H, s), 3.23-3.30 (2H, m), 3.12-3.23 (2H, m), 2.52 (3H, s), 2.36-2.48 (2H, m), 1.83-2.00 (3H, m), 1.40-1.57 (2H, m). LCMS (3) Rt 1.50 min; m/z (ESI⁺) 382 (MH⁺).

Synthesis 71

Methyl 6-(5-cyanopyrazin-2-ylamino)-4-((2S,4S)-2-(phenylcarbamoyl)piperidin-4-ylamino)nicotinate (Y-028)

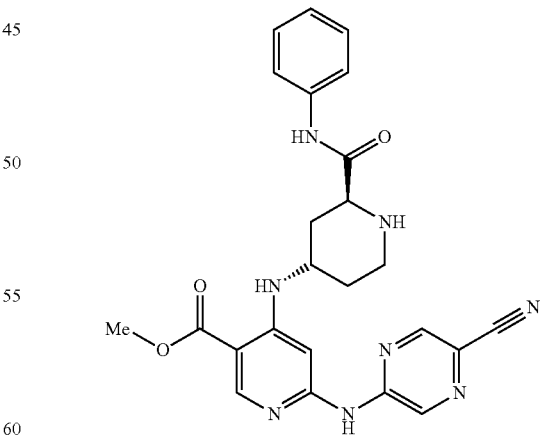

The title compound was prepared using methods analogous to those described in Synthesis 62, steps 62-A, 62-B and 62-C.

¹H NMR (500 MHz, DMSO) δ 10.78 (NH, br s), 9.67 (NH, s), 9.02 (1H, s), 8.85 (1H, s), 8.63 (1H, s), 7.92 (NH, d, J=7

Hz), 7.66 (2H, d, J=8.5 Hz), 7.37 (1H, s), 7.30 (2H, t, J=8.5 Hz), 7.05 (1H, t, J=7.0 Hz), 3.82 (3H, s), 3.52-3.62 (1H, m), 3.40-3.45 (1H, m), 3.28 (NH, s), 3.12-3.20 (1H, m), 2.70-2.80 (1H, m), 2.30-2.40 (1H, m), 1.98-2.05 (1H, m), 1.32-1.45 (2H, m). LCMS (3) Rt 2.54 min; m/z (ESI+) 473 (MH+).

Synthesis 72

Methyl 4-((1R,3s,5S)-8-benzyl-8-azabicyclo[3.2.1]octan-3-ylamino)-6-(5-cyanopyrazin-2-ylamino)nicotinate (Y-029)

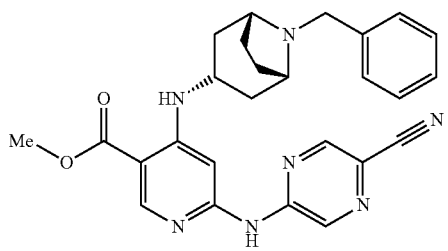

The title compound was prepared using methods analogous to those described in Synthesis 62, steps 62-A and 62-B.

¹H NMR (500 MHz, CDCl₃) δ 1.68-1.85 (4H, m), 1.98-2.03 (2H, m), 2.20-2.22 (2H, m), 3.36 (2H, s), 3.64 (2H, s), 3.78-3.84 (1H, m), 3.88 (3H, s), 7.23-7.44 (6H, m), 8.10 (1H, d, J=7.5), 8.50 (1H, d, J=1.4) 8.64 (1H, s), 8.68 (1H, s). LCMS (3) Rt 2.37 min; m/z (ESI+) 470 (MH+).

Synthesis 73

Methyl 4-((1R,3r,5S)-8-benzyl-8-azabicyclo[3.2.1]octan-3-ylamino)-6-(5-cyanopyrazin-2-ylamino)nicotinate (Y-030)

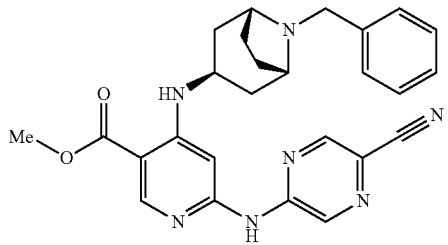 [SMILES: COC(=O)c1cnc(Nc2cnc(C#N)cn2)cc1N[C@H]1C[C@H]2CC[C@@H](C1)N2Cc1ccccc1]

The title compound was prepared using methods analogous to those described in Synthesis 62, steps 62-A and 62-B.

¹H NMR (500 MHz, CDCl₃) δ 1.81 (2H, d, J=13.8), 1.99-2.13 (2H, m), 2.17-2.19 (2H, m), 2.31-2.35 (2H, m), 3.27 (2H, s), 3.59 (2H, s), 3.79 (1H, q, J=6.5), 3.91 (3H, s), 7.07 (1H, s), 7.26-7.29 (1H, m), 7.35 (2H, t, J=7.5), 7.42-7.41 (2H, m), 8.50 (1H, d, J=1.4), 8.71-8.74 (3H, m). LCMS (3) Rt 2.38 min; m/z (ESI+) 470 (MH+).

Synthesis 74

Methyl 6-(5-cyanopyrazin-2-ylamino)-4-((3-methyloxetan-3-yl)methylamino)nicotinate (Y-031)

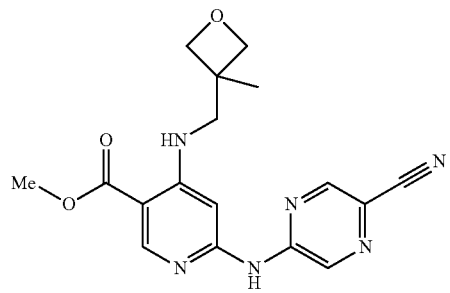 [SMILES: COC(=O)c1cnc(Nc2cnc(C#N)cn2)cc1NCC1(C)COC1]

The title compound was prepared using methods analogous to those described in Synthesis 62, steps 62-A and 62-B.

¹H NMR (500 MHz, DMSO) δ 1.36 (3H, s), 3.42 (2H, d, J=5.5 Hz), 3.82 (3H, s), 4.31 (2H, d, J=6.0 Hz), 4.45 (2H, d, J=6.0 Hz), 7.30 (1H, s), 8.25 (1H, t, J=5.5 Hz), 8.60 (1H, s), 8.80 (1H, d, J=1.0 Hz), 9.00 (1H, d, J=1.0 Hz), 10.78 (1H, s). LCMS (3) Rt 2.83 min; m/z (ESI+) 355 (MH+).

Synthesis 75-A tert-Butyl 4-((2-(5-cyanopyrazin-2-ylamino)-5-(phenylcarbamoyl)pyridin-4-ylamino)methyl)piperidine-1-carboxylate

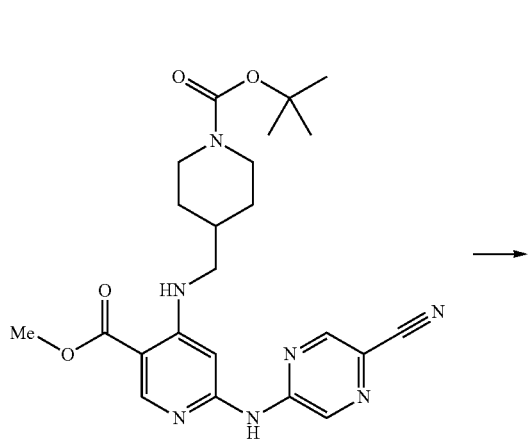

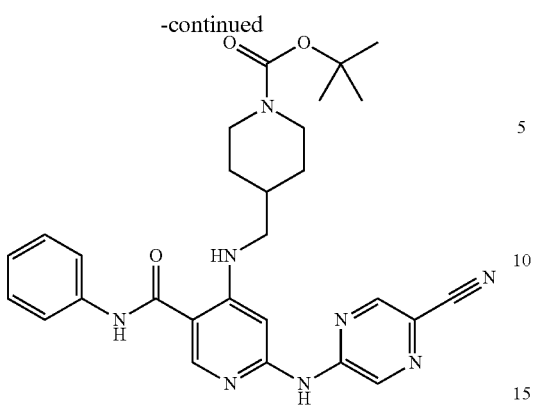

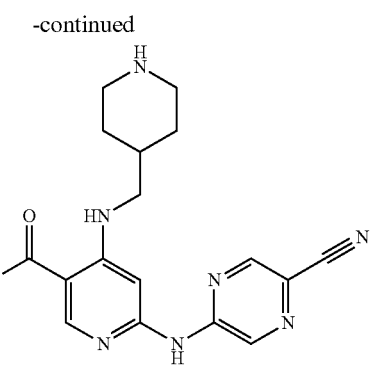

Lithium hydroxide (3 mg, 0.12 mmol) was added to a solution of methyl 6-(5-cyanopyrazin-2-ylamino)-4-(piperidin-4-ylmethylamino)nicotinate (30 mg, 0.06 mmol) in a mixture of tert-butanol and water (2:1, 0.3 mL). The reaction mixture was stirred for 4 days at room temperature then acidified to pH 3-4 with 1M HCl and extracted with ethyl acetate. The organic extract was dried ($Na_2SO_4$) and solvent was evaporated. The crude acid was used in the next step without further purification. Triethylamine (10.0 μL, 0.07 mmol) was added to a solution of the acid (29 mg, 0.06 mmol), aniline (4.8 μL, 0.05 mmol) and TBTU (24 mg, 0.06 mmol) in DMF (0.3 mL). The reaction mixture was stirred overnight at room temperature. The mixture was purified by ion exchange chromatography on SCX-II acidic resin (500 mg) eluting with methanol, then 2M ammonia-methanol. The basic fractions were combined and solvent was evaporated. Preparative TLC, eluting with ethyl acetate-hexane (1:1) gave tert-butyl 4-((2-(5-cyanopyrazin-2-ylamino)-5-(phenylcarbamoyl)pyridin-4-ylamino)methyl)piperidine-1-carboxylate as a yellow solid (12 mg, 42%).

$^1$H NMR (500 MHz, $(CD_3)_2CO$) δ 1.23-1.30 (3H, m), 1.44 (9H, s), 1.82 (2H, d, J=12.6 Hz), 1.91-1.97 (1H, m), 2.05-2.07 (1H, m), 2.74-2.85 (3H, m), 3.23 (2H, t, J=5.9 Hz), 4.13 (2H, d, J=11.1 Hz), 7.13 (1H, t, J=7.7 Hz), 7.77 (2H, d, J=7.7 Hz), 8.52 (1H, s), 8.63 (1H, s), 8.67 (1H, s). LCMS (3) $R_t$ 4.38 min; m/z ($ESI^+$) 529 ($MH^+$).

Synthesis 75-B 6-(5-Cyanopyrazin-2-ylamino)-N-phenyl-4-(piperidin-4-ylmethylamino) nicotinamide (Y-032)

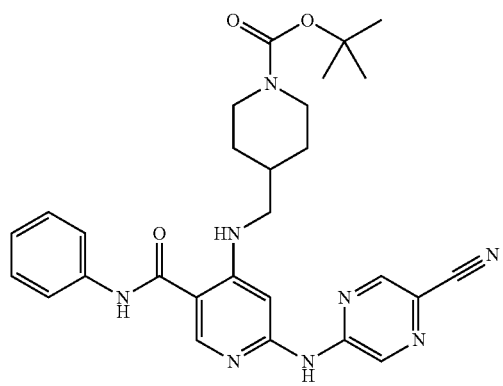

TFA (0.05 mL) was added to a solution of tert-butyl 4-((2-(5-cyanopyrazin-2-ylamino)-5-(phenylcarbamoyl)pyridin-4-ylamino)methyl)piperidine-1-carboxylate (11.0 mg, 0.02 mmol) in dichloromethane (0.5 mL) at room temperature. After 20 minutes, solvent was evaporated and the crude product was purified by ion exchange on SCX-II acidic resin (500 mg) eluting with methanol, then 2M ammonia-methanol. The basic fractions were combined and solvent was evaporated to give 6-(5-cyanopyrazin-2-ylamino)-N-phenyl-4-(piperidin-4-ylmethylamino)nicotinamide as a yellow solid (5.6 mg, 63%).

$^1$H NMR (500 MHz, MeOD) δ 1.32 (1H, d, J=9.5), 1.86 (2H, d, J=9.5), 2.65 (2H, dt, J=2.2, 12.5), 3.10-3.17 (4H, m), 3.33 (1H, dt, J=1.6, 3.3), 7.14-7.17 (2H, m), 7.38-7.35 (2H, m), 7.63 (2H, d, J=7.5), 8.51 (1H, s), 8.61 (1H, d, J=1.4), 9.00 (1H, d, J=1.4). LCMS (3) Rt 1.98 min; m/z ($ESI^+$) 429 ($MH^+$).

The following compounds were prepared from the appropriate substituted methyl nicotinate in a similar manner to that described in Synthesis 75, with the appropriate amine replacing aniline in Synthesis 75A.

Synthesis 76

6-(5-Cyanopyrazin-2-ylamino)-N-ethyl-4-(piperidin-4-ylmethylamino)nicotinamide (Y-033)

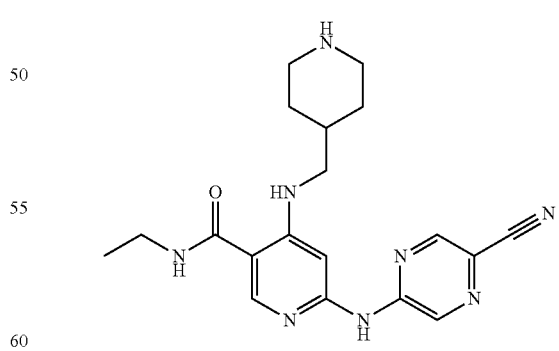

The title compound was prepared using methods analogous to those described in Synthesis 75, steps 75-A and 75-B.

$^1$H NMR (500 MHz, MeOD) 1.22 (3H, t, J=7.2), 1.32-1.34 (2H, m), 1.86-1.90 (2H, m), 2.68 (2H, t, J=11.3), 3.14-3.16 (4H, m), 3.32 (2H, dt, J=1.6, 3.3), 3.37 (2H, q, J=7.2), 7.10

(1H, s), 8.31 (1H, s), 8.59 (1H, d, J=1.3), 8.97 (1H, d, J=1.3). LCMS (3) Rt 1.46 min; m/z (ESI⁺) 381 (MH⁺).

Synthesis 77

6-(5-Cyanopyrazin-2-ylamino)-N-ethyl-4-(8-methyl-8-azabicyclo[3.2.1]octan-3-ylamino)nicotinamide (Y-034)

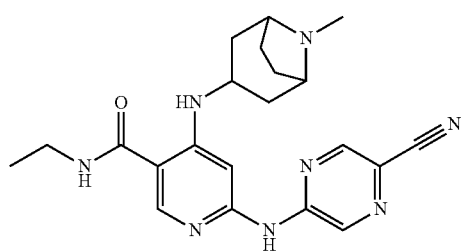 [SMILES: CCNC(=O)c1cnc(Nc2cnc(C#N)cn2)cc1NC1CC2CCC(C1)N2C]

The title compound was prepared using methods analogous to those described in Synthesis 75, step 75-A.

¹H NMR (500 MHz, MeOD) 1.23 (3H, t, J=7.3), 2.22 (2H, d, J=15.5), 2.41 (4H, m), 2.57 (2H, d, J=13.9), 2.85 (3H, s), 3.32 (1H, dt, J=1.6, 3.3) 3.40 (2H, q, J=7.2), 7.06 (1H, s), 8.40 (1H, s), 8.49 (1H, s), 8.58 (1H, s), 8.96 (1H, s). LCMS (3) Rt 1.63 min; m/z (ESI⁺) 407 (MH⁺).

Synthesis 78-A

5-Chloro-4-morpholinopyridin-2-amine

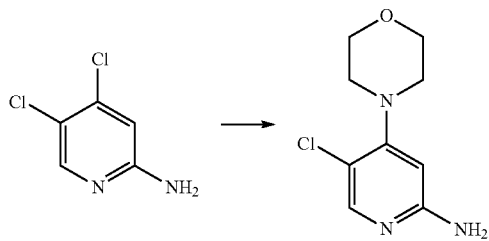 [SMILES: Nc1cc(Cl)c(Cl)cn1 ; Nc1cc(N2CCOCC2)c(Cl)cn1]

A mixture of 4,5-dichloropyridin-2-amine (300 mg, 1.84 mmol) and morpholine (480 mg, 5.52 mmol) in DMA (3.6 mL) was heated at 200° C. for 60 minutes by microwave irradiation. The mixture was purified by ion exchange chromatography on SCX-II acidic resin (2 g) eluting with methanol, then 2M ammonia-methanol. The basic fractions were combined and solvent was evaporated. Flash chromatography on silica, eluting with ethyl acetate-hexane (1:1) gave 5-chloro-4-morpholinopyridin-2-amine as a colourless solid (347 mg, 88%).

¹H NMR (500 MHz, (CD₃)₂CO) δ 3.07-3.09 (4H, m), 3.76-3.78 (4H, m), 5.39 (2H, s), 6.20 (1H, s), 7.78 (1H, s). LCMS (3) Rt 2.60 min; m/z (ESI⁺) 252 (MK⁺).

Synthesis 78-B

5-(5-Chloro-4-morpholinopyridin-2-ylamino)pyrazine-2-carbonitrile

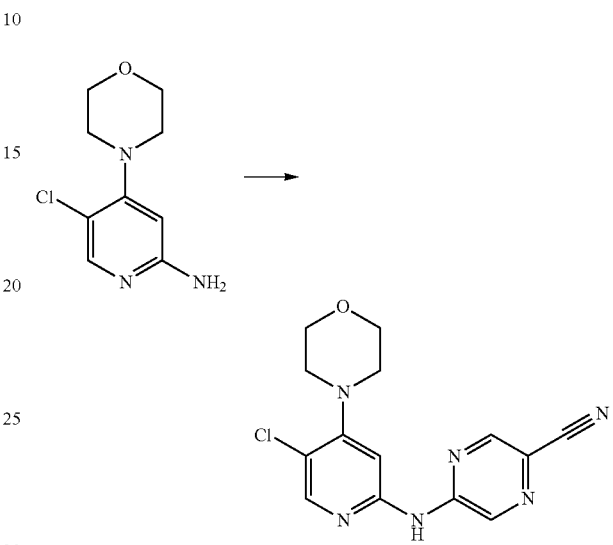

5-Chloro-4-morpholinopyridin-2-amine (68 mg, 0.31 mmol), 4-bromo-cyanopyrazine (30 mg, 0.20 mmol), sodium tert-butoxide (45 mg, 0.47 mmol), Pd(OAc)₂ (3 mg, 0.01 mmol) and BINAP (0.030 g, 0.05 mmol) were mixed under argon atmosphere before addition of mixture of DMF in toluene (2:1, 0.7 mL). The reaction mixture was heated to 140° C. by microwave irradiation for 20 minutes. The reaction mixture was purified by ion exchange chromatography on SCX-II acidic resin (500 mg) eluting with methanol, then 2M ammonia-methanol. The basic fractions were combined and solvent was evaporated. Flash chromatography on silica, eluting with ethyl acetate-hexane (1:1) gave 5-(5-chloro-4-morpholinopyridin-2-ylamino)pyrazine-2-carbonitrile as a yellow solid (20 mg, 20%).

¹H NMR (500 MHz, (CD₃)₂CO) δ 3.14-3.16 (4H, m), 3.76-3.79 (4H, m), 7.52 (1H, s), 8.22 (1H, s), 8.77 (1H, s), 9.02 (1H, s), 10.77 (1H, s). LCMS (3) Rt 4.55 min; m/z (ESI⁺) 317 (MH⁺).

Synthesis 78-C

5-(4-Morpholino-5-phenylpyridin-2-ylamino)pyrazine-2-carbonitrile (Y-035)

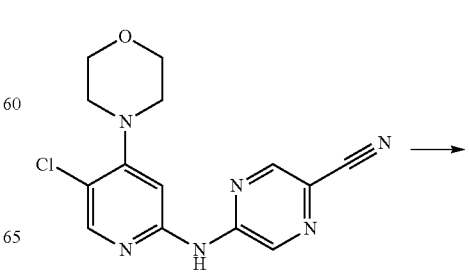

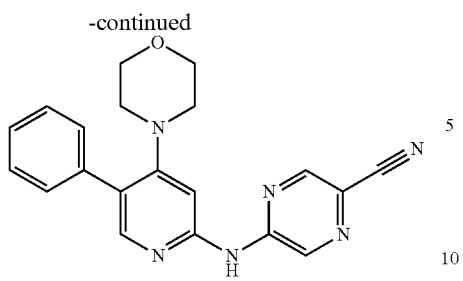

A mixture of 5-(5-chloro-4-morpholinopyridin-2-ylamino)pyrazine-2-carbonitrile (50 mg, 0.16 mmol), phenylboronic acid (38 mg, 0.31 mmol), sodium carbonate (41 mg, 0.39 mmol) and Bedford catalyst (1 mg, 0.01 mmol) in a mixture of acetonitrile-water (4:1, 2.5 mL) was heated at 150° C. by microwave irradiation for 30 minutes. The crude reaction mixture was purified by ion exchange chromatography on SCX-II acidic resin (500 mg) eluting with methanol, then 2M ammonia-methanol. The basic fractions were combined and solvent was evaporated. Preparative TLC, eluting with ethyl acetate-hexane (2:3) gave 5-(4-morpholino-5-phenylpyridin-2-ylamino)pyrazine-2-carbonitrile as a yellow solid (16 mg, 28%).

$^1$H NMR (500 MHz, CDCl$_3$) δ 2.94-3.00 (4H, m), 3.62-3.67 (4H, m), 7.22-7.62 (5H, m), 8.05 (1H, s), 8.52 (1H, s), 8.83 (1H, s), 9.00 (1H, s). LCMS (3) Rt 3.17 min; m/z (ESI$^+$) 359 (MH$^+$).

Synthesis 79-A 2-amino-5-bromopyrazine

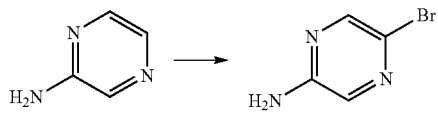

N-Bromosuccinimide (8.98 g, 50 mmol) was added portionwise over 15 minutes to a solution of 2-aminopyrazine (4.75 g, 50 mmol) in dichloromethane (300 mL) at 0° C. After 45 minutes at 0° C., and 3 hours at room temperature, the mixture was filtered through Celite and the filtrate was concentrated. The brown residue was purified by silica chromatography, eluting with 35% then 50% ethyl acetate in hexane, to give 2-amino-5-bromopyrazine (6.41 g, 74%) as a yellow solid.

$^1$H NMR (CDCl$_3$, 400 MHz) δ 8.02 (s, 1H), 7.71 (s, 1H), 4.58 (br s, 1H). LCMS (1) Rt=1.05 min; m/z (ESI$^+$) 174, 176 (MH$^+$).

Synthesis 79-B

2-Amino-5-(3-(tert-butyldimethylsilyloxy)prop-1-ynyl)pyrazine

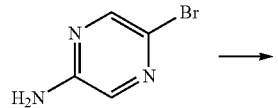

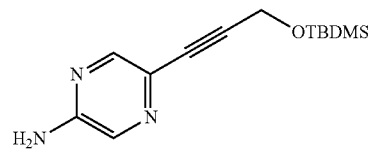

2-Amino-5-bromopyrazine (1.50 g, 8.6 mmol) was dissolved in anhydrous, deoxygenated DMF (24.5 mL) with triethylamine (10.5 mL). Copper(I) iodide (0.33 g, 1.7 mmol), tetrakis(triphenylphosphine)-palladium(0) (0.61 g, 0.51 mmol) and tert-butyldimethyl(prop-2-ynyloxy)silane (1.90 g, 11.2 mmol) were added and the solution was stirred overnight at 60° C., then cooled and partitioned between water and dichloromethane. The aqueous phase was extracted with dichloromethane and the combined organic phases were dried (Na$_2$SO$_4$) and evaporated. The residue was purified by silica chromatography to give 2-amino-5-(3-(tert-butyldimethylsilyloxy)prop-1-ynyl)pyrazine (2.06 g, 91%) as a brown solid.

$^1$H NMR (DMSO-d$_6$, 400 MHz) δ 7.87 (d, 1H, J=1.5 Hz), 7.71 (d, 1H, J=1.5 Hz), 6.74 (s, 2H), 4.41 (s, 2H), 0.77 (s, 9H), 0.00 (s, 6H). LCMS (1) Rt=2.29 min; m/z (ESI$^+$) 264 (MH$^+$).

Synthesis 79-C tert-Butyl 4-((6-chloropyrimidin-4-ylamino)methyl)-piperidine-1-carboxylate

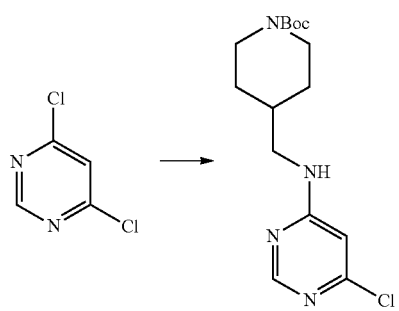 [SMILES: Clc1cc(Cl)ncn1 ; CC(C)(C)OC(=O)N1CCC(CNc2cc(Cl)ncn2)CC1]

4,6-Dichloropyrimidine (284 mg, 1.9 mmol), N-Boc-4-aminomethyl piperidine (409 mg, 1.9 mmol) and potassium carbonate (317 mg, 2.3 mmol) were dissolved in acetonitrile (5 mL) and the solution was heated for 30 minutes at 120° C. using microwave irradiation. The reaction mixture was partitioned between water and dichloromethane and the aqueous phase was extracted with dichloromethane. The combined organic phases were dried (Na$_2$SO$_4$) and evaporated to give tert-butyl 4-((6-chloropyrimidin-4-ylamino)methyl)-piperidine-1-carboxylate (656 mg, 100%) as a yellow oil which was used without further purification.

$^1$H NMR (DMSO-d$_6$, 400 MHz) δ 8.26 (s, 1H), 7.80 (br s, 1H), 6.51 (s, 1H), 3.92 (m, 2H), 3.23 (m, 2H), 2.68 (br s, 1H), 2.51 (m, 1H), 1.64 (m, 3H), 1.06-0.97 (m, 2H). LCMS (1) Rt=1.94 min; m/z (ESI⁺) 271, 227 (MH⁺), (ESI⁻) 325.

Synthesis 79-D tert-butyl 4-((6-(5-(3-(tert-butyldimethylsilyloxy) prop-1-ynyl)pyrazin-2-yl-amino)pyrimidin-4-ylamino)methyl)piperidine-1-carboxylate

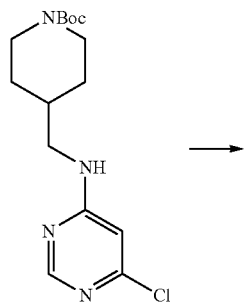

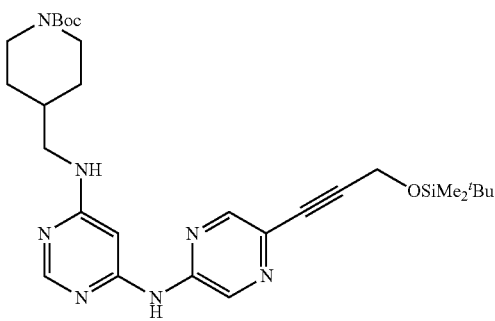

2,2'-Bis(diphenylphosphino)-1,1'-binaphthalene (56 mg, 0.09 mmol) and palladium acetate (4 mg, 0.015 mmol) were suspended in 5 mL toluene (5 mL) and degassed over 10 minutes under a stream of nitrogen gas. 2-Amino-5-(3-(tert-butyldimethyl-silyloxy)prop-1-ynyl)pyrazine (50 mg, 0.15 mmol) and tert-butyl 4-((6-chloropyrimidin-4-ylamino)methyl)-piperidine-1-carboxylate (40 mg, 0.15 mmol), in anhydrous and degassed DMF (500 µL), and sodium tert-butoxide (46 mg, 0.45 mmol) were added and the reaction mixture was heated at 145° C. for 30 minutes by microwave irradiation. The mixture was evaporated to dryness. The residue was partitioned between water and dichloromethane and the aqueous phase was extracted with dichloromethane. The combined organic phases were dried (Na₂SO₄) and concentrated. The residue was redissolved in methanol and filtered through a PS-SH column. The filtrate was evaporated to dryness to give crude tert-butyl 4-((6-(5-(3-(tert-butyldimethylsilyloxy) prop-1-ynyl)pyrazin-2-yl-amino)pyrimidin-4-ylamino)methyl)piperidine-1-carboxylate which was used directly for the next step.

LCMS (1) Rt=2.67 min; m/z (ESI⁺) 554 (MH⁺), (ESI⁻) 552.

Synthesis 79-E 3-(5-(6-(piperidin-4-ylmethylamino)pyrimidin-4-ylamino)pyrazin-2-yl)prop-2-yn-1-ol (Z-044)

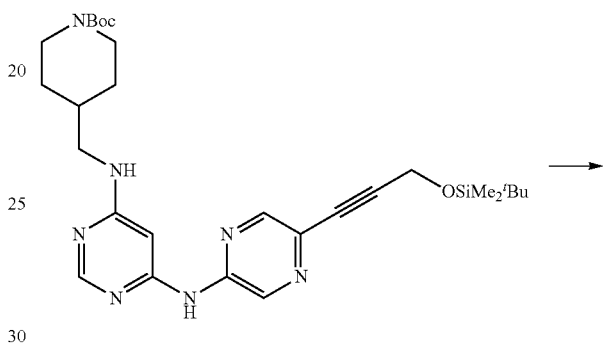

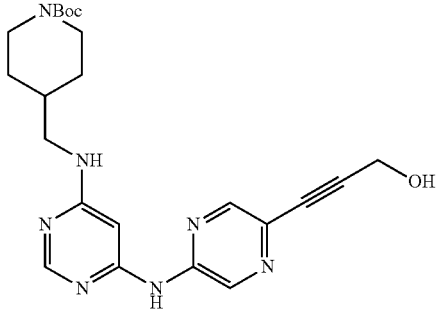

Crude tert-butyl 4-((6-(5-(3-(tert-butyldimethylsilyloxy) prop-1-ynyl)pyrazin-2-ylamino)pyrimidin-4-ylamino)-methyl)piperidine-1-carboxylate (0.15 mmol) was dissolved in tetra n-butylammonium fluoride (1M in THF, 225 µL). After 30 minutes the solution was evaporated and the residue was purified by preparative HPLC. The resulting solid was dissolved in 30% trifluoroacetic acid in dichloromethane and stirred at room temperature for 30 minutes. The mixture was adsorbed onto then MP-TsOH SPE cartridge and eluted with 2M ammonia in methanol. The basic fractions were concentrated to give 3-(5-(6-(piperidin-4-ylmethylamino)pyrimidin-4-ylamino)pyrazin-2-yl)prop-2-yn-1-ol (7.8 mg, 7.5% over two steps) as a white solid.

¹H NMR (DMSO-d₆, 400 MHz) δ 10.15 (br s, 1H), 8.79 (br s, 1H), 8.33 (s, 1H), 8.18 (s, 1H), 7.34 (br s, 1H), 6.94 (br s, 1H), 5.47 (s, 1H), 4.33 (s, 2H), 3.20-3.10 (m, 2H), 2.92 (d, 2H, J=12 Hz), 2.70 (s, 1H), 2.45-2.36 (t, 2H, J=12 Hz), 1.94-1.86

(m, 1H), 1.66-1.53 (m, 2H), 1.36-1.28 (m, 1H), 1.08-0.97 (m, 2H). LCMS (2) Rt=1.16 min; m/z (ESI$^+$) 340 (MH$^+$), (ESI$^-$) 338.

Synthesis 80

5-(6-(Piperidin-4-ylmethylamino)pyrimidin-4-ylamino)pyrazine-2-carboxamide (Z-045)

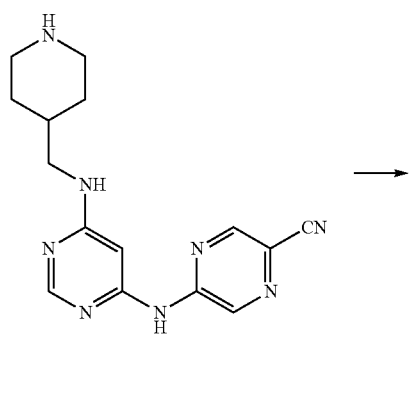

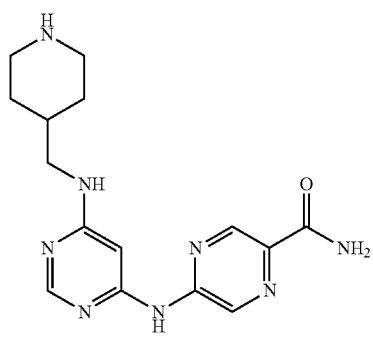

A mixture of tert-butyl-4-((6-(5-cyanopyrazin-2-ylamino)pyrimidin-4-ylamino)methyl)-piperidine-1-carboxylate (0.15 mmol) and trifluoroacetic acid was heated at 82° C. for 4 hours. The solution was evaporated to dryness and the residue was purified by preparative HPLC to give 5-(6-(piperidin-4-ylmethylamino)pyrimidin-4-ylamino)pyrazine-2-carboxamide (7.36 mg, 15%).

$^1$H NMR (DMSO-d$_6$, 400 MHz) δ 10.16 (br s, 1H), 8.83 (br s, 1H), 8.78 (s, 1H), 8.35 (s, 1H), 8.21 (s, 1H), 7.80 (br s, 1H), 7.42 (br s, 1H), 7.29 (t, 1H, J=5.8 Hz), 6.99 (s, 1H), 3.19 (t, 2H, J=5.8 Hz), 3.09 (d, 2H, J=12.0 Hz), 2.66-2.58 (m, 2H), 2.19 (t, 1H, J=7.8 Hz), 1.78-1.70 (m, 3H), 1.28-1.15 (m, 2H). LCMS (2) Rt=1.04 min; m/z (ESI$^+$) 329, (ESI$^-$) 327.

Synthesis 81

Methyl 6-(5-methylpyrazin-2-ylamino)-4-(piperidin-4-ylmethylamino)nicotinate (Y-036)

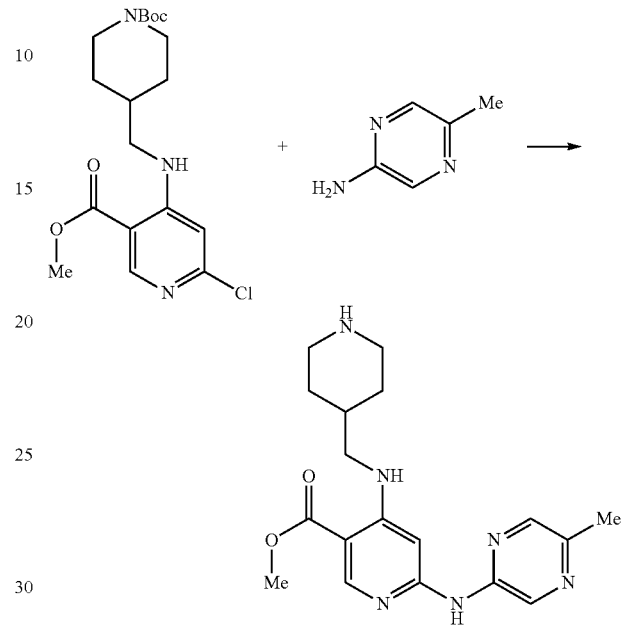

Methyl 4-((1-(tert-butoxycarbonyl)piperidin-4-yl)methylamino)-6-chloronicotinate (90 mg, 0.23 mmol), 5-methylpyrazin-2-amine (38 mg, 0.35 mmol, as described in Itoh et al., 2002), cesium carbonate (153 mg, 0.47 mmol), 4,5-bis(diphenyl phosphino)-9,9-dimethylxanthene (11 mg, 8 mol %), and tris(dibenzylidene acetone)dipalladium chloroform complex (10 mg, 4 mol %) were added to an oven-dried microwave reactor vial (2 mL) which was capped and flushed with nitrogen. Anhydrous toluene (1.35 mL) was added and nitrogen was bubbled through the stirred solution for 10 minutes. The mixture was heated at 130° C. for 30 minutes by microwave irradiation. The solution was cooled, diluted with dichloromethane-methanol and adsorbed onto a 2 g (solute SCX-II column. The resin was washed with methanol, then with 2M ammonia in methanol. The basic fractions were concentrated and the residue was purified by preparative TLC, eluting with 10% methanol-dichloromethane) to give methyl 6-(5-methylpyrazin-2-ylamino)-4-(1-Boc-piperidin-4-ylmethylamino)nicotinate (35 mg) as a light green powder.

LCMS (3) Rt 3.62 min; m/z (ESI$^+$) 457 (MH$^+$).

The material was dissolved in dichloromethane (1 mL) at 0° C. and trifluoroacetic acid (8 drops) was added. The temperature was allowed to rise to ambient. After 2.5 hours the mixture was adsorbed onto a 2 g Isolute SCX-II column. The resin was washed with methanol, then with 2M ammonia in methanol. The basic fractions were concentrated. Preparative TLC, eluting with 1% concentrated ammonia-10% methanol-89% dichloromethane, gave methyl 6-(5-methylpyrazin-2-ylamino)-4-(piperidin-4-ylmethylamino)nicotinate (18 mg, 22% over 2 steps) as a yellow powder.

$^1$H NMR (500 MHz, DMSO) δ 1.17-1.24 (2H, m), 1.66 (2H, d, J=12 Hz), 1.68-1.79 (1H, m), 2.40 (3H, s), 2.48 (2H, t, J=12 Hz), 2.98 (2H, d, J=12 Hz), 3.09 (2H, t, J=6 Hz), 3.22 (1H, t, J=6 Hz), 3.80 (3H, s), 7.11 (1H, s), 8.00 (1H, t, J=5.5 Hz), 8.14 (1H, s), 8.54 (1H, s), 8.84 (1H, s), 9.90 (1H, br s). LCMS (3) Rt 1.65 min; m/z (ESI$^+$) 357 (MH$^+$).

Synthesis 82-A

5-Methoxypyrazin-2-amine

5-Bromopyrazin-2-amine (0.11 g, 0.63 mmol) was dissolved in NaOMe/MeOH (0.23 g Na metal in 10 mL MeOH) and heated by microwave irradiation at 140° C. for 7 hours. After evaporation of the solvent, the residue was purified by preparative TLC, eluting with 30% ethyl acetate-n-hexane, to give 5-methoxypyrazin-2-amine (25 mg, 32%).

$^1$H NMR (500 MHz, MeOD) δ 7.64 (1H, s), 7.58 (1H, s), 3.85 (3H, s). LCMS (3) Rt 1.75 min; m/z (ESI$^+$) 126 (MH$^+$).

Synthesis 82-B

Methyl 6-(5-methoxypyrazin-2-ylamino)-4-(8-methyl-8-azabicyclo[3.2.1]octan-3-ylamino)nicotinate (Y-037)

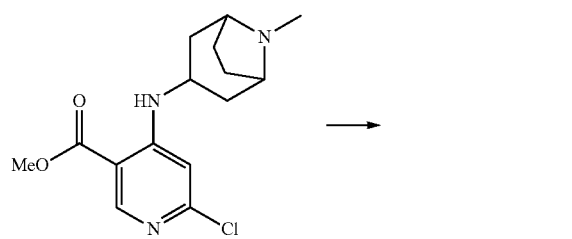

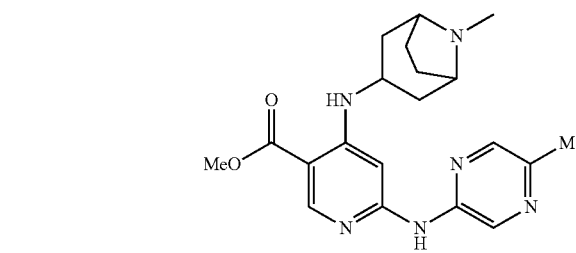

Methyl 6-chloro-4-(8-methyl-8-azabicyclo[3.2.1]octan-3-ylamino)nicotinate (26 mg, 0.084 mmol, prepared as described in Synthesis 62 and 63), 5-methoxypyrazin-2-amine (16 mg, 0.127 mmol), cesium carbonate (55 mg, 0.169 mmol), 4,5-bis(diphenylphosphino)-9,9-dimethylxanthene (3.9 mg, 7 mol %), and tris(dibenzylideneacetone)dipalladium chloroform complex (3.5 mg, 3.5 mol %) were added to a vial which was flushed with nitrogen and sealed. Anhydrous toluene (0.3 mL) and DMF (0.1 mL) were added and nitrogen was bubbled through the stirred solution for 10 minutes. The mixture was heated by microwave irradiation at 130° C. for 30 minutes. The cooled solution was diluted with methanol and adsorbed onto an Isolute SCX-II column. The column was washed with methanol, then with 2M ammonia in methanol. The basic fractions concentrated. Preparative TLC, eluting with ethyl acetate-methanol-concentrated ammonia 10:1:0.2, gave methyl 6-(5-methoxypyrazin-2-ylamino)-4-(8-methyl-8-azabicyclo[3.2.1]octan-3-ylamino)nicotinate (5 mg, 15%) as an oil.

$^1$H NMR (500 MHz, MeOH) δ 8.56 (1H, s), 8.43 (1H, s), 7.93 (1H, s), 7.00 (1H, s), 3.95 (3H, s), 3.84 (3H, s), 3.62-3.70 (2H, m), 2.60 (3H, s), 2.20-2.38 (4H, m), 2.00-2.10 (3H, m), 1.73-1.84 (2H, m). LCMS (3) Rt 1.70 min; m/z (ESI$^+$) 399 (MH$^+$).

Synthesis 83-A tert-Butyl 4-((2-bromo-5-nitropyridin-4-yloxy)methyl)piperidine-1-carboxylate

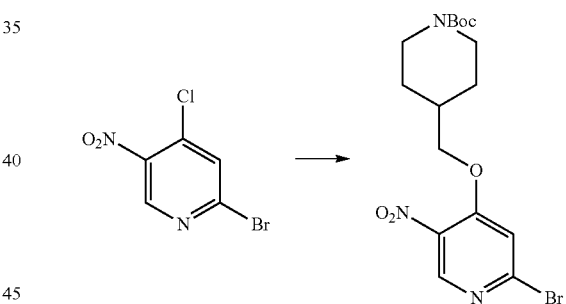

N-Boc-4-piperidinemethanol (860 mg, 4.0 mmol) was added to a suspension of 60% sodium hydride (160 mg, 4.0 mmol) in DMF (40 mmol) at room temperature. After 20 minutes, 2-bromo-4-chloro-5-nitropyridine (949 mg, 4.0 mmol) was added in one portion, and the resulting mixture was stirred overnight at room temperature. The mixture was diluted with ether and washed with water. The aqueous phase was extracted with ether. The combined organic phases were washed with water and brine, then dried (Na$_2$SO$_4$) and concentrated. Silica column chromatography, eluting with 20% ethyl acetate-hexane, gave tert-butyl 4-((2-bromo-5-nitropyridin-4-yloxy)methyl)piperidine-1-carboxylate (789 mg, 62%) as a viscous, pale yellow oil which solidified on standing.

$^1$H NMR (CDCl$_3$, 400 MHz) δ 8.80 (s, 1H), 7.20 (s, 1H), 4.05-4.15 (m, 2H), 4.00 (d, 2H, J=6.3 Hz), 2.75-2.85 (m, 2H), 2.10 (m, 1H), 1.80-1.90 (m, 2H), 1.45 (s, 9H), 1.20-1.30 (m, 2H). LCMS (1) Rt=2.45 min; m/z (ESI⁺) 316, 318 (MH⁺).

Synthesis 83-B tert-Butyl 4-((2-(5-cyanopyrazin-2-ylamino)-5-nitro-pyridin-4-yloxy)methyl)piperidine-1-carboxylate

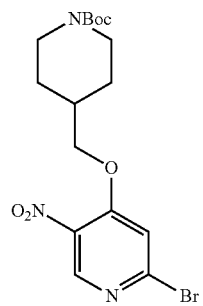

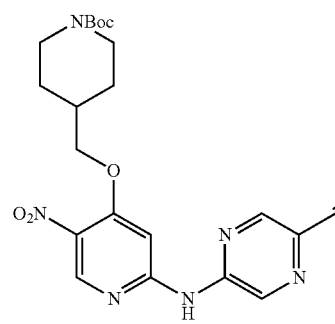

Palladium (II) acetate (14.7 mg, 0.07 mmol) was added to (±)-2,2"-bis(diphenylphosphino)-1,1"-binaphthalene (123 mg, 0.2 mmol) in DMF-toluene (1:1, 5 mL) and the mixture was degassed for 10 minutes under a stream of nitrogen gas. 2-Amino-5-cyanopyrazine (95 mg, 0.79 mmol), sodium-t-butoxide (76 mg, 0.79 mmol) and tert-butyl 4-((2-bromo-5-nitropyridin-4-yloxy)methyl)piperidine-1-carboxylate (273 mg, 0.67 mmol) were added and the mixture was degassed for a further 5 minutes before stirring at room temperature for 2 hours. The mixture was partitioned between ethyl acetate and water and the aqueous phase was extracted with ethyl acetate. The combined organic layers were washed with water and brine, then dried (Na₂SO₄) and concentrated to give crude tert-butyl 4-((2-(5-cyanopyrazin-2-ylamino)-5-nitropyridin-4-yloxy)methyl)piperidine-1-carboxylate (379 mg) which was used without further purification.

LCMS (1) Rt=2.39 min; m/z (ESI⁻) 454.

Synthesis 83-C tert-Butyl 4-((5-amino-2-(5-cyanopyrazin-2-ylamino)pyridin-4-yloxy)methyl)piperidine-1-carboxylate

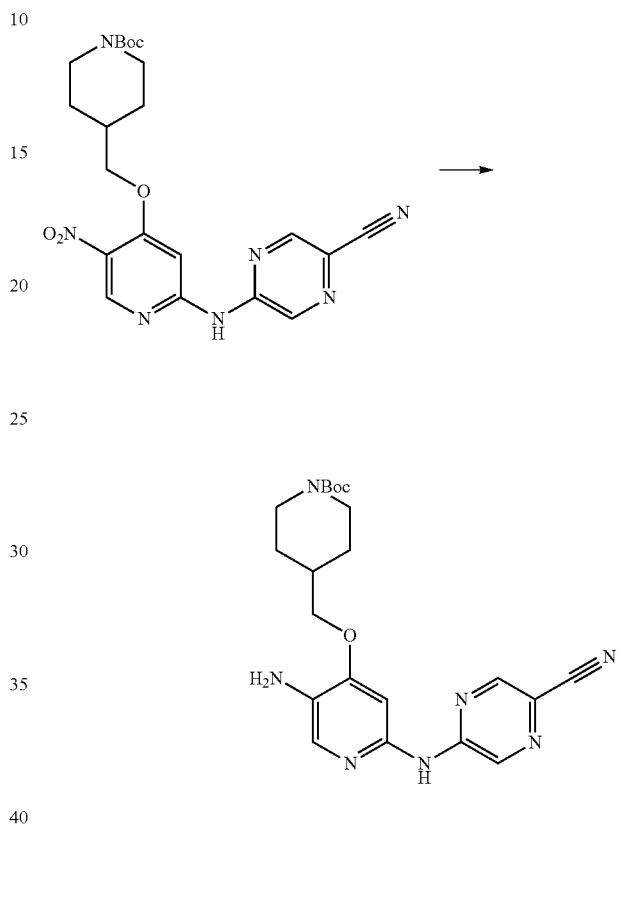

Tin (II) chloride dihydrate (745 mg, 3.3 mmol) was added to a solution of crude tert-butyl 4-((2-(5-cyanopyrazin-2-ylamino)-5-nitropyridin-4-yloxy)methyl)piperidine-1-carboxylate (301 mg, 0.66 mmol) in ethanol. After heating at 78° C. for 2 hours the mixture was cooled to room temperature and concentrated. The residue was diluted with ethyl acetate and water and the resulting precipitate was removed by filtration. The biphasic filtrate was separated and the aqueous phase was extracted with ethyl acetate. The combined organic layers were washed with brine, dried (Na₂SO₄) and concentrated to give a brown solid (250 mg). A portion of the crude material was purified by preparative HPLC to give tert-butyl 4-((2-(5-cyanopyrazin-2-ylamino)-5-nitropyridin-4-yloxy)methyl)piperidine-1-carboxylate (16 mg) as a yellow powder.

¹H NMR (CDCl₃, 400 MHz) δ 8.65 (s, 1H), 8.45 (s, 1H), 7.70 (s, 1H), 7.30 (s, 1H), 4.15-4.25 (m, 2H), 3.95 (d, 2H, J=6.3 Hz), 3.65 (br s, 2H), 2.75-2.80 (m, 2H), 2.00-2.10 (m, 1H), 1.70-1.80 (m, 2H), 1.50 (s, 9H), 1.30-1.40 (m, 2H). LCMS (1) Rt=2.05 min, m/z (ESI⁺) 426 (MH⁺), (ESI⁻) 424.

Synthesis 83-D 5-(5-Amino-4-(piperidin-4-ylmethoxy)pyridin-2-ylamino)pyrazine-2-carbonitrile (Y-038)

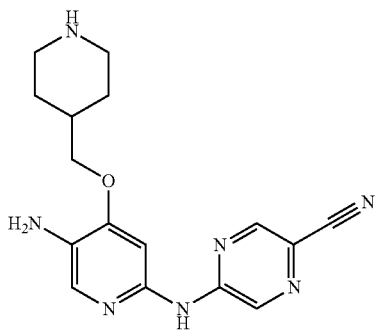 [SMILES: N#Cc1cnc(Nc2cc(OCC3CCNCC3)c(N)cn2)cn1]

A solution of tert-butyl 4-((5-amino-2-(5-cyanopyrazin-2-ylamino)pyridin-4-yloxy)methyl) piperidine-1-carboxylate (16 mg, 0.038 mmol) in 10 mL dichloromethane (10 mL) was treated over 45 minutes with 2 mL trifluoroacetic acid. After concentration of the solution in vacuo, the required product was isolated by SPE using a MP-TsOH cartridge, eluting with 2N ammonia in methanol. Concentration of the eluent gave the required product as a yellow solid (10 mg).

$^1$H NMR (CDCl$_3$, 400 MHz) δ 8.45 (s, 1H), 8.40 (s, 1H), 7.65 (s, 1H), 7.30 (s, 1H), 3.90 (d, 2H, J=6.4 Hz), 3.60 (br s, 2H), 3.05-3.15 (m, 2H), 2.55-2.65 (m, 2H), 1.90-2.00 (m, 1H), 2.70-2.80 (m, 2H), 1.20-1.30 (m, 2H). LCMS (2) Rt=1.33 min; m/z (ESI$^-$) 324.

Synthesis 84-A tert-Butyl 4-((2-(5-cyanopyrazin-2-ylamino)-5-(2-(dimethylamino)acetamido)pyridin-4-yloxy)methyl) piperidine-1-carboxylate

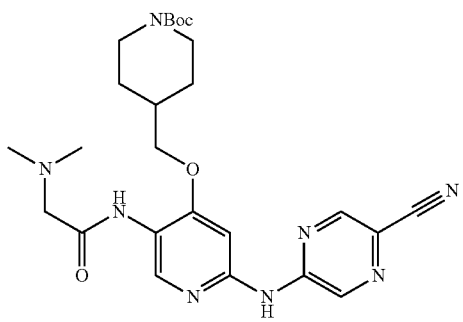 [SMILES: CN(C)CC(=O)Nc1cnc(Nc2cnc(C#N)cn2)cc1OCC1CCN(C(=O)OC(C)(C)C)CC1]

1-[3-(Dimethylamino)propyl]-3-ethylcarbodiimide (95 mg, 0.49 mmol) was added to a solution of tert-butyl 4-((5-amino-2-(5-cyanopyrazin-2-ylamino)pyridin-4-yloxy)methyl)piperidine-1-carboxylate (140 mg, 0.33 mmol), N,N-dimethylglycine (51 mg, 0.49 mmol), 1-hydroxybenzotriazole hydrate (76 mg, 0.49 mmol) and N-ethyldiisopropylamine (86 μL, 0.49 mmol) in DMF (4 mL). The mixture was stirred overnight at room temperature then partitioned between ethyl acetate and water. The organic phase was washed sequentially with water, dilute sodium bicarbonate solution and brine, then dried (Na$_2$SO$_4$) and concentrated. Preparative HPLC gave tert-butyl 4-((2-(5-cyanopyrazin-2-ylamino)-5-(2-(dimethylamino)acetamido)pyridin-4-yloxy)methyl)piperidine-1-carboxylate (24 mg, 14%) as an off-white powder.

$^1$H NMR (CDCl$_3$, 400 MHz) δ 9.70 (s, 1H), 9.10 (s, 1H), 8.65 (s, 1H), 8.50 (s, 1H), 8.00 (br s, 1H), 7.55 (s, 1H), 4.15-4.25 (m, 2H), 4.05 (d, 2H, J=5.90 Hz), 3.15 (s, 2H), 2.75-2.85 (m, 2H), 2.40 (s, 6H), 2.00-2.05 (m, 1H), 1.80-1.90 (m, 2H), 1.50 (s, 1H), 1.40-1.50 (m, 2H). LCMS (2) Rt=3.20 min; m/z (ESI$^+$) 511 (MH$^+$), (ESI$^-$) 509.

Synthesis 84-B

N-(6-(5-Cyanopyrazin-2-ylamino)-4-(piperidin-4-ylmethoxy)pyridin-3-yl)-2-(dimethylamino)acetamide (Y-039)

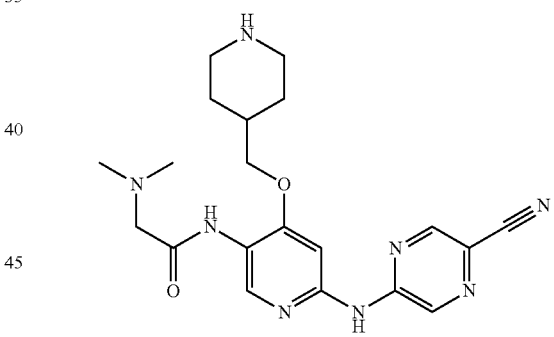

A solution of tert-butyl 4-((2-(5-cyanopyrazin-2-ylamino)-5-(2-(dimethylamino)acetamido) pyridin-4-yloxy) methyl)piperidine-1-carboxylate (24 mg, 0.047 mmol) and trifluoroacetic acid (2 mL) in dichloromethane (10 mL) was stirred for 45 minutes. The solution was concentrated and the residue was loaded onto a MP-TsOH SPE cartridge. Elution with 2M ammonia in methanol gave N-(6-(5-cyanopyrazin-2-ylamino)-4-(piperidin-4-ylmethoxy)pyridin-3-yl)-2-(dimethylamino)acetamide as a yellow solid (14 mg, 72%).

$^1$H NMR (CDCl$_3$, 400 MHz) δ 9.70 (s, 1H), 9.20 (s, 1H), 8.65 (s, 1H), 8.50, (s, 1H), 7.60 (s, 1H), 4.00 (d, 2H, J=6.6 Hz), 3.15-3.25 (m, 2H), 3.15 (s, 1H), 2.70-2.80 (m, 2H), 2.45

(s, 6H), 2.00-2.10 (m, 1H), 1.85-1.95 (m, 2H), 1.35-1.45 (m, 2H). LCMS (2) Rt=1.74 min; m/z (ESI⁺) 411 (MH⁺), (ESI⁻) 409.

Synthesis 85

5-(4-(1-Methylpiperidin-4-ylamino)-5-nitropyridin-2-ylamino)pyrazine-2-carbonitrile (Y-040)

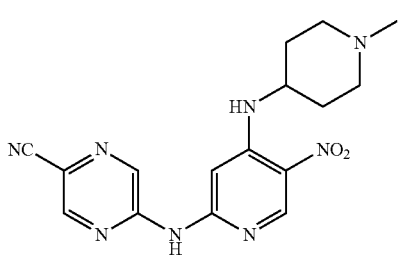 [SMILES: CN1CCC(Nc2cc(Nc3cnc(C#N)cn3)ncc2[N+](=O)[O-])CC1]

The title compound was prepared using methods analogous to those described in Synthesis 44, steps 44-A and 44-B.

LCMS (1) Rt=1.88 min; m/z (ESI⁺) 355 (MH⁺).

Synthesis 86

5-(5-Amino-4-(piperidin-3-ylmethylamino)pyridin-2-ylamino)pyrazine-2-carbonitrile (Y-041)

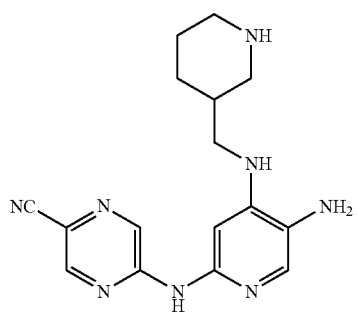

The title compound was prepared using methods analogous to those described in Synthesis 44, steps 44-A, 44-B, 44-C and 44-D.

¹H NMR (DMSO-d₆, 400 MHz) δ 8.95 (br. s, 1H), 8.63 (s, 1H), 8.36 (s, 2H), 7.45 (s, 1H), 6.83 (br. s, 1H), 5.74 (br. s, 1H) 3.23-3.17 (m, 1H), 3.11-2.98 (m, 3H), 2.71-2.60 (m, 1H), 2.02-1.92 (m, 1H), 1.90-1.81 (m, 1H), 1.78-1.70 (m, 1H), 1.59-1.46 (m, 1H), 1.26-1.15 (m, 1H). LC-MS (2) Rt=1.50 min; m/z (ESI⁺) 325 (MH⁺)

Synthesis 87

5-(5-Amino-4-(3-aminopropylamino)pyridin-2-ylamino)pyrazine-2-carbonitrile (Y-042)

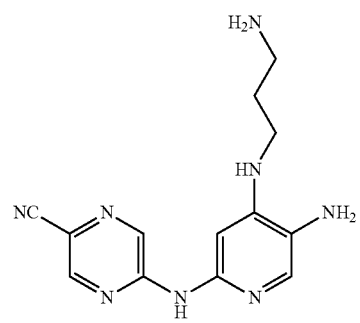 [SMILES: N#Cc1cnc(Nc2cc(NCCCN)c(N)cn2)cn1]

The title compound was prepared using methods analogous to those described in Synthesis 44, steps 44-A, 44-B, 44-C and 44-D.

LC-MS (2) Rt=2.57 min; m/z (ESI⁺) 285 (MH⁺).

Synthesis 88

(R)—N-(6-(5-Cyanopyrazin-2-ylamino)-4-(piperidin-3-ylamino)pyridin-3-yl)-2-(dimethylamino)acetamide (Y-043)

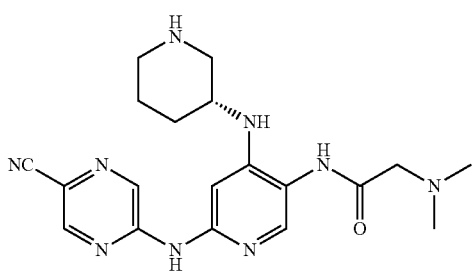 [SMILES: CN(C)CC(=O)Nc1cnc(Nc2cnc(C#N)cn2)cc1N[C@@H]1CCCNC1]

The title compound was prepared using methods analogous to those described in Synthesis 44, steps 44-A, 44-B, and 44-C, and Synthesis 53.

LC-MS (2) Rt=1.67 min; m/z (ESI⁺) 396 (MH⁺).

Synthesis 89

N-(6-(5-Cyanopyrazin-2-ylamino)-4-(piperidin-3-ylmethylamino)pyridin-3-yl)-2-(dimethylamino)acetamide (Y-044)

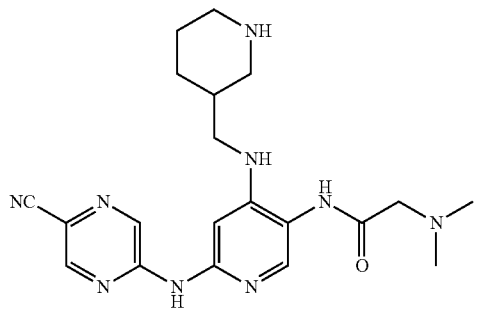 [SMILES: CN(C)CC(=O)Nc1cnc(Nc2cnc(C#N)cn2)cc1NCC1CCCNC1]

The title compound was prepared using methods analogous to those described in Synthesis 44, steps 44-A, 44-B, and 44-C, and Synthesis 53.

$^1$H NMR (DMSO-d$_6$, 400 MHz) δ 9.17 (s, 1H), 9.06 (s, 1H), 8.75 (s, 1H), 8.35 (s, 2H), 7.77 (s, 1H), 7.05 (br. s, 1H), 6.19-6.16 (m, 1H), 3.19-3.16 (m, 1H), 3.13-3.04 (m, 6H), 2.74-2.64 (m, 1H), 2.3 (s, 6H), 2.07-1.94 (m, 1H), 1.87-1.71 (m, 2H), 1.59-1.47 (m, 1H), 1.27-1.13 (m, 1H). LC-MS (2) Rt=1.82 min; m/z (ESI$^+$) 410 (MH$^+$).

Synthesis 90

5-(5-Amino-4-(cyclohexylamino)pyridin-2-ylamino)pyrazine-2-carbonitrile (Y-045)

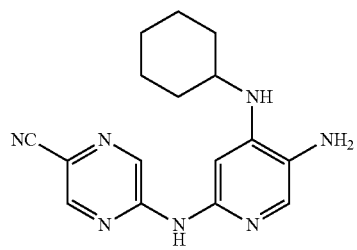 [SMILES: N#Cc1cnc(Nc2cc(NC3CCCCC3)c(N)cn2)cn1]

The title compound was prepared using methods analogous to those described in Synthesis 44, steps 44-A, 44-B and 44-C.

$^1$H NMR (DMSO-d$_6$, 400 MHz) δ 9.05-8.94 (br. s, 1H), 8.62 (s, 1H), 8.42 (s, 1H), 7.44 (s, 2H), 6.85-6.76 (br. s, 1H), 5.30-5.23 (m, 1H), 3.26-3.14 (m, 3H—occluded by broad water peak), 2.02-1.98 (m, 1H), 1.79-1.74 (m, 1H), 1.68-1.59 (m, 1H), 1.38-1.18 (m, 5H). LC-MS (2) Rt=2.58 min; m/z (ESI$^+$) 310 (MH$^+$).

Synthesis 91

(S)—N-(6-(5-Cyanopyrazin-2-ylamino)-4-(piperidin-3-ylamino)pyridin-3-yl)-2-(dimethylamino)acetamide (Y-046)

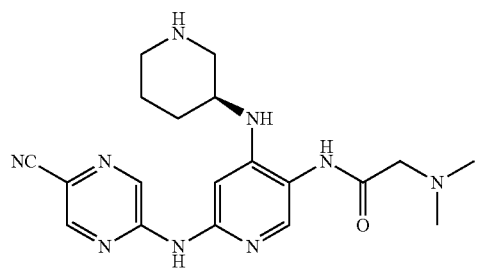 [SMILES: CN(C)CC(=O)Nc1cnc(Nc2cnc(C#N)cn2)cc1N[C@H]1CCCNC1]

The title compound was prepared using methods analogous to those described in Synthesis 44, steps 44-A, 44-B, 44-C and 44-D, and Synthesis 53.

$^1$H NMR (DMSO-d$_6$, 400 MHz) δ 9.23 (br. s, 1H), 9.07 (s, 1H), 8.72 (s, 1H), 8.34 (s, 2H), 7.82 (s, 1H), 7.08 (br. s, 1H), 5.63-5.57 (m, 1H), 3.17 (s, 2H), 3.10 (s, 2H), 2.91-2.80 (m, 2H), 2.72-2.57 (m, 1H), 2.30 (s, 6H), 1.92-1.85 (m, 1H), 1.77-1.64 (m, 1H), 1.56-1.44 (m, 2H). LC-MS (2) Rt=1.74 min; m/z (ESI$^+$) 396 (MH$^+$).

Synthesis 92

(S)-5-(5-Amino-4-(piperidin-3-ylmethylamino)pyridin-2-ylamino)pyrazine-2-carbonitrile (Y-047)

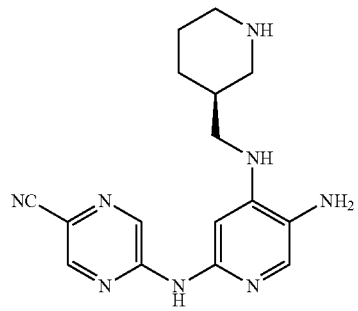 [SMILES: N#Cc1cnc(Nc2cc(NC[C@H]3CCCNC3)c(N)cn2)cn1]

The title compound was prepared using methods analogous to those described in Synthesis 44, steps 44-A, 44-B, 44-C and 44-D.

LC-MS (2) Rt=1.55 min; m/z (ESI$^+$) 325 (MH$^+$).

Synthesis 93

(R)-5-(5-Amino-4-(piperidin-3-ylmethylamino)pyridin-2-ylamino)pyrazine-2-carbonitrile (Y-048)

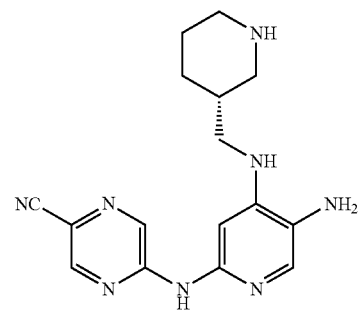 [SMILES: N#Cc1cnc(Nc2cc(NC[C@@H]3CCCNC3)c(N)cn2)cn1]

The title compound was prepared using methods analogous to those described in Synthesis 44, steps 44-A, 44-B, 44-C and 44-D.

LC-MS (2) Rt=1.55 min; m/z (ESI$^+$) 325 (MH$^+$).

Synthesis 94

5-(5-Amino-4-(cyclohexylmethylamino)pyridin-2-ylamino)pyrazine-2-carbonitrile (Y-049)

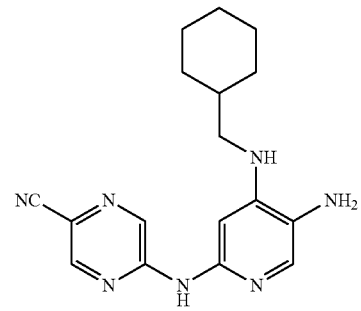 [SMILES: N#Cc1cnc(Nc2cc(NCC3CCCCC3)c(N)cn2)cn1]

The title compound was prepared using methods analogous to those described in Synthesis 44, steps 44-A, 44-B and 44-C.

$^1$H NMR (DMSO-d$_6$, 400 MHz) δ 9.00 (br. s, 1H), 8.61 (s, 1H), 8.24 (s, 1H), 7.44 (s, 1H), 6.76 (br. s, 1H), 5.61-5.80 (m, 1H), 2.95-2.92 (m, 2H), 1.83-1.62 (m, 5H), 1.32-1.18 (m, 4H), 0.97-0.94 (m, 2H). LC-MS (2) Rt=2.79 min; m/z (ESI$^+$) 324 (MH$^+$).

Synthesis 95

5-(5-Amino-4-(3-amino-3-phenylpropylamino)pyridin-2-ylamino)pyrazine-2-carbonitrile (Y-050)

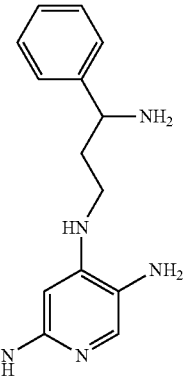

The title compound was prepared using methods analogous to those described in Synthesis 44, 44-A, 44-B, 44-C and 44-D.

$^1$H NMR (DMSO-d$_6$, 400 MHz) δ 10.20 (br. s, 1H), 8.94 (br. s, 1H), 8.59 (s, 1H), 7.47 (s, 1H), 7.41-7.19 (m, 5H), 6.86-6.79 (br. s, 1H), 5.56-5.49 (m, 1H), 4.55-4.40 (br. s, 1H), 3.79 (s, 2H), 3.24-3.17 (m, 1H), 2.84-2.77 (m, 1H). LC-MS (2) Rt=2.16 min; m/z (ESI$^+$) 361 (MH$^+$).

Synthesis 96

5-(5-Amino-4-(piperidin-2-ylmethylamino)pyridin-2-ylamino)pyrazine-2-carbonitrile (Y-051)

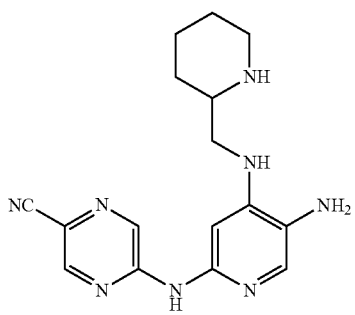 [SMILES: N#Cc1cnc(Nc2cc(NCC3CCCCN3)c(N)cn2)cn1]

The title compound was prepared using methods analogous to those described in Synthesis 44, steps 44-A, 44-B, 44-C and 44-D.

$^1$H NMR (DMSO-d$_6$, 400 MHz) δ 8.72 (br. s, 1H), 8.38 (s, 1H), 8.11 (s, 2H), 7.23 (s, 1H), 6.57 (br. s, 1H), 5.61-5.53 (m, 1H), 2.95-2.81 (m, 3H), 2.77-2.66 (m, 1H), 2.46-2.34 (m,

1H), 1.59-1.47 (m, 2H), 1.42-1.32 (m, 1H), 1.25-0.97 (m, 3H). LC-MS (2) Rt=1.81 min; m/z (ESI⁺) 325 (MH⁺).

Synthesis 97

(S)-2-Amino-5-(5-amino-2-(5-cyanopyrazin-2-ylamino)pyridin-4-ylamino)-N-phenylpentanamide (Y-052)

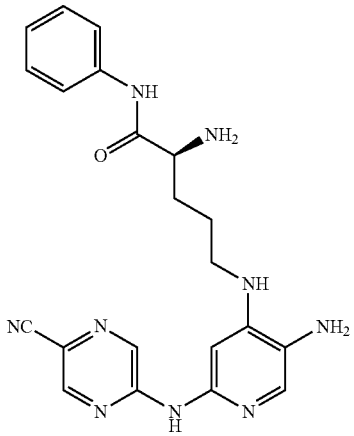 [SMILES: N#Cc1cnc(Nc2cc(NCCC[C@H](N)C(=O)Nc3ccccc3)c(N)cn2)cn1]

The title compound was prepared using methods analogous to those described in Synthesis 44, steps 44-A, 44-B, 44-C and 44-D.

¹H NMR (DMSO-d₆, 400 MHz) δ 10.18 (br. s, 1H), 8.93 (br. s, 1H), 8.61 (s, 1H), 7.67-7.59 (m, 2H), 7.45 (s, 1H), 7.35-7.24 (m, 2H), 7.08-7.00 (m, 1H), 6.83 (s, 1H), 5.65-5.57 (m, 1H), 4.55-4.40 (m, 2H), 3.20-3.06 (m, 3H), 1.84-1.52 (m, 4H). LC-MS (2) Rt=1.98 min; m/z (ESI⁺) 418 (MH⁺).

Synthesis 98

N-(6-(5-Cyanopyrazin-2-ylamino)-4-(piperidin-3-ylmethylamino)pyridin-3-yl)-3-(piperidin-4-yl)propanamide (Y-053)

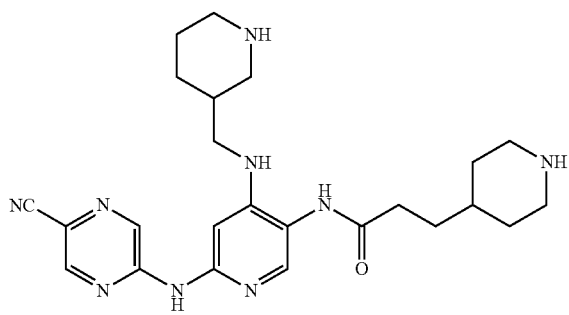 [SMILES: N#Cc1cnc(Nc2cc(NCC3CCCNC3)c(NC(=O)CCC3CCNCC3)cn2)cn1]

The title compound was prepared using methods analogous to those described in Synthesis 44, steps 44-A, 44-B, and 44-C, and Synthesis 53.

¹H NMR (DMSO-d₆, 400 MHz) δ 8.98 (s, 1H), 8.89 (s, 1H), 8.51 (s, 1H), 8.28 (s, 1H), 7.60 (s, 1H), 6.77 (s, 1H), 5.91-5.83 (m, 1H), 3.31-3.15 (m, 3H), 2.84-2.61 (m, 6H), 2.17-2.00 (m, 3H), 1.62-1.49 (m, 2H), 1.49-1.25 (m, 5H), 1.21-1.08 (m, 2H), 0.96-0.80 (m, 3H). LC-MS (2) Rt=1.41 min; m/z (ESI⁺) 464 (MH⁺)

Synthesis 99

N-(6-(5-Cyanopyrazin-2-ylamino)-4-(piperidin-3-ylmethylamino)pyridin-3-yl)-3-(4-methylthiazol-5-yl)propanamide (Y-054)

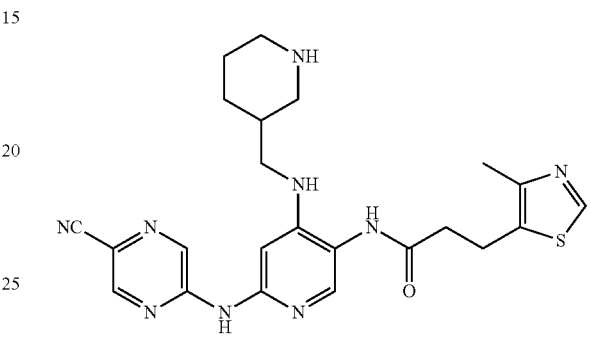

The title compound was prepared using methods analogous to those described in Synthesis 44, steps 44-A, 44-B, and 44-C, and Synthesis 53.

¹H NMR (DMSO-d₆, 400 MHz) δ 9.69 (br. s, 1H), 9.37 (br. s, 1H), 9.11 (s, 1H), 9.03 (s, 1H), 8.06 (s, 1H), 7.30 (br. s, 1H), 6.58-6.50 (m, 2H), 3.50-3.41 (m, 2H), 3.40-3.26 (m, 5H), 2.99-2.87 (m, 3H), 2.62 (s, 3H), 2.31-2.18 (m, 1H), 2.14-1.96 (m, 2H), 1.86-1.72 (m, 1H), 1.52-1.40 (m, 1H). LC-MS (2) Rt=1.59 min; m/z (ESI⁺) 478 (MH⁺).

Synthesis 100

N-(6-(5-Cyanopyrazin-2-ylamino)-4-(piperidin-3-ylmethylamino)pyridin-3-yl)-3-morpholinopropanamide (Y-055)

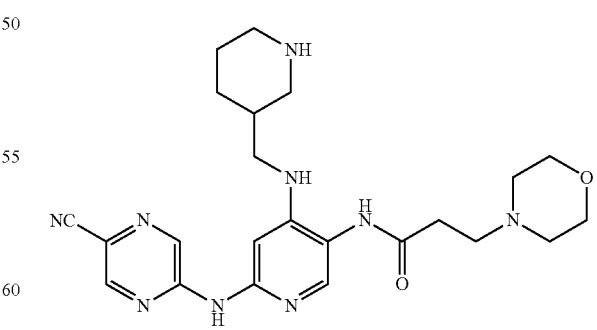

The title compound was prepared using methods analogous to those described in Synthesis 44, steps 44-A, 44-B, and 44-C, and Synthesis 53.

LC-MS (2) Rt=1.54 min; m/z (ESI⁺) 466 (MH⁺).

Synthesis 101-A tert-Butyl 3-((2-bromo-5-nitropyridin-4-ylamino)methyl)piperidine-1-carboxylate

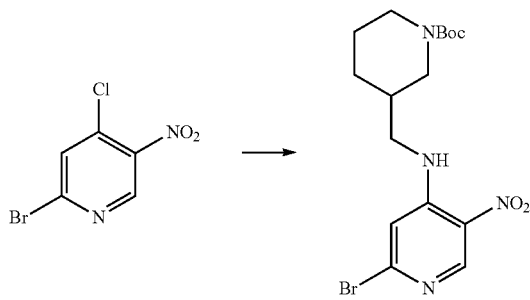 [SMILES: O=[N+]([O-])c1cnc(Br)cc1Cl ; CC(C)(C)OC(=O)N1CCCC(CNc2cc(Br)ncc2[N+](=O)[O-])C1]

A solution of 3-(aminomethyl)-1-boc-piperidine (409 mg, 1.91 mmol) in acetonitrile (2.5 mL) was added dropwise to a solution of 2-bromo-4-chloro-5-nitropyridine (431 mg, 1.82 mmol) and triethylamine (0.28 mL, 2.0 mmol) in acetonitrile (10 mL). The solution was stirred for 1 hr then partitioned between dichloromethane and water. The aqueous phase was extracted with dichloromethane (×3) and the combined organic phases were dried (Na$_2$SO$_4$) and concentrated to give tert-butyl 3-((2-bromo-5-nitropyridin-4-ylamino)methyl)piperidine-1-carboxylate as a yellow-brown solid (718 mg, 95%) which was used without further purification.

LCMS (1): Rt=2.38 min; m/z (ESI$^+$) 415, 417 (MH$^+$).

Synthesis 101-B tert-Butyl 3-((2-(5-cyanopyrazin-2-ylamino)-5-nitropyridin-4-ylamino)methyl)piperidine-1-carboxylate

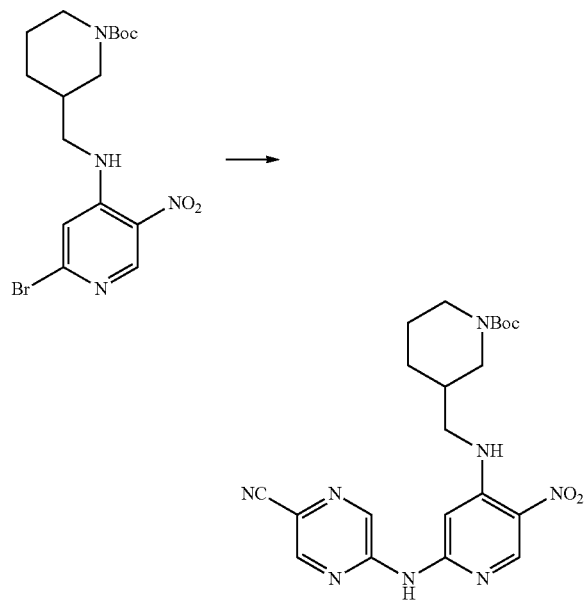

Palladium (II) acetate (39 mg, 0.17 mmol) was added to (±)-2,2″-bis(diphenylphosphino)-1,1″-binaphthalene (321 mg, 0.51 mmol) in DMF/toluene (1/1 15 mL) and the resulting mixture was degassed under a stream of nitrogen gas for 10 min. 2-Amino-5-cyanopyrazine (210 mg, 1.7 mmol), sodium tert-butoxide (250 mg, 2.6 mmol) and tert-butyl 3-((2-bromo-5-nitropyridin-4-ylamino)methyl)piperidine-1-carboxylate (713 mg, 1.7 mmol) were added and the mixture was degassed for a further 5 minutes then heated at 150° C. for 30 min using microwave irradiation. The mixture was concentrated in vacuo and water and ethyl acetate were added. The aqueous phase was extracted three times with ethyl acetate. The combined organic phases were dried (Na$_2$SO$_4$) and concentrated.

The residue was purified by flash column chromatography on silica, eluting with a gradient of ethyl acetate in hexane, 10-100% over 50 min. The fractions containing the product contaminated with 2-amino-5-cyanopyrazine were combined, evaporated and repurified by silica column chromatography, eluting with a gradient of ethyl acetate in hexane, 10-50% over 45 min. Tert-butyl 3-((2-(5-cyanopyrazin-2-ylamino)-5-nitropyridin-4-ylamino)methyl)piperidine-1-carboxylate was obtained as a yellow solid (265 mg, 34%).

LCMS (1): Rt=2.38 min; m/z (ESI$^+$) 455 (MH$^+$).

Synthesis 101-C tert-Butyl 3-((5-amino-2-(5-cyanopyrazin-2-ylamino)pyridin-4-ylamino)methyl)piperidine-1-carboxylate

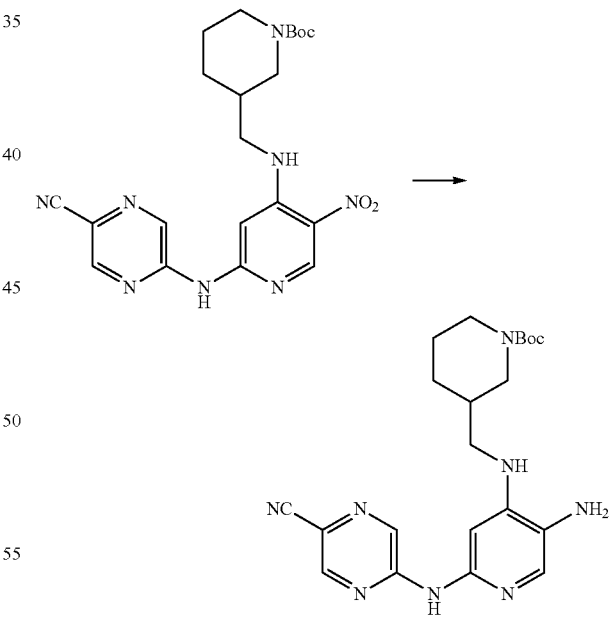

tert-Butyl 3-((2-(5-cyanopyrazin-2-ylamino)-5-nitropyridin-4-ylamino)methyl)piperidine-1-carboxylate (265 mg, 0.583 mmol) was dissolved in ethanol (20 mL) and tin (II) chloride hydrate (658 mg, 2.92 mmol) was added. The suspension was heated for 30 min at 70° C. Solvents were removed by evaporation and the residue was dissolved in ethyl acetate and aqueous saturated sodium hydrogen carbonate. The mixture was filtered and the residue was washed thoroughly with ethyl acetate. The two phases of the filtrate were separated and the aqueous phase was extracted twice with ethyl acetate. The combined organic phases were dried (Na$_2$SO$_4$) and solvent was removed by evaporation affording tert-butyl 3-((5-amino-2-(5-cyanopyrazin-2-ylamino)pyridin-4-ylamino)methyl)piperidine-1-carboxylate (139 mg, 56%). The crude product was used directly in the next step.

LCMS (1): Rt=1.97 min; m/z (ESI$^+$) 426 (MH$^+$).

Synthesis 101-D 5-(4-(Piperidin-3-ylmethylamino)-5-(1H-pyrrol-1-yl)pyridin-2-ylamino)pyrazine-2-carbonitrile (Y-056)

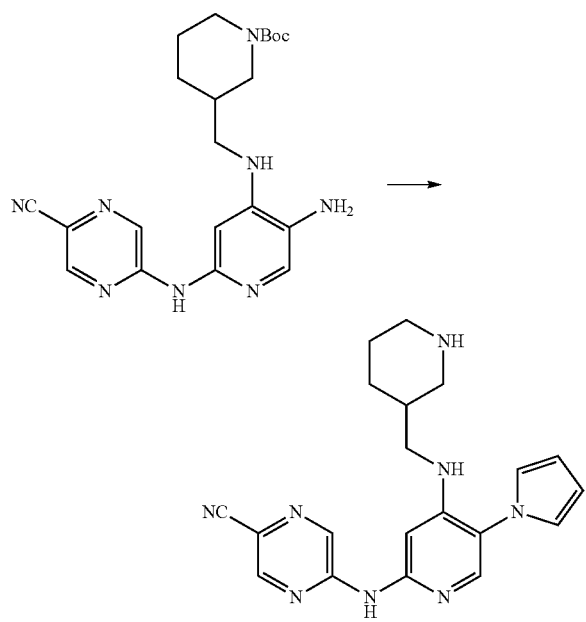

tert-Butyl 3-((5-amino-2-(5-cyanopyrazin-2-ylamino)pyridin-4-ylamino)methyl)piperidine-1-carboxylate (121 mg, 0.285 mmol) was dissolved in DCE (6 mL) and 2,5-dimethoxytetrahydrofuran (75.3 mg, 0.57 mmol) and acetic acid (2 mL) were added. The solution was heated for 1 h at 80° C. then a further aliquot of acetic acid (2 mL) was added. The solution was heated at 80° C. for a further 30 min then cooled to room temperature and partitioned between dichloromethane and water. The aqueous phase was extracted with dichloromethane and the combined organic phases were evaporated to give an orange oil. The residue was dissolved in methanol and absorbed onto a TsOH solid phase extraction cartridge, washed once with methanol and allowed to stand for 1 h. The cartridge was then eluted with a solution of 7M ammonia in methanol and the solution was evaporated to dryness. The residue was purified by HPLC to give 5-(4-(piperidin-3-ylmethylamino)-5-(1H-pyrrol-1-yl)pyridin-2-ylamino)pyrazine-2-carbonitrile (4.3 mg, 4%).

$^1$H NMR (DMSO-d$_6$, 400 MHz) δ 9.11 (s, 1H), 8.71 (s, 1H), 8.31 (s, 1H), 7.82 (s, 1H), 7.14 (s, 1H), 6.86 (s, 2H), 6.29 (s, 1H), 5.44 (m, 1H), 3.05-2.86 (m, 3H), 2.51 (m, 1H), 2.31 (m, 1H), 1.86-1.68 (m, 2H), 1.66-1.58 (m, 1H), 1.45-1.34 (m, 1H), 1.16-1.05 (m, 1H). LC-MS (2) Rt=2.57 min; m/z (ESI$^+$) 375 (MH$^+$).

Synthesis 102

(R)-5-(4-(Piperidin-3-ylamino)-5-(1H-pyrrol-1-yl)pyridin-2-ylamino)pyrazine-2-carbonitrile (Y-057)

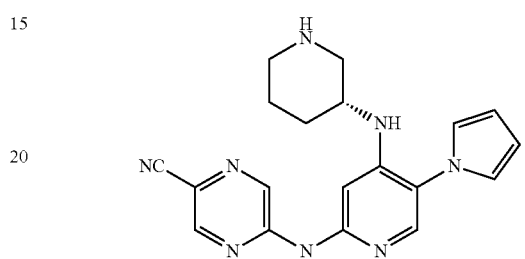

The title compound was prepared using methods analogous to those described in Synthesis 101, steps 101-A, 101-B, 101-C and 101-D.

$^1$H NMR (DMSO-d$_6$, 400 MHz) δ 9.13 (s, 1H), 8.77 (s, 1H), 8.24 (s, 1H), 7.89 (s, 1H), 7.15 (s, 1H), 6.91 (br. s, 2H), 6.30 (br. s, 2H), 5.16 (m, 1H), 2.95 (m, 1H), 2.72-2.56 (m, 3H), 1.78-1.38 (m, 4H). LC-MS (2) Rt=2.51 min; m/z (ESI$^+$) 361 (MH$^+$).

Synthesis 103

5-(4-(1-Methylpiperidin-4-ylamino)-5-(1H-pyrrol-1-yl)pyridin-2-ylamino)pyrazine-2-carbonitrile (Y-058)

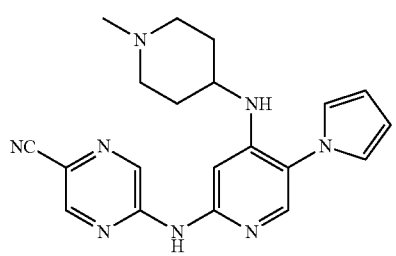 [SMILES: CN1CCC(Nc2cc(Nc3cnc(C#N)cn3)ncc2-n2cccc2)CC1]

The title compound was prepared using methods analogous to those described in Synthesis 101, steps 101-A, 101-B, 101-C and 101-D.

$^1$H NMR (DMSO-d$_6$, 400 MHz) δ 10.63-10.58 (br. S, 1H), 9.13 (s, 1H), 8.77 (s, 1H), 8.19 (s, 1H), 7.88 (s, 1H), 7.19 (s, 1H), 6.90-6.89 (m, 2H), 6.31-6.30 (m, 2H), 4.87-4.85 (m,

1H), 2.68-2.64 (m, 2H), 2.17 (s, 3H), 2.09-2.04 (m, 2H), 1.91-1.85 (m, 2H), 1.47-1.44 (m, 2H). LC-MS (2) Rt=2.68 min; m/z (ESI⁺) 375 (MH⁺).

Synthesis 104

5-(4-(Piperidin-3-ylmethylamino)-5-(pyrrolidin-1-yl)pyridin-2-ylamino)pyrazine-2-carbonitrile (Y-059)

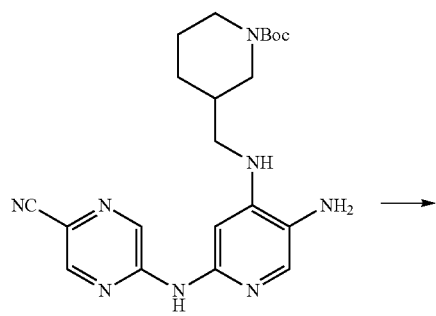

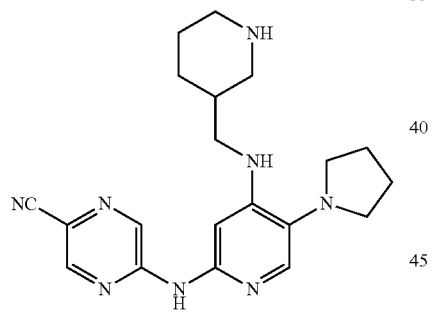

tert-Butyl 3-((5-amino-2-(5-cyanopyrazin-2-ylamino)pyridin-4-ylamino)methyl)piperidine-1-carboxylate (40 mg, 0.094 mmol) (Synthesis 101-C) was dissolved in ethanol (2 mL) and treated with sodium ethoxide (34 mg, 0.509 mmol) and 1,4-dibromobutane (44 mg, 0.208 mmol) at between 70 and 80° C. for 96 h. The reaction was quenched with water and the aqueous phase extracted with dichloromethane. The combined organic phases were evaporated and the residue was treated with a 20% solution of TFA in dichloromethane for 20 min. The solution was evaporated and the residue was purified by HPLC to give 5-(4-(piperidin-3-ylmethylamino)-5-(pyrrolidin-1-yl)pyridin-2-ylamino)pyrazine-2-carbonitrile (10.3 mg, 29%).

LC-MS (2) Rt=2.33 min; m/z (ESI⁺) 379 (MH⁺).

Synthesis 105

5-(5-((S)-3-Hydroxypyrrolidin-1-yl)-4-(piperidin-3-ylmethylamino)pyridin-2-ylamino)pyrazine-2-carbonitrile (Y-060)

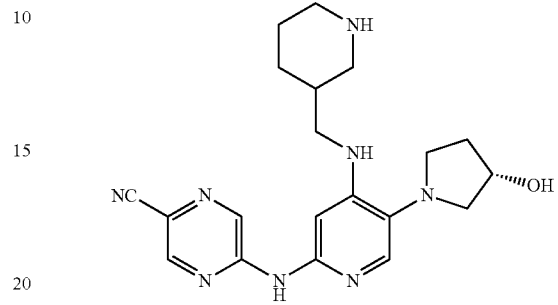

The title compound was prepared using methods analogous to those described in Synthesis 104, using (S)-1,4-dibromobutan-2-ol instead of 1,4-dibromobutane.

¹H NMR (DMSO-d₆, 400 MHz) δ 9.17 (s, 1H), 8.76 (s, 1H), 8.45 (s, 1H), 7.81 (s, 1H), 6.96 (s, 1H), 6.13-6.05 (m, 1H), 4.42-4.32 (m, 1H), 3.29-3.17 (m, 3H), 3.16-3.04 (m, 2H), 2.99-2.82 (m, 2H), 2.76-2.64 (m, 1H), 2.26-2.13 (m, 1H), 2.11-1.97 (m, 1H), 1.93-1.74 (m, 2H), 1.64-1.49 (m, 1H), 1.34-1.18 (m, 1H). LC-MS (2) Rt=1.74 min; m/z (ESI⁺) 395 (MH⁺).

Synthesis 106

5-(5-(3-Hydroxypyrrolidin-1-yl)-4-((R)-piperidin-3-ylmethylamino)pyridin-2-ylamino) pyrazine-2-carbonitrile (Y-061)

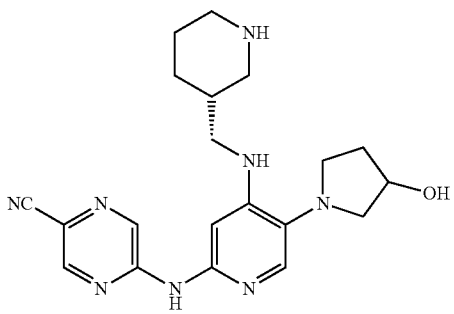

The title compound was prepared using methods analogous to those described in Synthesis 105.

¹H NMR (DMSO-d₆, 400 MHz) δ 9.11 (s, 1H), 8.70 (s, 1H), 8.41 (s, 1H), 7.76 (s, 1H), 6.90 (s, 1H), 6.09-6.01 (m, 1H), 4.36-4.26 (m, 1H), 3.21-3.13 (m, 3H), 3.12-3.00 (m, 2H), 2.92-2.77 (m, 2H), 2.76-2.63 (m, 1H), 2.20-1.97 (m,

2H), 1.89-1.70 (m, 2H), 1.62-1.46 (m, 1H), 1.29-1.15 (m, 1H). LC-MS (2) Rt=1.74 min; m/z (ESI⁺) 395 (MH⁺).

Synthesis 107-A tert-Butyl 3-((2-(5-cyanopyrazin-2-ylamino)-5-(3-formyl-1H-pyrrol-1-yl)pyridin-4-ylamino)methyl)piperidine-1-carboxylate

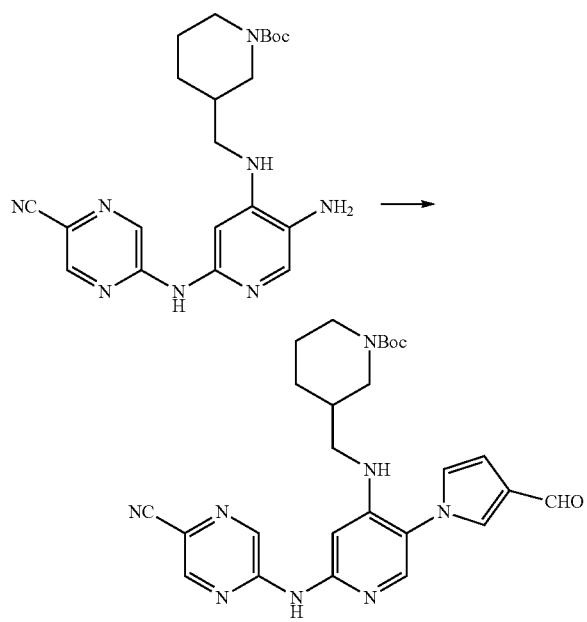

tert-Butyl 3-((5-amino-2-(5-cyanopyrazin-2-ylamino)pyridin-4-ylamino)methyl)piperidine-1-carboxylate (60 mg, 0.141 mmol) (Synthesis 101-C) was dissolved in DCE/AcOH (1/1, 5 mL). 2,5-Dimethoxytetrahydrofuran-3-carboxaldehyde (28 uL, 0.211 mmol) was added and the solution was stirred at 80° C. for 1 h. The solution was evaporated to dryness and the product (143 mg, approximately 50% purity) was used without further purification.

LC-MS (1) Rt=2.44 min; m/z (ESI⁺) 503 (MH⁺).

Synthesis 107-B tert-Butyl 3-((2-(5-cyanopyrazin-2-ylamino)-5-(3-(morpholinomethyl)-1H-pyrrol-1-yl)pyridin-4-ylamino)methyl)piperidine-1-carboxylate

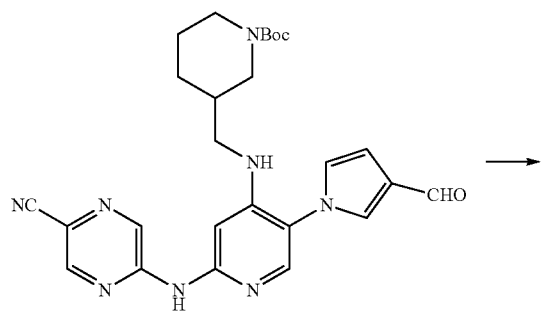

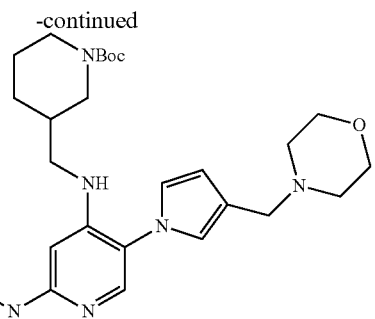

Crude tert-butyl 3-((2-(5-cyanopyrazin-2-ylamino)-5-(3-formyl-1H-pyrrol-1-yl)pyridin-4-ylamino)methyl)piperidine-1-carboxylate (143 mg of 50% pure material, approx. 0.142 mmol) was dissolved in DCE (1.5 mL) and AcOH (0.15 mL). Morpholine (18.5 uL, 0.213 mmol) and sodium triacetoxyborohydride (75 mg, 0.355 mmol) were added and the reaction mixture was stirred at room temperature for 30 min. The reaction mixture was partitioned between dichloromethane and 10% aqueous NaHCO₃. The two phases were separated and the aqueous phase was extracted with dichloromethane. The combined organic phases were evaporated to dryness and the product (90 mg) was used without further purification.

LC-MS (1) Rt=2.46 min; m/z (ESI⁺) 574 (MH⁺).

Synthesis 107-C 5-(5-(3-(Morpholinomethyl)-1H-pyrrol-1-yl)-4-(piperidin-3-ylmethylamino)pyridin-2-ylamino)pyrazine-2-carbonitrile (Y-062)

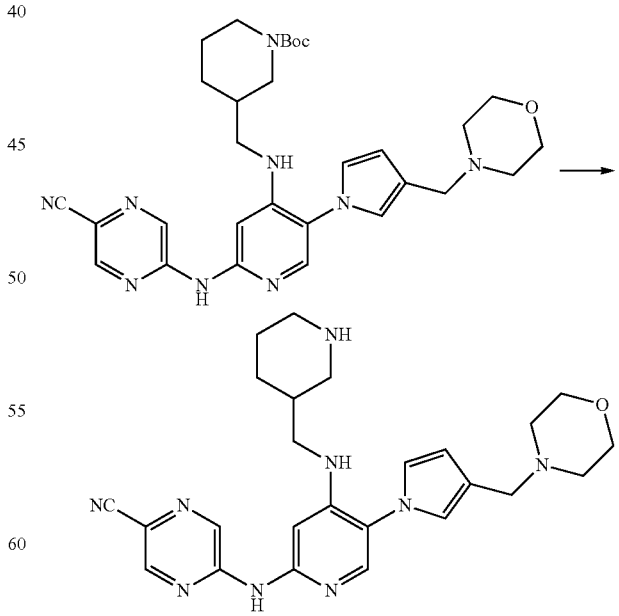

Crude tert-butyl 3-((2-(5-cyanopyrazin-2-ylamino)-5-(3-(morpholinomethyl)-1H-pyrrol-1-yl)pyridin-4-ylamino)methyl)piperidine-1-carboxylate (90 mg) was dissolved in methanol (1 mL) and absorbed onto a TsOH solid phase extraction cartridge and allowed to stand for 2 h. The cartridge was eluted with 7M ammonia in methanol. The basic fractions were evaporated to dryness. The crude product was purified by HPLC to give 5-(5-(3-(morpholinomethyl)-1H-pyrrol-1-yl)-4-(piperidin-3-ylmethylamino)pyridin-2-ylamino)pyrazine-2-carbonitrile (4.93 mg, 7% over 3 steps).

LC-MS (2) Rt=2.07 min; m/z (ESI+) 474 (MH+).

Synthesis 108

5-(5-(3-(Hydroxymethyl)-1H-pyrrol-1-yl)-4-(piperidin-3-ylmethylamino)pyridin-2-ylamino)pyrazine-2-carbonitrile (Y-063)

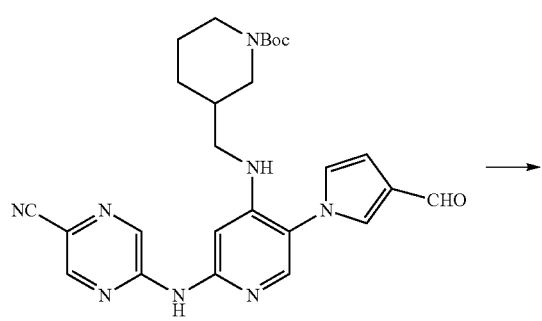

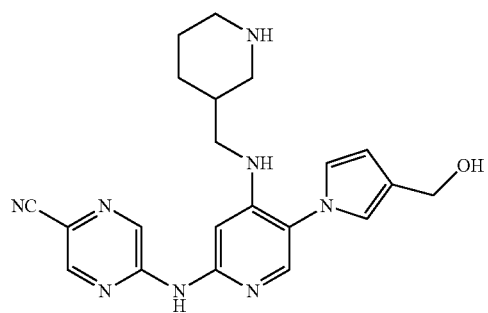

tert-Butyl 3-((5-amino-2-(5-cyanopyrazin-2-ylamino)pyridin-4-ylamino)methyl)piperidine-1-carboxylate (37 mg, 0.074 mmol) (Synthesis 107-A) was dissolved in methanol (1.5 mL) and cooled to 0° C. Sodium borohydride (15 mg, 0.396 mmol) was added and the reaction was stirred at 0° C. for 4 h. The solution was evaporated and the residue was partitioned between water and dichloromethane. The two phases were separated and the aqueous phase was extracted with dichloromethane. The combined organic phases were evaporated and the residue was dissolved in methanol (1 mL) and absorbed onto a TsOH solid phase extraction cartridge. After 1.5 h the cartridge was eluted with 7M ammonia in methanol. The basic eluent was evaporated to dryness. The residue was purified by HPLC to give 5-(5-(3-(hydroxymethyl)-1H-pyrrol-1-yl)-4-(piperidin-3-ylmethylamino)pyridin-2-ylamino)pyrazine-2-carbonitrile (3.18 mg, 11%).

$^1$H NMR (DMSO-d$_6$, 400 MHz) δ 10.66 (br. s, 1H), 9.13 (s, 1H), 8.78 (s, 1H), 8.43 (s, 1H), 7.81 (s, 1H), 7.15 (s, 1H), 6.88-6.79 (m, 1H), 6.27 (s, 1H), 5.82-5.73 (m, 1H), 4.29 (s, 2H), 3.27 (s, 2H), 3.06-2.90 (m, 2H), 2.39-2.28 (m, 1H), 1.92-1.61 (m, 2H), 1.49-1.35 (m, 1H), 1.16-1.04 (m, 1H). LC-MS (2) Rt=2.26 min; m/z (ESI+) 387 (MH+).

Synthesis 109-A

Ethyl 2,5-dimethoxy-2,5-dihydrofuran-3-carboxylate

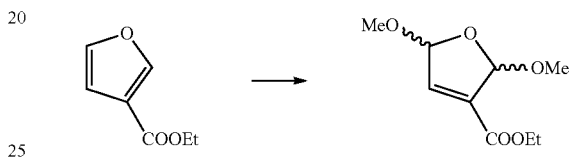

Ethylfuroate (500 mg, 3.568 mmol) and potassium carbonate (1233 mg, 8.92 mmol) were dissolved in methanol (10 mL), cooled to 0° C. Bromine (1140 mg, 7.136 mmol) was added dropwise. The reaction mixture was stirred for 30 min at 0° C. and was then allowed to warm to room temperature and stirred for an additional 2 h. The reaction mixture was evaporated and the residue was partitioned between dichloromethane and water. The phases were separated and the aqueous phase was extracted with dichloromethane. The combined organic phases were dried (Na$_2$SO$_4$), filtered and concentrated to give ethyl 2,5-dimethoxy-2,5-dihydrofuran-3-carboxylate as a mixture of isomers (659 mg, 91%).

$^1$H NMR (CDCl$_3$, 400 MHz) δ 6.83-6.80 (m, 1H), 6.03-5.98 (m, 1H), 5.76-5.69 (m, 1H), 4.29 (q, 2H), 3.51 (s), 3.50 (s), 3.47 (s), 3.44 (s, total for previous 4 singlets=6H), 1.33 (t, 3H). LC-MS (1) Rt=1.70 min; no ionisation.

Synthesis 109-B

Ethyl 2,5-dimethoxy-tetrahydrofuran-3-carboxylate

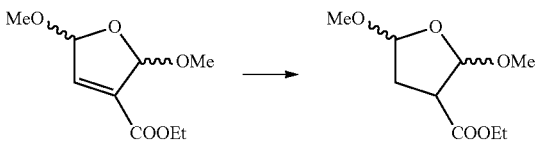 [SMILES: CCOC(=O)C1=CC(OC)OC1OC ; CCOC(=O)C1CC(OC)OC1OC]

Ethyl 2,5-dimethoxy-2,5-dihydrofuran-3-carboxylate (615 mg, 3.044 mmol) was dissolved in methanol (10 mL) and treated with hydrogen (10 bar) over Raney nickel at 40° C. for 2 h. The reaction mixture was evaporated to dryness to give ethyl 2,5-dimethoxy-tetrahydrofuran-3-carboxylate (564 mg, 91%) which was used directly in the next step.

LC-MS (1) Rt=1.47 min; no ionisation.

Synthesis 109-C tert-Butyl 3-((2-(5-cyanopyrazin-2-ylamino)-5-(3-(ethoxycarbonyl)-1H-pyrrol-1-yl)pyridin-4-ylamino)methyl)piperidine-1-carboxylate

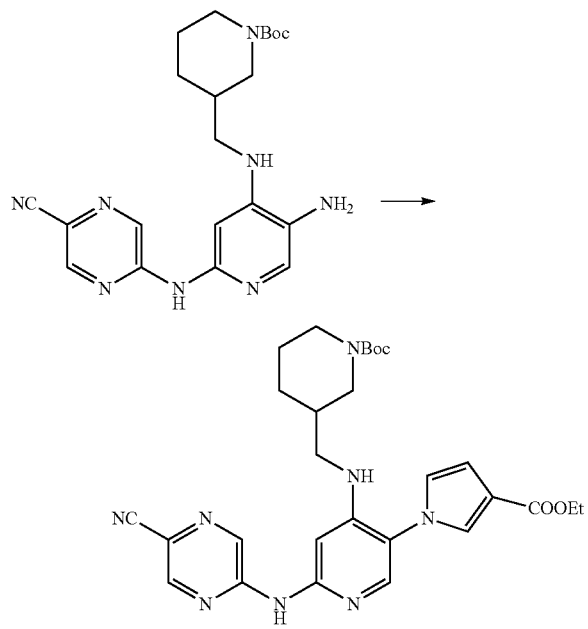

tert-Butyl 3-((5-amino-2-(5-cyanopyrazin-2-ylamino)pyridin-4-ylamino)methyl)piperidine-1-carboxylate (163 mg, 0.384 mmol) (Synthesis 101-C) and ethyl 2,5-dimethoxytetrahydrofuran-3-carboxylate (196 mg, 0.96 mmol) were dissolved in acetic acid (4 mL) and the solution was stirred at 80° C. for 6.5 h. The reaction mixture was evaporated to dryness and the residue was used directly in the next step.

LC-MS (1) Rt=3.52 min; m/z (ESI⁺) 547 (MH⁺).

Synthesis 109-D

Ethyl 1-(6-(5-cyanopyrazin-2-ylamino)-4-(piperidin-3-ylmethylamino)pyridin-3-yl)-1H-pyrrole-3-carboxylate (Y-064)

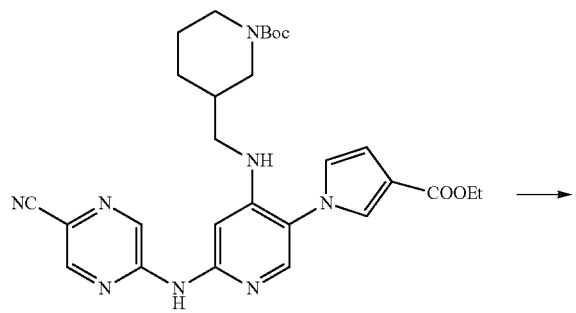

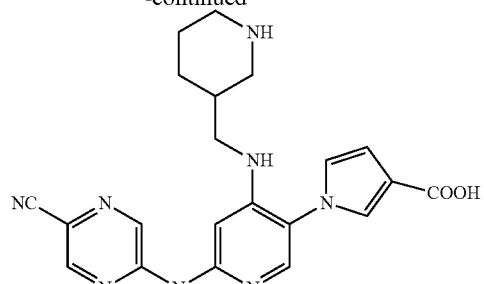

tert-Butyl 3-((2-(5-cyanopyrazin-2-ylamino)-5-(3-(ethoxycarbonyl)-1H-pyrrol-1-yl)pyridin-4-ylamino)methyl)piperidine-1-carboxylate (3 mg, 0.005 mmol) was dissolved in methanol (1 mL) and absorbed onto a TsOH solid phase extraction cartridge. After 1.5 h the cartridge was eluted with 7M ammonia in methanol. The eluent was evaporated to dryness to give ethyl 1-(6-(5-cyanopyrazin-2-ylamino)-4-(piperidin-3-ylmethylamino)pyridin-3-yl)-1H-pyrrole-3-carboxylate.

LC-MS (1) Rt=1.40 min; m/z (ESI⁺) 447 (MH⁺).

Synthesis 110-A 1-(4-((1-(tert-Butoxycarbonyl)piperidin-3-yl)methylamino)-6-(5-cyanopyrazin-2-ylamino)pyridin-3-yl)-1H-pyrrole-3-carboxylic acid

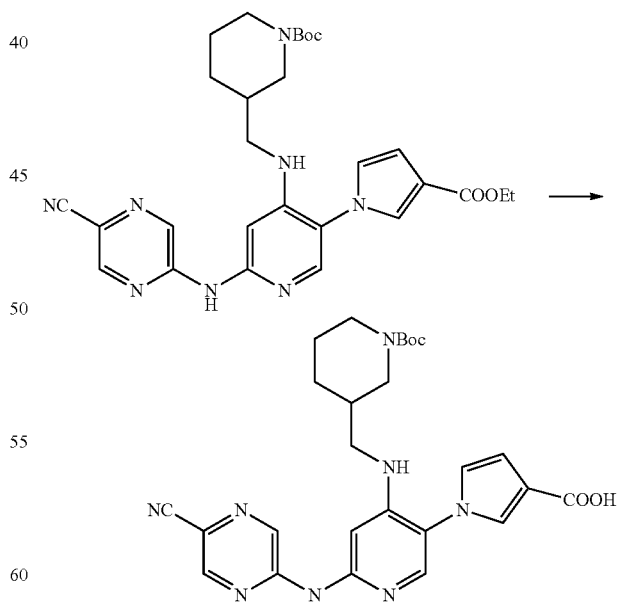

tert-Butyl 3-((2-(5-cyanopyrazin-2-ylamino)-5-(3-(ethoxycarbonyl)-1H-pyrrol-1-yl)pyridin-4-ylamino)methyl)piperidine-1-carboxylate (42 mg, 0.077 mmol) was dissolved in ethanol (1 mL). KOH (43 mg, 0.770 mmol) was added and the solution was stirred at 50° C. for 72 h. The reaction mixture was evaporated to dryness and the residue was partitioned between water and dichloromethane. The two phases were separated and the organic phase was extracted with water. The combined aqueous phases were neutralised to pH 7 by the addition of 1M HCl and then evaporated to dryness. The product (7 mg, 17%) was used directly in the next step without further purification.

LC-MS (1) Rt=1.96 min; m/z (ESI⁺) 519 (MH⁺).

Synthesis 110-B 1-(6-(5-Cyanopyrazin-2-ylamino)-4-(piperidin-3-ylmethylamino)pyridin-3-yl)-1H-pyrrole-3-carboxylic acid (Y-065)

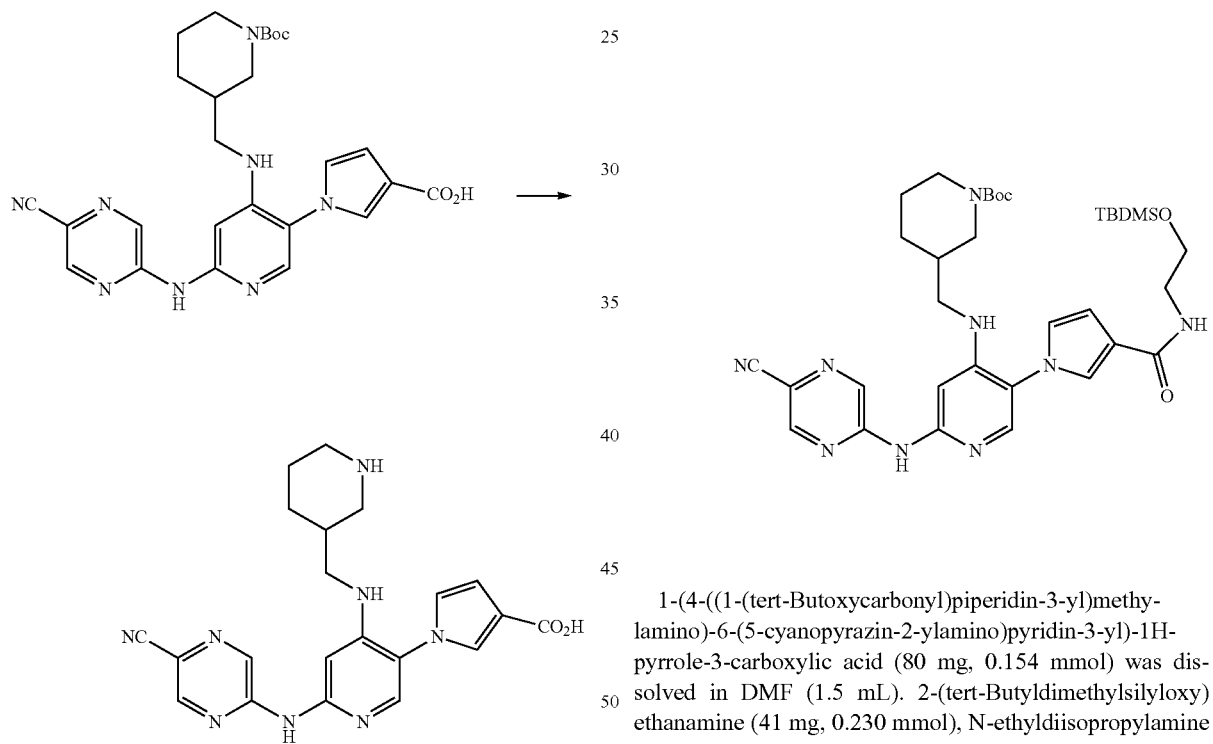

1-(4-((1-(tert-Butoxycarbonyl)piperidin-3-yl)methylamino)-6-(5-cyanopyrazin-2-ylamino)pyridin-3-yl)-1H-pyrrole-3-carboxylic acid (7 mg, 0.013 mmol) was dissolved in methanol (1 mL) and absorbed onto a TsOH solid phase extraction cartridge. After 1.5 h the cartridge was eluted with 7M ammonia in methanol. The eluent was evaporated to dryness to give 1-(6-(5-cyanopyrazin-2-ylamino)-4-(piperidin-3-ylmethylamino)pyridin-3-yl)-1H-pyrrole-3-carboxylic acid.

LC-MS (1) Rt=1.12 min; m/z (ESI⁺) 419 (MH⁺).

Synthesis 111-A tert-butyl 3-((5-(3-(2-(tert-butyldimethylsilyloxy)ethylcarbamoyl)-1H-pyrrol-1-yl)-2-(5-cyanopyrazin-2-ylamino)pyridin-4-ylamino)methyl)piperidine-1-carboxylate 1-(4-((1-(tert-Butoxycarbonyl)piperidin-3-yl)methylamino)-6-(5-cyanopyrazin-2-ylamino)pyridin-3-yl)-1H-pyrrole-3-carboxylic acid (80 mg, 0.154 mmol) was dissolved in DMF (1.5 mL). 2-(tert-Butyldimethylsilyloxy)ethanamine (41 mg, 0.230 mmol), N-ethyldiisopropylamine (30 mg, 0.230 mmol), 1-hydroxy benzotriazole hydrate (31 mg, 0.230 mmol) and 1-[3-(dimethylamino)propyl]-3-ethylcarbodiimide (44 mg, 0.23 mmol) were added to the solution and the reaction mixture was stirred for 14 h at room temperature. The solution was partitioned between dichloromethane and water. The two phases were separated and the aqueous phase was extracted with dichloromethane. The combined organic phases were dried (Na₂SO₄) and evaporated to give tert-butyl 3-((5-(3-(2-(tert-butyldimethylsilyloxy)ethylcarbamoyl)-1H-pyrrol-1-yl)-2-(5-cyanopyrazin-2-ylamino)pyridin-4-ylamino)methyl)piperidine-1-carboxylate (80 mg, 78%) which was used in the next step without purification.

LC-MS (2) Rt=3.99 min; m/z (ESI⁺) 676 (MH⁺).

Synthesis 111-B 1-(6-(5-Cyanopyrazin-2-ylamino)-4-(piperidin-3-ylmethylamino)pyridin-3-yl)-N-(2-hydroxyethyl)-1H-pyrrole-3-carboxamide (Y-066)

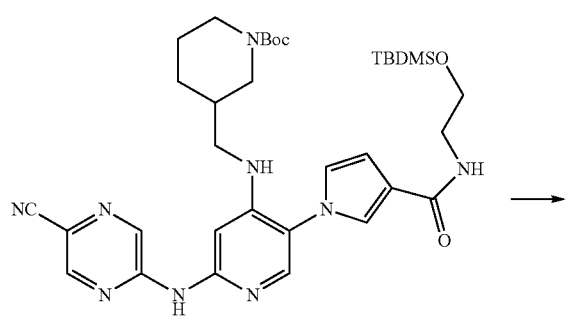

tert-Butyl 3-((5-(3-(2-(tert-butyldimethylsilyloxy)ethylcarbamoyl)-1H-pyrrol-1-yl)-2-(5-cyanopyrazin-2-ylamino)pyridin-4-ylamino)methyl)piperidine-1-carboxylate (80 mg, 0.118 mmol) was dissolved in THF (2 mL) and tetrabutylammonium fluoride on silica (1.5 mmol/g; 237 mg, 0.355 mmol) was added. The reaction mixture was stirred for 1 h at room temperature. The mixture was filtered and the solvent was evaporated. The residue was dissolved in methanol (1 mL) and absorbed on to a TsOH solid phase extraction cartridge. After 1.5 h the cartridge was eluted with 7M ammonia in methanol. The eluent was evaporated to dryness and the residue was purified by HPLC to give 1-(6-(5-cyanopyrazin-2-ylamino)-4-(piperidin-3-ylmethylamino)pyridin-3-yl)-N-(2-hydroxyethyl)-1H-pyrrole-3-carboxamide.

LC-MS (2) Rt=1.67 min; m/z (ESI$^+$) 462 (MH$^+$).

Synthesis 112

1-(6-(5-Cyanopyrazin-2-ylamino)-4-(piperidin-3-ylmethylamino)pyridin-3-yl)-N-(3-hydroxypropyl)-1H-pyrrole-3-carboxamide (Y-067)

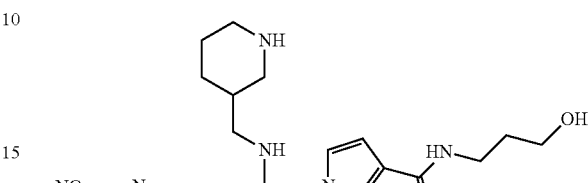

The title compound was prepared using methods analogous to those described in Synthesis Y-111, steps 111-A and 111-B.

$^1$H NMR (DMSO-d$_6$, 400 MHz) δ 9.11 (s, 1H), 8.78 (s, 1H), 8.38 (s, 1H), 7.98-7.90 (m, 1H), 7.84 (s, 1H), 7.37 (s, 1H), 7.18 (s, 1H), 6.85 (s, 1H), 6.70 (s, 1H), 6.08-5.99 (m, 1H), 3.49-3.42 (m, 2H), 3.32-3.24 (m, 2H), 3.18 (s, 2H), 3.12-2.95 (m, 3H), 2.65-2.55 (m, 1H), 2.44-2.32 (m, 1H), 1.99-1.85 (m, 1H), 1.82-1.59 (m, 3H), 1.53-1.40 (m, 1H), 1.20-1.06 (m, 1H). LC-MS (2) Rt=1.71 min; m/z (ESI$^+$) 476 (MH$^+$).

Synthesis 113

N-(6-(5-Cyanopyrazin-2-ylamino)-4-((tetrahydrofuran-3-yl)methoxy)pyridin-3-yl)-3-(piperidin-4-yl)propanamide (Y-068)

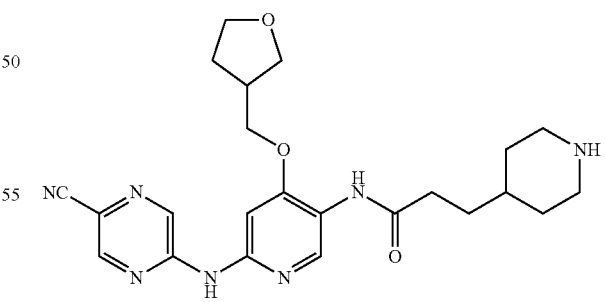

The title compound was prepared using methods analogous to those described in Synthesis 83, steps 83-A, 83-B and 83-C, and Synthesis 84, steps 84-A and 84-B.

LC-MS (2) Rt=1.68 min; m/z (ESI$^+$) 452 (MH$^+$).

Synthesis 114

N-(6-(5-Cyanopyrazin-2-ylamino)-4-((tetrahydro-2H-pyran-4-yl)methoxy)pyridin-3-yl)-3-(piperidin-4-yl)propanamide (Y-069)

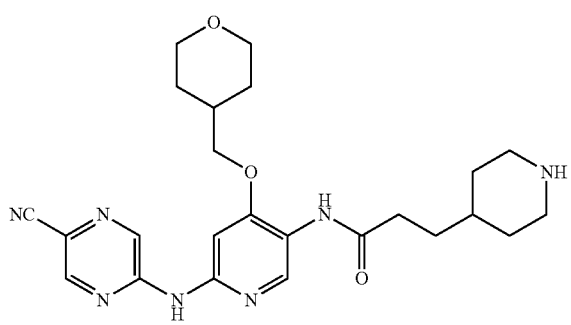 [SMILES: N#Cc1cnc(Nc2cc(OCC3CCOCC3)c(NC(=O)CCC3CCNCC3)cn2)cn1]

The title compound was prepared using methods analogous to those described in Synthesis 83, steps 83-A, 83-B and 83-C, and Synthesis 84, steps 84-A and 84-B.

$^1$H NMR (DMSO-d$_6$, 400 MHz) δ 9.18 (s, 1H), 9.03 (s, 1H), 8.77 (s, 1H), 8.43-8.38 (m, 2H), 7.52 (s, 1H), 3.97-3.87 (m, 4H), 3.39-3.29 (m, 4H), 3.19-3.10 (m, 2H), 2.73-2.64 (m, 2H), 2.43-2.32 (m, 2H), 2.13-2.02 (m, 1H), 1.79-1.67 (m, 3H), 1.58-1.25 (m, 4H), 1.27-1.14 (m, 2H). LC-MS (2) Rt=1.79 min; m/z (ESI$^+$) 466 (MH$^+$)

Synthesis 115

Methyl 6-(5-cyanopyrazin-2-ylamino)-4-(methyl(1-methylpiperidin-4-yl)amino)nicotinate (Y-070)

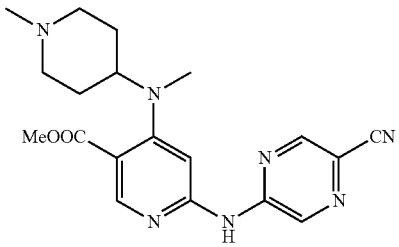 [SMILES: COC(=O)c1cnc(Nc2cnc(C#N)cn2)cc1N(C)C1CCN(C)CC1]

The title compound was prepared using methods analogous to those described in Synthesis 62, steps 62-A and 62-B.

$^1$H NMR (500 MHz, d$_4$-MeOD) δ 9.00 (1H, s), 8.62 (1H, s), 8.42 (1H, s), 7.46 (1H, s), 3.90 (3H, s), 3.40-3.50 (1H, m), 3.00-3.05 (2H, m), 2.83 (3H, s), 2.35 (3H, s), 2.10-2.20 (2H, m), 1.90-2.00 (2H, m) and 1.85-1.90 (2H, m). LCMS (3B) Rt=1.58 min; m/z (ESI$^+$) 382 (MH$^+$).

Synthesis 116

Methyl 6-(5-cyanopyrazin-2-ylamino)-4-(9-methyl-9-azabicyclo[3.3.1]-nonan-3-ylamino)nicotinate (Y-071)

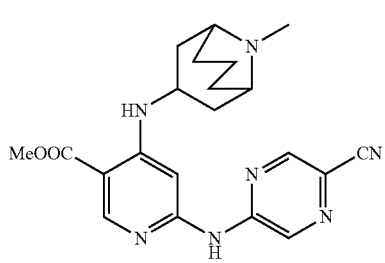 [SMILES: COC(=O)c1cnc(Nc2cnc(C#N)cn2)cc1NC1CC2CCCC(C1)N2C]

The title compound was prepared using methods analogous to those described in Synthesis 62, steps 62-A and 62-B.

$^1$H NMR (500 MHz, d$_4$-MeOD) δ 8.95 (1H, s), 8.65 (1H, s), 8.62 (1H, s), 7.22 (1H, s), 4.05-4.15 (1H, m), 3.88 (3H, s), 3.35-3.40 (2H, m), 2.75 (3H, s), 2.60-2.70 (2H, m), 2.05-2.20 (2H+1H, m), 1.45-1.55 (2H+1H, m) and 1.35-1.45 (2H, m). LCMS (3B) Rt=1.85 min; m/z (ESI$^+$) 408 (MH$^+$).

Synthesis 117-A ((1R,5S)-8-Methyl-8-azabicyclo[3.2.1]octan-3-yl)methanamine

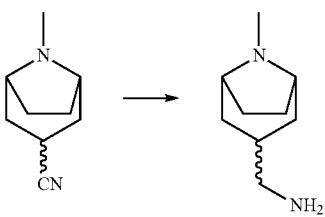

To a solution of (1R,5S)-8-methyl-8-azabicyclo[3.2.1]octane-3-carbonitrile (J. Org. Chem., 1977, 3114) (83 mg, 0.55 mmol) in NH$_3$/MeOH (0.5%) (10 mL) was added Raney Ni (ca. 50 mg). The reaction mixture was hydrogenated at atmospheric pressure for 16 hours. After filtration, the solvents were evaporated and the oil was purified by ion exchange on SCX-II acidic resin (2 g) eluting with methanol, then 2M ammonia-methanol. The basic fractions were combined and the solvent was removed in vacuo to give ((1R,5S)-8-methyl-8-azabicyclo[3.2.1]octan-3-Amethanamineas colourless oil (32 mg, 38%).

¹H NMR (500 MHz, d₄-MeOD) δ 2.45-2.55 (1H, m), 2.35-2.45 (1H, m), 2.28 (3H, s), 2.05-2.15 (2H, m), 1.70-1.80 (1H, m), 1.55-1.70 (4H, m) and 1.30-1.40 (2H, m).

Synthesis 117-B

Methyl 6-(5-cyanopyrazin-2-ylamino)-4-(((1R,5S)-8-methyl-8-azabicyclo[3.2.1]octan-3-yl)methylamino)nicotinate (Y-072)

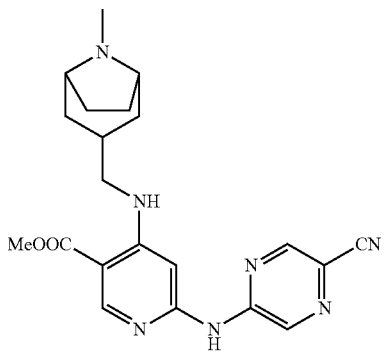 [SMILES: COC(=O)c1cnc(Nc2cnc(C#N)cn2)cc1NCC1CC2CCC(C1)N2C]

The title compound was prepared using methods analogous to those described in Synthesis 62, steps 62-A and 62-B.

¹H NMR (500 MHz, d₄-MeOD) δ 8.88 (1H, s), 8.67 (1H, s), 8.64 (1H, s), 7.34 (1H, s), 3.90-4.00 (2H, m), 3.88 (3H, s), 3.55-3.60 (2H, m), 2.80 (3H, s), 2.25-2.45 (3H, m), 1.95-2.05 (4H, m), and 1.75-1.85 (2H, m). LCMS (3B) Rt=1.64 min; m/z (ESI⁺) 408 (MH⁺).

Synthesis 118

Methyl 6-(5-cyanopyrazin-2-ylamino)-4-(piperidin-2-ylmethylamino)-nicotinate (Y-073)

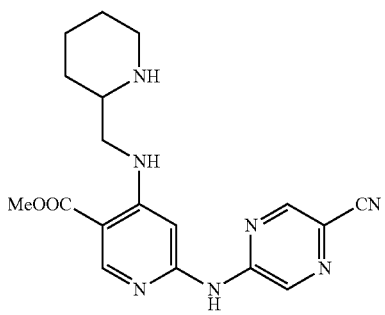 [SMILES: COC(=O)c1cnc(Nc2cnc(C#N)cn2)cc1NCC1CCCCN1]

The title compound was prepared using methods analogous to those described in Synthesis 62, steps 62-A, 62-B and 62-C.

¹H NMR (500 MHz, d₄-MeOD) δ 8.93 (1H, s), 8.60 (1H, s), 8.57 (1H, s), 7.16 (1H, s), 3.87 (3H, s), 3.25-3.30 (2H, m), 3.05-3.10 (1H, m), 2.85-2.95 (1H, m), 2.60-2.70 (1H, m), 1.75-1.90 (2H, m), 1.65-1.70 (1H, m), 1.40-1.55 (2H, m) and 1.20-1.30 (1H, m). LCMS (3B) Rt=1.76 min; m/z (ESI⁺) 368 (MH⁺).

Synthesis 119

(1R,5R)-tert-Butyl 3-(2-(5-cyanopyrazin-2-ylamino)-5-(methoxycarbonyl)pyridin-4-ylamino)-8-azabicyclo[3.2.1]octane-8-carboxylate (Y-074)

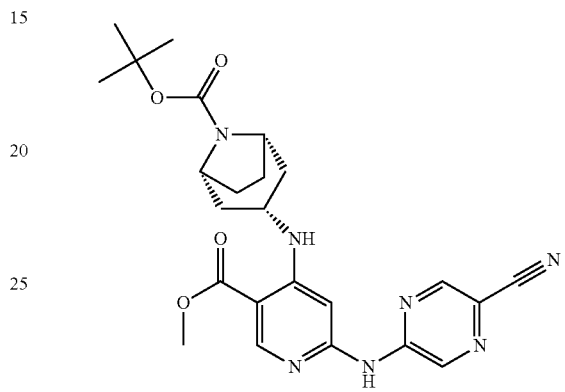

The title compound was prepared using methods analogous to those described in Synthesis 62, steps 62-A and 62-B.

¹H NMR (500 MHz, CDCl3) δ 8.68 (s, 2H), 8.49 (s, 1H), 8.09 (d, 1H, J=7.5 Hz), 7.41 (s, 1H), 4.37 (br s, 2H), 4.06-3.95 (m, 1H), 3.89 (s, 3H), 2.18-2.07 (m, 4H), 1.81-1.53 (m, 4H (under water peak)), 1.51 (s, 9H). LCMS (3B) Rt=4.78 min; m/z (ESI⁺) 480 (MH⁺).

Synthesis 120

Methyl 4-((1R,5R)-8-azabicyclo[3.2.1]octan-3-ylamino)-6-(5-cyanopyrazin-2-ylamino)nicotinate (Y-075)

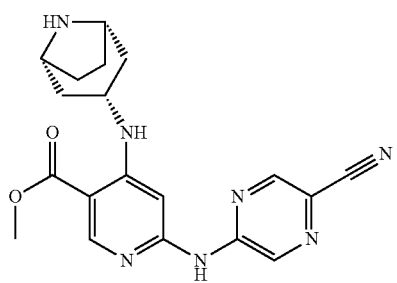 [SMILES: COC(=O)c1cnc(Nc2cnc(C#N)cn2)cc1N[C@@H]1C[C@H]2CC[C@@H](C1)N2]

The title compound was prepared using methods analogous to those described in Synthesis 62, steps 62-A, 62-B and 62-C.

¹H NMR (500 MHz, DMSO) δ 9.06 (s, 1H), 8.76 (s, 1H), 8.59 (s, 1H), 7.77 (d, 1H, J=7.5), 7.32 (s, 1H), 3.80 (s, 3H), 3.78-3.70 (m, 1H), 3.51-3.46 (m, 2H), 2.01-1.94 (m, 2H), 1.81-1.72 (m, 4H), 1.44-1.37 (m, 2H). LCMS (3B) Rt=1.81 min; m/z (ESI⁺) 380 (MH⁺).

2.10-2.25 (2H, m), 1.70-1.90 (2H, m), 1.50-1.70 (2H, m) and 0.88-1.00 (3H, t, J=6.5 Hz). LCMS (3B) R$_t$ 1.79 min; m/z (ESI⁺) 396 (MH⁺).

Synthesis 121

Methyl 4-(azepan-4-ylamino)-6-(5-cyanopyrazin-2-ylamino)nicotinate (Y-076)

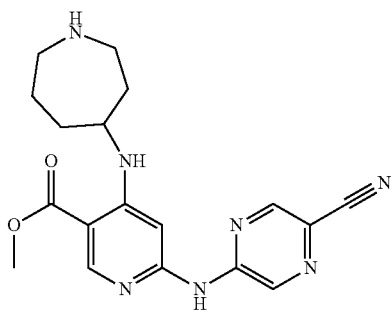 [SMILES: COC(=O)c1cnc(Nc2cnc(C#N)cn2)cc1NC1CCCNCC1]

The title compound was prepared using methods analogous to those described in Synthesis 62, steps 62-A, 62-B and 62-C.

¹H NMR (500 MHz, CDCl₃) δ 8.68 (d, 1H, J=1.0 Hz), 8.70 (s, 1H), 8.51 (d, 1H, J=1.0 Hz), 8.34 (d, 1H, J=7.5 Hz), 7.26 (s, 1H), 3.89 (s, 3H), 3.86-3.78 (m, 1H), 3.11-2.92 (m, 5H), 2.20-2.15 (m, 1H), 2.10-2.01 (m, 1H), 1.90-1.70 (m, 5H). LCMS (3B) Rt=1.76 min. m/z (ESI⁺) 368 (MH⁺).

Synthesis 122

Methyl 6-(5-cyanopyrazin-2-ylamino)-4-(1-propylpiperidin-4-ylamino)nicotinate (Y-077)

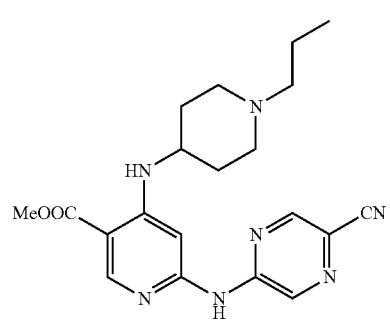 [SMILES: CCCN1CCC(Nc2cc(Nc3cnc(C#N)cn3)ncc2C(=O)OC)CC1]

The title compound was prepared using methods analogous to those described in Synthesis 62, steps 62-A and 62-B.

¹H NMR (500 MHz, CDCl₃) δ 8.80 (1H, s), 8.70 (1H, s), 8.52 (1H, s), 8.30 (1H, s, broad, NH), 7.20 (1H, s), 3.91 (3H, s), 3.50-3.60 (1H, m), 2.85-3.00 (2H, m), 2.30-2.50 (4H, m),

Synthesis 123

Methyl 6-(5-cyanopyrazin-2-ylamino)-4-(piperidin-4-ylamino)nicotinate (Y-078)

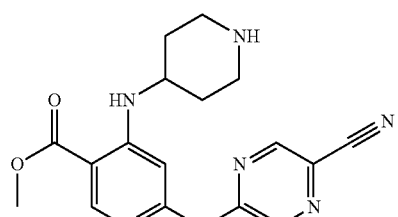

The title compound was prepared using methods analogous to those described in Synthesis 62, steps 62-A, 62-B and 62-C.

¹H NMR (500 MHz, MeOD) δ 8.94 (s, 1H), 8.64 (s, 1H), 8.59 (s, 1H), 7.23 (s, 1H), 3.87 (s, 3H), 3.68-3.59 (m, 1H), 3.16-3.09 (m, 2H), 2.86-2.76 (m, 2H), 2.15-2.08 (m, 2H), 1.58-1.50 (m, 2H). LCMS (3B) Rt=1.46 min; m/z (ESI⁺) 354 (MH⁺).

Synthesis 124

Methyl 6-(5-cyanopyrazin-2-ylamino)-4-(8-propyl-8-azabicyclo[3.2.1]octan-3-ylamino)nicotinate (Y-079)

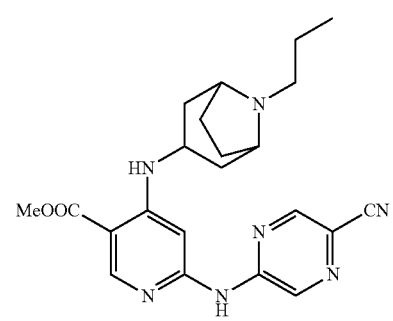 [SMILES: CCCN1C2CCC1CC(Nc1cc(Nc3cnc(C#N)cn3)ncc1C(=O)OC)C2]

The title compound was prepared using methods analogous to those described in Synthesis 62, steps 62-A and 62-B.

¹H NMR (500 MHz, d₄-MeOD) δ 8.93 (1H, s), 8.65 (1H, s), 8.59 (1H, s), 7.07 (1H, s), 3.90 (3H, s), 3.45-3.50 (1H, m), 2.50-2.60 (2H, m), 2.30-2.40 (2H, m), 2.00-2.20 (4H, m), 1.85-1.95 (2H, m), 1.70-1.80 (1H, m), 1.55-1.70 (2H, m), 1.25-1.40 (1H, m) and 0.95-1.05 (3H, t, J=6.5 Hz). LCMS (3B) Rt 1.96 min; m/z (ESI⁺) 422 (MH⁺).

Synthesis 125

Methyl 6-(5-cyanopyrazin-2-ylamino)-4-(8-(pyridin-2-ylmethyl)-8-azabicyclo[3.2.1]octan-3-ylamino)nicotinate (Y-080)

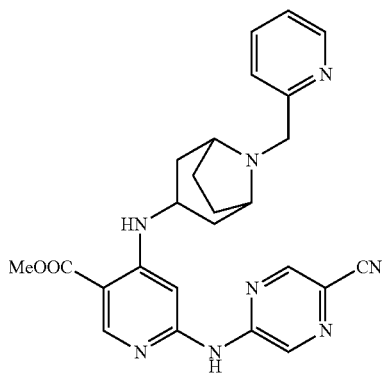 [SMILES: COC(=O)c1cnc(Nc2cnc(C#N)cn2)cc1NC1CC2CCC(C1)N2Cc1ccccn1]

The title compound was prepared using methods analogous to those described in Synthesis 62, steps 62-A and 62-B.

¹H NMR (500 MHz, d₄-MeOD) δ 8.92 (1H, s), 8.68 (1H, s), 8.60 (1H, s), 8.50-8.60 (1H, m), 7.85-7.90 (1H, m), 7.65-7.70 (1H, m), 7.35-7.40 (1H, m), 7.15 (1H, s), 4.03 (2H, s), 3.90 (3H, s), 3.50-3.65 (2H, m), 2.40-2.50 (1H, m), 2.30-2.40 (2H, m), 2.12-2.24 (2H, m), 1.90-2.10 (2H, m), 1.78-1.90 (1H, m), and 1.55-1.68 (1H, m). LCMS (3B) Rt 2.16 min; m/z (ESI⁺) 471 (MH⁺).

Synthesis 126

Methyl 6-(5-cyanopyrazin-2-ylamino)-4-(morpholin-2-ylmethylamino)nicotinate (Y-081)

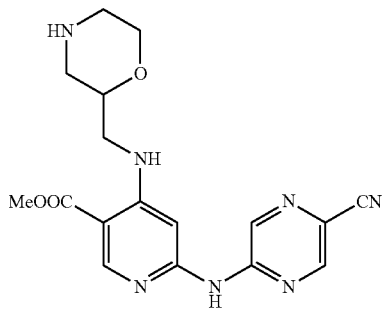 [SMILES: COC(=O)c1cnc(Nc2cnc(C#N)cn2)cc1NCC1CNCCO1]

The title compound was prepared using methods analogous to those described in Synthesis 62, steps 62-A, 62-B and 62-C.

¹H NMR (500 MHz, d₆-DMSO) δ 10.82 (1H, s, broad, NH), 9.00 (1H, s), 8.80 (1H, s), 8.60 (1H, s), 8.16 (1H, s, broad, NH), 7.24 (1H, s), 3.81 (3H, s), 3.75-3.80 (1H, m), 3.60-3.65 (1H, m), 3.42-3.50 (1H, m), 3.20-3.30 (1H, m), 3.10-3.20 (2H, m), 2.80-2.90 (1H, m), 2.60-2.70 (2H, m), and 2.42-2.50 (1H, m). LCMS (4) 1.16 min; m/z (ESI⁺) 370 (MH⁺).

Synthesis 127

(S)-Methyl 6-(5-cyanopyrazin-2-ylamino)-4-(2-(morpholin-2-yl)ethylamino)nicotinate (Y-082)

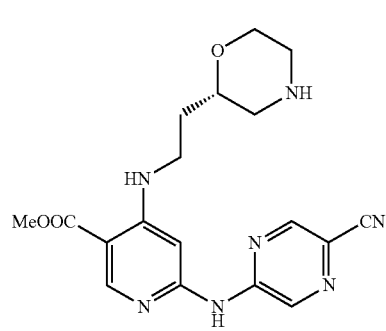 [SMILES: COC(=O)c1cnc(Nc2cnc(C#N)cn2)cc1NCC[C@H]1CNCCO1]

The title compound was prepared using methods analogous to those described in Synthesis 62, steps 62-A, 62-B and 62-C.

¹H NMR (500 MHz, d₄-MeOD) δ 8.90 (1H, s), 8.63 (1H, s), 8.60 (1H, s), 7.25 (1H, s), 3.88-3.95 (1H, m), 3.87 (3H, s), 3.50-3.70 (2H, m), 3.40-3.50 (2H, m), 2.85-2.95 (1H, m), 2.80-2.85 (2H, m), 2.55-2.65 (1H, m), and 1.70-1.85 (2H, m). LCMS (4) Rt 1.22 min; m/z (ESI⁺) 384 (MH⁺).

Synthesis 128

Methyl 6-(5-Cyanopyrazin-2-ylamino)-4-((4-fluoropiperidin-4-yl)methylamino)nicotinate (Y-083)

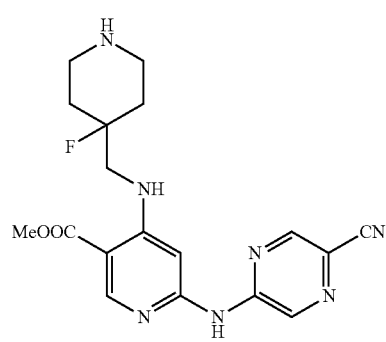 [SMILES: COC(=O)c1cnc(Nc2cnc(C#N)cn2)cc1NCC1(F)CCNCC1]

The title compound was prepared using methods analogous to those described in Synthesis 62, steps 62-A, 62-B and 62-C.

¹H NMR (500 MHz, d₄-MeOD) δ 8.92 (1H, s), 8.66 (1H, s), 8.64 (1H, s), 7.31 (1H, s), 3.90 (3H, s), 3.50-3.60 (2H, d,

J=21 Hz), 2.95-3.10 (4H, m), 1.97-2.05 (2H, m), and 1.75-1.90 (2H, m). LCMS (4) $R_t$ 1.28 min; m/z (ESI$^+$) 386 (MH$^+$).

Synthesis 129

6-(5-Cyanopyrazin-2-ylamino)-N-(2-methoxyethyl)-4-(piperidin-4-ylmethylamino)nicotinamide

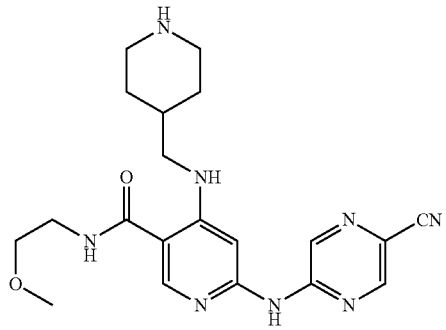

The title compound was prepared using methods analogous to those described in Synthesis 75, steps 75-A and 75-B.

$^1$H NMR (CDCl$_3$, 500 MHz) 8.97 (d, 1H, J=1.3 Hz), 8.61 (d, 1H, J=1.3 Hz), 8.34 (s, 1H), 7.14 (s, 1H), 3.59-3.57 (m, 2H), 3.55-3.53 (m, 2H), 3.41 (s, 3H), 3.33 (dt, 2H J=3.3, 1.6 Hz), 3.20-3.17 (m, 3H), 2.73 (dd, 2H J=12.5, 10.1 Hz), 1.90-1.88 (m, 3H), 1.37-1.35 (m, 3H); LC-MS (3B) Rt 1.48 min; m/z (ESI$^+$) 411 [MH$^+$].

Synthesis 130

6-(5-Cyanopyrazin-2-ylamino)-N-ethyl-4-(1-methylpiperidin-4-ylamino)nicotinamide (Y-085)

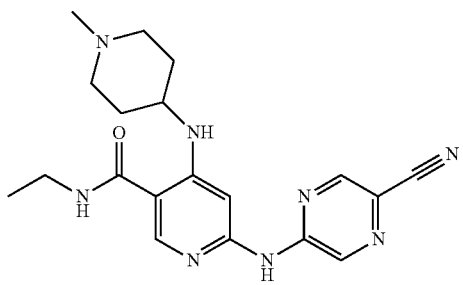 [SMILES: CCNC(=O)c1cnc(Nc2cnc(C#N)cn2)cc1NC1CCN(C)CC1]

The title compound was prepared using methods analogous to those described in Synthesis 75, steps 75-A.

LCMS (3B) Rt 1.11 min; m/z (ESI$^+$) 381 (MH$^+$).

Synthesis 131

6-(5-Cyanopyrazin-2-ylamino)-N-isopropyl-4-(piperidin-4-ylmethylamino)nicotinamide (Y-086)

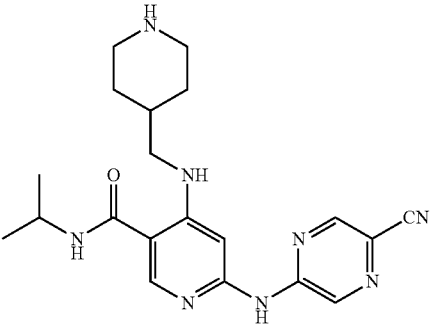 [SMILES: CC(C)NC(=O)c1cnc(Nc2cnc(C#N)cn2)cc1NCC1CCNCC1]

The title compound was prepared using methods analogous to those described in Synthesis 75, steps 75-A and 75-B.

$^1$H NMR (500 MHz, d-4-MeOD) δ 8.96 (1H, s), 8.58 (1H, s), 8.30 (1H, s), 7.07 (1H, s), 4.10-4.20 (1H, m), 3.10-3.20 (4H, m), 2.60-2.70 (2H, m), 1.80-1.90 (3H, m), 1.25-1.35 (2H, m) and 1.20 (6H, d, J=6.8 Hz). LCMS (3B) $R_t$ 1.68 min; m/z (ESI$^+$) 395 (MH$^+$).

Synthesis 132

5-(4-(Piperidin-4-ylmethylamino)-5-(pyrrolidine-1-carbonyl)pyridin-2-ylamino)pyrazine-2-carbonitrile (Y-087)

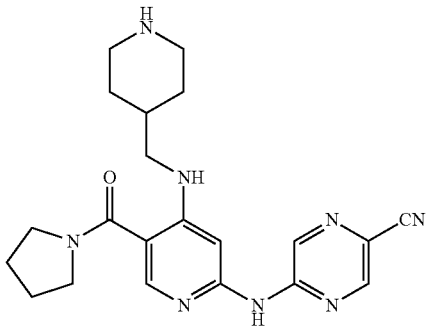 [SMILES: N#Cc1cnc(Nc2cc(NCC3CCNCC3)c(C(=O)N3CCCC3)cn2)cn1]

The title compound was prepared using methods analogous to those described in Synthesis 75, steps 75-A and 75-B.

$^1$H NMR (MeOD-d$_4$, 500 MHz,) 8.95 (s, 1H), 8.60 (s, 1H), 8.36 (s, 1H), 7.13 (s, 1H), 3.71 (t, 1H, J=5.8 Hz), 3.48 (t, 1H, J=5.8 Hz), 3.32-3.31 (m, 1H), 3.20-3.14 (m, 3H), 2.73 (t, 2H,

J=11.4 Hz), 2.00-1.89 (m, 3H), 1.39-1.33 (m, 3H); LCMS (3B) Rt 0.93 min; m/z (ESI$^+$) 407 [MH$^+$].

Synthesis 133

6-(5-Cyanopyrazin-2-ylamino)-N-(2-hydroxyethyl)-4-(piperidin-4-ylmethylamino)nicotinamide (Y-088)

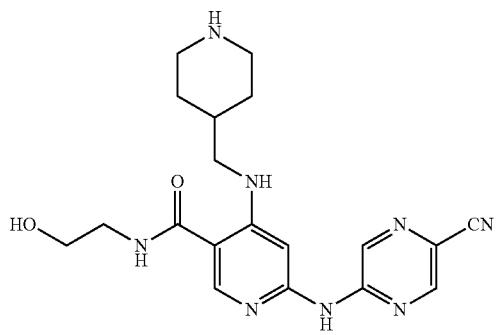 [SMILES: N#Cc1cnc(Nc2cc(NCC3CCNCC3)c(C(=O)NCCO)cn2)cn1]

The title compound was prepared using methods analogous to those described in Synthesis 75, steps 75-A and 75-B.

$^1$H NMR (MeOD-d$_4$, 500 MHz) 8.97 (s, 1H), 8.58 (s, 1H), 8.05 (s, 1H), 7.13 (s, 1H), 3.65-3.55 (m, 4H), 3.26-3.23 (m, 2H), 3.17-3.14 (m, 2H), 2.79 (t, 2H, J=11.4 Hz), 2.04-1.89 (m, 7H); LCMS (3B) Rt 1.08 min; m/z (ESI$^+$) 397 [MH$^+$].

Synthesis 134

5-(5-(Morpholine-4-carbonyl)-4-(piperidin-4-ylmethylamino)pyridin-2-ylamino)pyrazine-2-carbonitrile (Y-089)

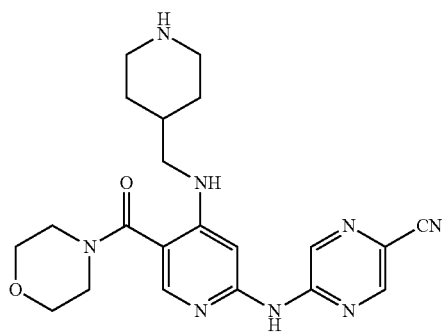 [SMILES: N#Cc1cnc(Nc2cc(NCC3CCNCC3)c(C(=O)N3CCOCC3)cn2)cn1]

The title compound was prepared using methods analogous to those described in Synthesis 75, steps 75-A and 75-B.

$^1$H NMR (MeOD-d$_4$, 500 MHz) 8.97 (d, 1H, J=1.2 Hz), 8.58 (d, 1H, J=1.2 Hz), 7.90 (s, 1H), 7.15 (s, 1H), 3.84-3.58 (m, 8H), 3.23-3.10 (m, 4H), 2.68 (dd, 2H, J=10.1, 12.5 Hz), 1.87-1.85 (m, 3H), 1.32-1.30 (m, 3H); LCMS (3B) Rt 0.66 min; m/z (ESI$^+$) 423 [MH$^+$].

Synthesis 135

6-(5-Cyanopyrazin-2-ylamino)-N,N-dimethyl-4-(piperidin-4-ylmethyl-amino)nicotinamide (Y-090)

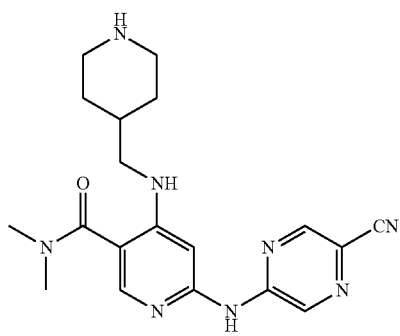 [SMILES: CN(C)C(=O)c1cnc(Nc2cnc(C#N)cn2)cc1NCC1CCNCC1]

The title compound was prepared using methods analogous to those described in Synthesis 75, steps 75-A and 75-B.

$^1$H NMR (500 MHz, d$_4$-MeOD) δ 8.97 (1H, s), 8.58 (1H, s), 7.90 (1H, s), 7.14 (1H, s), 3.12 (6H, s), 3.00-3.20 (4H, m), 2.55-2.75 (2H, m), 1.75-1.95 (3H, m) and 1.20-1.40 (2H, m). LCMS (3B) Rt 0.67 min; m/z (ESI$^+$) 381 (MH$^+$).

Synthesis 136

6-(5-Cyanopyrazin-2-ylamino)-N-(2-methoxyethyl)-N-methyl-4-(piperidin-4-ylmethylamino)nicotinamide (Y-091)

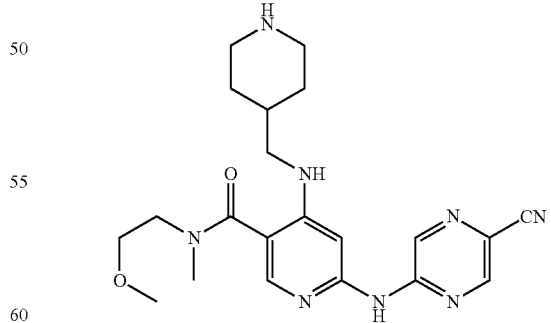

The title compound was prepared using methods analogous to those described in Synthesis 75, steps 75-A and 75-B.

$^1$H NMR (CDCl$_3$, 500 MHz) 8.84 (d, 1H, J=1.3 Hz), 8.50 (d, 1H, J=1.3 Hz), 7.93 (s, 1H), 7.18 (s, 1H), 3.69-3.68 (m, 2H), 3.61-3.60 (m, 2H), 3.36 (3H, s), 3.11-3.09 (m, 7H), 3.10

(t, 2H, J=6.0 Hz), 2.60 (t, 2H, J=11.7 Hz), 1.82-1.80 (m, 3H), 1.27-1.20 (m, 2H); LCMS (3B) Rt 0.87 min; m/z (ESI⁺) 425 [MH⁺].

Synthesis 137

6-(5-Cyanopyrazin-2-ylamino)-N-(4-fluorophenyl)-4-(piperidin-4-ylmethylamino)nicotinamide (Y-092)

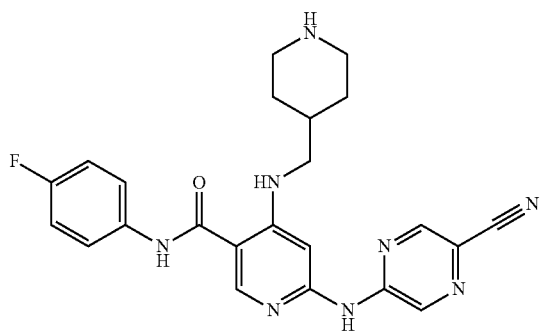 [SMILES: N#Cc1cnc(Nc2cc(NCC3CCNCC3)c(C(=O)Nc3ccc(F)cc3)cn2)cn1]

The title compound was prepared using methods analogous to those described in Synthesis 75, steps 75-A and 75-B.

¹H NMR (MeOD-d₄, 500 MHz) δ 8.99 (d, 1H, J=1.4 Hz), 8.60 (d, 1H, J=1.4 Hz), 8.49 (s, 1H), 7.95 (s, 1H), 7.63-7.60 (m, 2H), 7.14 (s, 1H), 7.10-7.07 (m, 2H), 3.16 (d, 2H, J=6.2 Hz), 3.12 (d, 2H, J=12.2 Hz), 2.68-2.63 (m, 2H), 1.89-1.84 (m, 2H), 1.36-1.29 (m, 3H). LCMS (3B) Rt=2.09 min; m/z (ESI⁺) 447 (MH⁺).

Synthesis 138

6-(5-Cyanopyrazin-2-ylamino)-N-(2-fluorophenyl)-4-(piperidin-4-ylmethylamino)nicotinamide (Y-093)

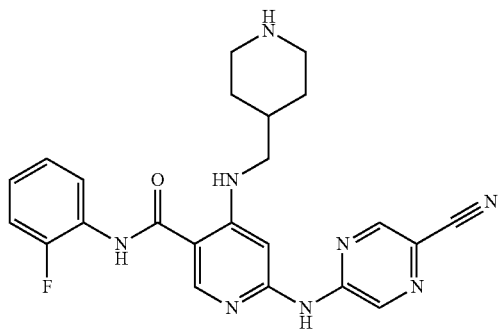 [SMILES: N#Cc1cnc(Nc2cc(NCC3CCNCC3)c(C(=O)Nc3ccccc3F)cn2)cn1]

The title compound was prepared using methods analogous to those described in Synthesis 75, steps 75-A and 75-B.

¹H NMR ((CD₃)₂SO-d₆, 500 MHz) δ 10.04 (br s, 1H), 9.08 (s, 1H), 8.80 (s, 1H), 8.67 (s, 1H), 8.46 (br s, 1H), 7.93 (s, 1H), 7.51 (t, 1H, J=7.6 Hz), 7.30-7.28 (m, 2H), 7.24-7.22 (m, 1H), 7.20 (s, 1H), 3.10-3.04 (m, 2H), 2.97 (d, 2H, J=12 Hz), 2.47-2.45 (m, 2H), 1.71-1.65 (m, 3H), 1.32-1.23 (m, 1H), 1.21-1.11 (m, 2H). LCMS (3B) Rt=1.97 min; m/z (ESI⁺) 447 (MH⁺).

Synthesis 139

6-(5-Cyanopyrazin-2-ylamino)-N-(3-fluorophenyl)-4-(piperidin-4-ylmethylamino)nicotinamide (Y-094)

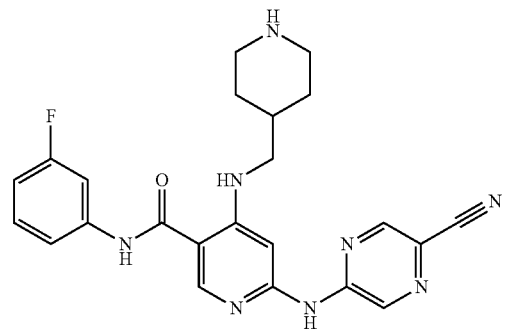 [SMILES: N#Cc1cnc(Nc2cc(NCC3CCNCC3)c(C(=O)Nc3cccc(F)c3)cn2)cn1]

The title compound was prepared using methods analogous to those described in Synthesis 75, steps 75-A and 75-B.

¹H NMR ((CD₃)₂SO-d₆, 500 MHz) δ 10.31 (s, 1H), 9.11 (s, 1H), 8.80 (s, 1H), 8.61 (s, 1H), 8.26 (br s, 1H), 7.93 (s, 1H), 7.66 (d, 1H, J=11.8 Hz), 7.51-7.46 (m, 1H), 7.41-7.36 (m, 1H), 7.20 (s, 1H), 6.95-6.92 (m, 1H), 3.12-3.08 (m, 2H), 3.02 (d, 2H, J=12 Hz), 2.55-2.53 (m, 2H), 1.72-1.69 (m, 3H), 1.24-1.16 (m, 3H). LCMS (3B) Rt=2.16 min; m/z (ESI⁺) 447 (MH⁺).

Synthesis 140

6-(5-Cyanopyrazin-2-ylamino)-N-(4-methoxyphenyl)-4-(piperidin-4-ylmethylamino)nicotinamide (Y-095)

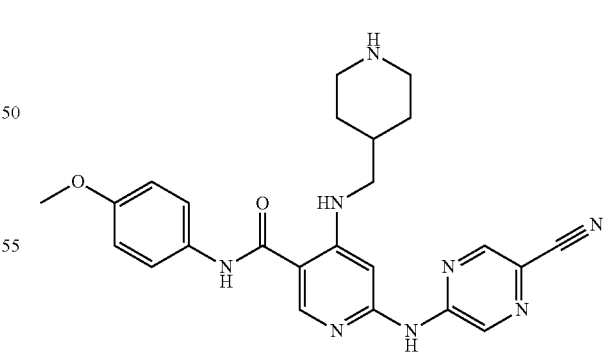

The title compound was prepared using methods analogous to those described in Synthesis 75, steps 75-A and 75-B.

¹H NMR ((CD₃)₂SO-d₆, 500 MHz) δ 10.04 (s, 1H), 9.11 (s, 1H), 8.79 (s, 1H), 8.59 (s, 1H), 8.37 (br s, 1H), 7.93 (s, 1H), 7.58 (d, 2H, J=8.8 Hz), 7.16 (s, 1H), 6.92 (d, 2H, J=8.8 Hz), 3.75 (s, 3H), 3.08 (m, 2H), 3.00 (d, 2H, J=11.8 Hz), 2.50-2.49

(m, 2H), 1.70-1.67 (m, 3H), 1.24-1.15 (m, 3H). LCMS (4) Rt=1.48 min; m/z (ESI+) 459 (MH+).

Synthesis 141

6-(5-Cyanopyrazin-2-ylamino)-N-(3-methoxyphenyl)-4-(piperidin-4-ylmethylamino)nicotinamide (Y-096)

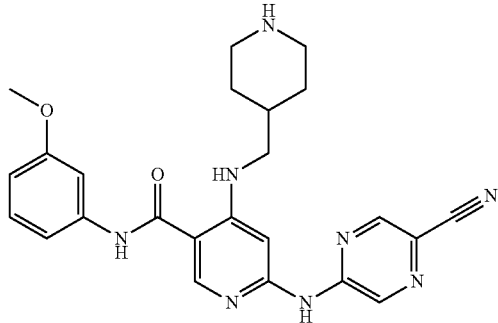 [SMILES: COc1cccc(NC(=O)c2cnc(Nc3cnc(C#N)cn3)cc2NCC2CCNCC2)c1]

The title compound was prepared using methods analogous to those described in Synthesis 75, steps 75-A and 75-B.

$^1$H NMR ((CD$_3$)$_2$SO-d$_6$, 500 MHz) δ 10.11 (s, 1H), 9.12 (s, 1H), 8.79 (d, 1H, J=1.2 Hz), 8.59 (s, 1H), 8.29 (t, 1H, J=5.6 Hz), 7.93 (s, 1H), 7.35 (s, 1H), 7.31 (d, 1H, J=8 Hz), 7.24 (t, 1H, J=8.1 Hz), 7.17 (s, 1H), 6.70-6.68 (m, 1H), 3.76 (s, 3H), 3.08 (t, 2H, J=5.7 Hz), 2.97 (d, 2H, J=12 Hz), 2.46 (t, 2H, J=12.2 Hz), 1.72-1.66 (m, 3H), 1.29-1.24 (m, 1H), 1.18-1.10 (m, 2H). LCMS (4) Rt=1.50 min; m/z (ESI+) 459 (MH+).

Synthesis 142

6-(5-Cyanopyrazin-2-ylamino)-N-(2-methoxyphenyl)-4-(piperidin-4-ylmethylamino)nicotinamide (Y-097)

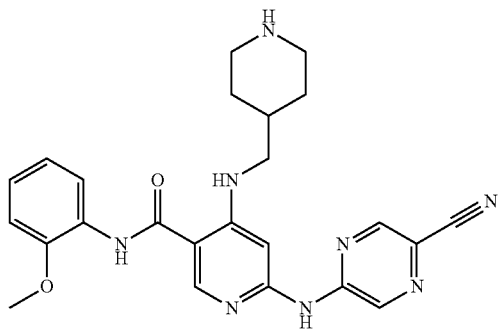 [SMILES: COc1ccccc1NC(=O)c1cnc(Nc2cnc(C#N)cn2)cc1NCC1CCNCC1]

The title compound was prepared using methods analogous to those described in Synthesis 75, steps 75-A and 75-B.

$^1$H NMR ((CD$_3$)$_2$SO-d$_6$, 500 MHz) δ 9.47 (s, 1H), 9.11 (s, 1H), 8.80 (s, 1H), 8.63 (s, 1H), 8.44 (t, 1H, J=5.4 Hz), 7.93 (s, 1H), 7.58 (d, 1H, J=7.7 Hz), 7.21 (t, 1H, J=7.8 Hz), 7.16 (s, 1H), 7.10 (d, 1H, J=8.2 Hz), 6.96 (t, 1H, J=7.6 Hz), 3.83 (s, 3H), 3.07 (t, 2H, J=5.5 Hz), 2.99 (d, 2H, J=12 Hz), 2.47-2.45 (m, 2H), 1.72-1.66 (m, 3H), 1.26-1.22 (m, 1H), 1.19-1.13 (m, 2H). LCMS (4) Rt=1.45 min; m/z (ESI+) 459 (MH+).

Synthesis 143

6-(5-Cyanopyrazin-2-ylamino)-N-(4-(2-morpholinoethoxy)phenyl)-4-(piperidin-4-ylmethylamino)nicotinamide (Y-098)

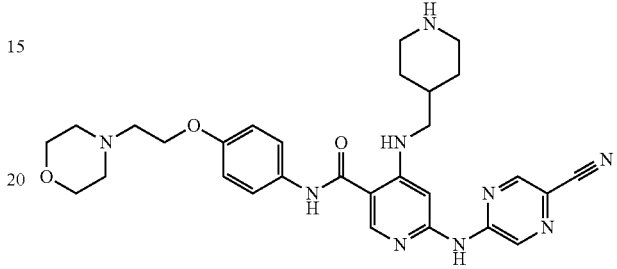

The title compound was prepared using methods analogous to those described in Synthesis 75, steps 75-A and 75-B.

$^1$H NMR ((CD$_3$)$_2$SO-d$_6$, 500 MHz) δ 10.05 (s, 1H), 9.10 (s, 1H), 8.79 (d, 1H, J=1.2 Hz), 8.57 (s, 1H), 8.35 (t, 1H, J=5.5 Hz), 7.92 (s, 1H), 7.56 (d, 2H, J=9 Hz), 7.15 (s, 1H), 6.92 (d, 2H, J=9 Hz), 4.06 (t, 2H, J=5.8 Hz), 3.59-3.57 (m, 4H), 3.05 (t, 2H, J=5.8 Hz), 2.96 (d, 2H, J=11.7 Hz), 2.67 (t, 2H, J=5.7 Hz), 2.47-2.43 (m, 6H), 1.70-1.64 (m, 3H), 1.27-1.23 (m, 1H), 1.16-1.10 (m, 2H). LCMS (4) Rt=1.08 min; m/z (ESI+) 558 (MH+).

Synthesis 144

6-(5-Cyanopyrazin-2-ylamino)-N-(3-morpholinophenyl)-4-(piperidin-4-ylmethylamino)nicotinamide (Y-099)

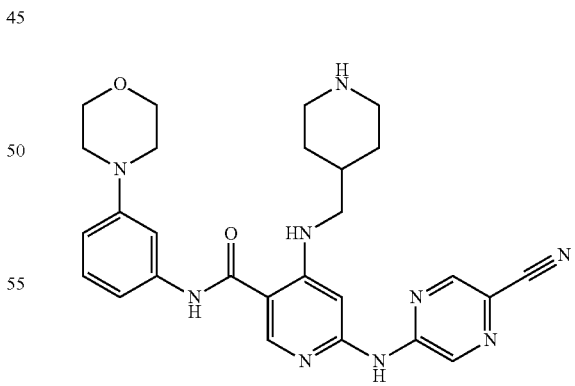

The title compound was prepared using methods analogous to those described in Synthesis 75, steps 75-A and 75-B.

$^1$H NMR ((CD$_3$)$_2$SO-d$_6$, 500 MHz) δ 10.02 (s, 1H), 9.10 (s, 1H), 8.79 (d, 1H, J=1.3 Hz), 8.56 (s, 1H), 8.29 (t, 1H, J=5.6 Hz), 7.92 (s, 1H), 7.27 (s, 1H), 7.22-7.16 (m, 3H), 6.70 (d, 1H, J=7.8 Hz), 3.75-3.73 (m, 4H), 3.09-3.05 (m, 6H), 2.95 (d, 2H,

J=12 Hz), 2.45 (t, 2H, J=11.2 Hz), 1.72-1.64 (m, 3H), 1.26-1.22 (m, 1H), 1.16-1.09 (m, 2H). LCMS (4) Rt=1.48 min; m/z (ESI$^+$) 514 (MH$^+$).

Synthesis 145

6-(5-Cyanopyrazin-2-ylamino)-N-(4-morpholinophenyl)-4-(piperidin-4-ylmethylamino)nicotinamide (Y-100)

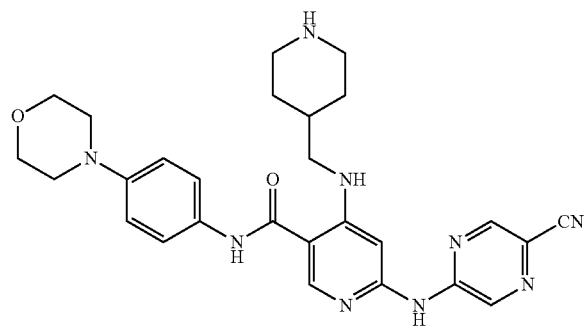 [SMILES: N#Cc1cnc(Nc2cc(NCC3CCNCC3)c(C(=O)Nc3ccc(N4CCOCC4)cc3)cn2)cn1]

The title compound was prepared using methods analogous to those described in Synthesis 75, steps 75-A and 75-B.

$^1$H NMR (500 MHz, d$_4$-MeOD) δ 9.00 (1H, s), 8.60 (1H, s), 8.46 (1H, s), 7.50 (2H, d, J=8.5 Hz), 7.10 (1H, s), 7.00 (2H, d, J=8.5 Hz), 3.80-3.90 (4H, m), 3.05-3.20 (8H, m), 2.60-2.75 (2H, m), 1.80-1.95 (1H+2H, m), and 1.25-1.45 (2H, m). LCMS (4) Rt=2.11 min; m/z (ESI$^+$) 514 [MH$^+$].

Synthesis 146

6-(5-Cyanopyrazin-2-ylamino)-4-(piperidin-4-ylmethylamino)nicotinamide (Y-101)

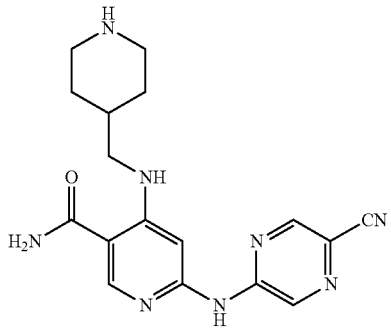 [SMILES: N#Cc1cnc(Nc2cc(NCC3CCNCC3)c(C(N)=O)cn2)cn1]

The title compound was prepared using methods analogous to those described in Synthesis 75, steps 75-A and 75-B.

$^1$H NMR (MeOD-d$_4$, 500 MHz) δ 8.97 (s, 1H), 8.60 (s, 1H), 8.41 (s, 1H), 7.12 (s, 1H), 3.14 (d, 2H, J=6 Hz), 3.09 (d, 2H, J=11.8 Hz), 2.62 (t, 2H, J=11.6 Hz), 1.83 (d, 2H, J=10.8 Hz), 1.30-1.28 (m, 3H). LCMS (4) Rt=0.98 min; m/z (ESI$^+$) 353 (MH$^+$).

Synthesis 147

6-(5-Cyanopyrazin-2-ylamino)-4-(morpholin-2-ylmethylamino)-N-phenylnicotinamide (Y-102)

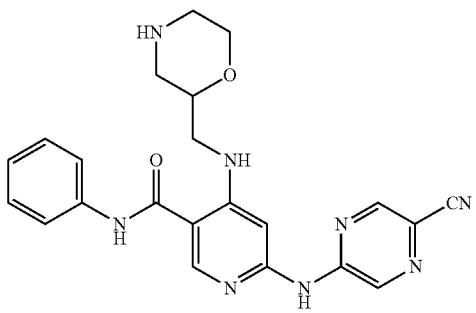 [SMILES: N#Cc1cnc(Nc2cc(NCC3CNCCO3)c(C(=O)Nc3ccccc3)cn2)cn1]

The title compound was prepared using methods analogous to those described in Synthesis 75, steps 75-A and 75-B.

$^1$H NMR (500 MHz, d$_4$-MeOD) δ 9.00 (1H, s), 8.65 (1H, s), 8.57 (1H, s), 7.60-7.65 (2H, dd, J=1.5 and 8.3 Hz), 7.35-7.40 (2H, dd, J=7.8 and 8.3 Hz), 7.26 (1H, s), 7.15-7.20 (1H, m), 4.10-4.20 (1H, m), 4.00-4.10 (1H, m), 3.84-3.94 (1H, m), 3.68-3.77 (1H, m), 3.40-3.50 (2H, m), 3.26-3.30 (1H, m), 3.20-3.26 (1H, m), and 3.05-3.15 (1H, m). LCMS (4) Rt=1.81 min; m/z (ESI$^+$) 431.1 [MH$^+$].

Synthesis 148

6-(5-Cyanopyrazin-2-ylamino)-4-(1-methylpiperidin-4-ylamino)-N-phenylnicotinamide (Y-103)

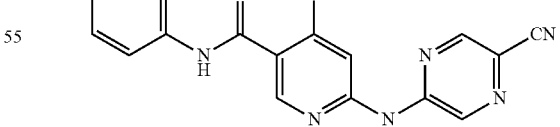

The title compound was prepared using methods analogous to those described in Synthesis 75, steps 75-A.

$^1$H NMR ((CD$_3$)$_2$SO-d$_6$, 500 MHz) δ 10.67 (s, 1H), 10.13 (s, 1H), 9.11 (d, 1H, J=1.2 Hz), 8.79 (d, 1H, J=1.4 Hz), 8.62 (s, 1H), 8.22 (d, 1H, J=7.1 Hz), 7.67 (dd, 2H, J=8.4, 1.0 Hz), 7.34 (t, 2H, J=8.0 Hz), 7.20 (s, 1H), 7.10 (t, 1H, J=8.0 Hz), 2.71 (d, 2H, J=10.8 Hz), 2.22 (s, 3H), 2.19-2.15 (m, 2H), 1.98 (d, 2H, J=9.8 Hz), 1.52-1.50 (m, 2H). LCMS (4) Rt=1.50 min; m/z (ESI+) 429 (MH+).

Synthesis 149

6-(5-Cyanopyrazin-2-ylamino)-4-(1-methylpiperidin-4-ylamino)nicotinic acid (Y-104)

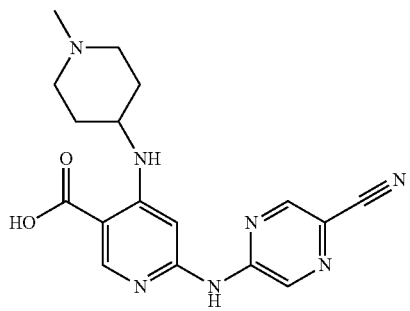 [SMILES: CN1CCC(Nc2cc(Nc3cnc(C#N)cn3)ncc2C(=O)O)CC1]

Methyl 6-(5-cyanopyrazin-2-ylamino)-4-(1-methylpiperidin-4-ylamino)nicotinate (Synthesis 66) (50 mg, 0.136 mmol) and lithium iodide (36 mg, 2 eq.) in dry pyridine (1.4 mL) were heated at 150° C. in a sealed Biotage microwave vial for 2.5 hr. The volatiles were removed in vacuo and the crude mixture was partitioned between EtOAc and 1M aqueous NaHCO₃. The aqueous layer was retained, washed with fresh EtOAc and then carefully neutralised with 1M HCl. The volatiles were then removed and a portion of the residue was purified by HPLC to give the title compound as a yellow powder (5 mg, 10%).

¹H NMR (500 MHz, DMSO) δ 9.03 (s, 1H), 8.88 (br s, 1H), 8.75 (s, 1H), 8.54 (s, 1H), 8.18 (s, 1H), 7.11 (s, 1H), 3.45-3.39 (m, 1H), 2.96-2.87 (m, 2H), 2.48-2.39 (m, 2H), 2.39 (s, 3H), 2.08-2.01 (m, 2H), 1.61-1.52 (m, 2H). LCMS (3B) Rt=1.09 min; m/z (ESI+) 354 (MH+).

Synthesis 150 methyl 4-(1-methylpiperidin-4-ylamino)-6-(5-methylpyrazin-2-ylamino)nicotinate (Y-105)

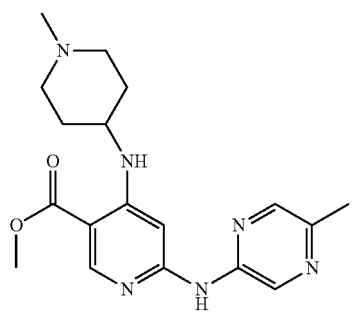 [SMILES: COC(=O)c1cnc(Nc2cnc(C)cn2)cc1NC1CCN(C)CC1]

The title compound was prepared using methods analogous to those described in Synthesis 81.

¹H NMR (500 MHz, CDCl₃) δ 8.68 (s, 1H), 8.52 (d, 1H, J=1.0 Hz), 8.15 (d, 1H, J=7.0 Hz), 8.07 (s, 1H), 7.23 (s, 1H), 3.86 (s, 3H), 3.64 (s, 1H), 3.53 (br s, 1H), 2.87-2.80 (m, 2H), 2.49 (s, 3H), 2.39 (s, 3H), 2.41-2.34 (m, 2H), 2.18-2.11 (m, 2H), 1.83-1.71 (m, 2H). LCMS (3B) Rt=1.56 min; m/z (ESI+) 357 (MH+).

Synthesis 151

Methyl 6-(5-methoxypyrazin-2-ylamino)-4-(morpholin-2-ylmethylamino)nicotinate (Y-106)

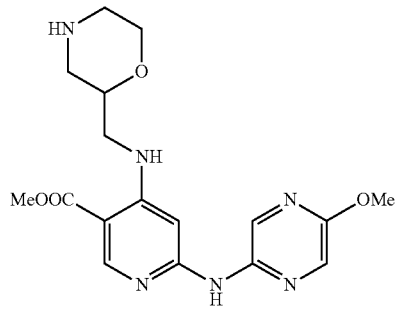 [SMILES: COC(=O)c1cnc(Nc2cnc(OC)cn2)cc1NCC1CNCCO1]

The title compound was prepared using methods analogous to those described in Synthesis 82, steps 82-A and 82-B, and Synthesis 75, step 75-B.

¹H NMR (500 MHz, d₄-MeOD) δ 8.58 (1H, s), 8.46 (1H, s), 7.96 (1H, s), 6.77 (1H, s), 3.98-4.02 (1H, m), 3.97 (3H, s), 3.87 (3H, s), 3.80-3.85 (1H, m), 3.70-3.75 (1H, m), 3.35-3.40 (1H, m), 3.25-3.32 (1H, m), 3.02-3.12 (1H, m), 2.88-2.95 (2H, m) and 2.70-2.80 (1H, m). LCMS (4) Rt=1.29 min; m/z (ESI+) 375 [MH+].

Synthesis 152-A

(E)-tert-Butyl 4-((5-((1-aminoethylideneaminooxy)carbonyl)-2-(5-cyanopyrazin-2-ylamino)pyridin-4-ylamino)methyl)piperidine-1-carboxylate

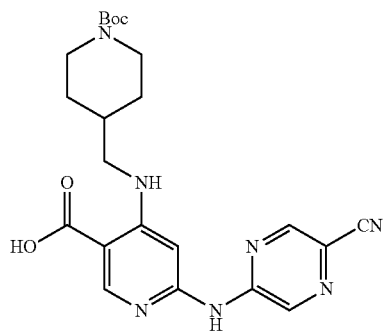

-continued

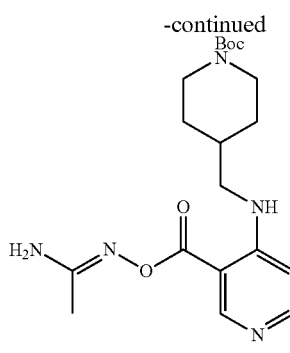

DIPEA (96 µL, 0.55 mmol) was added to a solution of 4-((1-(tert-butoxycarbonyl)piperidin-4-yl)methylamino)-6-(5-cyanopyrazin-2-ylamino)nicotinic acid (Synthesis 75-A) (50 mg, 0.11 mmol), HATU (54 mg, 0.14 mmol) in DMF (6 mL) under argon. The reaction mixture was stirred for 15 min at r.t. and (E)-N'-hydroxyacetimidamide (25 mg, 0.34 mmol) in DMF (0.5 mL) was added. The resulting solution was stirred at r.t. for 12 hr. Aqueous NaCl solution (15 mL) was added and the resulting precipitate was collected. The solid was washed with water and n-hexane to give a yellow powder (43 mg, 77%).

$^1$H NMR (500 MHz, $d_6$-DMSO) δ 10.70 (1H, s, broad, NH), 9.10 (1H, s), 8.86 (1H, s), 8.78 (1H, s), 8.20 (1H, s, broad, NH), 7.18 (1H, s), 6.50 (2H, s, broad, NH$_2$), 3.91-4.00 (2H, m), 3.05-3.15 (2H, m), 2.60-2.70 (2H, m), 1.80 (3H, s), 1.60-1.70 (2H, m), 1.40 (9H, s) and 1.00-1.30 (2H, m). LCMS Rt=4.02 min; m/z (ESI$^+$) 510 [MH$^+$].

Synthesis 152-B tert-Butyl 4-((2-(5-cyanopyrazin-2-ylamino)-5-(3-methyl-1,2,4-oxadiazol-5-yl)pyridin-4-ylamino)methyl)piperidine-1-carboxylate

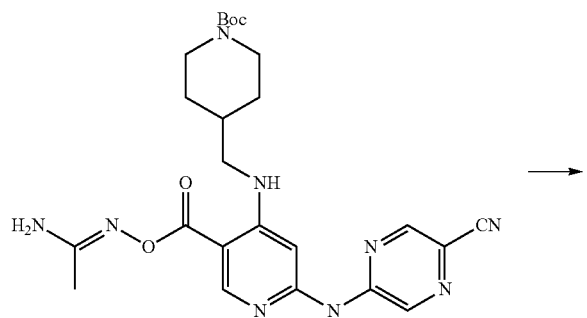

A solution of (E)-tert-Butyl 4-((5-(((1-aminoethylidene-aminooxy)carbonyl)-2-(5-cyanopyrazin-2-ylamino)pyridin-4-ylamino)methyl)piperidine-1-carboxylate (40 mg, 0.078 mmol) in pyridine (3 mL) was heated at 120° C. for 8 hr using microwave irradiation. After evaporation of the solvent, the crude product was purified by column chromatography (Biotage), eluting with EtOAc/n-hexane (1/1), to give the title compound as a yellow solid (9 mg, 23%).

$^1$H NMR (500 MHz, CDCl$_3$) δ 8.79 (1H, s), 8.77 (1H, s), 8.53 (1H, s), 8.30 (1H, s, broad, NH), 7.32 (1H, s), 4.15-4.25 (2H, m), 3.25-3.30 (2H, m), 2.70-2.80 (2H, m), 2.48 (3H, s), 1.90-2.00 (1H, m), 1.80-1.85 (2H, m), 1.48 (9H, s) and 1.20-1.35 (2H, m). LCMS Rt=5.32 min; m/z (ESI$^+$) 492 [MH$^+$].

Synthesis 152-C 5-(5-(3-Methyl-1,2,4-oxadiazol-5-yl)-4-(piperidin-4-ylmethylamino)pyridin-2-ylamino)pyrazine-2-carbonitrile (Y-107)

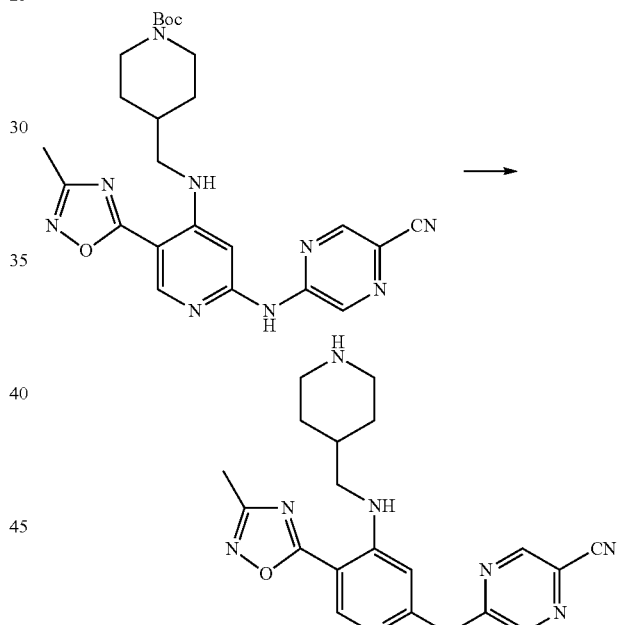

To a solution of tert-butyl 4-((2-(5-cyanopyrazin-2-ylamino)-5-(3-methyl-1,2,4-oxadiazol-5-yl)pyridin-4-ylamino)methyl)piperidine-1-carboxylate (9 mg, 0.018 mmol) in dichloromethane (3 mL) was added trifluoroacetic acid (0.15 mL) at r.t. After 3 hr, the solution was evaporated to dryness and purified by ion exchange on SCX-II acidic resin (500 mg) eluting with methanol, then 2M ammonia-methanol. The basic fractions were combined and the solvent was removed in vacuo to give the title compound as a yellow solid (4 mg, 56%).

$^1$H NMR (500 MHz, $d_6$-DMSO) δ 9.03 (1H, s), 8.82 (1H, s), 8.71 (1H, s), 8.07 (1H, s, broad, NH), 7.34 (1H, s), 3.15-

3.25 (4H, m), 2.90-3.00 (2H, m), 2.45 (3H, s), 1.60-1.80 (1H+2H, m), and 1.10-1.25 (2H, m). LCMS Rt=2.18 min; m/z (ESI$^+$) 392 [MH$^+$].

Synthesis 153-A

N-(4-Chloropyridin-2-yl)pivalamide

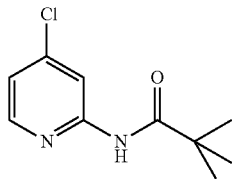

Trimethylacetyl chloride (4.22 g, 35.0 mmol) was added dropwise to a solution of 2-amino-4-chloropyridine (3.00 g, 23.3 mmol) in pyridine (11 mL) at 0° C. The resulting solution was stirred for 12 h at r.t. Water (20 mL) was added and the aqueous phase was extracted with ethyl acetate (3×10 mL). The combined organic extracts were dried (MgSO$_4$). The solvent was removed in vacuo and the crude mixture was purified by flash chromatography on silica, eluting with ethyl acetate and hexane (2/8), to give the title compound as a colourless solid (4.9 g, 99%).

$^1$H NMR (CDCl$_3$, 500 MHz) δ 8.37 (d, 1H, J=1.9 Hz), 8.17 (s, 1H), 8.15 (d, 1H, J=5.3 Hz), 7.05 (1H, dd, J=1.9, 5.3 Hz), 1.33 (9H, s). LCMS (3B) Rt=2.45 min; m/z (ESI$^+$) 213 [MH$^+$].

Synthesis 153-B

N-(4,5-Dichloropyridin-2-yl)pivalamide

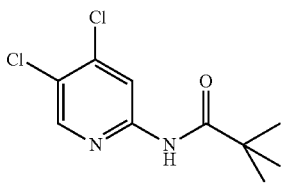

NCS (3.14 g. 23.5 mmol) was added to a solution of N-(4-chloropyridin-2-yl)pivalamide (1.00 g, 4.7 mmol) in dry acetonitrile (10 mL). The resulting suspension was heated for 3 h and then cooled to r.t. The solvent was removed in vacuo and the crude mixture was diluted with ethyl acetate (50 mL). The organic phase was washed with aqueous NaOH (10%, 2×20 mL), water (20 mL) and dried (MgSO$_4$). The solvent was removed in vacuo and the crude mixture was purified by flash chromatography on silica, eluting with ethyl acetate and hexane (1/9), to give the title compound as a colourless solid (0.87 g, 75%).

$^1$H NMR (CDCl$_3$, 500 MHz) δ 8.46 (s, 1H), 8.24 (s, 1H), 1.31 (9H, s). LCMS (3B) Rt=2.72 min; m/z (ESI$^+$) 247 [MH$^+$].

Synthesis 153-C

N-(5-Chloro-4-(1-methylpiperidin-4-ylamino)pyridin-2-yl)pivalamide

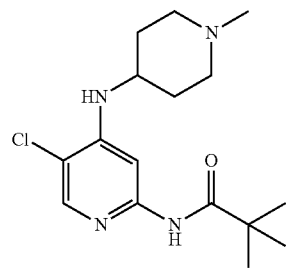 [SMILES: CN1CCC(Nc2cc(NC(=O)C(C)(C)C)ncc2Cl)CC1]

A solution of N-(4,5-dichloropyridin-2-yl)pivalamide (0.400 g, 1.62 mmol), N-methyl-4-aminopiperidine (0.185 g, 1.62 mmol) in NMP (3 mL) was heated at 220° C. under microwave irradiation for 3 h. The crude reaction mixture was purified by ion exchange on SCX-II acidic resin (2 g) eluting with methanol/dichloromethane (1/1), then 2M ammonia-methanol. The basic fractions were combined and the solvent was removed in vacuo. The crude mixture was purified by flash chromatography on silica, eluting with methanol and dichloromethane (1/9), to give the title compound as a colourless solid (0.384 g, 73%).

$^1$H NMR (Acetone-d$_6$, 500 MHz) δ 8.51 (s, 1H), 7.88 (s, 1H), 7.70 (s, 1H), 5.46 (d, 1H, J=7.9 Hz), 3.56-3.49 (1H, m), 3.04-3.01 (m, 2H), 2.50-2.45 (m, 2H), 2.42 (s, 3H), 2.09-2.06 (m, 2H), 1.89-1.86 (m, 2H). LCMS (3B) Rt=1.00 min; m/z (ESI$^+$) 325 [MH$^+$].

Synthesis 153-D

5-Chloro-N4-(1-methylpiperidin-4-yl)pyridine-2,4-diamine

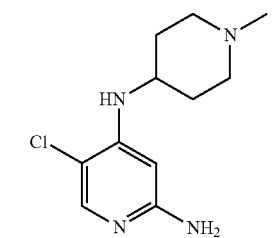 [SMILES: CN1CCC(Nc2cc(N)ncc2Cl)CC1]

A solution of N-(5-chloro-4-(1-methylpiperidin-4-ylamino)pyridin-2-yl)pivalamide (0.609 g, 1.87 mmol) in 6M HCl (5 mL) was heated under microwave irradiation at 105° C. for 50 min. The solution was basified with Na$_2$CO$_3$ and extracted with ethyl acetate (3×20 mL). The crude mixture was purified by flash chromatography on silica, eluting with methanol and dichloromethane (1/9), to give the title compound as a colourless solid (0.300 g, 66%).

$^1$H NMR (MeOD-d$_4$, 500 MHz) δ 7.58 (s, 1H), 5.87 (s, 1H), 3.44-3.28 (m, 1H), 2.86 (d, 2H, J=11.8 Hz), 2.30 (s, 3H), 2.20 (t, 2H, J=11.0 Hz), 2.01 (d, 2H, J=14.2 Hz), 1.60-1.62 (m, 2H). LCMS (3B) Rt=0.52 min; m/z (ESI⁺) 241 [MH⁺].

Synthesis 153-E 5-(5-Chloro-4-(1-methylpiperidin-4-ylamino)pyridin-2-ylamino)pyrazine-2-carbonitrile (Y-108)

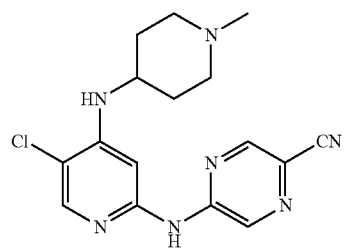 [SMILES: CN1CCC(Nc2cc(Nc3cnc(C#N)cn3)ncc2Cl)CC1]

A solution of 5-chloro-N4-(1-methylpiperidin-4-yl)pyridine-2,4-diamine (0.080 g, 0.33 mmol), 2-bromo-cyanopyrazine (0.040 g, 0.22 mmol), BINAP (0.005 g, 0.02 mmol), sodium tert-butoxide (0.030 g, 0.31 mmol), tris(dibenzylideneacetone)dipalladium chloroform complex (0.009 g, 0.01 mmol) in dioxane (1.6 mL) was stirred at r.t. under nitrogen for 10 min before being heated under microwave irradiation for 30 min at 90° C. The crude reaction mixture was purified by ion exchange on SCX-II acidic resin (1 g) eluting with methanol/dichloromethane (1/1), then 2M ammonia-methanol. The basic fractions were combined and the solvent was removed in vacuo. The crude mixture was purified by preparative thin layer chromatography eluting with methanol/dichloromethane (1/9) to give the title compound as a yellow solid (0.023 g, 30%).

¹H NMR (MeOD-d₄, 500 MHz) δ 8.94 (s, 1H), 8.57 (s, 1H), 7.96 (s, 1H), 7.18 (s, 1H), 3.53-3.47 (m, 1H), 3.00-2.98 (m, 2H), 2.40 (s, 3H), 2.38-2.35 (m, 2H), 2.13-2.09 (m, 2H), 1.75-1.67 (m, 2H). LC-MS (3B) Rt=0.67 min; m/z (ESI⁺) 344 [MH⁺].

Synthesis 154

5-(5-Chloro-4-(methyl(1-methylpiperidin-4-yl)amino)pyridin-2-ylamino)pyrazine-2-carbonitrile (Y-109)

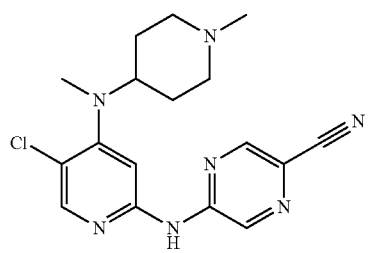 [SMILES: CN1CCC(N(C)c2cc(Nc3cnc(C#N)cn3)ncc2Cl)CC1]

The title compound was prepared using methods analogous to those described in Synthesis 153, steps 153-A, 153-B, 153-C, 153-D and 153-E.

¹H NMR (500 MHz, MeOD) δ 8.94 (d, 1H, J=1.0 Hz). 8.59 (d, 1H, J=1.0 Hz), 8.12 (s, 1H), 7.55 (s, 1H), 3.94-3.84 (m, 1H), 3.48-3.41 (m, 2H), 2.98-2.89 (m, 2H), 2.87 (s, 3H), 2.76 (s, 3H), 2.20-2.09 (m, 2H), 2.06-1.97 (m, 2H). LCMS (4) Rt=1.43 min; m/z (ESI⁺) 358 (MH⁺).

Synthesis 155-A

N-(5-Bromo-4-chloropyridin-2-yl)pivalamide

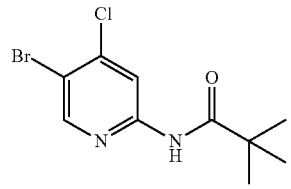

NBS (8.37 g. 47.0 mmol) was added to a solution of N-(4-chloropyridin-2-yl)pivalamide (2.00 g, 9.40 mmol) in dry acetonitrile (20 mL). The resulting suspension was heated for 3 hr and then cooled to r.t. The solvent was removed in vacuo and the crude mixture was diluted with ethyl acetate (100 mL). The organic phase was washed with aqueous NaOH (10%, 2×40 mL), water (40 mL) and dried (MgSO₄). The solvent was removed in vacuo and the crude mixture was purified by flash chromatography on silica, eluting with ethyl acetate and hexane (1/9), to give the title compound as a colourless solid (1.82 g, 66%).

¹H NMR (CDCl₃, 500 MHz) δ 8.46 (s, 1H), 8.34 (s, 1H). LCMS (3B) Rt=2.73 min; m/z (ESI⁺) 292 [MH⁺].

Synthesis 155-B

N-(5-Bromo-4-(1-methylpiperidin-4-ylamino)pyridin-2-yl)pivalamide

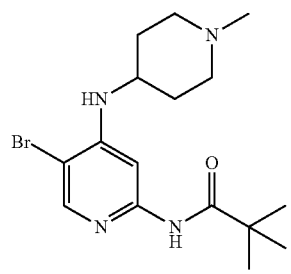

A solution of N-(5-bromo-4-chloropyridin-2-yl)pivalamide (0.547 g, 1.87 mmol), 1-methylpiperidin-4-amine (0.600 g, 5.25 mmol) in NMP (3.3 mL) was heated under microwave irradiation for 3 hr at 220° C. The crude mixture was purified by flash chromatography on silica, eluting with methanol and dichloromethane (1/9), to give the title compound as a colourless oil (0.684 g, 99%).

¹H NMR (CDCl₃, 500 MHz) δ 8.00 (s, 1H), 7.84 (s, 1H), 7.70 (s, 1H), 3.57-3.42 (m, 1H), 3.42-3.35 (1H, m), 2.80-2.78

(m, 2H), 2.31 (s, 3H), 2.24 (t, 2H, J=9.8 Hz), 2.09-2.05 (m, 2H), 1.64-1.58 (m, 2H). LCMS (3B) Rt=1.04 min; m/z (ESI⁺) 369 [MH⁺].

Synthesis 155-C

5-Bromo-N4-(1-methylpiperidin-4-yl)pyridine-2,4-diamine

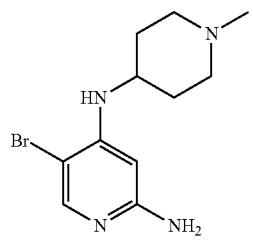

A solution of N-(5-bromo-4-(1-methylpiperidin-4-ylamino)pyridin-2-yl)pivalamide (0.526, 1.42 mmol) in 6M HCl (6 mL) was heated under microwave irradiation at 105° C. for 50 min. The solution was basified with Na$_2$CO$_3$ and extracted with ethyl acetate (3×20 mL). The crude mixture was purified by flash chromatography on silica, eluting with methanol and dichloromethane (1/9), to give the title compound as a colourless solid (0.288 g, 70%).

$^1$H NMR (CDCl$_3$, 500 MHz) δ 7.86 (s, 1H), 5.70 (s, 1H), 4.58 (d, 1H, J=7.3 Hz), 3.35-3.24 (m, 1H), 2.80-2.77 (m, 2H), 2.31 (s, 3H), 2.18 (t, 2H, J=10.4 Hz), 2.08-1.98 (m, 2H), 1.64-1.57 (m, 2H). LC-MS (3B) Rt=0.52 min; m/z (ESI⁺) 284 [MH⁺].

Synthesis 155-D 5-(5-Bromo-4-(1-methylpiperidin-4-ylamino)pyridin-2-ylamino)pyrazine-2-carbonitrile (Y-110)

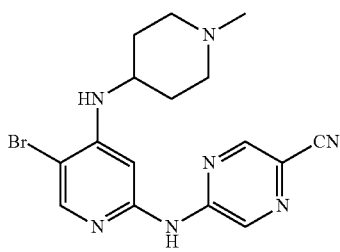 [SMILES: CN1CCC(Nc2cc(Nc3cnc(C#N)cn3)ncc2Br)CC1]

A solution of 5-bromo-N4-(1-methylpiperidin-4-yl)pyridine-2,4-diamine (0.020 g, 0.070 mmol), 2-bromo-cyanopyrazine (0.013 g, 0.070 mmol), BINAP (0.002 g, 0.005 mmol), sodium tert-butoxide (0.009 g, 0.098 mmol), tris(dibenzylideneacetone)dipalladium chloroform complex (0.003 g, 0.003 mmol) in dioxane (0.5 mL was stirred at r.t. under nitrogen for 10 min before being heated for 6 h at 90° C. The crude reaction mixture was purified by ion exchange on SCX-II acidic resin (1 g) eluting with methanol/dichloromethane (1/1), then 2M ammonia-methanol. The basic fractions were combined and the solvent was removed in vacuo. The crude mixture was purified by preparative thin layer chromatography eluting with methanol/dichloromethane (1/9) to give the title compound as a yellow solid (0.002 g, 7%).

$^1$H NMR (MeOD-d$_4$, 500 MHz) δ 8.87 (s, 1H), 8.60 (s, 1H), 8.12 (s, 1H), 7.31 (s, 1H), 3.86-3.77 (m, 1H), 3.61-3.56 (m, 2H), 2.94 (s, 3H), 2.37-2.31 (m, 2H), 2.03-1.91 (m, 2H), 1.30-1.28 (m, 2H). LCMS (4) Rt=1.06 min; m/z (ESI⁺) 387 [MH⁺].

Synthesis 156-A

N4-(1-Methylpiperidin-4-yl)-5-phenylpyridine-2,4-diamine

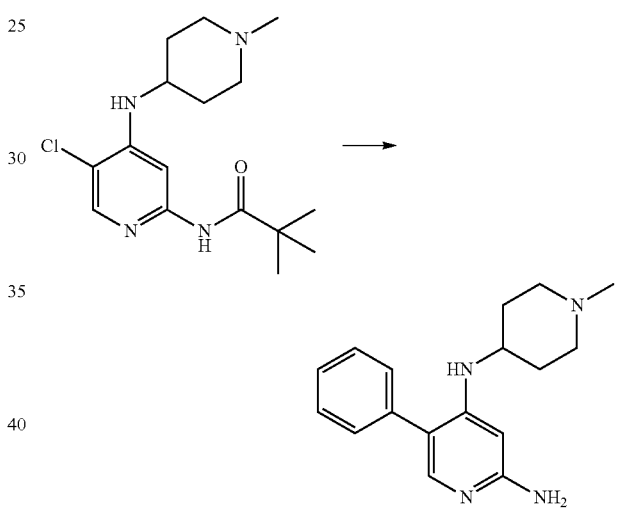

A solution of the N-(5-chloro-4-(1-methylpiperidin-4-ylamino)pyridin-2-yl)pivalamide (Synthesis 153-C) (0.187 g, 0.57 mmol), phenyl boronic acid (0.140 g, 1.15 mmol), sodium carbonate (0.153 g, 1.43 mmol) and Bedford catalyst (0.003 g, 0.005 mmol) in a mixture of acetonitrile/water (4/1, 3.1 mL) was heated under microwave irradiation for 30 min at 130° C. The crude reaction mixture was purified by ion exchange on SCX-II acidic resin (1 g) eluting with methanol/dichloromethane (1/1), then 2M ammonia-methanol. The basic fractions were combined and the solvent was removed in vacuo. The crude mixture was used without further purification. A solution of the protected amine in 6 M HCl (3 mL) was heated under microwave irradiation at 105° C. for 50 min. The solution was basified with Na$_2$CO$_3$ and extracted with ethyl acetate (3×10 mL). The crude mixture was purified by flash chromatography on silica, eluting with methanol and dichloromethane (1/9), to give the title compound as a colourless solid (0.384 g, 73%).

$^1$H NMR (MeOD-d$_4$, 500 MHz) δ 7.50-7.47 (m, 2H), 7.41-7.40 (m, 1H), 7.38 (s, 1H), 7.35-7.34 (m, 2H), 6.06 (s, 1H), 3.51-3.49 (m, 1H), 2.88-2.75 (m, 2H), 2.38-2.27 (m,

5H), 2.05-1.96 (m, 2H), 1.53-1.49 (m, 2H). LCMS (3B) Rt=2.11 min; m/z (ESI⁺) 480 [MH⁺].

Synthesis 156-B 5-(4-(1-Methylpiperidin-4-ylamino)-5-phenylpyridin-2-ylamino)pyrazine-2-carbonitrile (Y-111)

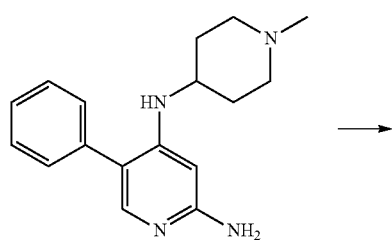

→

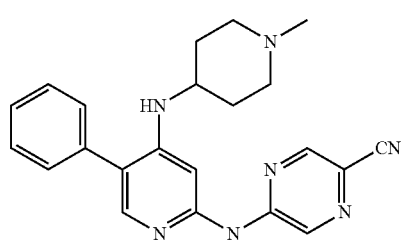

A solution of N4-(1-methylpiperidin-4-yl)-5-phenylpyridine-2,4-diamine (0.050 g, 0.17 mmol), 2-bromo-5-cyanopyrazine (0.022 g, 0.12 mmol), BINAP (0.003 g, 0.01 mmol), sodium tert-butoxide (0.016 g, 0.16 mmol), tris(dibenzylideneacetone)dipalladium chloroform complex (0.005 g, 0.01 mmol) in toluene (0.7 mL) was stirred at r.t. under nitrogen for 10 min before being heated under microwave irradiation for 30 min at 90° C. The crude reaction mixture was purified by ion exchange on SCX-II acidic resin (0.5 g) eluting with methanol/dichloromethane (1/1), then 2M ammonia-methanol. The basic fractions were combined and the solvent was removed in vacuo. The crude mixture was purified by preparative thin layer chromatography eluting with methanol/dichloromethane (1/9) to give the desired compound as a yellow solid (0.008 g, 17%).

¹H NMR (500 MHz, MeOD-d₄) δ 8.73 (d, 1H, J=1.2 Hz), 8.63 (d, 1H, J=1.2 Hz), 7.78 (s, 1H), 7.60-7.46 (m, 5H), 6.89 (s, 1H), 4.06-4.00 (m, 1H), 3.62-3.59 (m, 2H), 3.36-3.30 (m, 2H), 2.91 (s, 3H), 2.31-2.28 (m, 2H), 1.96-1.88 (m, 2H). LCMS (3B) Rt=1.61 min; m/z (ESI⁺) 386 [MH⁺].

Synthesis 157

5-(4-(1-methylpiperidin-4-ylamino)-5-(thiophen-3-yl)pyridin-2-ylamino)pyrazine-2-carbonitrile (Y-112)

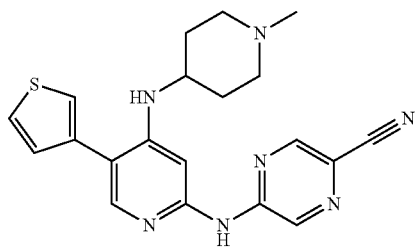 [SMILES: CN1CCC(Nc2cc(Nc3cnc(C#N)cn3)ncc2-c2ccsc2)CC1]

The title compound was prepared using methods analogous to those described in Synthesis 156, steps 156-A and 156-B.

¹H NMR (500 MHz, MeOD) δ 8.91 (s, 1H), 8.57 (s, 1H), 7.88 (s, 1H), 7.62 (dd, 1H, J=5.0, 3.0 Hz), 7.50 (dd, 1H, J=3.0, 1.5 Hz), 7.23 (dd, 1H, J=5.0, 1.5 Hz), 7.15 (s, 1H), 3.65-3.58 (m, 1H), 3.16-3.08 (m, 2H), 2.75-2.66 (m, 2H), 2.58 (s, 3H), 2.22-2.15 (m, 2H), 1.71-1.61 (m, 2H). LCMS (3B) Rt=1.59 min; m/z (ESI⁺) 392 (MH⁺).

Synthesis 158

5-(4-(methyl(1-methylpiperidin-4-yl)amino)-5-phenylpyridin-2-ylamino)pyrazine-2-carbonitrile (Y-113)

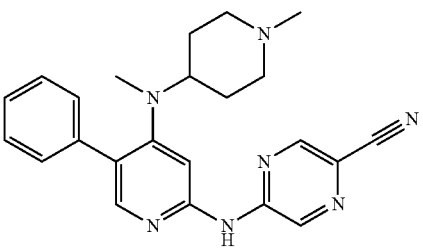 [SMILES: CN1CCC(N(C)c2cc(Nc3cnc(C#N)cn3)ncc2-c2ccccc2)CC1]

The title compound was prepared using methods analogous to those described in Synthesis 156, steps 156-A and 156-B.

¹H NMR (500 MHz, MeOD) δ 9.01 (d, 1H, J=1.0 Hz), 8.61 (d, 1H, J=1.0 Hz), 7.95 (s, 1H), 7.49 (s, 1H), 7.50-7.46 (m, 5H), 7.41-7.35 (m, 1H), 3.46-3.37 (s, 1H), 3.29-3.20 (m, 2H), 2.73 (s, 3H), 2.61 (s, 3H), 2.43-2.32 (m, 2H), 1.98-1.86 (m, 2H), 1.67-1.59 (m, 2H). LCMS (4) Rt=1.35 min; m/z (ESI+) 400 (MH+).

Synthesis 159

5-(5-(4-methoxyphenyl)-4-(1-methylpiperidin-4-ylamino)pyridin-2-ylamino)pyrazine-2-carbonitrile (Y-114)

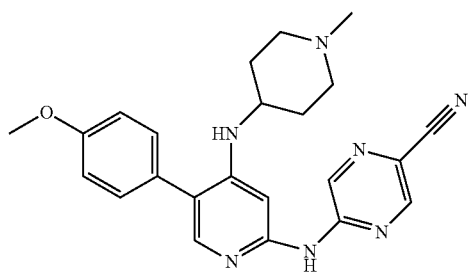 [SMILES: COc1ccc(-c2cnc(Nc3cnc(C#N)cn3)cc2NC2CCN(C)CC2)cc1]

The title compound was prepared from the product of Synthesis 155-D using methods analogous to those described in Synthesis 156, steps 156-A and 156-B.

¹H NMR (500 MHz, MeOD) δ 8.89 (s, 1H), 8.56 (s, 1H), 7.75 (s, 1H), 7.32 (d, 2H, J=8.5 Hz), 7.06 (d, 2H, J=8.5 Hz), 7.11 (s, 1H), 3.86 (s, 3H), 3.64-3.54 (m, 1H), 3.16-3.04 (m, 2H), 2.72-2.62 (m, 2H), 2.55 (s, 3H), 2.19-2.11 (s, 2H), 1.69-1.56 (m, 2H). LCMS (4) Rt=1.36 min; m/z (ESI+) 416 (MH+).

Synthesis 160

5-(5-(3-(methoxymethyl)phenyl)-4-(1-methylpiperidin-4-ylamino)pyridin-2-ylamino)pyrazine-2-carbonitrile (Y-115)

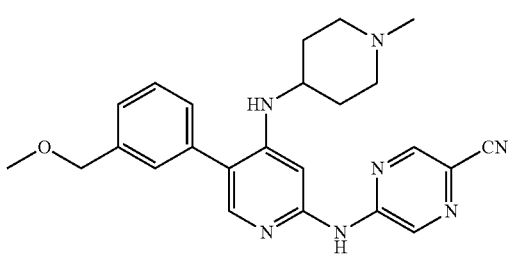 [SMILES: COCc1cccc(-c2cnc(Nc3cnc(C#N)cn3)cc2NC2CCN(C)CC2)c1]

The title compound was prepared from the product of Synthesis 155-C using methods analogous to those described in Synthesis 167, steps 167-C and 167-D.

¹H NMR (CDCl₃, 500 MHz) δ 8.81 (s, 1H), 8.47 (s, 1H), 8.11 (s, 1H), 7.83 (s, 1H), 7.51-7.48 (m, 1H), 7.42-7.38 (m, 1H), 7.31-7.32 (m, 1H), 7.12 (s, 1H), 4.53 (s, 2H), 3.58-3.45

(m, 2H), 2.83-2.81 (m, 2H), 2.38 (s, 3H), 2.33-2.29 (m, 2H), 2.12-2.09 (m, 2H), 1.65-1.60 (m, 2H). LCMS (4) Rt 1.32 min; m/z (ESI+) 430 [MH+].

Synthesis 161

5-(5-(3-Methoxyphenyl)-4-(1-methylpiperidin-4-ylamino)pyridin-2-ylamino)pyrazine-2-carbonitrile (Y-116)

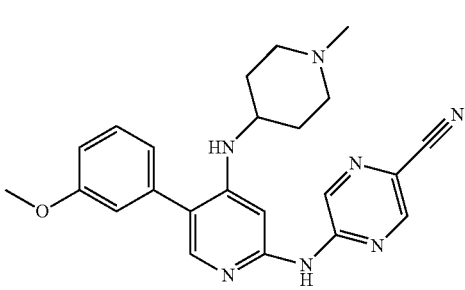 [SMILES: COc1cccc(-c2cnc(Nc3cnc(C#N)cn3)cc2NC2CCN(C)CC2)c1]

The title compound was prepared from the product of Synthesis 155-C using methods analogous to those described in Synthesis 167, steps 167-C and 167-D.

¹H NMR (500 MHz, MeOD) δ 8.92 (s, 1H), 8.57 (s, 1H), 7.80 (s, 1H), 7.42 (dd, 1H, J=8.0, 8.0 Hz), 7.14 (s, 1H), 7.02-6.93 (m, 3H), 3.85 (s, 3H), 3.63-3.55 (m, 1H), 3.12-2.99 (m, 2H), 2.69-2.58 (m, 2H), 2.52 (s, 3H), 2.20-2.11 (s, 2H), 1.68-1.56 (m, 2H). LCMS (4 min) Rt=1.32 min; m/z (ESI+) 416 (MH+).

Synthesis 162

5-(5-(4-(2-Methoxyethoxy)phenyl)-4-(1-methylpiperidin-4-ylamino)pyridin-2-ylamino)pyrazine-2-carbonitrile (Y-117)

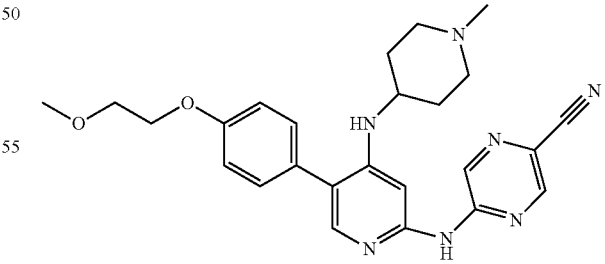

The title compound was prepared from the product of Synthesis 155-C using methods analogous to those described in Synthesis 167, steps 167-C and 167-D.

¹H NMR (500 MHz, MeOD) δ 8.93 (m, 1H). 8.55 (s, 1H), 7.73 (s, 1H), 7.31 (d, 2H, J=8.5 Hz), 7.06 (s, 1H), 7.08 (2H, d, J=8.5 Hz), 4.20-4.17 (m, 2H), 3.80-3.77 (m, 2H), 3.45 (s, 3H), 2.87-2.76 (m, 2H), 2.31 (s, 3H), 2.35-2.23 (s, 2H), 2.09-2.01 (m, 2H), 1.57-1.46 (m, 2H). LCMS (4) Rt=1.95 min; m/z (ESI⁺) 460 (MH⁺).

Synthesis 163

5-(5-(3-(2-methoxyethoxy)phenyl)-4-(1-methylpiperidin-4-ylamino)pyridin-2-ylamino)pyrazine-2-carbonitrile (Y-118)

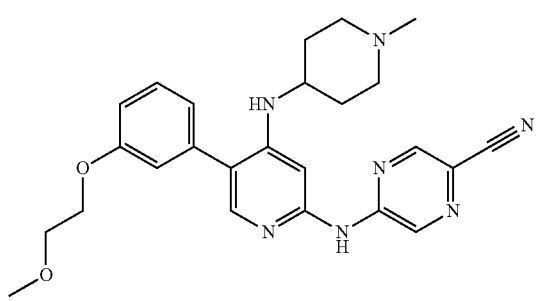 [SMILES: COCCOc1cccc(-c2cnc(Nc3cnc(C#N)cn3)cc2NC2CCN(C)CC2)c1]

The title compound was prepared using methods analogous to those described in Synthesis 156, steps 156-A and 156-B.

¹H NMR (500 MHz, MeOD) δ 8.93 (s, 1H), 8.55 (s, 1H), 7.78 (s, 1H), 7.42 (t, 1H, J=8.0 Hz), 7.10 (s, 1H), 7.03-6.95 (m, 3H), 4.19-4.16 (m, 2H), 3.79-3.76 (m, 2H), 3.57-3.49 (m, 1H), 3.44 (s, 3H), 2.98-2.87 (m, 2H), 2.50-2.40 (m, 2H), 2.42 (s, 3H), 2.14-2.07 (m, 2H), 1.62-1.52 (m, 2H). LCMS (4) Rt=1.60 min; m/z (ESI⁺) 460 (MH⁺).

Synthesis 164

5-(5-(4-(Methoxymethyl)phenyl)-4-(1-methylpiperidin-4-ylamino)pyridin-2-ylamino)pyrazine-2-carbonitrile (Y-119)

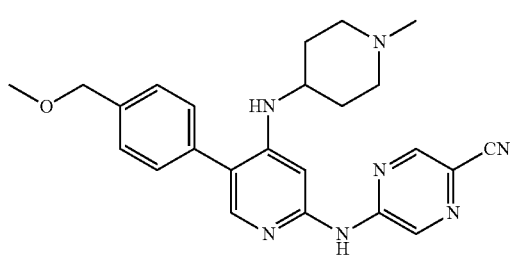 [SMILES: COCc1ccc(-c2cnc(Nc3cnc(C#N)cn3)cc2NC2CCN(C)CC2)cc1]

The title compound was prepared using methods analogous to those described in Synthesis 156, steps 156-A and 156-B.

¹H NMR (CDCl₃, 500 MHz) δ 8.74 (s, 1H), 8.46 (s, 1H), 7.82 (s, 1H), 7.48-7.45 (m, 2H), 7.38-7.36 (m, 2H), 7.16 (s, 1H), 4.54 (s, 2H), 3.48-3.39 (m, 2H), 2.79-2.77 (m, 2H), 2.33 (s, 3H), 2.21-2.19 (m, 2H), 2.08-2.06 (m, 2H), 1.57-1.50 (m, 2H). LCMS (4) Rₜ 1.32 min; m/z (ESI⁺) 430 [MH⁺].

Synthesis 165

5-(4-(1-Methylpiperidin-4-ylamino)-5-(4-morpholinophenyl)pyridin-2-ylamino)pyrazine-2-carbonitrile (Y-120)

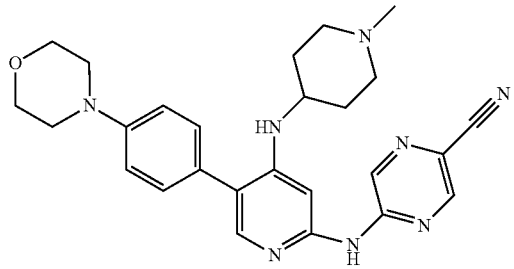 [SMILES: CN1CCC(Nc2cc(Nc3cnc(C#N)cn3)ncc2-c2ccc(N3CCOCC3)cc2)CC1]

The title compound was prepared from the product of Synthesis 155-C using methods analogous to those described in Synthesis 167, steps 167-C and 167-D.

¹H NMR (500 MHz, MeOD) δ 8.90 (s, 1H), 8.54 (s, 1H), 7.73 (s, 1H), 7.28 (d, 2H, J=8.5), 7.09 (d, 2H, J=8.5), 7.05 (s, 1H), 3.78-3.85 (m, 4H), 3.53-3.45 (m, 1H), 3.24-3.20 (m, 4H), 2.91-2.81 (m, 2H), 2.39-2.30 (m, 2H), 2.35 (s, 3H), 2.11-2.04 (m, 2H), 1.58-1.47 (m, 2H). LCMS (4) Rt=2.00 min; m/z (ESI⁺) 471 (MH⁺).

Synthesis 166

5-(4-(1-Methylpiperidin-4-ylamino)-5-o-tolylpyridin-2-ylamino)pyrazine-2-carbonitrile (Y-121)

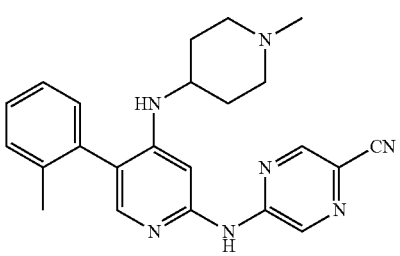 [SMILES: Cc1ccccc1-c1cnc(Nc2cnc(C#N)cn2)cc1NC1CCN(C)CC1]

The title compound was prepared using methods analogous to those described in Synthesis 156, steps 156-A and 156-B.

¹H NMR (MeOD-d₄, 500 MHz) δ 8.94 (s, 1H), 8.55 (d, 1H, J=1.4 Hz), 7.67 (s, 1H), 7.36-7.31 (m, 3H), 7.18-7.16 (m, 1H), 7.09 (s, 1H), 3.49-3.45 (m, 1H), 2.81-2.79 (m, 2H), 2.34-2.32

(m, 2H), 2.17 (s, 3H), 2.05-1.98 (m, 2H), 1.50-1.38 (m, 2H). LCMS (4) R$_t$ 1.65 min; m/z (ESI$^+$) 400 [MH$^+$].

Synthesis 167-A

Benzyl 4-(5-bromo-2-pivalamidopyridin-4-ylamino)piperidine-1-carboxylate

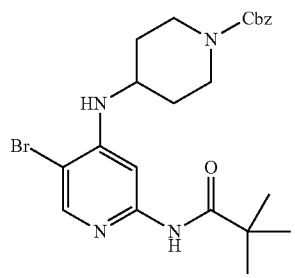 [SMILES: CC(C)(C)C(=O)Nc1cc(NC2CCN(C(=O)OCc3ccccc3)CC2)c(Br)cn1]

N-(5-Bromo-4-chloropyridin-2-yl)pivalamide (Synthesis 155-A) (1.08 g, 3.70 mmol), benzyl 4-aminopiperidine-1-carboxylate (1.736 g, 7.41 mmol), and triethylamine (1.041 mL, 7.41 mmol) in NMP (7.41 mL) in a sealed vial was heated to 210° C. by microwave irradiation for 1.5 hr. The cooled solution was diluted with MeOH and purified by ion exchange on Isolute SCX II acidic resin eluting with MeOH then 2M NH$_3$ in MeOH. He basic fractions were combined and volatiles were removed in vacuo. The crude product was dissolved in dichloromethane and loaded onto a Biotage silica column. Flash column chromatography eluting with a gradient of EtOAc in hexanes gave N-(5-bromo-4-(1-methylpiperidin-4-ylamino)pyridin-2-yl)pivalamide (0.536 g, 1.095 mmol, 30%) as a clear glass.

$^1$H NMR (500 MHz, CDCl$_3$) δ 8.03 (s, 1H), 7.95 (s, 1H), 7.69 (s, 1H), 7.39-7.30 (m, 5H), 5.15 (s, 2H), 4.74 (d, 1H, J=7.7 Hz), 4.13 (q, 3H, J=7.0 Hz), 3.73-3.64 (m, 1H), 3.12 (t, 2H, J=11.5 Hz), 2.13-2.06 (m, 2H), 1.54-1.43 (m, 2H), 1.33 (s, 9H). LCMS (4) Rt=2.48 min; m/z (ESI$^+$) 489/491 (MH$^+$).

Synthesis 167-B tert-Butyl 4-(2-amino-5-bromopyridin-4-ylamino)piperidine-1-carboxylate

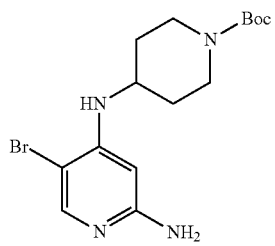 [SMILES: CC(C)(C)OC(=O)N1CCC(Nc2cc(N)ncc2Br)CC1]

N-(5-Bromo-4-(1-methylpiperidin-4-ylamino)pyridin-2-yl)pivalamide (526 mg, 1.075 mmol) in 6M HCl (10 mL, 60.0 mmol) was heated by microwave irradiation to 105° C. for 1.5 hr. After cooling the volatiles were removed in vacuo. The residue was purified by ion exchange on Isolute SCX II acidic resin, washing with MeOH and then with 2M NH$_3$ in MeOH. The basic fractions were concentrated to give crude 5-bromo-N4-(1-methylpiperidin-4-yl)pyridine-2,4-diamine (290 mg, 1.069 mmol, 100% yield) as a cream powder. LCMS (4) Rt=0.56 min; m/z (ESI$^+$) 271/273 (MH$^+$). Di-tert-butyl dicarbonate (73.6 μl, 0.317 mmol) dissolved in the minimum amount of dichloromethane was slowly added to an ice-cooled solution of 5-bromo-N4-(piperidin-4-yl)pyridine-2,4-diamine (86 mg, 0.317 mmol) in triethylamine (134 μL, 0.951 mmol) and dichloromethane (2.44 mL). The mixture was stirred at 0° C. for 30 min followed by 1 hr at r.t. Solvents were removed in vacuo and the crude material was purified by preparative thin layer chromatography, eluting with 7% MeOH, 1% NH3 in dichloromethane, to give tert-butyl 4-(2-amino-5-bromopyridin-4-ylamino)piperidine-1-carboxylate (91 mg, 0.245 mmol, 77%) as a colourless foam.

$^1$H NMR (500 MHz, CDCl$_3$) δ 7.82 (s, 1H), 5.69 (s, 1H), 4.51 (d, 1H, J=7.5 Hz), 4.31 (br s, 2H), 4.05-3.91 (m, 2H), 3.41.3.32 (m, 1H), 2.98-2.86 (m, 2H), 1.99-1.90 (m, 1H), 1.44 (s, 9H), 1.44-1.36 (m, 1H). LCMS (4) Rt=1.87 min; m/z (ESI$^+$) 371/373 (MH$^+$).

Synthesis 167-C tert-Butyl 4-(2-amino-5-(4-methoxyphenyl)pyridin-4-ylamino)piperidine-1-carboxylate

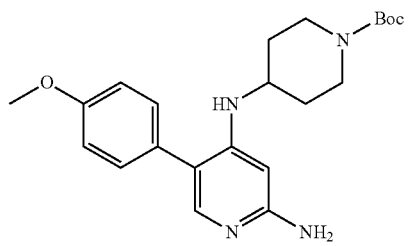 [SMILES: COc1ccc(-c2cnc(N)cc2NC2CCN(C(=O)OC(C)(C)C)CC2)cc1]

Acetonitrile (1212 μL) and 0.5M sodium carbonate solution (0.36 mL, 1.5 eq) were added to tert-butyl 4-(2-amino-5-bromopyridin-4-ylamino)piperidine-1-carboxylate (45 mg, 0.121 mmol), 4-methoxyphenylboronic acid (27.6 mg, 0.182 mmol), and tetrakis(triphenylphosphine) palladium(0) (7.00 mg, 6.06 μmol) in a microwave vial (0.5 mL). The capped vial was heated to 150° C. by microwave irradiation for 20 min. After cooling the solution was diluted with MeOH and purified by ion exchange on SCX-II acidic resin (2 g) column, eluting with MeOH then 2M ammonia in MeOH. The basic fractions were combined and concentrated. The crude product was dissolved in dichloromethane and loaded onto a Biotage SNAP silica column (10 g) which was eluted with a gradient of MeOH/NH$_3$ (99/1) in dichloromethane to give tert-butyl 4-(2-amino-5-(4-methoxyphenyl)pyridin-4-ylamino)piperidine-1-carboxylate (19 mg, 0.048 mmol, 39%) as a colourless foam.

$^1$H NMR (500 MHz, CDCl$_3$) δ 7.60 (s, 1H), 7.23 (d, 2H, J=8.5 Hz), 6.97 (d, 2H, J=8.5 Hz), 5.75 (s, 1H), 4.45 (br s, 2H), 4.20 (d, 1H, J=7.5 Hz), 3.98-3.88 (m, 2H), 3.85 (s, 3H), 3.47-3.39 (m, 1H), 2.96 (t, 2H, J=11.0 Hz), 1.99-1.92 (m, 2H), 1.45 (s, 9H), 1.34-1.24 (m, 2H). LCMS (4) Rt=2.20 min; m/z (ESI⁺) 399 (MH⁺).

Synthesis 167-D tert-butyl 4-(2-(5-cyanopyrazin-2-ylamino)-5-(4-methoxyphenyl)pyridin-4-ylamino)piperidine-1-carboxylate

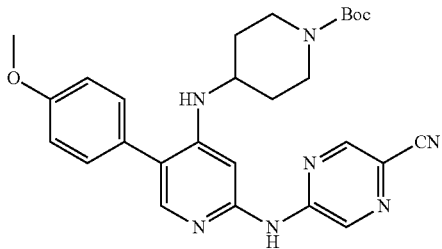 [SMILES: COc1ccc(-c2cnc(Nc3cnc(C#N)cn3)cc2NC2CCN(C(=O)OC(C)(C)C)CC2)cc1]

Dry DME (402 µL) was added to a mixture of tert-butyl 4-(2-amino-5-(4-methoxyphenyl)pyridin-4-ylamino)piperidine-1-carboxylate (16 mg, 0.040 mmol), 5-bromopyrazine-2-carbonitrile (7.39 mg, 0.040 mmol), xantphos (1.859 mg, 3.21 µmol), tris(dibenzylideneacetone)dipalladium(0) (1.471 mg, 1.606 µmol), and cesium carbonate (26.2 mg, 0.080 mmol) in a nitrogen purged, sealed microwave vial. Nitrogen gas was bubbled through the mixture for 5 min. The reaction mixture was heated for 1 hr at 100° C. by microwave irradiation. Upon cooling the mixture was diluted with MeOH and purified by ion exchange on Isolute SCX II acidic resin (5 g), eluting with MeOH. The eluent was concentrated and further purified by preparative thin layer chromatography, eluting with 7% MeOH, 1% NH3, 92% DCM, to give 5-(5-(4-methoxyphenyl)-4-(1-methylpiperidin-4-ylamino)pyridin-2-ylamino)pyrazine-2-carbonitrile (4 mg, 7.97 µmol, 20% yield) as a light yellow powder.

¹H NMR (500 MHz, CDCl₃) δ 8.83 (s, 1H), 8.46 (s, 1H), 7.77 (s, 1H), 7.29 (d, 2H, J=8.5 Hz), 7.15 (s, 1H), 7.05 (d, 2H, J=8.5 Hz), 4.62 (d, 1H, J=7.0 Hz), 4.05-3.94 (m, 2H), 3.90 (s, 3H), 3.65-3.55 (m, 1H), 3.08-2.97 (m, 2H), 2.08-2.00 (d, 2H, J=12.5 Hz), 1.43 (s, 9H), 1.43-1.32 (m, 2H). LCMS (4) Rt=2.36 min; m/z (ESI⁺) 502 (MH⁺).

Synthesis 167-E 5-(5-(4-Methoxyphenyl)-4-(piperidin-4-ylamino)pyridin-2-ylamino)pyrazine-2-carbonitrile (Y-122)

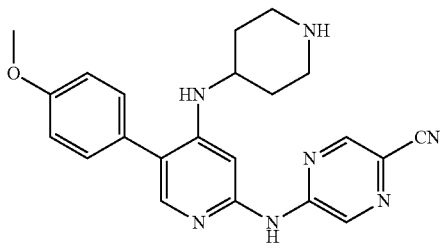 [SMILES: COc1ccc(-c2cnc(Nc3cnc(C#N)cn3)cc2NC2CCNCC2)cc1]

Trifluoroacetic acid (0.1 µL, 1.298 µmol) was added to tert-butyl 4-(2-(5-cyanopyrazin-2-ylamino)-5-(4-methoxyphenyl)pyridin-4-ylamino)piperidine-1-carboxylate (4 mg, 7.97 µmol) dissolved in dichloromethane (0.45 mL) and the mixture was stirred for 1 hr. The mixture was concentrated and purified by ion exchange on (solute SCX II acidic resin (1 g), eluting with MeOH then 2M NH₃-MeOH. The basic fractions were combined and concentrated. Preparative thin layer chromatography, eluting with 10% MeOH/1% NH₃/89% dichloromethane) gave 5-(5-(4-methoxyphenyl)-4-(piperidin-4-ylamino)pyridin-2-ylamino)pyrazine-2-carbonitrile (2 mg, 4.98 µmol, 62.5% yield) as a yellow powder.

¹H NMR (500 MHz, MeOD) δ 8.93 (s, 1H), 8.56 (s, 1H), 7.74 (s, 1H), 7.32 (d, 2H, J=9.0 Hz), 7.07 (d, 2H, J=9.0 Hz), 7.07 (s, 1H), 3.87 (s, 3H), 3.61-3.53 (s, 1H), 3.10-3.03 (m, 2H), 2.79-2.72 (m, 2H), 2.10-2.02 (m, 2H), 1.43-1.32 (m, 2H). LCMS (4) Rt=1.97 min; m/z (ESI⁺) 402 (MH⁺).

Synthesis 168-A (E)-5-(3-Methoxyprop-1-enyl)-N4-(1-methylpiperidin-4-yl)pyridine-2,4-diamine

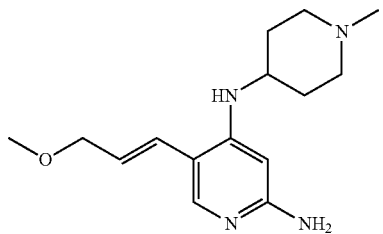

A solution of 5-bromo-N4-(1-methylpiperidin-4-yl)pyridine-2,4-diamine (Synthesis 155-C) (0.100 g, 0.35 mmol), sodium carbonate (0.5 M, 1.05 mL) and tetrakis(triphenylphosphine) palladium(0) (0.020 g, 0.02 mmol) in acetonitrile (3.40 mL) was heated for 20 min at 130° C. by microwave irradiation. The reaction mixture was concentrated in vacuo. The crude product was purified by ion exchange on SCX-II acidic resin (1 g) eluting with methanol/dichloromethane (1/1), then 2M ammonia-methanol. The basic fractions were combined and the solvent was removed in vacuo. The crude mixture was used without further purification.

¹H NMR (CDCl₃, 500 MHz) δ 7.68 (s, 1H), 6.35 (d, 1H, J=15.7 Hz), 5.98 (dt, 1H, J=5.8, 15.7 Hz), 5.67 (s, 1H), 4.03 (d, 2H, J=7.2 Hz), 3.36 (s, 3H), 3.32-3.18 (m, 1H), 2.86-2.67 (m, 2H), 2.27 (s, 3H), 2.10 (t, 2H, J=10.5 Hz), 2.06-1.92 (m, 2H), 1.51 (td, 2H, J=3.6, 13.6 Hz). LCMS (4) R_t 0.82 min; m/z (ESI⁺) 277 [MH⁺].

Synthesis 168-B (E)-5-(5-(3-methoxyprop-1-enyl)-4-(1-methylpiperidin-4-ylamino)pyridin-2-ylamino)pyrazine-2-carbonitrile (Y-123)

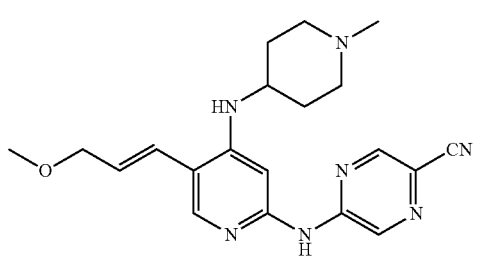 [SMILES: COC/C=C/c1cnc(Nc2cnc(C#N)cn2)cc1NC1CCN(C)CC1]

A solution of (E)-5-(3-methoxyprop-1-enyl)-N4-(1-methylpiperidin-4-yl)pyridine-2,4-diamine (0.090 g, 0.32 mmol), 2-bromo-cyanopyrazine (0.060 g, 0.32 mmol), BINAP (0.007 g, 0.02 mmol), sodium tert-butoxide (0.043 g, 0.45 mmol), tris(dibenzylideneacetone)dipalladium chloroform complex (0.013 g, 0.01 mmol) in dioxane (3 mL) was stirred at room temperature under nitrogen for 10 min, then heated for 30 min at 90° C. under microwave irradiation. The crude reaction mixture was purified by ion exchange on SCX-II acidic resin (1 g) eluting with methanol/dichloromethane (1/1), then 2M ammonia-methanol. The basic fractions were combined and the solvent was removed in vacuo. The crude mixture was purified by preparative thin layer chromatography, eluting with methanol/dichloromethane (1/9), to give the title compound as a yellow solid (0.004 g, 3%).

$^1$H NMR (CDCl$_3$, 500 MHz) δ 8.81 (s, 1H), 8.76 (s, 1H), 8.44 (m, 1H), 7.93 (s, 1H), 7.02 (s, 1H), 6.45 (d, 1H, J=15.8 Hz), 6.15 (1H, dt, J=15.8, 5.5 Hz), 4.40 (d, 1H, J=7.2 Hz), 4.12 (2H, J=5.5, 1.5 Hz), 3.45 (s, 3H), 2.90-2.88 (m, 2H), 2.37 (s, 3H), 2.23 (t, 2H, J=11.1 Hz), 2.14-2.11 (m, 2H), 1.66-1.64 (m, 2H). LCMS (4) R$_t$ 1.72 min; m/z (ESI$^+$) 380 [MH$^+$].

Synthesis 169-A

Benzyl 4-((5-chloro-2-pivalamidopyridin-4-ylamino)methyl)piperidine-1-carboxylate

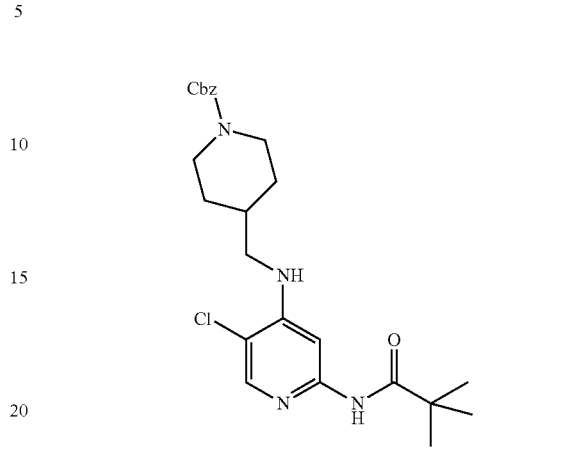

A capped microwave reaction vial containing a solution of N-(4,5-dichloropyridin-2-yl)pivalamide (0.38 g, 1.54 mmol) (Synthesis 153-B), benzyl 4-(aminomethyl)piperidine-1-carboxylate (0.76 g, 2 eq) and triethylamine (0.43 mL, 2 eq) in NMP (3 mL) was heated at 210° C. for 1.75 hr under microwave irradiation, and then allowed to cooled. The reaction mixture was diluted with MeOH and adsorbed onto Isolute SCX-II acidic resin (10 g). The resin was washed with methanol, then 2M ammonia in methanol. The basic fractions were concentrated and the crude product was further purified by column chromatography, using a Biotage 40+silica column eluted with a gradient of EtOAc in hexane. The product contained residual NMP which was removed by a second ion exchange purification on Isolute SCX-II acidic resin, eluting with methanol, then 2M ammonia in methanol, to give benzyl 4-((5-chloro-2-pivalamidopyridin-4-ylamino)methyl)piperidine-1-carboxylate as a light yellow gum (0.53 g, 68%).

$^1$H NMR (500 MHz, MeOD) δ 7.91 (s, 1H), 7.86 (br s, 1H), 7.67 (s, 1H), 7.39-7.30 (m, 5H), 5.15 (s, 2H), 4.83 (t, 1H, J=5.5 Hz), 4.25 (br s, 2H), 3.20 (dd, 2H, J=6.0, 6.0 Hz), 2.89-2.76 (m, 2H), 1.87-1.76 (m, 2H, 1H), 1.31-1.18 (m, 2H). LCMS (3B) Rt=4.19 min; m/z (ESI$^+$) 459 (MH$^+$).

Synthesis 169-B tert-Butyl 4-((2-amino-5-chloropyridin-4-ylamino)methyl)piperidine-1-carboxylate

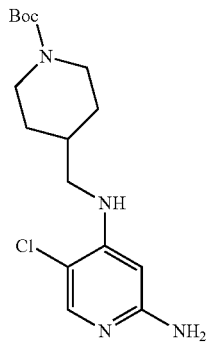 [SMILES: CC(C)(C)OC(=O)N1CCC(CNc2cc(N)ncc2Cl)CC1]

Benzyl 4-((5-chloro-2-pivalamidopyridin-4-ylamino)methyl)piperidine-1-carboxylate (0.52 g, 1.12 mmol) was refluxed in 6M HCl (20 mL) for 2 hr. The volatiles were removed in vacuo and the residue was dissolved in MeOH and adsorbed onto Isolute SCX-II acidic resin. The resin was washed with methanol, then 2M ammonia in methanol. The basic fractions were concentrated to give crude 5-chloro-N4-(piperidin-4-ylmethyl)pyridine-2,4-diamine (0.234 g, 96%). LCMS (4) Rt=0.51 min; m/z (ESI$^+$) 241 (MH$^+$). Di-tert-butyl dicarbonate (0.21 g, 1 eq.) in dichloromethane (1 mL) was added dropwise to 5-chloro-N4-(piperidin-4-ylmethyl)pyridine-2,4-diamine (0.228 g, 0.95 mmol) and triethylamine (0.40 ml, 3 eq.) in dichloromethane (6.5 mL). The solution was stirred at room temperature for 2 hr. Solvents were evaporated and the crude product was purified by preparative thin layer chromatography, eluting with 8% MeOH, 1% NH$_3$, 91% dichloromethane, to give tert-butyl 4-((2-amino-5-chloropyridin-4-ylamino)methyl)piperidine-1-carboxylate (109 mg, 34%) as a white powder.

$^1$H NMR (500 MHz, CDCl$_3$) δ 7.69 (s, 1H), 5.65 (s, 1H), 4.68 (t, 1H, J=5.5 Hz), 4.44 (br s, 2H), 4.10 (br s, 2H), 2.98 (dd, 2H, J=6.0, 6.0 Hz), 2.73-2.60 (m, 2H), 1.76-1.65 (m, 1H, 2H), 1.47 (s, 9H), 1.20-1.05 (m, 2H), LCMS (4) Rt=1.95 min; m/z (ESI$^+$) 341 (MH$^+$).

Synthesis 169-C tert-Butyl 4-((5-chloro-2-(5-cyanopyrazin-2-ylamino)pyridin-4-ylamino)methyl)piperidine-1-carboxylate

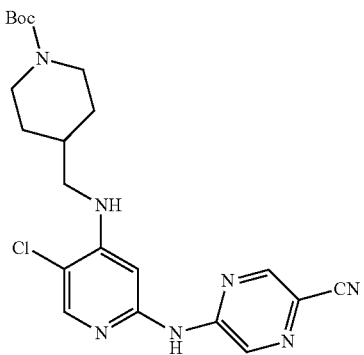 [SMILES: CC(C)(C)OC(=O)N1CCC(CNc2cc(Nc3cnc(C#N)cn3)ncc2Cl)CC1]

Dry dioxane (0.45 mL) was added to a microwave reaction vial containing tert-butyl 4-((2-amino-5-chloropyridin-4-ylamino)methyl)piperidine-1-carboxylate (23 mg, 0.067 mmol), 5-bromopyrazine-2-carbonitrile (8.3 mg, 0.045 mmol), tris(dibenzylideneacetone)-dipalladium chloroform complex (1.9 mg, 4 mol %), (±)-2,2'-bis(diphenylphosphino)-1,1'-binaphthalene (2.2 mg, 8 mol %) and sodium tert-butoxide (6.1 mg, 1.4 eq.) under nitrogen. The vial was sealed and nitrogen gas was bubbled through the suspension with stirring for 5 min. The mixture was heated at 90° C. for 30 min under microwave irradiation. The mixture was diluted with methanol and adsorbed onto Isolute SCX-II acidic resin (2 g). The resin was washed with methanol, then 2M ammonia in methanol. The basic fractions were concentrated and the residue was further purified by preparative thin layer chromatography, eluting with 5% MeOH in dichloromethane, to give tert-butyl 4-((5-chloro-2-(5-cyanopyrazin-2-ylamino)pyridin-4-ylamino)methyl)piperidine-1-carboxylate (12 mg, 60%) as an off-white solid.

$^1$H NMR (500 MHz, CDCl$_3$) δ 8.80 (s, 1H), 8.47 (s, 1H), 8.19 (br s, 1H), 8.00 (s, 1H), 7.09 (s, 1H), 4.99 (dd, 1H, J=5.5, 5.5 Hz), 4.20 (br s, 2H), 3.20 (dd, 2H, J=6.0, 6.0 Hz), 2.79-2.69 (m, 2H), 1.91-1.76 (m, 1H, 2H), 1.48 (s, 9H), 1.31-1.21 (m, 2H). LCMS (4) Rt=2.21 min; m/z (ESI$^+$) 444 (MH$^+$).

Synthesis 169-D 5-(5-chloro-4-(piperidin-4-ylmethylamino)pyridin-2-ylamino)pyrazine-2-carbonitrile (Y-124)

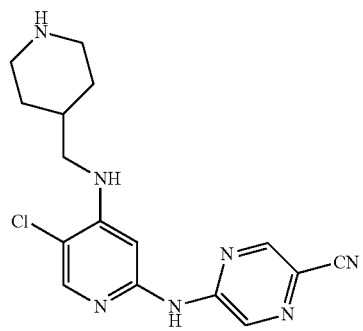 [SMILES: N#Cc1cnc(Nc2cc(NCC3CCNCC3)c(Cl)cn2)cn1]

Trifluoroacetic acid (0.1 mL) was added to tert-butyl 4-((5-chloro-2-(5-cyanopyrazin-2-ylamino)pyridin-4-ylamino)methyl)piperidine-1-carboxylate (12 mg, 0.027 mmol) in dichloromethane (1 mL) and the mixture was stirred at r.t. for 2 hr. Solvent was removed in vacuo and the residue was redissolved in MeOH and adsorbed onto Isolute SCX-II acidic resin (500 mg). The resin was washed with methanol, then 2M ammonia in methanol. The basic fractions were evaporated to dryness to give 5-(5-chloro-4-(piperidin-4-ylmethylamino)pyridin-2-ylamino)pyrazine-2-carbonitrile (2 mg, 22%) as a yellow powder.

$^1$H NMR (500 MHz, MeOD) δ 8.89 (d, 1H, J=1.5 Hz), 8.57 (d, 1H, J=1.5 Hz), 7.92 (s, 1H), 7.19 (s, 1H), 3.19 (d, 2H, J=6.5 Hz), 3.16-3.10 (m, 2H), 2.69-2.61 (m, 2H), 1.94-1.80 (m, 1H, 2H), 1.35-1.24 (m, 2H). LCMS (4) Rt=1.03 min; m/z (ESI$^+$) 344 (MH$^+$).

Synthesis 170-A

2-Chloro-5-iodopyridin-4-amine

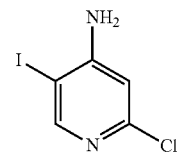

Iodine monochloride (0.758 g, 4.67 mmol) was added to a solution of 2-chloro-4-amino pyridine (0.500 g, 3.89 mmol) and potassium acetate (0.763 g, 7.78 mmol) in acetic acid (30 mL). The reaction mixture was heated under reflux for 4 hr. The solvent was removed in vacuo and the residue was partitioned between aqueous sodium hydrogenocarbonate (50 mL) and ethyl acetate (50 mL). The organic phase was dried (MgSO$_4$) and the solvent was removed in vacuo. The crude product was purified by flash silica chromatography, eluting with ethyl acetate and hexane (1/9), to give the title compound as a pink solid (0.394 g, 40%).

$^1$H NMR (CDCl$_3$, 500 MHz) δ 8.33 (s, 1H), 6.63 (s, 1H), 4.85 (brs, 2H). LCMS (4) R$_t$ 1.66 min; m/z (ESI$^+$) 254 [MH$^+$].

Synthesis 170-B tert-Butyl 4-((2-chloro-5-iodopyridin-4-ylamino)methyl)piperidine-1-carboxylate

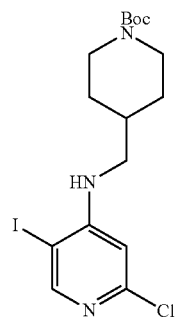 [SMILES: CC(C)(C)OC(=O)N1CCC(CNc2cc(Cl)ncc2I)CC1]

NaH (0.098 g, 3.9 mmol) was added to a solution of 2-chloro-5-iodopyridin-4-amine (0.500 g, 1.96 mmol) in DMF (12 mL) and the mixture was stirred for 30 min at r.t. The temperature was then raised to 80° C. and a solution of tert-butyl 4-(bromomethyl)-piperidine-1-carboxylate (1.093 g, 3.93 mmol) in DMF (2 mL) was added. The reaction mixture was stirred at 80° C. for 2 h, then cooled to r.t. NaH (0.050 g, 2.00 mmol) was added and the reaction mixture was heated for 1 h at 80° C. After cooling, water (40 mL) was added and the reaction mixture was partitioned between ethyl acetate and aq. NaHCO$_3$. The organic phase was washed with brine, dried (MgSO$_4$) and concentrated. The crude product was purified by flash silica chromatography, eluting with ethyl acetate and hexane (1/9), to give the title compound as a pink solid (0.405 g, 46%).

$^1$H NMR (CDCl$_3$, 500 MHz) δ 8.28 (s, 1H), 6.41 (s, 1H), 4.85 (t, 1H, J=5.2 Hz), 4.27-4.08 (m, 2H), 3.12 (t, 2H, J=6.2 Hz), 2.76-2.71 (m, 2H), 1.88-1.70 (m, 3H), 1.47 (s, 9H), 1.29-1.13 (m, 2H); LCMS (4) R$_t$ 2.78 min; m/z (ESI$^+$) 395 [MH$^+$].

Synthesis 170-C tert-Butyl 4-((2-chloro-5-phenylpyridin-4-ylamino)methyl)piperidine-1-carboxylate

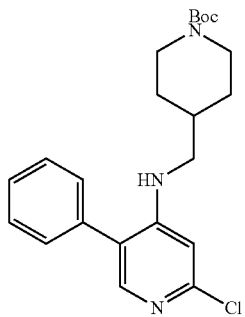 [SMILES: CC(C)(C)OC(=O)N1CCC(CNc2cc(Cl)ncc2-c2ccccc2)CC1]

A solution of tert-butyl 4-((2-chloro-5-iodopyridin-4-ylamino)methyl)piperidine-1-carboxylate (0.100 g, 0.22 mmol), sodium carbonate (0.5 M, 0.66 mL), phenyl boronic acid (0.027 g, 0.221 mmol) and tetrakis(triphenylphosphine)palladium(0) (0.011 g, 0.01 mmol) in acetonitrile (2 mL) was heated at 100° C. for 20 min under microwave irradiation. The reaction mixture was concentrated in vacuo. The crude product was purified by chromatography on a short silica column, eluting with ethyl acetate/petroleum ether (3/7), to give the title compound as a colourless oil (0.088 g, 98%).

$^1$H NMR (CDCl$_3$, 500 MHz) δ 7.83 (s, 1H), 7.51-7.48 (m, 2H), 7.44-7.41 (m, 1H), 7.36-7.32 (m, 2H), 6.52 (s, 1H), 4.57 (t, 1H, J=5.7 Hz), 4.19-4.02 (m, 2H), 3.03 (t, 2H, J=6.3 Hz), 2.68 (t, 2H, J=11.9 Hz), 1.75-1.68 (m, 1H), 1.66-1.63 (m, 2H), 1.45 (s, 9H), 1.16-1.08 (m, 2H). LC-MS (4) R$_t$ 2.71 min; m/z (ESI$^+$) 402 [MH$^+$].

Synthesis 170-D tert-Butyl 4-((2-(5-cyanopyrazin-2-ylamino)-5-phenylpyridin-4-ylamino)methyl)piperidine-1-carboxylate

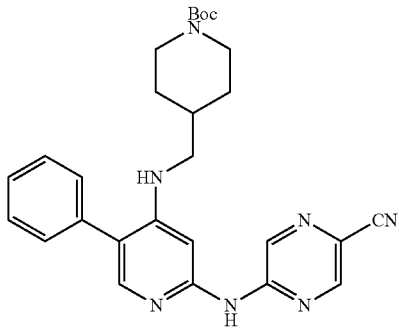 [SMILES: CC(C)(C)OC(=O)N1CCC(CNc2cc(Nc3cnc(C#N)cn3)ncc2-c2ccccc2)CC1]

A solution of tert-butyl 4-((2-chloro-5-phenylpyridin-4-ylamino)methyl)piperidine-1-carboxylate (0.040 g, 0.100 mmol), 2-amino-4-cyanopyrazine (0.018 g, 0.149 mmol), Xantphos (0.009 g, 0.016 mmol), cesium carbonate (0.065 g, 0.19 mmol), tris(dibenzylideneacetone)dipalladium chloroform complex (0.007 g, 0.008 mmol) in dioxane (0.7 mL) was stirred at r.t. under nitrogen for 10 min, then heated under microwave irradiation for 60 min at 150° C. The reaction mixture was purified by ion exchange on SCX-II acidic resin (1 g), eluting with methanol/dichloromethane (1/1), then 2M ammonia-methanol. The basic fractions were combined and solvent was removed in vacuo. The crude product was purified by preparative thin layer chromatography, eluting with ethyl acetate/hexane (1/1), to give the title compound as a yellow solid (0.020 g, 41%).

$^1$H NMR (CDCl$_3$, 500 MHz) δ 8.67 (s, 1H), 8.46 (s, 1H), 7.84 (s, 1H), 7.52 (t, 2H, J=7.4 Hz), 7.44 (t, 1H, J=7.4 Hz), 7.38 (d, 2H, J=7.0 Hz), 7.28 (s, 1H), 7.21 (s, 1H), 4.71 (t, 1H, J=5.7 Hz), 3.11 (t, 2H, J=6.2 Hz), 2.78-2.62 (m, 2H), 1.79-1.82 (m, 1H), 1.69 (d, 2H, J=12.4 Hz), 1.47 (s, 9H), 1.27 (t, 2H, J=7.1 Hz), 1.13-1.18 (m, 2H). LCMS (4) R$_t$ 2.18 min; m/z (ESI$^+$) 486 [MH$^+$].

Synthesis 170-E tert-Butyl 4-((2-(5-cyanopyrazin-2-ylamino)-5-phenylpyridin-4-ylamino)methyl)piperidine-1-carboxylate (Y-125)

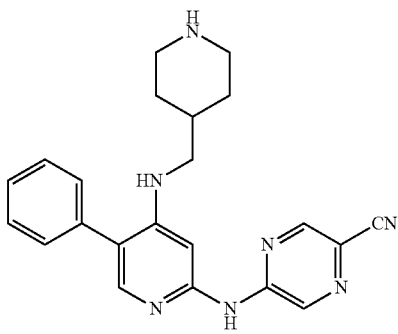 [SMILES: N#Cc1cnc(Nc2cc(NCC3CCNCC3)c(-c3ccccc3)cn2)cn1]

TFA (0.2 mL) was added at room temperature to a solution of tert-butyl 4-((2-(5-cyanopyrazin-2-ylamino)-5-phenylpyridin-4-ylamino)methyl)piperidine-1-carboxylate (0.020 g, 0.041 mmol) in dichloromethane (2 mL). The reaction mixture was stirred for 20 min. Solvent was removed in vacuo and the mixture was purified by ion exchange on SCX-II acidic resin (500 mg), eluting with methanol, then 2M ammonia-methanol. The basic fractions were combined and solvent was removed in vacuo. The crude product was purified by preparative thin layer chromatography, eluting with methanol/dichloromethane/NH$_3$ (0.9/9/0.01), to give the title compound as a yellow solid (0.012 g, 76%).

$^1$H NMR (MeOD-d$_4$, 500 MHz) 8.90 (s, 1H), 8.56 (s, 1H), 7.73 (s, 1H), 7.51-7.40 (m, 5H), 7.11 (s, 1H), 3.15-3.12 (m, 4H), 2.66 (t, 2H, J=13.5 Hz), 1.92-1.78 (m, 3H), 1.33-1.22 (m, 2H). LCMS (4) R$_t$ 1.24 min; m/z (ESI$^+$) 386 [MH$^+$].

Synthesis 171-A

Benzyl 4-((5-bromo-2-pivalamidopyridin-4-ylamino)methyl)piperidine-1-carboxylate

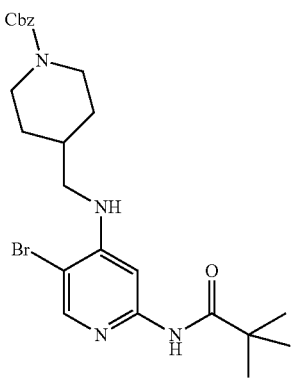 [SMILES: CC(C)(C)C(=O)Nc1cc(NCC2CCN(C(=O)OCc3ccccc3)CC2)c(Br)cn1]

Two capped microwave reaction vials each containing a solution of N-(5-bromo-4-chloropyridin-2-yl)pivalamide (0.55 g, 1.89 mmol), benzyl 4-(aminomethyl)piperidine-1-carboxylate (1.07 g, 2 eq.) and triethylamine (0.80 mL, 3 eq.) in NMP (3.8 mL) were heated at 210° C. by microwave irradiation for 1.5 hr and then allowed to cool. The contents of the two vials were combined and partitioned between EtOAc (15 mL) and sat. NaHCO$_3$ (150 mL). The organic layer was retained whilst the aqueous was further extracted with EtOAc (15 mL). The organic extracts were combined, washed with brine (50 mL), dried (MgSO$_4$) and concentrated. The crude material was purified by chromatography on a 40+M Biotage silica column, eluting with a gradient of EtOAc in dichloromethane, to give the title compound as a clear oil (0.83 g, 43%)

$^1$H NMR (500 MHz, CDCl$_3$) δ 8.01 (s, 1H), 7.87 (s, 1H), 7.65 (s, 1H), 7.39-7.35 (m, 4H), 7.34-7.30 (m, 1H), 5.14 (s, 2H), 4.86 (t, 1H, J=5.5 Hz), 4.25 (br s, 2H), 3.19 (t, 2H, J=6.0 Hz), 2.88-2.77 (m, 2H), 1.92-1.76 (m, 2H, 1H), 1.32 (s, 9H), 1.30-1.19 (m, 2H). LCMS (3.5 min) Rt=2.42 min; m/z (ESI$^+$) 503/505 (MH$^+$).

Synthesis 171-B tert-Butyl 4-((2-amino-5-bromopyridin-4-ylamino)methyl)piperidine-1-carboxylate

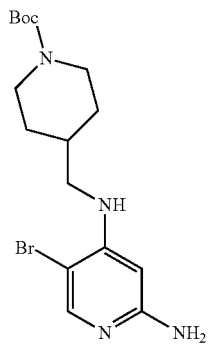 [SMILES: CC(C)(C)OC(=O)N1CCC(CNc2cc(N)ncc2Br)CC1]

A mixture of benzyl 4-((5-bromo-2-pivalamidopyridin-4-ylamino)methyl)piperidine-1-carboxylate (0.695 g, 1.24 mmol) and 6M HCl (10 mL) was heated at 105° C. for 45 mins by microwave irradiation. After cooling the volatiles were removed in vacuo. The residue was redissolved in MeOH and adsorbed onto Isolute SCX-II acidic resin. The resin was washed with methanol, then 2M ammonia in methanol. The basic fractions were concentrated to give crude 5-bromo-N4-(piperidin-4-ylmethyl)pyridine-2,4-diamine (0.326 g, 92%), LCMS (4) Rt=0.51 min; m/z (ESI$^+$) 285/287 (MH$^+$). A solution of di-tert-butyl dicarbonate (0.249 g, 1 eq.) in dichloromethane (1 mL) was added dropwise to an ice-cooled solution of 5-bromo-N4-(piperidin-4-ylmethyl)pyridine-2,4- diamine (0.326 g, 1.14 mmol) and triethylamine (0.48 mL, 3 eq.) in dichloromethane (7.79 mL). The solution was stirred at 0° C. for 30 mins and then warmed to room temperature and stirred for a further 30 min. The mixture was concentrated. The crude product was purified by preparative TLC, eluting with 7% MeOH, 1% NH$_3$, 92% dichloromethane, to give tert-butyl 4-((2-amino-5-bromopyridin-4-ylamino)methyl)piperidine-1-carboxylate (234 mg, 53%) as a white powder.

$^1$H NMR (500 MHz, CDCl$_3$) δ 7.86 (s, 1H), 5.68 (s, 1H), 4.74-6.68 (m, 1H), 4.40-4.07 (m, 4H), 3.05 (dd, 2H, J=6.0, 6.0 Hz), 2.84-2.63 (m, 2H), 1.83-1.72 (m, 2H, 1H), 1.47 (s, 9H), 1.25-1.14 (m, 2H). LCMS (4) Rt=1.90 min; m/z (ESI$^+$) 385/387 (MH$^+$).

Synthesis 171-C tert-Butyl 4-((2-amino-5-(4-methoxyphenyl)pyridin-4-ylamino)methyl)piperidine-1-carboxylate

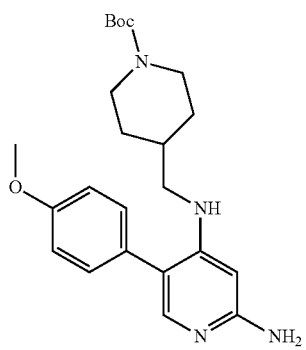 [SMILES: COc1ccc(-c2cnc(N)cc2NCC2CCN(C(=O)OC(C)(C)C)CC2)cc1]

Two capped 0.5 mL microwave reaction vials each containing a solution of tert-butyl 4-((2-amino-5-bromopyridin-4-ylamino)methyl)piperidine-1-carboxylate (30 mg, 0.078 mmol), 4-methoxyphenyl boronic acid (17.8 mg, 1.5 eq.), Pd(PPh$_3$)$_4$ (4.5 mg, 5 mol %), 0.5M aqueous sodium carbonate (0.23 mL, 1.5 eq.) in acetonitrile (0.78 mL) were heated at 150° C. for 20 min by microwave irradiation. After cooling, the contents of the two reaction vials were combined and solvents were removed in vacuo. The crude product was purified by chromatography using a Biotage SNAP silica (10 g) column, eluting with a gradient of methanol/NH$_3$ (99/1) in dichloromethane, to give the title compound as a yellow solid (48 mg, 75%).

$^1$H NMR (500 MHz, CDCl$_3$) δ 7.53 (s, 1H), 7.21 (d, 2H, J=8.5), 6.96 (d, 2H, J=8.5), 5.75 (s, 1H), 4.92 (br s, 2H), 4.40 (t, 1H, J=6.0 Hz), 4.10 (br s, 2H), 3.83 (s, 3H), 2.97 (dd, 2H, J=6.0, 6.0 Hz), 2.70-2.59 (m, 2H), 1.75-1.59 (m, 1H+2H), 1.44 (s, 9H), 1.14-1.03 (m, 2H). LCMS (4) Rt=2.15 min; m/z (ESI$^+$) 413 (MH$^+$).

Synthesis 171-D tert-Butyl 4-((2-(5-cyanopyrazin-2-ylamino)-5-(4-methoxyphenyl)pyridin-4-ylamino)methyl)piperidine-1-carboxylate

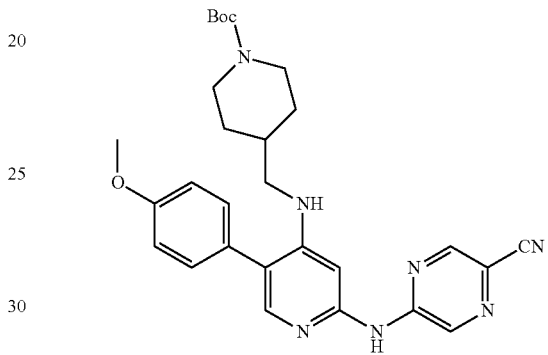

Dry DME (0.87 mL) was added to a microwave reaction vial containing tert-butyl 4-((2-(5-cyanopyrazin-2-ylamino)-5-(4-methoxyphenyl)pyridin-4-ylamino)methyl)piperidine-1-carboxylate (36 mg, 0.087 mmol), 5-bromopyrazine-2-carbonitrile (19 mg, 0.105 mmol), tris(dibenzylideneacetone) dipalladium chloroform complex (3.6 mg, 4 mol %), Xantphos (4.0 mg, 8 mol %) and cesium carbonate (57 mg, 2 eq.) under nitrogen. The vial was sealed and nitrogen was bubbled through the stirred suspension for 10 min. The mixture was heated at 100° C. for 1 hr by microwave irradiation. The mixture was diluted with methanol and adsorbed onto Isolute SCX-II acidic resin (2 g). The resin was washed with methanol, then 2M ammonia in methanol. The basic fractions were concentrated and further purified by preparative thin layer chromatography, eluting with 5% MeOH, 0.5% NH$_3$, 94.5% dichloromethane, to give the title compound as a yellow solid (15 mg, 33%).

$^1$H NMR (500 MHz, MeOD) δ 8.86 (s, 1H), 8.55 (s, 1H), 7.69 (s, 1H), 7.31 (d, 2H, J=9.0 Hz), 7.06 (d, 2H, J=9.0 Hz), 7.01 (s, 1H), 4.13-4.08 (m, 2H), 3.86 (s, 3H), 3.33-3.30 (m, 1H), 3.11 (d, 2H, J=7.0 Hz), 2.74 (br s, 2H), 1.94-1.83 (m, 1H), 1.77-1.69 (m, 2H), 1.46 (s, 9H), 1.19-1.08 (m, 2H). LCMS (4) Rt=2.22 min; m/z (ESI$^+$) 516 (MH$^+$).

Synthesis 171-E 5-(5-(4-Methoxyphenyl)-4-(piperidin-4-ylmethylamino)pyridin-2-ylamino)pyrazine-2-carbonitrile (Y-126)

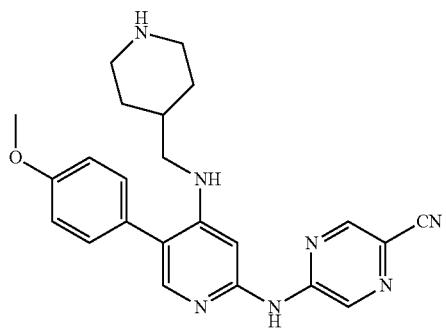 [SMILES: COc1ccc(-c2cnc(Nc3cnc(C#N)cn3)cc2NCC2CCNCC2)cc1]

The title compound was prepared using methods analogous to those described in Synthesis 169, step 169-D.

$^1$H NMR (500 MHz, MeOD) δ 8.85 (s, 1H), 8.58 (d, 1H, J=1.4 Hz), 7.71 (s, 1H), 7.31 (d, 2H, J=8.5 Hz), 7.14 (s, 1H), 7.06 (d, 2H, J=8.5 Hz), 3.86 (s, 3H), 3.32-3.26 (m, 2H), 3.16 (d, 2H, J=6.5 Hz), 2.89-2.80 (m, 2H), 2.01-1.87 (s, 2H+1H), 1.42-1.29 (s, 2H). LCMS (4) Rt=1.33 min; m/z (ESI$^+$) 416 (MH$^+$).

Synthesis 172

5-(5-(4-(Methoxymethyl)phenyl)-4-(piperidin-4-ylmethylamino)pyridin-2-ylamino)pyrazine-2-carbonitrile (Y-127)

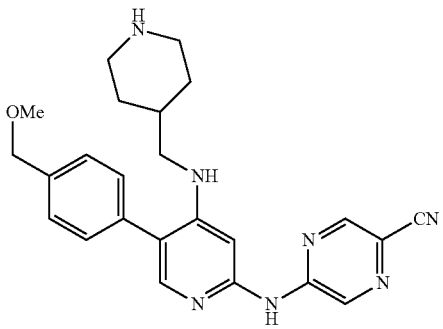 [SMILES: COCc1ccc(-c2cnc(Nc3cnc(C#N)cn3)cc2NCC2CCNCC2)cc1]

The title compound was prepared using methods analogous to those described in Synthesis 171, steps 171-A, 171-B, 171-C, 171-D and 171-E.

$^1$H NMR (MeOD-d$_4$, 500 MHz) δ 8.90 (s, 1H), 8.56 (s, 1H), 7.73 (s, 1H), 7.48 (d, 2H, J=8.1), 7.40 (d, 2H, J=8.1), 7.11 (s, 1H), 4.84 (m, 3H), 4.53 (s, 2H), 3.33 (t, 1H, J=3.3), 3.11-3.09 (m, 4H), 2.65 (dt, 2H, J=12.4, 2.5 Hz), 1.94-1.71 (m, 2H), 1.38-1.18 (m, 2H). LCMS (4) Rt=1.34 min; m/z (ESI$^+$) 430 [MH$^+$].

Synthesis 173

Ethyl 4-(6-(5-cyanopyrazin-2-ylamino)-4-(piperidin-4-ylmethylamino)pyridin-3-yl)thiophene-2-carboxylate (Y-128)

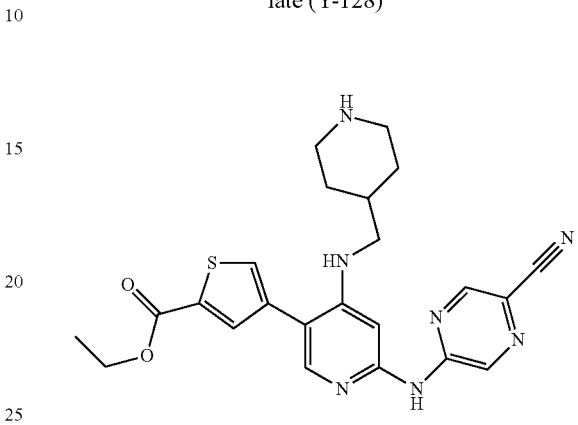

The title compound was prepared using methods analogous to those described in Synthesis 171, steps 171-A, 171-B, 171-C, 171-D and 171-E.

$^1$H NMR (500 MHz, MeOD) δ 8.91 (d, 1H, J=1.5 Hz), 8.57 (d, 1H, J=1.5 Hz), 7.86 (d, 1H, J=1.5 Hz), 7.83 (s, 1H), 7.77 (d, 1H, J=1.5 Hz), 7.17 (s, 1H), 4.38 (q, 2H, J=7.0 Hz), 3.38-3.33 (m, 2H), 3.19 (d, 2H, J=6.5 Hz), 2.90 (td, 2H, J=3.0, 13.0 Hz), 2.06-1.94 (m, 2H, 1H), 1.49-1.40 (m, 2H), 1.39 (t, 4H, J=7.0 Hz). LCMS (4) Rt=1.42 min; m/z (ESI$^+$) 464 (MH$^+$).

Synthesis 174

5-(5-(4-(2-hydroxyethoxy)phenyl)-4-(piperidin-4-ylmethylamino)pyridin-2-ylamino)pyrazine-2-carbonitrile (Y-129)

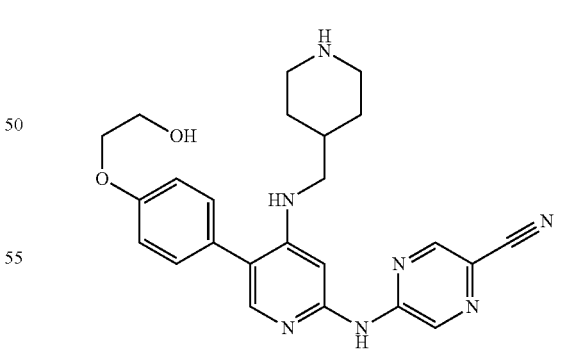

The title compound was prepared using methods analogous to those described in Synthesis 171, steps 171-A, 171-B, 171-C, 171-D and 171-E.

$^1$H NMR (500 MHz, MeOD) δ 8.86 (d, 1H, J=1.0 Hz), 8.55 (d, 1H, J=1.0 Hz), 7.69 (s, 1H), 7.30 (d, 2H, J=8.5 Hz), 7.09 (d, 2H, J=8.5 Hz), 7.07 (s, 1H), 4.11 (t, 2H, J=5.0 Hz), 3.91 (t, 2H, J=5.0 Hz), 3.11 (d, 4H, J=6.5 Hz), 2.62 (td, 2H, J=2.5, 12.5 Hz), 1.89-1.72 (m, 2H, 1H), 1.23 (qd, 2H, J=4.0, 12.5 Hz). LCMS (4) Rt=1.25 min; m/z (ESI⁺) 446 (MH⁺).

Synthesis 175

5-(5-(4-(methylsulfonyl)phenyl)-4-(piperidin-4-ylmethylamino)pyridin-2-ylamino)pyrazine-2-carbonitrile (Y-130)

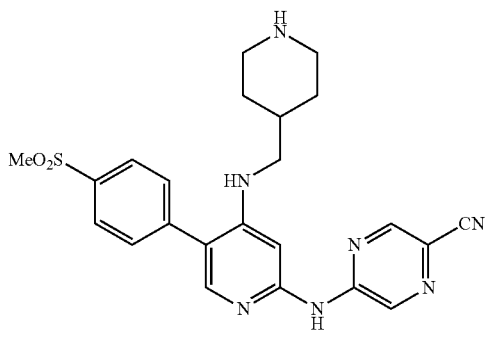 [SMILES: CS(=O)(=O)c1ccc(-c2cnc(Nc3cnc(C#N)cn3)cc2NCC2CCNCC2)cc1]

The title compound was prepared using methods analogous to those described in Synthesis 170, steps 170-A, 170-B, 170-C, 170-D and 170-E.

¹H NMR (DMSO-d₆, 500 MHz) δ 9.15 (s, 1H), 8.74 (s, 1H), 8.00 (d, 2H, J=8.3 Hz), 7.78 (s, 1H), 7.66 (d, 2H, J=8.3 Hz), 7.11 (s, 1H), 3.26 (s, 3H), 3.08 (d, 2H, J=12.2 Hz), 3.01-2.98 (m, 2H), 2.59 (t, 2H, J=11.3 Hz), 1.88-1.76 (m, 2H), 1.73-1.70 (m, 2H), 1.19-1.12 (m, 1H); LC-MS (4) Rt=1.13 min; m/z (ESI⁺) 464 [MH⁺].

Synthesis 176

(S)-5-(5-(4-methoxyphenyl)-4-(morpholin-2-ylmethylamino)pyridin-2-ylamino)pyrazine-2-carbonitrile (Y-131)

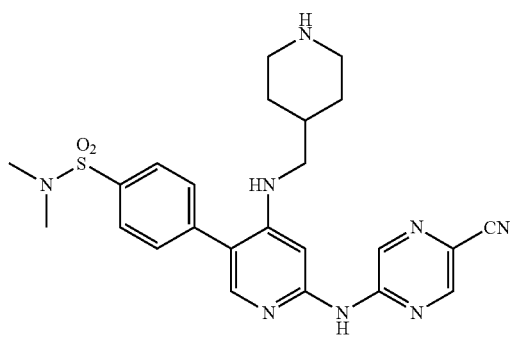 [SMILES: CN(C)S(=O)(=O)c1ccc(-c2cnc(Nc3cnc(C#N)cn3)cc2NCC2CCNCC2)cc1]

The title compound was prepared using methods analogous to those described in Synthesis 170, steps 170-A, 170-B, 170-C, 170-D and 170-E.

¹H NMR (MeOD-d₄, 500 MHz) δ 8.93 (s, 1H), 8.56 (s, 1H), 7.90 (d, 2H, J=8.3 Hz), 7.77 (s, 1H), 7.66 (d, 2H, J=8.3 Hz), 7.17 (s, 1H), 3.12-3.10 (m, 3H), 2.76 (s, 6H), 2.63 (t, 2H, J=11.5 Hz), 1.81 (2H, d, J=14.4 Hz), 1.30-1.24 (m, 2H), 0.91-0.89 (m, 2H). LCMS Rt=1.28 min; m/z (ESI⁺) 493 [MH⁺].

Synthesis 177

5-(5-(3-(Methylsulfonyl)phenyl)-4-(piperidin-4-ylmethylamino)pyridin-2-ylamino)pyrazine-2-carbonitrile (Y-132)

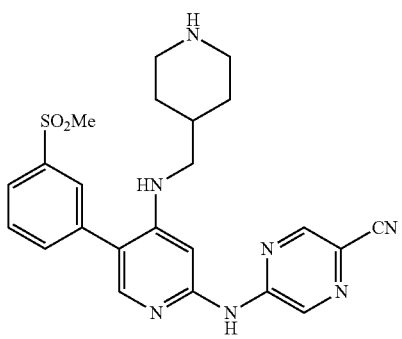 [SMILES: CS(=O)(=O)c1cccc(-c2cnc(Nc3cnc(C#N)cn3)cc2NCC2CCNCC2)c1]

The title compound was prepared using methods analogous to those described in Synthesis 170, steps 170-A, 170-B, 170-C, 170-D and 170-E.

¹H NMR (MeOD-d₄, 500 MHz) δ 8.94 (s, 1H), 8.55 (s, 1H), 8.09-7.93 (m, 2H), 7.77-7.76 (m, 3H), 7.14 (s, 1H), 3.19 (s, 3H), 3.12-3.09 (m, 4H), 2.63 (dt, 2H, J=12.6, 2.5 Hz), 1.93-1.75 (m, 3H), 1.25 (ddd, 2H, J=4.0, 12.6, 16.3 Hz). LCMS (4) Rt=1.13 min; m/z (ESI⁺) 464 [MH⁺].

Synthesis 178

5-(5-(4-(3-Methoxypropoxy)phenyl)-4-(piperidin-4-ylmethylamino)pyridin-2-ylamino)pyrazine-2-carbonitrile (Y-133)

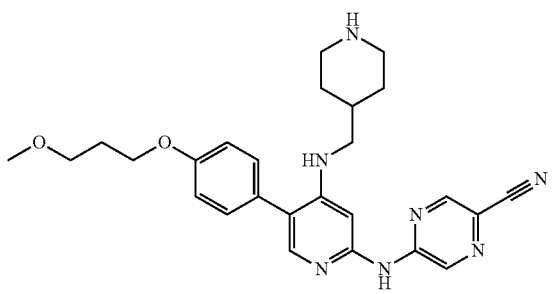 [SMILES: COCCCOc1ccc(-c2cnc(Nc3cnc(C#N)cn3)cc2NCC2CCNCC2)cc1]

The title compound was prepared using methods analogous to those described in Synthesis 171, steps 171-A, 171-B, 171-C, 171-D and 171-E.

¹H NMR (500 MHz, MeOD) δ 8.88 (s, 1H), 8.56 (s, 1H), 7.70 (s, 1H), 7.30 (d, 2H, J=8.2 Hz), 7.09-7.03 (m, 2H, 1H), 4.14-4.10 (m, 2H), 3.63-3.59 (m, 2H), 3.38 (s, 3H), 3.14-3.06

(s, 2H, 2H), 2.62 (t, 2H, J=12.5 Hz), 2.10-2.04 (m, 2H), 1.90-1.73 (m, 2H, 1H), 1.29-1.18 (m, 2H). LCMS (4) Rt=1.47 min; m/z (ESI⁺) 474 (MH⁺).

Synthesis 179

5-(5-(2,3-Dihydrobenzo[b][1,4]dioxin-6-yl)-4-(piperidin-4-ylmethylamino)pyridin-2-ylamino)pyrazine-2-carbonitrile (Y-134)

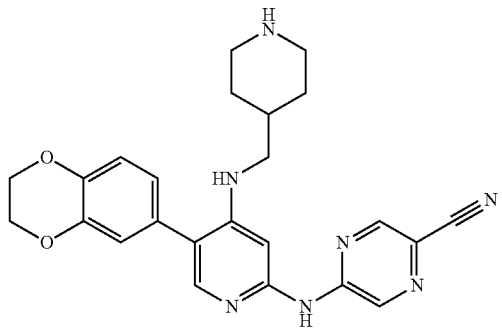 [SMILES: N#Cc1cnc(Nc2cc(NCC3CCNCC3)c(-c3ccc4c(c3)OCCO4)cn2)cn1]

The title compound was prepared using methods analogous to those described in Synthesis 171, steps 171-A, 171-B, 171-C, 171-D and 171-E.

¹H NMR (500 MHz, DMSO) δ 9.18 (s, 1H), 8.70 (s, 1H), 7.67 (s, 1H), 7.00-6.92 (m, 1H, 1H), 6.85-6.79 (m, 1H, 1H), 5.68 (t, 1H, J=6.0 Hz), 4.27 (s, 4H), 3.01-2.90 (m, 2H, 2H), 2.44 (t, 2H, J=11.0 Hz), 1.77-1.67 (m, 1H), 1.66-1.56 (m, 2H), 1.10-1.00 (m, 2H). LCMS (4) Rt=1.34 min; m/z (ESI⁺) 444 (MH⁺).

Synthesis 180

5-(5-(3-Fluorophenyl)-4-(piperidin-4-ylmethylamino)pyridin-2-ylamino)pyrazine-2-carbonitrile (Y-135)

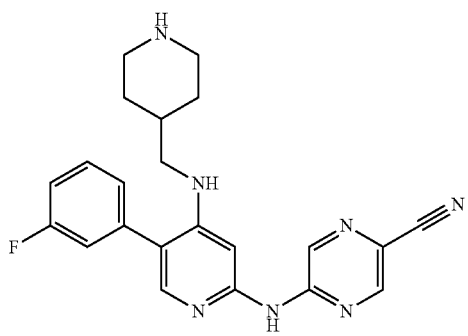 [SMILES: N#Cc1cnc(Nc2cc(NCC3CCNCC3)c(-c3cccc(F)c3)cn2)cn1]

The title compound was prepared using methods analogous to those described in Synthesis 170, steps 170-A, 170-B, 170-C, 170-D and 170-E.

¹H NMR (CDCl₃, 500 MHz) δ 8.78 (s, 1H), 8.39 (s, 1H), 7.75 (s, 1H), 7.40 (td, 1H, J=8.0, 6.0 Hz), 7.10 (ddd, 1H, J=7.5, 1.5, 1.0 Hz), 7.07-7.01 (m, 2H), 6.92 (s, 1H), 4.56 (t, 1H, J=5.5 Hz), 3.05 (ddd, 2H, J=12.0, 6.0, 3.0 Hz), 3.01 (t, 2H J=6.0 Hz), 2.53 (td, 2H, J=12.0, 2.5 Hz), 1.72-1.61 (m, 4H), 1.13 (ddd, 2H, J=24.5, 12.5, 4.0 Hz). LCMS (4) Rt=1.66 min; m/z (ESI⁺) 404 (MH⁺).

Synthesis 181-A tert-Butyl 4-fluoro-4-(hydroxymethyl)piperidine-1-carboxylate

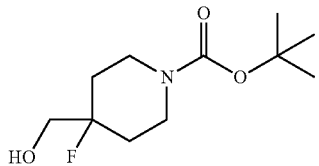 [SMILES: CC(C)(C)OC(=O)N1CCC(F)(CO)CC1]

Lithium aluminium hydride (1M in THF) (2.36 mL, 2.361 mmol) was added dropwise to a stirred solution of 1-tert-butyl 4-ethyl 4-fluoropiperidine-1,4-dicarboxylate (325 mg, 1.180 mmol) in THF (5.90 mL) cooled to 0° C. After 10 min ether (15 mL) was added and the reaction was quenched by sequential dropwise addition of water (0.1 mL), 10% NaOH (0.1 mL) and water (0.3 mL). The mixture was stirred at room temperature and the lithium salts that had precipitated were filtered off and washed with fresh ether. The organic filtrates were combined and solvent was removed in vacuo to leave a clear gum. The crude product was taken up in chloroform and loaded onto a 25+M Biotage silica column. Chromatography, eluting with a gradient of EtOAc in hexanes, gave tert-butyl 4-fluoro-4-(hydroxymethyl)piperidine-1-carboxylate (189 mg, 0.810 mmol, 69%) as a clear gum.

¹H NMR (500 MHz, CDCl₃) δ 3.92 (d, 2H, J=11.0 Hz), 3.59 (d, 2H, J=20.0 Hz), 3.09 (t, 2H, J=12.0 Hz), 2.17 (br s, 1H), 1.87 (m, 2H), 1.64-1.48 (m, 2H), 1.45 (s, 9H).

Synthesis 181-B tert-Butyl 4-fluoro-4-(tosyloxymethyl)piperidine-1-carboxylate

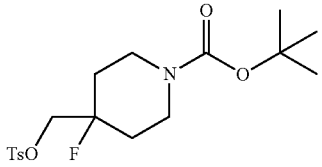 [SMILES: Cc1ccc(S(=O)(=O)OCC2(F)CCN(C(=O)OC(C)(C)C)CC2)cc1]

p-Toluenesulfonyl chloride (230 mg, 1.209 mmol) was added portionwise to tert-butyl 4-fluoro-4-(hydroxymethyl) piperidine-1-carboxylate (188 mg, 0.806 mmol), triethylamine (227 µL, 1.612 mmol), and DMAP (9.85 mg, 0.081 mmol) in dichloromethane (2015 µL) at 0° C. The solution was stirred at room temperature overnight and then partitioned between dichloromethane and water. The organic layer was washed with 0.2M HCl and then dried (MgSO$_4$) and concentrated. The residue was dissolved in dichloromethane and loaded onto a 25+M Biotage silica column. Chromatography, eluting with a gradient of EtOAc in hexanes, gave tert-butyl 4-fluoro-4-(tosyloxymethyl)piperidine-1-carboxylate (251 mg, 0.648 mmol, 80%) as a clear semi-solid.

$^1$H NMR (500 MHz, CDCl$_3$) δ 7.81 (d, 2H, J=8.0 Hz), 7.38 (d, 2H, J=8.0 Hz), 4.00 (d, 2H, J=19.0 Hz), 3.95 (br s, 2H), 3.04 (t, 2H, J=12.5 Hz), 2.47 (s, 3H), 1.82 (t, 2H, J=11.5 Hz), 1.63-1.47 (s, 2H), 1.46 (s, 9H). LCMS (4) Rt=2.68 min; m/z (ESI$^+$) 410 (M+Na$^+$).

Synthesis 181-C tert-Butyl 4-((2-chloro-5-iodopyridin-4-ylamino)methyl)-4-fluoropiperidine-1-carboxylate

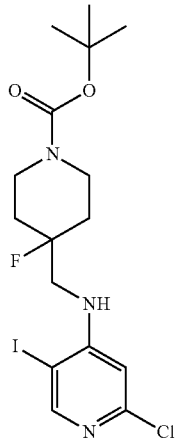 [SMILES: CC(C)(C)OC(=O)N1CCC(F)(CNc2cc(Cl)ncc2I)CC1]

Sodium hydride (60% by wt) (32.7 mg, 0.817 mmol) was added to a solution of 2-chloro-5-iodopyridin-4-amine (160 mg, 0.629 mmol) in DMF (3930 µL) at room temperature and the mixture was stirred for 10 min. The temperature was raised to 80° C. and tert-butyl 4-fluoro-4-(tosyloxymethyl)piperidine-1-carboxylate (244 mg, 0.629 mmol) in DMF (1 mL) was added. The reaction mixture was stirred at 80° C. for 2 hr before further NaH (1.3 eq.) was added after first cooling the reaction to room temperature again. The reaction mixture was heated at 120° C. for 10 hr. After cooling, the solution was partitioned between EtOAc (150 mL) and 1M aqueous NaHCO$_3$. The organic layer was washed with 1M NaHCO$_3$ aq., sat. NaHCO$_3$ and brine, then dried (MgSO$_4$) and concentrated. The residue was dissolved in dichloromethane/hexane and loaded onto a 25+M Biotage silica column. Chromatography, eluting with 1% MeOH in dichloromethane gave partial purification. Further purification by preparative thin layer chromatography, eluting with 16% EtOAc in dichloromethane, gave tert-butyl 4-((2-chloro-5-iodopyridin-4-ylamino)methyl)-4-fluoropiperidine-1-carboxylate (39 mg, 0.083 mmol, 13%) as a colourless solid.

$^1$H NMR (500 MHz, CDCl$_3$) δ 8.32 (s, 1H), 6.48 (s, 1H), 5.05 (t, 1H, J=6.0 Hz), 4.02 (br s, 2H), 3.39 (dd, 2H, J=6.0, 19.5 Hz), 3.16-3.05 (m, 2H), 1.99-1.91 (m, 2H), 1.70-1.53 (m, 2H), 1.48 (s, 9H). LCMS (4) Rt=2.76 min; m/z (ESI$^+$) 470 (MH$^+$).

Synthesis 181-D tert-Butyl 4-((2-chloro-5-(4-methoxyphenyl)pyridin-4-ylamino)methyl)-4-fluoropiperidine-1-carboxylate

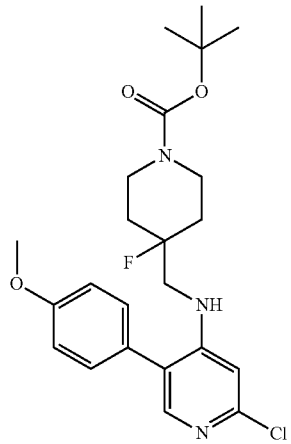 [SMILES: COc1ccc(-c2cnc(Cl)cc2NCC2(F)CCN(C(=O)OC(C)(C)C)CC2)cc1]

MeCN (0.72 mL) and 0.5M aqueous sodium carbonate (0.24 mL, 1.5 eq.) were added to a mixture of tert-butyl 4-((2-chloro-5-iodopyridin-4-ylamino)methyl)-4-fluoropiperidine-1-carboxylate (37 mg, 0.079 mmol), 4-methoxyphenylboronic acid (11.97 mg, 0.079 mmol), and tetrakis(triphenylphosphine) palladium(0) (4.55 mg, 3.94 µmol) in a 0.5 mL microwave reaction vial. The sealed vial was heated at 100° C. for 20 mins by microwave irradiation. The volatiles were removed in vacuo. The residue was dissolved in dichloromethane and loaded onto a 12+S Biotage silica column. Chromatography, eluting with a gradient of EtOAc in hexanes, gave tert-butyl 4-((2-chloro-5-(4-methoxyphenyl)pyridin-4-ylamino)methyl)-4-fluoropiperidine-1-carboxylate (17 mg, 0.038 mmol, 48%) as a colourless solid.

$^1$H NMR (500 MHz, CDCl$_3$) δ 7.85 (s, 1H), 7.27 (d, 2H, J=8.5 Hz), 7.03 (d, 2H, J=8.5 Hz), 6.57 (s, 1H), 4.76 (t, 1H, J=6.0 Hz), 4.01 (br s, 2H), 3.87 (s, 3H), 3.29 (dd, 2H, J=6.0, 20.0 Hz), 3.11-2.98 (m, 2H), 1.90-1.80 (m, 2H), 1.65-1.49 (m, 2H), 1.47 (s, 9H). LCMS (4) Rt=2.78 min; m/z (ESI⁺) 450 (MH⁺).

Synthesis 181-E 5-(4-((4-Fluoropiperidin-4-yl)methylamino)-5-(4-methoxyphenyl)pyridin-2-ylamino)pyrazine-2-carbonitrile (Y-136)

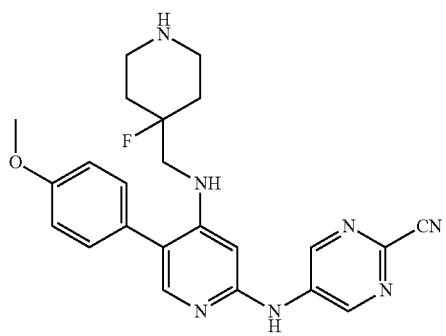 [SMILES: COc1ccc(-c2cnc(Nc3cnc(C#N)nc3)cc2NCC2(F)CCNCC2)cc1]

5-Aminopyrazine-2-carbonitrile (5.45 mg, 0.045 mmol), Xantphos (1.749 mg, 3.02 µmol), tris(dibenzylideneacetone)dipalladium(0) (1.384 mg, 1.511 µmol), and cesium carbonate (24.62 mg, 0.076 mmol) were added to tert-butyl 4-((2-chloro-5-(4-methoxyphenyl)pyridin-4-ylamino)methyl)-4-fluoropiperidine-1-carboxylate (17 mg, 0.038 mmol) in a 0.2 mL microwave reaction vial. The vial was sealed and an inert atmosphere was introduced before dry dioxane (291 µL) was added. Nitrogen was bubbled through the mixture for 5 min. The mixture was heated at 150° C. for 1 hr by microwave irradiation. After cooling the mixture was diluted with 20% dichloromethane in MeOH and loaded onto a preparative thin layer chromatography plate. Elution with 50% EtOAc in hexane gave tert-butyl 4-((2-(5-cyanopyrazin-2-ylamino)-5-(4-methoxyphenyl)pyridin-4-ylamino)methyl)-4-fluoropiperidine-1-carboxylate (1.5 mg, 2.81 µmol, 7% yield) as a light yellow powder. LCMS (4) Rt=2.35 min; m/z (ESI⁺) 534 (MH⁺). Trifluoroacetic acid (0.1 mL, 1.298 mmol) was added to tert-butyl 4-((2-(5-cyanopyrazin-2-ylamino)-5-(4-methoxyphenyl)pyridin-4-ylamino)methyl)-4-fluoropiperidine-1-carboxylate (1.5 mg, 2.81 µmol) dissolved in dichloromethane (0.5 mL) and the solution was stirred for 1 hr. The volatiles were removed in vacuo and the crude product was purified by ion exchange on Isolute SCX II acidic resin (1 g), followed by preparative thin layer chromatography, eluting with 10% MeOH/1% NH₃/89% dichloromethane, to give 5-(4-((4-fluoropiperidin-4-yl)methylamino)-5-(4-methoxyphenyl)pyridin-2-ylamino)pyrazine-2-carbonitrile (1 mg, 2.307 µmol, 82% yield) as a yellow powder.

¹H NMR (500 MHz, MeOD) δ 8.87 (s, 1H), 8.59 (s, 1H), 7.75 (s, 1H), 7.33 (d, 2H, J=8.5 Hz), 7.21 (s, 1H), 7.07 (d, 2H, J=8.5 Hz), 3.86 (s, 3H), 3.44 (d, 2H, J=19.5 Hz), 3.08-2.93 (m, 4H), 1.96-1.69 (m, 4H). LCMS (4) Rt=1.62 min; m/z (ESI⁺) 434 (MH⁺).

Synthesis 182

5-(5-(4-methoxyphenyl)-4-(2-(morpholin-2-yl)ethylamino)pyridin-2-ylamino)pyrazine-2-carbonitrile (Y-137)

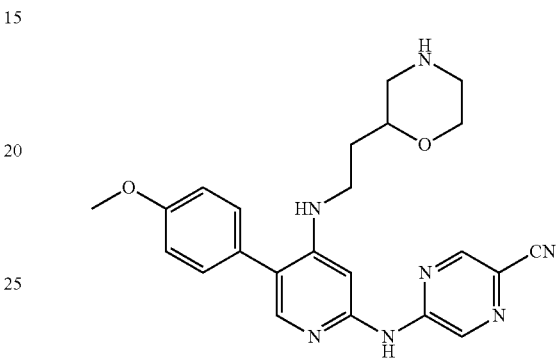

The title compound was prepared using methods analogous to those described in Synthesis 171, steps 171-A, 171-B, 171-C, 171-D and 171-E.

¹H NMR (MeOD-d₄, 500 MHz,) δ 8.85 (s, 1H), 8.54 (s, 1H), 7.69 (s, 1H), 7.30 (d, 2H, J=11.4 Hz), 7.05 (d, 2H, J=11.5 Hz), 6.99 (s, 1H), 3.85 (s, 3H), 3.73-3.70 (m, 1H), 3.61-3.51 (m, 2H), 3.35-3.26 (m, 2H), 2.99-2.79 (m, 2H), 2.63 (dd, 1H, J=10.8, 12.5 Hz), 1.82-1.67 (m, 2H). LCMS (4) Rt=1.64 min; m/z (ESI⁺) 432 [MH⁺].

Synthesis 183

5-(4-(2-(Morpholin-2-yl)ethylamino)-5-phenylpyridin-2-ylamino)pyrazine-2-carbonitrile (Y-138)

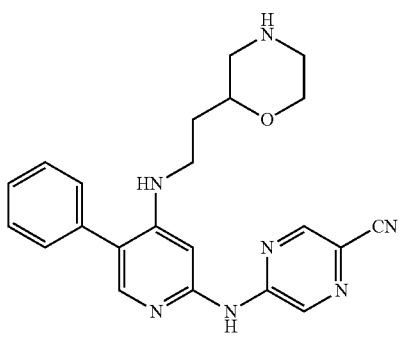 [SMILES: N#Cc1cnc(Nc2cc(NCCC3CNCCO3)c(-c3ccccc3)cn2)cn1]

The title compound was prepared using methods analogous to those described in Synthesis 171, steps 171-A, 171-B, 171-C, 171-D and 171-E.

¹H NMR (CDCl₃, 500 MHz) δ 8.88 (s, 1H), 8.54 (s, 1H), 7.71 (s, 1H), 7.50-7.47 (m, 3H), 7.00 (s, 1H), 3.62-3.52 (m, 2H), 3.48-3.43 (m, 1H), 3.29-3.23 (m, 2H), 2.85-2.70 (m,

3H), 2.53 (dd, 2H, J=12.5, 10.6 Hz), 1.82-1.62 (m, 2H). LCMS (4) Rt=1.35 min; m/z (ESI⁺) 402 [MH⁺].

Synthesis 184-A (E)-tert-Butyl 4-((2-chloro-5-(3-methoxyprop-1-enyl)pyridin-4-ylamino)methyl)piperidine-1-carboxylate

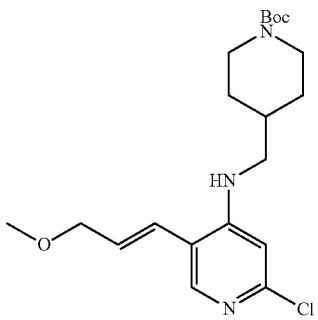 [SMILES: COC/C=C/c1cnc(Cl)cc1NCC1CCN(C(=O)OC(C)(C)C)CC1]

A solution of tert-butyl 4-((2-chloro-5-iodopyridin-4-ylamino)methyl)piperidine-1-carboxylate (Synthesis 170-B) (0.100 g, 0.22 mmol), (E)-2-(3-methoxyprop-1-enyl)-4,4,5,5-tetramethyl-1,3,2-dioxaborolane (0.044 g, 0.22 mmol), sodium carbonate (0.5 M, 0.66 mL) and tetrakis(triphenylphosphine) palladium(0) (0.013 g, 0.01 mmol) in acetonitrile (2.00 mL) was heated under microwave irradiation for 20 min at 100° C. The solvent was removed in vacuo and the crude product was purified by silica column chromatography, eluting with ethyl acetate and hexane (1/1). to give the title compound as a colourless oil (0.057 g, 65%).

¹H NMR (CDCl₃, 500 MHz) δ 7.90 (s, 1H), 6.42 (s, 1H), 6.42-6.38 (s, 1H), 6.11 (dt, 1H, J=5.3, 15.7 Hz), 4.64 (t, 1H, J=5.7 Hz), 4.13 (s, 2H), 4.06 (d, 2H, J=6.9 Hz), 3.40 (s, 3H), 3.05 (t, 2H, J=6.2 Hz), 2.69 (s, 2H), 1.78-1.71 (m, 3H), 1.44 (s, 9H), 1.18-1.12 (m, 4H). LCMS (4) Rt=2.59 min; m/z (ESI⁺) 396 [MH⁺].

Synthesis 184-B (E)-tert-butyl 4-((2-(5-cyanopyrazin-2-ylamino)-5-(3-methoxyprop-1-enyl)pyridin-4-ylamino)methyl)piperidine-1-carboxylate

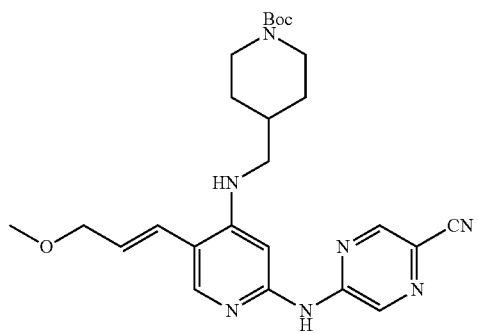 [SMILES: COC/C=C/c1cnc(Nc2cnc(C#N)cn2)cc1NCC1CCN(C(=O)OC(C)(C)C)CC1]

A solution of (E)-tert-butyl 4-((2-chloro-5-(3-methoxyprop-1-enyl)pyridin-4-ylamino)methyl)piperidine-1-carboxylate (0.040 g, 0.101 mmol), 2-amino-4-cyanopyrazine (0.018 g, 0.152 mmol), Xantphos (0.009 g, 0.016 mmol), cesium carbonate (0.065 g, 0.20 mmol), tris(dibenzylideneacetone)dipalladium chloroform complex (0.007 g, 0.008 mmol) in dioxane (0.7 mL) was stirred at room temperature under nitrogen for 10 min, then heated under microwave irradiation for 60 min at 150° C. The reaction mixture was purified by ion exchange on SCX-II acidic resin (1 g), eluting with methanol/DCM (1/1) then 2M ammonia-methanol. The basic fractions were combined and the solvent was removed in vacuo. The crude product was purified by preparative thin layer chromatography, eluting with ethyl acetate/hexane (1/1), to give the title compound as a yellow solid (0.020 g, 41%).

¹H NMR (CDCl₃, 500 MHz) δ 8.73 (s, 1H), 8.44 (s, 1H), 7.92 (s, 1H), 7.06 (s, 1H), 6.46 (d, 1H, J=15.7 Hz), 6.15 (dt, 1H, J=5.3, 15.6 Hz), 4.63 (t, 1H, J=5.4 Hz), 4.23-4.11 (m, 5H), 3.45 (s, 3H), 3.16 (t, 2H, J=6.1 Hz), 2.73 (t, 2H, J=11.5 Hz), 1.92-1.73 (m, 3H), 1.48 (s, 9H), 1.36-1.18 (m, 4H). LCMS (4) Rt=2.14 min; m/z (ESI⁺) 480 [MH⁺].

Synthesis 184-C (E)-5-(5-(3-Methoxyprop-1-enyl)-4-(piperidin-4-ylmethylamino)pyridin-2-ylamino)pyrazine-2-carbonitrile (Y-139)

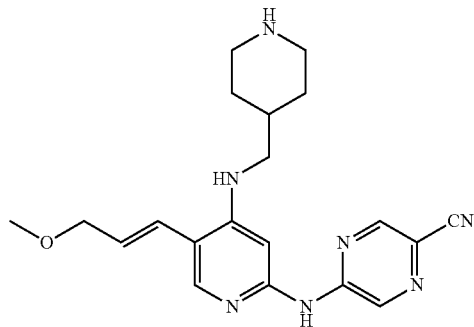 [SMILES: COC/C=C/c1cnc(Nc2cnc(C#N)cn2)cc1NCC1CCNCC1]

TFA (0.2 mL) was added at room temperature to a solution of (E)-tert-butyl 4-((2-(5-cyanopyrazin-2-ylamino)-5-(3-methoxyprop-1-enyl)pyridin-4-ylamino)methyl)piperidine-1-carboxylate (0.020 g, 0.041 mmol) in dichloromethane (2 mL). The reaction mixture was stirred for 20 min. Solvent was removed in vacuo and the mixture was purified by ion exchange on SCX-II acidic resin (500 mg) eluting with methanol, then 2M ammonia-methanol. The basic fractions were combined and the solvent was removed in vacuo. The crude product was purified by preparative thin layer chromatography, eluting with methanol/dichloromethane/NH₃ (9%/90%/1%) to give the title compound as a yellow solid (0.008 g, 51%).

¹H NMR (MeOD-d₄, 500 MHz) δ 8.83 (s, 1H), 8.53 (s, 1H), 7.93 (s, 1H), 7.01 (s, 1H), 6.75-6.55 (m, 1H), 6.14 (dt, 1H, J=6.0, 15.6 Hz), 4.11 (dd, 2H, J=1.2, 6.0 Hz), 3.41 (s,

3H), 3.19-3.09 (m, 4H), 2.66 (td, 2H, J=2.3, 12.4 Hz), 1.96-1.78 (m, 3H), 1.36-1.22 (m, 2H). LCMS (4) Rt=1.20 min; m/z (ESI⁺) 380 [MH⁺].

Synthesis 185

(E)-5-(5-(4-Hydroxybut-1-enyl)-4-(piperidin-4-ylmethylamino)pyridin-2-ylamino)pyrazine-2-carbonitrile (Y-140)

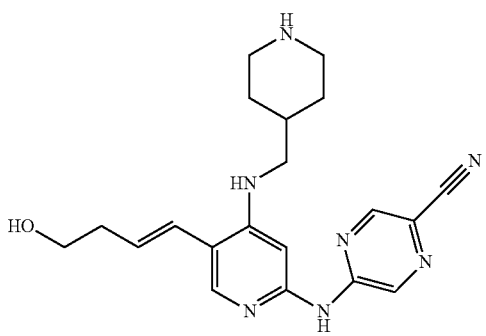 [SMILES: N#Cc1cnc(Nc2cc(NCC3CCNCC3)c(/C=C/CCO)cn2)cn1]

The title compound was prepared using methods analogous to those described in Synthesis 184, steps 184-A, 184-B and 184-C.
¹H NMR (500 MHz, MeOD) δ 8.80 (s, 1H), 8.55 (s, 1H), 7.90 (s, 1H), 7.01 (s, 1H), 6.44 (d, 1H, J=15.5 Hz), 6.08 (dt, 1H, J=6.5, 15.5 Hz), 3.71 (t, 2H, J=6.5 Hz), 3.27 (s, 2H), 3.18 (d, 2H, J=6.5 Hz), 2.81 (td, 2H, J=2.0, 12.5 Hz), 2.48 (td, 2H, J=1.0, 7.5 Hz), 2.02-1.91 (m, 2H, 1H), 1.44-1.34 (m, 2H). LCMS (4) Rt=1.14 min; m/z (ESI⁺) 380 (MH⁺).

Synthesis 186

5-(5-(3-methoxypropyl)-4-(piperidin-4-ylmethylamino)pyridin-2-ylamino)pyrazine-2-carbonitrile (Y-141)

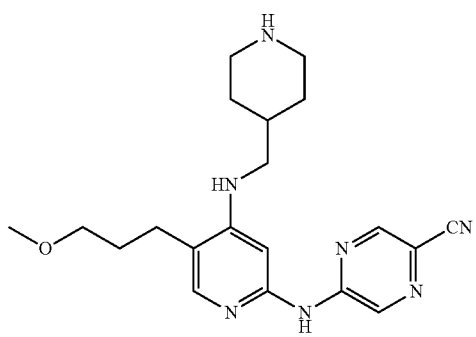 [SMILES: COCCCc1cnc(Nc2cnc(C#N)cn2)cc1NCC1CCNCC1]

A solution of (E)-tert-butyl 4-((2-(5-cyanopyrazin-2-ylamino)-5-(3-methoxyprop-1-enyl)pyridin-4-ylamino)methyl)piperidine-1-carboxylate (Synthesis 183-B) (0.035 g, 0.073 mmol), palladium on carbon (0.035 g) in methanol (2 mL) was stirred overnight under hydrogen (1 atm). The reaction mixture was filtered through celite and the solvent was removed in vacuo. The crude product was used without further purification. TFA (0.2 mL) was added to a solution of the crude material dissolved in dichloromethane (2 mL) at room temperature. The reaction mixture was stirred for 20 min. Solvent was removed in vacuo and the mixture was purified by ion exchange on SCX-II acidic resin (500 mg) eluting with methanol, then 2M ammonia-methanol. The basic fractions were combined and the solvent was removed in vacuo. The crude product was purified by preparative thin layer chromatography, eluting with methanol/dichloromethan/NH₃ (9%/90%/1%), to give the title compound as a yellow solid (0.020 g, 84%).
¹H NMR (MeOD-d₄, 500 MHz,) δ 8.74 (s, 1H), 8.50 (s, 1H), 7.68 (s, 1H), 6.91 (s, 1H), 3.46 (t, 1H, J=6.5 Hz), 3.38 (s, 3H), 3.16-3.14 (m, 4H), 2.69 (dd, 2H, J=10.1, 12.5 Hz), 2.56 (t, 2H, 7.5 Hz), 2.00-1.75 (m, 5H), 1.41-1.22 (m, 2H). LCMS (4) Rt=1.20 min; m/z (ESI⁺) 382 [MH⁺].

Synthesis 187

5-(5-(4-hydroxybutyl)-4-(piperidin-4-ylmethylamino)pyridin-2-ylamino)pyrazine-2-carbonitrile (Y-142)

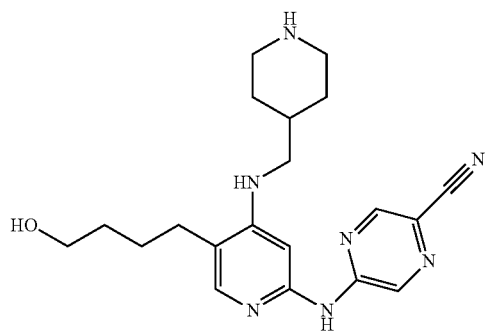 [SMILES: N#Cc1cnc(Nc2cc(NCC3CCNCC3)c(CCCCO)cn2)cn1]

The title compound was prepared using methods analogous to those described in Synthesis 184 and Synthesis 186.
¹H NMR (500 MHz, MeOD) δ 8.68 (s, 1H), 8.56 (s, 1H), 7.74 (s, 1H), 6.67 (s, 1H), 3.65 (t, 2H, J=6.0 Hz), 3.49-3.44 (s, 2H), 3.36-3.32 (m, 2H), 3.02 (td, 2H, J=3.0, 13.0), 2.60 (t, 2H, J=7.5 Hz), 2.19-2.02 (m, 2H, 1H), 1.74-1.62 (m, 2H+2H), 1.60-1.49 (m, 2H). LCMS (4) Rt=1.12 min; m/z (ESI⁺) 382 (MH⁺).

Synthesis 188

5-(5-(3-hydroxypropyl)-4-(piperidin-4-ylmethylamino)pyridin-2-ylamino)pyrazine-2-carbonitrile (Y-143)

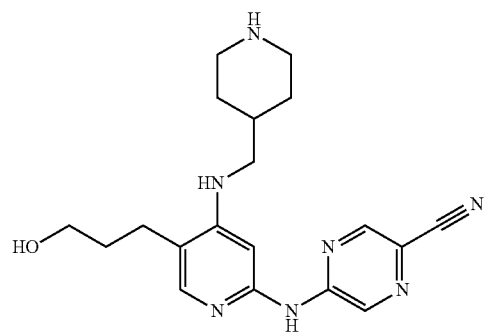 [SMILES: N#Cc1cnc(Nc2cc(NCC3CCNCC3)c(CCCO)cn2)cn1]

The title compound was prepared using methods analogous to those described in Synthesis 184 and Synthesis 186.

¹H NMR (500 MHz, MeOD) δ 8.73 (s, 1H), 8.51 (d, 1H, J=1.5 Hz), 7.70 (s, 1H), 6.92 (s, 1H), 3.63 (t, 2H, J=6.0 Hz), 3.18-3.11 (m, 4H), 2.66 (td, 2H, J=2.5, 12.5 Hz), 2.59-2.54 (m, 2H), 1.96-1.75 (m, 1H, 2H, 2H), 1.35-1.24 (m, 2H).

Synthesis 189-A tert-Butyl 4-((2-(5-cyanopyrazin-2-ylamino)-5-(3-hydroxy-3-methylbut-1-ynyl)pyridin-4-ylamino)methyl)piperidine-1-carboxylate

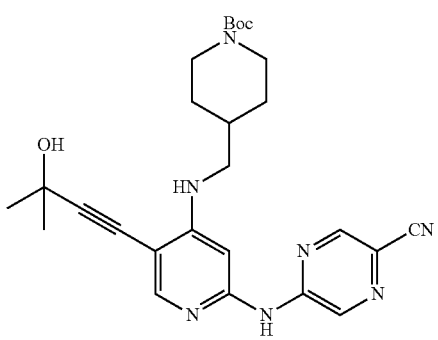 [SMILES: CC(C)(O)C#Cc1cnc(Nc2cnc(C#N)cn2)cc1NCC1CCN(C(=O)OC(C)(C)C)CC1]

A solution of tert-butyl 4-((2-chloro-5-iodopyridin-4-ylamino)methyl)piperidine-1-carboxylate (Synthesis 170-B) (0.100 g, 0.22 mmol), dichlorobis(triphenylphosphine)-palladium (II) (0.009 g, 0.01 mmol), trimethyl(2-methylbut-3-yn-2-yloxy)silane (0.048 mL, 0.24 mmol) and copper iodide (0.002 g, 0.01 mmol) was heated under microwave irradiation for 5 min at 120° C. The crude mixture was concentrated in vacuo and filtered through a pad of silica, eluting with hexane/ethyl acetate (8/2), to give the crude product which was used without further purification. The crude pyridine (0.085 g, 0.163 mmol), 2-amino-4-cyanopyrazine (0.023 g, 0.195 mmol), Xantphos (0.015 g, 0.026 mmol), cesium carbonate (0.106 g, 0.326 mmol), dichlorobis(triphenylphosphine)-palladium (II) (0.012 g, 0.013 mmol) in dioxane (1.2 mL) were stirred at room temperature under nitrogen for 10 min, then heated under microwave irradiation for 60 min at 150° C. The reaction mixture was purified by ion exchange on SCX-II acidic resin (2 g), eluting with methanol/dichloromethane (1/1), then 2M ammonia-methanol. The basic fractions were combined and solvent was removed in vacuo. The crude product was purified by preparative thin layer chromatography, eluting with methanol/dichloromethane (1/19), to give the title compound as a yellow solid (0.024 g, 27%).

¹H NMR (CDCl₃, 500 MHz) δ 8.62 (s, 1H), 8.44 (s, 1H), 8.00 (s, 1H), 7.17 (s, 1H), 5.19 (t, 1H, J=5.8 Hz) 4.19-4.16 (m, 2H), 3.17 (t, 2H, J=6.1 Hz), 2.72 (t, 2H, J=11.3 Hz), 1.84-1.75 (m, 3H), 1.66 (s, 6H), 1.47 (s, 9H), 1.27-1.21 (m, 2H), 0.90-0.84 (m, 1H). LCMS (4) Rt=2.17 min; m/z (ESI⁺) 492 [MH⁺].

Synthesis 189-B 5-(5-(3-Hydroxy-3-methylbut-1-ynyl)-4-(piperidin-4-ylmethylamino)pyridin-2-ylamino)pyrazine-2-carbonitrile (Y-144)

TFA (0.2 mL) was added at room temperature to a solution of tert-butyl 4-((2-(5-cyanopyrazin-2-ylamino)-5-(3-hydroxy-3-methylbut-1-ynyl)pyridin-4-ylamino)methyl)piperidine-1-carboxylate (0.020 g, 0.041 mmol) dissolved in dichloromethane (2 mL). The reaction mixture was stirred for 20 min. Solvent was removed in vacuo and the crude mixture was purified by ion exchange on SCX-II acidic resin (500 mg), eluting with methanol then 2M ammonia-methanol. The basic fractions were combined and solvent was removed in vacuo. The crude product was purified by preparative thin layer chromatography, eluting with methanol/dichloromethane (1/19), to give the title compound as a yellow solid (0.008 g, 50%).

¹H NMR (MeOD-d₄, 500 MHz) δ 8.89 (s, 1H), 8.55 (s, 1H), 7.93 (s, 1H), 7.06 (s, 1H), 3.36 (s, 1H), 3.18 (d, 2H, J=6.4 Hz), 3.10 (d, 2H, J=12.4 Hz), 2.62 (dt, 2H, J=12.4, 2.2 Hz), 1.87-1.89 (m, 2H), 1.60 (s, 6H), 1.32-1.26 (m, 2H). LC-MS (4) Rt=1.85 min; m/z (ESI⁺) 392 [MH⁺].

Synthesis 190

5-(5-(3-Hydroxyprop-1-ynyl)-4-(piperidin-4-ylmethylamino)pyridin-2-ylamino)pyrazine-2-carbonitrile (Y-145)

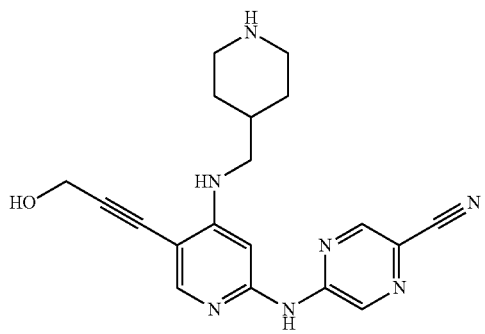 [SMILES: N#Cc1cnc(Nc2cc(NCC3CCNCC3)c(C#CCO)cn2)cn1]

The title compound was prepared using methods analogous to those described in Synthesis 189, steps 189-A and 189-B.

$^1$H NMR (500 MHz, DMSO) δ 9.09 (s, 1H), 8.73 (s, 1H), 7.96 (s, 1H), 7.02 (s, 1H), 6.23 (t, 1H, J=6.0 Hz), 5.28 (br s, 1H), 4.35 (s, 2H), 3.07 (t, 2H, J=6.5 Hz), 3.00-2.95 (m, 2H), 2.49-2.41 (m, 2H), 1.77-1.67 (m, 1H), 1.67-1.61 (m, 2H), 1.16-1.06 (m, 2H). LCMS (4) Rt=1.02 min; m/z (ESI$^+$) 364 (MH$^+$).

Synthesis 191-A (S)-2-Chloro-N-(2,3-dihydroxypropyl)acetamide

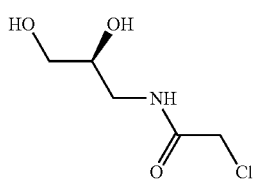

Triethylamine (4.0 ml, 28.9 mmol) was added to a solution of (S)-3-amino-1,2-propanediol (2.2 g, 24.1 mmol) in a mixture of CH$_3$CN/MeOH (80 mL/13 mL) at −10° C. under nitrogen. Chloroacetyl chloride (2.1 mL, 26.5 mmol) was then added dropwise at −10° C. over 30 min. The reaction mixture was allowed to reach room temperature and stirred for 16 h. The mixture was concentrated under vacuum and purified by flash column chromatography on silica gel, eluting with methanol/ethyl acetate (8/92), to give the title compound as a white solid (3.63 g, 90%).

$^1$H NMR (DMSO-d$_6$, 500 MHz,) δ 9.10 (s, 1H), 4.79 (d, 1H, J=5.0 Hz), 4.53 (t, 1H, J=5.6 Hz), 4.07 (s, 1H), 3.53-3.47 (m, 2H), 3.33-3.23 (m, 3H), 3.02-2.97 (m, 1H).

Synthesis 191-B (S)-6-(Hydroxymethyl)morpholin-3-one

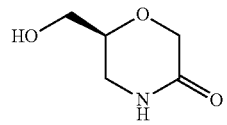

(S)-2-Chloro-N-(2,3-dihydroxypropyl)acetamide (4.77 g, 28.45 mmol) in tert-amyl alcohol (75 mL) was added over 2 h to a stirred solution of potassium tert-butoxide (3.59 g, 21.4 mmol) in tert-amyl alcohol (25 mL) at room temperature under nitrogen. After 1 hr, methanol (12 mL) and water (0.7 mL) were added and the reaction mixture was stirred for an additional 20 min. The mixture was concentrated under vacuum and purified by flash column chromatography on silica gel, eluting with methanol/ethyl acetate (2/8), to give the title compound as a white solid (1.26 g, 45%).

$^1$H NMR (DMSO-d$_6$, 500 MHz) δ 7.90 (s, 1H), 4.83 (t, 1H, J=5.7 Hz), 4.04 (AB, 2H, J=16.4 Hz), 3.66-3.62 (m, 1H), 3.50-3.38 (m, 2H), 3.19-3.15 (m, 1H), 3.09-3.05 (m, 1H).

Synthesis 191-C (S)-Morpholin-2-ylmethanol

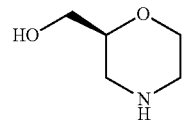

A solution of Red-Al (bis(2-methoxyethoxy)aluminum hydride) (65 wt. % in toluene, 0.46 mL, 1.52 mmol) was slowly added over 1 h to a suspension of (S)-6-(hydroxymethyl)morpholin-3-one (0.050 g, 0.38 mmol) in anhydrous THF (2 mL) at 0° C. under nitrogen. The reaction mixture was stirred for 16 h room temperature and then cooled to 0° C. before the addition of water (0.5 mL) followed by 4M potassium hydroxide (1 mL). The resulting precipitate was filtered through celite and rinsed with dichloromethane. The filtrate was concentrated under vacuum and purified by flash column chromatography on silica gel, eluting with methanol/chloroform (25/75), to give the title compound as a pale yellow oil (0.015 g, 33%).

$^1$H NMR (Acetone-d$_6$, 500 MHz,) δ 3.73 (dt, 1H, J=10.7, 2.5 Hz), 3.51-3.38 (m, 4H), 3.16 (s, 1H), 2.90-2.87 (m, 1H), 2.72-2.70 (m, 2H), 2.50-2.45 (m, 1H).

Synthesis 191-D (S)-tert-Butyl 2-(hydroxymethyl)morpholine-4-carboxylate

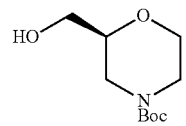 [SMILES: CC(C)(C)OC(=O)N1CCO[C@H](CO)C1]

Di-tert-butyl dicarbonate (0.606 g, 2.77 mmol was added to a solution of (S)-morpholin-2-ylmethanol (0.316 g, 2.69 mmol) and triethylamine (0.54 mL, 3.71 mmol) in dichloromethane (12 mL). The reaction mixture was stirred for 16 h at room temperature. The organic solution was washed with 2M HCl (12 mL), and the aqueous phase was extracted with dichloromethane (2×10 mL). The combined organic phases were dried (MgSO$_4$) and the solvent was removed in vacuo. The crude product was purified by flash column chromatography on silica gel, eluting with ethyl acetate/hexane (1/1), to give the title compound as a colourless oil (0.500 g, 85%).

¹H NMR (CDCl₃, 500 MHz) δ 3.91-3.86 (m, 3H), 3.68-3.65 (m, 1H), 3.59-3.49 (m, 3H), 2.95-2.93 (m, 1H), 2.77-2.75 (m, 2H), 2.10 (s, 1H), 1.46 (s, 9H).

Synthesis 191-E (S)-tert-Butyl 2-(tosyloxymethyl)morpholine-4-carboxylate

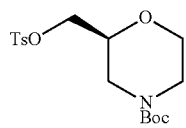 [SMILES: Cc1ccc(S(=O)(=O)OC[C@@H]2CN(C(=O)OC(C)(C)C)CCO2)cc1]

Toluene sulphonyl chloride (0.513 g, 2.69 mmol) was added to a solution of (S)-tert-butyl 2-(hydroxymethyl)morpholine-4-carboxylate (0.390 g, 1.79 mmol), triethylamine (0.50 mL, 3.59 mmol) and DMAP (cat.) in dichloromethane (11 mL). The reaction mixture was stirred for 24 h then diluted with dichloromethane (25 ml) and washed sequentially with water (25 mL) and 0.2M HCl (25 mL). The organic phase was dried (Na₂SO₄) and the solvent was removed in vacuo. The crude product was purified by flash column chromatography on silica gel, eluting with ethyl acetate/hexane (1/5), to give the title compound as a colourless solid (0.650 g, 97%).
¹H NMR (CDCl₃, 500 MHz,) δ 7.76 (d, 2H, J=8.5 Hz), 7.31 (d, 2H, J=8.5 Hz), 4.00-3.96 (m, 2H), 3.89-3.76 (m, 3H), 3.62-3.58 (m, 1H), 3.48-3.43 (m, 1H), 2.91-2.87 (m, 1H), 2.69-2.65 (m, 1H), 2.45 (s, 3H), 1.41 (s, 9H). LCMS (4) Rt=2.53 min; m/z (ESI⁺) 394 [M+Na⁺].

Synthesis 191-F (R)-tert-Butyl 2-((2-chloro-5-(4-methoxyphenyl)pyridin-4-ylamino)methyl)morpholine-4-carboxylate

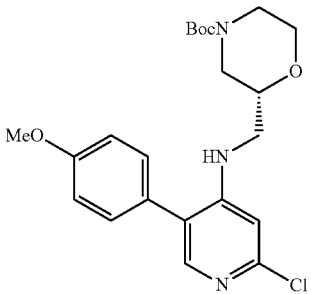 [SMILES: COc1ccc(-c2cnc(Cl)cc2NC[C@@H]2CN(C(=O)OC(C)(C)C)CCO2)cc1]

NaH (0.024 g, 0.569 mmol) was added to a solution of 2-chloro-5-iodopyridin-4-amine (0.121 g, 0.474 mmol) in DMF (2.8 mL) at room temperature and stirred for 10 min. The temperature was raised to 80° C. and (R)-tert-butyl 2-(tosyloxymethyl)morpholine-4-carboxylate (0.264 g, 0.711 mmol) in DMF (0.6 mL) was added. The reaction mixture was stirred for 2 h before further NaH (0.024 g, 0.569 mmol) was added at room temperature. The reaction mixture was heated at 80° C. for a further 1 h then cooled. Water was added and the mixture was partitioned between ethyl acetate (20 mL) and aq. NaHCO₃ (20 mL). The organic phase was washed with brine, dried (MgSO₄) and concentrated. The mixture was purified by flash column chromatography on silica gel, eluting with ethyl acetate and hexane (2/4), to give an inseparable mixture of starting material and product. LC-MS (4) Rt=2.66 min; m/z (ESI⁺) 397 [MH⁺]. A solution of the crude (R)-tert-butyl 2-((2-chloro-5-iodopyridin-4-ylamino)methyl)morpholine-4-carboxylate (0.040 g, 0.088 mmol), sodium carbonate (0.5 M, 0.26 mL), 4-methoxyphenyl boronic acid (0.013 g, 0.088 mmol) and tetrakis(triphenylphosphine) palladium(0) (0.011 g, 0.01 mmol) in acetonitrile (2 mL) was heated under microwave irradiation at 100° C. for 20 min. The reaction mixture was concentrated in vacuo. The mixture was purified by flash column chromatography on silica gel, eluting with ethyl acetate/hexane (1/1), to give the title compound as colorless oil (0.036 g, 94%).
¹H NMR (CDCl₃, 500 MHz) δ 7.83 (s, 1H), 7.27 (d, 1H, J=11.6 Hz), 7.01 (d, 1H, J=11.6 Hz), 6.53 (s, 1H), 4.85 (t, 1H, J=5.3 Hz), 3.89-3.82 (m, 5H), 3.56-3.50 (m, 1H), 3.48 (dd, 1H, J=2.4, 11.4 Hz), 3.27-3.11 (m, 2H), 2.96-2.83 (m, 1H), 2.75-2.61 (m, 1H), 2.40 (s, 1H), 1.46 (s, 9H). LCMS (4) Rt=2.66 min; m/z (ESI⁺) 434 [MH⁺].

Synthesis 191-G (R)-tert-Butyl 2-((2-(5-cyanopyrazin-2-ylamino)-5-(4-methoxyphenyl)pyridin-4-ylamino)methyl)morpholine-4-carboxylate

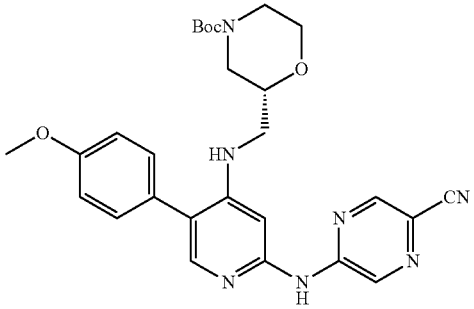 [SMILES: COc1ccc(-c2cnc(Nc3cnc(C#N)cn3)cc2NC[C@@H]2CN(C(=O)OC(C)(C)C)CCO2)cc1]

A solution of (R)-tert-butyl 2-((2-chloro-5-(4-methoxyphenyl)pyridin-4-ylamino)methyl)morpholine-4-carboxylate (0.036 g, 0.083 mmol), 2-amino-4-cyanopyrazine (0.014 g, 0.116 mmol), Xantphos (0.008 g, 0.013 mmol), cesium carbonate (0.054 g, 0.166 mmol), tris(dibenzylideneacetone)dipalladium chloroform complex (0.007 g, 0.008 mmol) in dioxane (0.7 mL) was stirred at room temperature under nitrogen for 10 min, then heated under microwave irradiation for 60 min at 150° C. The reaction mixture was purified by ion exchange on SCX-II acidic resin (1 g), eluting with methanol/dichloromethane (1/1) then 2M ammonia-methanol. The basic fractions were combined and solvent was removed in vacuo. The crude product was purified by preparative thin layer chromatography, eluting with ethyl acetate/hexane (1/1), to give the title compound as a yellow solid (0.014 g, 32%).
¹H NMR (CDCl₃, 500 MHz) δ 8.82 (s, 1H), 8.46 (s, 1H), 7.79 (s, 1H), 7.31 (d, 2H, J=8.7 Hz), 7.06 (s, 1H), 7.03 (d, 2H, J=8.7 Hz), 5.01 (t, 1H, J=5.3 Hz), 3.85 (s, 3H), 3.86-3.84 (m, 1H), 3.74-3.64 (m, 1H), 3.30-3.50 (m, 1H), 3.26-3.17 (m, 2H), 2.99 (d, 1H, J=13.7 Hz), 2.86 (2H, d, J=6.9 Hz), 2.73-2.63 (m, 1H). LCMS (4) Rt=2.17 min; m/z (ESI⁺) 518 [MH⁺].

Synthesis 191-H (S)-5-(5-(4-Methoxyphenyl)-4-(morpholin-2-ylmethylamino)pyridin-2-ylamino)pyrazine-2-carbonitrile (Y-146)

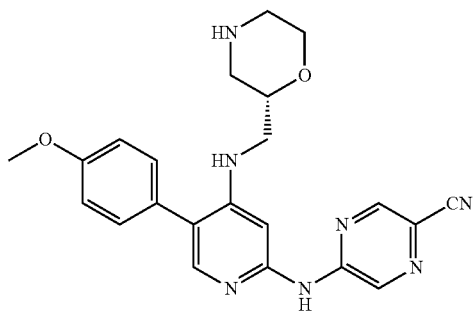 [SMILES: COc1ccc(-c2cnc(Nc3cnc(C#N)cn3)cc2NC[C@@H]2CNCCO2)cc1]

TFA (0.2 mL) was added to a solution of (R)-tert-butyl 2-((2-(5-cyanopyrazin-2-ylamino)-5-(4-methoxyphenyl)pyridin-4-ylamino)methyl)morpholine-4-carboxylate (0.014 g, 0.027 mmol) dissolved in dichloromethane (2 mL) at room temperature. The reaction mixture was stirred for 20 min. Solvent was removed in vacuo and the mixture was purified by ion exchange on SCX-II acidic resin (500 mg), eluting with methanol then 2M ammonia-methanol. The basic fractions were combined and solvent was removed in vacuo. The crude product was purified by preparative thin layer chromatography, eluting with methanol/dichloromethane (1/19), to give the title compound as a yellow solid (0.007 g, 62%).
¹H NMR (CDCl₃, 500 MHz) δ 8.78 (s, 1H), 8.46 (s, 1H), 7.79 (s, 1H), 7.31 (d, 2H, J=8.7 Hz), 7.06 (s, 1H), 7.03 (d, 2H, J=8.7 Hz), 5.01 (t, 1H, J=5.3 Hz), 3.85 (s, 3H), 3.86-3.84 (m, 1H), 3.74-3.64 (m, 1H), 3.30-3.50 (m, 1H), 3.26-3.17 (m, 2H), 2.99 (d, 1H, J=13.7 Hz), 2.86 (2H, d, J=6.9 Hz), 2.73-2.63 (m, 1H). LCMS Rt=1.33 min; m/z (ESI⁺) 418 [MH⁺].

Synthesis 192-A (R)-2-Chloro-N-(2,3-dihydroxypropyl)acetamide

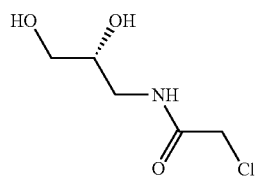

Triethylamine (1.83 mL, 13.2 mmol) was added to a solution of (R)-3-amino-1,2-propanediol (1.00 g, 11.0 mmol) in a mixture CH₃CN/MeOH (36 mL/16 mL) at −10° C. under nitrogen. Chloroacetyl chloride (0.98 ml, 12.0 mmol) was added dropwise at −10° C. over 30 min. The reaction mixture was allowed to reach room temperature and stirred for 16 h. The mixture was concentrated and purified by flash column chromatography on silica gel, eluting with methanol/ethyl acetate (8/92), to give the title compound as a white solid (1.43 g, 78%).

¹H NMR (Acetone-d₆, 500 MHz,) δ 7.59 (s, 1H), 4.12 (s, 2H), 4.08 (brs, 1H), 3.84 (s, 1H), 3.73 (q, 1H, J=5.4 Hz), 3.50 (q, 1H, J=5.4 Hz), 3.47-3.42 (m, 1H), 3.32-3.27 (m, 1H).

Synthesis 192-B (R)-6-(Hydroxymethyl)morpholin-3-one

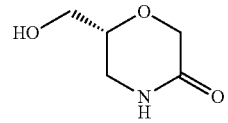

(R)-2-Chloro-N-(2,3-dihydroxypropyl)acetamide (1.31 g, 8.20 mmol) in tert-amyl alcohol (34 mL) was added dropwise over 2 h to a stirred solution of potassium tert-butoxide (2.30 g, 20.6 mmol) in tert-amyl alcohol (16 mL) at room temperature under nitrogen. After 1 hr, MeOH (8 mL) and water (0.5 mL) were added and the reaction mixture was stirred for an additional 20 min. The mixture was concentrated under vacuum and purified by flash column chromatography on silica gel, eluting with methanol/ethyl acetate (2/8) to give the title compound as a white solid (0.59 g, 54%).
¹H NMR (DMSO-d₆, 500 MHz) δ 7.90 (s, 1H), 4.83 (t, 1H, J=5.7 Hz), 4.04 (AB, 2H, J=16.4 Hz), 3.66-3.62 (m, 1H), 3.50-3.38 (m, 2H), 3.19-3.15 (m, 1H), 3.09-3.05 (m, 1H).

Synthesis 192-C (R)-Morpholin-2-ylmethanol

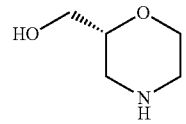

A solution of Red-Al (bis(2-methoxyethoxy)aluminum hydride) (65 wt. % in toluene, 0.93 mL, 3.04 mmol) was slowly added over 1 h to a suspension of (S)-6-(hydroxymethyl)morpholin-3-one (0.100 g, 0.76 mmol) in anhydrous THF (4 mL) at 0° C. under nitrogen. The reaction mixture was stirred for 16 h at room temperature, then cooled to 0° C. before the addition of water (1 mL) followed by 4M potassium hydroxide (2 mL). The resulting precipitate was filtered through celite and rinsed with dichloromethane. The organic filtrate was concentrated under vacuum and purified by flash column chromatography on silica gel, eluting with methanol/chloroform (25/75), to give the title compound as a pale yellow oil (0.040 g, 44%).

¹H NMR (Acetone-d₆, 500 MHz,) δ 3.73 (dt, 1H, J=10.7, 2.5 Hz), 3.51-3.38 (m, 4H), 3.16 (s, 1H), 2.90-2.87 (m, 1H), 2.72-2.70 (m, 2H), 2.50-2.45 (m, 1H).

Synthesis 192-D (R)-tert-Butyl 2-(hydroxymethyl)morpholine-4-carboxylate

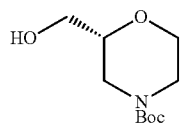 [SMILES: CC(C)(C)OC(=O)N1CCO[C@@H](CO)C1]

Di-tert-butyl dicarbonate (0.558 g, 2.55 mmol) was added to a solution of (R)-morpholin-2-ylmethanol (0.291 g, 2.48 mmol) and triethylamine (0.47 mL, 3.42 mmol) in dichloromethane (11 mL). The reaction mixture was stirred for 16 h at room temperature. The organic solution was washed with 2M HCl (10 mL), and the aqueous phase was extracted with dichloromethane (2×10 mL). The combined organic extracts were dried (MgSO₄) and solvent was removed in vacuo. The crude product was purified by flash column chromatography on silica gel, eluting with ethyl acetate/hexane (1/1). to give the title compound as a colourless oil (0.360 g, 64%).

¹H NMR (CDCl₃, 500 MHz) δ 3.91-3.86 (m, 3H), 3.68-3.65 (m, 1H), 3.59-3.49 (m, 3H), 2.95-2.93 (m, 1H), 2.77-2.75 (m, 2H), 2.10 (s, 1H), 1.46 (s, 9H).

Synthesis 192-E (R)-tert-Butyl 2-(tosyloxymethyl)morpholine-4-carboxylate

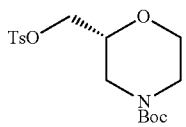

Toluene sulphonyl chloride (0.473, 2.48 mmol) was added to a solution of (R)-tert-butyl 2-(hydroxymethyl)morpholine-4-carboxylate (0.360, 1.65 mmol), triethylamine (0.45 mL, 3.30 mmol) and DMAP (cat.) in dichloromethane (10 mL). The reaction mixture was stirred for 24 h then diluted with dichloromethane (20 mL) and washed sequentially with water (20 mL) and 0.2M HCl (20 mL). The organic phase was dried (Na₂SO₄) and solvent was removed in vacuo. The crude product was purified by flash column chromatography on silica gel, eluting with ethyl acetate/hexane (1/5), to give the title compound as a colourless solid (0.542 g, 88%).

¹H NMR (CDCl₃, 500 MHz,) δ 7.81 (d, 2H, J=8.5 Hz), 7.35 (d, 2H, J=8.5 Hz), 4.06-3.89 (m, 2H), 3.89-3.81 (m, 3H), 3.62-3.58 (m, 1H), 3.48-3.43 (m, 1H), 2.91-2.87 (m, 1H), 2.69-2.65 (m, 1H), 2.45 (s, 3H), 1.46 (s, 9H). LC-MS (4) Rt=2.53 min; m/z (ESI⁺) 394 [M+Na⁺].

Synthesis 192-F (S)-tert-Butyl 2-((2-chloro-5-(4-methoxyphenyl)pyridin-4-ylamino)methyl)morpholine-4-carboxylate

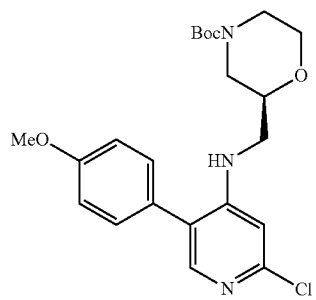 [SMILES: COc1ccc(-c2cnc(Cl)cc2NC[C@H]2CN(C(=O)OC(C)(C)C)CCO2)cc1]

NaH (0.024 g, 0.569 mmol) was added to a solution of 2-chloro-5-iodopyridin-4-amine (0.121 g, 0.474 mmol) in DMF (2.8 mL) at room temperature and stirred for 10 min. The temperature was raised to 80° C. and (S)-tert-butyl 2-(tosyloxymethyl)morpholine-4-carboxylate (0.264 g, 0.711 mmol) in DMF (0.6 mL) was added. The reaction mixture was stirred for 2 h, then further NaH (0.024 g, 0.569 mmol) was added at room temperature. The reaction mixture was further heated at 80° C. for 1 h then cooled. Water was added and the mixture was partitioned between ethyl acetate (20 mL) and aq. NaHCO₃ (20 mL). The organic phase was washed with brine, dried (MgSO₄) and concentrated. The mixture was purified by flash column chromatography on silica gel, eluting with ethyl acetate/hexane (2/4), to give an inseparable mixture of starting material and product. LCMS (4) Rt=2.66 min; m/z (ESI⁺) 397 [MH⁺]. A solution of the crude (R)-tert-butyl 2-((2-chloro-5-iodopyridin-4-ylamino)methyl)morpholine-4-carboxylate (0.040 g, 0.088 mmol), sodium carbonate (0.5 M, 0.26 mL), 4-methoxyphenyl boronic acid (0.013 g, 0.088 mmol) and tetrakis(triphenylphosphine) palladium(0) (0.011 g, 0.01 mmol) in acetonitrile (2 mL) was heated under microwave irradiation at 100° C. for 20 min. The reaction mixture was concentrated. The crude product was purified by flash column chromatography on silica gel, eluting with ethyl acetate/hexane (1/1), to give the title compound as a colorless oil (0.036 g, 94%).

¹H NMR (CDCl₃, 500 MHz) δ 7.82 (s, 1H), 7.27 (d, 1H, J=11.6 Hz), 7.01 (d, 1H, J=11.6 Hz), 6.53 (s, 1H), 4.86 (t, 1H, J=5.3 Hz), 3.89-3.82 (m, 5H), 3.56-3.50 (m, 1H), 3.48 (dd, 1H, J=2.4, 11.4 Hz), 3.27-3.11 (m, 2H), 2.96-2.83 (m, 1H), 2.75-2.61 (m, 1H), 2.40 (s, 1H), 1.46 (s, 9H). LCMS (4) Rt=2.66 min; m/z (ESI⁺) 434 [MH⁺].

Synthesis 192-G (S)-tert-Butyl 2-((2-(5-cyanopyrazin-2-ylamino)-5-(4-methoxyphenyl)pyridin-4-ylamino)methyl)morpholine-4-carboxylate

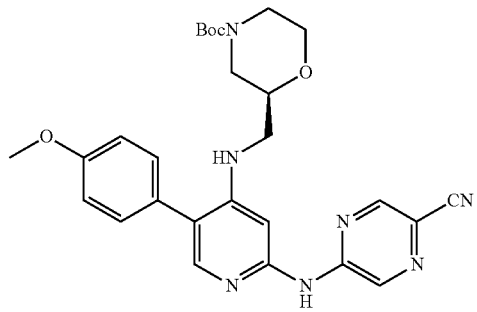 [SMILES: COc1ccc(-c2cnc(Nc3cnc(C#N)cn3)cc2NC[C@H]2CN(C(=O)OC(C)(C)C)CCO2)cc1]

A solution of (S)-tert-butyl 2-((2-chloro-5-(4-methoxyphenyl)pyridin-4-ylamino)methyl)morpholine-4-carboxylate (0.036 g, 0.083 mmol), 2-amino-4-cyanopyrazine (0.014 g, 0.116 mmol), Xantphos (0.008 g, 0.013 mmol), cesium carbonate (0.054 g, 0.166 mmol), tris(dibenzylideneacetone)dipalladium chloroform complex (0.007 g, 0.008 mmol) in dioxane (0.7 mL) was stirred at room temperature under nitrogen for 10 min then heated under microwave irradiation for 60 min at 150° C. The reaction mixture was purified by ion exchange on SCX-II acidic resin (1 g), eluting with methanol/dichloromethane (1/1), then 2M ammonia-methanol. The basic fractions were combined and the solvent was removed in vacuo. The crude product was purified by preparative thin layer chromatography, eluting with ethyl acetate/hexane (1/1), to give the title compound as a yellow solid (0.014 g, 32%).

¹H NMR (CDCl₃, 500 MHz) δ 8.81 (s, 1H), 8.51 (s, 1H), 7.79 (s, 1H), 7.30 (d, 2H, J=8.5 Hz), 7.06 (s, 1H), 7.02 (d, 2H, J=8.5 Hz), 4.95 (t, 1H, J=5.2 Hz), 3.87 (s, 3H), 3.88-3.84 (m, 1H), 3.65-3.60 (m, 1H), 3.52-3.48 (m, 2H), 3.33-3.20 (m, 2H), 2.97-2.90 (m, 1H), 2.76-2.67 (m, 1H), 1.47 (s, 9H). LCMS (4) Rt=2.17 min; m/z (ESI⁺) 518 [MH⁺].

Synthesis 192-H (R)-5-(5-(4-Methoxyphenyl)-4-(morpholin-2-ylmethylamino)pyridin-2-ylamino)pyrazine-2-carbonitrile (Y-147)

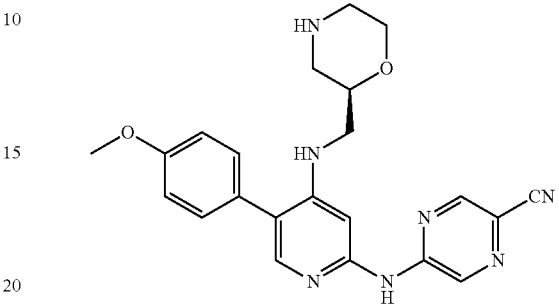

TFA (0.1 mL) was added to a solution of tert-butyl (S)-tert-butyl 2-((2-(5-cyanopyrazin-2-ylamino)-5-(4-methoxyphenyl)pyridin-4-ylamino)methyl)morpholine-4-carboxylate (0.006 g, 0.012 mmol) dissolved in dichloromethane (1 mL) at room temperature. The reaction mixture was stirred for 20 min. Solvent was removed in vacuo and the mixture was purified by ion exchange on SCX-II acidic resin (500 mg), eluting with methanol then 2M ammonia-methanol. The basic fractions were combined and solvent was removed in vacuo. The crude product was purified by preparative thin layer chromatography, eluting with methanol/dichloromethane (1/19), to give the title compound as a yellow solid (0.003 g, 62%).

¹H NMR (CDCl₃, 500 MHz) δ 8.82 (s, 1H), 8.46 (s, 1H), 7.79 (s, 1H), 7.31 (d, 2H, J=8.7 Hz), 7.06 (s, 1H), 7.03 (d, 2H, J=8.7 Hz), 5.11 (t, 1H, J=5.3 Hz), 3.85 (s, 3H), 3.86-3.84 (m, 1H), 3.74-3.71 (m, 1H), 3.65-3.62 (m, 1H), 3.30-3.24 (m, 2H), 2.99 (d, 1H, J=13.7 Hz), 2.86 (d, 2H, J=6.9 Hz), 2.73-2.66 (m, 1H). LCMS Rt=1.33 min; m/z (ESI⁺) 418 [MH⁺].

Synthesis 193

(S)-5-(5-(4-(Methoxymethyl)phenyl)-4-(morpholin-2-ylmethylamino)pyridin-2-ylamino)pyrazine-2-carbonitrile (Y-148)

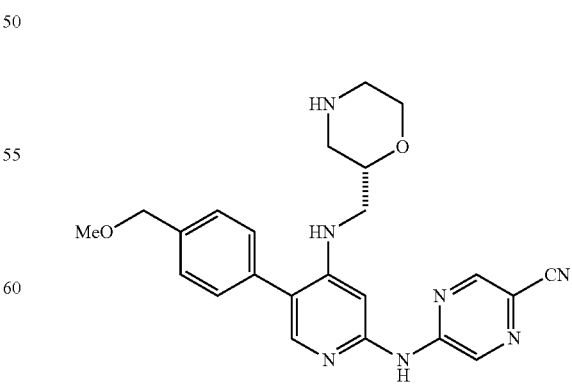

Prepared using methods analogous to those in Synthesis 191, steps 191-F, 191-G and 191-H.

¹H NMR (MeOD-d₄, 500 MHz) δ 8.92 (d, 1H, J=0.9 Hz), 8.57 (d, 1H, J=1.4 Hz), 7.77 (s, 1H), 7.48 (d, 2H, J=8.2 Hz), 7.40 (d, 2H, J=8.2 Hz), 7.10 (s, 1H), 4.53 (s, 2H), 3.84 (d, 1H, J=11.3 Hz), 3.73-3.67 (m, 1H), 3.60-3.55 (m, 1H), 3.43 (s, 3H), 3.30-3.27 (m, 1H), 3.20 (dd, 1H, J=13.6, 6.9 Hz), 2.93 (dd, 1H, J=12.5, 2.3 Hz), 2.77 (dd, 2H, J=8.3, 2.7 Hz), 2.58 (dd, 1H, J=12.5, 10.4 Hz). LCMS (4) Rt=1.32 min; m/z (ESI⁺) 432 (MH⁺).

Synthesis 194

(S)-5-(5-(4-(2-Methoxyethoxy)phenyl)-4-(morpholin-2-ylmethylamino)pyridin-2-ylamino)pyrazine-2-carbonitrile (Y-149)

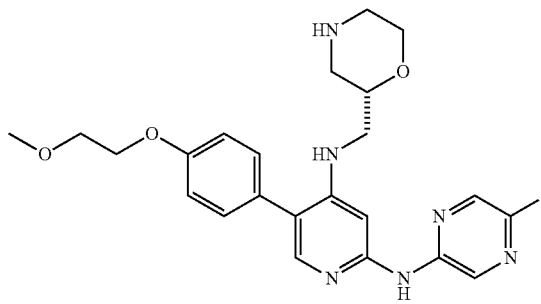

Prepared using methods analogous to those in Synthesis 191, steps 191-F, 191-G and 191-H.

¹H NMR (MeOD-d₄, 500 MHz) δ 8.87 (s, 1H), 8.58 (d, 1H, J=1.1 Hz), 7.74 (s, 1H), 7.32 (d, 2H, J=8.7 Hz), 7.11 (s, 1H), 7.08 (d, 2H, J=8.7 Hz), 4.19-4.17 (m, 2H), 3.94 (dd, 1H, J=12.1, 2.5 Hz), 3.80-3.78 (m, 3H), 3.69-3.63 (m, 1H), 3.46 (s, 3H), 3.36-3.33 (m, 1H), 3.26 (dd, 1H, J=13.9, 6.7 Hz), 3.09 (d, 1H, J=11.2 Hz), 2.97-2.88 (m, 2H), 2.73 (dd, 1H, J=12.5, 10.8 Hz). LCMS (4) Rt=1.47 min; m/z (ESI⁺) 462 (MH⁺).

Synthesis 195

(S)-5-(5-(3-Fluorophenyl)-4-(morpholin-2-ylmethylamino)pyridin-2-ylamino)pyrazine-2-carbonitrile (Y-150)

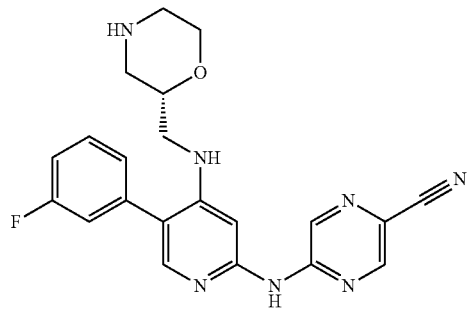 [SMILES: N#Cc1cnc(Nc2cc(NC[C@@H]3CNCCO3)c(-c3cccc(F)c3)cn2)cn1]

Prepared using methods analogous to those in Synthesis 191, steps 191-F, 191-G and 191-H.

¹H NMR (CDCl₃, 500 MHz) δ 8.65 (s, 1H), 8.40 (s, 1H), 7.77 (s, 1H), 7.38 (dd, 1H, J=14.0, 8.0 Hz), 7.12-7.09 (m, 2H), 7.05-7.01 (m, 2H), 4.93 (t, 1H, J=5.0 Hz), 3.78 (dt, 1H, J=11.0, 2.0 Hz), 3.67-3.62 (m, 1H), 3.52 (dt, 1H, J=11.0, 7.0 Hz), 3.22 (ddd, 1H, J=13.0, 6.0, 4.0 Hz), 3.12 (ddd, 1H, J=13.0, 7.5, 5.0 Hz), 2.89 (dd, 1H, J=12.0, 2.0 Hz), 2.77 (dd, 2H, J=7.5, 2.5 Hz), 2.60 (dd, 1H, J=12.0, 10.0 Hz). LCMS (4) Rt=1.36 min; m/z (ESI⁺) 406 (MH⁺).

Synthesis 196

(S)-5-(5-(4-Fluorophenyl)-4-(morpholin-2-ylmethylamino)pyridin-2-ylamino)pyrazine-2-carbonitrile (Y-151)

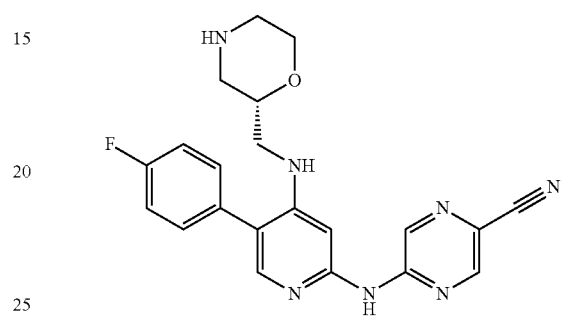

Prepared using methods analogous to those in Synthesis 191, steps 191-F, 191-G and 191-H.

¹H NMR (CDCl₃, 500 MHz) δ 8.72 (s, 1H), 8.39 (s, 1H), 7.73 (s, 1H), 7.31-7.27 (m, 2H), 7.13-7.09 (m, 2H), 6.98 (s, 1H), 4.81 (t, 1H, J=5.3), 3.77 (dt, 1H, J=11.5, 2.5, Hz), 3.65-3.61 (m, 1H), 3.52 (ddd, 1H, J, 14.0, 6.5, 5.0 Hz), 3.20 (ddd, 1H, J=13.0, 6.0, 4.0 Hz), 3.10 (ddd, 1H, J=13.0, 7.5, 5.0 Hz), 2.89 (dd, 1H, J=12.0, 2.5 Hz), 2.78-2.76 (m, 2H), 2.59 (dd, 1H, J=12.0, 10.0 Hz). LCMS (4) Rt=1.25 min; m/z (ESI⁺) 406 (MH⁺).

Synthesis 197

(S)-5-(5-(1-Methyl-1H-pyrazol-4-yl)-4-(morpholin-2-ylmethylamino)pyridin-2-ylamino)pyrazine-2-carbonitrile (Y-152)

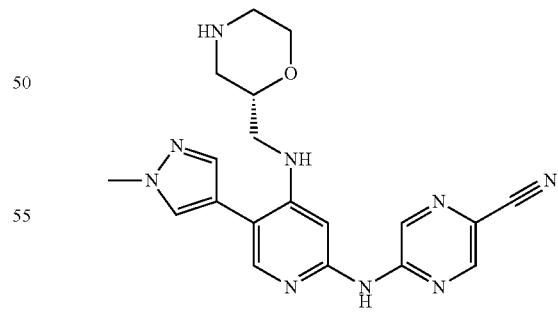

Prepared using methods analogous to those in Synthesis 191, steps 191-F, 191-G and 191-H.

¹H NMR (CDCl₃, 500 MHz) δ 8.81 (s, 1H), 8.38 (s, 1H), 7.76 (s, 1H), 7.54 (s, 1H), 7.41 (s, 1H), 6.80 (s, 1H), 5.00 (t, 1H, J=5.0 Hz), 3.92 (s, 3H), 3.81 (dt, 1H, J=11.5, 2.5 Hz), 3.67-3.62 (m, 1H), 3.54 (ddd, 1H, J=11.5, 10.0, 4.0 Hz), 3.20 (ddd, 1H, J=13.0, 6.5, 4.0 Hz), 3.11 (ddd, 1H, J=13.0, 7.5, 4.5

Hz), 2.89 (dd, 1H, J=12.0, 2.5 Hz), 2.82-2.77 (m, 1H), 2.62 (dd, 1H, J=12.0, 10.0 Hz). LCMS (4) Rt=1.31 min; m/z (ESI⁺) 392 (MH⁺).

Synthesis 198

(S)-5-(5-(3-Hydroxy-3-methylbut-1-ynyl)-4-(morpholin-2-ylmethylamino)pyridin-2-ylamino)pyrazine-2-carbonitrile (Y-153)

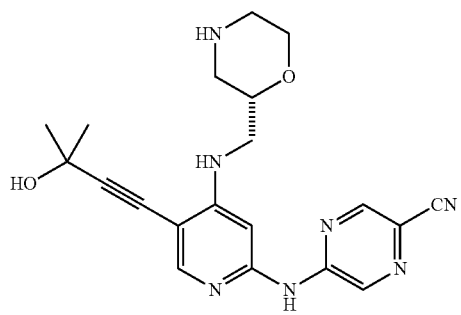 [SMILES: CC(C)(O)C#Cc1cnc(Nc2cnc(C#N)cn2)cc1NC[C@@H]1CNCCO1]

Prepared using methods analogous to those in Synthesis 190, step 190-E, and Synthesis 189, steps 189-A and 189-B.

¹H NMR (MeOD-d₄, 500 MHz) δ 8.92 (d, 1H, J=1.3 Hz), 8.58 (d, 1H, J=1.4 Hz), 7.96 (s, 1H), 7.06 (s, 1H), 3.92 (d, 1H, J=11 Hz), 3.78-3.73 (m, 1H), 3.68-3.61 (m, 1H), 3.37 (dd, 1H, J=13.5, 4.4 Hz), 3.26 (dd, 1H, J=13.5, 7 Hz), 2.97 (dd, 1H, J=12.4, 2.1 Hz), 2.88-2.81 (m, 2H), 2.66 (d, 1H, J=12.5, 10.5 Hz), 1.61 (s, 6H). LCMS (4) Rt=1.38 min; m/z (ESI⁺) 394 (MH⁺).

Synthesis 199

(S)-5-(5-(3-Methoxyprop-1-ynyl)-4-(morpholin-2-ylmethylamino)pyridin-2-ylamino)pyrazine-2-carbonitrile (Y-154)

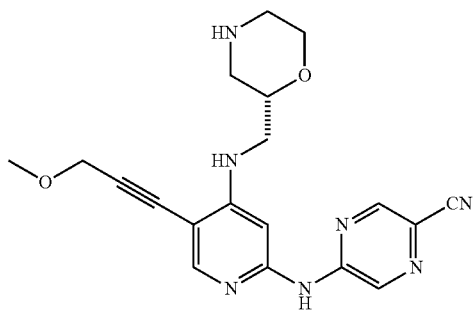 [SMILES: COCC#Cc1cnc(Nc2cnc(C#N)cn2)cc1NC[C@@H]1CNCCO1]

Prepared using methods analogous to those in Synthesis 190, steps 190-F, 190-G and 190-H and Synthesis 188, steps 188-A and 188-B.

¹H NMR (MeOD-d₄, 500 MHz) δ 8.93 (s, 1H), 8.58 (s, 1H), 8.02 (s, 1H), 7.10 (s, 1H), 4.41 (s, 2H), 3.93 (d, 1H, J=9.4 Hz), 3.79-3.75 (m, 1H), 3.68-3.64 (m, 1H), 3.46 (s, 3H), 3.38 (dd, 1H, J=13.8, 4.6 Hz), 3.30 (dd, 1H, J=13.8, 6.7 Hz), 3.00 (dd, 1H, J=12.6, 2.0 Hz), 2.87-2.85 (m, 2H), 2.68 (dd, 1H, J=12.4, 10.8 Hz). LCMS (4) Rt=1.37 min; m/z (ESI⁺) 380 (MH⁺).

Synthesis 200

(S)-5-(5-(3-Methoxy-3-methylbut-1-ynyl)-4-(morpholin-2-ylmethylamino)pyridin-2-ylamino)pyrazine-2-carbonitrile (Y-155)

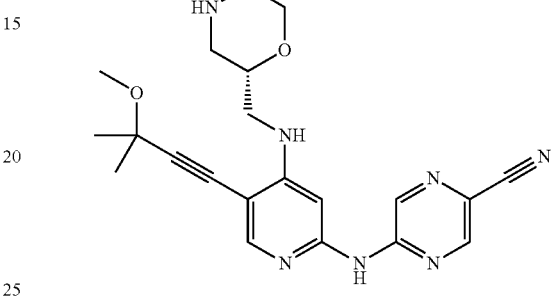

Prepared from (R)-tert-butyl 2-((2-chloro-5-iodopyridin-4-ylamino)methyl)morpholine-4-carboxylate (Synthesis 191-E) using methods analogous to those described in Synthesis 189, steps 189-A and 189-B.

¹H NMR (CDCl₃, 500 MHz) δ 8.75 (s, 1H), 8.41 (s, 1H), 7.99 (s, 1H), 6.85 (s, 1H), 5.46 (t, 1H, J=5.0 Hz), 3.87-3.85 (m, 1H,), 3.73-3.68 (m, 1H), 3.60 (td, 1H, J=11.0, 3.5 Hz), 3.37 (s, 3H), 3.26 (ddd, 1H, J=12.5, 6.0, 4.0 Hz), 3.14 (ddd, 1H, J=12.5, 7.5, 4.0 Hz), 2.93-2.90 (m, 1H), 2.87-2.76 (m, 2H), 2.69 (dd, 1H, J=12.0, 10.5 Hz), 1.52 (s, 6H). LCMS (4) Rt=1.55 min; m/z (ESI⁺) 408 (MH⁺).

Synthesis 201

(R)-5-(5-(4-(Methoxymethyl)phenyl)-4-(morpholin-2-ylmethylamino)pyridin-2-ylamino)pyrazine-2-carbonitrile (Y-156)

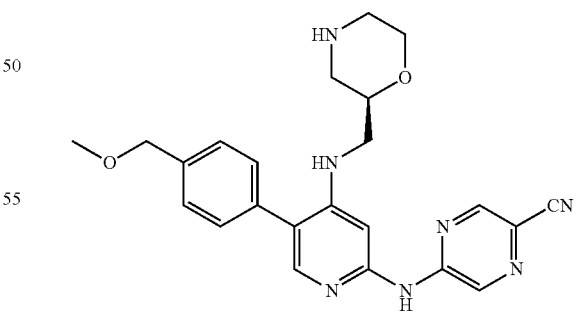

Prepared using methods analogous to those in Synthesis 192, steps 192-F, 192-G and 192-H.

¹H NMR (MeOD-d₄, 500 MHz) δ 8.92 (s, 1H), 8.57 (s, 1H), 7.77 (s, 1H), 7.48 (d, 2H, J=8.2 Hz), 7.40 (d, 2H, J=8.2 Hz), 1.86 (s, 2H), 3.85-3.82 (m, 1H), 3.72-3.67 (m, 1H), 3.60-3.55 (m, 1H), 2.82 (s, 3H), 3.22-3.18 (m, 1H), 2.93 (dd,

1H, J=2.3, 12.5 Hz), 2.78-2.76 (m, 2H), 2.58 (dd, 1H, J=10.4, 12.5 Hz). LCMS (4) Rt=1.36 min; m/z (ESI$^+$) 432 [MH$^+$].

Synthesis 202

(R)-5-(5-(4-(2-Methoxyethoxy)phenyl)-4-(morpholin-2-ylmethylamino)pyridin-2-ylamino)pyrazine-2-carbonitrile (Y-157)

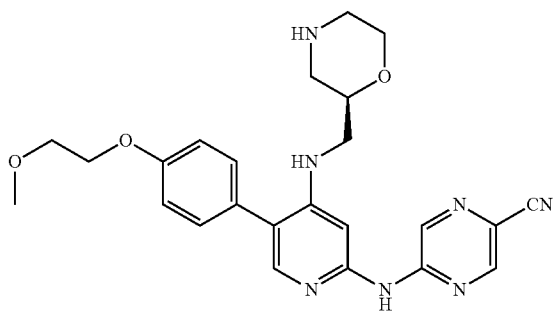 [SMILES: COCCOc1ccc(-c2cnc(Nc3cnc(C#N)cn3)cc2NC[C@H]2CNCCO2)cc1]

Prepared using methods analogous to those in Synthesis 192, steps 192-F, 192-G and 192-H.

LCMS (4) Rt=1.39 min; m/z (ESI$^+$) 462 [MH$^+$].

Synthesis 203

(R)-5-(5-(3-hydroxy-3-methylbut-1-ynyl)-4-(morpholin-2-ylmethylamino)pyridin-2-ylamino)pyrazine-2-carbonitrile (Y-158)

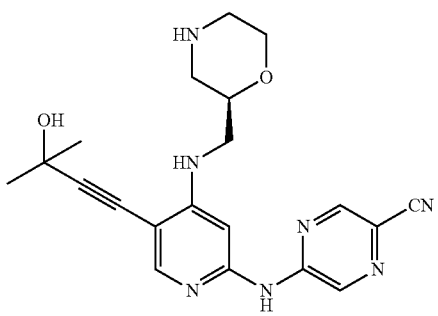 [SMILES: CC(C)(O)C#Cc1cnc(Nc2cnc(C#N)cn2)cc1NC[C@H]1CNCCO1]

Prepared from (S)-tert-butyl 2-((2-chloro-5-iodopyridin-4-ylamino)methyl)morpholine-4-carboxylate (Synthesis 192-E) using methods analogous to those described in Synthesis 189, steps 189-A and 189-B.

$^1$H NMR (MeOD-d$_4$, 500 MHz) δ 8.92 (s, 1H), 8.60 (s, 1H), 8.00 (s, 1H), 7.16 (s, 1H), 4.14-4.12 (m, 1H), 4.03-3.92 (m, 1H), 3.83 (td, 1H, J=2.6, 12.4 Hz), 3.56-3.38 (m, 2H), 3.36-3.33 (m, 2H), 3.27-3.08 (m, 2H), 2.98 (t, 1H, J=11.8 Hz), 1.62 (s, 6H). LCMS Rt=1.25 min; m/z (ESI$^+$) 394 [MH$^+$].

Synthesis 204

(R)-5-(5-(3-Methoxypropyl)-4-(morpholin-2-ylmethylamino)pyridin-2-ylamino)pyrazine-2-carbonitrile (Y-159)

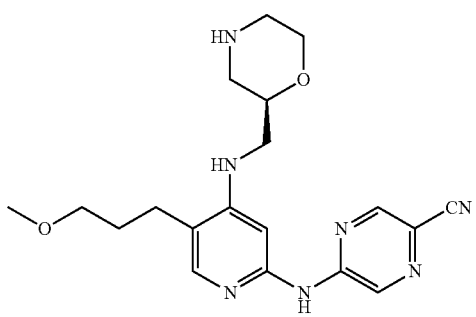 [SMILES: COCCCc1cnc(Nc2cnc(C#N)cn2)cc1NC[C@H]1CNCCO1]

Prepared using methods analogous to those in Synthesis 198 and Synthesis 185.

$^1$H NMR (MeOD-d$_4$, 500 MHz) δ 8.78 (s, 1H), 8.55 (s, 1H), 7.72 (s, 1H), 6.96 (s, 1H), 3.93 (dd, 1H, J=11.3, 1.7 Hz), 3.84-3.74 (m, 1H), 3.70-3.61 (m, 1H), 3.45 (t, 2H, J=6.1 Hz), 3.39 (s, 3H), 3.37-3.28 (m, 2H), 3.01 (d, 1H, J=12.4 Hz), 2.91-2.90 (m, 2H), 2.67-2.56 (m, 3H), 1.86-1.81 (m, 2H). LCMS (4) Rt=1.72 min; m/z (ESI$^+$) 384 [MH$^+$].

Synthesis 205-A

5-Amino-3-methoxypyrazine-2-carbonitrile

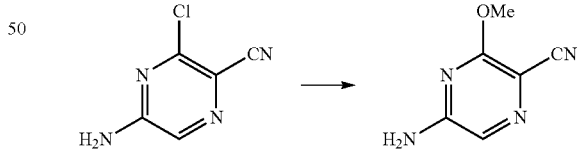

5-Amino-3-chloropyrazine-2-carbonitrile (52 mg, 0.34 mmol) was suspended in NaOMe/MeOH (2M, 2 mL). The reaction mixture was heated at 80° C. for 30 min using microwave irradiation. After cooling, the mixture was diluted with MeOH (3 mL) and water (2 mL). The solvents were concentrated and the resulting precipitate was filtered off, washed with water (3 mL) and dried in vacuo to give the title compound as a yellow solid (33 mg, 58%).

$^1$H NMR (500 MHz, d$_6$-DMSO) δ 7.65 (2H, s, broad), 7.52 (1H, s) and 3.90 (3H, s). LCMS (3B) Rt=2.60 min; m/z (ESI$^+$) 151 [MH$^+$].

Synthesis 205-B 5-(6-Chloropyrimidin-4-ylamino)-3-methoxypyrazine-2-carbonitrile

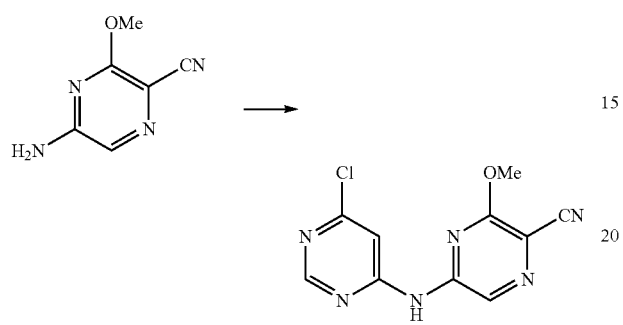

5-Amino-3-methoxypyrazine-2-carbonitrile (9.2 mg, 0.061 mmol), 4,6-dichloropyrimidine (10 mg, 0.067 mmol), lithium bis(trimethylsilyl)amide (1M, 75 uL, 0.075 mmol), Pd$_2$(dba)$_3$ (3.5 mg, 5.5% mol) and 2-(di-tert-butyl-phosphino)biphenyl (2 mg, 0.0067 mmol) were mixed in THF (0.5 mL). The reaction mixture was heated at 135° C. for 60 minutes using microwave irradiation. The crude product was purified by preparative thin layer chromatography, eluting with EtOAc/n-hexane (1/2), to give the title compound as an oil (4.5 mg, 28%).

$^1$H NMR (500 MHz, d$_4$-MeOD) δ 8.68 (1H, s), 8.61 (1H, s), 7.95 (1H, s), 4.16 (3H, s). LCMS (3B) Rt=4.32 min; m/z (ESI$^+$) 263 [MH$^+$].

Synthesis 205-C tert-Butyl 4-((6-(5-cyano-6-methoxypyrazin-2-ylamino)pyrimidin-4-ylamino)methyl)piperidine-1-carboxylate

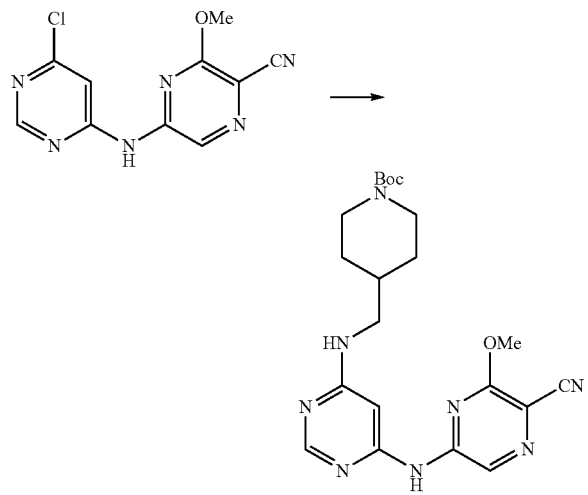

A solution of 5-(6-chloropyrimidin-4-ylamino)-3-methoxypyrazine-2-carbonitrile (4.5 mg, 0.017 mmol), tert-butyl 4-(aminomethyl)piperidine-1-carboxylate (4 mg, 0.034 mmol) and triethylamine (12 uL, 0.085 mmol) in acetonitrile (1.5 mL) was heated at 145° C. for 90 min using microwave irradiation. The solvent was removed in vacuo and the crude mixture was purified by preparative thin layer chromatography, eluting with dichloromethane/MeOH (10/1), to give the title compound as a yellow oil (3 mg, 40%).

$^1$H NMR (500 MHz, CDCl$_3$) δ 8.38 (1H, s), 8.30 (1H, s), 7.05 (1H, s), 5.24-5.58 (1H+1H, m, NH), 4.15-4.26 (2H, m), 4.13 (3H, s), 3.18-3.32 (2H, m), 2.64-2.84 (3H, m), 1.79-1.85 (2H, m), 1.46 (9H, s), 1.14-1.26 (2H, m). LCMS (3B) Rt=4.87 min; m/z (ESI$^+$) 441 [MH$^+$].

Synthesis 205-D

3-Methoxy-5-(6-(piperidin-4-ylmethylamino)pyrimidin-4-ylamino)-pyrazine-2-carbonitrile (Z-046)

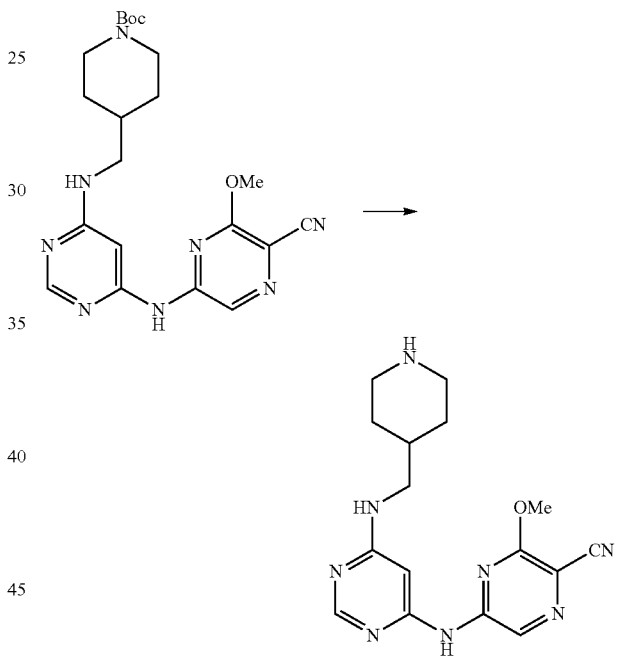

TFA (0.1 mL) was added to a solution of tert-butyl 4-((6-(5-cyano-6-methoxypyrazin-2-ylamino)-pyrimidin-4-ylamino)methyl)piperidine-1-carboxylate (3 mg, 0.0068 mmol) in dichloromethane (3 mL) at room temperature. After 2 hr, the solution was evaporated to dryness and purified by ion exchange on SCX-II acidic resin (500 mg), eluting with methanol then 2M ammonia-methanol. The basic fractions were combined and the solvent was removed in vacuo to give the title compound as yellow oil (1.5 mg, 65%).

$^1$H NMR (500 MHz, d$_4$-MeOD) δ 8.38 (1H, s), 8.22 (1H, s), 7.02 (1H, s), 4.16 (3H, s), 3.20-3.30 (2H, m), 3.10-3.20 (4H, m), 2.62-2.76 (2H, m), 1.78-1.88 (3H, m). LCMS (3B) Rt=2.02 min; m/z (ESI$^+$) 341.2 [MH$^+$].

Biological Methods

Measurement of Inhibition of CHK1 Kinase Function

CHK1 kinase function was measured in a DELFIA® assay in order to monitor phosphorylation of a CDC25C peptide using a specific phospho antibody.

The enzyme reaction was carried out in polypropylene plates (Greiner) using a reaction mix (25 μL) containing enzyme and peptide mix (CHK1, 1 nM; Biotin-KKKVSRS-GLYRSPSMPENLNRPR, 1 μM or 15 μL), ATP (30 μM or 5 μL) and either DMSO (2.5%) or test compound (5 μL) diluted to a give a range of concentrations (from 0 to 100 μM in 2.5% DMSO, final concentrations) in assay buffer (40 mM Tris, 40 mM NaCl, 2 mM $MgCl_2$, 1 mM DTT and 0.1% Tween 20). The reaction mixture was incubated for 30 minutes at room temperature and then stopped by the addition of buffer (125 μL) containing 40 mM EDTA, 0.05% Tween 20, 0.1% BSA in TBS (10× concentrate, Sigma). An aliquot (100 μL) of the stopped reaction mixture was transferred to a black neutravidin-coated plate (Perbio) and incubated for 1 hour on a shaker (Titertek, Flow Laboratories) at room temperature. The plates were washed four times with wash buffer (25 mM Tris (pH 8), 150 mM NaCl, and 0.1% Tween 20) (WellWash4, Thermo Life Sciences) and incubated for 1 hour as before with an antibody mixture (100 μL) consisting of anti-phospho CDC25C (1.25 nM, #9528, Cell Signalling Technology) and europium-labelled anti-rabbit IgG (0.3 μg/mL, AD0105, PerkinElmer Life Sciences) diluted in DELFIA assay buffer (PerkinElmer Life Sciences). The plates were washed a further four times with wash buffer before the addition of enhancement solution (100 μL/well, PerkinElmer Life Sciences). The plate was read on a $Victor^2$ 1420 multilabel counter (Perkin Elmer Life Sciences) using a time-resolved measurement mode reading fluorescence at 615 nm.

Measurement of Cytotoxicity

HT29 colon carcinoma cells were obtained from ATCC (Rockville, Md., USA). Cells were grown in DMEM supplemented with 10% foetal calf serum and containing L-glutamine 5 mM, glucose, penicillin, and streptomycin. Cells were grown at 37° C. in a dry 5% $CO_2$ atmosphere. Cytotoxicity assays were carried out in 96-well plates using quadruplicate wells for each dose. Cells were seeded at 1.6× $10^3$ per well in 160 μL medium and were allowed to attach for 36 hours prior to treatment. Test compounds were dissolved in DMSO at 10 mM and serially diluted in culture medium to 5× final concentration prior to addition in a volume of 40 μl per well. Cells were left for 4 doublings (96 hours) in the presence of the test compounds and then fixed in 10% TCA for 30 minutes, washed in water, and dried. The fixed cells were stained with Sulfurhodamine B (SRB, 0.4% in 1% acetic acid, Sigma, Dorset, UK) for 30 minutes, washed in 1% acetic acid, and dried. SRB was resolubilised in 10 mM Tris base and the OD was measured at 490 nm. Results were expressed relative to untreated controls and the concentration of compound required to inhibit growth by 50% (SRB $IC_{50}$) was calculated.

Mitosis Inhibition Assay (MIA)

Checkpoint abrogation by CHK1 kinase function inhibitors in combination with genotoxic agents was assessed using a europium based ELISA assay designed to quantify the number of cells trapped in mitosis after treatment with a genotoxic agent (to induce G2 arrest) followed by a test compound in combination with nocodazole to abrogate this arrest.

HT29 cells were seeded at $10^4$ cells per well into 96 well plates in a volume of 160 μL and left to attach for 36 hours. Etoposide (10 mM stock in DMSO) was diluted in medium to 250 μM and then 40 μL was added to appropriate wells to give a final concentration of 50 μM and incubated for 1 hour. This treatment had previously been optimised to induce a G2 arrest in 80% of cells 16 hours following treatment. After genotoxic drug exposure, the medium was removed and replaced with fresh medium (160 μL). Cells were either untreated (untreated control or etoposide pre-treatment alone), exposed to nocodazole following etoposide pre-treatment or nocodazole alone (100 ng/mL final concentration), or exposed to increasing concentrations of test compound (200 μM-0.01 nM final concentration) in combination with nocodazole (100 ng/mL final concentration). Test compounds were added in 40 μL using quadruplicate wells for each dose. After 21 hours exposure, the medium was removed and cells were fixed in 4% formaldehyde in phosphate buffered saline (PBS, pH 7.4, pre-cooled to 4° C.) for 30 minutes at 4° C., followed by 100% methanol (pre-cooled to −20° C.) for 10 minutes at ambient temperature. Wells were washed with PBS and blocked with 5% dried milk (Marvel) in Tris-buffered saline (TBS, pH 7.4) at 37° C. for 30 minutes. Each well was washed three times with water containing 0.1% tween 20. Primary antibody (MPM-2, Upstate cat#05-368, 1 μg/mL in 5% milk in TBS) was added to each well and incubated overnight with shaking at 4° C. Primary antibody was removed and wells were washed with water containing 0.1% Tween 20. The secondary antibody (europium labelled anti-mouse, Perkin-Elmer cat#AD0124, 333 ng/mL in assay buffer Perkin-Elmer cat#1244-111) was added to each well and incubated at 37° C. for 1 hour. Each well was washed with water 0.1% containing tween 20 and treated with enhancement solution (Perkin-Elmer cat#1244-105). Europium emissions were counted on a Wallac, $Victor^2$ counter (Perkin-Elmer, Bucks UK). Appropriate controls were included and results were expressed as the concentration of test compound required to allow 50% of cells to enter mitosis (MIA $IC_{50}$).

Biological Data

Biological data were obtained using the CHK1 kinase function inhibition assay described above for the following compounds: Y-001 through Y-039 and Z-001 through Z-045.

For the CHK1 kinase function inhibition assay, all of the compounds had IC50 values of less than 100 μM.

For the CHK1 kinase function inhibition assay, the following compounds had IC50 values of 1 μM or less: Y-001, Y-003, Y-005, Y-007, Y-008, Y-010, Y-016, Y-019, Y-020, Y-021, Y-022, Y-023, Y-024, Y-025, Y-026, Y-027, Y-028, Y-029, Y-031, Y-032, Y-033, Y-034, Y-036, Y-037, Z-007, Z-008, Z-010, Z-011, Z-012, Z-016, Z-021, Z-022, Z-025, Z-026, Z-027, Z-029, Z-039.

For the CHK1 kinase function inhibition assay, the following compounds had IC50 values of more than 1 μM and less than 10 μM: Y-004, Y-006, Y-009, Y-011, Y-012, Y-013, Y-015, Y-030, Y-038, Y-039, Z-004, Z-005, Z-006, Z-009, Z-013, Z-014, Z-015, Z-018, Z-019, Z-020, Z-024, Z-028, Z-031, Z-032, Z-038, Z-040, Z-041.

One compound, compound Y-003, has an IC50 value of 0.66 μM.

One compound, compound Z-016, has an IC50 value of 0.60 μM.

Biological data were obtained using the CHK1 kinase function inhibition assay described above for the following compounds: Y-001 through Y-159 and Z-001 through Z-046.

For the CHK1 kinase function inhibition assay, all of the compounds had IC50 values of less than 100 μM.

For the CHK1 kinase function inhibition assay, the following compounds had IC50 values of 0.1 μM or less: Y-007, Y-019, Y-020, Y-021, Y-022, Y-023, Y-025, Y-026, Y-027, Y-029, Y-032, Y-033, Y-037, Y-040, Y-041, Y-042, Y-047, Y-048, Y-053, Y-056, Y-058, Y-059, Y-060, Y-061, Y-062, Y-063, Y-064, Y-067, Y-070, Y-072, Y-073, Y-075, Y-076, Y-077, Y-078, Y-079, Y-080, Y-081, Y-082, Y-083, Y-084, Y-085, Y-086, Y-087, Y-095, Y-096, Y-098, Y-099, Y-100, Y-102, Y-103, Y-105, Y-107, Y-108, Y-110, Y-111, Y-112, Y-114, Y-115, Y-116, Y-117, Y-118, Y-119, Y-120, Y-122, Y-123, Y-124, Y-125, Y-126, Y-127, Y-128, Y-129, Y-130, Y-131, Y-135, Y-136, Y-137, Y-138, Y-139, Y-140, Y-141, Y-144, Y-145, Y-146, Y-147, Y-148, Y-149, Y-150, Y-151, Y-152, Y-153, Y-154, Y-155, Y-156, Y-157, Y-158, Y-159, Z-027.

For the CHK1 kinase function inhibition assay, the following compounds had IC50 values of more than 0.1 µM and less than or equal to 1 µM: Y-001, Y-003, Y-005, Y-008, Y-010, Y-016, Y-024, Y-028, Y-031, Y-034, Y-036, Y-043, Y-044, Y-055, Y-057, Y-065, Y-066, Y-071, Y-088, Y-091, Y-092, Y-093, Y-094, Y-097, Y-101, Y-106, Y-109, Y-113, Y-121, Y-132, Y-133, Y-134, Y-142, Y-143, Z-007, Z-008, Z-010, Z-011, Z-012, Z-016, Z-021, Z-022, Z-025, Z-026, Z-029, Z-039.

For the CHK1 kinase function inhibition assay, the following compounds had IC50 values of more than 1 µM and less than 10 µM: Y-004, Y-006, Y-009, Y-011, Y-012, Y-013, Y-015, Y-030, Y-038, Y-039, Y-045, Y-046, Y-050, Y-051, Y-052, Y-054, Y-068, Y-069, Y-074, Y-089, Y-090, Y-104, Z-004, Z-005, Z-006, Z-009, Z-013, Z-014, Z-015, Z-018, Z-019, Z-020, Z-024, Z-028, Z-031, Z-032, Z-038, Z-040, Z-041, Z-046.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

REFERENCES

A number of patents and publications are cited above in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Balaint and Vousden, 2001, "Activation and activities of the p53 tumour suppressor protein," *Br. J. Cancer*, Vol. 85, pp. 1813-1823.
Bartek and Lukas, 2003, "Chk1 and Chk2 kinases in checkpoint control and cancer," *Cancer Cell*, Vol. 3, pp. 421-429.
Carson and Lois, 1995, "Cancer progression and p53," *Lancet*, Vol. 346, pp. 1009-1011.
Dixon and Norbury, 2002, "Therapeutic exploitation of checkpoint defects in cancer cells lacking p53 function," *Cell Cycle*, Vol. 1, pp. 362-368.
Greenblatt et al., 1994, "Mutations in the p53 tumor suppressor gene: clues to cancer etiology and molecular pathogenesis," *Cancer Res.*, Vol. 54, pp. 4855-4878.
Itoh et al., 2002, "Efficient synthesis of substituted 2-aminopyrazines: FeCl3-promoted condensation of hydroxyiminoketones with aminoacetonitriles", *Tetrahedron Lett.*, Vol. 43, pp 9287-9290.
Liu et al., 2000, "Chk1 is an essential kinase that is regulated by Atr and required for the G(2)/M DNA damage checkpoint," *Genes Dev.*, Vol. 14, pp. 1448-1459.
Sanchez et al., 1997, "Conservation of the Chk1 checkpoint pathway in mammals: linkage of DNA damage to Cdk regulation through Cdc25," *Science*, Vol. 277, pp. 1497-1501.
Sorensen et al., 2005, "Cell-cycle checkpoint kinase Chk1 is required for mammalian homologous recombination repair," *Nat. Cell Biol.*, Vol 7, pp. 195-201.
Tao and Lin, 2006, "Chk1 inhibitors for novel cancer treatment," *Anti-Cancer Agents in Medicinal Chemistry*, Vol. 6, pp. 377-388.
Wang et al., 1996, "UCN-01: a potent abrogator of G2 checkpoint function in cancer cells with disrupted p53," *J. Natl. Cancer Inst.*, Vol. 8, pp. 956-965.
Wang et al., 2005, "Polycyclic Pyrazines as Potassium Channel Modulators", international patent application publication number WO 2005/121126 A1, published 22 Dec. 2005.
Weinert and Hartwell, 1989, "Control of G2 delay by the rad9 gene of *Saccharomyces cerevisiae*," *J. Cell Sci. Suppl.*, Vol. 12, pp. 145-148.
Xiao et al., 2006, "Differential roles of checkpoint kinase 1, checkpoint kinase 2, and mitogen-activated protein kinase-activated protein kinase 2 in mediating DNA damage-induced cell cycle arrest: implications for cancer therapy," *Mol. Cancer Ther.*, Vol. 5, pp. 1935-1943.
Zachos et al., 2003, "Chk1-deficient tumour cells are viable but exhibit multiple checkpoint and survival defects," *EMBO J.*, Vol. 22, pp. 713-723.
Zhao et al., 2002, "Disruption of the checkpoint kinase 1/cell division cycle 25A pathway abrogates ionizing radiation-induced S and G2 checkpoints," *Proc. Natl. Acad. Sci. USA*, Vol. 99, pp. 14795-14800.

The invention claimed is:

1. A method of inhibiting CHK1 kinase function in a cell, in vitro or in vivo, comprising contacting the cell with an effective amount of a compound selected from compounds of the following formula, and pharmaceutically acceptable salts thereof:

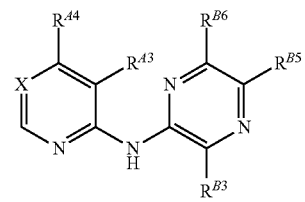

wherein:
—X= is —CR$^{A5}$=;
—R$^{A5}$ is -Q$^{A5}$;
—R$^{A3}$ is —H;
—R$^{A4}$ is independently -Q$^{A4N}$ or —O-Q$^{A4O}$;
—R$^{B3}$ is —H;
—R$^{B5}$ is -Q$^{B5}$;
-Q$^{B5}$ is —CN; and
—R$^{B6}$ is independently —H or -Q$^{B6}$;
and wherein:
-Q$^{A4N}$ is independently -Q$^{A4N1}$ or -Q$^{A4N2}$;
-Q$^{A4N1}$ is independently —NHR$^{QN1}$ or —NR$^{QN1}{}_2$;
-Q$^{A4N2}$ is —NR$^{QN2}$R$^{QN3}$;
each —R$^{QN1}$ is independently:
—R$^{J1}$, —R$^{J4}$, —R$^{J6}$, —R$^{J7}$, —R$^{J8}$,
-L$^{J}$-R$^{J4}$, -L$^{J}$-R$^{J6}$, -L$^{J}$-R$^{J7}$, or -L$^{J}$-R$^{J8}$;
wherein:
each —R$^{J1}$ is saturated aliphatic C$_{1-6}$alkyl;
each —R$^{J4}$ is saturated C$_{3-6}$cycloalkyl;
each —R$^{J6}$ is non-aromatic C$_{3-8}$heterocyclyl;
each —R$^{J7}$ is phenyl;
each —R$^{J8}$ is C$_{5-6}$heteroaryl;

each -$L^I$- is saturated aliphatic $C_{1-3}$alkylene;
and wherein:
  each $C_{1-6}$alkyl, $C_{3-6}$cycloalkyl, non-aromatic $C_{3-8}$heterocyclyl, phenyl, $C_{5-6}$heteroaryl, and $C_{1-3}$alkylene is optionally substituted with one or more substituents —$R^{J9}$, wherein each —$R^{J9}$ is independently:
    —$R^{L1}$,
    —OH, —$OR^{L1}$,
    —$NH_2$, —$NHR^{L1}$, —$NR^{L1}_2$, —$NR^{L2}R^{L3}$,
    —C(=O)$NH_2$, —C(=O)$NHR^{L1}$, —C(=O)$NR^{L1}_2$, or —C(=O)$NR^{L2}R^{L3}$;
  wherein:
    each —$NR^{L2}R^{L3}$ is independently pyrrolidino, piperidino, piperazino, or morpholino, and is optionally substituted with one or more groups selected from $C_{1-3}$alkyl and —$CF_3$;
    each —$R^{L1}$ is independently:
      —$R^{Z1}$, —$R^{Z7}$, or -$L^Z$-$R^{Z7}$;
    wherein:
      each —$R^{Z1}$ is saturated aliphatic $C_{1-6}$alkyl;
      each —$R^{Z7}$ is phenyl;
      each -$L^Z$- is saturated aliphatic $C_{1-3}$alkylene;
    and wherein:
      each $C_{1-6}$alkyl, $C_{6-10}$carboaryl, and $C_{1-3}$alkylene is optionally substituted with one or more substituents —$R^{Z9}$, wherein each —$R^{Z9}$ is independently:
        —F, —Cl, —Br, —I,
        —$R^{ZZ1}$,
        —$CF_3$, —$OCF_3$,
        —OH, -$L^{ZZ}$-OH,
        —$OR^{ZZ1}$, -$L^{ZZ}$-$OR^{ZZ1}$,
        —$NH_2$, —$NHR^{ZZ1}$, —$NR^{ZZ1}_2$, —$NR^{ZZ2}R^{ZZ3}$,
        -$L^{ZZ}$-$NH_2$, -$L^{ZZ}$-$NHR^{ZZ1}$, -$L^{ZZ}$-$NR^{ZZ1}_2$, -$L^{ZZ}$-$NR^{ZZ2}R^{ZZ3}$,
        —C(=O)OH, —C(=O)$OR^{ZZ1}$,
        —C(=O)$NH_2$, —C(=O)$NHR^{ZZ1}$, —C(=O)$NR^{ZZ1}_2$, or —C(=O)$NR^{ZZ2}R^{ZZ3}$;
      wherein:
        each —$R^{ZZ1}$ is independently saturated aliphatic $C_{1-4}$alkyl, phenyl, or benzyl;
        each -$L^{ZZ}$- is saturated aliphatic $C_{1-5}$alkylene; and
        each —$NR^{ZZ2}R^{ZZ3}$ is independently pyrrolidino, piperidino, piperazino, or morpholino, and is optionally substituted with one or more groups selected from $C_{1-3}$alkyl and —$CF_3$;
    and wherein:
      —$NR^{QN2}R^{QN3}$ is independently piperidino, piperazino, or morpholino, and is optionally substituted with one or more substituents —$R^{QNR}$, wherein each —$R^{QNR}$ is independently:
        —$R^{AA1}$,
        —$NH_2$, —$NHR^{AA1}$, —$NR^{AA1}_2$, —$NR^{AA2}R^{AA3}$,
        -$L^{AA}$-$NH_2$, -$L^{AA}$-$NHR^{AA1}$, -$L^{AA}$-$NR^{AA1}_2$, or -$L^{AA}$-$NR^{AA2}R^{AA3}$;
      wherein:
        each -$L^{AA}$- is saturated aliphatic $C_{1-5}$alkylene;
        each —$NR^{AA2}R^{AA3}$ is independently pyrrolidino, piperidino, piperazino, or morpholino, and is optionally substituted with one or more groups selected from $C_{1-3}$alkyl and —$CF_3$;
        each —$R^{AA1}$ is independently —$R^{BB1}$, —$R^{BB7}$, or -$L^{BB}$-$R^{BB7}$;
      wherein:
        each —$R^{BB1}$ is saturated aliphatic $C_{1-6}$alkyl;
        each —$R^{BB7}$ is phenyl;
        each -$L^{BB}$- is saturated aliphatic $C_{1-3}$alkylene;
      and wherein:
        each $C_{1-6}$alkyl, phenyl, and $C_{1-3}$alkylene is optionally substituted with one or more substituents —$R^{BB9}$, wherein each —$R^{BB9}$ is independently:
          —F, —Cl, —Br, —I,
          —$R^{CC1}$,
          —$CF_3$, —$OCF_3$,
          —OH, -$L^{CC}$-OH,
          —$OR^{CC1}$, -$L^{CC}$-$OR^{CC1}$,
          —$NH_2$, —$NHR^{CC1}$, —$NR^{CC1}_2$, —$NR^{CC2}R^{CC3}$,
          -$L^{CC}$-$NH_2$, -$L^{CC}$-$NHR^{CC1}$, -$L^{CC}$-$NR^{CC1}_2$, -$L^{CC}$-$NR^{CC2}R^{CC3}$,
          —C(=O)OH, —C(=O)$OR^{CC1}$,
          —C(=O)$NH_2$, —C(=O)$NHR^{CC1}$, —C(=O)$NR^{CC1}_2$, or —C(=O)$NR^{CC2}R^{CC3}$;
        wherein:
          each —$R^{CC1}$ is independently saturated aliphatic $C_{1-4}$alkyl, phenyl, or benzyl;
          each -$L^{CC}$- is saturated aliphatic $C_{1-5}$alkylene; and
          each —$NR^{CC2}R^{CC3}$ is independently pyrrolidino, piperidino, piperazino, or morpholino, and is optionally substituted with one or more groups selected from $C_{1-3}$alkyl and —$CF_3$;
and wherein:
  -$Q^{44O}$ is independently —$R^{C1}$, wherein —$R^{C1}$ is independently:
    —$R^{D1}$, —$R^{D6}$, —$R^{D7}$, —$R^{D8}$,
    -$L^D$-$R^{D6}$, -$L^D$-$R^{D7}$, or -$L^D$-$R^{D8}$;
wherein:
  each —$R^{D1}$ is independently saturated aliphatic $C_{1-6}$alkyl;
  each —$R^{D6}$ is non-aromatic $C_{3-8}$heterocyclyl;
  each —$R^{D7}$ is phenyl;
  each —$R^{D8}$ is $C_{5-6}$heteroaryl;
  each -$L^D$- is saturated aliphatic $C_{1-3}$alkylene;
and wherein:
  each $C_{1-6}$alkyl, non-aromatic $C_{3-8}$heterocyclyl, phenyl, $C_{6-10}$carboaryl, $C_{5-6}$heteroaryl, and $C_{1-3}$alkylene is optionally substituted with one or more substituents —$R^{D9}$, wherein each —$R^{D9}$ is independently:
    —F, —Cl, —Br, —I,
    —$R^{E1}$,
    —$CF_3$, —$OCF_3$,
    —OH, -$L^E$-OH, —O-$L^E$-OH,
    —$OR^{E1}$, -$L^E$-$OR^{E1}$, —O-$L^E$-$OR^{E1}$,
    —$NH_2$, —$NHR^{E1}$, —$NR^{E1}_2$, —$NR^{E2}R^{E3}$,
    -$L^E$-$NH_2$, -$L^E$-$NHR^{E1}$, -$L^E$-$NR^{E1}_2$, -$L^E$-$NR^{E2}R^{E3}$,
    —O-$L^E$-$NH_2$, —O-$L^E$-$NHR^{E1}$, —O-$L^E$-$NR^{E1}_2$,
    —O-$L^E$-$NR^{E2}R^{E3}$,
    —C(=O)OH, —C(=O)$OR^{E1}$,
    —C(=O)$NH_2$, —C(=O)$NHR^{E1}$, —C(=O)$NR^{E1}_2$, or —C(=O)$NR^{E2}R^{E3}$;
  wherein:
    each —$R^{E1}$ is independently saturated aliphatic $C_{1-4}$alkyl, phenyl, or benzyl;
    each -$L^E$- is saturated aliphatic $C_{1-5}$alkylene; and
    each —$NR^{E2}R^{E3}$ is independently pyrrolidino, piperidino, piperazino, or morpholino, and is optionally substituted with one or more groups selected from $C_{1-3}$alkyl and —$CF_3$;
and wherein:
  -$Q^{45}$ is independently:
    —F, —Cl, —Br, —I,
    —$R^{J1}$,
    —$CF_3$, —$OCF_3$,
    —OH, -$L^J$-OH, —O-$L^J$-OH,
    —$OR^{J1}$, -$L^J$-$OR^{J1}$, —O-$L^J$-$OR^{J1}$,
    —CN,
    —$NH_2$, —$NHR^{J1}$, —$NR^{J1}_2$, —$NR^{J2}R^{J3}$, -L$^J$-NH$_2$, -L$^J$-NHR$^{J1}$, -L$^J$-NR$^{J1}{}_2$, -L$^J$-NR$^{J2}$R$^{J3}$,
—O-L$^J$-NH$_2$, —O-L$^J$-NHR$^{J1}$, —O-L$^J$-NR$^{J1}{}_2$, —O-L$^J$-NR$^{J2}$R$^{J3}$,
—C(=O)OH, —C(=O)OR$^{J1}$,
—C(=O)NH$_2$, —C(=O)NHR$^{J1}$, —C(=O)NR$^{J1}{}_2$, —C(=O)NR$^{J2}$R$^{J3}$,
—NHC(=O)R$^{J1}$, —NR$^{J1}$C(=O)R$^{J1}$,
—NHS(=O)$_2$R$^{J1}$, —NR$^{J1}$S(=O)$_2$R$^{J1}$, or
—C(=O)R$^{J1}$;

wherein:
each -L$^J$- is saturated aliphatic C$_{1-5}$alkylene;
each —NR$^{J2}$R$^{J3}$ is independently pyrrolidino, piperidino, piperazino, or morpholino, and is optionally substituted with one or more groups selected from C$_{1-3}$alkyl and —CF$_3$;
each —R$^{J1}$ is independently:
—R$^{K1}$, —R$^{K2}$, —R$^{K3}$, —R$^{K4}$, —R$^{K5}$, —R$^{K6}$, —R$^{K7}$, —R$^{K8}$,
-L$^K$-R$^{K4}$, -L$^K$-R$^{K5}$, -L$^K$-R$^{K6}$, -L$^K$-R$^{K7}$, or -L$^K$-R$^{K8}$;
wherein:
each —R$^{K1}$ is saturated aliphatic C$_{1-6}$alkyl;
each —R$^{K2}$ is aliphatic C$_{2-6}$alkenyl;
each —R$^{K3}$ is aliphatic C$_{2-6}$alkynyl;
each —R$^{K4}$ is saturated C$_{3-6}$cycloalkyl;
each —R$^{K5}$ is C$_{3-6}$cycloalkenyl;
each —R$^{K6}$ is non-aromatic C$_{3-8}$heterocyclyl;
each —R$^{K7}$ is phenyl;
each —R$^{K8}$ is C$_{5-6}$heteroaryl;
each -L$^K$- is saturated aliphatic C$_{1-3}$alkylene;
and wherein:
each C$_{1-6}$alkyl, C$_{2-6}$alkenyl, C$_{2-6}$alkynyl, C$_{3-6}$cycloalkyl, C$_{3-6}$cycloalkenyl, non-aromatic C$_{3-8}$heterocyclyl, phenyl, C$_{5-6}$heteroaryl, and C$_{1-3}$alkylene is optionally substituted with one or more substituents —R$^{K9}$, wherein each —R$^{K9}$ is independently:
—F, —Cl, —Br, —I,
—R$^{M1}$,
—CF$_3$, —OCF$_3$,
—OH, -L$^M$-OH,
—OR$^{M1}$, -L$^M$-OR$^{M1}$, —O-L$^M$-OR$^{M1}$,
—NH$_2$, —NHR$^{M1}$, —NR$^{M1}{}_2$, —NR$^{M2}$R$^{M3}$,
-L$^M$-NH$_2$, -L$^M$-NHR$^{M1}$, -L$^M$-NR$^{M1}{}_2$, -L$^M$-NR$^{M2}$R$^{M3}$,
—C(=O)OH, —C(=O)OR$^{M1}$,
—C(=O)NH$_2$, —C(=O)NHR$^{M1}$, —C(=O)NR$^{M1}{}_2$, or —C(=O)NR$^{M2}$R$^{M3}$;
wherein:
each —R$^{M1}$ is independently saturated aliphatic C$_{1-4}$alkyl, phenyl, or benzyl;
each -L$^M$- is saturated aliphatic C$_{1-5}$alkylene; and
each —NR$^{M2}$R$^{M3}$ is independently pyrrolidino, piperidino, piperazino, or morpholino, and is optionally substituted with one or more groups selected from C$_{1-3}$alkyl and —CF$_3$;
and wherein:
-Q$^{B6}$ is independently:
—R$^{W1}$,
—CF$_3$, —OCF$_3$,
—OH, -L$^W$-OH, —O-L$^W$-OH,
—OR$^{W1}$, -L$^W$-OR$^{W1}$, —O-L$^W$-OR$^{W1}$,
—CN,
—NH$_2$, —NHR$^{W1}$, —NR$^{W1}{}_2$, —NR$^{W2}$R$^{W3}$,
-L$^W$-NH$_2$, -L$^W$-NHR$^{W1}$, -L$^W$-NR$^{W1}{}_2$, -L$^W$-NR$^{W2}$R$^{W3}$,
—O-L$^W$-NH$_2$, —O-L$^W$-NHR$^{W1}$, —O-L$^W$-NR$^{W1}{}_2$, or —O-L$^W$-NR$^{W2}$R$^{W3}$;

wherein:
each -L$^W$- is saturated aliphatic C$_{1-5}$alkylene;
each —NR$^{W2}$R$^{W3}$ is independently pyrrolidino, piperidino, piperazino, or morpholino, and is optionally substituted with one or more groups selected from C$_{1-3}$alkyl and —CF$_3$;
each —R$^{W1}$ is independently:
—R$^{X1}$, —R$^{X4}$, —R$^{X6}$, —R$^{X7}$, —R$^{X8}$,
-L$^X$-R$^{X4}$, -L$^X$-R$^{X6}$, -L$^X$-R$^{X7}$ or -L$^X$-R$^{X8}$;
wherein:
each —R$^{X1}$ is saturated aliphatic C$_{1-6}$alkyl;
each —R$^{X4}$ is saturated C$_{3-6}$cycloalkyl;
each —R$^{X6}$ is non-aromatic C$_{3-8}$heterocyclyl;
each —R$^{X7}$ is C$_{6-10}$carboaryl;
each —R$^{X8}$ is C$_{5-10}$heteroaryl;
each -L$^X$- is saturated aliphatic C$_{1-3}$alkylene;
and wherein:
each C$_{1-6}$alkyl, C$_{3-6}$cycloalkyl, non-aromatic C$_{3-8}$heterocyclyl, C$_{6-10}$carboaryl, C$_{5-10}$heteroaryl, and C$_{1-3}$alkylene is optionally substituted with one or more substituents —R$^{X9}$, wherein each —R$^{X9}$ is independently:
—F, —Cl, —Br, —I,
—R$^{Y1}$,
—CF$_3$, —OCF$_3$,
—OH, -L$^Y$-OH,
—OR$^{Y1}$, -L$^Y$-OR$^{Y1}$,
—NH$_2$, —NHR$^{Y1}$, —NR$^{Y1}{}_2$, —NR$^{Y2}$R$^{Y3}$,
-L$^Y$-NH$_2$, -L$^Y$-NHR$^{Y1}$, -L$^Y$-NR$^{Y1}{}_2$, -L$^Y$-NR$^{Y2}$R$^{Y3}$,
—C(=O)OH, —C(=O)OR$^{Y1}$,
—C(=O)NH$_2$, —C(=O)NHR$^{Y1}$, —C(=O)NR$^{Y1}{}_2$, or —C(=O)NR$^{Y2}$R$^{Y3}$;
wherein:
each —R$^{Y1}$ is independently saturated aliphatic C$_{1-4}$alkyl, phenyl, or benzyl;
each -L$^Y$- is saturated aliphatic C$_{1-5}$alkylene; and
each —NR$^{Y2}$R$^{Y3}$ is independently pyrrolidino, piperidino, piperazino, or morpholino, and is optionally substituted with one or more groups selected from C$_{1-3}$alkyl and —CF$_3$.

2. A method according to claim 1, wherein —R$^{A4}$ is -Q$^{A4N}$.

3. A method according to claim 1, wherein —R$^{A4}$ is —O-Q$^{A4O}$.

4. A method according to claim 1, wherein —R$^{B6}$ is —H.

5. A method according to claim 1, wherein —R$^{B6}$ is -Q$^{B6}$.

6. A method according to claim 2, wherein -Q$^{A4N}$ is -Q$^{A4N1}$.

7. A method to claim 6, wherein:
each —R$^{QN1}$ is —R$^{J1}$; and
each —R$^{J1}$ is saturated aliphatic C$_{1-5}$alkyl.

8. A method according to claim 6, wherein -Q$^{A4N1}$ is independently selected from groups of the following formulae:

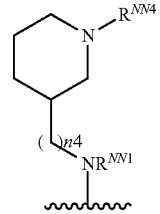

(A4N1-H)

-continued

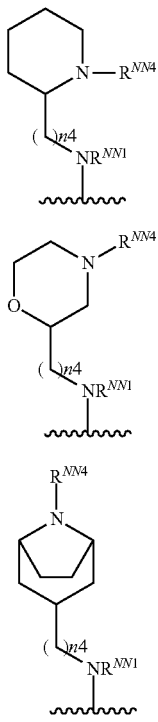

(A4N1-I)

(A4N1-J)

(A4N1-K)

wherein:
n4 is independently 1 or 2
$R^{NN1}$ is independently —H or saturated aliphatic $C_{1-4}$alkyl; and
$R^{NN4}$ is independently —H, saturated aliphatic $C_{1-4}$alkyl, phenyl, or benzyl.

9. A method according to claim 8, wherein -$Q^{A4N1}$ is a group of formula (A4N1-J).

10. A method according to claim 9, wherein:
n4 is 1;
—$R^{NN1}$ is —H or -Me; and
—$R^{NN4}$ is —H or -Me.

11. A method according to claim 1, wherein -$Q^{A5}$ is independently:
—F, —Cl, —Br, —I,
—$R^{J1}$,
—$NH_2$, —$NHR^{J1}$, —$NR^{J1}_2$, —$NR^{J2}R^{J3}$,
—C(=O)OH, —C(=O)$OR^{J1}$
—C(=O)$NH_2$, —C(=O)$NHR^{J1}$, —C(=O)$NR^{J1}_2$,
—C(=O)$NR^{J2}R^{J3}$,
—NHC(=O)$R^{J1}$, —$NR^{J1}$C(=O)$R^{J1}$,
—NHS(=O)$_2R^{J1}$, or —$NR^{J1}$S(=O)$_2R^{J1}$.

12. A method according to claim 1, wherein -$Q^{A5}$ is independently: —F, —Cl, —Br, —I, or —$R^{J1}$.

13. A method according to claim 1, wherein -$Q^{A5}$ is —$R^{J1}$.

14. A method according to claim 13, wherein each —$R^{J1}$ is independently:
—$R^{K1}$, —$R^{K4}$, —$R^{K6}$, —$R^{K7}$, —$R^{K8}$,
-$L^K$-$R^{K4}$, -$L^K$-$R^{K6}$, -$L^K$-$R^{K7}$, or -$L^K$-$R^{K8}$.

15. A method according to claim 13, wherein each —$R^{J1}$ is —$R^{K8}$.

16. A method according to claim 15, wherein each —$R^{K8}$ is independently thienyl or pyrazolyl, and is optionally substituted.

17. A method according to claim 15, wherein each —$R^{K8}$ is independently selected from:

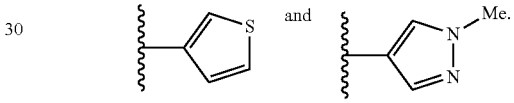

18. A method according to claim 1, wherein each —$R^{W1}$ is —$R^{X1}$; and each —$R^{X1}$ is saturated aliphatic $C_{1-3}$alkyl.

19. A method according to claim 1, which is a method of inhibiting CHK1 kinase function in a cell, in vitro.

\* \* \* \* \*